(12) United States Patent
Snyder et al.

(10) Patent No.: US 11,883,393 B2
(45) Date of Patent: Jan. 30, 2024

(54) COMPOUNDS AND METHODS FOR THE TARGETED DEGRADATION OF ANDROGEN RECEPTOR

(71) Applicant: Arvinas Operations, Inc., New Haven, CT (US)

(72) Inventors: Lawrence B. Snyder, Killingworth, CT (US); Hanqing Dong, Madison, CT (US)

(73) Assignee: Arvinas Operations, Inc., New Haven, CT (US)

( * ) Notice: Subject to any disclaimer, the term of this patent is extended or adjusted under 35 U.S.C. 154(b) by 242 days.

(21) Appl. No.: 17/126,501

(22) Filed: Dec. 18, 2020

(65) Prior Publication Data

US 2021/0196710 A1    Jul. 1, 2021

Related U.S. Application Data

(60) Provisional application No. 63/089,497, filed on Oct. 8, 2020, provisional application No. 63/032,473, filed
(Continued)

(51) Int. Cl.
*A61K 31/496*    (2006.01)
*A61K 47/54*    (2017.01)
(Continued)

(52) U.S. Cl.
CPC .......... *A61K 31/496* (2013.01); *A61K 31/167* (2013.01); *A61K 31/277* (2013.01); *A61K 31/337* (2013.01); *A61K 31/417* (2013.01); *A61K 31/4523* (2013.01); *A61K 31/4545* (2013.01); *A61K 31/497* (2013.01);
(Continued)

(58) Field of Classification Search
CPC .. A61K 31/167; A61K 31/277; A61K 31/337; A61K 31/417; A61K 31/4523; A61K 31/4545; A61K 31/497; A61K 31/5377; A61K 31/5386; A61K 31/57; A61K 31/661; A61K 31/663; A61K 31/675; A61K 47/545; A61P 35/00;
(Continued)

(56) References Cited

U.S. PATENT DOCUMENTS 4,522,811 A    6/1985  Eppstein et al.
5,492,922 A    2/1996  Palkowitz et al.
(Continued)

FOREIGN PATENT DOCUMENTS

CA    2945975 A1    4/2015
CL    202200302 A1    2/2023
(Continued)

OTHER PUBLICATIONS

Albrecht, B., et al. "Identification of a Benzoisoxazoloazepine Inhibitor (CPI-0610) of the Bromodomain and Extra-Terminal (BET) Family as a Candidate for Human Clinical Trials", J. Med. Chem., Jan. 27, 2016, 59, 1330-1339.
(Continued)

*Primary Examiner* — Sarah Pihonak
*Assistant Examiner* — Padmaja S Rao
(74) *Attorney, Agent, or Firm* — COOLEY LLP

(57) ABSTRACT

This disclosure pertains to compounds, the preparation thereof, and the use of these compounds in the treatment of prostate cancer, including metastatic and/or castrate-resistant prostate cancer, in subjects in need thereof.

4 Claims, 4 Drawing Sheets

Specification includes a Sequence Listing.

Related U.S. Application Data on May 29, 2020, provisional application No. 62/950,815, filed on Dec. 19, 2019.

(51) Int. Cl.

| | | |
|---|---|---|
| *A61K 31/167* | (2006.01) | |
| *A61K 31/277* | (2006.01) | |
| *A61K 31/4523* | (2006.01) | |
| *A61K 31/4545* | (2006.01) | |
| *C07D 401/14* | (2006.01) | |
| *A61K 31/337* | (2006.01) | |
| *A61K 31/417* | (2006.01) | |
| *A61K 31/497* | (2006.01) | |
| *A61K 31/501* | (2006.01) | |
| *A61K 31/5377* | (2006.01) | |
| *A61K 31/5386* | (2006.01) | |
| *A61K 31/57* | (2006.01) | |
| *A61K 31/661* | (2006.01) | |
| *A61K 31/663* | (2006.01) | |
| *A61K 31/675* | (2006.01) | |
| *A61K 38/09* | (2006.01) | |
| *C07D 401/12* | (2006.01) | |
| *A61K 31/506* | (2006.01) | |
| *C07D 413/12* | (2006.01) | |
| *C07D 413/14* | (2006.01) | |
| *C07D 498/10* | (2006.01) | |

(52) U.S. Cl.
CPC .......... *A61K 31/501* (2013.01); *A61K 31/506* (2013.01); *A61K 31/5377* (2013.01); *A61K 31/5386* (2013.01); *A61K 31/57* (2013.01); *A61K 31/661* (2013.01); *A61K 31/663* (2013.01); *A61K 31/675* (2013.01); *A61K 38/09* (2013.01); *A61K 47/545* (2017.08); *C07D 401/12* (2013.01); *C07D 401/14* (2013.01); *C07D 413/12* (2013.01); *C07D 413/14* (2013.01); *C07D 498/10* (2013.01)

(58) Field of Classification Search
CPC .. C07D 401/12; C07D 401/14; C07D 413/12; C07D 413/14; C07D 498/10
See application file for complete search history.

(56) References Cited

U.S. PATENT DOCUMENTS

| | | |
|---|---|---|
| 6,306,663 B1 | 10/2001 | Kenten et al. |
| 6,642,251 B1 | 11/2003 | Tang et al. |
| 6,670,348 B1 | 12/2003 | Rosen et al. |
| 7,030,141 B2 | 4/2006 | Bigge et al. |
| 7,041,298 B2 | 5/2006 | Deshaies et al. |
| 7,208,157 B2 | 4/2007 | Dashaies et al. |
| 8,067,473 B2 | 11/2011 | Erez et al. |
| 9,500,653 B2 | 11/2016 | Sabapathy et al. |
| 9,632,089 B2 | 4/2017 | Crews et al. |
| 9,938,264 B2 | 4/2018 | Crews et al. |
| 10,071,164 B2 | 9/2018 | Crew et al. |
| 10,584,101 B2 | 3/2020 | Crew et al. |
| 10,844,021 B2 | 11/2020 | Crew et al. |
| 11,149,007 B2 | 10/2021 | Ammirante et al. |
| 11,220,515 B2 | 2/2022 | Crews et al. |
| 11,236,051 B2 | 2/2022 | Crew et al. |
| 11,312,702 B2 | 4/2022 | Fan et al. |
| 11,325,889 B2 | 5/2022 | Ammirante et al. |
| 11,420,956 B2 | 8/2022 | Fan et al. |
| 11,535,606 B2 | 12/2022 | Fan et al. |
| 11,634,407 B2 | 4/2023 | Alexander et al. |
| 2007/0254933 A1 | 11/2007 | Jung et al. |
| 2008/0051432 A1 | 2/2008 | Zhang |
| 2008/0214501 A1 | 9/2008 | Pan et al. |
| 2008/0219929 A1 | 9/2008 | Wischik et al. |
| 2009/0035362 A1 | 2/2009 | Shih et al. |
| 2009/0142297 A1 | 6/2009 | Muller et al. |
| 2010/0048517 A1 | 2/2010 | Hu et al. |
| 2010/0286127 A1 | 11/2010 | Miyoshi et al. |
| 2011/0269793 A1 | 11/2011 | Macconi et al. |
| 2012/0270800 A1 | 10/2012 | Verdine et al. |
| 2014/0088143 A1 | 3/2014 | Jain |
| 2014/0256700 A1 | 9/2014 | Poss et al. |
| 2014/0302523 A1 | 10/2014 | Crews et al. |
| 2014/0356322 A1 | 12/2014 | Crews et al. |
| 2014/0371206 A1 | 12/2014 | Albrecht et al. |
| 2015/0119435 A1 | 4/2015 | Crews et al. |
| 2015/0141470 A1 | 5/2015 | Garraway et al. |
| 2015/0148342 A1 | 5/2015 | Combs et al. |
| 2015/0259288 A1 | 9/2015 | Nam et al. |
| 2015/0291562 A1 | 10/2015 | Crew et al. |
| 2015/0344473 A1 | 12/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0176864 A1 | 6/2016 | Norris et al. |
| 2016/0214972 A1 | 7/2016 | Jin et al. |
| 2016/0243247 A1 | 8/2016 | Bradner et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0015087 A1 | 1/2018 | Liu et al. |
| 2018/0072711 A1 | 3/2018 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0193470 A1 | 7/2018 | Crew et al. |
| 2018/0215731 A1 | 8/2018 | Crew et al. |
| 2018/0228907 A1 | 8/2018 | Crew et al. |
| 2018/0237418 A1 | 8/2018 | Crew et al. |
| 2018/0256586 A1 | 9/2018 | Crew et al. |
| 2019/0233433 A1 | 8/2019 | Crews et al. |
| 2021/0147387 A1 | 5/2021 | Arlt et al. |
| 2021/0171470 A1 | 6/2021 | Crew et al. |
| 2021/0380591 A1 | 12/2021 | Koolman et al. |
| 2022/0112211 A1 | 4/2022 | Crews et al. |
| 2022/0220124 A1 | 7/2022 | Fan et al. |
| 2022/0257774 A1 | 8/2022 | Du et al. |
| 2022/0259154 A1 | 8/2022 | Berlin et al. |
| 2022/0313826 A1 | 10/2022 | Phillips et al. |
| 2022/0380368 A1 | 12/2022 | Wang et al. |
| 2023/0002321 A1 | 1/2023 | Ammirante et al. |
| 2023/0011726 A1 | 1/2023 | Li et al. |
| 2023/0087008 A1 | 3/2023 | Pouletty et al. |
| 2023/0111119 A1 | 4/2023 | Lu et al. |
| 2023/0112499 A1 | 4/2023 | Panknin et al. |
| 2023/0119316 A1 | 4/2023 | Kurhade et al. |
| 2023/0142285 A1 | 5/2023 | Cai et al. |
| 2023/0159519 A1 | 5/2023 | Gerusz et al. |
| 2023/0183209 A1 | 6/2023 | Crew et al. |
| 2023/0203009 A1 | 6/2023 | Waetzig et al. |
| 2023/0241227 A1 | 8/2023 | Desantis et al. |
| 2023/0242509 A1 | 8/2023 | Alexander et al. |

FOREIGN PATENT DOCUMENTS

| | | |
|---|---|---|
| CL | 202200303 A1 | 2/2023 |
| CL | 202201583 A1 | 2/2023 |
| CL | 202201644 A1 | 2/2023 |
| CL | 202203305 A1 | 2/2023 |
| CL | 202201642 A1 | 3/2023 |
| CL | 202201660 A1 | 3/2023 |
| CL | 202201670 A1 | 3/2023 |
| CL | 202201739 A1 | 3/2023 |

(56) References Cited

FOREIGN PATENT DOCUMENTS

| | | |
|---|---|---|
| CL | 202203353 A1 | 7/2023 |
| CN | 1844118 A | 10/2006 |
| CN | 102477033 A | 5/2012 |
| CN | 103688176 A | 3/2014 |
| CN | 110746399 A | 2/2020 |
| CN | 113582974 A | 11/2021 |
| CN | 113912589 A | 1/2022 |
| CN | 114133379 A | 3/2022 |
| CN | 114163444 A | 3/2022 |
| DE | 2460304 A1 | 7/1976 |
| EP | 2985285 A1 | 2/2016 |
| EP | 3971176 A1 | 3/2022 |
| JP | 2002-523455 A | 7/2002 |
| JP | 2004-525889 A | 8/2004 |
| JP | 2010-502627 A | 1/2010 |
| JP | 2010-515771 A | 5/2010 |
| JP | 7061135 B2 | 4/2022 |
| RU | 2310651 C2 | 11/2007 |
| RU | 2008112221 A | 10/2009 |
| RU | 2418800 C2 | 5/2011 |
| RU | 2448101 C2 | 4/2012 |
| RU | 2011121567 A | 10/2012 |
| RU | 2012138709 A | 3/2014 |
| WO | WO 1998/003502 A1 | 1/1998 |
| WO | WO 99/15521 A1 | 4/1999 |
| WO | WO 99/31061 A1 | 6/1999 |
| WO | WO 2000/066119 A1 | 11/2000 |
| WO | WO 2002/000617 A2 | 1/2002 |
| WO | WO-0222577 A2 | 3/2002 |
| WO | WO 2002/066512 A1 | 8/2002 |
| WO | WO 2002/100845 A1 | 12/2002 |
| WO | WO-03097052 A2 | 11/2003 |
| WO | WO 2005/007141 A2 | 1/2005 |
| WO | WO 2006/113942 A2 | 10/2006 |
| WO | WO 2007/106670 A2 | 9/2007 |
| WO | WO 2008/011392 A1 | 1/2008 |
| WO | WO 2009/015254 A1 | 1/2009 |
| WO | WO 2010/053732 A1 | 5/2010 |
| WO | WO 2010/141805 A1 | 12/2010 |
| WO | WO 2011/008260 A2 | 1/2011 |
| WO | WO 2011/119565 A1 | 9/2011 |
| WO | WO 2011/143660 A2 | 11/2011 |
| WO | WO 2011/143669 A2 | 11/2011 |
| WO | WO 2012/003281 A2 | 1/2012 |
| WO | WO 2012/040389 A2 | 3/2012 |
| WO | WO 2012/040527 A2 | 3/2012 |
| WO | WO 2012/078559 A2 | 6/2012 |
| WO | WO 2012/090104 A1 | 7/2012 |
| WO | WO 2013/106643 A2 | 7/2013 |
| WO | WO 2013/106646 A2 | 7/2013 |
| WO | WO-2013097224 A1 | 7/2013 |
| WO | WO 2013/170147 A1 | 11/2013 |
| WO | WO 2014/001356 A1 | 1/2014 |
| WO | WO 2014/015157 A2 | 1/2014 |
| WO | WO 2014/108452 A1 | 7/2014 |
| WO | WO 2014/123418 A1 | 8/2014 |
| WO | WO 2014/128111 A1 | 8/2014 |
| WO | WO 2015/000868 A1 | 1/2015 |
| WO | WO 2015/011084 A1 | 1/2015 |
| WO | WO 2015/015318 A2 | 2/2015 |
| WO | WO 2015/022332 A1 | 2/2015 |
| WO | WO 2015/067770 A1 | 5/2015 |
| WO | WO 2015/074064 A2 | 5/2015 |
| WO | WO 2015/160845 A1 | 10/2015 |
| WO | WO 2015/195863 A1 | 12/2015 |
| WO | WO 2016/050821 A1 | 4/2016 |
| WO | WO 2016/069578 A1 | 5/2016 |
| WO | WO 2016/097071 A1 | 6/2016 |
| WO | WO 2016/105518 A1 | 6/2016 |
| WO | WO 2016/118666 A1 | 7/2016 |
| WO | WO 2016/146985 A1 | 9/2016 |
| WO | WO 2016/169989 A1 | 10/2016 |
| WO | WO 2016/172134 A2 | 10/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/011371 A1 | 1/2017 |
| WO | WO 2017/011590 A1 | 1/2017 |
| WO | WO 2017/030814 A1 | 2/2017 |
| WO | WO-2017024319 A1 | 2/2017 |
| WO | WO 2017/046036 A1 | 3/2017 |
| WO | WO 2017/079267 A1 | 5/2017 |
| WO | WO 2017/161119 A1 | 9/2017 |
| WO | WO 2017/185036 A1 | 10/2017 |
| WO | WO-2017176957 A1 | 10/2017 |
| WO | WO 2017/197051 A1 | 11/2017 |
| WO | WO 2018/053354 A1 | 3/2018 |
| WO | WO-2018071606 A1 | 4/2018 |
| WO | WO-2018098280 A1 | 5/2018 |
| WO | WO 2018/144649 A1 | 8/2018 |
| WO | WO 2018/200981 A1 | 11/2018 |
| WO | WO-2020132014 A1 | 6/2020 |
| WO | WO-2020132016 A1 | 6/2020 |
| WO | WO-2020198711 A1 | 10/2020 |
| WO | WO-2020198712 A1 | 10/2020 |
| WO | WO-2021249534 A1 | 12/2021 |
| WO | WO-2022048605 A1 | 3/2022 |
| WO | WO-2022111526 A1 | 6/2022 |

OTHER PUBLICATIONS

Allan, G. F., et al., "Therapeutic androgen receptor ligands", Nuclear Receptor Signaling, 2003, 1, e009, 9, 1-4.

Ariza, M. et al., "Tau Positron Emission Tomography (PET) Imaging: Past, Present, and Future", J. Med. Chem., Feb. 11, 2015, 58, 4365-4382.

Baratta, M. G. et al., "An in-tumor genetic screen reveals that the BET bromodomain protein, BRD4, is a potential therapeutic target in ovarian carcinoma", PNAS, Jan. 6, 2015, 112(1), 232-237.

Battista, M. J., et al., "Fulvestrant for the treatment of endometrial cancer", Expert Opinion on Investigational Drugs, 2016, 25(4), 475-483.

Beaumont, K., et al. "Design of Ester Prodrugs to Enhance Oral Absorption of Poorly Permeable Compounds: Challenges to the Discovery Scientist", Current Drug Metabolism, 2003, 4(6), 461-485.

Belkina, A. C. et al., "BET domain co-regulators in obesity, inflammation and cancer", Nat. Rev. Cancer, 2012, 12(7), 465-477.

Boi, M. et al., "The BET Bromodomain inhibitor OTX015 Affects Pathogenetic Pathways in Preclinical B-cell Tumor Models and Synergizes with Targeted Drugs", Clin Cancer Res., Apr. 1, 2015, 21(7), 1628-1638.

Boichenko, I., et al., "A FRET-Based Assay for the Identification and Characterization of Cereblon Ligands," J. Med. Chem., Jan. 5, 2016, 59, 770-774.

Boitano, et al., "Aryl Hydrocarbon Receptor Antagonists Promote the Expansion of Human Hematopoietic Stem Cells", Sep. 10, 2010, 329, 1345-1348.

Bondeson D. P., et al., "Lessons in PROTAC Design from Selective Degradation with a Promiscuous Warhead," Cell Chemical Biology, Jan. 18, 2018, 25(1), 78-87.

Brough, et al., "4,5-Diarylisoxazole Hsp90 Chaperone Inhibitors: Potential Therapeutic Agents for the Treatment of Cancer", J. Med. Chem., Jan. 24, 2008, 51(2), 196-218.

Burslem G. M., et al., "The Advantages of Targeted Protein Degradation Over Inhibition: An RTK Case Study." Cell Chemical Biology, Jan. 18, 2018, 25(1), 67-77.

Ceribelli, M. et al., "Blockade of oncongenic IκB kinase activity in diffuse large B-cell lymphoma by bromodomain and extraterminal domain protein inhibitors", PNAS, Aug. 5, 2014, 111(31), 11365-11370.

Chan, et al., "Impact of Target Warhead and Linkage Vector on Inducing Protein Degradation: Comparison of Bromodomain and Extra-Terminal (BET) Degraders Derived from Triazolodiazepine (JQ1) and Tetrahydroquinoline (I-BET726) BET Inhibitor Scaffolds," J. Med. Chem., Jun. 8, 2017, 61(2), 504-513.

Chang, et al., "Structural basis for G9a-like protein lysine methyltransferase inhibition by BIX-01294", Nat Struct Mol Biol., Mar. 2009, 16(3), 312-317.

(56) References Cited

OTHER PUBLICATIONS

Chapuy, B. et al., "Discovery and Characterization of Super-Enhancer-Associated Dependencies in Diffuse Large B Cell Lymphoma", Cancer Cell, Dec. 9, 2013, 24, 777-790.
Chung, C. et al., "Discovery and Characterization of Small Molecule Inhibitors of the BET Family Bromodomains", J. Med. Chem., May 13, 2011, 54(11), 3827-3838.
Churcher, I., "Protac-Induced Protein Degradation in Drug Discovery: Breaking the Rules or Just Making New Ones?" J. Med. Chem., Nov. 16, 2017, 61(2), 444-452.
Crew, A. P., et al. "Identification and Characterization of Von Hippel-Lindau-Recruiting Proteolysis Targeting Chimeras (PROTACs) of TANK-Binding Kinase 1." Journal of Medical Chemistry, Jul. 10, 2017, 61(2), 583-598.
Dawson, et al., "Inhibition of BET recruitment to chromatin as an effective treatment for MLL-fusion leukemia", Nature, Oct. 27, 2011, 478, 529-533.
Delmore, J. E. et al., "BET Bromodomain Inhibition as a Therapeutic Strategy to Target c-Myc", Cell, Sep. 16, 2011, 146, 904-917.
Deroo, B. J., et al., "Estrogen receptors and human disease", The Journal of Clinical Investigation, Mar. 2006, 116(3), 561-570.
Di, J. et al. "Reactivation of p53 by Inhibiting Mdm2 E3 Ligase: A Novel Antitumor Approach", Current Cancer Drug Targets, 2011, 11(8), 987-994.
Dixon, S. J. et al., "Identifying Druggable Disease-Modifying Gene Products", Curr. Opin. Chem. Biol., Dec. 2009, 13(5-6), 549-555.
Filippakopoulos, et al., "Selective inhibition of BET bromodomains", Nature, Dec. 23, 2010, 468, 1067-1073.
Finnin, et al., "Structures of a histone deacetylase homologue bound to the TSA and SAHA inhibitors", Nature, Sep. 9, 1999, 401, 188-193.
Gangjee, A. et al., "The contribution of a 2-amino group on receptor tyrosine kinase inhibition and antiangiogenic activity in 4-anilinosubstituted pyrrolo[2,3-d]pyrimidines", Bioorg Med Chem Lett., May 15, 2010, 20(10), 3177-3181.
Hewings, et al., "3,5-Dimethylisoxazoles Act as Acetyl-lysine-mimetic Bromodomain Ligands", J. Med. Chem., Aug. 18, 2011, 54(19), 6761-6770.
Hoffmann, J. et al., "Characterization of New Estrogen Receptor Destabilizing Compounds: Effects on Estrogen-Sensitive and Tamoxifen-Resistant Breast Cancer", Journal of the National Cancer Institute, Feb. 4, 2004, 96(3), 210-218.
Hu, J., et al. "Discovery of ERD-308 as a Highly Potent Proteolysis Targeting Chimera (PROTAC) Degrader of Estrogen Receptor (ER)," J. Med. Chem., Jan. 18, 2019, 62, 1420-1442.
Huang H.T., et al., "A Chemoproteomic Approach to Query the Degradable Kinome Using a Multi-kinase Degrader." Cell Chemical Biology, Jan. 18, 2018, 25(1), 88-99.
Ishikawa, T. et al., "Design and Synthesis of Novel Human Epidermal Growth Factor Receptor 2 (HER2)/Epidermal Growth Factor Receptor (EGFR) Dual Inhibitors Bearing a Pyrrolo[3,2-d]pyrimidine Scaffold", J. Med. Chem., Oct. 17, 2011, 54(23), 8030-8050.
Kim, A. et al., "Heat Shock Protein as Molecular Targets for Breast Cancer Therapeutics", J. Breast Cancer, Sep. 2011, 14(3), 167-174.
Konecny, G. E., et al., "Activity of the Dual Kinase Inhibitor Lapatinib (GW572016) against HER-2-Overexpressing and Trastuzumab-Treated Breast Cancer Cells", Cancer Research, Feb. 1, 2006, 66(3), 1630-1639.
Kurimchak, A. M. et al., "Resistance to BET Bromodomain Inhibitors Is Mediated by Kinome Reprogramming in Ovarian Cancer", Cell Reports, Aug. 2, 2016, 16, 1273-1286.
Liu, et al., "Discovery of a 2,4-Diamino-7-aminoalkoxyquinazoline as a Potent and Selective Inhibitor of Histone Lysine Methyltransferase G9a", J. Med. Chem., 2009, 52(24), 7950-7953.
Liu, H., et al., "Bioactivation of the Selective Estrogen Receptor Modulator Desmethylated Arzoxifene to Quinoids: 4'-Fluoro Substitution Prevents Quinoid Formation", Chem. Res. Toxicol., 2005, 18, 162-173.

Llinàs-Brunet, et al., "Discovery of a Potent and Selective Noncovalent Linear Inhibitor of the Hepatitis C Virus NS3 Protease (BI 201335)", J. Med. Chem., 53(17), 2010, 6466-6476.
Lountos, et al., "Structural Characterization of Inhibitor Complexes with Checkpoint Kinase 2 (Chk2), a Drug Target for Cancer Therapy", J Struct Biol., Dec. 2011, 176(3), 292-301.
Loven, J. et al., "Selective Inhibition of Tumor Oncogenes by Disruption of Super-Enhancers", Cell, Apr. 11, 2013, 153, 320-334.
Martin-Kohler, A. et al., "Furo[2,3-d] pyrimidines and Oxazolo[5,4-d]pyrimidines as Inhibitors of Receptor Tyrosine Kinases (RTK)", Helvetica Chimica Acta, 2004, 87(4), 956-975.
Maximov, P.Y. et al., "The Discovery and Development of Selective Estrogen Receptor Modulators (SERMs) for Clinical Practice," Current Clinical Pharmacology, 2013, 8(2), 135-155.
Mehellou, Y., et al., "Twenty-six years of anti-HIV drug discovery: where do we stand and where do we go?", J. Med. Chem., 2010, 53(2), 521-538.
Mertz, J. A. et al., "Targeting MYC dependence in cancer by inhibiting BET bromodomains", PNAS, 2011, 108, 16669-16674.
Millan, et al. "Design and Synthesis of Inhaled p38 Inhibitors for the Treatment of Chronic Obstructive Pulmonary Disease", J. Med. Chem., Sep. 5, 2011, 54(22), 7797-7814.
Nathan, M. R., et al., "A Review of Fulvestrant in Breast Cancer", Oncol Ther, 2017, 5, 17-29.
Nicodeme, et al., "Suppression of inflammation by a synthetic histone mimic", Nature, Dec. 2010, 468, 1119-1123.
Noel, J., "Abstract C244: Development of the BET bromodomain inhibitor OTX015", Molecular Cancer Therapeutics, 2013; 12(11 Suppl);C244, 1-4.
Powell, C. E. et al., "Chemically Induced Degradation of Anaplastic Lymphoma Kinase (ALK)", J. Med. Chem., 2018, 61, 4249-4255.
Puissant, A. et al., "Targeting MYCN in Neuroblastoma by BET Bromodomain Inhibition", Cancer Discovery, 2013, 3, 308-323.
Qin, Z., et al., "Benzothiophene Selective Estrogen Receptor Modulators with Modulated Oxidative Activity and Receptor Affinity", J. Med Chem., 2007, 50, 2682-2692.
Rautio, et al., "Prodrugs: design and clinical applications," Nature Reviews Drug Discovery, Mar. 2008, 7, 255-270.
Richters, A., et al., "Identification and Further Development of Potent TBK1 Inhibitors", ACS Chem. Biol., Dec. 26, 2014, 10(1), 289-298.
Robertson, J. F. R., "Fulvestrant (Faslodex®)—How to Make a Good Drug Better," Oncologist, 2007, 12, 774-784.
Rusch, M., et al., "Identification of Acyl Protein Thioesterases 1 and 2 as the Cellular Targets of the Ras-Signaling Modulators Palmostatin B and M", Angew. Chem. Int. Ed., 2011, 50, 9838-9842.
Scagliotti, G., et al., "Phase III Multinational, Randomized, Double-Blind, Placebo-Controlled Study of Tivantinib (ARQ 197) Plus Erlotinib Versus Erlotinib Alone in Previously Treated Patients With Locally Advanced or Metastatic Nonsquamous Non-Small-Cell Lung Cancer", Journal of Clinical Oncology, Aug. 20, 2015, 33(24), 2667-2674.
Schenkel, et al., "Discovery of Potent and Highly Selective Thienopyridine Janus Kinase 2 Inhibitors", J Med Chem., Nov. 16, 2011, 54(24), 8440-8450.
Sequist, L.V., et al., "Randomized Phase II Study of Erlotinib Plus Tivantinib Versus Erlotinib Plus Placebo in Previously Treated Non-Small-Cell Lung Cancer", Journal of Clinical Oncology, Aug. 20, 2011, 29(24), 3307-3315.
Shangary, S. et al. "Temporal activation of p53 by a specific MDM2 inhibitor is selectively toxic to tumors and leads to complete tumor growth inhabitation", PNAS USA, Mar. 11, 2008, 105(10), 3933-3938.
Stanton, et al., "Chemically induced proximity in biology and medicine." Science, Mar. 9, 2018, 359(117), 1-11.
Stuhlmiller, T., et al., "Inhibition of Lapatinib-Induced Kinome Reprogramming in ERBB2-Positive Breast Cancer by Targeting BET Family Bromodomains", Cell Reports, Apr. 21, 2015, 11, 390-404.
Suh, N. et al., "Arzoxifene, a New Selective Estrogen Receptor Modulator for Chemoprevention of Experimental Breast Cancer," Cancer Res., Dec. 1, 2001, 61, 8412-8415.

(56) References Cited

OTHER PUBLICATIONS

Sun, B. et al., "BET protein proteolysis targeting chimera (PROTAC) exerts potent lethal activity against mantle cell lymphoma cells," Leukemia, 2018, 32, 343-352.
Vallee, et al., "Tricyclic Series of Heat Shock Protein 90 (HSP90) Inhibitors Part I: Discovery of Tricyclic Imidazo [4,5-c] Pyridines as Potent Inhibitors of the Hsp90 Molecular Chaperone", J Med Chem., Oct. 5, 2011, 54(20), 7206-7219.
Van Eis, et al., "2,6-Naphthyridines as potent and selective inhibitors of the novel protein kinase C isozymes", Bioorganic & Medicinal Chemistry Letters, 2011, 21(24), 7367-7372.
Vassilev, et al., "In vivo activation of the p53 pathway by small-molecule antagonists of MDM2", Science, Feb. 6, 2004, 303, 844-848.
Vu, B. et al. "Discovery of RG7112: A Small-Molecule MDM2 Inhibitor in Clinical Development", ACS Med. Chem. Lett. Apr. 2, 2013, 4, 466-469.
Wang, C. et al., "Estrogen induces c-myc gene expression via an upstream enhancer activated by the estrogen receptor and the AP-1 transcription factor", Mol. Endocrinol., Sep. 2011, 25(9), 1527-1538.
Willson, T. M. et al., "3-[4-(1,2-Diphenylbut-1-enyl)phenyl]acrylic Acid: A Non-Steroidal Estrogen with Functional Selectivity for Bone over Uterus in Rats", J. Med. Chem., 1994, 37, 1550-1552.
Wolff, M., "Burger's Medicinal Chemistry", 5$^{th}$ Ed., Part 1, John Wiley & Sons, 1995, 975-977.
Wright, et al., "Structure-Activity Relationships in Purine-Based Inhibitor Binding to HSP90 Isoforms", Chem Biol., Jun. 2004, 11(6), 775-785.
Zhang, B. et al., "Small-molecule MDM2-p53 inhibitors: recent advances", Future Med. Chem., 2015, 7(5), 631-645.
Zhao, Y. et al. "Small-molecule Inhibitors of the MDM2-p53 Protein-Protein Interaction (MDM2 Inhibitors) in Clinical Trials for Cancer Treatment", J. Med. Chem., Nov. 14, 2014, 58, 1038-1052.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem., 2018, 61(2), 462-481.
Zillhardt, M., et al., "Foretinib (GSK1363089), an Orally Available Multikinase Inhibitor of c-Met and VEGFR-2, Blocks Proliferation, Induces Anoikis, and Impairs Ovarian Cancer Metastasis", Clinical Cancer Research, Jun. 15, 2011, 17(12), 4042-4051.
Ahn, et al. "HIF-1α peptide derivatives with modifications at the hydroxyproline residue as activators of HIF-1α" Bioorg Med Chem Lett. 19(15), 2009, 4403-4405.
Allan, et. al. "Therapeutic androgen receptor ligands" Nuclear Receptor Signaling, 2003, 1, e009 DOI:10.621.01009 9 1-4.
Asangani, et al. "Therapeutic Targeting of BET Bromodomain Proteins in Castration-Resistant Prostate Cancer" Nature. (2014), 510: 278-282.
Bargagna-Mohan, et al. "Use of PROTACS as molecular probes of angiogenesis" Bioorg. Med. Chem. Lett. (2005); 15(11) 2724-2727.
Bondeson, et al. "Targeted Protein Degradation by Small Molecules" Annu Rev Pharmacol Toxicol (2017) 57:107-123.
Bondeson, et al. "Catalytic in vivo protein knockdown by small-molecule PROTACS" National Chem Biol. (2015); 11(8), 611-617.
Bradbury, et al. "Small-molecule androgen receptor downregulators as an approach to treatment of advanced prostate cancer" Bioorganic & Medicinal Chemistry Letters. (2011). 21: 5442-5445.
Buckley, et al. "HaloPROTACS: use of small molecule PROTACS to induce degradation of HaloTag fusion proteins" ACS Chem Biol. (2015); 10(8),1831-1837.
Buckley, et al. "Small-molecule inhibitors of the interaction between the E3 ligase VHL and HIF1α" Angew Chem Int Ed Engl. (2012); 51(46), 11463-11467.
Buckley, et al. "Targeting the von Hippel-Lindau E3 ubiquitin ligase using small molecules to disrupt the VHL/HIF-1α interaction" Journal of the American Chemical Society, (2012); 134(10): 4465-4468.

Burslem, et al. "Small-Molecule Modulation of Protein Homeostasis" Chem Rev. (2017); 117(17):11269-11301.
Capitosti, S. et al. "Thalidomide analogues demonstrate dual inhibition of both angiogenesis and prostate cancer" Bioorganic & Medicinal Chemistry 12, (2004); 327-336.
Carmony, et al. "PROTAC-Induced Proteolytic Targeting" Methods Mol. Biol. (2012); vol. 832, pp. 627-638.
CAS 155180-53-3, published 1994.
CAS 155255-73-5, published 1995.
CAS 186040-53-9, published 1997.
CAS 186798-71-0, published 1997.
CAS 186798-85-6, published 1997.
CAS 534612-78-7, published 2003.
CAS Registry No. 1004933-70-3, entered STN on Feb. 21, 2008.
CAS Registry No. 871986-52-6, entered STN Jan. 16, 2006.
CAS Registry No. 1226974-40-8, indexed in the Registry file on STN CAS Online Jun. 4, 2010.
CAS Registry No. 1818885-25-4, indexed in the Registry file on STN CAS Online Nov. 10, 2015.
Contino-Pepin, et al. "Preliminary biological evaluations of new thalidomide analogues for multiple sclerosis application" Bioorganic & Medicinal Chemistry Letter 19 (2009); 878-881.
Corson, et al. "Design and applications of bifunctional small molecules: why two heads are better than one" ACS Chemical Biology (2008); vol. 3 No. 11, pp. 677-692.
Crews, C. M. "Targeting the undruggable proteome: the small molecules of my dreams" Chem Biol (2010); 17, 551-555.
Cromm, et al. "Targeted Protein Degradation: from Chemical Biology to Drug Discovery" Cell Chem Biol (2017); 24(9):1181-1190.
Cyrus, et al. "Jostling for position: optimizing linker location in the design of estrogen receptor-targeting PROTACs" Chem Med Chem. (2010); 5(7), 979-985.
Cyrus, et al. "Impact of Linker Length on the Activity of PROTACs" Mol. Biosyst., (2011); vol. 7, No. 2, pp. 359-364.
Cyrus, K. et al, "Two-Headed PROTAC: An Effective New Tool for Targeted Protein Degradation" Chembiochem. (2010); vol. 11, pp. 1531-1534.
Fischer, et al. "Structure of the DDB1-CRBN E3 Ubiquitin ligase in complex with thalidomide" Nature (2014): 1-5.
Gadd, M.S., et al. "Structural basis of PROTAC cooperative recognition for selective protein degradation" Nat Chem Biol (2017); 13, 514-521.
Galdeano, et al. "Structure-guided design and optimization of small molecules targeting the protein-protein interaction between the von hippel-lindau (VHL) E3 ubiquitin ligase and the Hypoxia inducible factor (HIF) alpha subunit with in Vitro nanomolar affinities" Journal Med Chem, Aug. 2014; vol. 57, pp. 8657-8663.
Golub, et al. "Molecular classification of cancer: class discovery and class prediction by gene expression monitoring" Science (1999); 286, 531-537.
Gosink, M., et al. "Redirecting the specificity of ubiquitination by modifying ubiquitin-conjugating enzymes" Pro. Natl. Acad. Sci. (1995); vol. 92, pp. 9117-9121.
Guo C., et. al, "Design of oxobenzimidazoles and oxindoles as novel androgen receptor antagonists" Bioorganic & Medicinal Chemistry Letters, (2012); 22:2572-2578.
Guo, C. et al "Discovery of Aryloxy Tetramethylcyclobutanes as Novel Androgen Receptor Antagonists" J. Med. Chem. (2011); 54, 7693-7704.
Gustafson, et al. "Small-Molecule-Mediated Degradation of the Androgen Receptor through Hydrophobic Tagging" Agnew. Chem. Int. Ed., (2015); 54: 9659-9662.
Hines, J., et al. "Posttranslational protein knockdown coupled to receptor tyrosine kinase activation with phosphoPROTACs" Proc Natl Acad Sci USA (2013); 110, 8942-8947.
Hon, et al. "Structural basis for the recognition of hydroxyproline in HIF1α by pVHL." Nature 417, (Jun. 27, 2002), 975-978.
Huang, et al. "Drugging the undruggables: exploring the ubiquitin system for drug development" Cell Res (2016); 26(4):484-498.
Hughes, et al. "Molecular recognition of ternary complexes: a new dimension in the structure-guided design of chemical degraders" Essays Biochem (2017); 61(5):505-516.

(56) References Cited

OTHER PUBLICATIONS

Ivan, et al. "HIFα Targeted for VHL-Mediated Destruction by Praline Hydroxylation: Implications for $O_2$ Sensing" Science (2001); vol. 292, No. 5516, pp. 464-468.
Jang, et al. "Targeted Degradation of Proteins by PROTACS" Curr. Protoc. Chem. Biol. (2010), vol. 2, No. 2, pp. 71-87.
Jung, et al "Structure-Activity Relationship for Thioydantoin Androgen Receptor Antagonists for Castration-Resistant Prostate Cancer (CRPC)" J. Med. Chem. 2010, 53, 2779-2796.
Knott, E. B. "Compounds containing sulphur chromophores. Part V. Complex Cyanines" Journal of The Chemical Society (1955); pp. 949-954.
Kronke, et al. "Lenalidomide Causes Selective Degradation of IKZF1 and IKZF3 in Multiple Myeloma Cells" Science (2014); 343, 301-305.
Lai, et al. "Modular PROTAC Design for the Degradation of Oncogenic BCR-ABL" Angew Chem Int Ed Engl(2016); 55, 807-810.
Lai, et al. "Induced protein degradation: an emerging drug discovery paradigm" Nat. Rev. Drug Discov. (2017); 16(2):101-114.
Lala, et al., "Role of nitric oxide in tumor progression: Lessons from experimental tumors" Cancer and Metastasis Reviews 17:291-106 (1998).
Lebraud, et al. "Protein Degradation by In-Cell Self-Assembly of Proteolysis Targeting Chimeras" ACS Central Science (2016); 2, 927-934.
Lee, et al. "Targeted Degradation of the Aryl Hydrocarbon Receptor by the PROTAC Approach: A Useful Chemical Genetic Tool" ChemBioChem (2007); vol. 8, Issue 17, pp. 2058-2062.
Lee, B. Y. "FAK signaling in human cancer as a target for therapeutics" Pharmacol. Ther. (2015); 146, 132-149.
Lelais, G. et al. "Discovery of (R,E)-N-(7-Chloro-1-(1-[4-(dimethylamino)but-2-enoyl]azepan-3-y1)-1H-benzo[d]imidazol-2-yl)-2-methylisonicotinamide (EGF816), a novel, potent, and WT sparing covalent inhibitor of oncogenic (L858R, eX19del) and resistant (T790M) EGFR mutants for the treatment of EGFR mutant non-small-cell lung cancers" Journal of Medicinal Chemistry (2016); 59(14), 6671-6689.
Lemmon, M. A., et al. "Cell Signaling by Receptor Tyrosine Kinases" Cell (2010); 141, 1117-1134.
Levine, et al. "Targeting the androgen receptor with steroid conjugates" J. Med. Chem. (2014); vol. 57. No. 20. pp. 8224-8237.
Li, Yan, et al. "Single polymer-drug conjugate carrying two drugs for fixed-dose co-delivery" Medicinal Chemistry, (2014); vol. 4(10): 676-683.
Liu, K. et al. "Design and biological characterization of hybrid compounds of curcumin and thalidomide for multiple myeloma" Org. Biomol. Chem. (2013); 11, 4757-4763.
Lopez-Girona, A., et al. "Cereblon is a direct protein target for immunomodulatory and antiproliferative activities of lenalidomide and pomalidomide" Leukemia (2012); 26: 2326-2335.
Lu, et al. "Hijacking the E3 ubiquitin ligase cereblon to efficiently target BRD4" Chemistry & Biology 22(6), 2015, 755-763.
Lu, et al. "The myeloma drug lenalidonlide promotes the cereblon-dependent destruction of ikaros proteins" Science (2014); 343, 305-309.
Lu, et al. "International Union of Pharmacology. LXV. The pharmacology and classification of the nuclear receptor superfamily: glucocorticoid, mineralocorticoid, progesterone, and androgen receptors" Pharmacol Rev. (2006); 58(4):782-797.
Maniaci, C., et al. "Homo-PROTACS: bivalent small-molecule dimerizers of the VHL E3 ubiquitin ligase to induce self-degradation" Nat Commun (2017); 8(1):830 1-14.
Medline Plus Trusted Health Information for You. (2007). URL: www.nlm.nih.gov/medlineplus/cancer.html pp. 1-10.
Min, Jung-hyun, et al. "Structure of an HIF-1α-pVHL complex: hydroxyproline recognition in signaling" (2002); 296: 1886-1889.
Mohler, M.L., et al. "Androgen receptor antagonists: a patent review (2008-2011)" Expert Opinion on Therapeutic Patents (2012); vol. 22, No. 5. pp. 541-565.

Muller, G. et al. "Amino-Substituted Thalodomide Analogs: Potent Inhibitors of TNF-α Production" Bioorganic & Medicinal ChemistrV Letters 9 (1999): 1625-1630.
Neklesa, T.K., et al. "Chemical biology: Greasy tags for protein removal" Nature (2012); 487, 308-309.
Neklesa, T. K. et al. "Targeted protein degradation by PROTACS" Pharmacology & Therapeutics (2017): 174, 138-144.
Office Action and Prior Art Search Report for RU Application No. 2020106066, filing date of Oct. 11, 2017, dated Jul. 30, 2020, English Translation, 8 pages.
Ohoka, N., et al. "SNIPER(TACC3) induces cytoplasmic vacuolization and sensitizes cancer cells to Bortezomib" Cancer Sci. (2017); 108, 1032-1041.
Ottis, et al. "Assessing Different E3 Ligases for Small Molecule Induced Protein Ubiquitination and Degradation" ACS Chem Biol (2017); 12(10):2570-2578.
Ottis, et al. "Proteolysis-Targeting Chimeras: Induced Protein Degradation as a Therapeutic Strategy" ACS Chem Biol (2017); 12(4):892-898.
Pepe, A. et. al. "Synthesis and structure-activity relationship studies of novel dihydropyridones as androgen receptor modulators" J. Med. Chem. (2013); 56, 8280-8297.
Poutiainen, P. K., et. al. "Design, synthesis, and biological evaluation of nonsteroidal cycloalkane[d]isoxazole-containing androgen receptor modulators" J. Med. Chem. (2012), 55, 6316-6327.
Puppala, D., et al. "Development of an Aryl Hydrocarbon Receptor Antagonist Using the Proteolysis-Targeting chimeric Molecules Approach: A Potential Tool for Chemoprevention" Mol. Pharmacol. (2008), vol. 73, No. 4, pp. 1064-1071.
Raina, et al. "Targeted protein knockdown using small molecule degraders" Curr Opin Chem Biol (2017); 39:46-53.
Raina, K. et al. "PROTAC-induced BET protein degradation as a therapy for castration-resistant prostate cancel" Proc Natl Acad Sci USA (2016); 113, 7124-7129.
Remillard D., et al. "Degradation of the BAF Complex Factor BRD9 by Heterobifunctional Ligands" Angew Chem Int Ed Engl (2017); 56(21):5738-5743.
Rodriguez-Gonzalez, et al. "Targeting steroid hormone receptors for ubiquitination and degradation in breast and prostate cancer" Oncogene. 27 (57), (2008):7201-7211.
Rotili, D., et al. "Photoactivable peptides for identifying enzyme-substrate and protein-protein interactions" Chem. Commun. 47(5), (2011): 1488-1490.
Ruchelman, A., et al. "Isosteric analogs of lenalidonlinde and pomalidomide: Synthesis and biological activity" Bioorganic & Medicinal Chemistry Letters 23 (2013): 360-365.
Sakamoto, et al. "Development of Protacs to target cancer-promoting proteins for ubiquitination and degradation" Mol Cell Proteomics. (2003); 2(12), 1350-1358.
Sakamoto, et al. "Protacs: chimeric molecules that target proteins to the Skp1-Cullin-F box complex for ubiquitination and degradation" Proc Natl Acad Sci USA. (2001); 98(15), 8554-8559.
Salami, J. & Crews, C. M. "Waste disposal—An attractive strategy for cancer therapy" Science (2017); 355, 1163-1167.
Schiedel, M., et al. "Chemically Induced Degradation of Sirtuin 2 (Sirt2) by a Proteolysis Targeting Chimera (PROTAC) Based on Sirtuin Rearranging Ligands (SirReals)" J Med Chem. (2017); 61:482-491.
Schneekloth, et al. "Chemical Genetic Control of Protein Levels: Selective in Vivo Targeted Degradation" J Am Chem Soc. (2004); 126(12), 3748-3754.
Schneekloth, et al. "Targeted intracellular protein degradation induced by a small molecule: En route to chemical proteomics" Bioorg. Med. Chem. Lett. 18 (2008); 5904-5908.
Smith, et al. "Targeted Intracellular Protein Degradation Induced by a Small Molecule: En Route to Chemical Proteomics" Bioorg Med Chem Lett. (2008);18(22), 5904-5908.
Stewart, Scott G. et al. "Efforts toward elucidating Thalidomide's molecular target: An Expedient Synthesis of the first Thalidomide Biotin Analogue" Org. Biomol. Chem. (2010); 8, 4059-4062.
STN transcript excerpt Nov. 24, 2017 "Compounds containing sulfur Chromophores V. Complex cyanines".

(56) References Cited

OTHER PUBLICATIONS

Stoppler, Melissa Conrad. Endometriosis [online], "Endometriosis Definition and Facts" retrieved on Apr. 5, 2017.
Stoppler, Melissa Conrad. Endometriosis [online], "What about surgery for Endometriosis?" Retrieved on Apr. 5, 2017.
Toure, et al. "Small-Molecule PROTACS: New Approaches to Protein Degradation" Angew Chem Int Ed Engl. (2016);55(6):1966-1973.
Trewartha, et al. "Advances in prostate cancer treatment" Nat Rev Drug Discov. (2013); (11):823-824.
Turk, B. E. et al. "Binding of thalidomide to $\alpha_1$-acid glycoprotein may be involved in its inhibition of tumor necrosis factor alpha production" Proc. Natl. Acad. Sci. U.S.A. (1996); 93, 7552-7556.
Van Molle, et al. "Dissecting fragment-based lead discovery at the von Hippel-Lindau protein:hypoxia inducible factor 1α protein-protein interface" Chem Biol. (2012); 19(10): 1300-1312.
Winter, et al. "Phthalimide Conjugation as a strategy for in vivo target protein degradation" Science, (2015) vol. 348 (6241), pp. 1376-1381.
Zengerle, et al. "Selective Small Molecule Induced Degradation of the BET Bromodomain Protein BRD4" ACS Chemical Biology, (2015); vol. 10, pp. 1770-1777.
Zhang, D., et al. "Targeted Degradation of Proteins by Small Molecules: A Novel Tool for Functional Proteomics" Comb Chem. High Throughput Screen. (2004); vol. 7, No. 7, pp. 689-697.
Arvinas Presentation, "ARV-110 Phase ½ Dose Escalation: Interim Update" [online] https://ir.arvinas.com/events-and-presentations?page=0%2C0%2C0 (May 29, 2020); 30 pages.
Arvinas Presentation, "Clinical Program Update: ARV-471 & ARV-110" [online] https://ir.arvinas.com/events-and-presentations?page=0%2C0%2C0 (Dec. 14, 2020); 43 pages.
Banker, G. S. et al. (Ed.)., "Modern Pharmaceutics", Third Edition, Revised and Expanded, Marcel Dekker, Inc. (1996); pp. 450-453 and 596-597; 10 pages.
Berlin, M./Arvinas Presentation, "Targeted Protein Degradation as a Clinical-stage Modality: Insights From ARV-110 and Other PROTAC® Protein Degraders", North American Protein Degradation Congress [online] https://ir.arvinas.com/events-and-presentations?page=0%2C0%2C0 (Feb. 5-6, 2020); 35 pages.
Bogush, T. A. et al., "Expression of estrogen receptors in tumors other than cancer mammary gland", Antibiotics and Chemotherapy (2009); 54(7-8): 41-49; 10 pages with English summary.
ClinicalTrials.gov Identifier: NCT01587703, "A Study to Investigate the Safety, Pharmacokinetics, Pharmacodynamics, and Clinical Activity of GSK525762 in Subjects With NUT Midline Carcinoma (NMC) and Other Cancers" [online] https://classic.clinicaltrials.gov/ct2/show/NCT01587703 (First Posted—Apr. 30, 2012, Access Date—Jul. 11, 2023); 59 pages.
ClinicalTrials.gov Identifier: NCT01713582, "A Dose-finding Study of the Bromodomain (Brd) Inhibitor OTX015/ Birabresib (MK-8628) in Hematologic Malignancies (MK-8628-001)" [online] https://classic.clinicaltrials.gov/ct2/show/NCT01713582 (First Posted—Oct. 22, 2012, Access Date—Jul. 11, 2023); 26 pages.
ClinicalTrials.gov Identifier: NCT01949883, "A Phase 1 Study Evaluating CPI-0610 in Patients With Progressive Lymphoma" [online] https://classic.clinicaltrials.gov/ct2/show/NCT01949883 (First Posted—Sep. 25, 2013, Access Date—Jul. 11, 2023); 12 pages.
ClinicalTrials.gov Identifier: NCT01987362, "A Two Part Study of RO6870810. Dose-Escalation Study in Participants With Advanced Solid Tumors and Expansion Study in Participants With Selected Malignancies" [online] https://classic.clinicaltrials.gov/ct2/show/NCT01987362 (First Posted—Nov. 19, 2013, Access Date—Jul. 11, 2023); 15 pages.
ClinicalTrials.gov Identifier: NCT05067140, "A Study of ARV-766 Given by Mouth in Men With Metastatic Castration-resistant Prostate Cancer Who Have Progressed on Prior Approved Systemic Therapies" [online] https://clinicaltrials.gov/ct2/show/NCT05067140?term=arv-766&draw=2&rank=1 (First Posted—Oct. 5, 2021, Last Update Posted—Feb. 2, 2023); 8 pages.

Durnov, L. A., et al., Pediatric Oncology, Second Edition, Moscow: Medicine Publishing House (2002); pp. 139-140; 5 pages with English summary.
Dyson, G. M., et al., "May's Chemistry of Synthetic Drugs", Longmans, Fifth Edition, Moscow, MIR (1964); pp. 12-19; 12 pages with English summary.
French, C.A., et al., "BRD-NUT oncoproteins: a family of closely related nuclear proteins that block epithelial differentiation and maintain the growth of carcinoma cells", Oncogene (2008); 27: 2237-2242.
Gabay, M., et al., "MYC Activation is a hallmark of cancer initiation and maintenance", Cold Spring Harbor Perspectives In Medicine (2014); 4(a014241): 1-14.
Garrido, J., "Influencia de los agentes exteriores sobre la forma de los cristales", Forma y estructura de los cristales, Exedra (1973); Chapter V: 204-225; 34 pages with English Translation.
Giron, D., "Thermal analysis and calorimetric methods in the characterisation of polymorphs and solvates", Thermochimica Acta (1995); 248: 1-59.
Heinlein, C. A., et al., "Androgen receptor in prostate cancer", Endocrine Reviews (2004); 25(2): 276-308.
Heinlein, C. A., et al., "The roles of androgen receptors and androgen-binding proteins in nongenomic androgen actions", Molecular Endocrinology (2002); 16(10): 2181-2187.
Houston, J. G./Arvinas Presentation, "The Promise of PROTAC® Protein Degraders: What's Next for Arvinas' Pipeline & Platform" [online] https://ir.arvinas.com/events-and-presentations?page=0%2C0%2C0 (Oct. 14, 2020); 23 pages.
Kiselev, F. L., "Regarding Molecular Mechanisms of Tumors", Priroda (2014); 4: 19-20; 4 pages with English summary.
Klapproth, K., et al., "Advances in the understanding of MYC-induced lymphomagenesis", British Journal of Hematology (2010); 149: 484-497.
Kümmerer, K., "Pharmaceuticals in the Environment", Annual Review of Environment and Resources (2010); 35: 57-75.
Lien, E. J., "Atomic and Molecular Structure and the States of Matter", Remington's Pharmaceutical Sciences, 16th Edition (1980); pp. 160-181.
Mooradian, A. D., et al., "Biological actions of androgens", Endocrine Reviews (1987); 8(1): 1-28.
Mullard, A., "First targeted protein degrader hits the clinic", Nature Reviews, Drug Discovery (Apr. 2019); 18: 237-239.
Nies, A. S., et al., "Principios de Terapeutica", Las Bases Farmacológicas De La Terapéutica (1996); Chapter 3; p. 47; 2 pages with English Translation.
Pandian, R. S., et al., "In-silico analysis and QSAR studies of tacrine hybrids with ubiquitin ligase on Alzheimer's disease", International Journal of Bioinformatics Research and Applications (2010); 6(6): 556-570.
Pantoliano, M. W., et al., "High-density miniaturized thermal shift assays as a general strategy for drug discovery", Journal of Biomolecular Screening (2001); 6(6): 429-440.
Papulov, Y. G., "Relationship of Substance Properties and Molecular Structure: Mathematical Simulation", Advances of Contemporary Natural Science (2006); 2: 75-76; 3 pages with English summary.
Patch, R. J., et al., "Identification of diaryl ether-based ligands for estrogen-related receptor α as potential antidiabetic agents", Journal of Medicinal Chemistry (2011); 54(3): 788-808.
PubChem CID 46916268, "4-(4-((2,4-Dioxothiazolidin-5-ylidene)methyl)-2-methoxyphenoxy)-3-(trifluoromethyl)benzonitrile", National Center for Biotechnology Information, Create date Oct. 21, 2010 [online] https://pubchem.ncbi.nlm.nih.gov/compound/E3-ligase-Ligand-5; 13 pages.
Roy, A. K., et al., "Regulation of androgen action", Vitamins & Hormones (1998); 55: 309-352.
Scudellari, M., "The protein slayers", Nature (Mar. 21, 2019); 567: 298-300.
Shi, J., et al., "The mechanisms behind the therapeutic activity of BET bromodomain inhibition", Molecular Cell (2014); 54(5): 728-736.

(56) References Cited

OTHER PUBLICATIONS

Suñé-Negre, J. M., "Nuevas aportaciones galénicas a las formas de administración", Formación Continuada para Farmacéuticos de Hospital (2002); 3(2): 1-29; 49 pages with English Translation.

Wyce, A et al., "Inhibition of BET bromodomain proteins as a therapeutic approach in prostate cancer", Oncotarget (Dec. 2013); 4(12): 2419-2429.

Zuber, J., et al., "RNAi screen identifies Brd4 as a therapeutic target in acute myeloid leukaemia", Nature (2011); 478(7370): 524-528.

Romanel, A., et al., "Plasma AR and abiraterone-resistant prostate cancer", Science Translational Medicine (2015); 7(312): 312re10; 9 pages.

Wyatt, A. W., et al., "Genomic alterations in cell-free DNA and enzalutamide resistance in castration-resistant prostate cancer", JAMA Oncology (2016); 2(12): 1598-1606.

Co-Pending U.S. Appl. No. 18/460,063, inventor Snyder; Lawrence B., filed on Sep. 1, 2023.

Cucchiara, V., et al., "Genomic markers in prostate cancer decision making", European Urology (2018); 73(4): 572-582.

Azad, A. A., et al., "Androgen receptor gene aberrations in circulating cell-free DNA: biomarkers of therapeutic resistance in castration-resistant prostate cancer", Clinical Cancer Research (2015); 21(10): 2315-2324.

Catalona, W. J., et al., "Comparison of digital rectal examination and serum prostate specific antigen in the early detection of prostate cancer: results of a multicenter clinical trial of 6,630 men", The Journal of Urology (1994); 15(5): 1283-1290.

Chen, C. D., et al., "Molecular determinants of resistance to antiandrogen therapy", Nature Medicine (2004); 10(1): 33-39.

Cleutjens, K. B. J. M., et al., "Two Androgen Response Regions Cooperate in Steriod Hormone Regulated Activity of the Prostate-specific Antigen Promoter", Journal of Biological Chemistry (1996); 271(11): 6379-6388.

Co-pending U.S. Appl. No. 18/493,773, inventors Peck; Ronald et al., filed on Oct. 24, 2023.

Gottlieb, B., et al., "The androgen receptor gene mutations database (ARDB): 2004 update", Human Mutation (2004); 23(6): 527-533.

Jenster, G., et al., "Functional domains of the human androgen receptor", The Journal of Steriod Biochemistry and Molecular Biology (1992); 41(3-8): 671-675.

Ledet, E. M., et al., "Comprehensive analysis of AR alterations in circulating tumor DNA from patients with advanced prostate cancer", The Oncologist (2020); 25(4): 327-333.

Li, J., et al., "Aberrant corticosteroid metabolism in tumor cells enables GR takeover in enzalutamide resistant prostate cancer", eLife (2017); 6: e20183; 17 pages.

Maclean, H. E., et al., "Localization of functional domains in the androgen receptor", The Journal of Steriod Biochemistry and Molecular Biology (1997); 62(4): 233-242.

Marcelli, M., et al., "Androgen receptor mutations in prostate cancer", Cancer Research (2000); 60(4): 944-949.

Page, S. T., et al., "Persistent intraprostatic androgen concentrations after medical castration in healthy men", The Journal of Clinical Endocrinology & Metabolism (2006); 91(10): 3850-3856.

Robinson, D., et al., "Integrative clinical genomics of advanced prostate cancer", Cell (2015); 161(5): 1215-1228.

Taplin, M., et al., "Mutation of the androgen-receptor gene in metastatic androgen-independent prostate cancer", New England Journal of Medicine (1995); 332(21): 1393-1398.

SEQUENCE LISTING

<160> NUMBER OF SEQ ID NOS: 1

<210> SEQ ID NO 1
<211> LENGTH: 920
<212> TYPE: PRT
<213> ORGANISM: Homo sapiens

<400> SEQUENCE: 1

```
Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
            85                  90                  95
```

-continued

```
Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350

Leu Asp Glu Ala Ala Ala Tyr Gln Ser Arg Asp Tyr Tyr Asn Phe Pro
        355                 360                 365

Leu Ala Leu Ala Gly Pro Pro Pro Pro Pro Pro Pro His Pro His
    370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly Gly Gly
    450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
```

```
            515                 520                 525
Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
            580                 585                 590

Lys Tyr Leu Cys Ala Ser Arg Asn Asp Cys Thr Ile Asp Lys Phe Arg
        595                 600                 605

Arg Lys Asn Cys Pro Ser Cys Arg Leu Arg Lys Cys Tyr Glu Ala Gly
    610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
                645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
        675                 680                 685

Gly His Asp Asn Asn Gln Pro Asp Ser Phe Ala Ala Leu Leu Ser Ser
    690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
                725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
        755                 760                 765

Leu Val Phe Asn Glu Tyr Arg Met His Lys Ser Arg Met Tyr Ser Gln
    770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
                805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
        835                 840                 845

Asn Pro Thr Ser Cys Ser Arg Arg Phe Tyr Gln Leu Thr Lys Leu Leu
    850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
                885                 890                 895

Ala Glu Ile Ile Ser Val Gln Val Pro Lys Ile Leu Ser Gly Lys Val
            900                 905                 910

Lys Pro Ile Tyr Phe His Thr Gln
        915                 920
```

COMPOUNDS AND METHODS FOR THE TARGETED DEGRADATION OF ANDROGEN RECEPTOR

CROSS-REFERENCE TO RELATED APPLICATIONS

This application claims priority to, and the benefit of, U.S. Application No. 63/089,497, filed Oct. 8, 2020, U.S. Application No. 63/032,473, filed May 29, 2020, U.S. Application No. 62/950,815, filed Dec. 19, 2019, the entirety of each of which is incorporated by reference herein.

INCORPORATION BY REFERENCE OF SEQUENCE LISTING

The contents of the text file named "ARVN-007_001US_SeqList_ST25", which was created on Dec. 16, 2020 and is 9 KB in size, are hereby incorporated by reference in their entirety.

TECHNICAL FIELD

The disclosure provides imide-based compounds, including bifunctional compounds comprising the same, and associated methods of use. The bifunctional compounds are useful as modulators of targeted ubiquitination, especially with respect to a variety of polypeptides and other proteins, which are degraded and/or otherwise inhibited by bifunctional compounds according to the present disclosure.

BACKGROUND OF THE DISCLOSURE

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and are therefore attractive therapeutic targets. The development of ligands of E3 ligases has proven challenging, in part due to the fact that they must disrupt protein-protein interactions. However, recent developments have provided specific ligands which bind to these ligases.

One E3 ubiquitin ligase with therapeutic potential is cereblon. Cereblon is a protein that in humans is encoded by the CRBN gene. Thalidomide and its analogs, e.g., pomalidomide and lenalidomide, are known to bind cereblon. These agents bind to cereblon, altering the specificity of the complex to induce the ubiquitination and degradation of transcription factors essential for multiple myeloma growth. Indeed, higher expression of cereblon has been linked to an increase in efficacy of imide drugs in the treatment of multiple myeloma.

Androgen Receptor (AR) belongs to a nuclear hormone receptor family that is activated by androgens, such as testosterone and dihydrotestosterone (Pharmacol. Rev. 2006, 58(4), 782-97; Vitam. Horn. 1999, 55:309-52). In the absence of androgens, AR is bound by Heat Shock Protein 90 (Hsp90) in the cytosol. When an androgen binds AR, its conformation changes to release AR from Hsp90 and to expose the Nuclear Localization Signal (NLS). The latter enables AR to translocate into the nucleus where AR acts as a transcription factor to promote gene expression responsible for male sexual characteristics (Endocr. Rev. 1987, 8(1): 1-28; Mol. Endocrinol. 2002, 16(10), 2181-7). AR deficiency leads to Androgen Insensitivity Syndrome, formerly termed testicular feminization.

While AR is responsible for development of male sexual characteristics, it is also a well-documented oncogene in certain forms of cancers including prostate cancers (Endocr. Rev. 2004, 25(2), 276-308). A commonly measured target gene of AR activity is the secreted Prostate Specific Antigen (PSA) protein. The current treatment regimen for prostate cancer involves inhibiting the androgen-AR axis by two methods. The first approach relies on reduction of androgens, while the second strategy aims to inhibit AR function (Nat. Rev. Drug Discovery, 2013, 12, 823-824). Despite the development of effective targeted therapies, most patients develop resistance and the disease progresses. An alternative approach for the treatment of prostate cancer involves eliminating the AR protein.

Because AR is a critical driver of tumorigenesis in many forms of prostate cancers, its elimination should lead to a therapeutically beneficial response. There exists an ongoing need in the art for effective treatments for diseases, especially cancer, prostate cancer, and Kennedy's Disease.

However, non-specific effects, and the inability to target and modulate certain classes of proteins altogether, such as transcription factors, remain as obstacles to the development of effective anti-cancer agents. As such, small molecule therapeutic agents that leverage or potentiate cereblon's substrate specificity and, at the same time, are "tunable" such that a wide range of protein classes can be targeted and modulated with specificity would be very useful as a therapeutic.

SUMMARY

The present disclosure describes bifunctional compounds which function to recruit endogenous proteins to an E3 Ubiquitin Ligase for degradation, and methods of using the same. In particular, the present disclosure provides bifunctional or proteolysis targeting chimeric compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer, e.g., multiple myeloma or prostate cancer.

In one aspect, the present application provides bifunctional compound having the structure:

ABM-L-CLM, or a pharmaceutically acceptable salt, solvate, enantiomer, stereoisomer, or isotopic derivative thereof, wherein:

(a) ABM is an androgen receptor (AR) binding moiety having the structure:

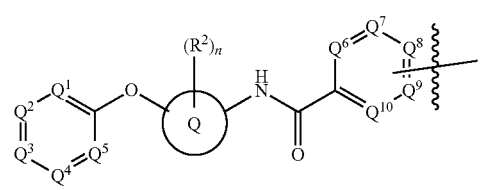

wherein:

$Q^1$, $Q^2$, $Q^3$, $Q^4$, and $Q^5$ are each independently $CR^1$, or N;

is 4-6 membered cycloalkyl, $C_6$-$C_{10}$ aryl, 4-6 membered heterocycloalkyl, or 4-6 membered heteroaryl, wherein the heterocycloalkyl or heteroaryl comprises 0-4 heteroatoms;

$Q^6$, $Q^7$, $Q^8$, $Q^9$, and $Q^{10}$ are each independently $CR^3$, or N;

Each $R^1$ is independently selected from the group consisting of H, optionally substituted linear or branched $C_1$-$C_6$ alkyl, cyano, halogen, and optionally substituted linear or branched $C_1$-$C_6$ alkoxy, wherein the alkyl or alkoxy group is optionally substituted with one or more halo;

Each $R^2$ is independently selected from the group consisting of optionally substituted linear or branched $C_1$-$C_6$ alkyl, cyano, halogen, and optionally substituted linear or branched $C_1$-$C_6$ alkoxy, wherein the alkyl or alkoxy group is optionally substituted with one or more halo;

Each $R^3$ is independently selected from the group consisting of optionally substituted H, linear or branched $C_1$-$C_6$ alkyl, cyano, halogen, and optionally substituted linear or branched $C_1$-$C_6$ alkoxy, wherein the alkyl or alkoxy group is optionally substituted with one or more halo; and n is 0, 1, 2, 3, or 4;

(b) L is a chemical linking moiety having the structure:

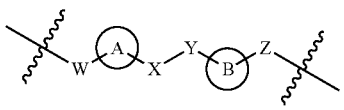

wherein:

the ABM is linked to W, and the CLM is linked to Z or
the ABM is linked to Z, and the CLM is linked to W;

W is absent or

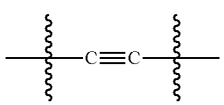 [SMILES: *C#C*]

is 4-7 membered cycloalkyl, 4-7 membered heterocycle, or spiro-bicyclic heterocycloalkyl, where each ring in the spiro-bicycle is 4-7 membered;

X is —CH$_2$— or absent;

Y is —NR$^6$—, —O—, or absent;

is 4-7 membered cycloalkyl or 4-7 membered heterocycle;

Z is —C(R$^7$)$_2$—, —NR$^7$—, —O—, or absent;

R$^6$ is H, linear or branched $C_{1-6}$ alkyl, linear or branched $C_{1-6}$ alkoxy-$C_{1-6}$ alkyl, or

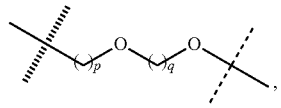

wherein

indicates a bond to Y, and

indicates a bond to

each R$^7$ is independently selected from the group consisting of H, linear or branched $C_{1-6}$ alkyl, and linear or branched $C_{1-6}$ alkoxy;

p is 1, 2, 3, or 4; and q is 1, 2, 3, 4, or 5;

(c) CLM is cereblon E3 ubiquitin ligase binding moiety having the structure:

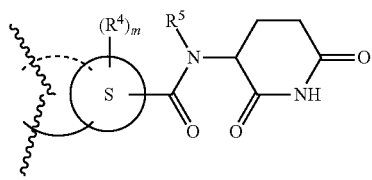

wherein:

is $C_6$-$C_{10}$ aryl, 4-7 membered heteroaryl, or bridged bicyclic cycloalkyl;

indicates that linking moiety L is connected to ring S by one or two covalent bonds;

Each $R^4$ is independently selected from the group consisting of optionally substituted linear or branched $C_1$-$C_6$ alkyl, cyano, halogen, and optionally substituted linear or branched $C_1$-$C_6$ alkoxy, wherein the alkyl or alkoxy group is optionally substituted with one or more halo;

$R^5$ is H, optionally substituted linear or branched $C_1$-$C_6$ alkyl, or optionally substituted linear or branched $C_1$-$C_6$ alkoxy, wherein the alkyl or alkoxy group is optionally substituted with one or more halo; and m is 0, 1, 2, 3, or 4.

In some embodiments, when

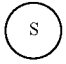

is pyridyl,

is tetramethylcyclobutyl, Q2 is CR1, and Q4 is CR1; that R1 is not chloro.

In some embodiments, further provided that the compound is not N-(4-(3-chloro-4-cyanophenoxy)cyclohexyl)-6-(4-((4-(4-((2,6-dioxopiperidin-3-yl)carbamoyl)phenyl)piperazin-1-yl)methyl)piperidin-1-yl)pyridazine-3-carboxamide.

In another aspect, this application provides a bifunctional compound of claim 1, wherein the compound is a compound of Formula (I):

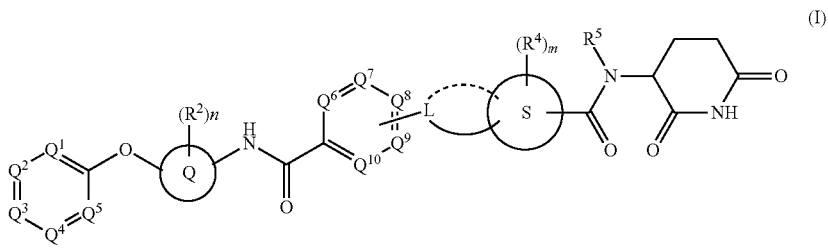

or a pharmaceutically acceptable salt, solvate, enantiomer, stereoisomer, or isotopic derivative thereof.

In some embodiments, L is

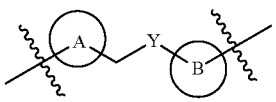

wherein:

is 4-7 membered cycloalkyl or 4-7 membered heterocycle;

Y is —$NR^6$—, —O—, or absent;

$R^6$ is H, linear or branched $C_{1-6}$ alkyl, or linear or branched $C_{1-6}$ alkoxy; and

is 4-7 membered cycloalkyl or 4-7 membered heterocycle.

In some embodiments, L is

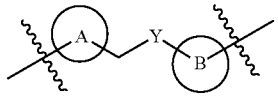

wherein:

is 4-7 membered cycloalkyl or 4-7 membered heterocycle;

Y is —$NR^6$— or —O—;

$R^6$ is H, linear or branched $C_{1-6}$ alkyl, or linear or branched $C_{1-6}$ alkoxy; and

is 4-7 membered cycloalkyl or 4-7 membered heterocycle.

In some embodiments, L is

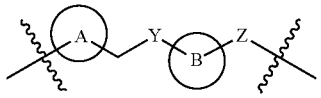

Wherein:

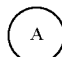

is piperidinyl or morpholinyl;

Y is —NR$^6$— or —O—;

R$^6$ is

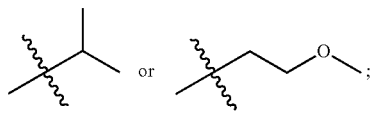

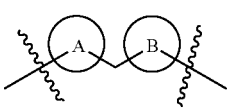

is cyclobutyl; and

Z is —O—.

In some embodiments, L is

Wherein:

is piperidinyl or morpholinyl; and


is piperazinyl.

In some embodiments,

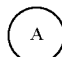

is piperidinyl.

In some embodiments, the compound is a compound of Formula (Ib):

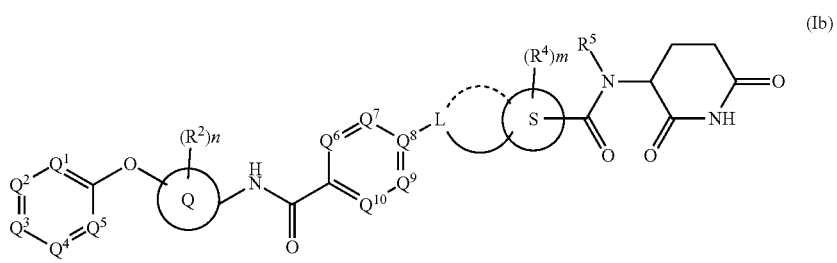

or a pharmaceutically acceptable salt, solvate, enantiomer, stereoisomer, or isotopic derivative thereof.

In some embodiments, the compound is a compound of Formula (Ic):

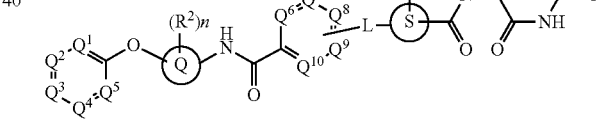

or a pharmaceutically acceptable salt, solvate, enantiomer, stereoisomer, or isotopic derivative thereof.

In some embodiments, $Q^1$-$Q^5$ are each $CR^1$.

In some embodiments, exactly 1 of $Q^1$-$Q^5$ is N.

In some embodiments, exactly 2 of $Q^1$-$Q^5$ are N.

In some embodiments, exactly 3 of $Q^1$-$Q^5$ are N.

In some embodiments, $Q^6$-$Q^{10}$ are each $CR^3$.

In some embodiments, exactly 1 of $Q^6$-$Q^{10}$ is N.

In some embodiments, exactly 2 of $Q^6$-$Q^{10}$ are N.

In some embodiments, exactly 3 of $Q^6$-$Q^{10}$ are N.

In some embodiments, $Q^1$ is CH, $Q^2$ is $C(CH_3)$, $Q^3$ is C(CN), $Q^4$ is $C(CH_3)$, and $Q^5$ is CH.

In some embodiments, $Q^1$ is CH, $Q^2$ is $C(OCH_3)$, $Q^3$ is C(CN), $Q^4$ is CH, and $Q^5$ is CH.

In some embodiments, $Q^1$ is CH, $Q^2$ is C(Cl), $Q^3$ is C(CN), $Q^4$ is CH, and $Q^5$ is CH.

In some embodiments, (Q)

is 4-6 membered cycloalkyl.
In some embodiments, (Q)

is cyclobutyl or cyclohexyl.
In some embodiments, (Q)

is cyclobutyl.
In some embodiments, n is 4.
In some embodiments, each $R^2$ is methyl.
In some embodiments, Q is cyclohexyl.
In some embodiments, n is 0.
In some embodiments, $R^2$ is linear or branched $C_1$-$C_6$ alkyl.
In some embodiments, (S)

is phenyl, pyridinyl, pyridazinyl, pyrimidinyl, or pyrazinyl.
In some embodiments, (S)

is phenyl.

In some embodiments, (S)

is pyridinyl.
In some embodiments, (S)

is pyridazinyl.
In some embodiments, (S)

is pyrimidinyl.
In some embodiments, (S)

is pyrazinyl.
In some embodiments, each $R^4$ is independently selected from the group consisting of F, methoxy, ethoxy, methyl, and ethyl.
In some embodiments, each $R^4$ is independently selected from the group consisting of F, methoxy, and methyl.
In some embodiments, m is 0, 1, or 2.
In some embodiments, m is 0.
In some embodiments, m is 1.
In some embodiments, m is 2.
In one aspect, the application provides a bifunctional compound, wherein the compound is:

-continued
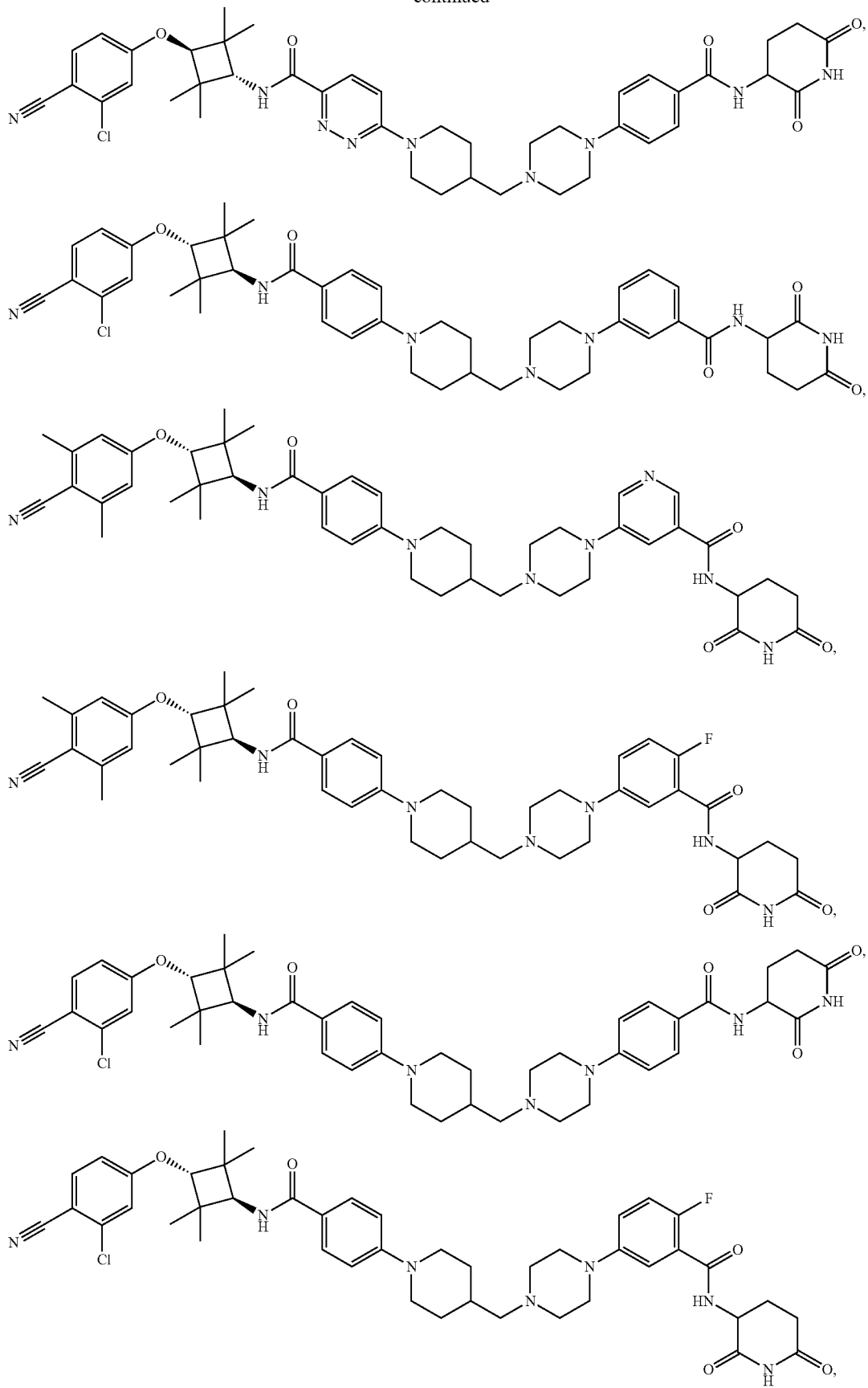

-continued
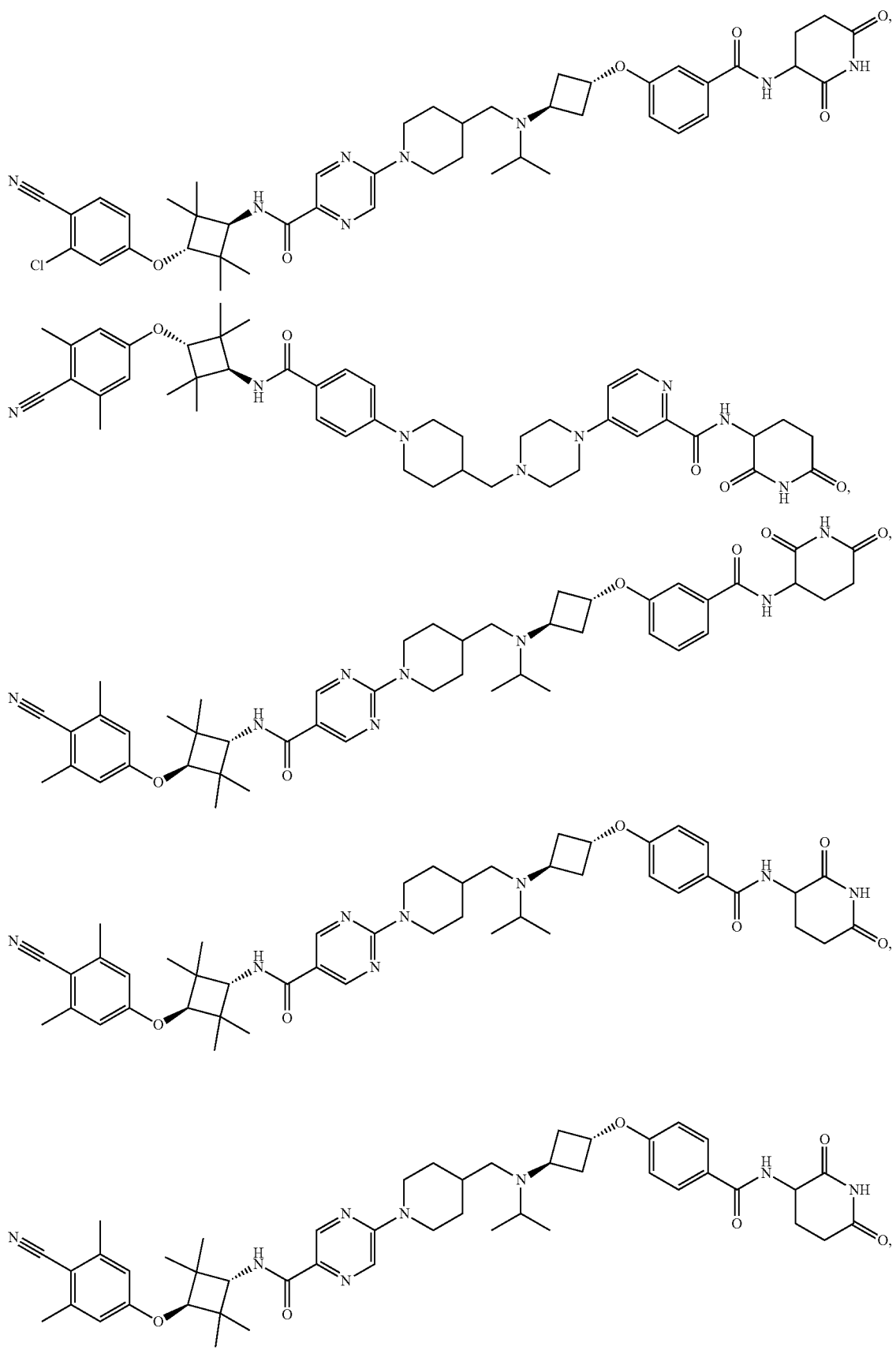

-continued
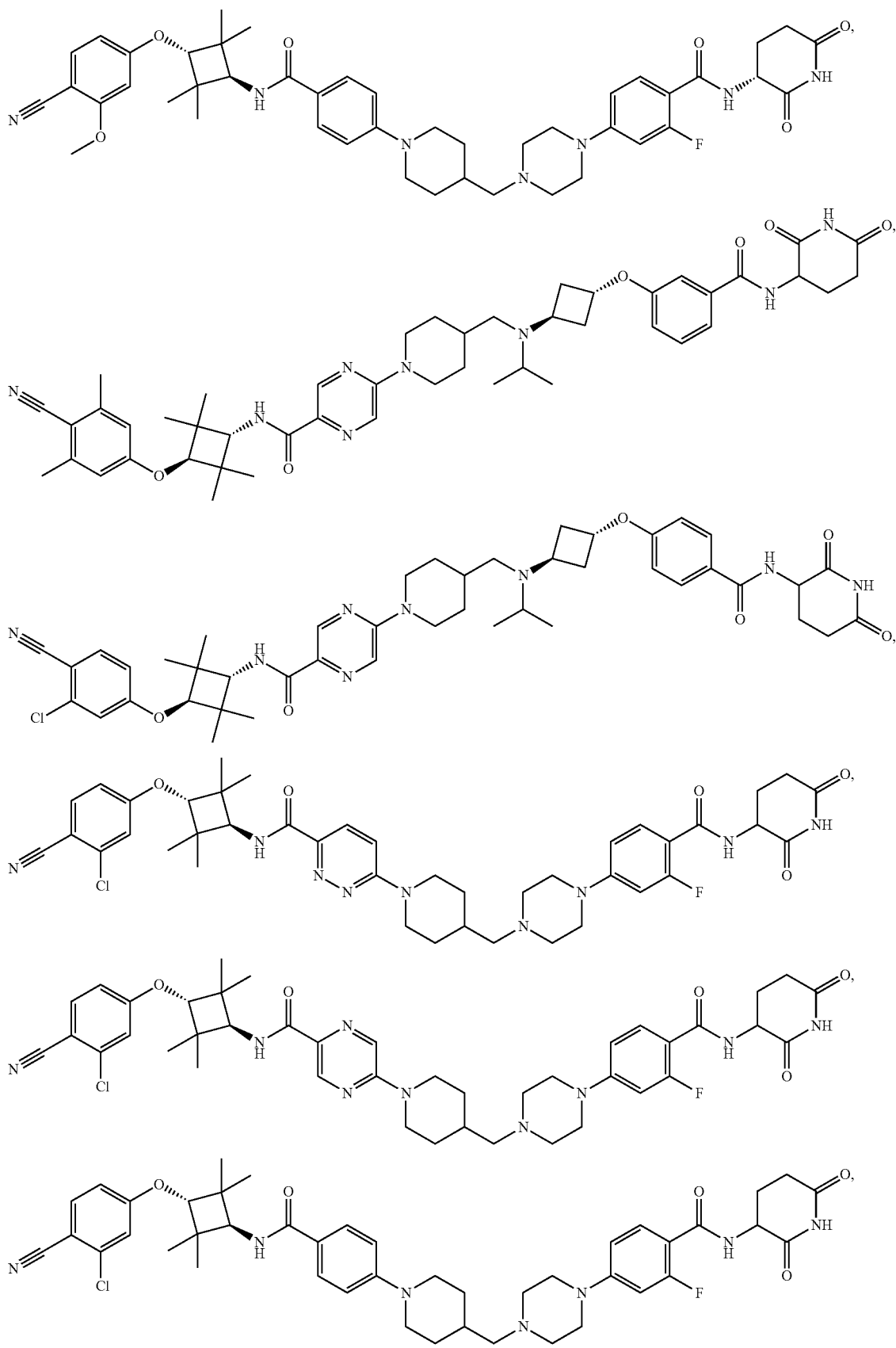

-continued
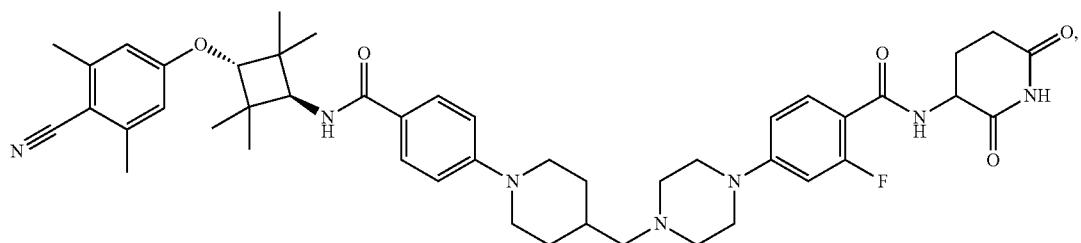
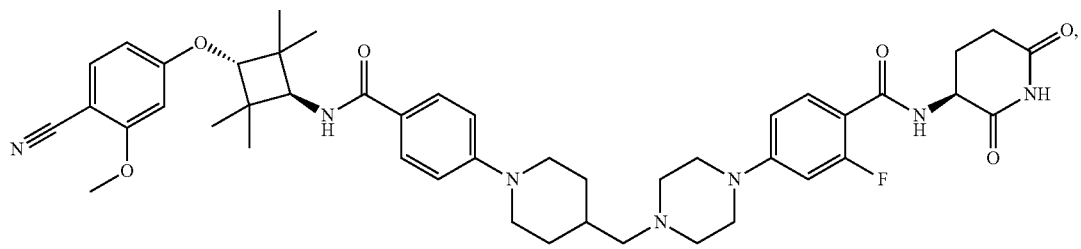
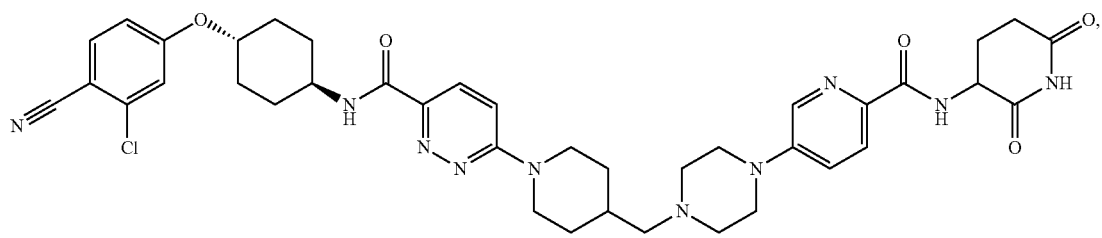
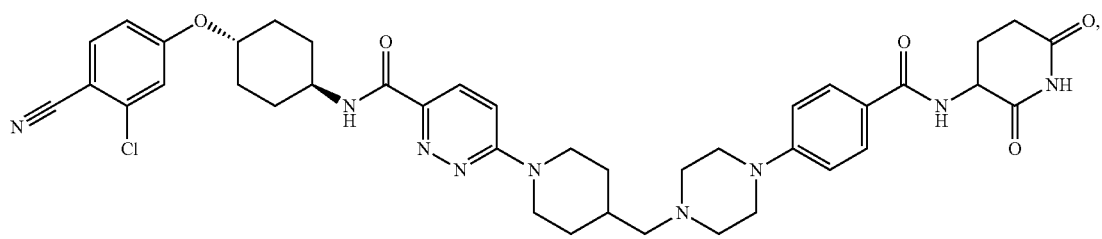
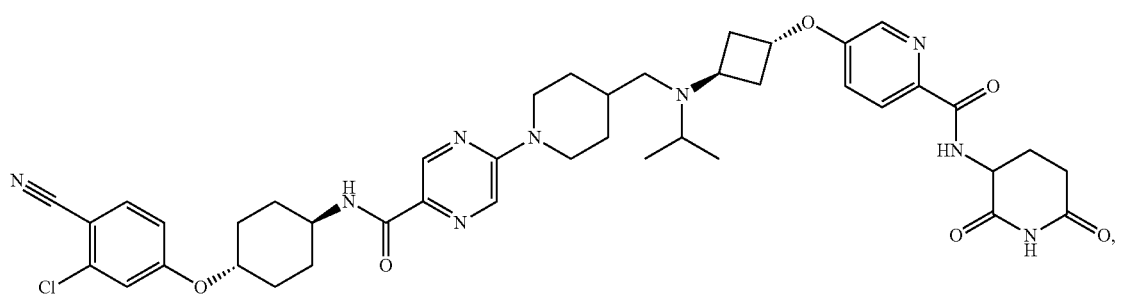
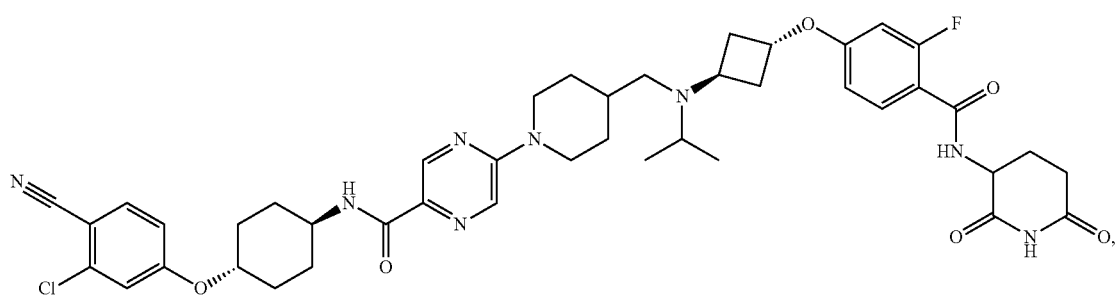

-continued
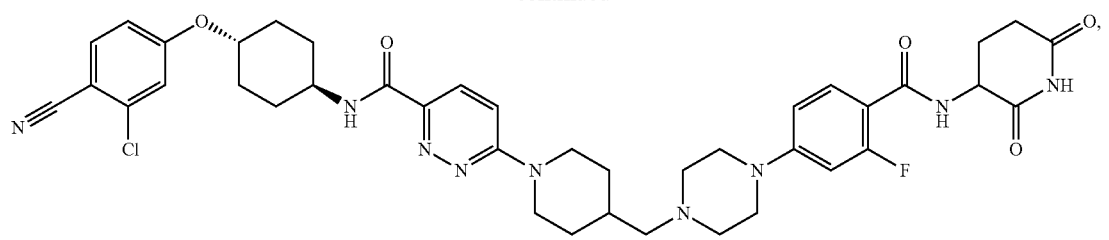
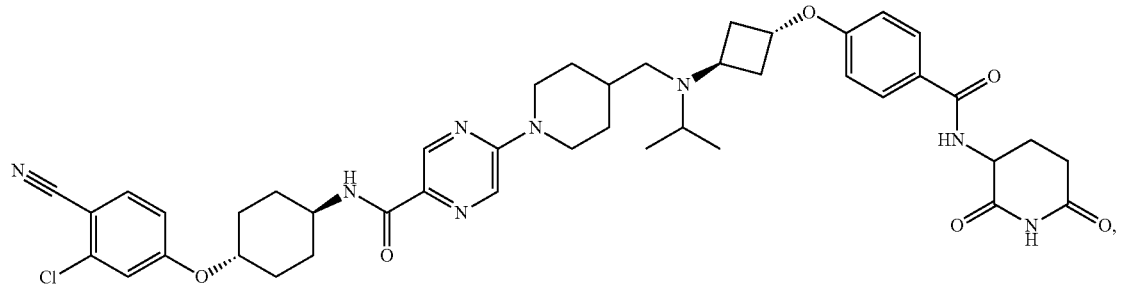
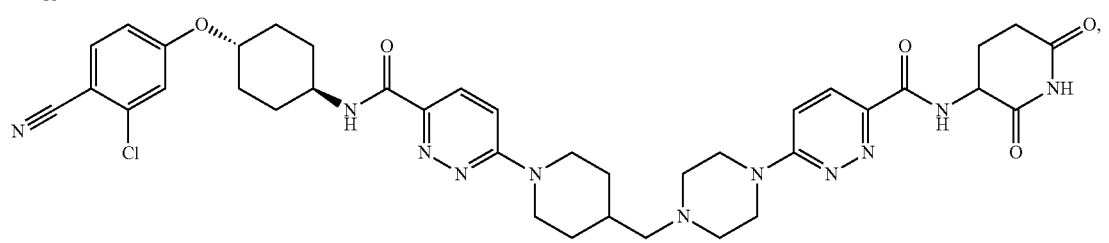
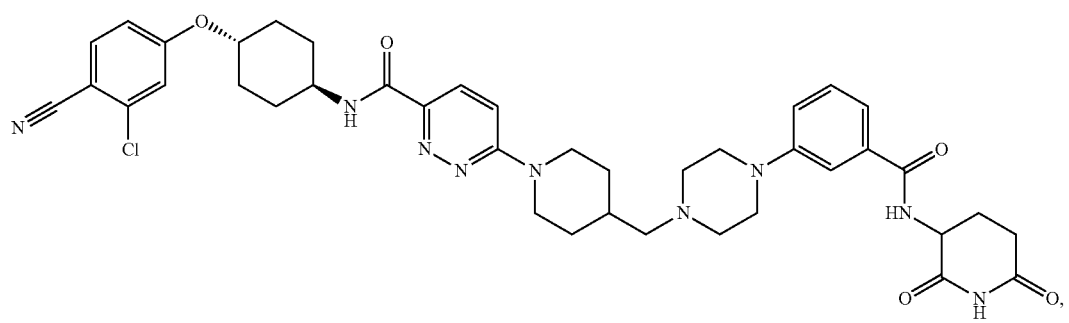
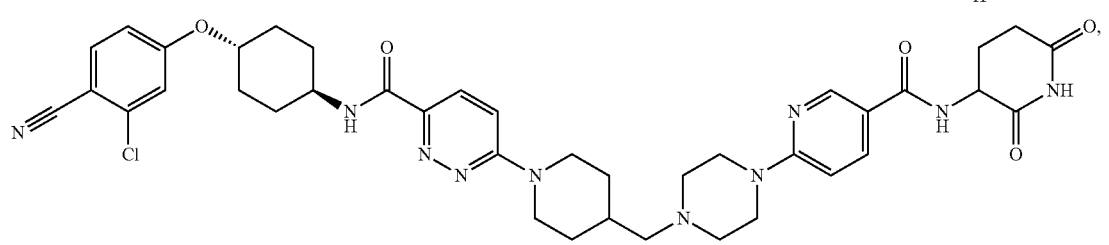
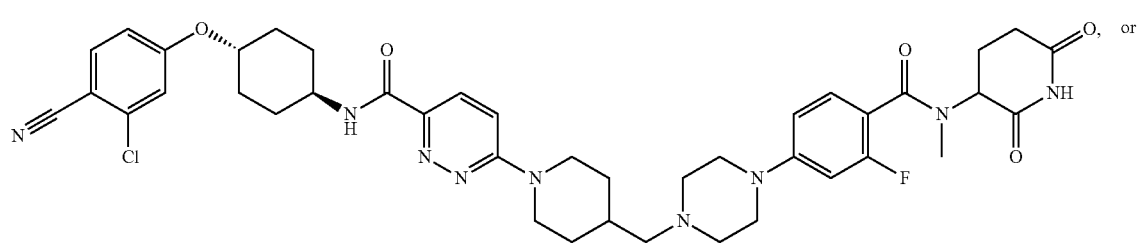

21
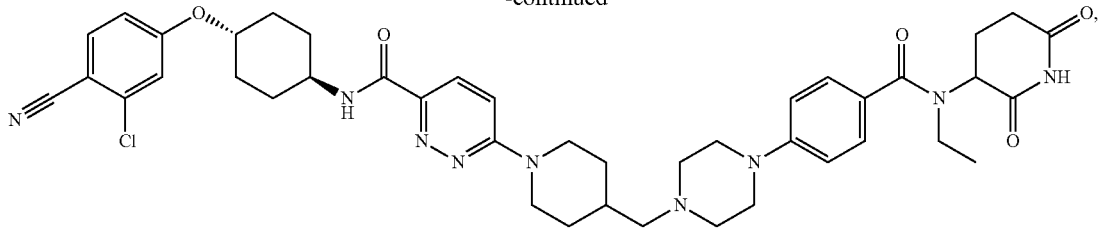
or a pharmaceutically acceptable salt, enantiomer, stereoisomer, or isotopic derivative of any of the foregoing.
22
In one aspect, the application provides bifunctional compound, wherein the compound is:
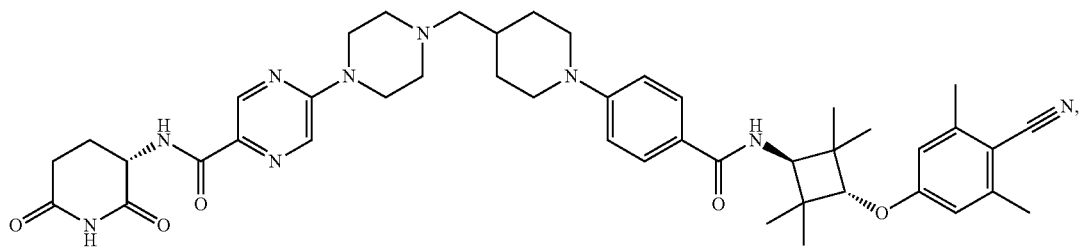
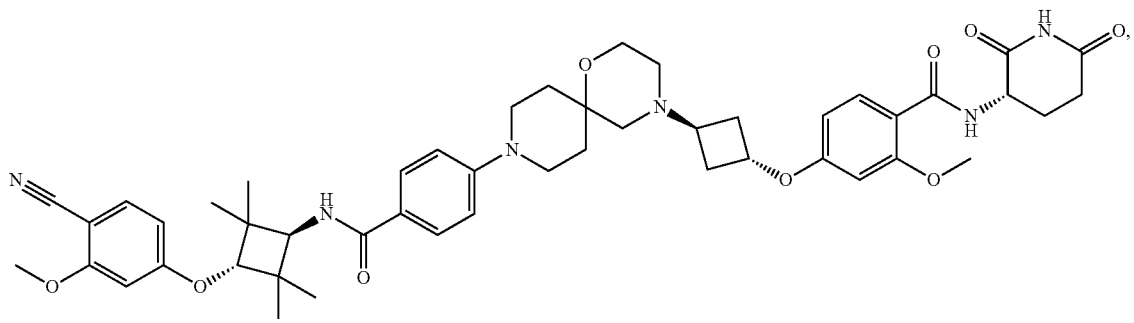
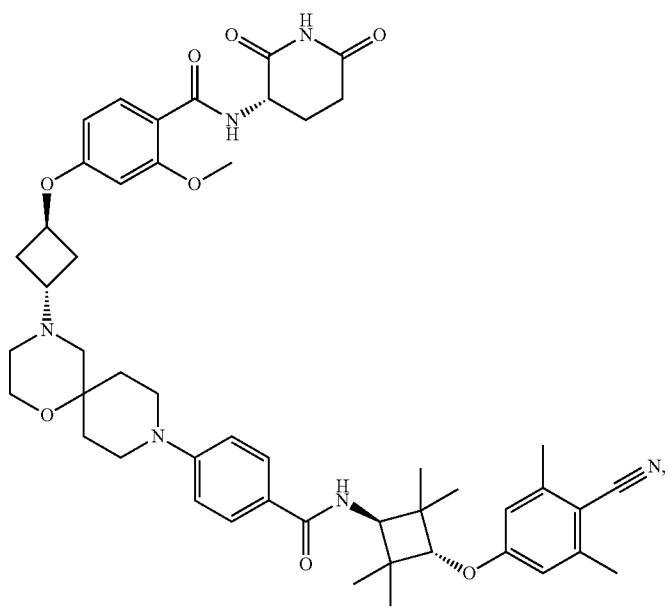

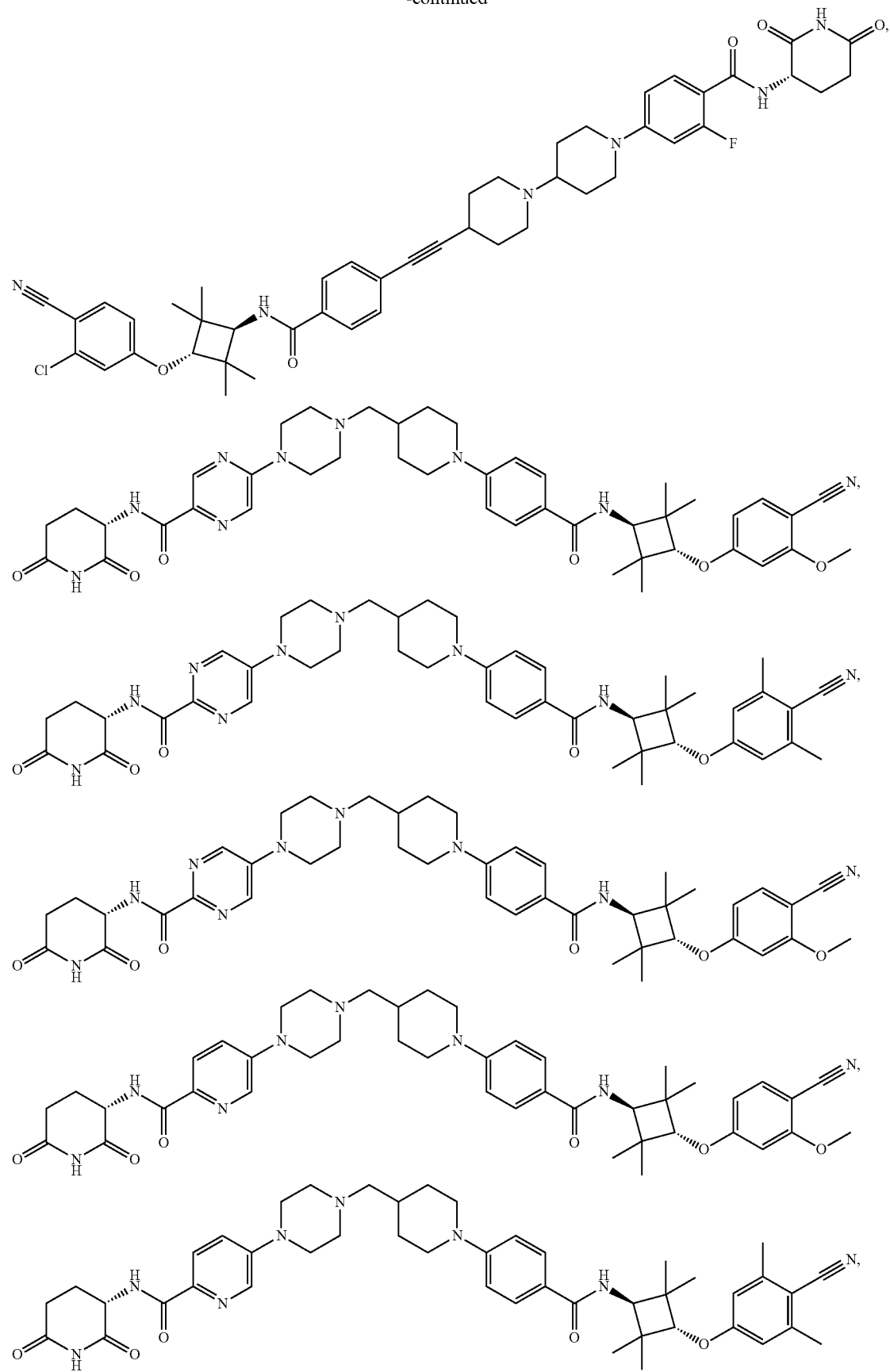

-continued
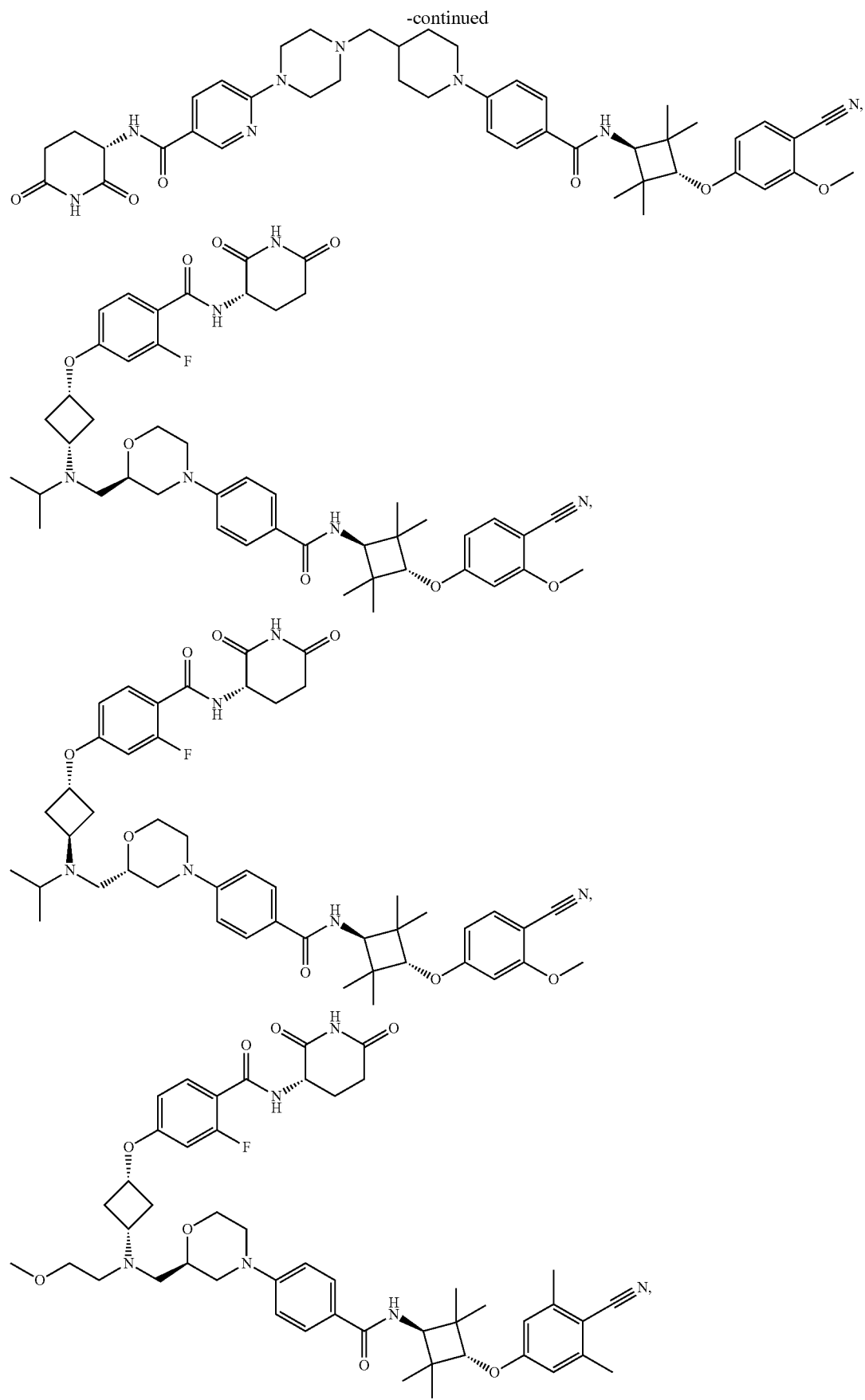

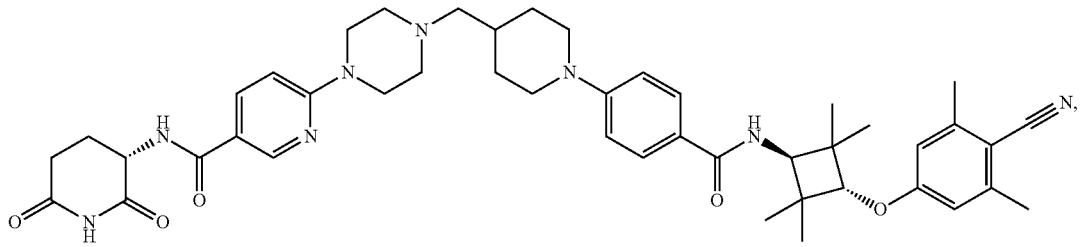
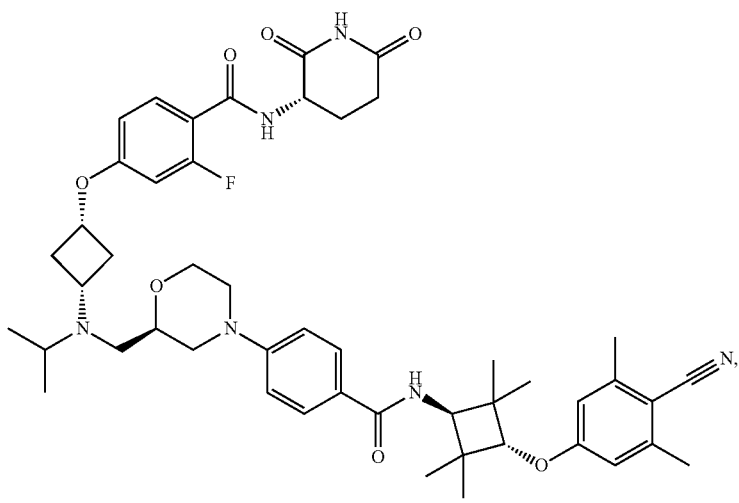
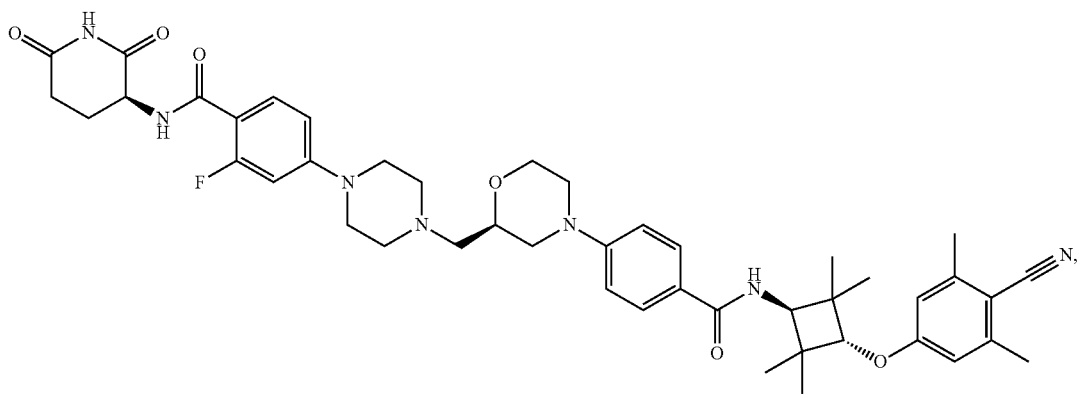
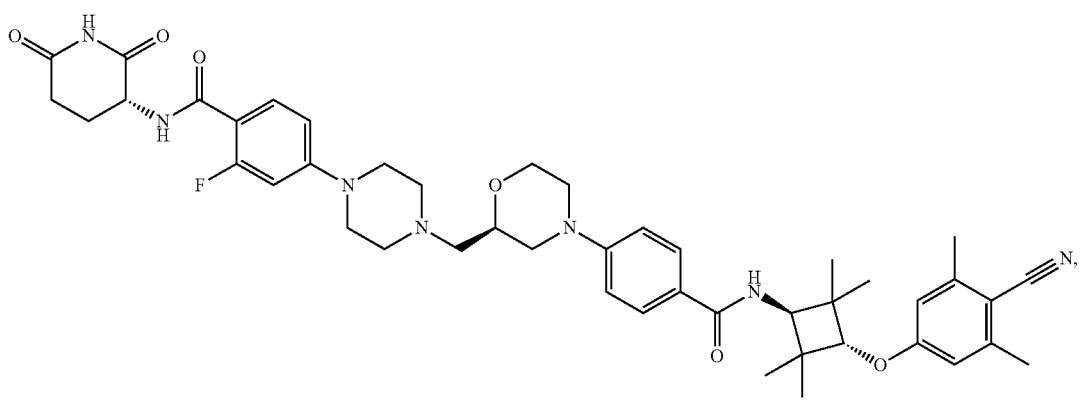

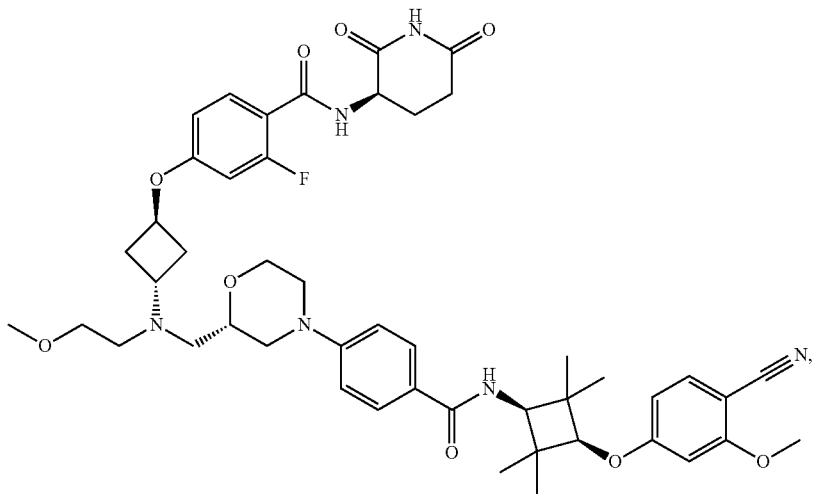
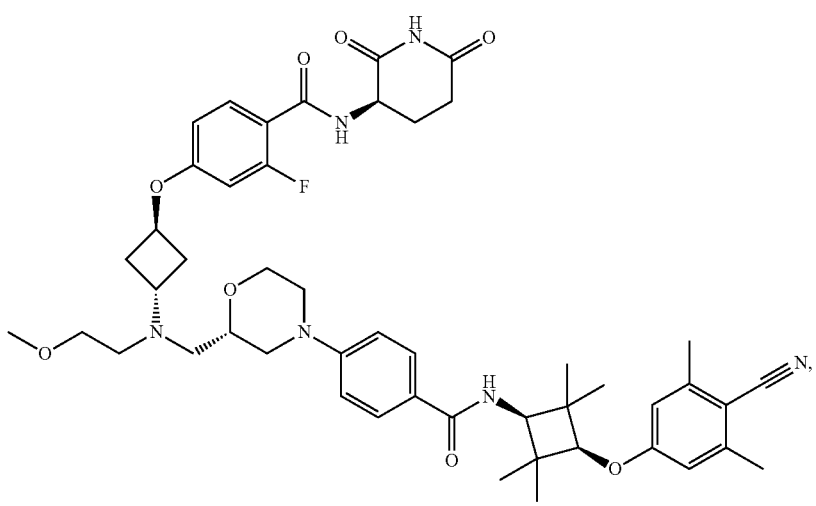
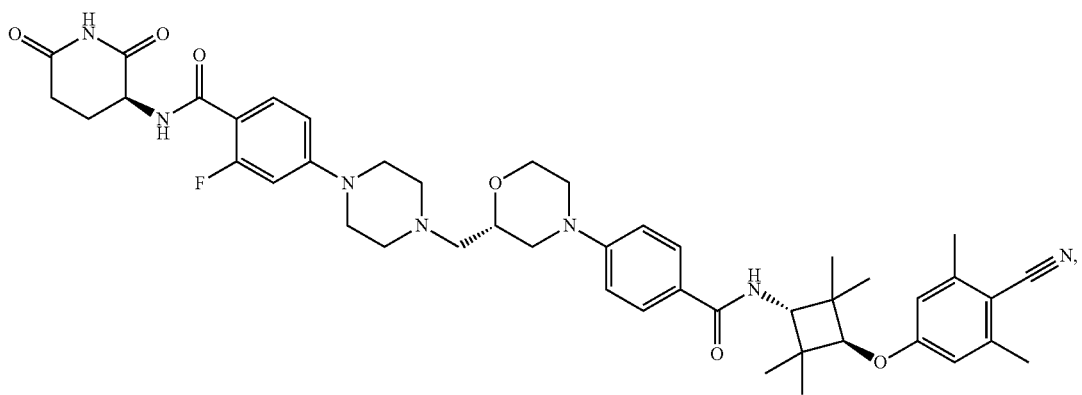

-continued
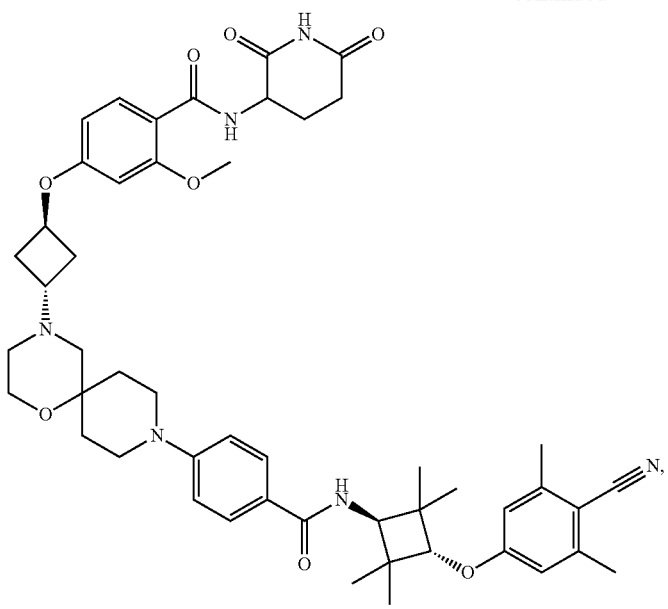
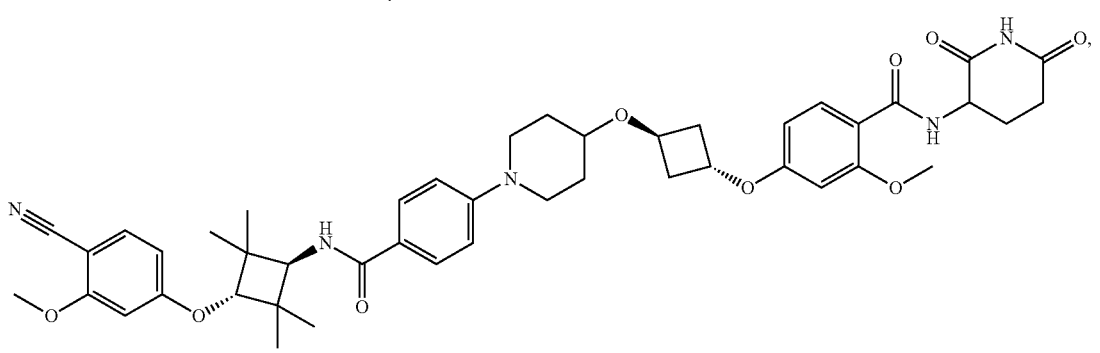
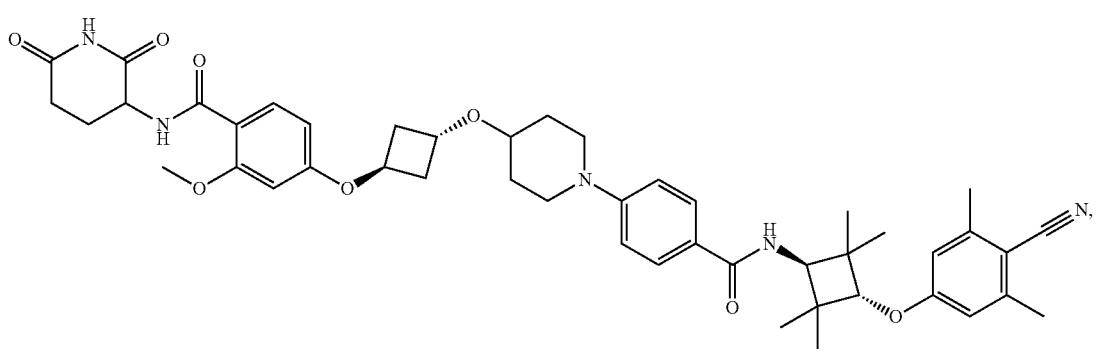
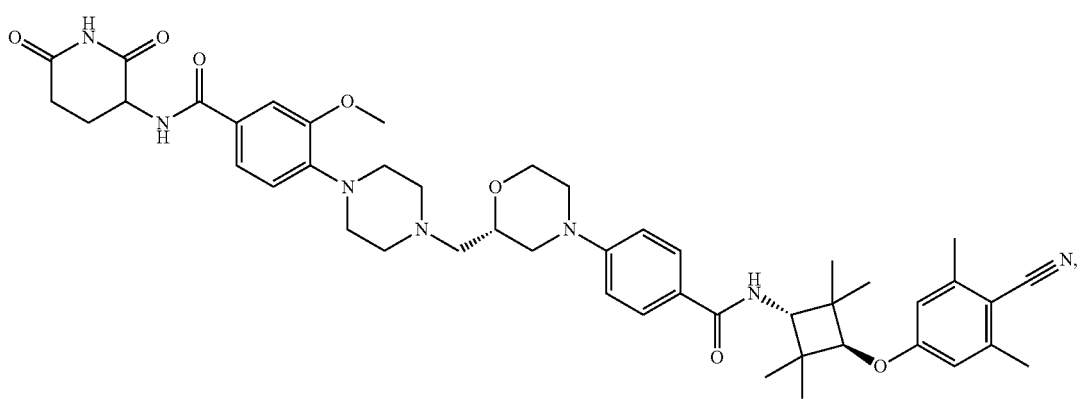

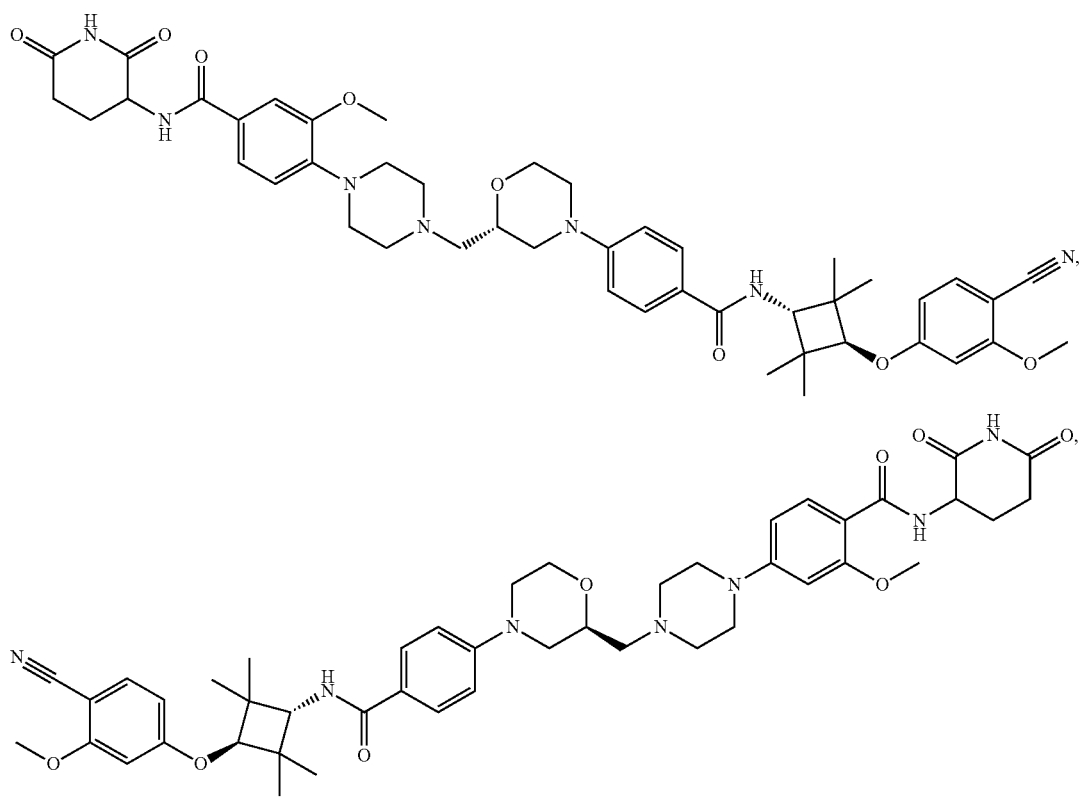
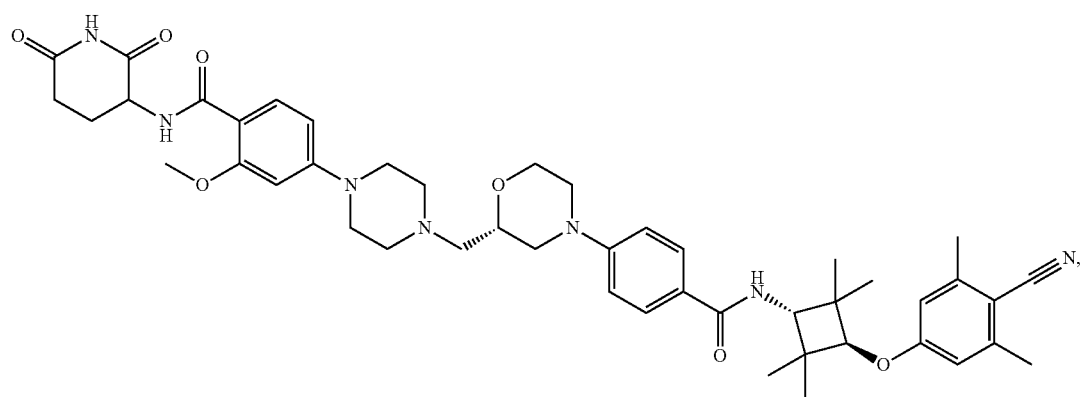
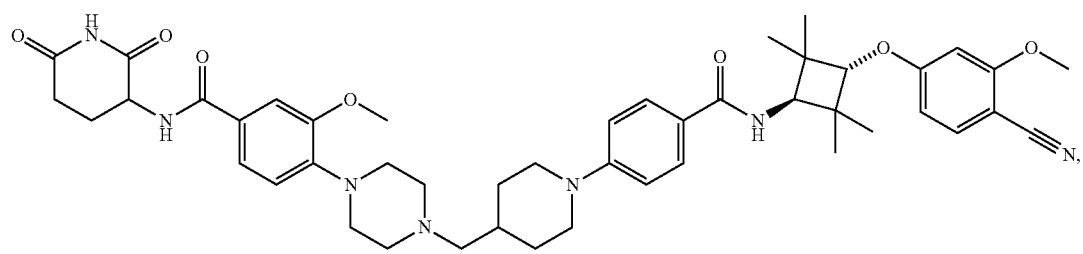

-continued
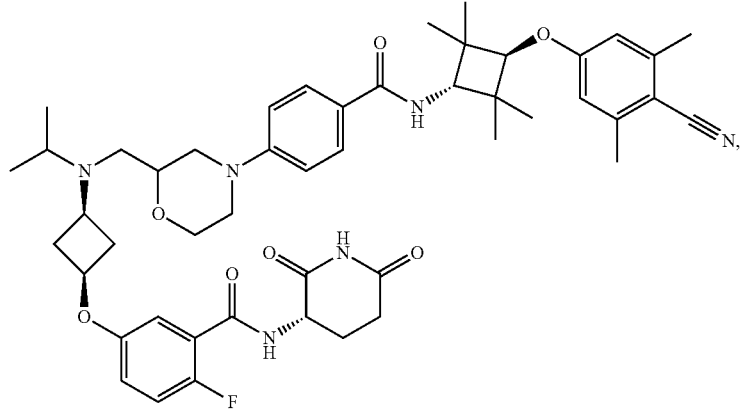
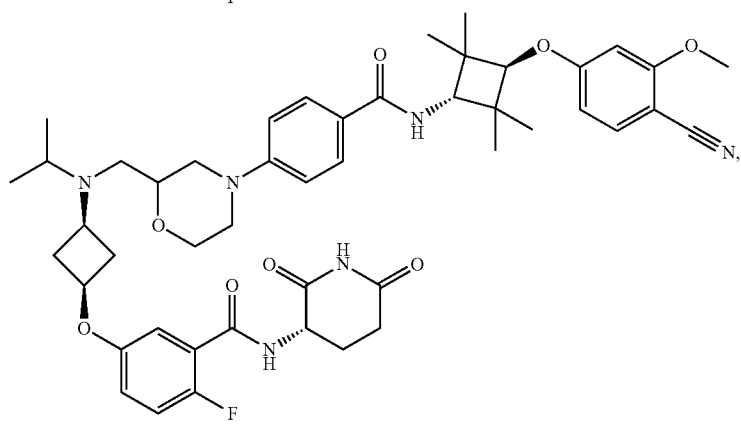
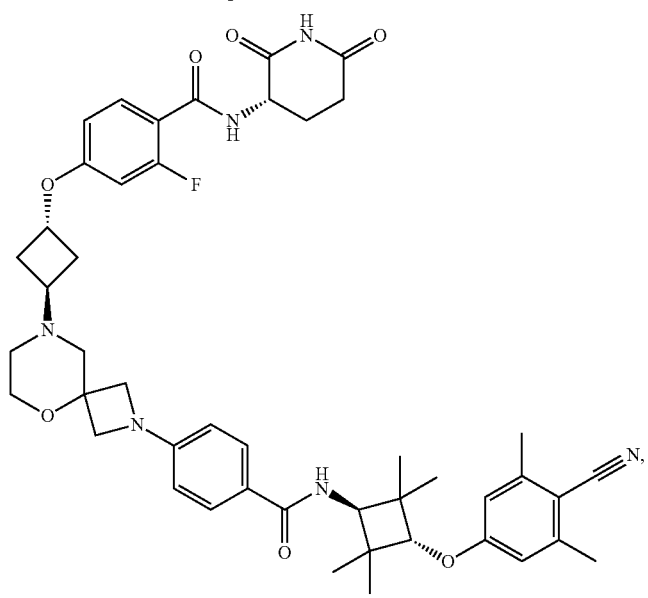
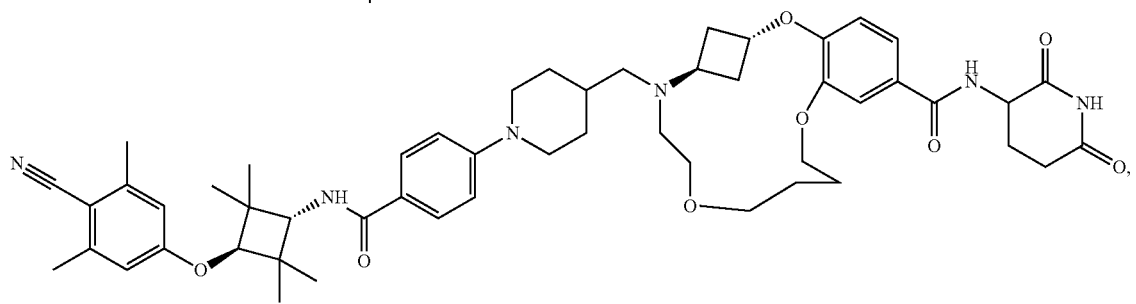

-continued
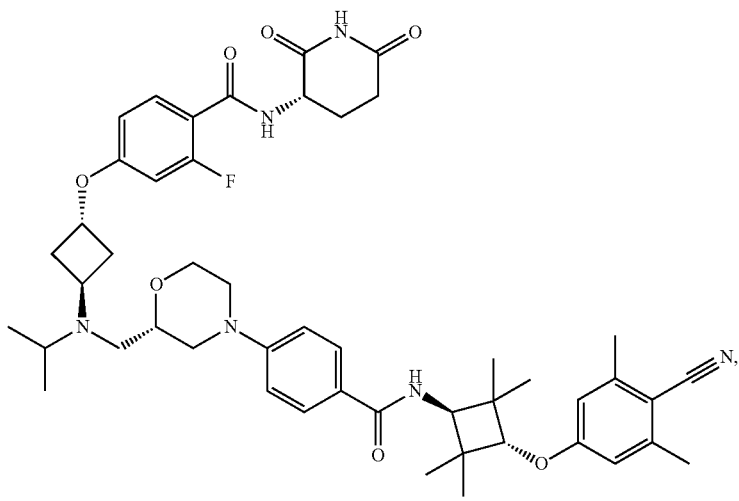
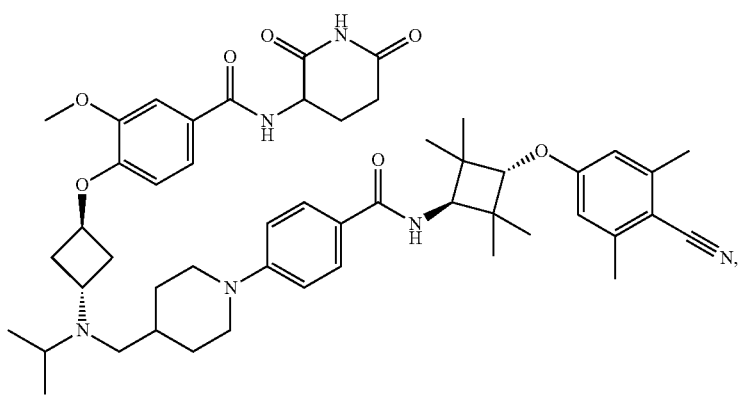
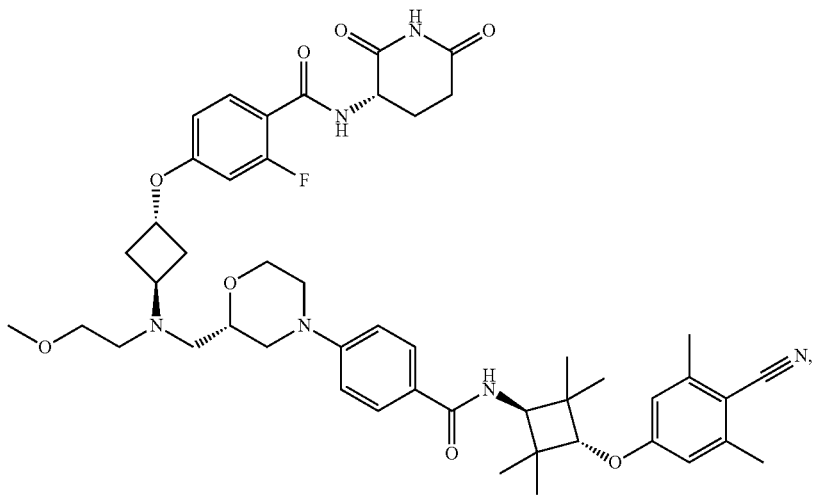

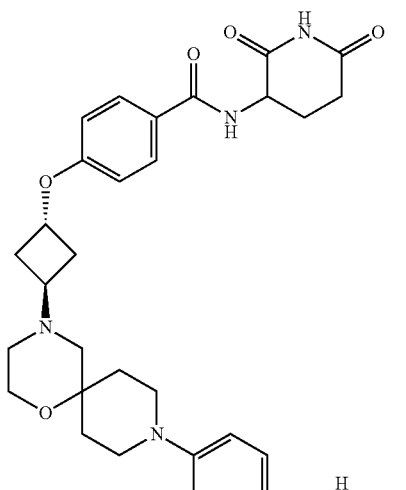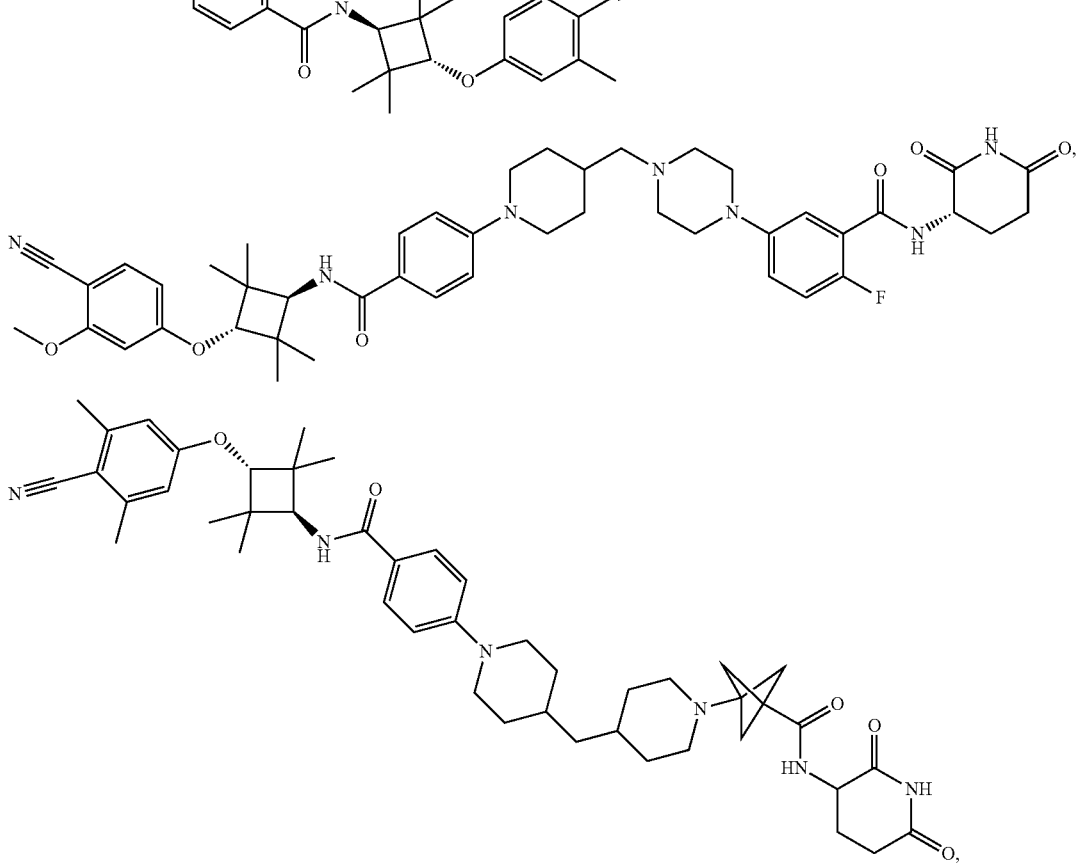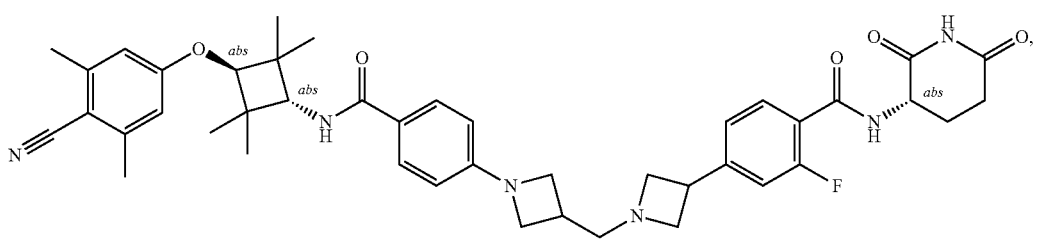

41 42
-continued
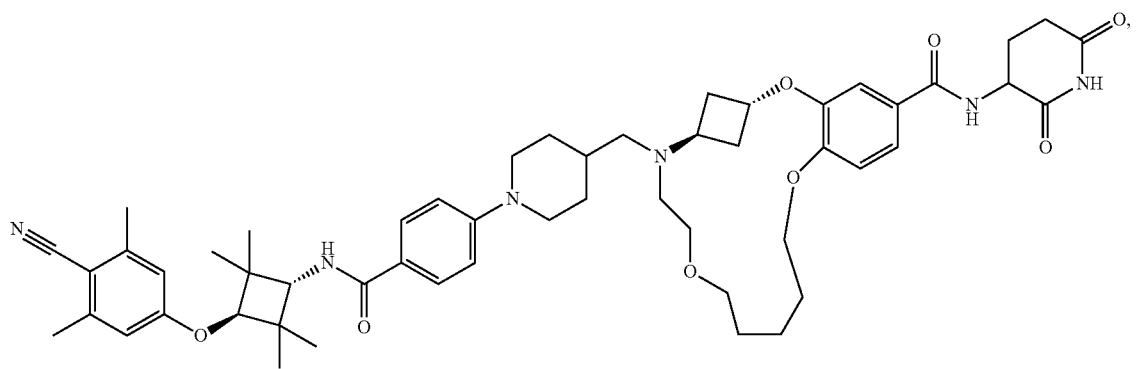
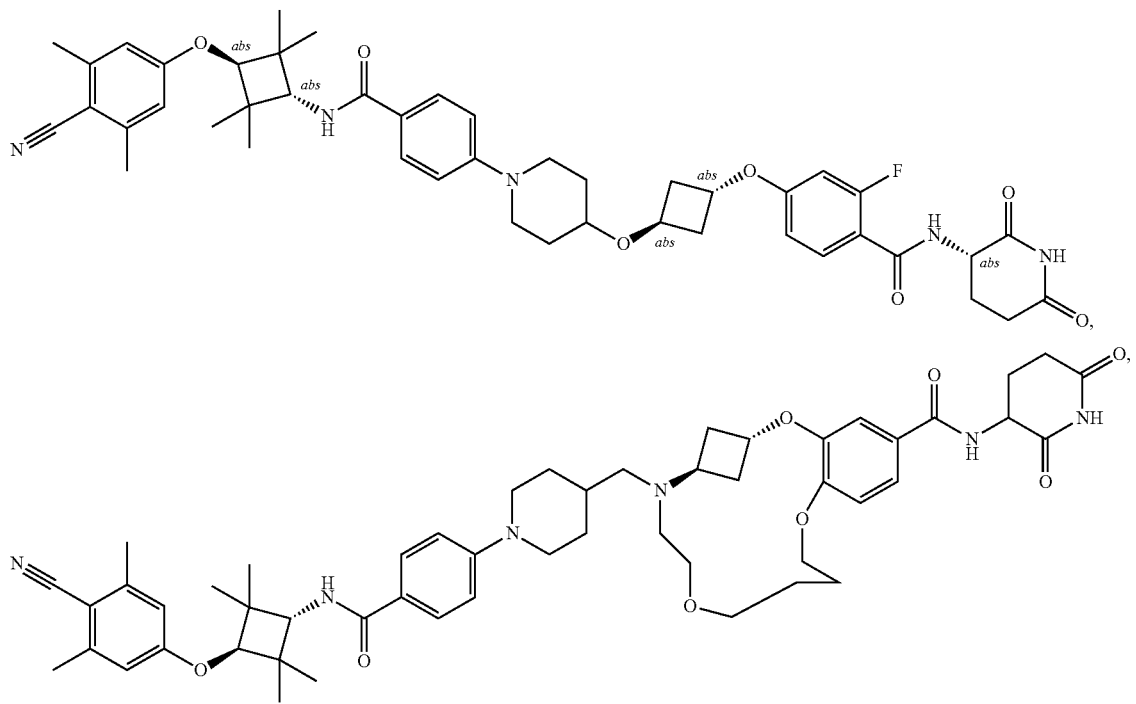
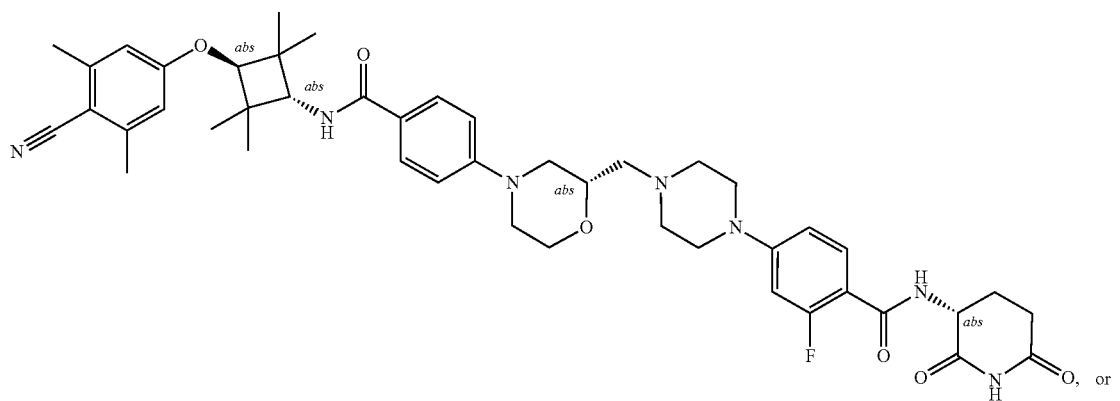

-continued

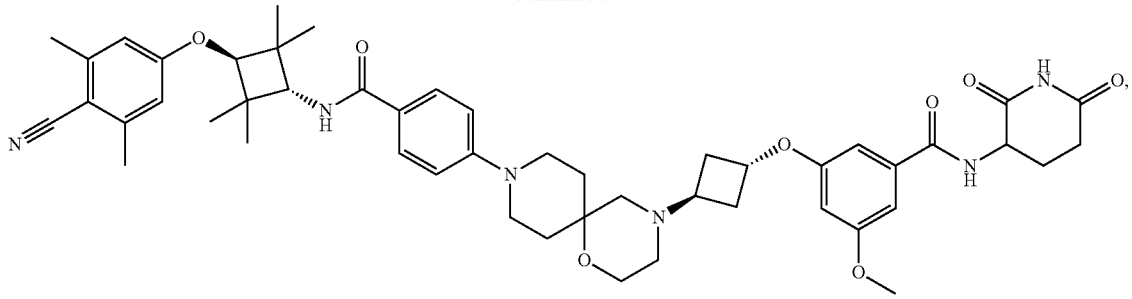 [SMILES: COc1cc(O[C@H]2C[C@H](N3CCOC4(CCN(c5ccc(C(=O)N[C@H]6C(C)(C)[C@H](Oc7cc(C)c(C#N)c(C)c7)C6(C)C)cc5)CC4)C3)C2)cc(C(=O)NC2CCC(=O)NC2=O)c1]

or a pharmaceutically acceptable salt, enantiomer, stereoisomer, or isotopic derivative of any of the foregoing.

In one embodiment, the application provides a pharmaceutical composition comprising a bifunctional compound described herein and one or more pharmaceutically acceptable excipients.

In one embodiment, the composition is formulated as a tablet, and comprises one or more of the following: emulsifier; surfactant; binder; disintegrant; glidant; and lubricant.

In one embodiment, the composition further comprises an effective amount of at least one additional anti-cancer agent.

In one embodiment, the anti-cancer agent is estramustine, docetaxel, ketoconazole, goserelin, histrelin, triptorelin, buserelin, cyproterone, flutamide, bicalutamide, nilutamide, pamidronate, or zolendronate.

In one embodiment, the application provides a method of treating prostate cancer in a subject comprising administering to a subject in need thereof a therapeutically effective amount of a bifunctional compound described herein or a therapeutically effective amount of a pharmaceutical composition described herein.

In one embodiment, the therapeutically effective amount of the bifunctional compound is administered orally to the subject.

In one embodiment, the therapeutically effective amount of the bifunctional compound is administered to the subject once a day, twice a day, three times a day, or four times a day.

In one embodiment, the therapeutically effective amount of the bifunctional compound is administered to the subject once a day.

In one embodiment, the therapeutically effective amount of the bifunctional compound is administered to the subject all at once or is administered in two, three, or four divided doses.

In one embodiment, the therapeutically effective amount of the bifunctional compound is about 1 mg to about 1000 mg.

In one embodiment, the therapeutically effective amount of the bifunctional compound is about 5 mg to about 750 mg.

In one embodiment, the therapeutically effective amount of the bifunctional compound is about 10 mg to about 500 mg.

In one embodiment, the therapeutically effective amount of the bifunctional compound is about 20 mg to about 250 mg.

In one embodiment, the subject is in a fed state at the time of administration.

In one embodiment, the subject is in a fasted state at the time of administration.

In one embodiment, the method further comprises administering an effective amount of at least one additional anti-cancer agent to the subject in need thereof.

In one embodiment, the anti-cancer agent is abiraterone, estramustine, docetaxel, ketoconazole, goserelin, histrelin, triptorelin, buserelin, cyproterone, flutamide, bicalutamide, nilutamide, pamidronate, or zolendronate.

In one embodiment, the subject with prostate cancer comprises at least one somatic AR tumor mutation.

In one embodiment, the prostate cancer is castrate-resistant prostate cancer.

In one embodiment, the prostate cancer is metastatic prostate cancer.

In one embodiment, the application provides a method of treating prostate cancer in a subpopulation of prostate cancer subjects, comprising:
selecting a prostate cancer subject for treatment based on the subject's somatic AR tumor biomarker status; and
administering a therapeutically effective amount of a bifunctional compound of Formula (I), or a pharmaceutical composition comprising an effective amount of a bifunctional compound of Formula (I).

In one embodiment, the subject's somatic AR tumor biomarker status comprises at least one somatic AR tumor mutation.

In one embodiment, the AR biomarker status of the subject is determined by ctDNA analysis, fluorescent in situ hybridization, immunohistochemistry, PCR analysis, or sequencing.

In one embodiment, the AR biomarker status of the subject is determined in a blood sample derived from the subject.

In one embodiment, the AR biomarker status of the subject is determined in a solid biopsy derived from the tumor of the subject.

In one embodiment, the prostate cancer is castrate-resistant prostate cancer.

In one embodiment, the prostate cancer is metastatic prostate cancer.

In one embodiment, the at least one somatic AR tumor mutation is selected from the group consisting of L702H, M895V, M896V, T878A, F877L, and H875Y.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating an embodiment of the disclosure and are not to be construed as limiting the disclosure. Further objects, features and advantages of the disclosure will become apparent from the following detailed description taken in conjunction with the accompanying figures showing illustrative embodiments of the disclosure, in which:

FIG. 1A represents exemplary proteolysis targeting chimeric compounds comprise a protein targeting moiety (PTM; darkly shaded rectangle), a cereblon ubiquitin ligase binding moiety (CLM; unshaded triangle), and a linker moiety (black line) coupling or tethering the PTM to the CLM. FIG. 1B illustrates the functional use of the proteolysis targeting chimeric compounds as described herein. Briefly, the CLM recognizes and binds to cereblon, an E3 Ubiquitin Ligase, and the PTM binds and recruits an intracellular target protein bringing it into close proximity to the cereblon E3 Ubiquitin Ligase. Typically, the cereblon E3 Ubiquitin Ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degradation by the proteosomal machinery of the cell.

DETAILED DESCRIPTION

Definitions

Figure 1A:
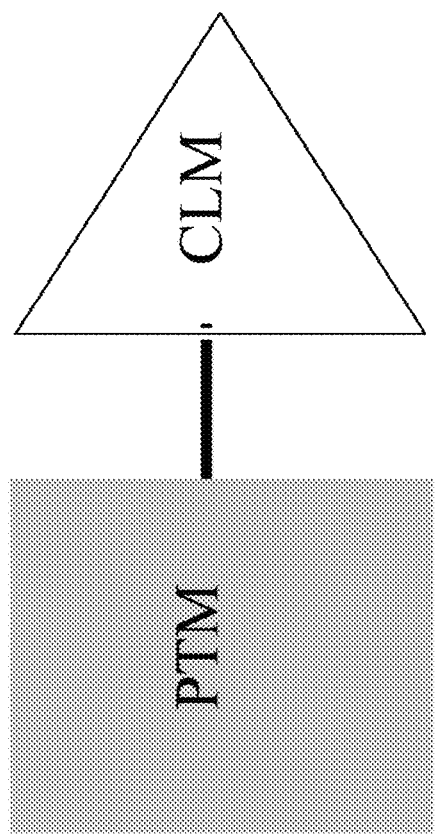
FIGS. 1A and 1B are illustrations of the general principle for the function of proteolysis targeting chimeric compounds.
Figure 1B:
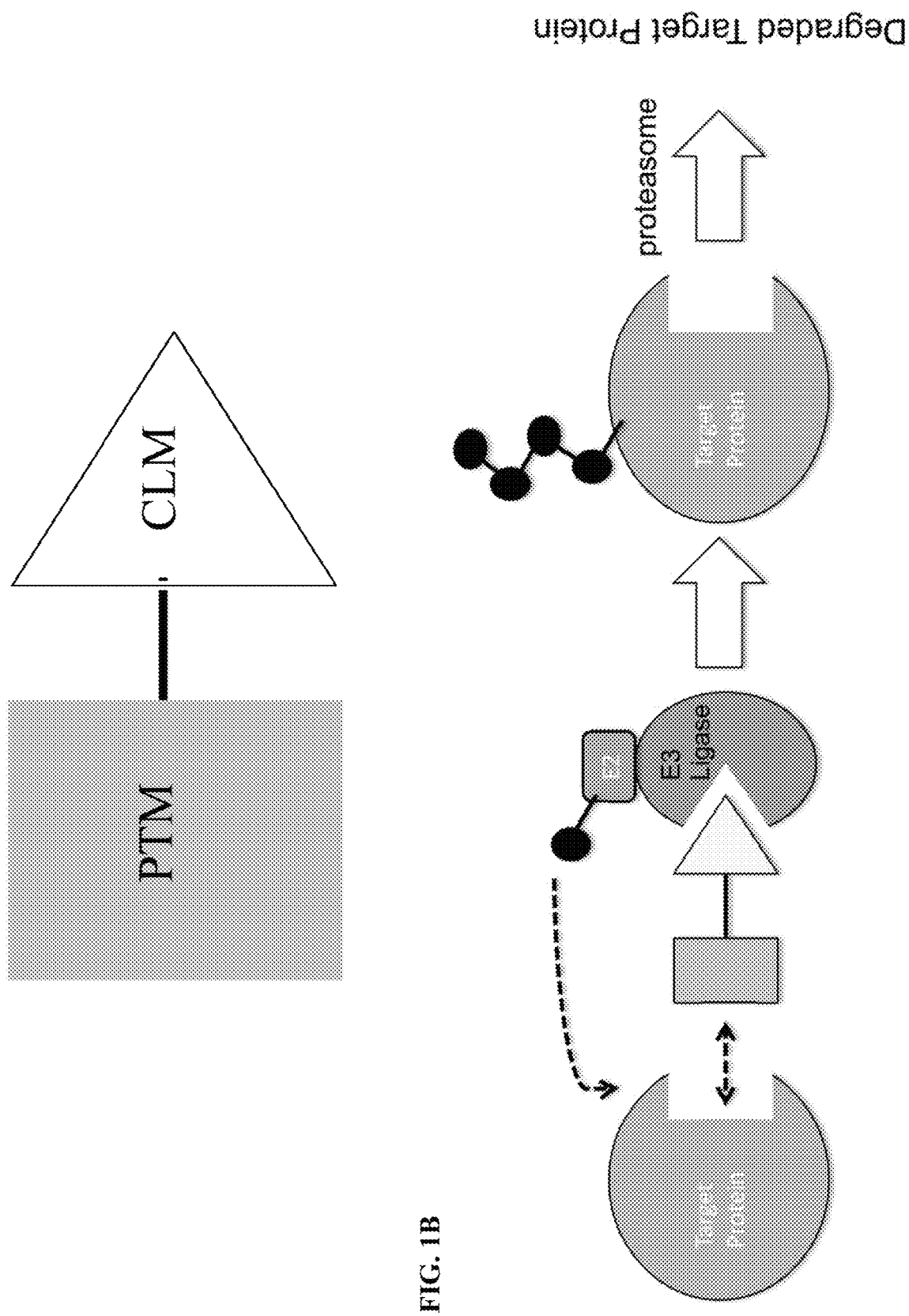

All references to amino acid mutations in the Androgen Receptor are numbered relative to SEQ ID NO: 1, which is provided herewith.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, "Compound", "bifunctional compound", or "Compound of the Disclosure", as used herein, refers to the compounds disclosed by structure in the following tables and examples.

The term "substituted" or "optionally substituted" shall mean independently (i.e., where more than substituent occurs, each substituent is independent of another substituent) one or more substituents (independently up to five substituents, preferably up to three substituents, often 1 or 2 substituents on a moiety in a compound according to the present disclosure and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a Q-C3 alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a sidechain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, $C_1$-$C_6$ alkyl, —(CH$_2$)$_n$O—$C_1$-$C_6$ alkyl), —(CH$_2$)$_n$C(O)—($C_1$-$C_6$ alkyl), —(CH$_2$)$_n$OC(O)—($C_1$-$C_6$ alkyl), —(CH$_2$)$_n$C(O)O—($C_1$-$C_6$ alkyl), —(CH$_2$)$_n$NHC(O)—$R_1$, —(CH$_2$)$_n$C(O)—$NR_1R_2$, —(OCH$_2$)$_n$OH, —(CH$_2$O)$_n$COOH, $C_1$-$C_6$ alkyl, —(OCH$_2$)$_n$O—($C_1$-$C_6$ alkyl), —(CH$_2$O)$_n$C(O)—($C_1$-$C_6$ alkyl), —(OCH$_2$)$_n$NHC(O)—$R_1$, —(CH$_2$O)$_n$C(O)—$NR_1R_2$, —S(O)$_2$—$R_S$, —S(O)—$R_S$ ($R_S$ is $C_1$-$C_6$ alkyl or a —(CH$_2$)$_m$—$NR_1R_2$ group), NO$_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted Ci-Ce alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —(CH$_2$)$_n$OH, —(CH$_2$)$_n$—O—($C_1$-$C_6$)alkyl, —(CH$_2$)$_n$—O—(CH$_2$)$_n$—($C_1$-$C_6$)alkyl, —(CH$_2$)$_n$—C(O)(C$_0$-$C_6$) alkyl, —(CH$_2$)$_n$—C(O)O(C$_0$-$C_6$) alkyl, —(CH$_2$)$_n$—OC(O)(C$_0$-$C_6$)alkyl, amine, mono- or di-($C_1$-$C_6$ alkyl) amine wherein the alkyl group on the amine is optionally substituted with 1 or 2 hydroxyl groups or up to three halo (preferably F, Cl) groups, OH, COOH, $C_1$-$C_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably substituted with a linker group attached to a ABM group, including a ULM group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methyl substituted isoxazole, an optionally substituted oxazole including a methyl substituted oxazole, an optionally substituted thiazole including a methyl substituted thiazole, an optionally substituted isothiazole including a methyl substituted isothiazole, an optionally substituted pyrrole including a methyl substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methyl substituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

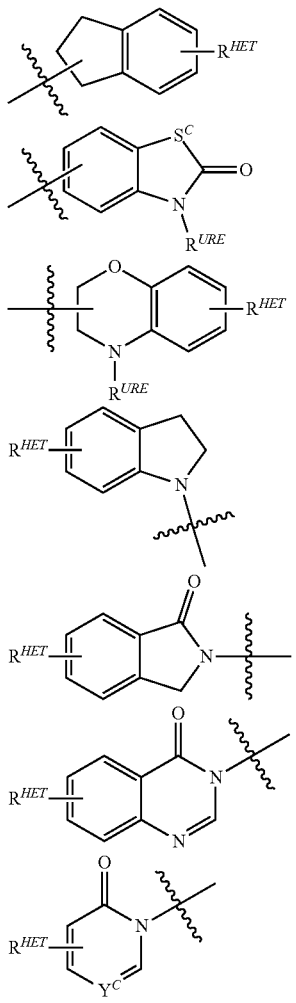

wherein $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$, alkyl group (preferably $C_1$-$C_3$ alkyl);

$R^{SS}$ is H, CN, $NO_2$, halo (preferably F or Cl), optionally substituted $C_1$-$C_6$, alkyl (preferably substituted with one or two hydroxyl groups or up to three halo groups), optionally substituted O—($C_1$-$C_6$, alkyl) (preferably substituted with one or two hydroxyl groups or up to three halo groups) or an optionally substituted —C(O) ($C_1$-$C_6$ alkyl) (preferably substituted with one or two hydroxyl groups or up to three halo groups);

$R^{URE}$ is H, $C_1$-$C_6$ alkyl (preferably H or $C_1$-$C_3$ alkyl) or a —C(O)($C_1$-$C_6$, alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^c$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$, alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl).

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO-heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyL and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S and P. "Substituted heterocycloalkyl" refers to a monocyclic or polycyclic alkyl group in which at least one ring carbon atom of its cyclic structure being replaced with a heteroatom selected from the group consisting of N, O, S and P and the group is containing one or more substituents selected from the group consisting of halogen, alkyl, substituted alkyl, carbyloxy, carbylmercapto, aryl, nitro, mercapto and sulfo, whereas these generic substituent group have meanings which are identical with definitions of the corresponding groups as defined in this legend.

The term "spirocycle" or "spiro-fused cycloalkyl" refers to a polycyclic alkyl group confining at least two rings, in which two rings share exactly one ring atom. The term "spiroheterocycle" or "spiro-fused heterocycloalkyl" refers to spiro-fused cycloakyl group in which at least one ring carbon atom of its cyclic structure is replaced with a heteroatom selected from the group consisting of N, O, S and P. Spiro-fused cycloalkyl and spiro-fused heterocycloalkyl groups may be further defined by their number of rings, e.g. bicyclic, tricyclic, tetracyclic, etc.

The term "bridged cycloalkyl" or refers to a polycyclic alkyl group confining at least two rings, in which two rings share at least three ring atoms. The term "bridged heterocycle" refers to bridged cycloakyl groups in which at least one ring carbon atom of its cyclic structure is replaced with a heteroatom selected from the group consisting of N, O, S and P. Bridged cycloalkyl and spiro-fused heterocycloalkyl groups may be further defined by their number of rings, e.g. bicyclic, tricyclic, tetracyclic, etc.

"Halogen" or "halo" refers to fluorine (F), chlorine (Cl), bromine (Br), or iodine (I).

"$C_1$-$C_6$ alkyl" refers to a straight or branched chain saturated hydrocarbon containing 1-6 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Pharmaceutically acceptable salt", as used herein with respect to a compound of the disclosure, means a salt form of the compound of the disclosure as well as hydrates of the salt form with one or more water molecules present. Such salt and hydrated forms retain the biological activity of the compound of the disclosure and are not biologically or otherwise undesirable, i.e., exhibit minimal, if any, toxicological effects. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methyl sulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "isomer" refers to salts and/or compounds that have the same composition and molecular weight but differ in physical and/or chemical properties. The structural difference may be in constitution (geometric isomers) or in the ability to rotate the plane of polarized light (stereoisomers). With regard to stereoisomers, the salts of the compounds of the disclosure may have one or more asymmetric carbon atom and may occur as racemates, racemic mixtures and as individual enantiomers or diastereomers.

The compounds of the disclosure may exist in unsolvated as well as solvated forms such as, for example, hydrates.

"Solvate" means a solvent addition form that contains either a stoichiometric or non-stoichiometric amounts of solvent. Non-limiting examples of suitable solvates include ethanolate, methanolate, and the like. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H2O, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the disclosure.

"Isotopic derivative", as referred to herein, relates to a compound of the disclosure that is isotopically enriched or labelled (with respect to one or more atoms of the compound) with one or more stable isotopes. Thus, in this application, the compounds of the disclosure include, for example, compounds that are isotopically enriched or labelled with one or more atoms such as deuterium.

Metastatic prostate cancer, or metastases, refers to prostate cancer that has spread beyond the prostate to other parts of the body, e.g., bones, lymph nodes, liver, lungs, brain.

Castrate-resistant prostate cancer or castration-resistant prostate cancer (or prostate cancer that is castrate- or castration-resistant) is a type of prostate cancer that keeps growing even when the amount of testosterone in the body is reduced to very low levels.

Metastatic, castrate-resistant prostate cancer is a type of prostate cancer that has metastasized and continues to grow even when the amount of testosterone in the body is reduced to very low levels.

As used herein, "treating" describes the management and care of a subject for the purpose of combating a disease, condition, or disorder and includes decreasing or alleviating the symptoms or complications, or eliminating the disease, condition or disorder.

As used herein, "preventing" describes stopping the onset of the symptoms or complications of the disease, condition or disorder.

"Administration" refers to introducing an agent, such as a compound of the disclosure into a subject. The related terms "administering" and "administration of" (and grammatical equivalents) refer both to direct administration, which may be administration to a subject by a medical professional or by self-administration by the subject, and/or to indirect administration, which may be the act of prescribing a drug. For example, a physician who instructs a patient to self-administer a drug and/or provides a patient with a prescription for a drug is administering the drug to the patient.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anti-cancer agent. In particularly preferred aspects, the co-administration of compounds results in synergistic activity and/or therapy, including anti-cancer activity.

"Therapeutically effective amount", as used herein means an amount of the free base of a compound of the disclosure that is sufficient to treat, ameliorate, or prevent a specified disease (e.g., prostate cancer), disease symptom, disorder or condition, or to exhibit a detectable therapeutic or inhibitory effect. The effect can be detected by any assay method known in the art. The effective amount for a particular subject may depend upon the subject's body weight, size, and health; the nature and extent of the condition; and whether additional therapeutics are to be administered to the subject. Therapeutically effective amounts for a given situation can be determined by routine experimentation that is within the skill and judgment of the clinician.

"$C_{max}$", as used herein, refers to the observed maximum (peak) plasma concentration of a specified compound in the subject after administration of a dose of that compound to the subject.

"AUC", as used herein, refers to the total area under the plasma concentration-time curve, which is a measure of exposure to a compound of interest, and is the integral of the concentration-time curve after a single dose or at steady state. AUC is expressed in units of ng*H/mL (ng×H/mL), where "H" refers to hours.

"$AUC_{tau}$", as used herein, refers to the AUC from 0 hours to the end of a dosing interval.

"$AUC_{0-24}$" means the AUC from 0 hours to 24 hours after administration of a single dose.

"Controlled release" or "CR" as used herein with respect to an oral dosage form refers to where a compound of the disclosure is released from the dosage form according to a predetermined profile that may include when and where release occurs after oral administration and/or a specified rate of release over a specified time period "Controlled release agent" as used herein with respect to an oral dosage form of the disclosure refers to one or more substances or materials that modulate release of a compound of the disclosure from the dosage form. Controlled release agents may be materials which are organic or inorganic, naturally occurring or synthetic, such as polymeric materials, triglycerides, derivatives of triglycerides, fatty acids and salts of fatty acids, talc, boric acid, colloidal silica, and combinations thereof.

"Enteric coating" as used herein with respect to a dosage form of the disclosure refers to a pH-dependent material that surrounds a core comprising a compound of the disclosure and which remains substantially intact in the acid environment of the stomach, but which dissolves in the pH environment of the intestines.

"Gastro-resistant" or "GR" as applied to a CR oral dosage form described herein means that release of a compound of the disclosure in the stomach of a subject shall not exceed 5%, 2.5%, 1% or 0.5% of the total amount of the compound of the disclosure in the dosage form.

"Oral dosage form" as used herein refers to a pharmaceutical drug product that contains a specified amount (dose) of a compound of the disclosure as the active ingredient, or a pharmaceutically acceptable salt and/or solvate thereof, and inactive components (excipients), formulated into a particular configuration that is suitable for oral administration, such as an oral tablet, liquid, or capsule. In one embodiment, the compositions are in the form of a tablet that can be scored.

The term "carrier", as used in this disclosure, encompasses pharmaceutically acceptable excipients and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "about" as part of a quantitative expression such as "about X", includes any value that is 10% higher or lower than X, and also includes any numerical value that falls between X−10% and X+10%. Thus, for example, a weight of about 40 g includes a weight of between 36 to 44 g.

"Comprising" or "comprises" as applied to a particular dosage form, composition, use, method or process described or claimed herein means that the dosage form, composition, use, method, or process includes all of the recited elements in a specific description or claim, but does not exclude other elements. "Consists essentially of" and "consisting essentially of" means that the described or claimed composition, dosage form, method, use, or process does not exclude other materials or steps that do not materially affect the recited physical, pharmacological, pharmacokinetic properties or therapeutic effects of the composition, dosage form, method, use, or process. "Consists of" and "consisting of" means the exclusion of more than trace elements of other ingredients and substantial method or process steps.

"Fasted condition" or "fasted state" as used to describe a subject means the subject has not eaten for at least 4 hours before a time point of interest, such as the time of administering a compound of the disclosure. In an embodiment, a subject in the fasted state has not eaten for at least any of 6, 8, 10 or 12 hours prior to administration of a compound of the disclosure.

"Fed condition" or "fed state" as used to describe a subject herein means the subject has eaten less than 4 hours before a time point of interest, such as the time of administering a compound of the disclosure. In an embodiment, a subject in the fed state has eaten within at least any of 3, 2, 1 or 0.5 hours prior to administration of a compound of the disclosure.

As used herein, the term "anti-cancer agent" is used to describe an anti-cancer agent, or a therapeutic agent administered concurrently with an anti-cancer agent (e.g., palonosetron), with which may be co-administered and/or co-formulated with a compound of the disclosure to treat cancer, and the side effects associated with the cancer treatment. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitor, an ART inhibitor, an mTORC1/2 inhibitor, a JAK/STAT inhibitor, a checkpoint-1 or 2 inhibitor, a focal adhesion kinase inhibitor, a Map kinase (mek) inhibitor, a VEGF trap antibody, pemetrexed, erlotinib, dasatinib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, IL13-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafamib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa, and mixtures thereof. In one embodiment, the anti-cancer agent is selected from the group consisting of abiraterone, estramustine, docetaxel, ketoconazole, goserelin, histrelin, triptorelin, buserelin, cyproterone, flutamide, bicalutamide, nilutamide, pamidronate, and zolendronate. In one embodiment, the anti-cancer agent is selected from the group consisting of FLT-3 inhibitor, androgen receptor inhibitor, VEGFR inhibitor, EGFR TK inhibitor, aurora kinase inhibitor, PIK-1 modulator, Bcl-2 inhibitor, HDAC inhibitor, c-Met inhibitor, PARP inhibitor, CDK 4/6 inhibitor, anti-HGF antibody, IGFR TK inhibitor, PI3 kinase inhibitor, AKT inhibitor, JAK/STAT inhibitor, checkpoint 1 inhibitor, checkpoint 2 inhibitor, focal adhesion kinase inhibitor, Map kinase kinase inhibitor, VEGF trap antibody, and chemical castration agent.

In one embodiment, the anti-cancer agent is selected from the group consisting of temozolomide, capecitabine, irinotecan, tamoxifen, anastrazole, exemestane, letrozole, DES, Estradiol, estrogen, bevacizumab, goserelin acetate, leuprolide acetate, triptorelin pamoate, medroxyprogesterone acetate, hydroprogesterone caproate, raloxifene, megestrol acetate, carboplatin, cisplatin, dacarbazine, methotrexate, vinblastine, vinorelbine, topotecan, finasteride, arzoxifene, fulvestrant, prednisone, abiraterone, enzalutamide, apalutamide, darolutamide, sipuleucel-T, pembrolizumab, nivolumab, cemiplimab, atezolizumab (Tecentriq), avelumab (Bavencio), durvalumab (Imfinzi), docetaxel (Taxotere), cabazitaxel (Jevtana), mitoxantrone (Novantrone), estramustine (Emcyt), docetaxel, ketoconazole, histrelin, triptorelin, buserelin, cyproterone, flutamide, bicalutamide, nilutamide, pamidronate, and zolendronate.

Abiraterone acetate is a commercially available drug for the treatment of metastatic castration-resistant prostate cancer developed by Janssen and sold under the brand name Zytiga®.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The terms "patient" and "subject" are used interchangeably herein, and refer to a mammal, e.g., a human, mouse, rat, guinea pig, dog, cat, horse, cow, pig, or non-human primate, such as a monkey, chimpanzee, baboon or rhesus.

In one embodiment, the subject is a human.

In one embodiment, the subject is a human who has been diagnosed with prostate cancer.

In one embodiment, the subject is a human who has been diagnosed with metastatic prostate cancer.

In one embodiment, the subject is a human who has been diagnosed with castrate-resistant prostate cancer.

In one embodiment, the subject is a human who has been diagnosed with metastatic, castrate-resistant prostate cancer.

Compounds of the Disclosure

In one aspect, the application pertains to a bifunctional or multifunctional compounds useful for regulating protein activity by inducing the degradation of a target protein. In some embodiments, the bifunctional compound comprises an E3 ubiquitin ligase binding moiety and a protein targeting moiety, preferably linked through a linker moiety, as otherwise described herein, wherein the E3 ubiquitin ligase binding moiety is coupled to the protein targeting moiety and wherein the E3 ubiquitin ligase binding moiety recognizes a ubiquitin pathway protein (e.g., an ubiquitin ligase, preferably an E3 ubiquitin ligase) and the protein targeting moiety recognizes the target protein such that degradation of the target protein will occur when the target protein is placed in proximity to the ubiquitin ligase, thus resulting in degradation/inhibition of the effects of the target protein and the control of protein levels. In certain embodiments, the bifunctional compound comprises a CLM coupled, e.g., linked covalently, directly, or indirectly, to a chemical linker L, and a PTM, which can be depicted as:

PTM-L-CLM

The CLM recognizes and binds to cereblon, an E3 Ubiquitin Ligase. The PTM is a small molecule protein binding moiety that binds and recruits an intracellular target protein or polypeptide bringing it into close proximity to the CLM to effect the degradation of the target protein, resulting in target protein ubiquitination. In certain embodiments, the PTM is an AR binding moiety (ABM).

In any of the compounds described herein, the PTM comprises the following chemical structure:

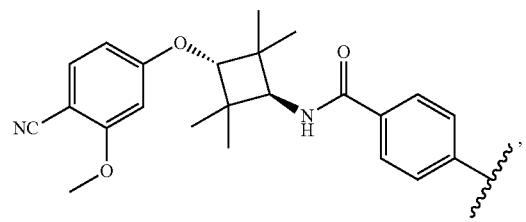

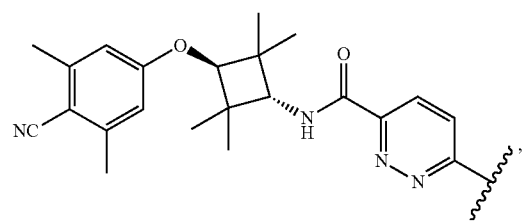

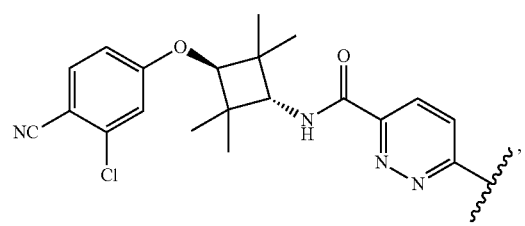

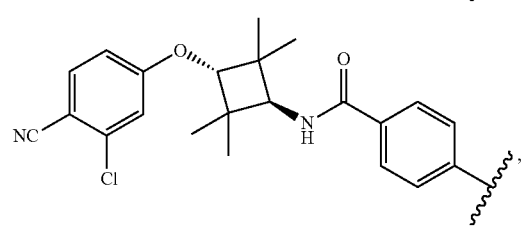

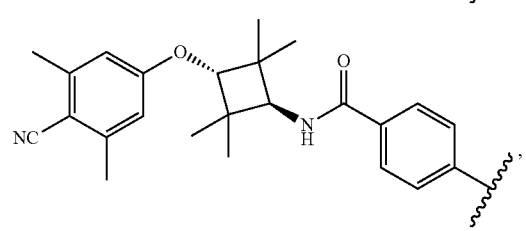

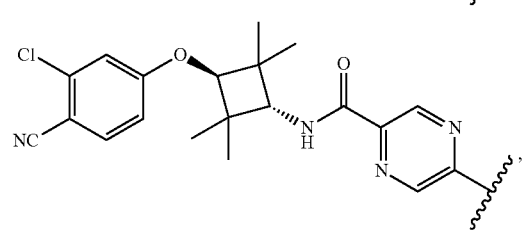

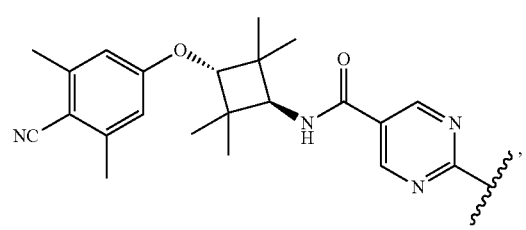

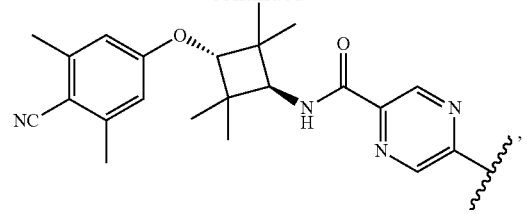
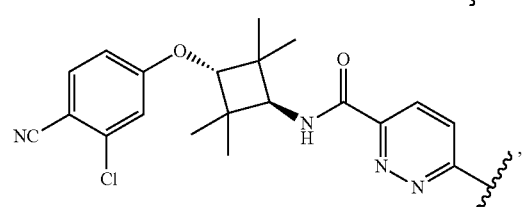
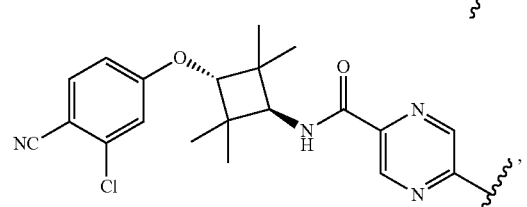
, and
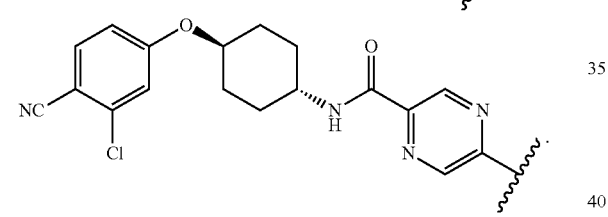.
In any of the compounds described herein, the L comprises the following chemical structure:
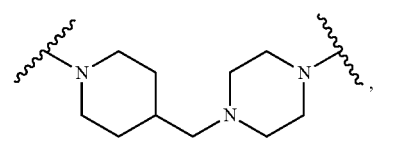,
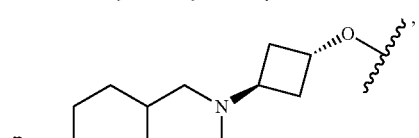,
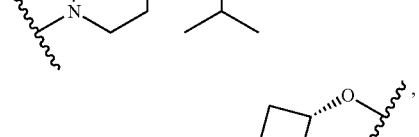,
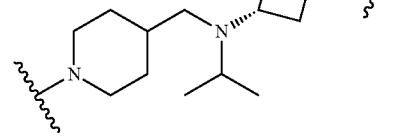,
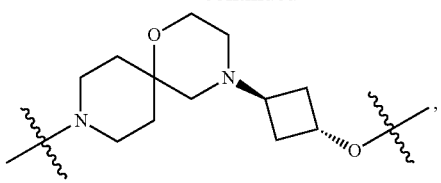,
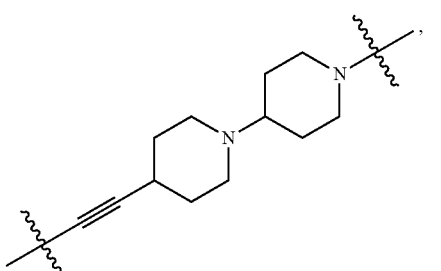,
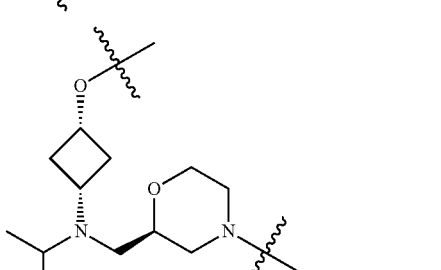,
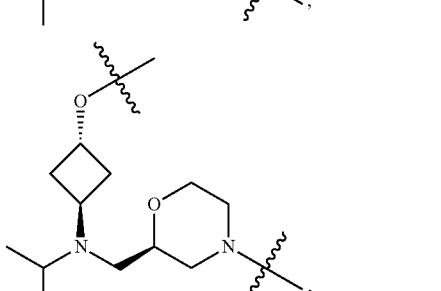,
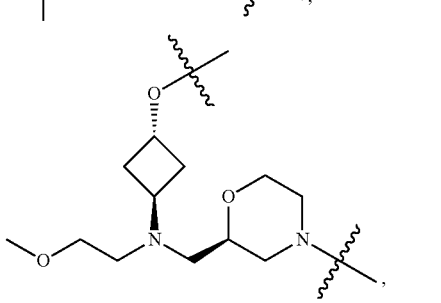,
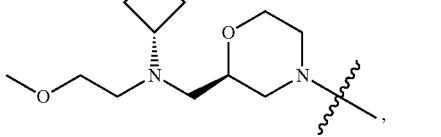,

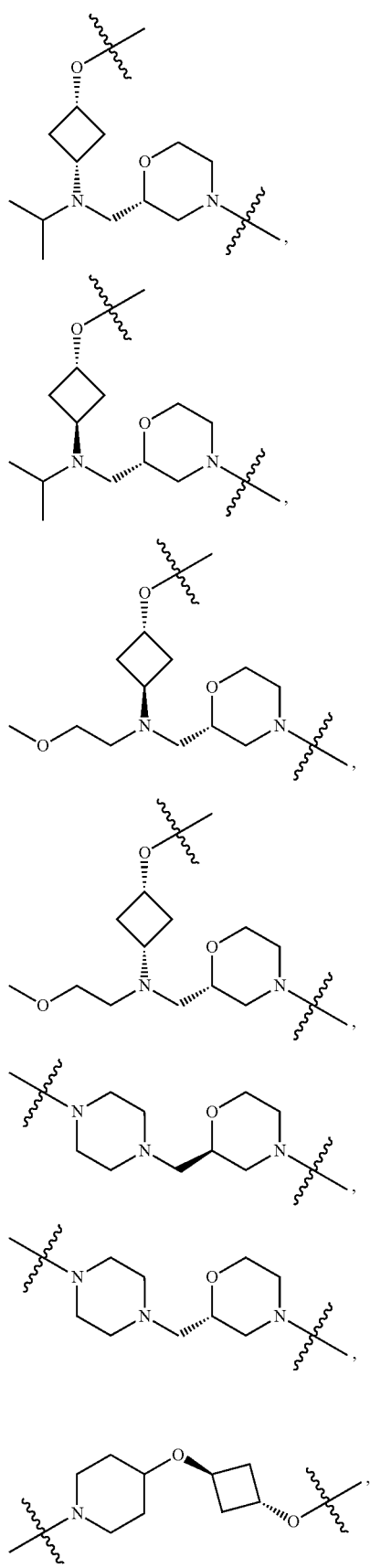
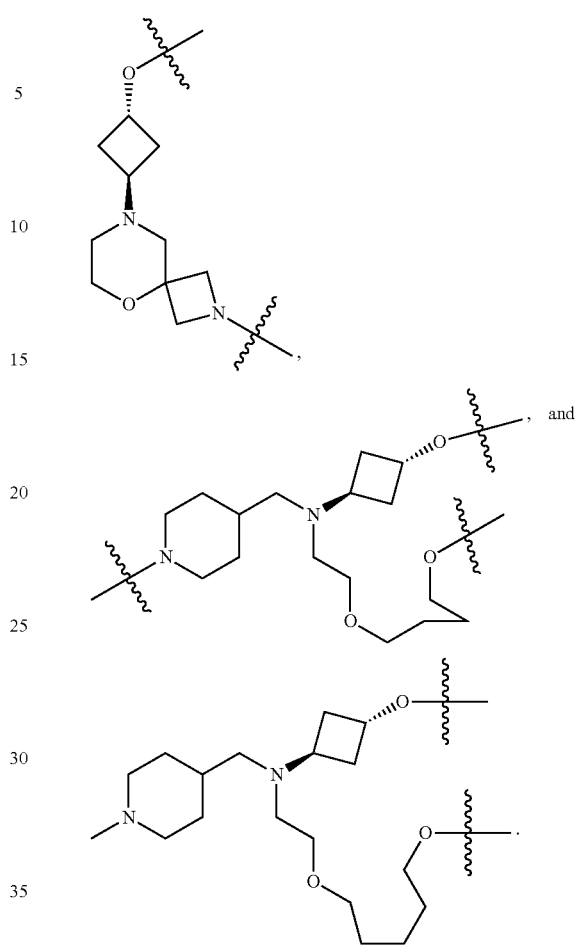
In any of the compounds described herein, the CLM comprises the following chemical structures:
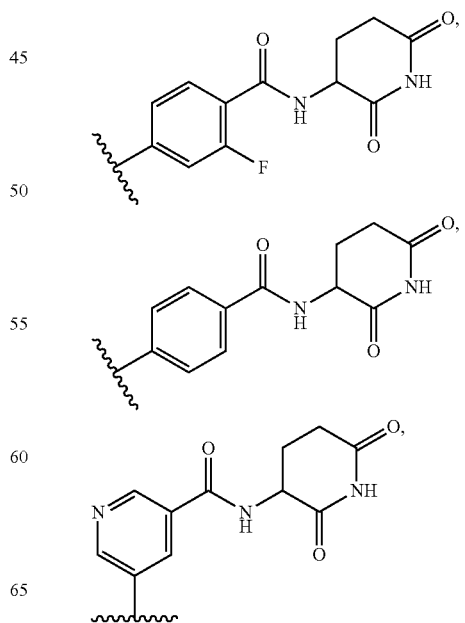

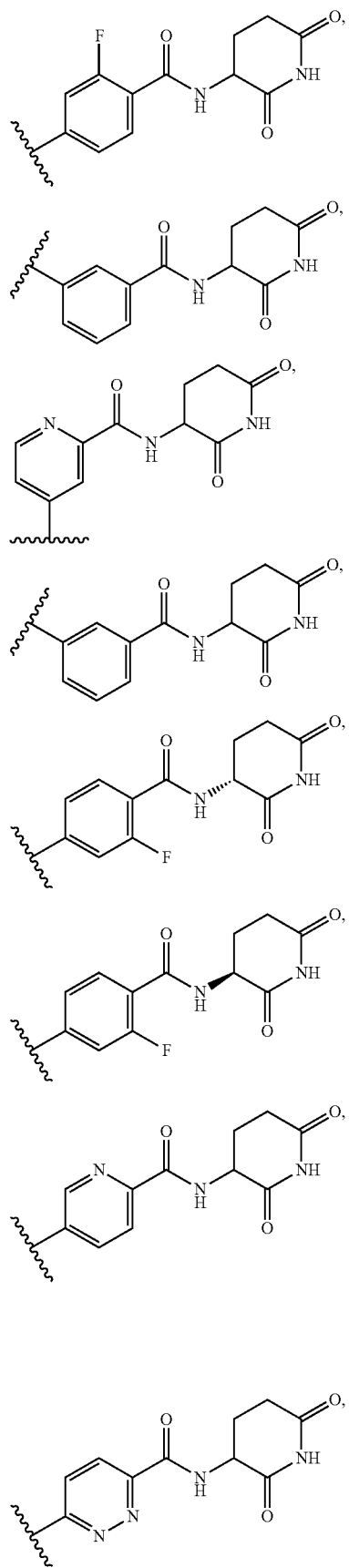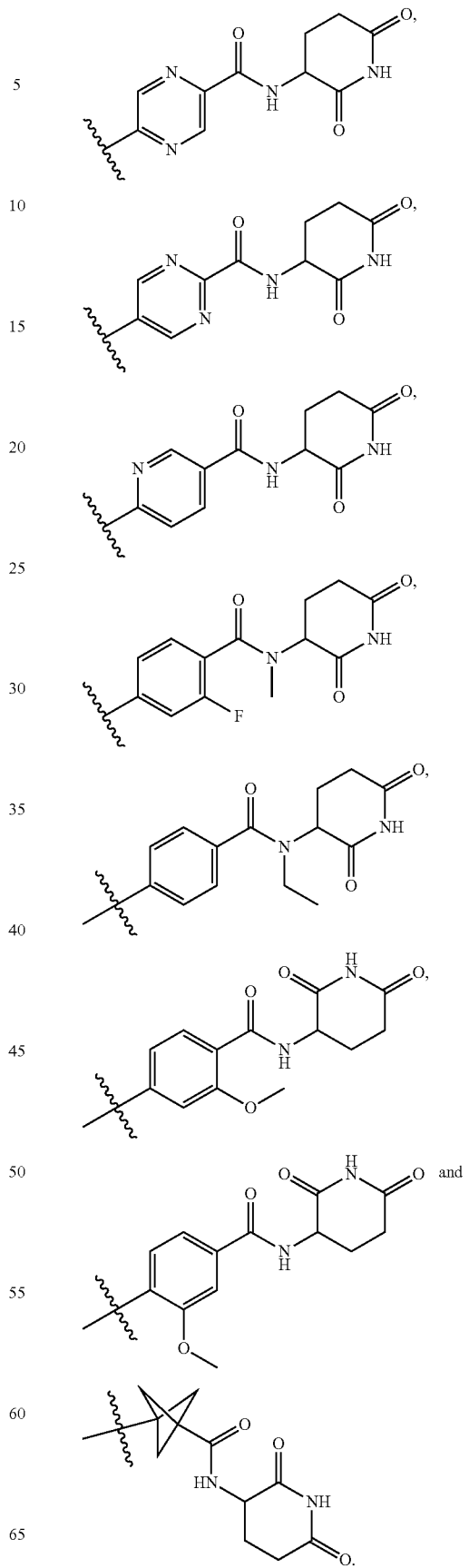

In another aspect, the application pertains to a bifunctional compound having the structure:

ABM-L-CLM, or a pharmaceutically acceptable salt, solvate, enantiomer, stereoisomer, or isotopic derivative thereof,
wherein:
(a) ABM is an androgen receptor (AR) binding moiety having the structure:

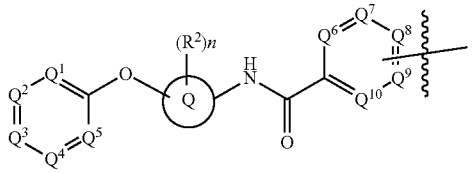

wherein:
$Q^1$, $Q^2$, $Q^3$, $Q^4$, and $Q^5$ are each independently $CR^1$, or N;

is 4-6 membered cycloalkyl, $C_6$-$C_{10}$ aryl, 4-6 membered heterocycloalkyl, or 4-6 membered heteroaryl, wherein the heterocycloalkyl or heteroaryl comprises 0-4 heteroatoms;
$Q^6$, $Q^7$, $Q^8$, $Q^9$, and $Q^{10}$ are each independently $CR^3$, or N;
Each $R^1$ is independently selected from the group consisting of H, optionally substituted linear or branched $C_1$-$C_6$ alkyl, cyano, halogen, and optionally substituted linear or branched $C_1$-$C_6$ alkoxy, wherein the alkyl or alkoxy group is optionally substituted with one or more halo;
Each $R^2$ is independently selected from the group consisting of optionally substituted linear or branched $C_1$-$C_6$ alkyl, cyano, halogen, and optionally substituted linear or branched $C_1$-$C_6$ alkoxy, wherein the alkyl or alkoxy group is optionally substituted with one or more halo;
Each $R^3$ is independently selected from the group consisting of optionally substituted H, linear or branched $C_1$-$C_6$ alkyl, cyano, halogen, and optionally substituted linear or branched $C_1$-$C_6$ alkoxy, wherein the alkyl or alkoxy group is optionally substituted with one or more halo; and
n is 0, 1, 2, 3, or 4;
(b) L is a chemical linking moiety having the structure:

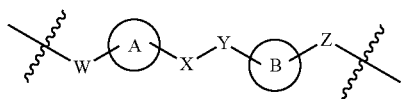

wherein:
the ABM is linked to W, and the CLM is linked to Z or the ABM is linked to Z, and the CLM is linked to W;
W is absent or

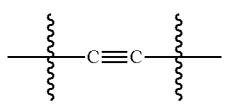 [SMILES: *C#C*]

is 4-7 membered cycloalkyl, 4-7 membered heterocycle, or spiro-bicyclic heterocycloalkyl, where each ring in the spiro-bicycle is 4-7 membered;
X is —$CH_2$— or absent;
Y is —$NR^6$—, —O—, or absent;

is 4-7 membered cycloalkyl or 4-7 membered heterocycle;
Z is —$C(R^7)_2$—, —$NR^7$—, —O—, or absent;
$R^6$ is H, linear or branched $C_{1-6}$ alkyl, linear or branched $C_{1-6}$ alkoxy-$C_{1-6}$ alkyl, or

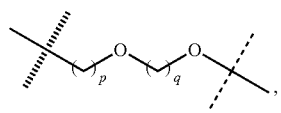

wherein

indicates a bond to Y, and

indicates a bond to

each $R^7$ is independently selected from the group consisting of H, linear or branched $C_{1-6}$ alkyl, and linear or branched $C_{1-6}$ alkoxy;
p is 1, 2, 3, or 4; and
q is 1, 2, 3, 4, or 5;
(c) CLM is cereblon E3 ubiquitin ligase binding moiety having the structure:

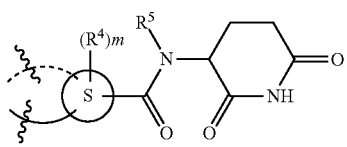

Wherein:

$C_6$-$C_{10}$ aryl, 4-7 membered heteroaryl, or bridged bicyclic cycloalkyl;

indicates that linking moiety L is connected to ring S by one or two covalent bonds;

Each $R^4$ is independently selected from the group consisting of optionally substituted linear or branched $C_1$-$C_6$ alkyl, cyano, halogen, and optionally substituted linear or branched $C_1$-$C_6$ alkoxy, wherein the alkyl or alkoxy group is optionally substituted with one or more halo;

$R^5$ is H, optionally substituted linear or branched $C_1$-$C_6$, alkyl, or optionally substituted linear or branched $C_1$-$C_6$ alkoxy, wherein the alkyl or alkoxy group is optionally substituted with one or more halo; and m is 0, 1, 2, 3, or 4.

In another aspect, the application pertains to a compound of Formula (I):

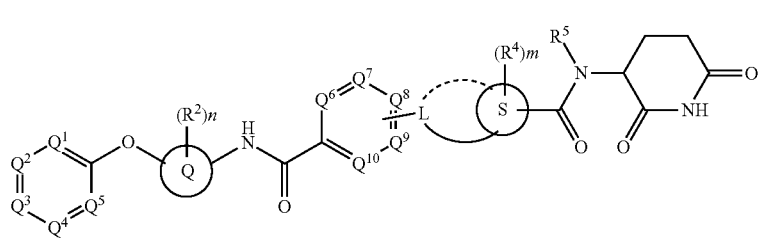

(I)

or a pharmaceutically acceptable salt, solvate, enantiomer, stereoisomer, or isotopic derivative thereof,
wherein all variables are as defined herein.
In some embodiments, when

is pyridyl,

is tetramethylcyclobutyl, $Q^2$ is $CR^1$, and $Q^4$ is $CR^1$, then $R^1$ is not chloro In some embodiments, the compound of Formula (I) is not N-(4-(3-chloro-4-cyanophenoxy)cyclohexyl)-6-(4-((4-(4-((2,6-dioxopiperidin-3-yl)carbamoyl)phenyl)piperazin-1-yl)methyl)piperidin-1-yl)pyridazine-3-carboxamide.

In some embodiments, the compound of Formula (I) is not

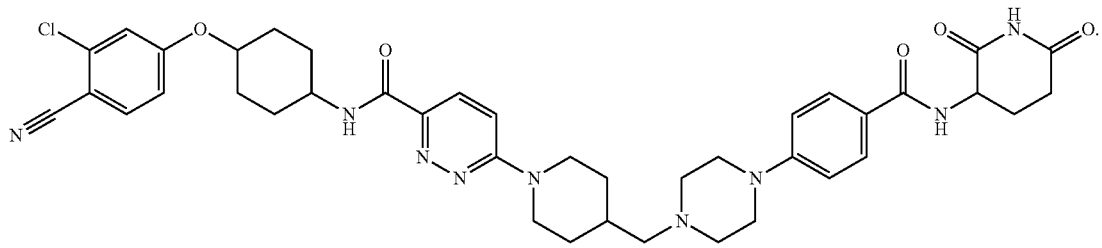 [SMILES: N#Cc1ccc(OC2CCC(NC(=O)c3ccc(N4CCC(CN5CCN(c6ccc(C(=O)NC7CCC(=O)NC7=O)cc6)CC5)CC4)nn3)CC2)cc1Cl]

In some embodiments, L is

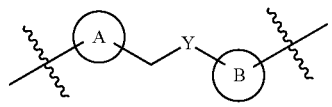

wherein:

is 4-7 membered cycloalkyl or 4-7 membered heterocycle;

Y is —NR$^6$—, —O—, or absent;

R$^6$ is H, linear or branched C$_{1-6}$ alkyl, or linear or branched C$_{1-6}$ alkoxy; and

is 4-7 membered cycloalkyl or 4-7 membered heterocycle.

In some embodiments, L is

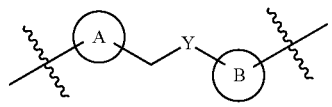

wherein:

is 4-7 membered cycloalkyl or 4-7 membered heterocycle;

Y is —NR$^6$— or —O—;

R$^6$ is H, linear or branched C$_{1-6}$ alkyl, or linear or branched C$_{1-6}$ alkoxy; and

is 4-7 membered cycloalkyl or 4-7 membered heterocycle.

In some embodiments, L is

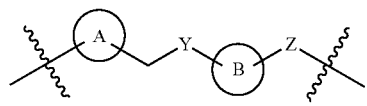

Wherein:

is piperidinyl or morpholinyl;

Y is —NR$^6$— or -Q-;

R$^6$ is

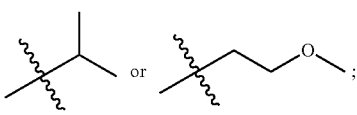

is cyclobutyl; and

Z is —O—.

In some embodiments, L is

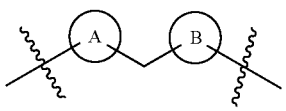

Wherein:

is piperidinyl or morpholinyl; and

is piperazinyl.

In some embodiments

is piperidinyl.

In some embodiments, the compound is a compound of Formula (Ib):

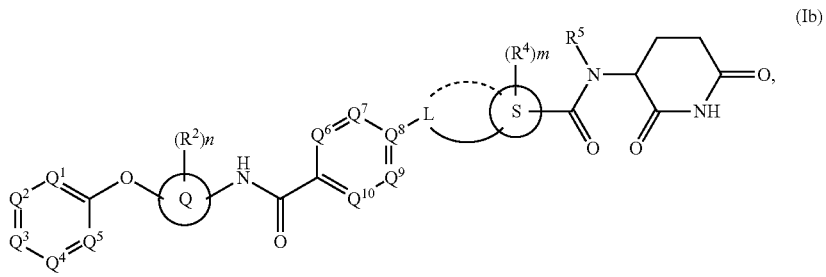

(Ib)

wherein all variables are as defined herein.

In some embodiments, the compound is a compound of Formula (Ic):

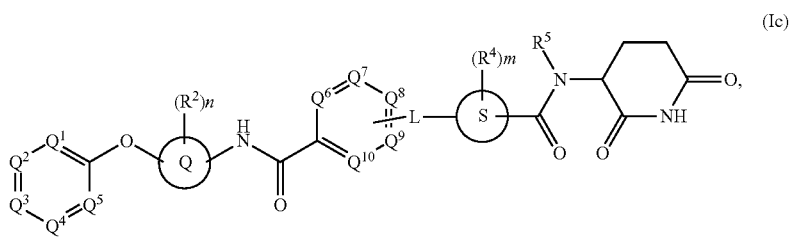

(Ic)

wherein all variables are as defined herein.

In some embodiments, $Q^1$-$Q^5$ are each $CR^1$. In some embodiments, between 1-3 of $Q^1$-$Q^5$ is N. In some embodiments, exactly 1 of $Q^1$-$Q^5$ is N. In some embodiments, exactly 2 of $Q^1$-$Q^5$ is N. In some embodiments, exactly 3 of $Q^1$-$Q^5$ is N.

In some embodiments, $Q^6$-$Q^{10}$ are each $CR^1$. In some embodiments, between 1-3 of $Q^6$-$Q^{10}$ is N. In some embodiments, exactly 1 of $Q^6$-$Q^{10}$ is N. In some embodiments, exactly 2 of $Q^6$-$Q^{10}$ is N. In some embodiments, exactly 3 of $Q^6$-$Q^{10}$ is N.

In some embodiments, $Q^1$ is CH, $Q^2$ is $C(CH_3)$, $Q^3$ is C(CN), $Q^4$ is $C(CH_3)$, and $Q^5$ is CH.

In some embodiments, $Q^1$ is CH, $Q^2$ is $C(OCH_3)$, $Q^3$ is C(CN), $Q^4$ is CH, and $Q^5$ is CH.

In some embodiments, $Q^1$ is CH, $Q^2$ is C(Cl), $Q^3$ is C(CN), $Q^4$ is CH, and $Q^5$ is CH.

In some embodiments, $R^1$ is selected from the group consisting of CN and $CH_3$. In some embodiments, 1e is selected from the group consisting of CN and $OCH^3$. In some embodiments, $R^1$ is selected from the group consisting of CN and Cl. In some embodiments, at least one R1 is $CF_3$.

In some embodiments,

is 4-6 membered cycloalkyl. In some embodiments,

is cyclobutyl or cyclohexyl. In some embodiments,

is cyclobutyl. In some embodiments,

is cyclopentyl. In some embodiments,

is cyclohexyl.

In some embodiments, n is 0. In some embodiments, n is 1. In some embodiments, n is 2. In some embodiments, n is 3. In some embodiments, n is 4.

In some embodiments, $R^2$ is linear or branched $C_1$-$C_6$ alkyl. In some embodiments, $R^2$ is methyl. In some embodiments, $R^2$ is ethyl. In some embodiments, $R^2$ is propyl. In some embodiments, $R^2$ is n-propyl. In some embodiments, $R^2$ is isopropyl. In some embodiments, $R^2$ is butyl. In some embodiments, $R^2$ is n-butyl. In some embodiments, $R^2$ is isobutyl. In some embodiments, $R^2$ is sec-butyl. In some embodiments, $R^2$ is tert-butyl. In some embodiments, $R^2$ is pentyl. In some embodiments, $R^2$ is hexyl.

In some embodiments,

is phenyl, pyridinyl, pyridazinyl, pyrimidinyl, or pyrazinyl. In some embodiments,

is phenyl. In some embodiments,

is pyridinyl. In some embodiments,

is pyridazinyl. In some embodiments,

is pyrimidinyl. In some embodiments,

is pyrazinyl.

In some embodiments, each $R^4$ is independently selected from the group consisting of F, methoxy, ethoxy, methyl, and ethyl. In some embodiments, each $R^4$ is independently selected from the group consisting of F, methoxy, and methyl.

In some embodiments, m is 0, 1, or 2. In some embodiments, m is 0. In some embodiments, m is 1. In some embodiments, m is 2.

In one aspect, the application pertains to a compound of Formula (Id):

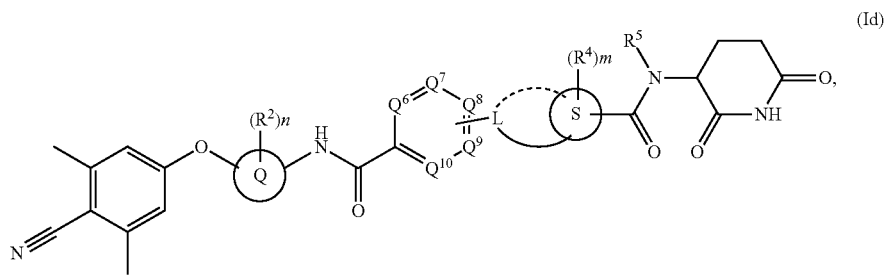

wherein all variables are as defined herein.

In one aspect, the application pertains to a compound of Formula (Ie):

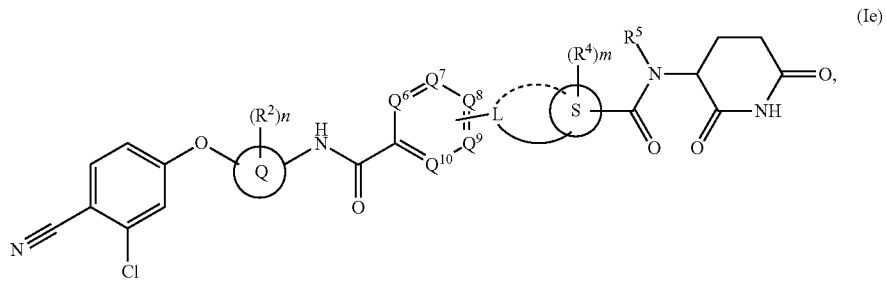

wherein all variables are as defined herein.

In one aspect, the application pertains to a compound of Formula (If):

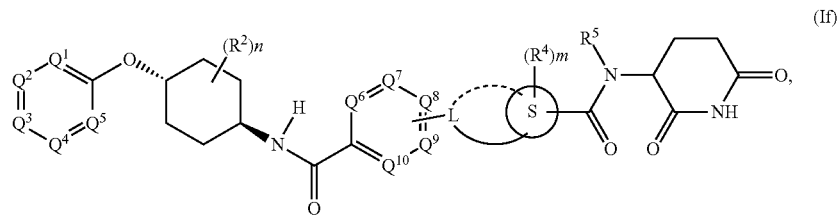

(If)

wherein all variables are as defined herein.

In one aspect, the application pertains to a compound of Formula (Ig):

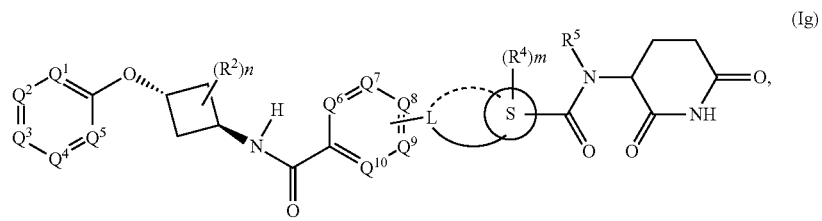

(Ig)

wherein all variables are as defined herein.

In one aspect, the application pertains to a compound of Formula (Ih):

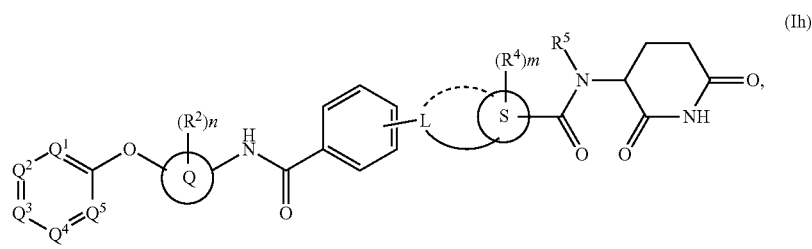

(Ih)

wherein all variables are as defined herein.

In one aspect, the application pertains to a compound of Formula (Ii):

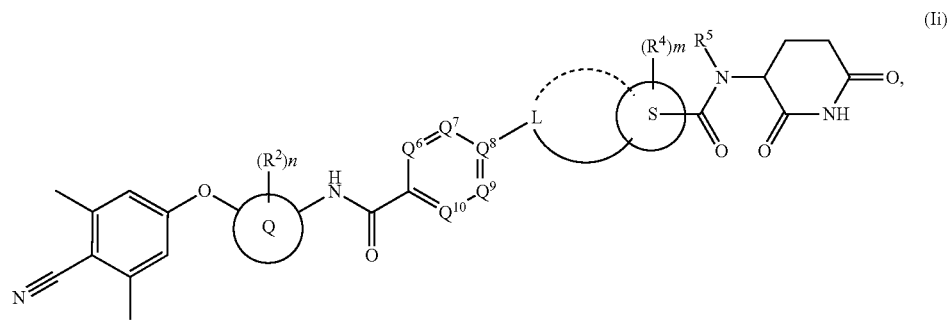

(Ii)

wherein all variables are as defined herein.

In one aspect, the application pertains to a compound of Formula (Ij):
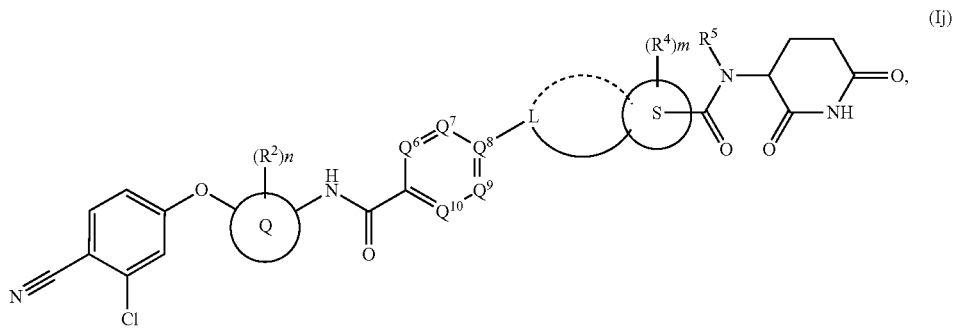
wherein all variables are as defined herein.
In one aspect, the application pertains to a compound of Formula (Ik):
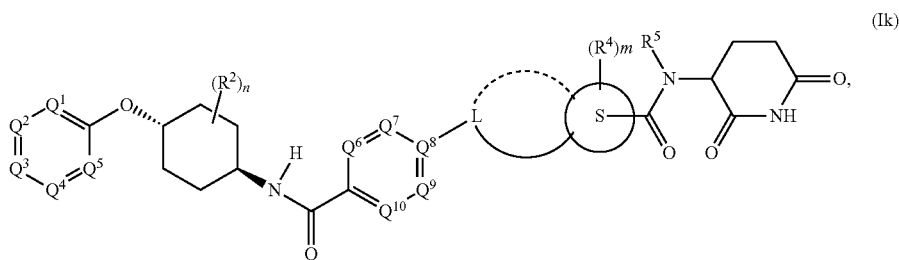
wherein all variables are as defined herein.
In one aspect, the application pertains to a compound of Formula (Il):
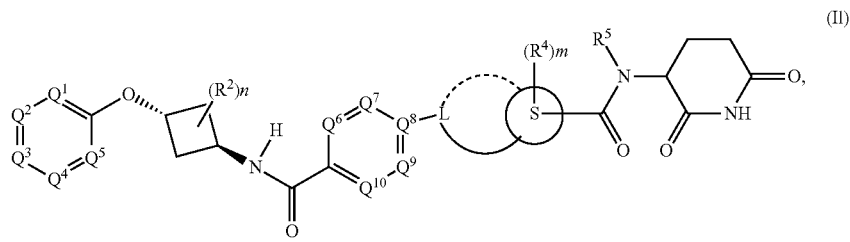
wherein all variables are as defined herein.

In one aspect, the application pertains to a compound of Formula (Im):

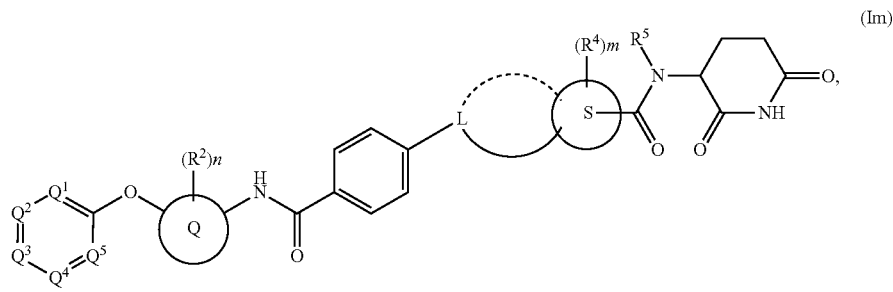

(Im)

wherein all variables are as defined herein.
In one aspect, the application pertains to a compound of Formula (In):

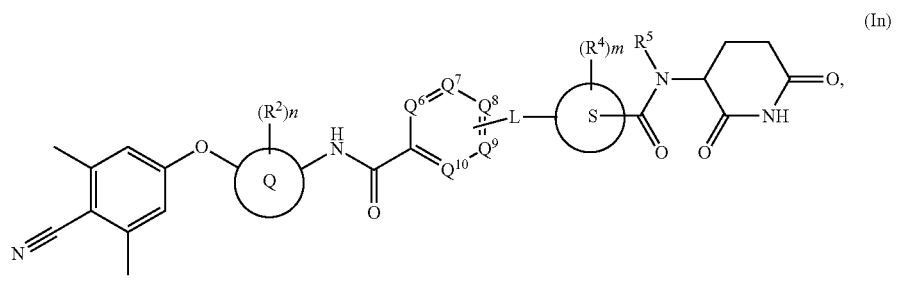

(In)

wherein all variables are as defined herein.
In one aspect, the application pertains to a compound of Formula (Io):

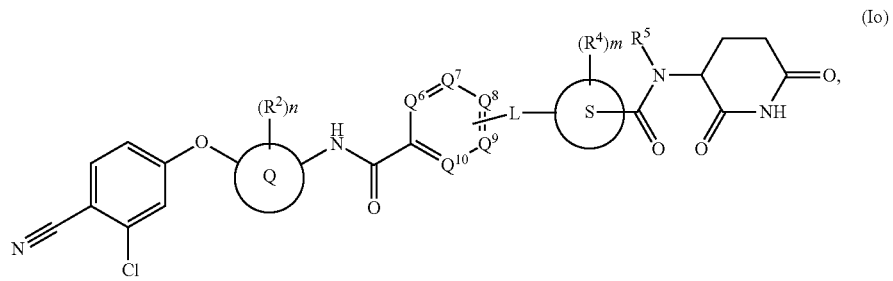

(Io)

wherein all variables are as defined herein.
In one aspect, the application pertains to a compound of Formula (Ip):

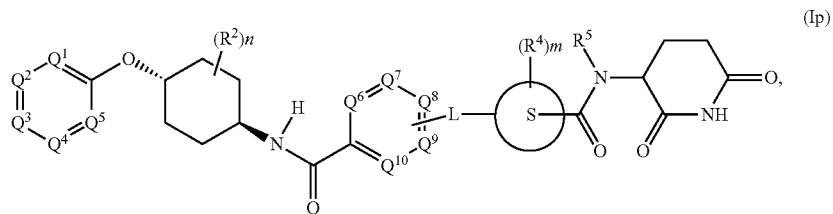

(Ip)

wherein all variables are as defined herein.
In one aspect, the application pertains to a compound of Formula (Iq):

In one aspect, the application pertains to a compound of Formula (Ir):
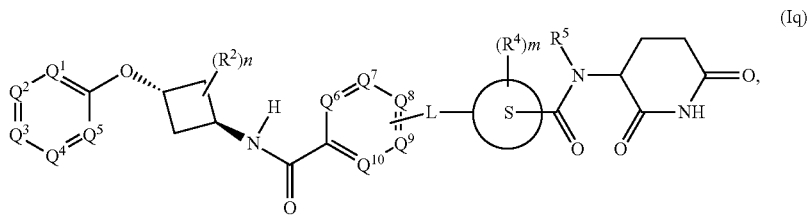
(Iq)
wherein all variables are as defined herein.
In one aspect, the application pertains to a compound of Formula (Is):
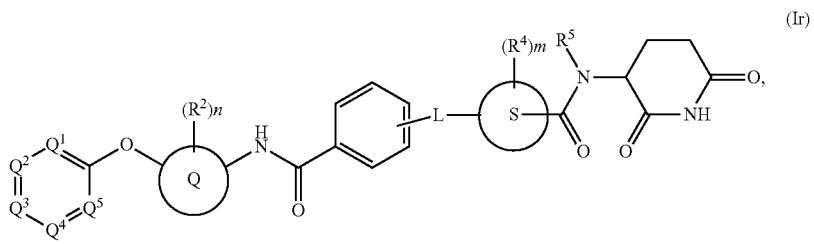
(Ir)
wherein all variables are as defined herein.
In another aspect, the application pertains to a compound, wherein the compound is:
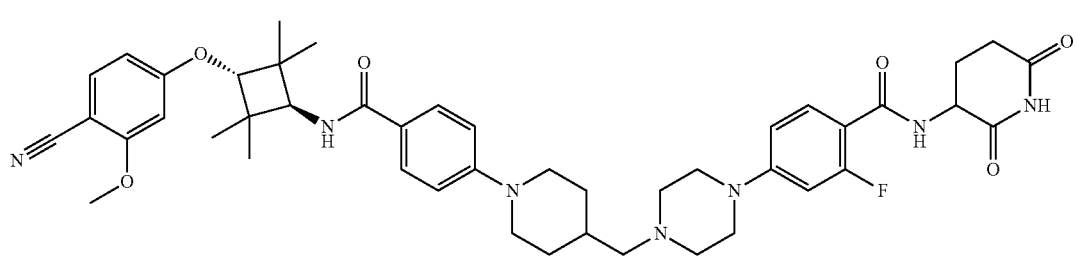 [SMILES: COc1cc(O[C@H]2C(C)(C)[C@H](NC(=O)c3ccc(N4CCC(CN5CCN(c6ccc(C(=O)NC7CCC(=O)NC7=O)c(F)c6)CC5)CC4)cc3)C2(C)C)ccc1C#N]
1
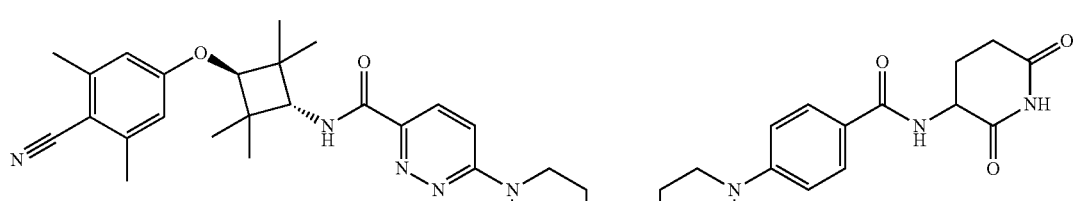
2
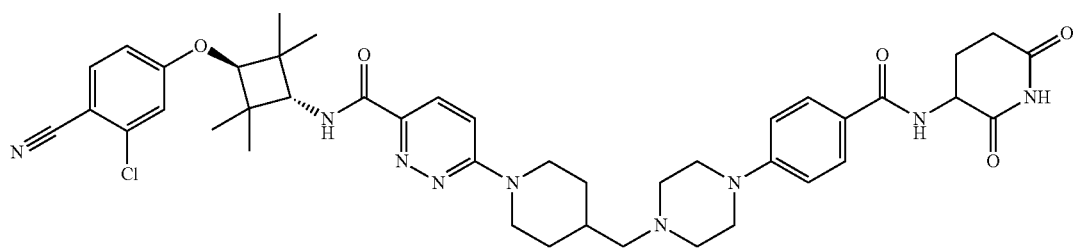 [SMILES: CC1(C)[C@H](NC(=O)c2ccc(N3CCC(CN4CCN(c5ccc(C(=O)NC6CCC(=O)NC6=O)cc5)CC4)CC3)nn2)C(C)(C)[C@H]1Oc1ccc(C#N)c(Cl)c1]
3

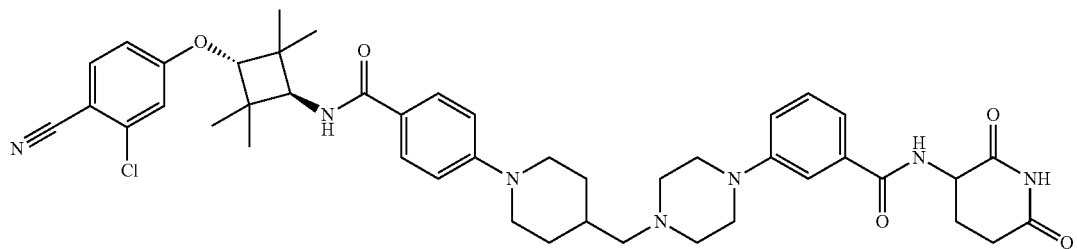 [SMILES: CC1(C)[C@H](NC(=O)c2ccc(N3CCC(CN4CCN(c5cccc(C(=O)NC6CCC(=O)NC6=O)c5)CC4)CC3)cc2)C(C)(C)[C@H]1Oc1ccc(C#N)c(Cl)c1]
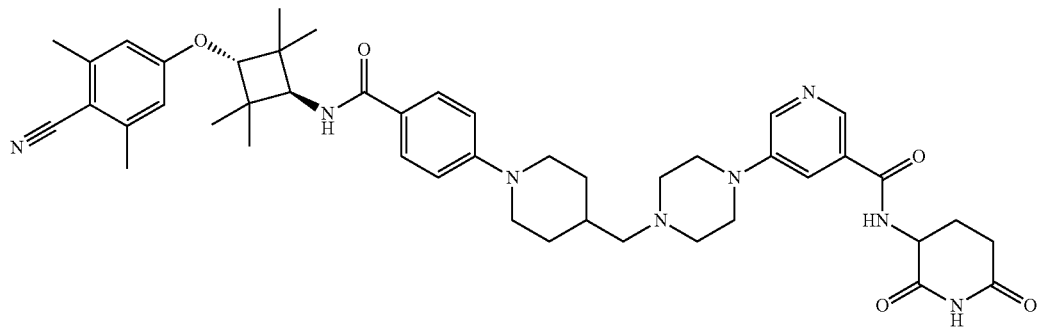 [SMILES: Cc1cc(O[C@H]2C(C)(C)[C@H](NC(=O)c3ccc(N4CCC(CN5CCN(c6cncc(C(=O)NC7CCC(=O)NC7=O)c6)CC5)CC4)cc3)C2(C)C)cc(C)c1C#N]
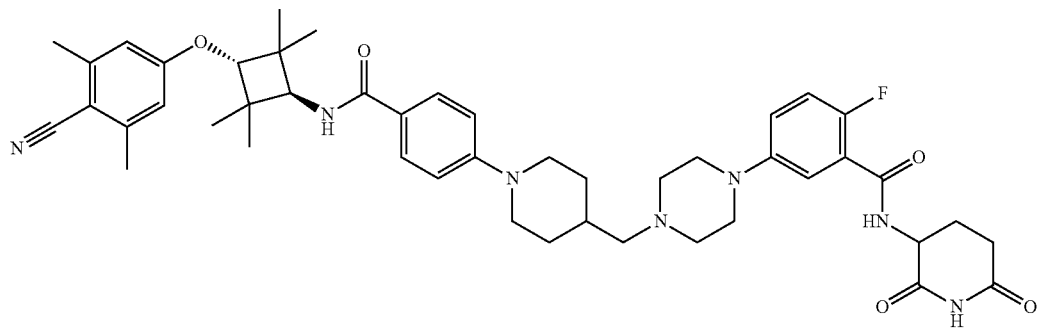 [SMILES: Cc1cc(O[C@H]2C(C)(C)[C@H](NC(=O)c3ccc(N4CCC(CN5CCN(c6ccc(F)c(C(=O)NC7CCC(=O)NC7=O)c6)CC5)CC4)cc3)C2(C)C)cc(C)c1C#N]
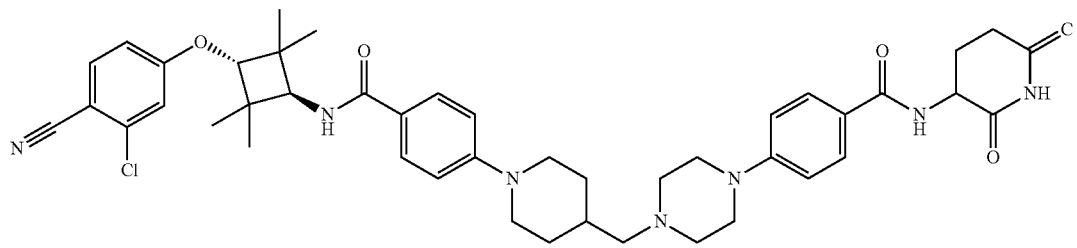 [SMILES: CC1(C)[C@H](NC(=O)c2ccc(N3CCC(CN4CCN(c5ccc(C(=O)NC6CCC(=O)NC6=O)cc5)CC4)CC3)cc2)C(C)(C)[C@H]1Oc1ccc(C#N)c(Cl)c1]
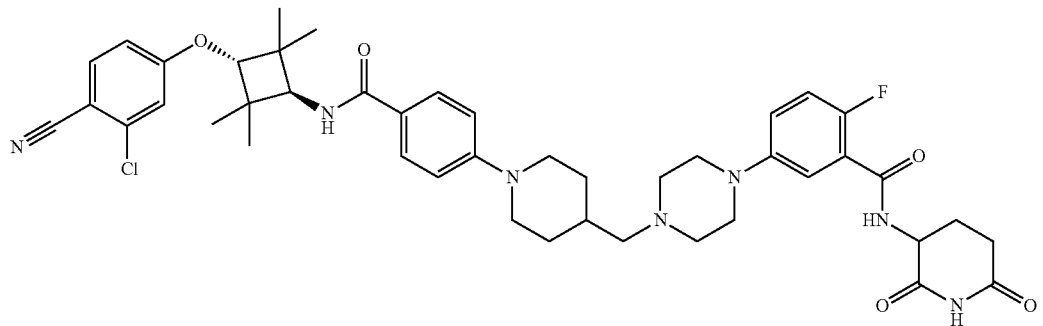 [SMILES: CC1(C)[C@H](NC(=O)c2ccc(N3CCC(CN4CCN(c5ccc(F)c(C(=O)NC6CCC(=O)NC6=O)c5)CC4)CC3)cc2)C(C)(C)[C@H]1Oc1ccc(C#N)c(Cl)c1]

9
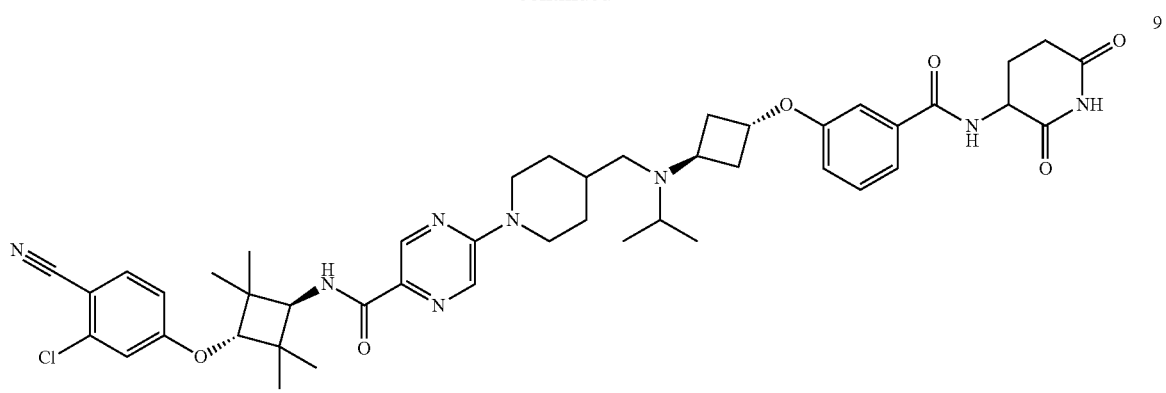
10
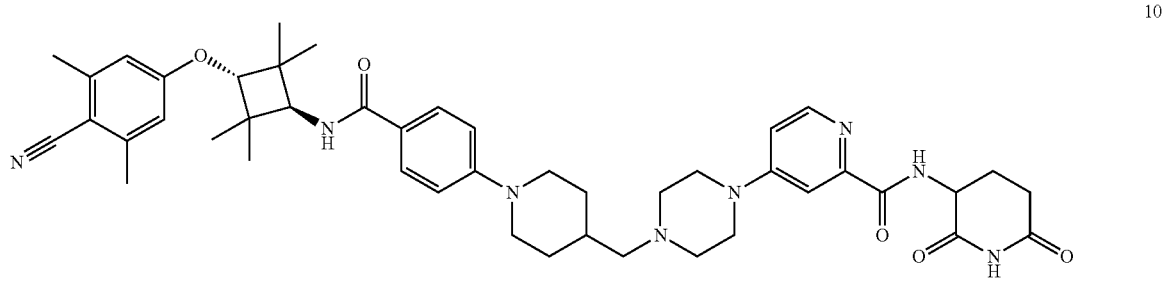
11
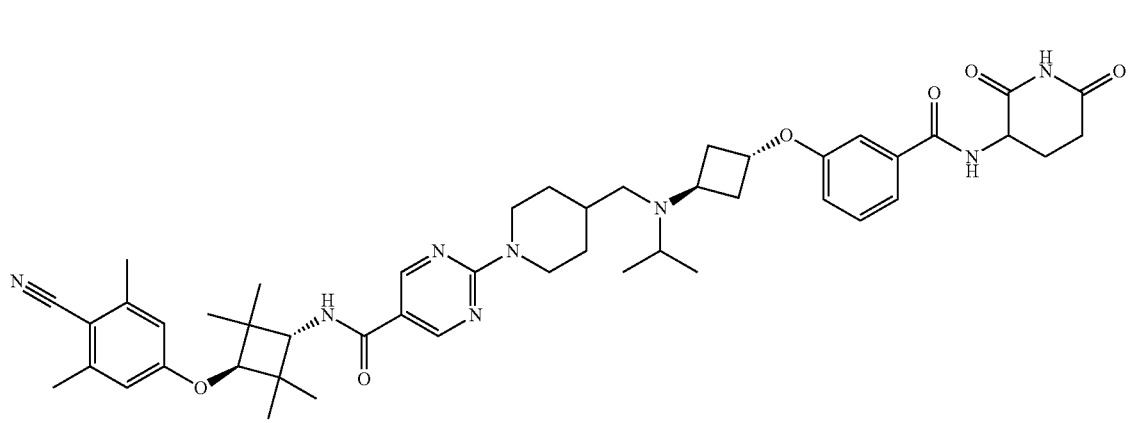
12
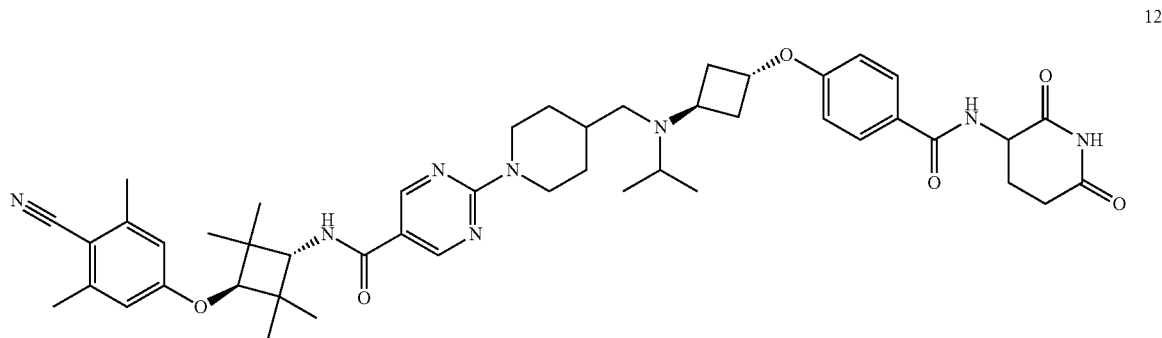

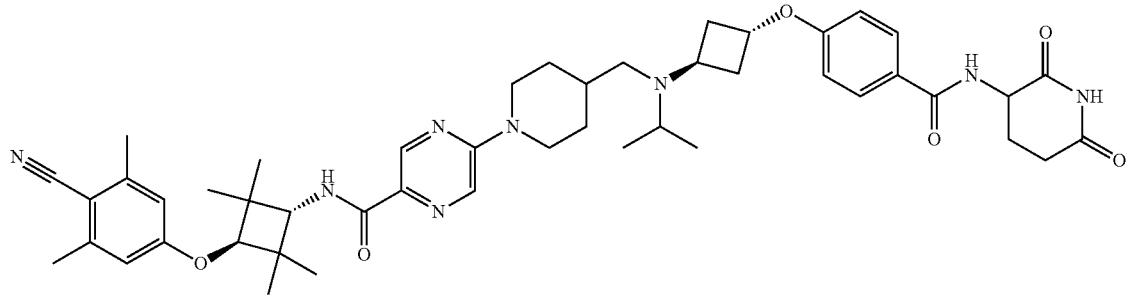
13
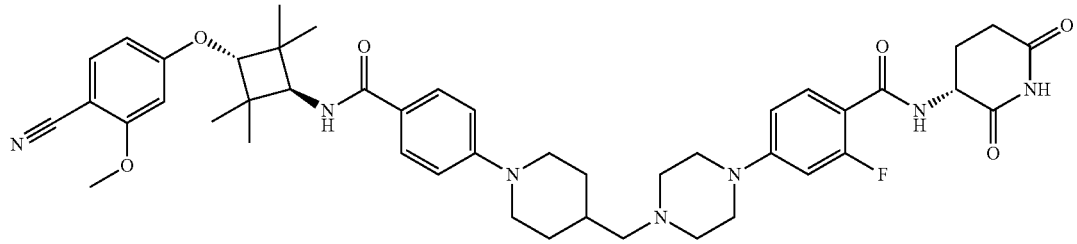
14
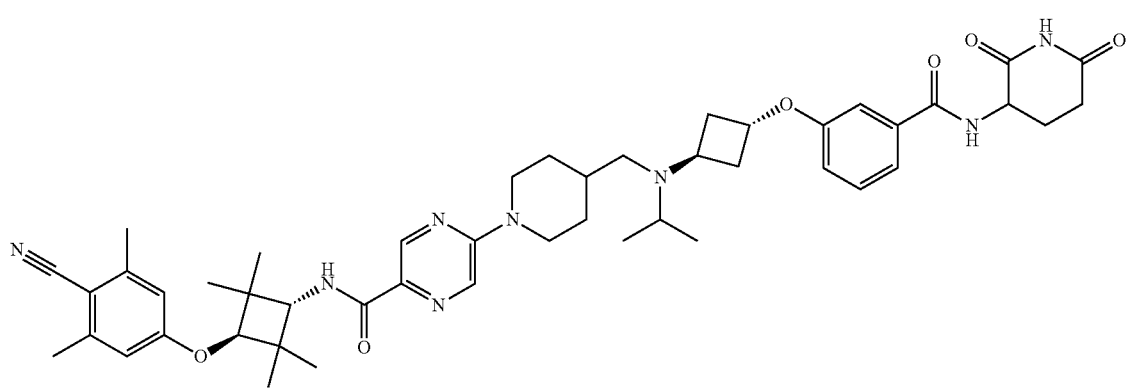
15
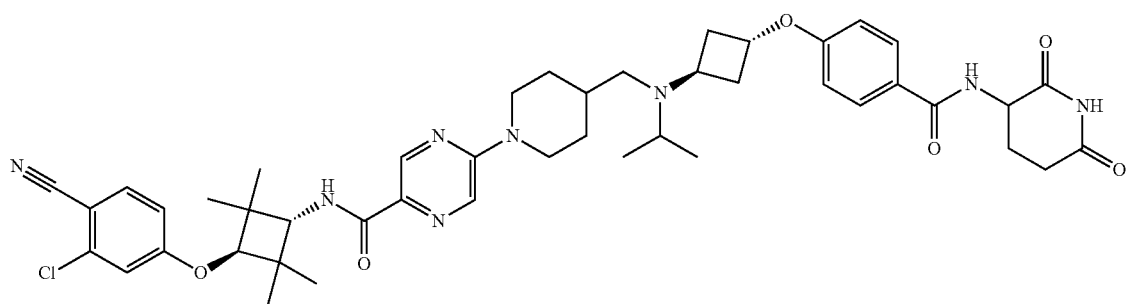
16
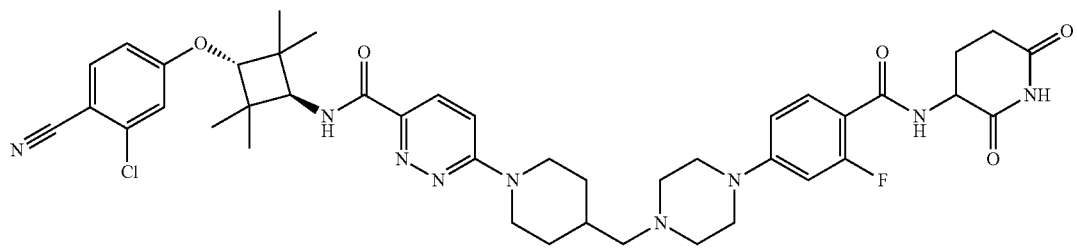
17

-continued
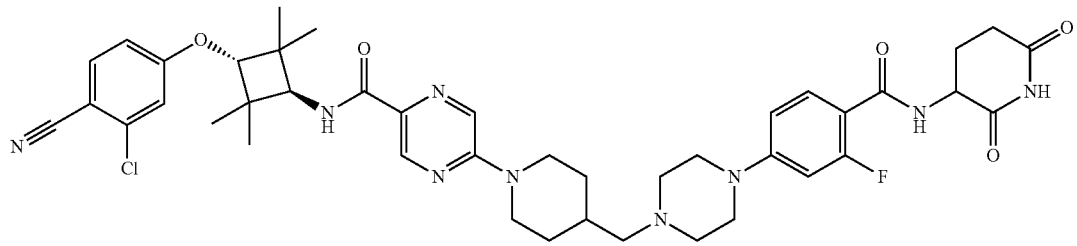
18
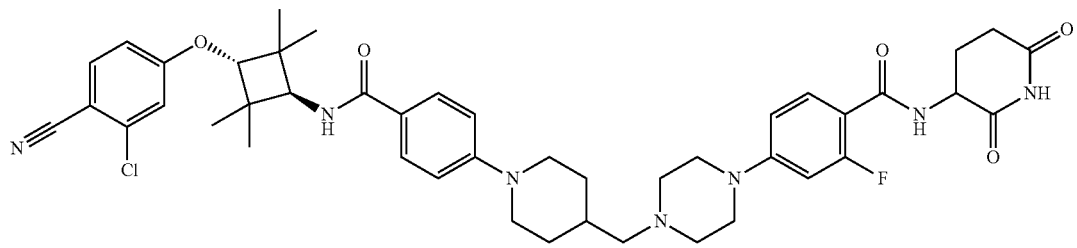
19
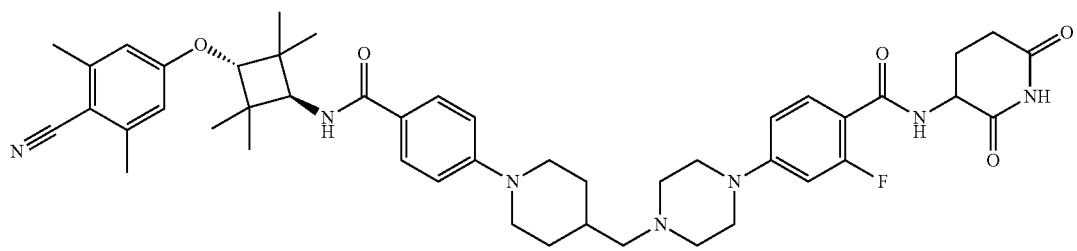
20
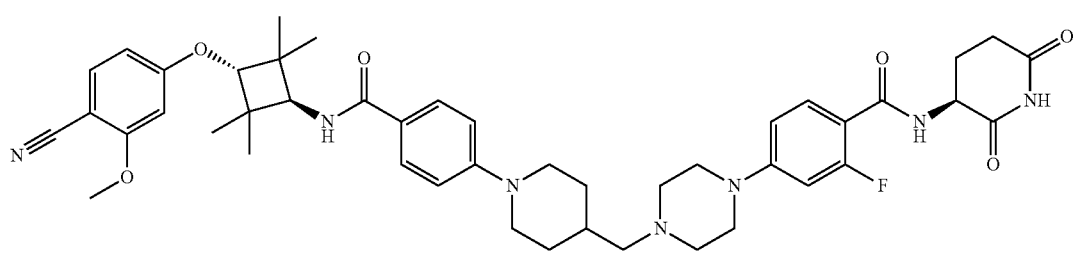
21
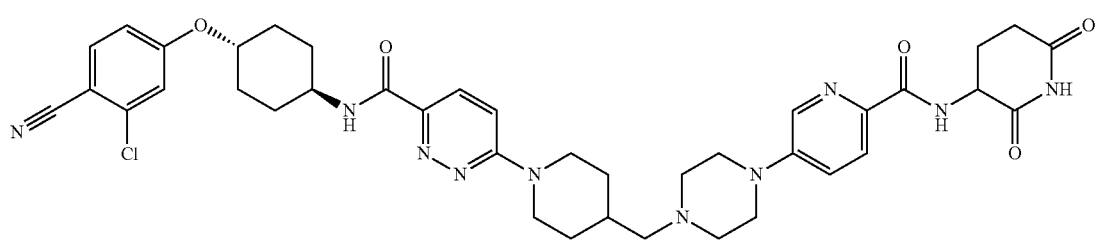
22
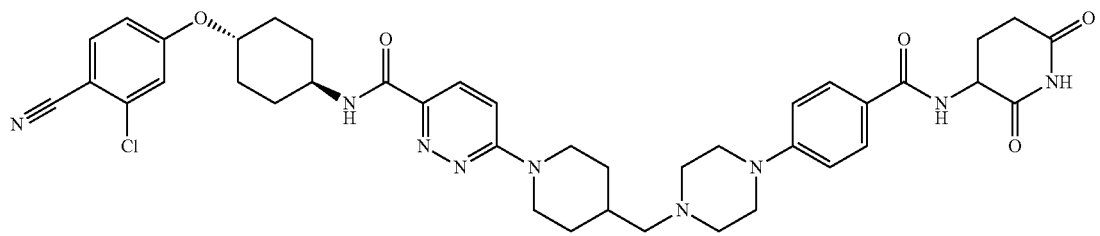
23

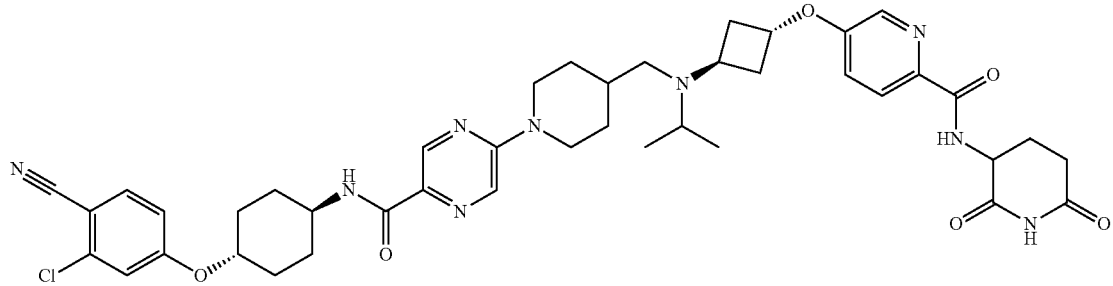
24
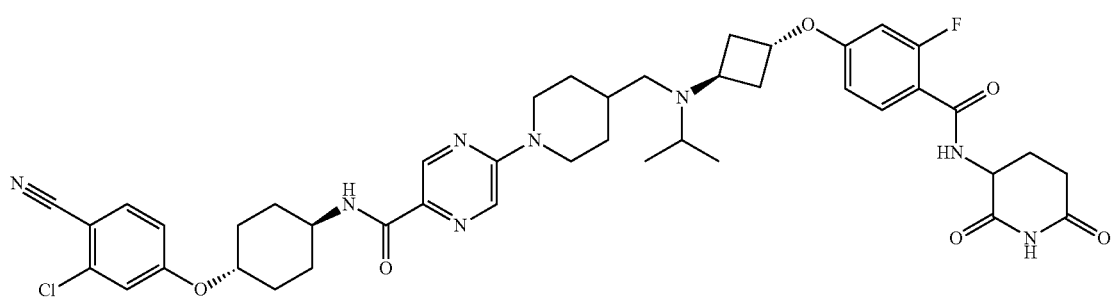
25
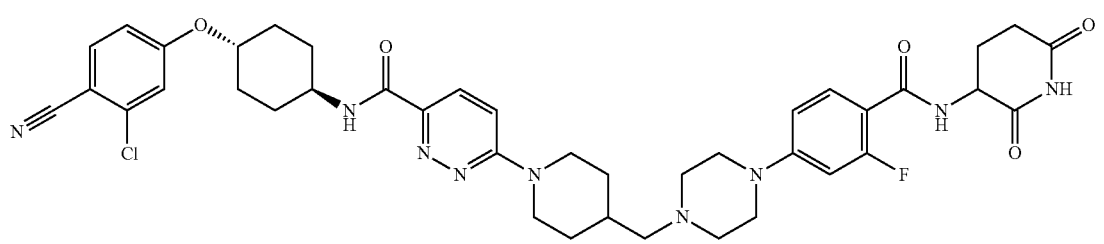
26
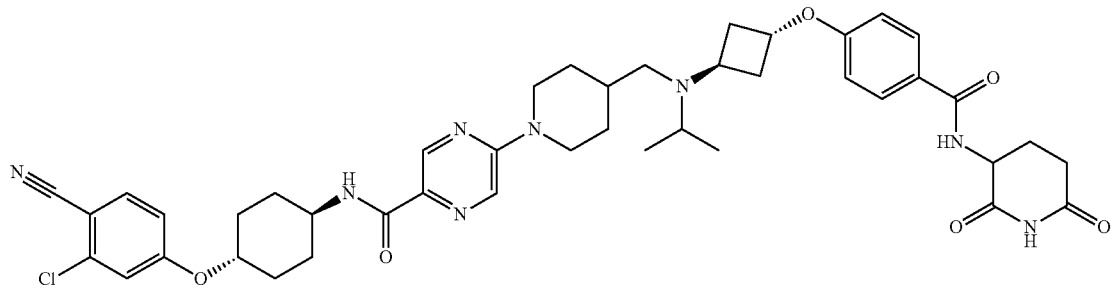
27
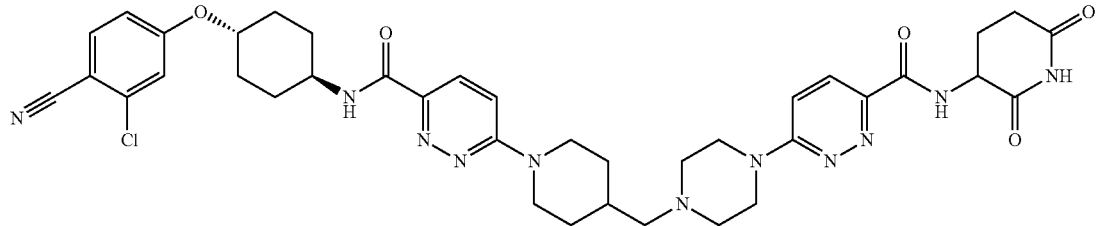
28

-continued
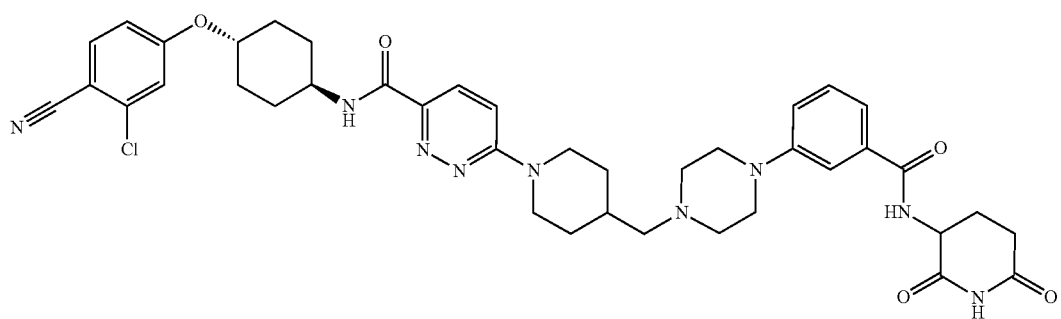
29
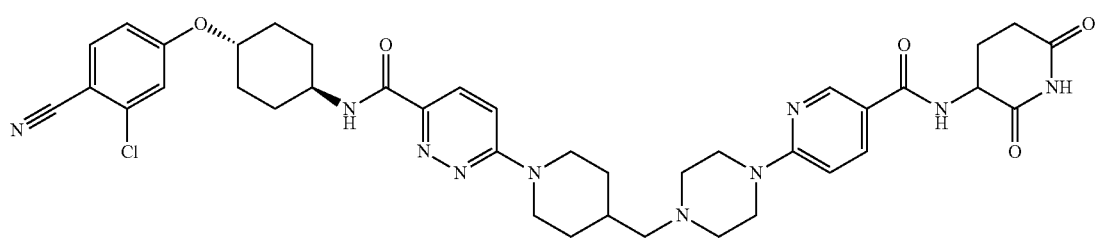
30
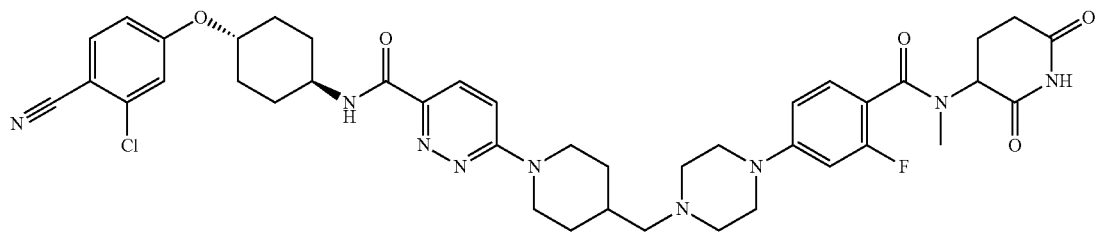
31
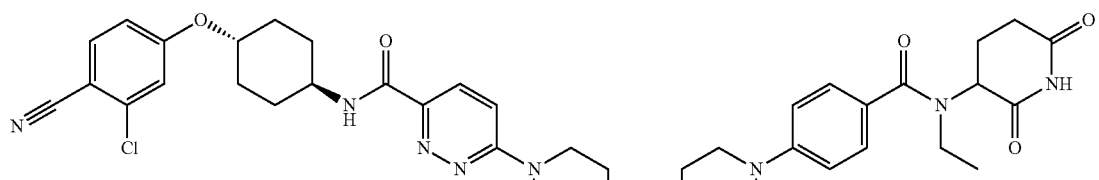
32
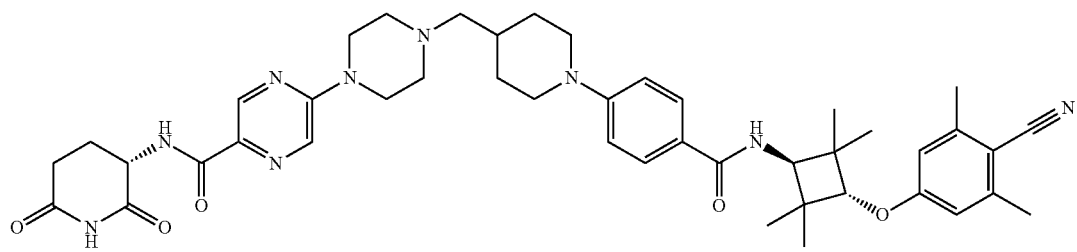
33
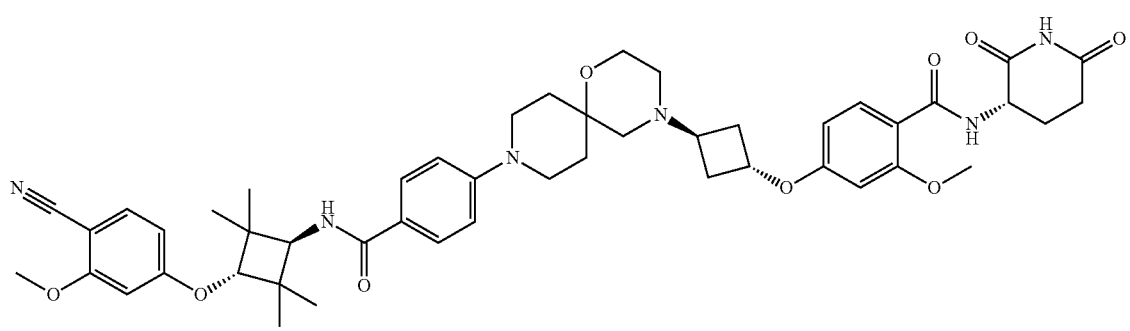
34

35
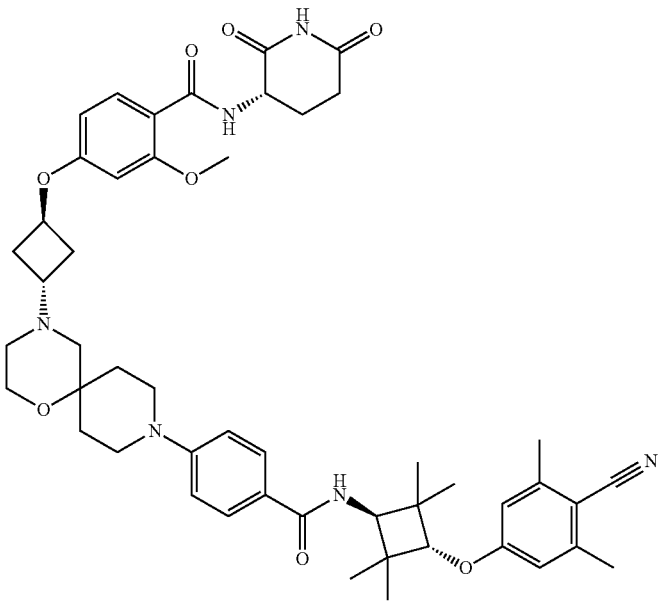
36
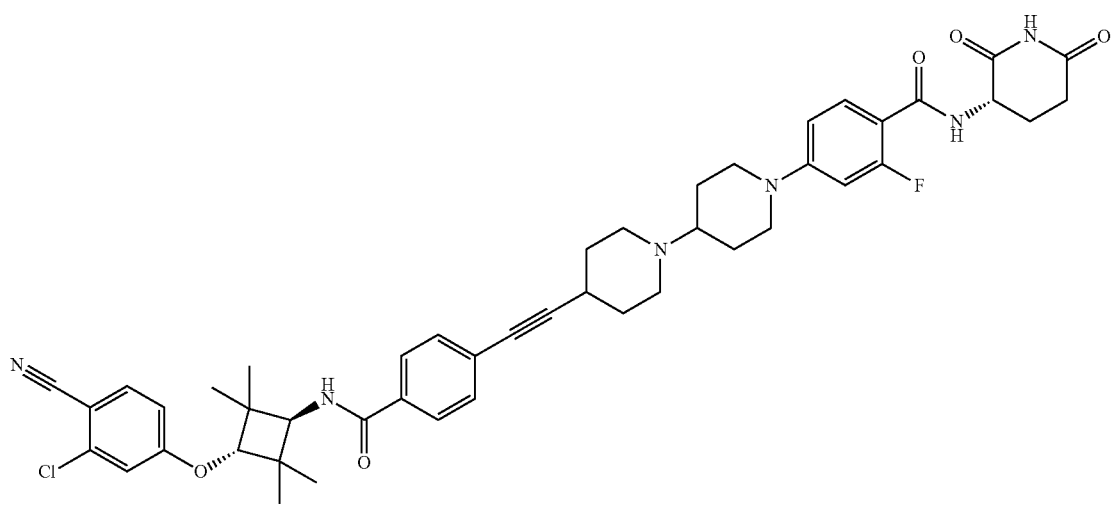
37
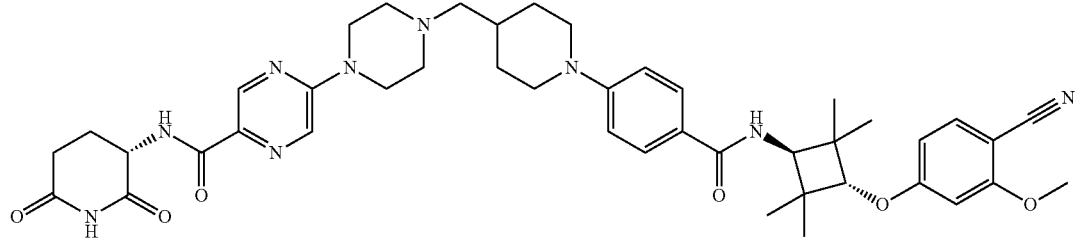
38
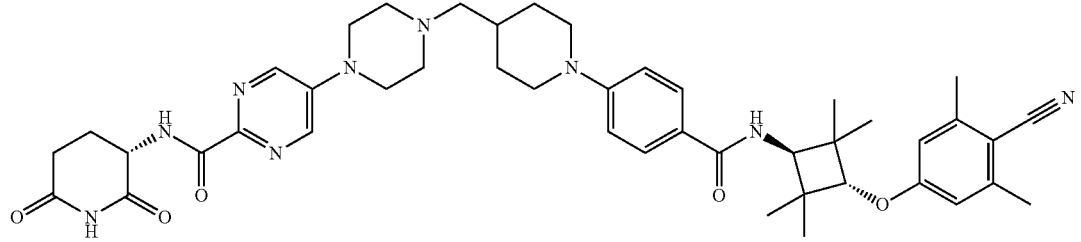

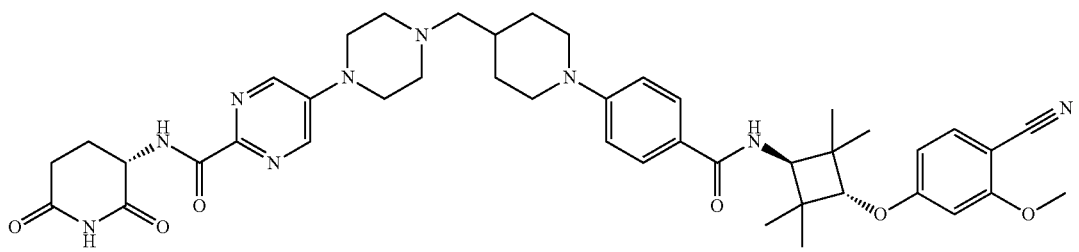
39
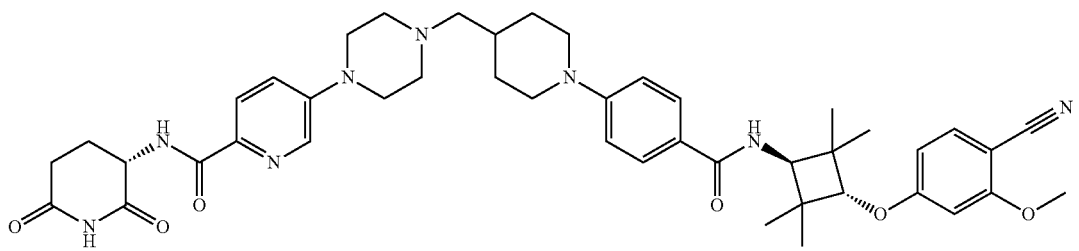
40
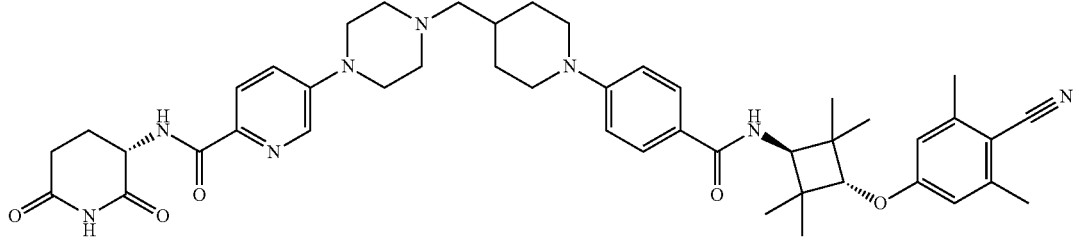
41
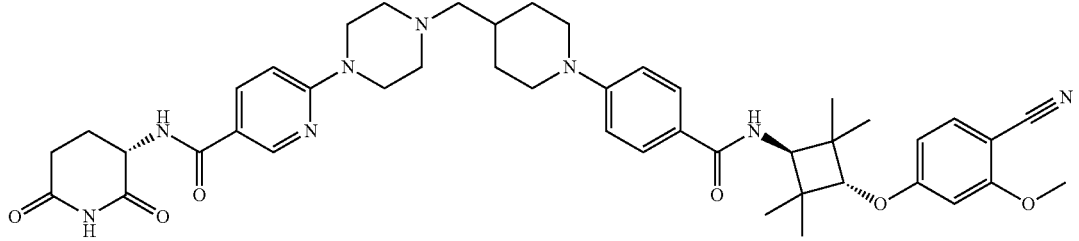
42
43
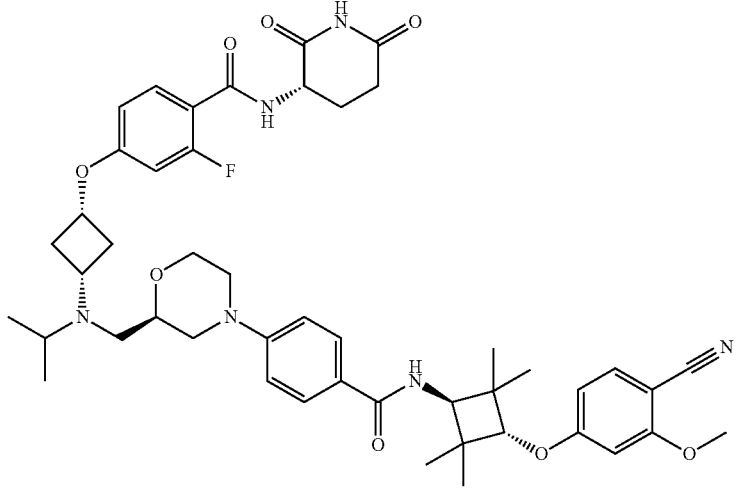

44
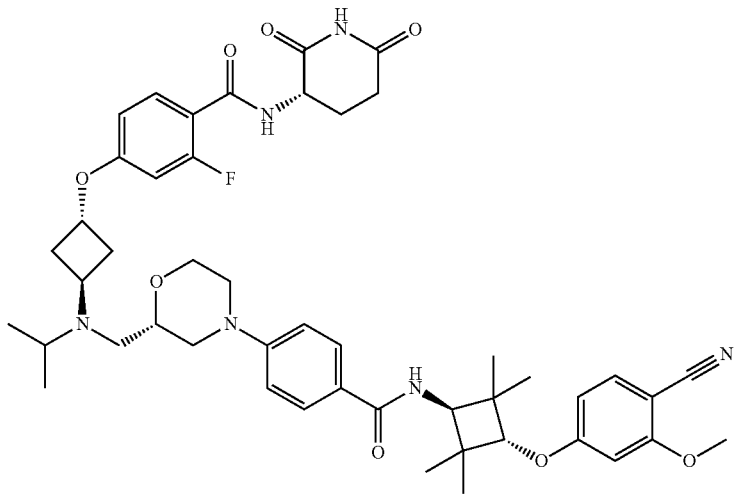
45
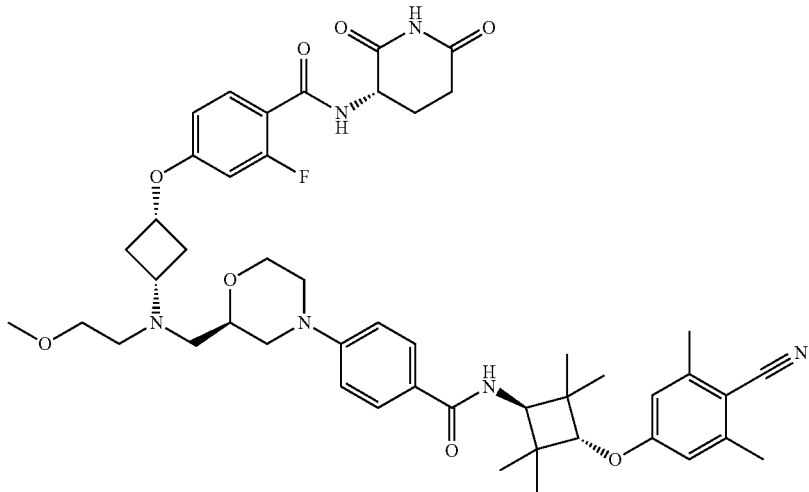
46
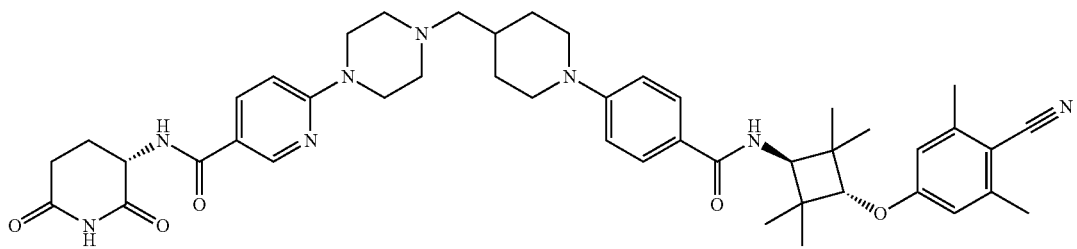

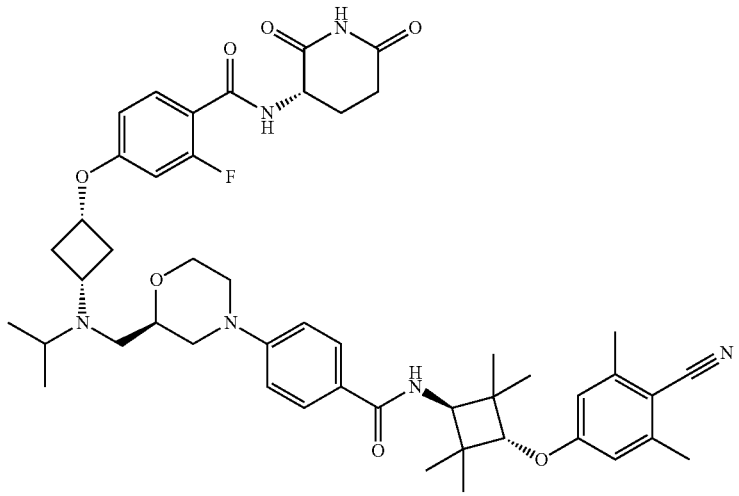
47
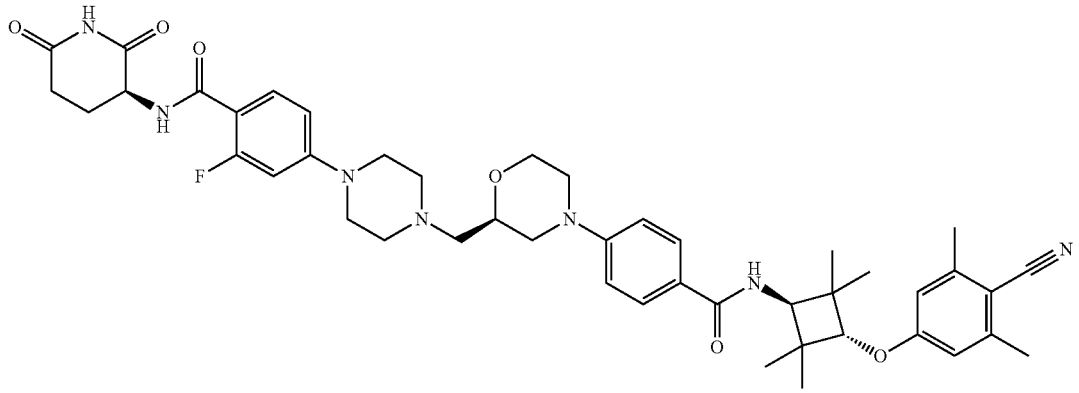
48
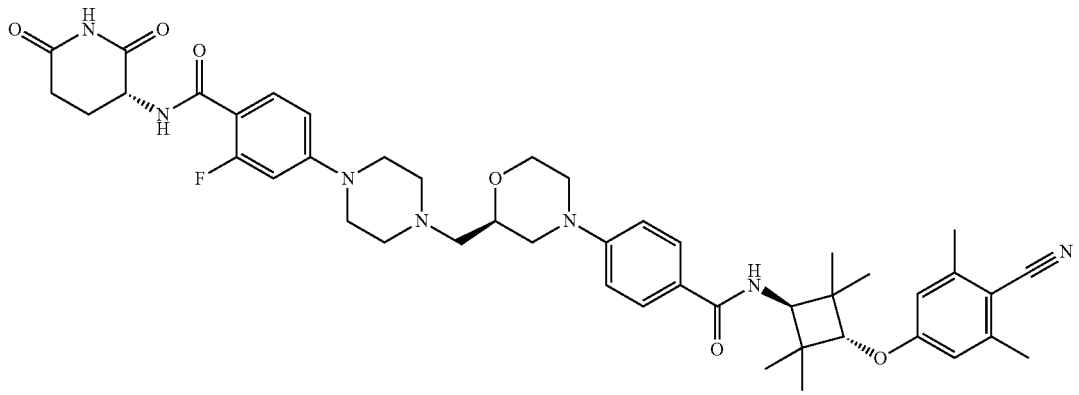
49

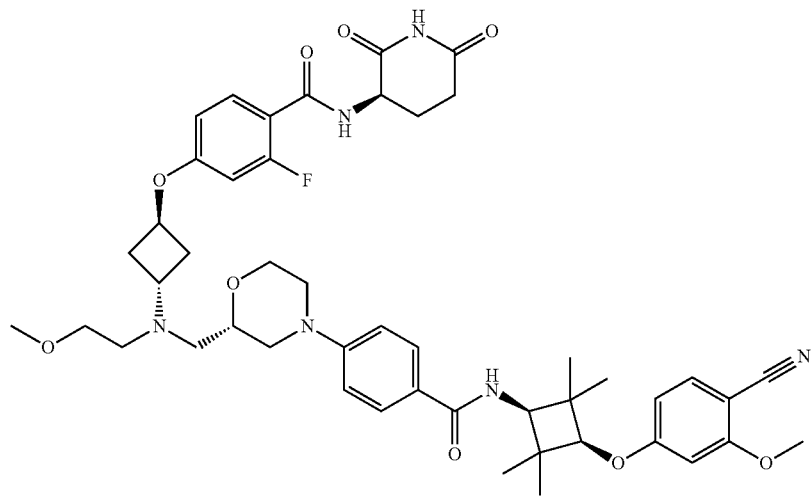
50
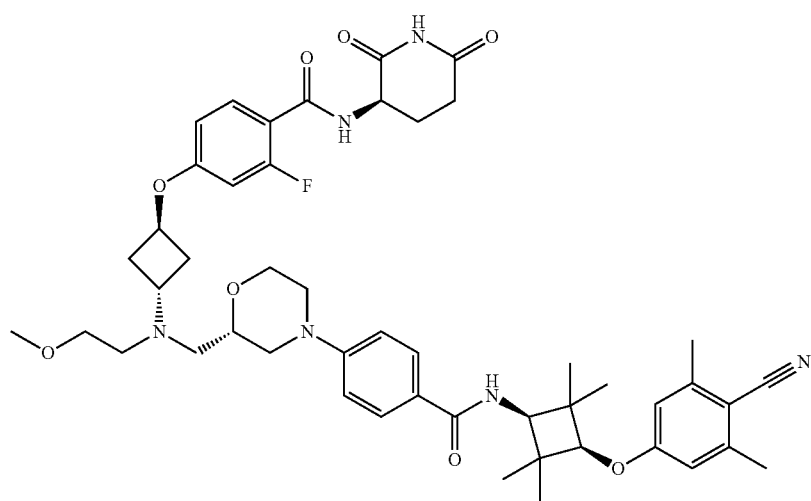
51
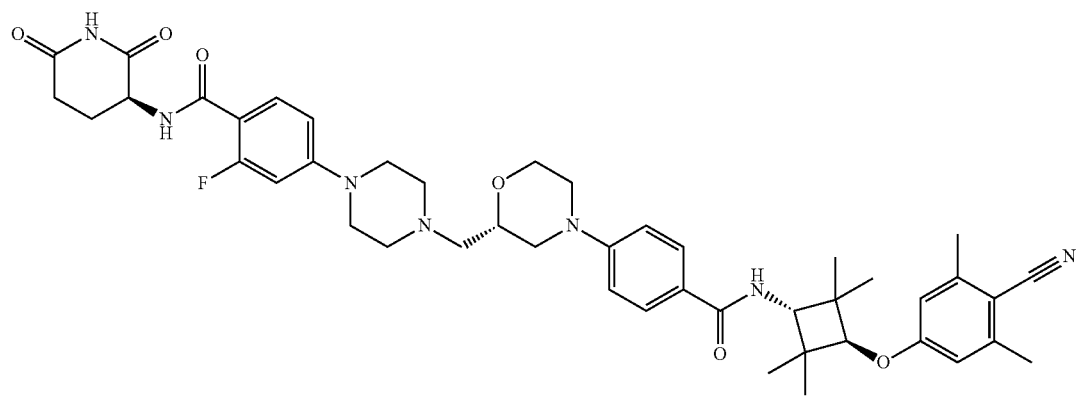
52

53
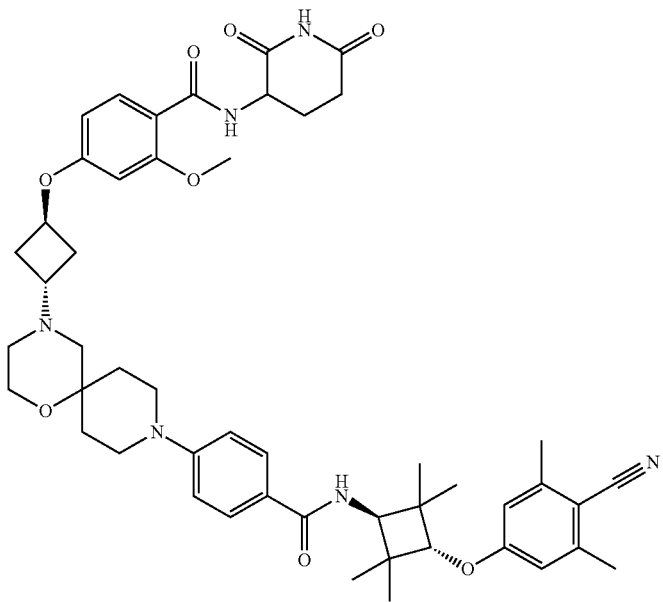
54
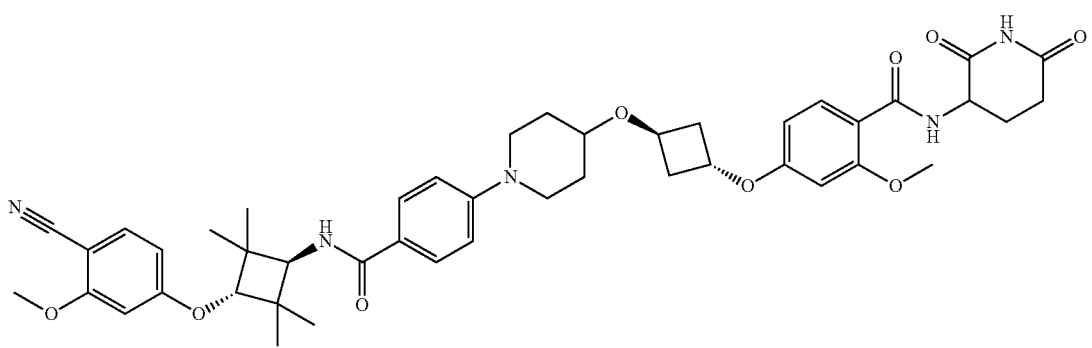
55
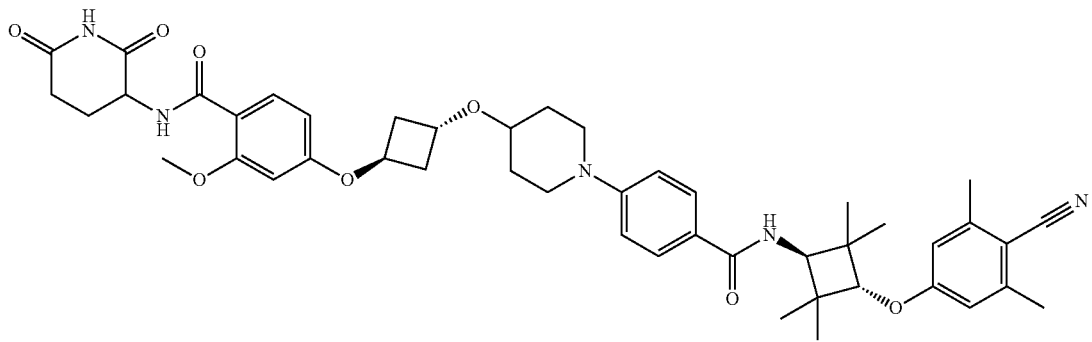

56
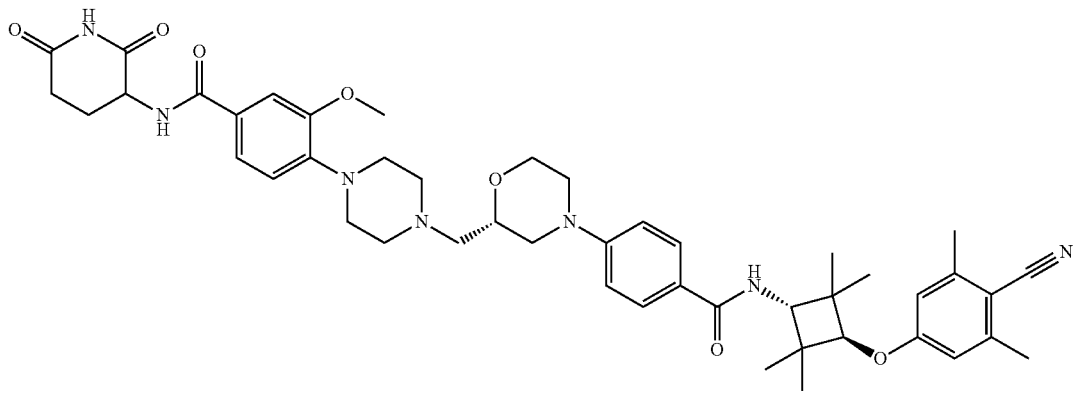
57
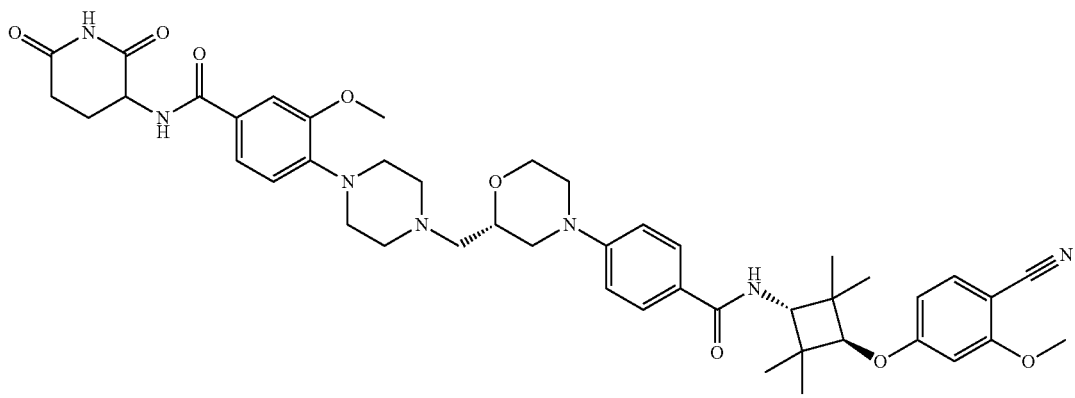
58
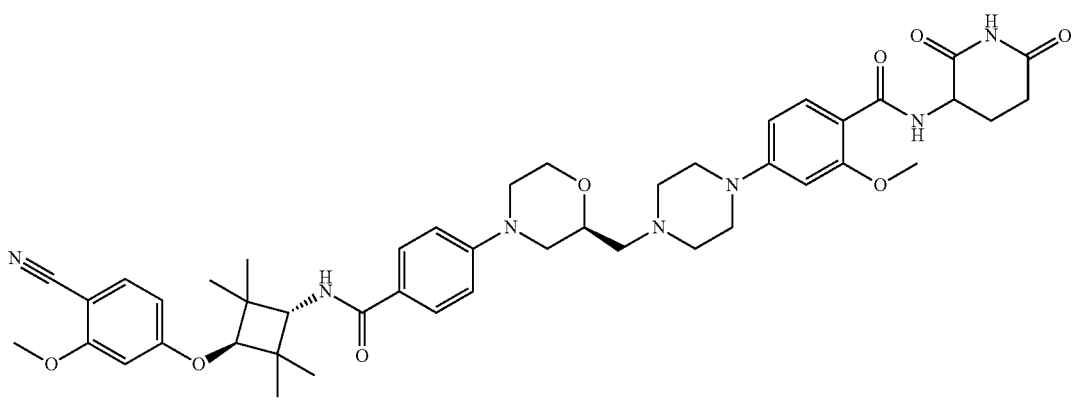
59
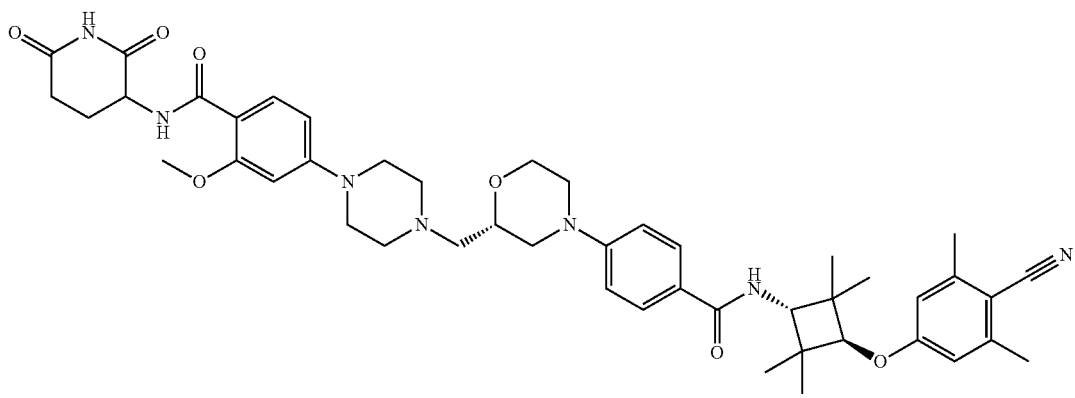

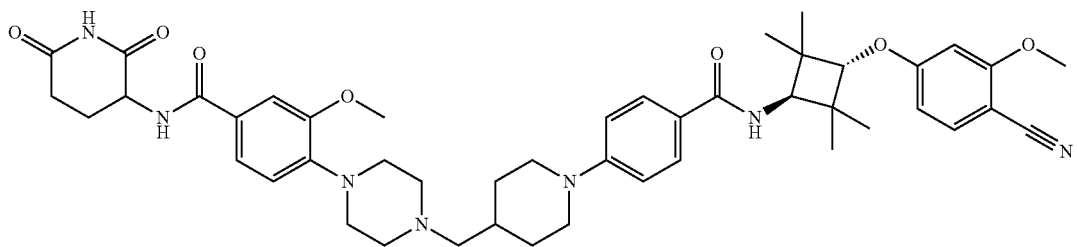
60
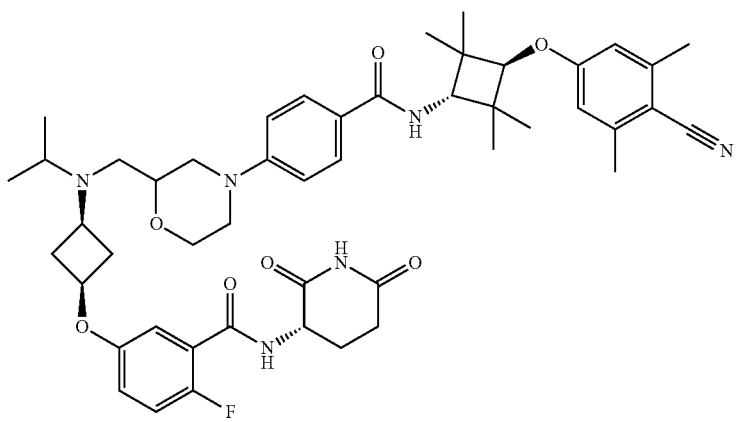
61
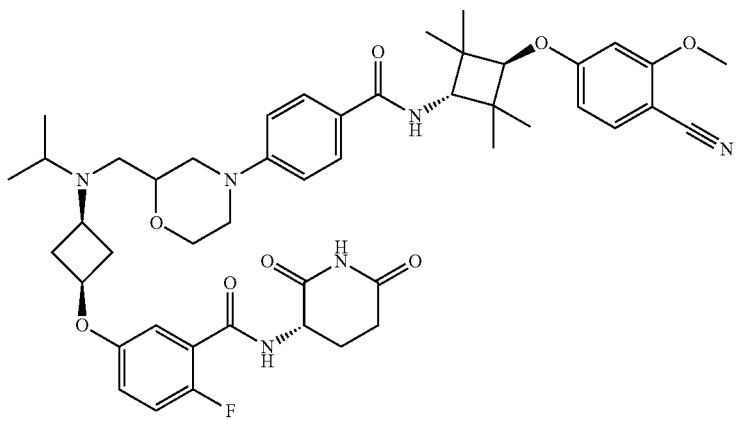
62

63
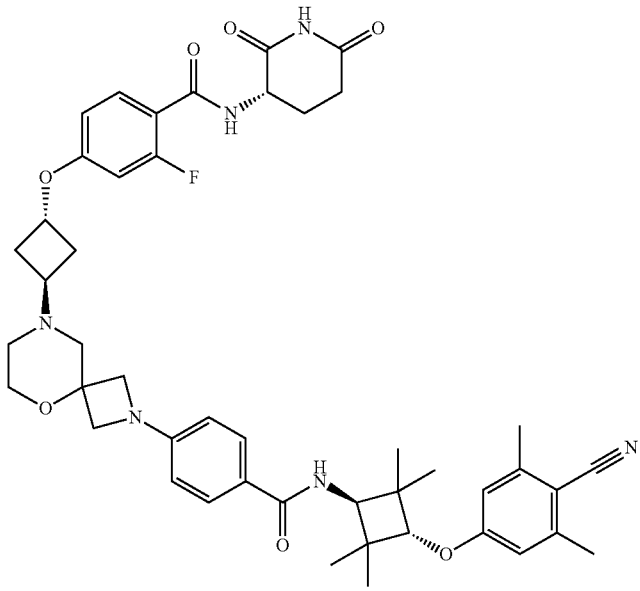
64
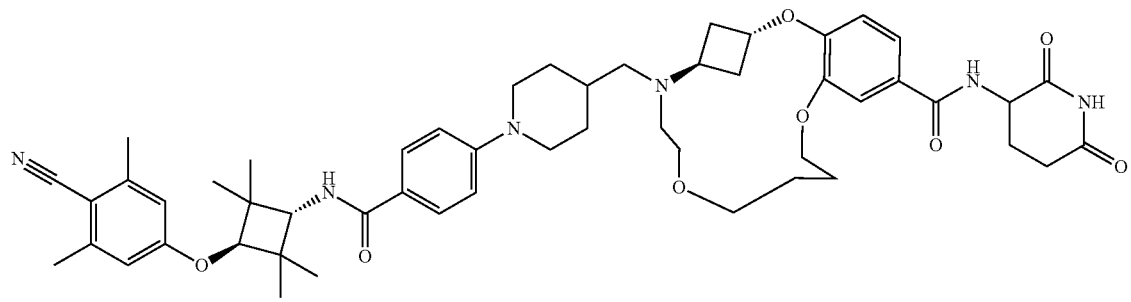
65
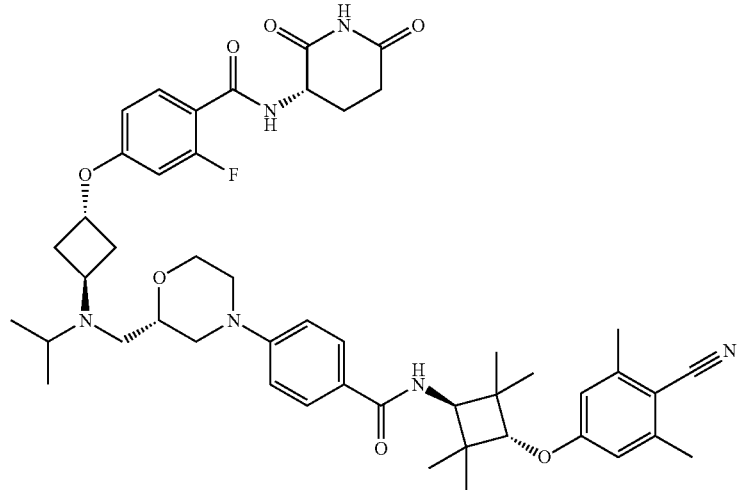

66
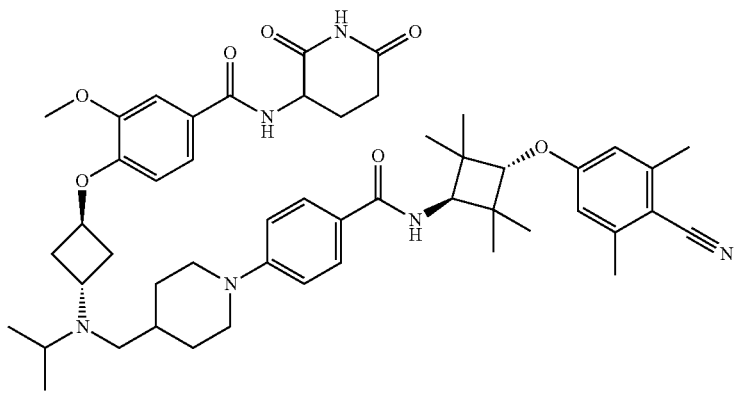
67
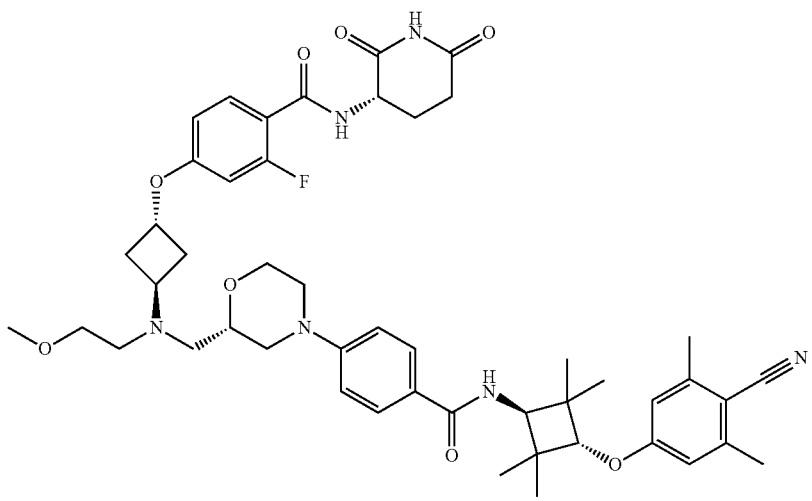
68
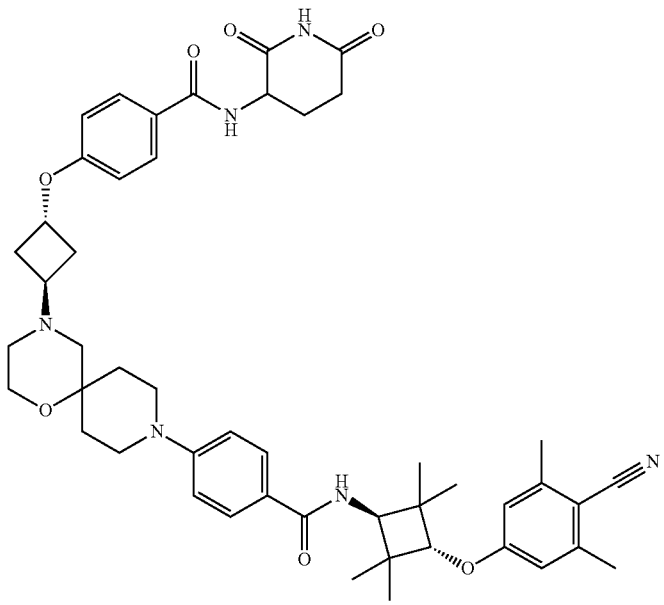

69
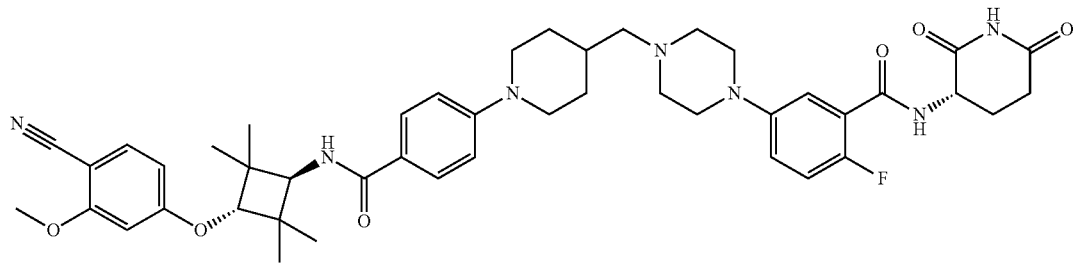
70
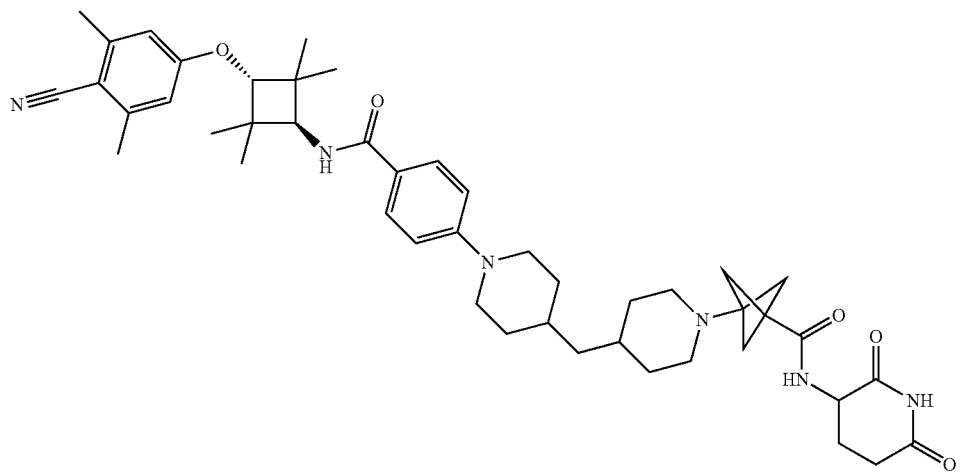
71
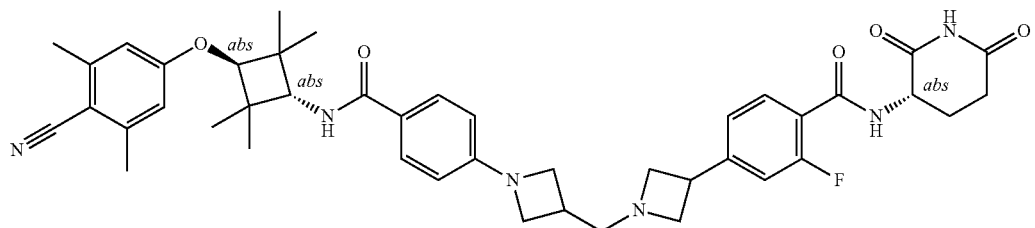
72
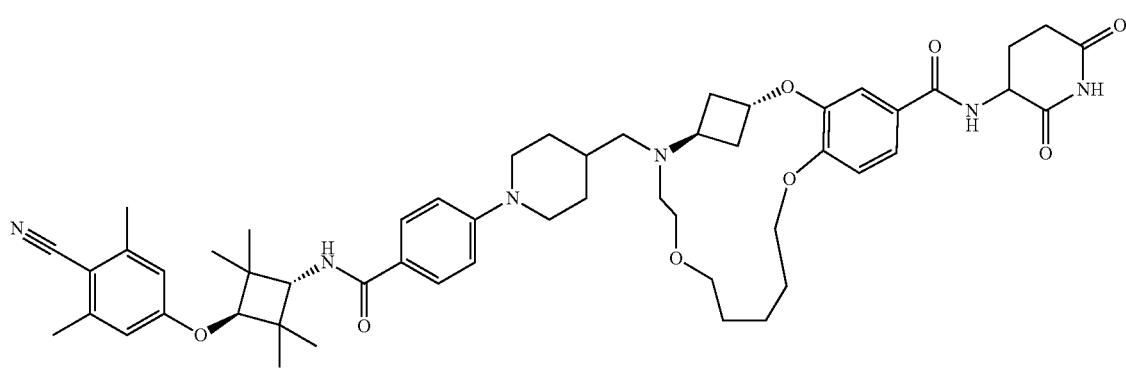

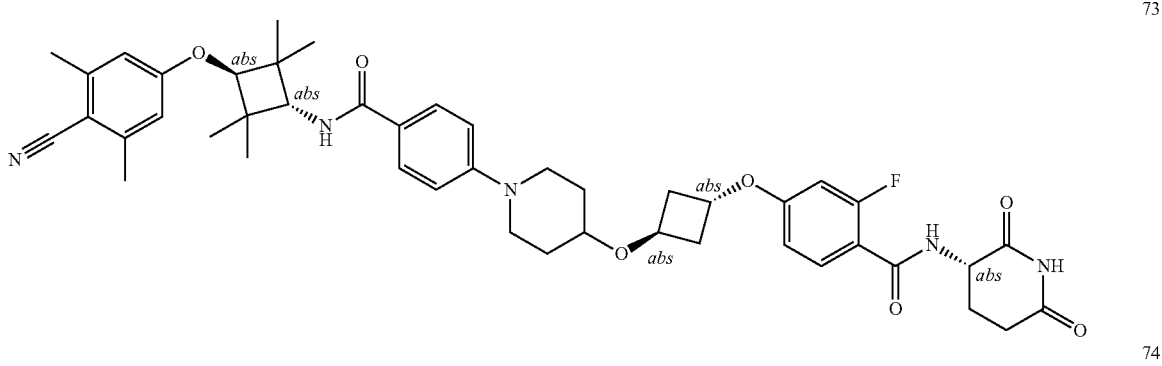

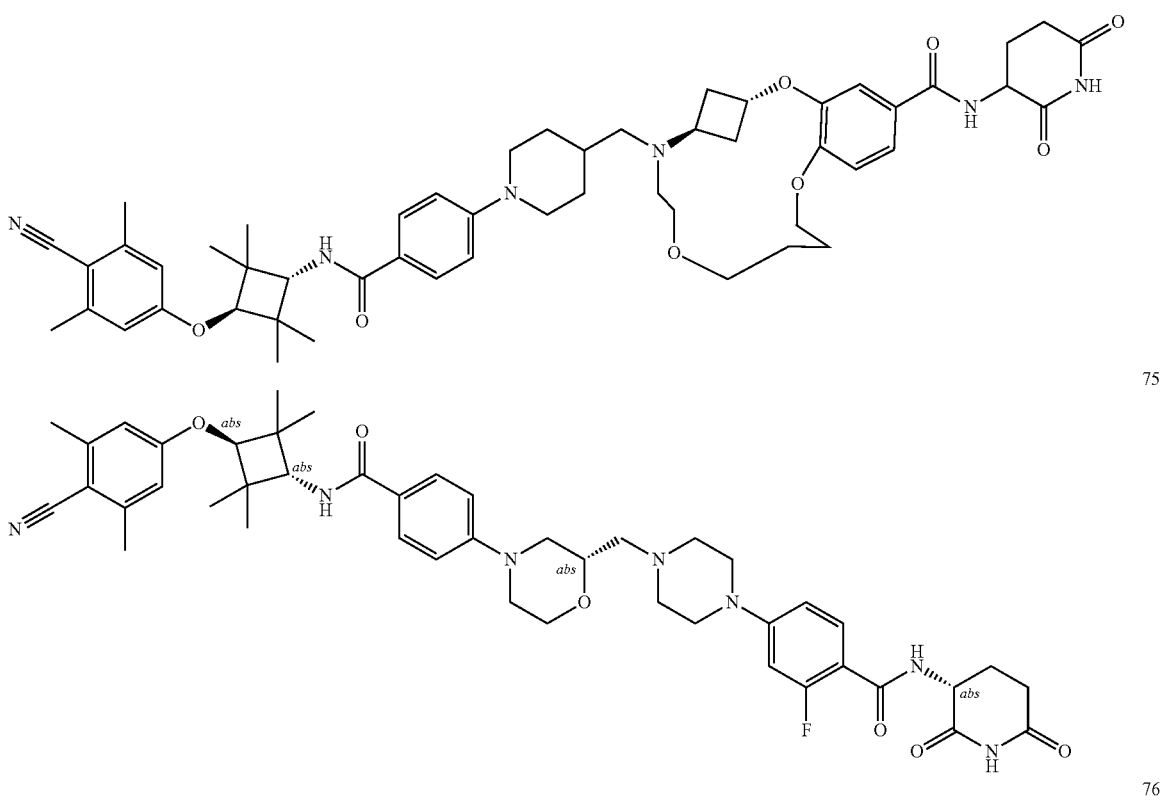

or a pharmaceutically acceptable salt, enantiomer, stereoisomer, solvate, or isotopic derivative thereof.

A compound of the disclosure may be synthesized using standard synthetic methods and procedures for the preparation of organic molecules and functional group transformations and manipulations, including the use of protective groups, as can be obtained from the relevant scientific literature or from standard reference textbooks in the field in view of this disclosure. Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$; John Wiley & Sons: New York, 1999. The synthetic methods described in U.S. Patent Application Publication No. 2018/0099940 and International Publication No. 2018/144649 are incorporated herein by reference in their entireties.

In one embodiment, the compounds of the disclosure may be prepared according to the procedures and methods disclosed herein, including, for example, where indicated in Table 1. Other bifunctional compounds of the disclosure can be prepared using similar methods from common intermediates or derivatives thereof.

TABLE 1

SYNTHETIC ROUTES TO PREPARE VARIOUS COMPOUNDS OF THE DISCLOSURE

Figure 2:
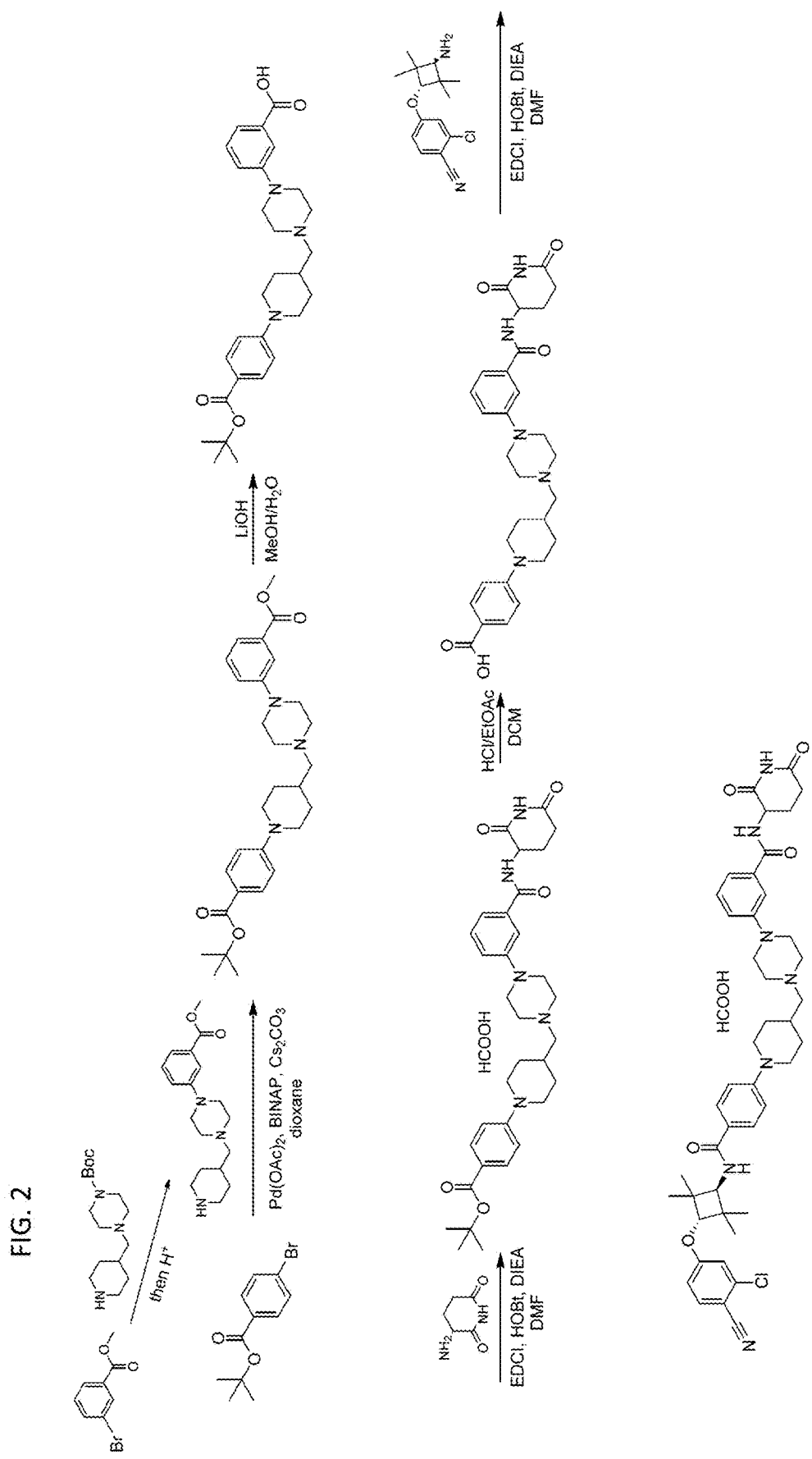
FIG. 2 is a scheme showing the synthesis of Compound No. 4.
Figure 3:
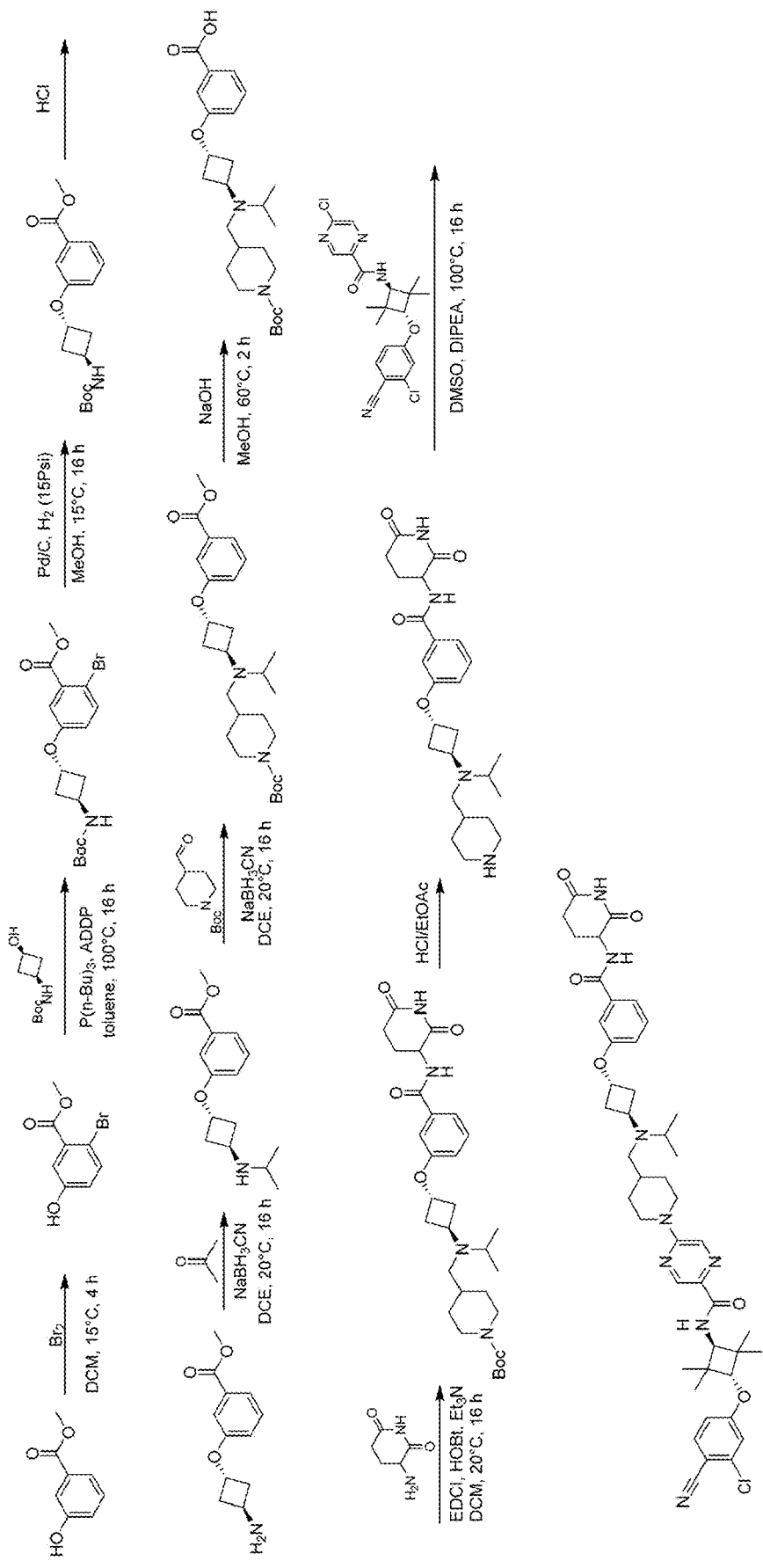
FIG. 3 is a scheme showing the synthesis of Compound No. 9.
Figure 4:
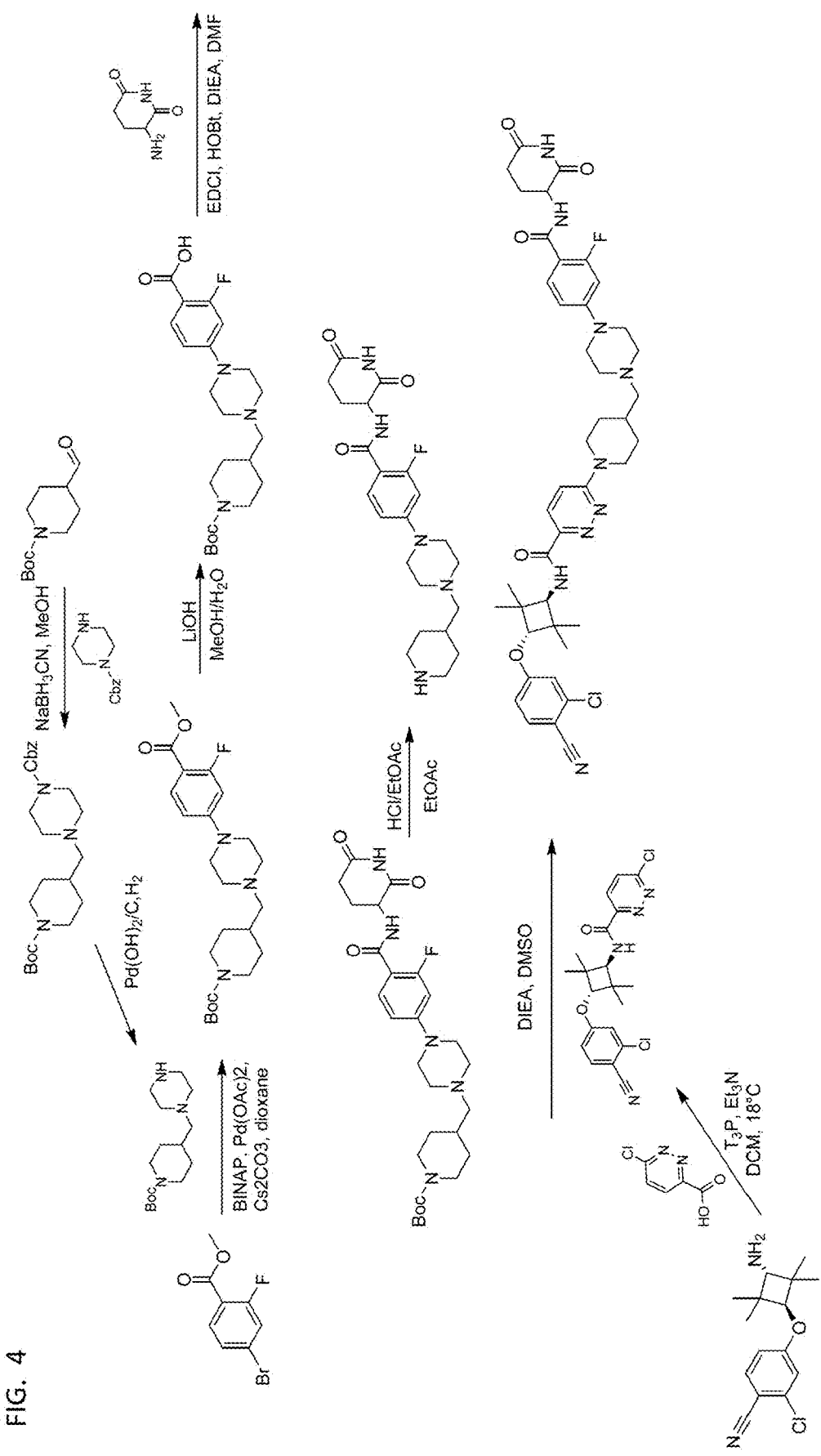
FIG. 4 is a scheme showing the synthesis of Compound No. 17.

| Compound No. | Synthetic Route |
|---|---|
| 1 | Example 3 |
| 3 | Example 4 |
| 4 | FIG. 2 |
| 5 | Example 5 |
| 9 | FIG. 3 |
| 14 | Example 6 |
| 15 | Example 7 |
| 16 | FIG. 4 |
| 21 | Example 8 |
| 23 | Example 9 |
| 24 | Example 10 |
| 27 | Example 11 |
| 28 | Example 12 |
| 33 | Example 13 |
| 34 | Example 14 |
| 35 | Example 15 |
| 37 | Example 16 |
| 38 | Example 17 |
| 39 | Example 18 |
| 40 | Example 19 |
| 41 | Example 20 |
| 43 and 44 | Example 21 |
| 48 and 49 | Example 22 |
| 64 | Example 23 |
| 70 | Example 24 |

Methods of Ubiquitinating/Degrading a Target Protein in a Cell

The present disclosure provides a method of ubiquitinating/degrading a target protein in a cell. The method comprises administering a bifunctional composition comprising an E3 ubiquitin ligase binding moiety and a protein targeting moiety, preferably linked through a linker moiety, as otherwise described herein, wherein the E3 ubiquitin ligase binding moiety is coupled to the protein targeting moiety and wherein the E3 ubiquitin ligase binding moiety recognizes a ubiquitin pathway protein (e.g., an ubiquitin ligase, preferably an E3 ubiquitin ligase) and the protein targeting moiety recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In one aspect, this application provides a compound of Formula (I), or a pharmaceutically acceptable salt, enantiomer, stereoisomer, solvate, polymorph, isotopic derivative, or prodrug thereof, that degrades the androgen receptor (AR) protein. In one embodiment, the AR that is degraded by the compound of Formula (I) is wild type AR. In one embodiment, the AR that is degraded by the compound of Formula (I) is a mutant form of AR.

In one embodiment, the mutant form of AR that is degraded by the compound of Formula (I) comprises at least one AR somatic tumor mutation. In one embodiment, the at least one somatic AR tumor mutation is selected from L702H, M895V, M896V, T878A, F877L, and H875Y.

In one embodiment, the mutant form of AR that is degraded by the compound of Formula (I) comprises at least two AR somatic tumor mutations. In one embodiment, the at least two somatic AR tumor mutation are selected from L702H, M895V, M896V, T878A, F877L, and H875Y In one embodiment, the present disclosure is directed to a method of treating a patient in need for a disease state or condition modulated through a protein where the degradation of that protein will produce a therapeutic effect in that patient, the method comprising administering to a patient in need an effective amount of a compound of Formula (I), optionally in combination with another anti-cancer agent. The disease state or condition may be a disease caused by a microbial agent or other exogenous agent such as a virus, bacteria, fungus, protozoa, or other microbe or may be a disease state caused by overexpression of a protein, which leads to a disease state and/or condition.

Methods of Treatment

In one aspect, the present application pertains to a method of treating and/or preventing cancer comprising administering to a subject in need thereof a therapeutically effective amount of a compound of the disclosure, or a pharmaceutically acceptable salt, enantiomer, stereoisomer, solvate, or isotopic derivative thereof.

In one aspect, the present application pertains to a method of treating and/or preventing cancer comprising administering to a subject in need thereof a therapeutically effective amount of a compound of Formula (I), or a pharmaceutically acceptable salt, enantiomer, stereoisomer, solvate, polymorph, isotopic derivative, or prodrug thereof, in combination with one or more additional anti-cancer agents.

The methods of treating cancer described herein result in a reduction in tumor size. Alternatively, or in addition, the cancer is metastatic cancer and this method of treatment includes inhibition of metastatic cancer cell invasion.

In one embodiment, the cancer is prostate cancer.

In one embodiment, the cancer is metastatic prostate cancer.

In one embodiment, the cancer is castrate-resistant prostate cancer.

In one embodiment, the cancer is metastatic, castrate-resistant prostate cancer (mCRPC).

In one embodiment, the subject suffering from prostate cancer (e.g., mCRPC) will have a different response to treatment with a compound of the disclosure or a pharmaceutically acceptable salt, enantiomer, stereoisomer, solvate, polymorph, isotopic derivative, or prodrug thereof, depending on the AR biomarker status of the subject, i.e., whether the subject has one or more somatic tumor mutations to AR.

In one embodiment, the subject with prostate cancer comprises at least one somatic AR tumor mutation.

In one embodiment, the subject with prostate cancer comprises at least the somatic AR tumor mutation of L702.

In one embodiment, the subject with prostate cancer comprises at least the somatic AR tumor mutation of L702H.

In one embodiment, the subject with prostate cancer comprises at least the somatic AR tumor mutation of M895.

In one embodiment, the subject with prostate cancer comprises at least the somatic AR tumor mutation of M895V.

In one embodiment, the subject with prostate cancer comprises at least the somatic AR tumor mutation of M896.

In one embodiment, the subject with prostate cancer comprises at least the somatic AR tumor mutation of M896V.

In one embodiment, the subject with prostate cancer comprises at least the somatic AR tumor mutation of T878.

In one embodiment, the subject with prostate cancer comprises at least the somatic AR tumor mutation of T878A.

In one embodiment, the subject with prostate cancer comprises at least the somatic AR tumor mutation of F877.

In one embodiment, the subject with prostate cancer comprises at least the somatic AR tumor mutation of F877L.

In one embodiment, the subject with prostate cancer comprises at least the somatic AR tumor mutation of H875.

In one embodiment, the subject with prostate cancer comprises at least the somatic AR tumor mutation of H875Y.

In one embodiment, the subject with prostate cancer comprises at least two somatic AR tumor mutations.

In one aspect, the application pertains to a method of treating prostate cancer with a compound of the disclosure, wherein the compound of the disclosure is:

1
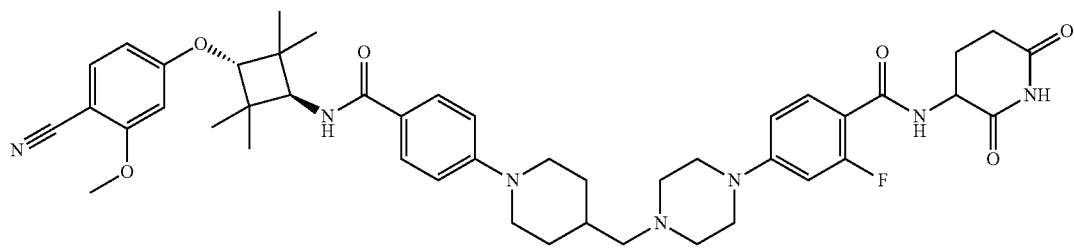

2
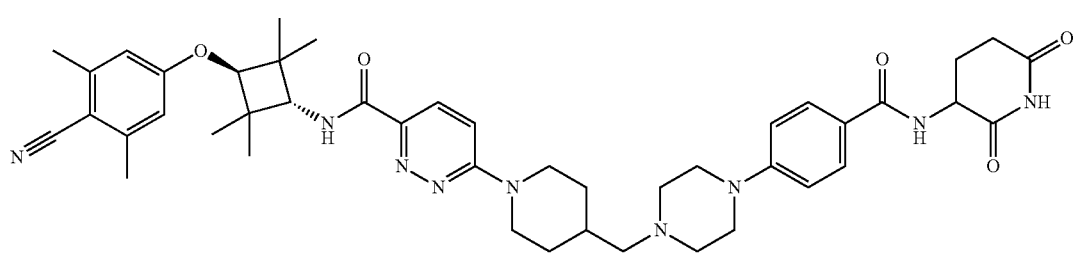

3
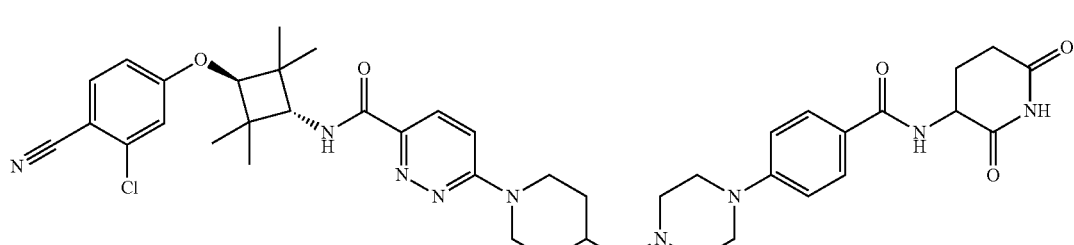

4
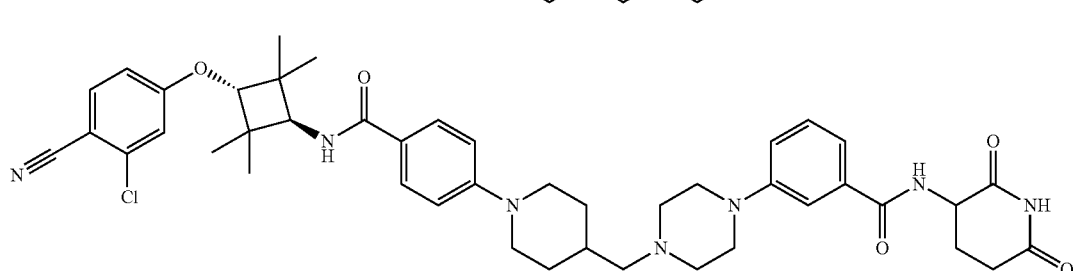

5
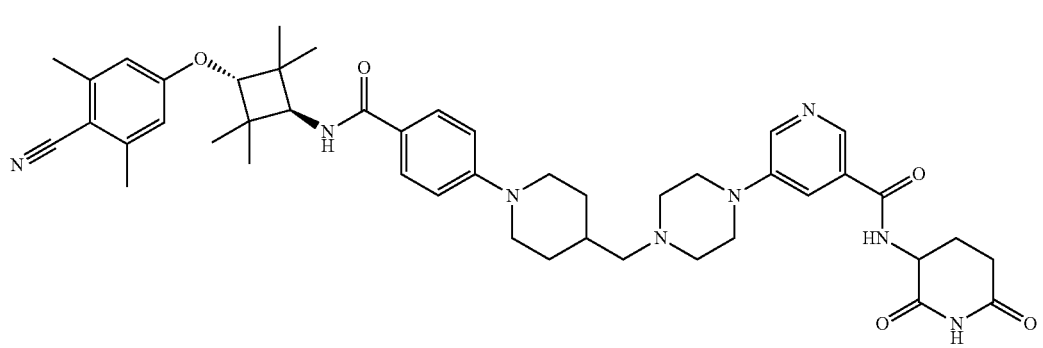

-continued
6
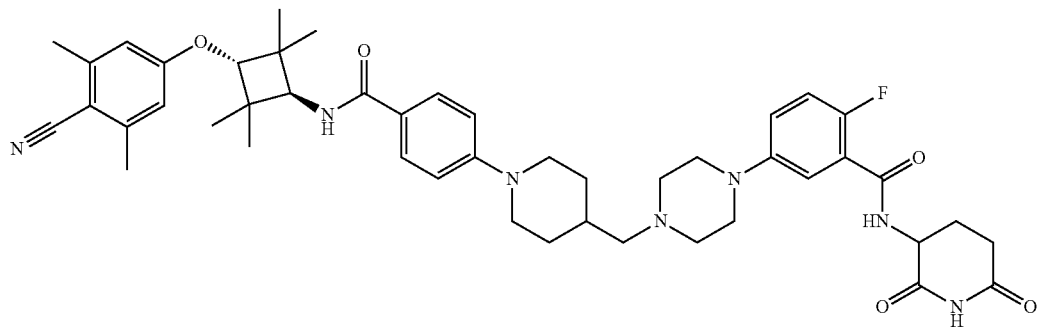
7
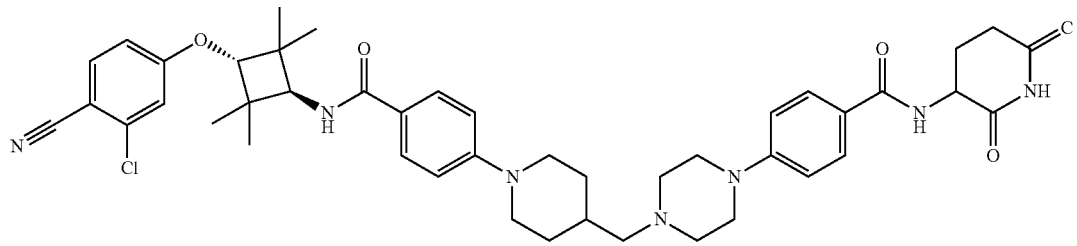
8
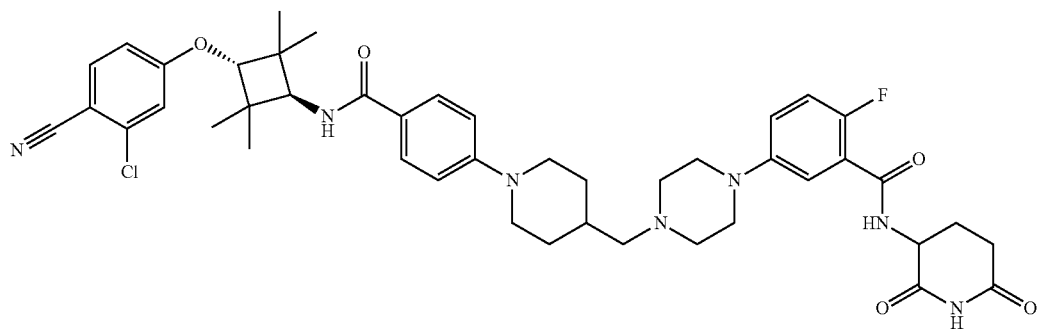
9
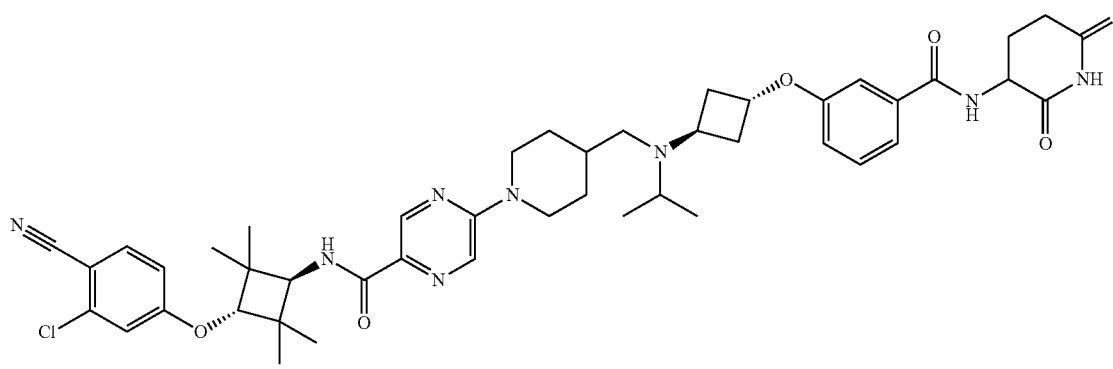
10
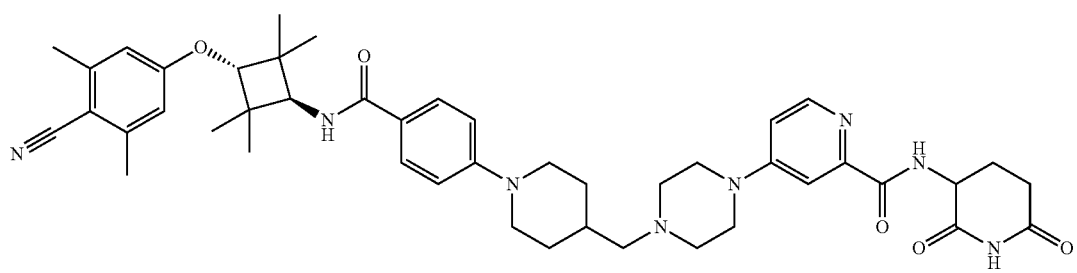 [SMILES: Cc1cc(O[C@H]2C(C)(C)[C@H](NC(=O)c3ccc(N4CCC(CN5CCN(c6ccnc(C(=O)NC7CCC(=O)NC7=O)c6)CC5)CC4)cc3)C2(C)C)cc(C)c1C#N]

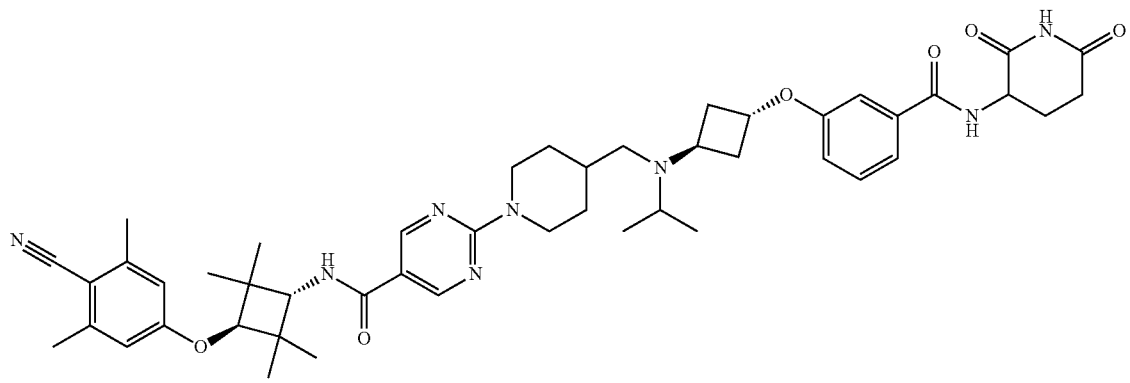 [SMILES: Cc1cc(O[C@H]2C(C)(C)[C@H](NC(=O)c3cnc(N4CCC(CN(C(C)C)[C@H]5C[C@H](Oc6cccc(C(=O)NC7CCC(=O)NC7=O)c6)C5)CC4)nc3)C2(C)C)cc(C)c1C#N]
11
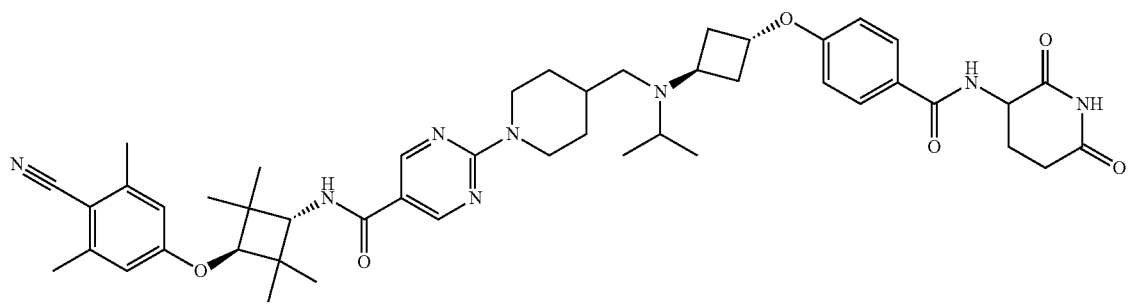 [SMILES: Cc1cc(O[C@H]2C(C)(C)[C@H](NC(=O)c3cnc(N4CCC(CN(C(C)C)[C@H]5C[C@H](Oc6ccc(C(=O)NC7CCC(=O)NC7=O)cc6)C5)CC4)nc3)C2(C)C)cc(C)c1C#N]
12
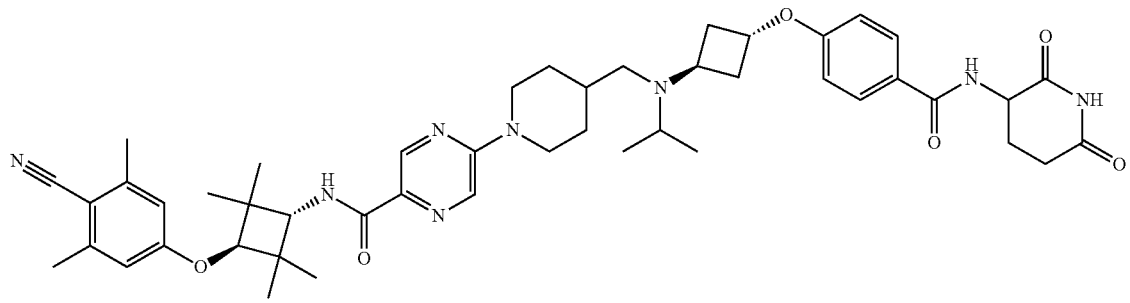 [SMILES: Cc1cc(O[C@H]2C(C)(C)[C@H](NC(=O)c3cnc(N4CCC(CN(C(C)C)[C@H]5C[C@H](Oc6ccc(C(=O)NC7CCC(=O)NC7=O)cc6)C5)CC4)cn3)C2(C)C)cc(C)c1C#N]
13
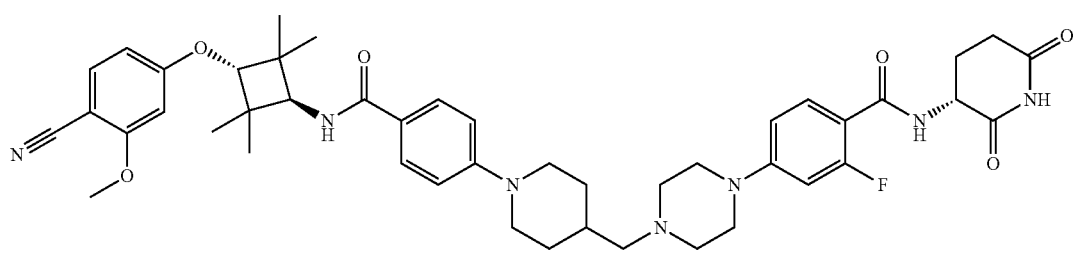 [SMILES: COc1cc(O[C@H]2C(C)(C)[C@H](NC(=O)c3ccc(N4CCC(CN5CCN(c6ccc(C(=O)N[C@@H]7CCC(=O)NC7=O)c(F)c6)CC5)CC4)cc3)C2(C)C)ccc1C#N]
14

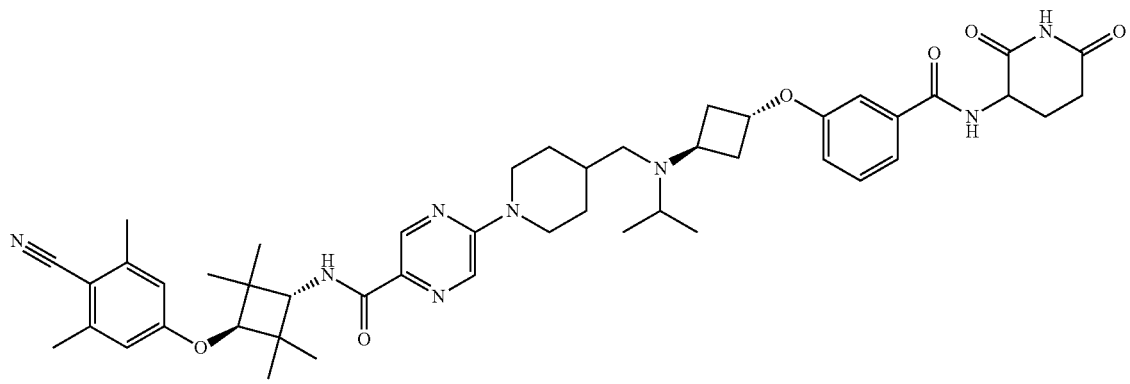 [SMILES: Cc1cc(O[C@H]2C(C)(C)[C@H](NC(=O)c3cnc(N4CCC(CN(C(C)C)[C@H]5C[C@H](Oc6cccc(C(=O)NC7CCC(=O)NC7=O)c6)C5)CC4)cn3)C2(C)C)cc(C)c1C#N]
15
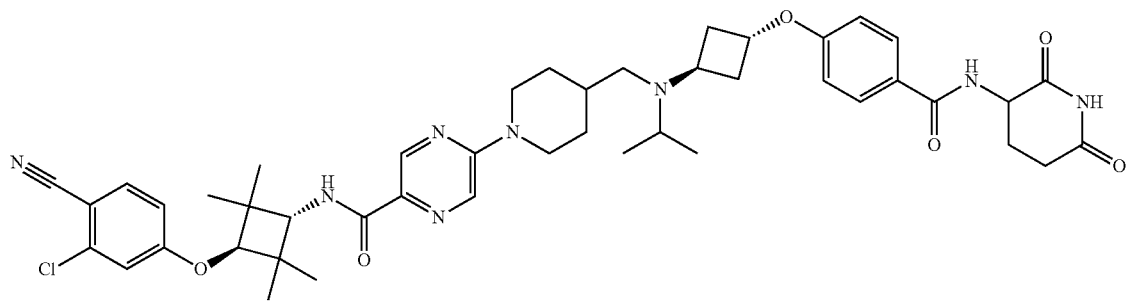 [SMILES: CC(C)N(CC1CCN(c2cnc(C(=O)N[C@H]3C(C)(C)[C@H](Oc4ccc(C#N)c(Cl)c4)C3(C)C)cn2)CC1)[C@H]1C[C@H](Oc2ccc(C(=O)NC3CCC(=O)NC3=O)cc2)C1]
16
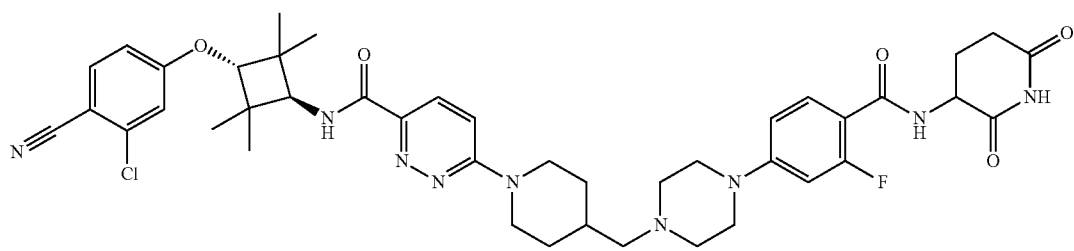 [SMILES: CC1(C)[C@H](NC(=O)c2ccc(N3CCC(CN4CCN(c5ccc(C(=O)NC6CCC(=O)NC6=O)c(F)c5)CC4)CC3)nn2)C(C)(C)[C@H]1Oc1ccc(C#N)c(Cl)c1]
17
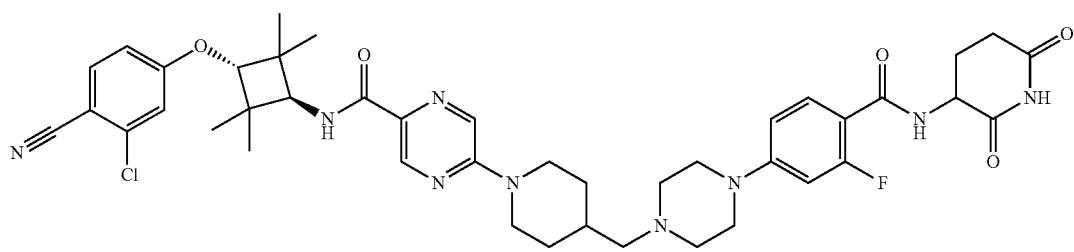 [SMILES: CC1(C)[C@H](NC(=O)c2cnc(N3CCC(CN4CCN(c5ccc(C(=O)NC6CCC(=O)NC6=O)c(F)c5)CC4)CC3)cn2)C(C)(C)[C@H]1Oc1ccc(C#N)c(Cl)c1]
18
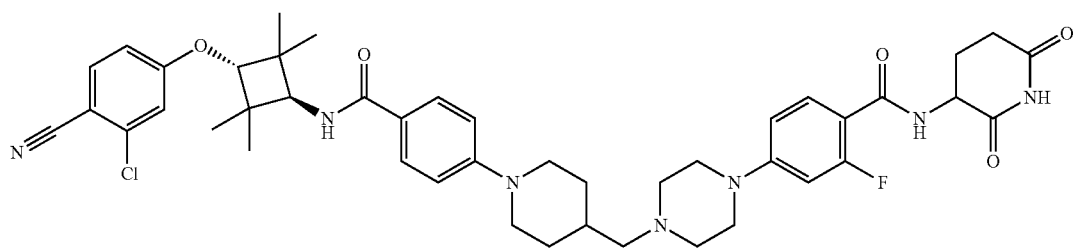 [SMILES: CC1(C)[C@H](NC(=O)c2ccc(N3CCC(CN4CCN(c5ccc(C(=O)NC6CCC(=O)NC6=O)c(F)c5)CC4)CC3)cc2)C(C)(C)[C@H]1Oc1ccc(C#N)c(Cl)c1]
19

-continued
| | |
|---|---|
| 20 | 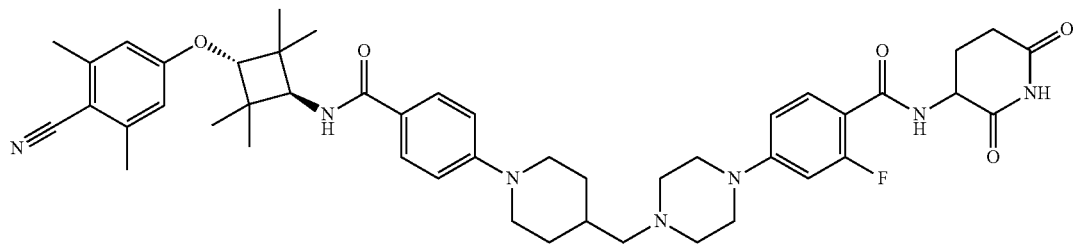 [SMILES: Cc1cc(O[C@H]2C(C)(C)[C@H](NC(=O)c3ccc(N4CCC(CN5CCN(c6ccc(C(=O)NC7CCC(=O)NC7=O)c(F)c6)CC5)CC4)cc3)C2(C)C)cc(C)c1C#N] |
| 21 | 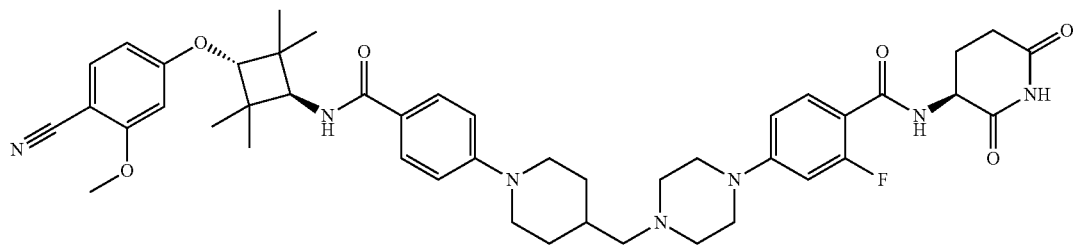 [SMILES: COc1cc(O[C@H]2C(C)(C)[C@H](NC(=O)c3ccc(N4CCC(CN5CCN(c6ccc(C(=O)N[C@H]7CCC(=O)NC7=O)c(F)c6)CC5)CC4)cc3)C2(C)C)ccc1C#N] |
| 22 | 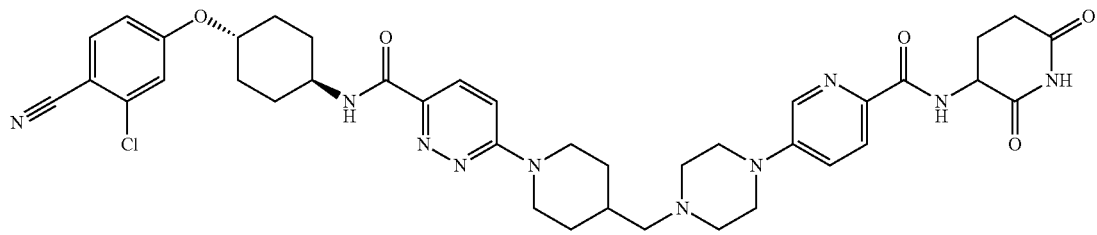 |
| 23 | 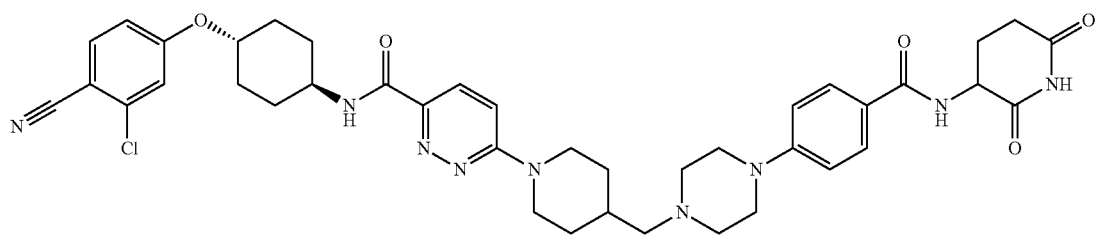 [SMILES: N#Cc1ccc(O[C@H]2CC[C@H](NC(=O)c3ccc(N4CCC(CN5CCN(c6ccc(C(=O)NC7CCC(=O)NC7=O)cc6)CC5)CC4)nn3)CC2)cc1Cl] |
| 24 | 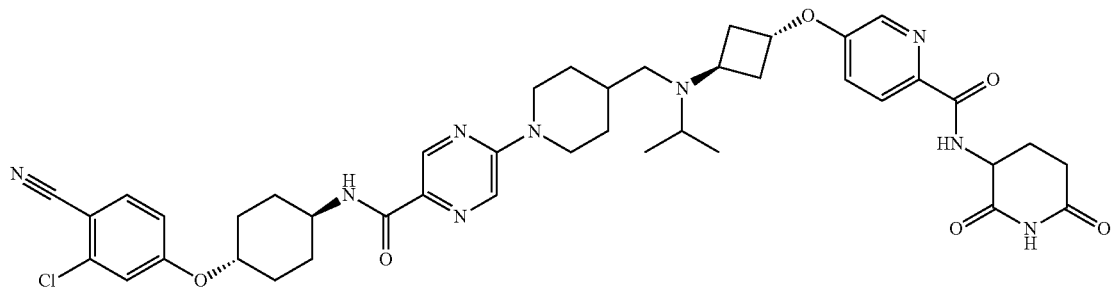 |
| 25 | 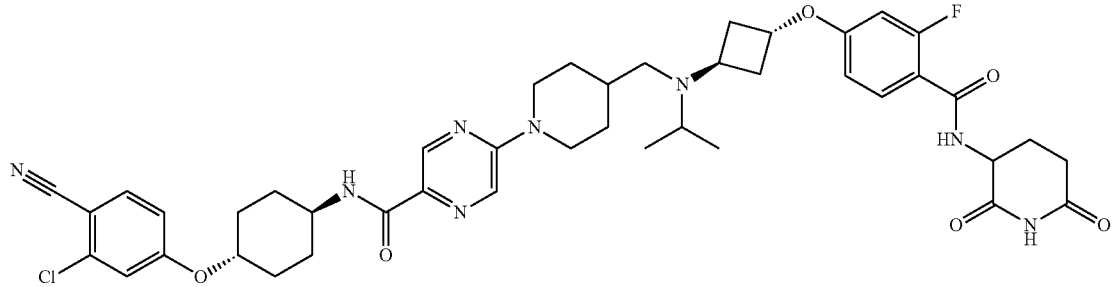 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc(C(=O)NC3CCC(=O)NC3=O)c(F)c2)C1] |

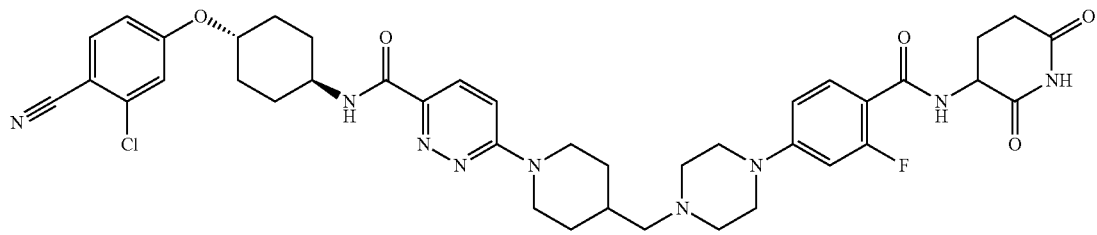 [SMILES: N#Cc1ccc(O[C@H]2CC[C@H](NC(=O)c3ccc(N4CCC(CN5CCN(c6ccc(C(=O)NC7CCC(=O)NC7=O)c(F)c6)CC5)CC4)nn3)CC2)cc1Cl]
26
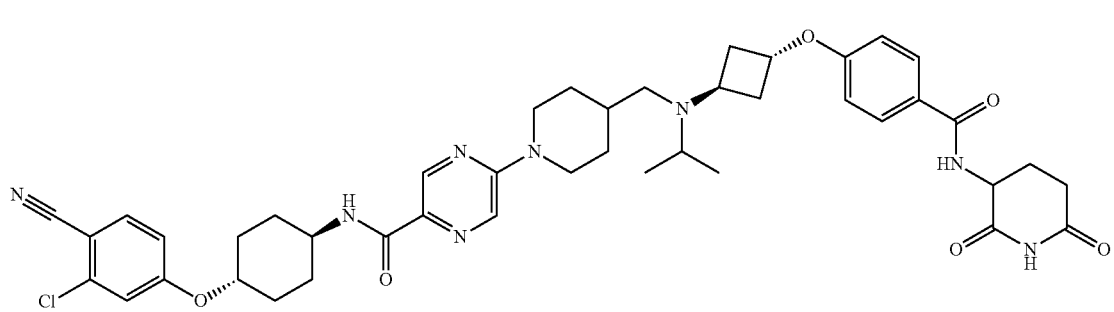 [SMILES: CC(C)N(CC1CCN(c2cnc(C(=O)N[C@H]3CC[C@H](Oc4ccc(C#N)c(Cl)c4)CC3)cn2)CC1)[C@H]1C[C@H](Oc2ccc(C(=O)NC3CCC(=O)NC3=O)cc2)C1]
27
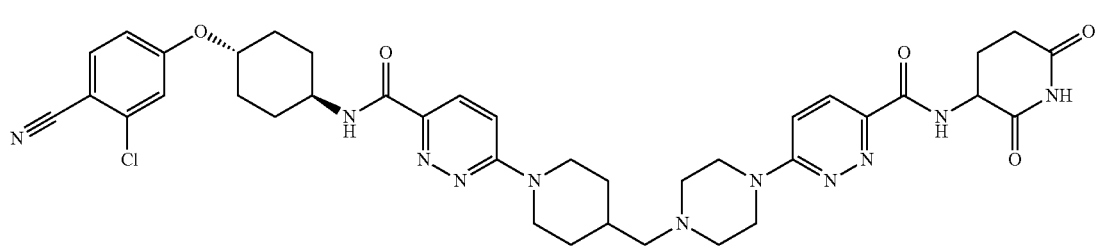 [SMILES: N#Cc1ccc(O[C@H]2CC[C@H](NC(=O)c3ccc(N4CCC(CN5CCN(c6ccc(C(=O)NC7CCC(=O)NC7=O)nn6)CC5)CC4)nn3)CC2)cc1Cl]
28
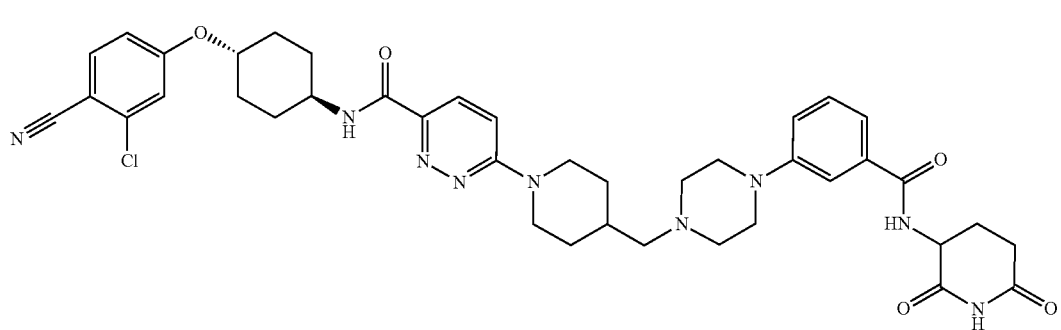 [SMILES: N#Cc1ccc(O[C@H]2CC[C@H](NC(=O)c3ccc(N4CCC(CN5CCN(c6cccc(C(=O)NC7CCC(=O)NC7=O)c6)CC5)CC4)nn3)CC2)cc1Cl]
29
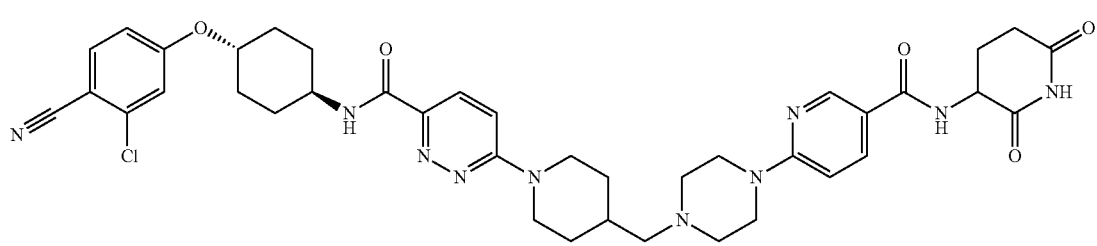 [SMILES: N#Cc1ccc(O[C@H]2CC[C@H](NC(=O)c3ccc(N4CCC(CN5CCN(c6ccc(C(=O)NC7CCC(=O)NC7=O)cn6)CC5)CC4)nn3)CC2)cc1Cl]
30
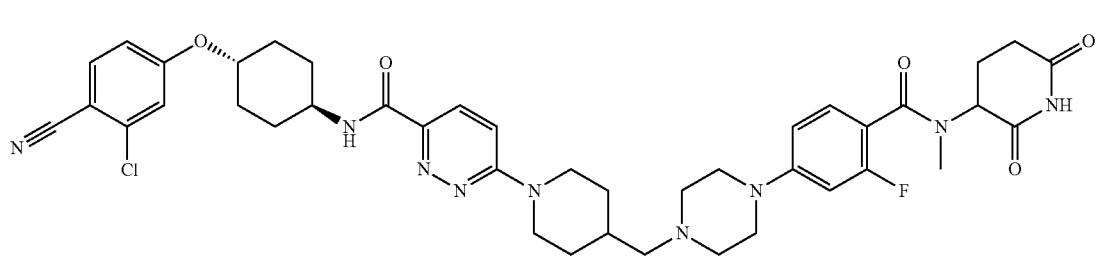 [SMILES: CN(C(=O)c1ccc(N2CCN(CC3CCN(c4ccc(C(=O)N[C@H]5CC[C@H](Oc6ccc(C#N)c(Cl)c6)CC5)nn4)CC3)CC2)cc1F)C1CCC(=O)NC1=O]
31

-continued
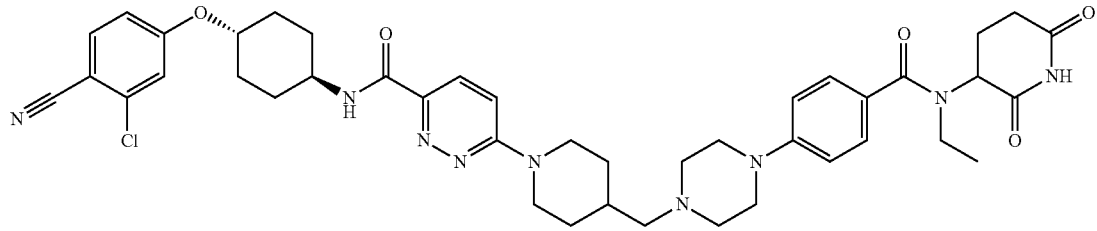 [SMILES: CCN(C(=O)c1ccc(N2CCN(CC3CCN(c4ccc(C(=O)N[C@H]5CC[C@H](Oc6ccc(C#N)c(Cl)c6)CC5)nn4)CC3)CC2)cc1)C1CCC(=O)NC1=O]
32
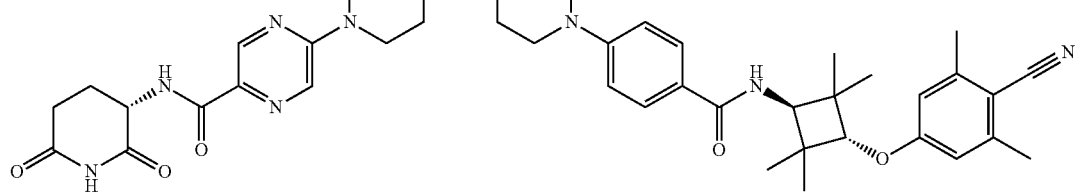
33
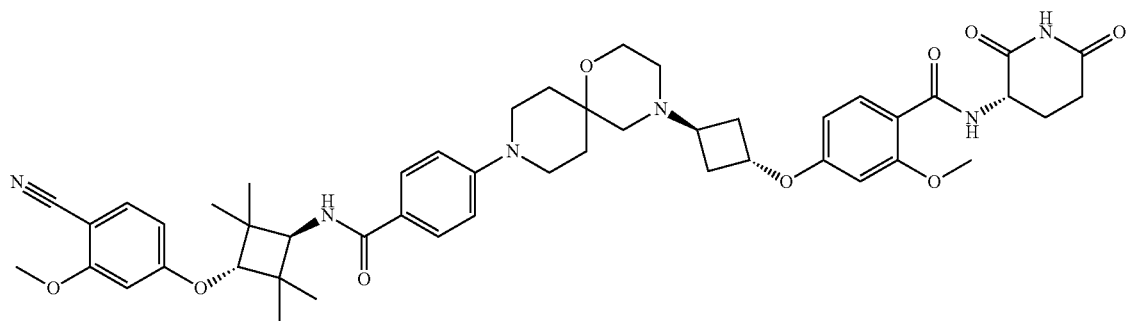 [SMILES: COc1cc(O[C@H]2C(C)(C)[C@H](NC(=O)c3ccc(N4CCC5(CC4)CN([C@H]4C[C@H](Oc6ccc(C(=O)N[C@H]7CCC(=O)NC7=O)c(OC)c6)C4)CCO5)cc3)C2(C)C)ccc1C#N]
34
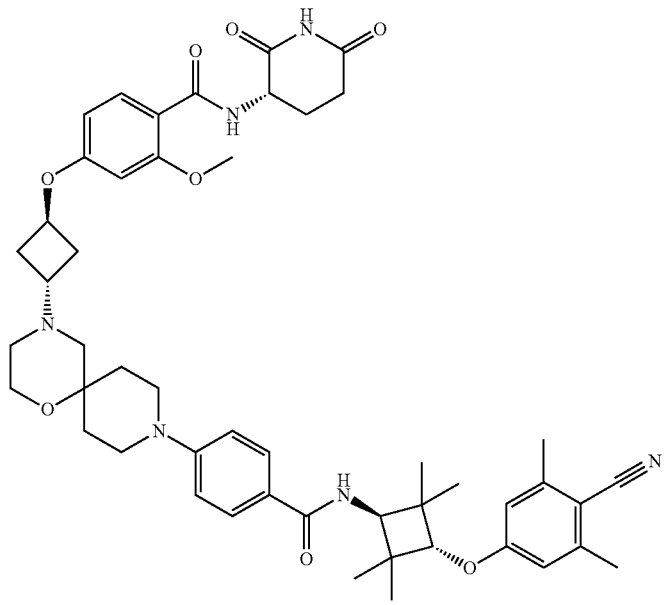 [SMILES: COc1cc(O[C@H]2C[C@H](N3CCOC4(CCN(c5ccc(C(=O)N[C@H]6C(C)(C)[C@H](Oc7cc(C)c(C#N)c(C)c7)C6(C)C)cc5)CC4)C3)C2)ccc1C(=O)N[C@H]1CCC(=O)NC1=O]
35

36
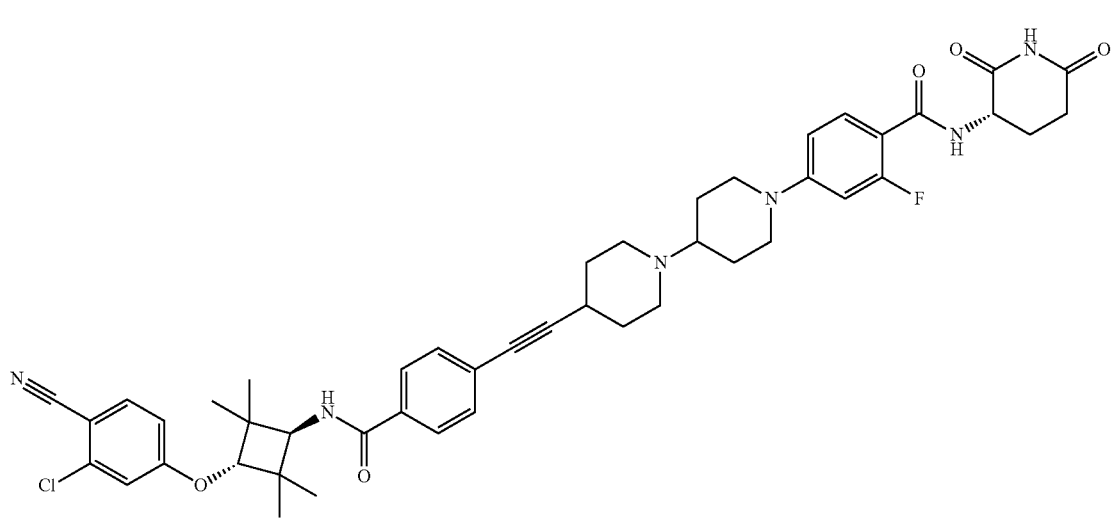 [SMILES: CC1(C)[C@H](NC(=O)c2ccc(C#CC3CCN(C4CCN(c5ccc(C(=O)N[C@H]6CCC(=O)NC6=O)c(F)c5)CC4)CC3)cc2)C(C)(C)[C@H]1Oc1ccc(C#N)c(Cl)c1]
37
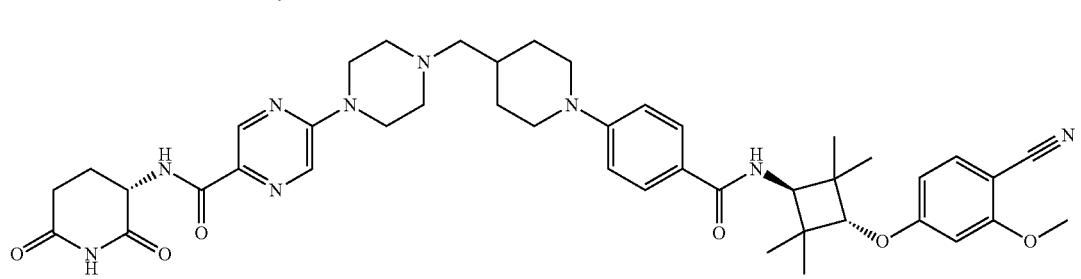
38
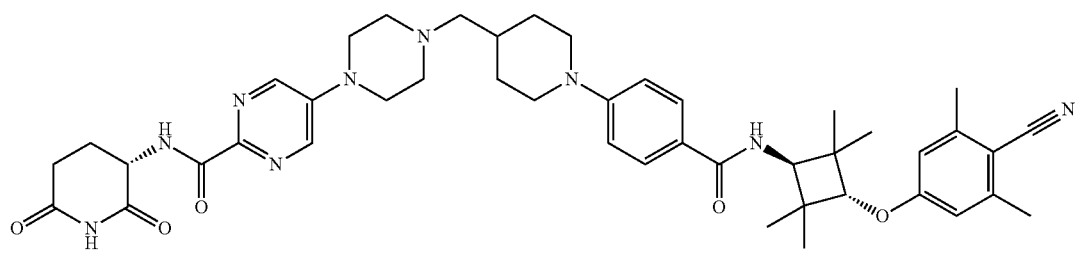
39
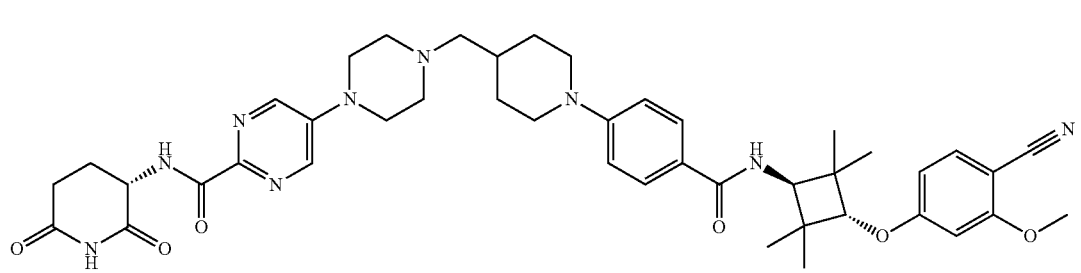 [SMILES: COc1cc(O[C@H]2C(C)(C)[C@H](NC(=O)c3ccc(N4CCC(CN5CCN(c6cnc(C(=O)N[C@H]7CCC(=O)NC7=O)nc6)CC5)CC4)cc3)C2(C)C)ccc1C#N]
40
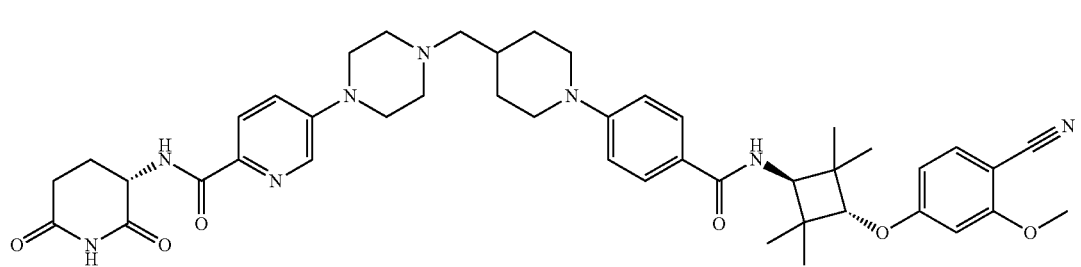 [SMILES: COc1cc(O[C@H]2C(C)(C)[C@H](NC(=O)c3ccc(N4CCC(CN5CCN(c6ccc(C(=O)N[C@H]7CCC(=O)NC7=O)nc6)CC5)CC4)cc3)C2(C)C)ccc1C#N]

-continued
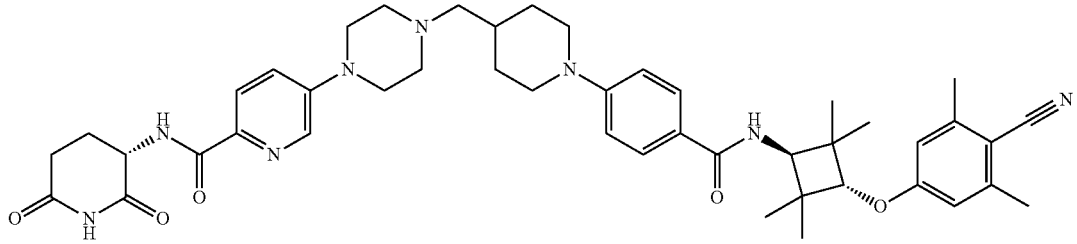 [SMILES: Cc1cc(O[C@H]2C(C)(C)[C@H](NC(=O)c3ccc(N4CCC(CN5CCN(c6ccc(C(=O)N[C@H]7CCC(=O)NC7=O)nc6)CC5)CC4)cc3)C2(C)C)cc(C)c1C#N]
41
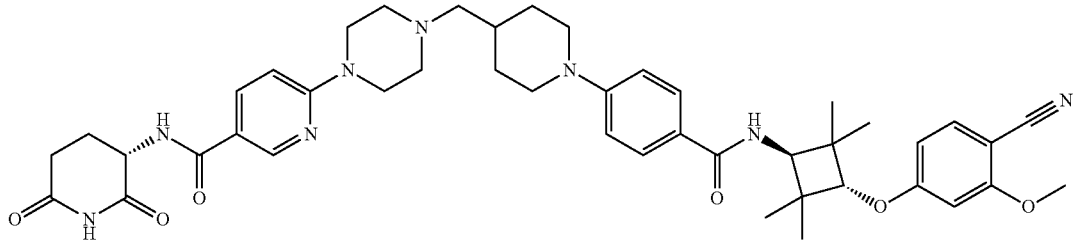 [SMILES: COc1cc(O[C@H]2C(C)(C)[C@H](NC(=O)c3ccc(N4CCC(CN5CCN(c6ccc(C(=O)N[C@H]7CCC(=O)NC7=O)cn6)CC5)CC4)cc3)C2(C)C)ccc1C#N]
42
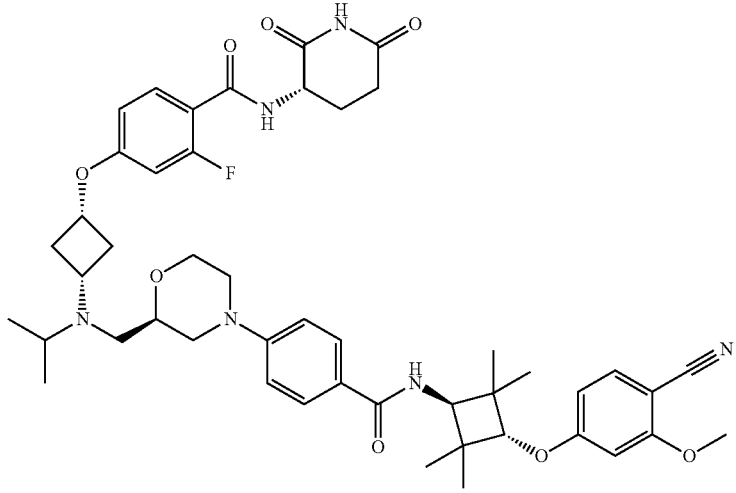 [SMILES: COc1cc(O[C@H]2C(C)(C)[C@H](NC(=O)c3ccc(N4CCO[C@H](CN(C(C)C)[C@H]5C[C@@H](Oc6ccc(C(=O)N[C@H]7CCC(=O)NC7=O)c(F)c6)C5)C4)cc3)C2(C)C)ccc1C#N]
43
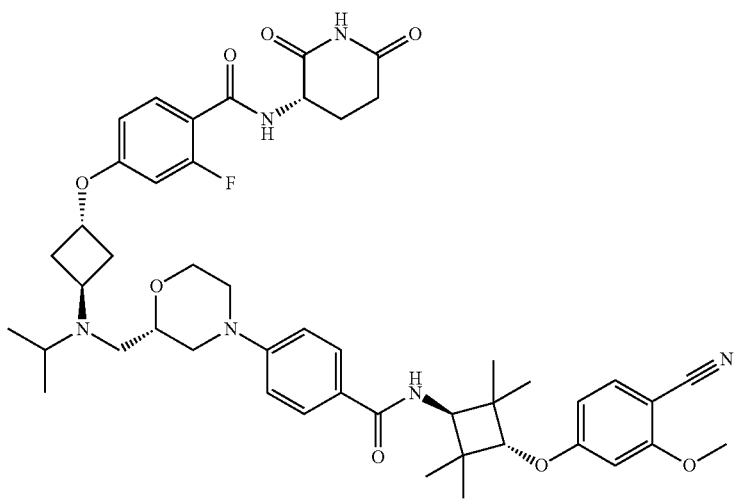 [SMILES: COc1cc(O[C@H]2C(C)(C)[C@H](NC(=O)c3ccc(N4CCO[C@@H](CN(C(C)C)[C@H]5C[C@H](Oc6ccc(C(=O)N[C@H]7CCC(=O)NC7=O)c(F)c6)C5)C4)cc3)C2(C)C)ccc1C#N]
44

45
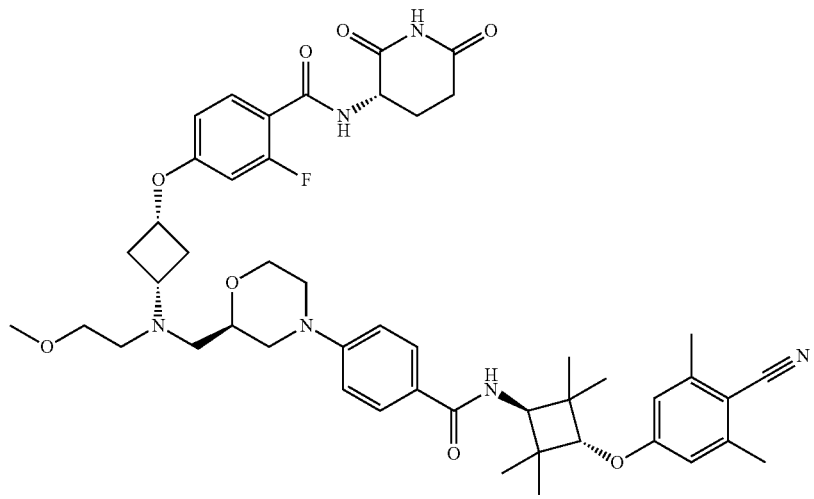 [SMILES: COCCN(C[C@@H]1CN(c2ccc(C(=O)N[C@H]3C(C)(C)[C@H](Oc4cc(C)c(C#N)c(C)c4)C3(C)C)cc2)CCO1)[C@H]1C[C@@H](Oc2ccc(C(=O)N[C@H]3CCC(=O)NC3=O)c(F)c2)C1]
46
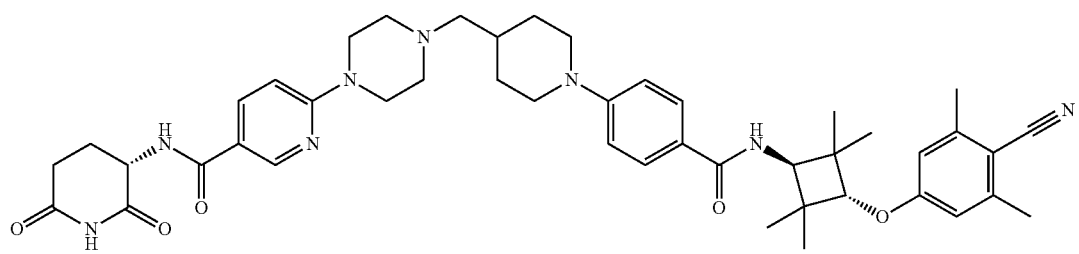 [SMILES: Cc1cc(O[C@H]2C(C)(C)[C@H](NC(=O)c3ccc(N4CCC(CN5CCN(c6ccc(C(=O)N[C@H]7CCC(=O)NC7=O)cn6)CC5)CC4)cc3)C2(C)C)cc(C)c1C#N]
47
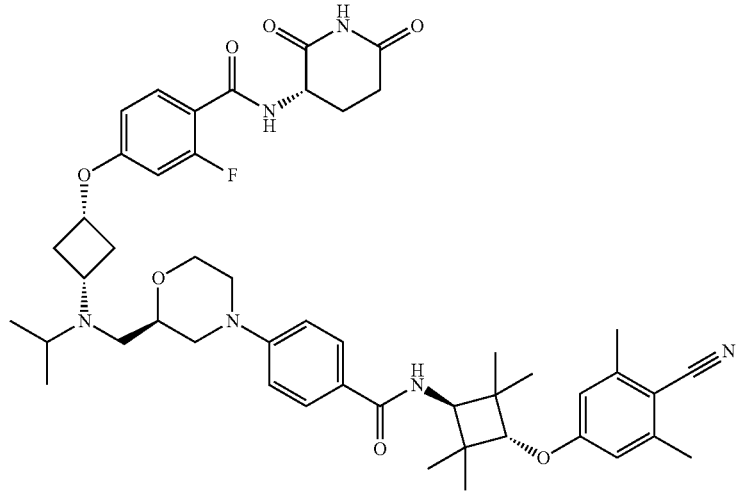 [SMILES: Cc1cc(O[C@H]2C(C)(C)[C@H](NC(=O)c3ccc(N4CCO[C@H](CN(C(C)C)[C@H]5C[C@@H](Oc6ccc(C(=O)N[C@H]7CCC(=O)NC7=O)c(F)c6)C5)C4)cc3)C2(C)C)cc(C)c1C#N]
48
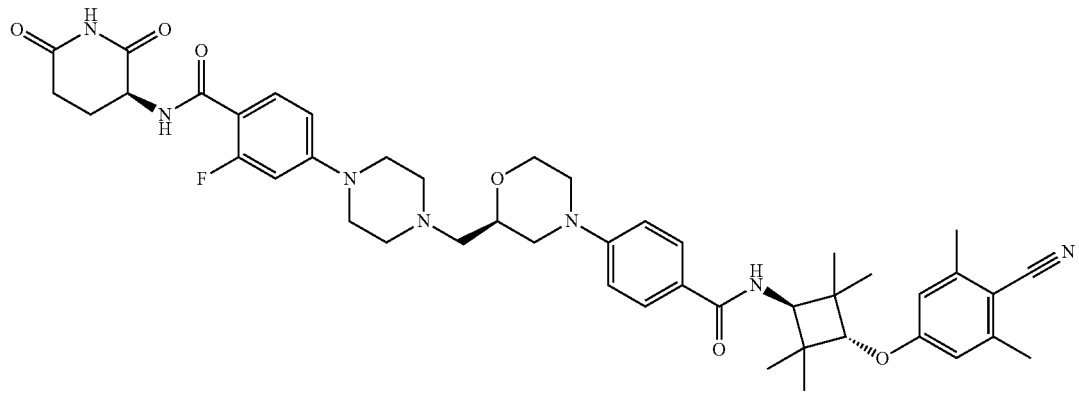 [SMILES: Cc1cc(O[C@H]2C(C)(C)[C@H](NC(=O)c3ccc(N4CCO[C@H](CN5CCN(c6ccc(C(=O)N[C@H]7CCC(=O)NC7=O)c(F)c6)CC5)C4)cc3)C2(C)C)cc(C)c1C#N]

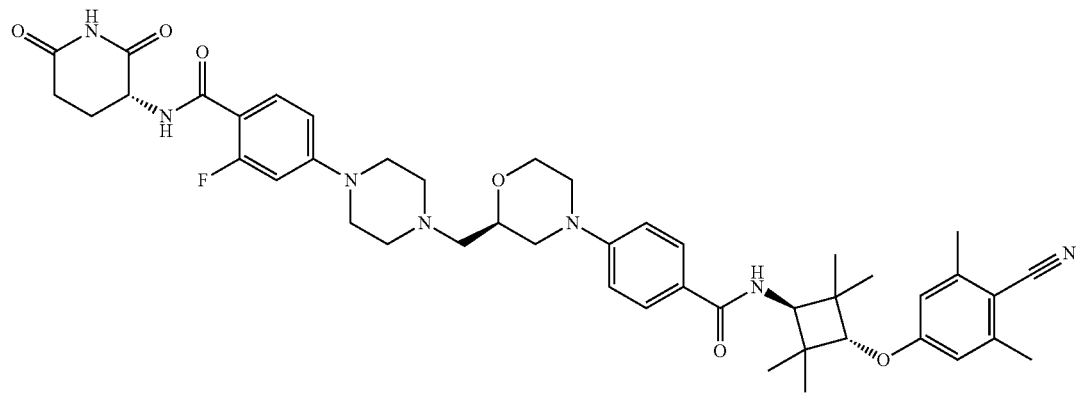 [SMILES: Cc1cc(O[C@H]2C(C)(C)[C@H](NC(=O)c3ccc(N4CCO[C@H](CN5CCN(c6ccc(C(=O)N[C@@H]7CCC(=O)NC7=O)c(F)c6)CC5)C4)cc3)C2(C)C)cc(C)c1C#N]
49
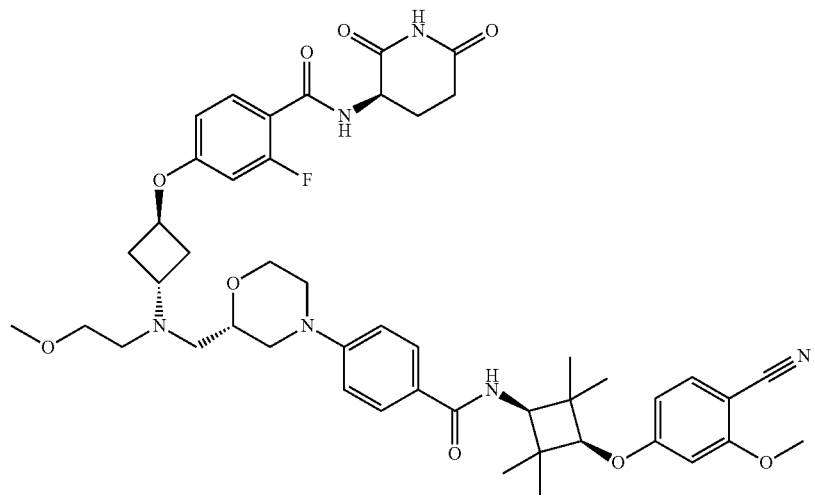
50
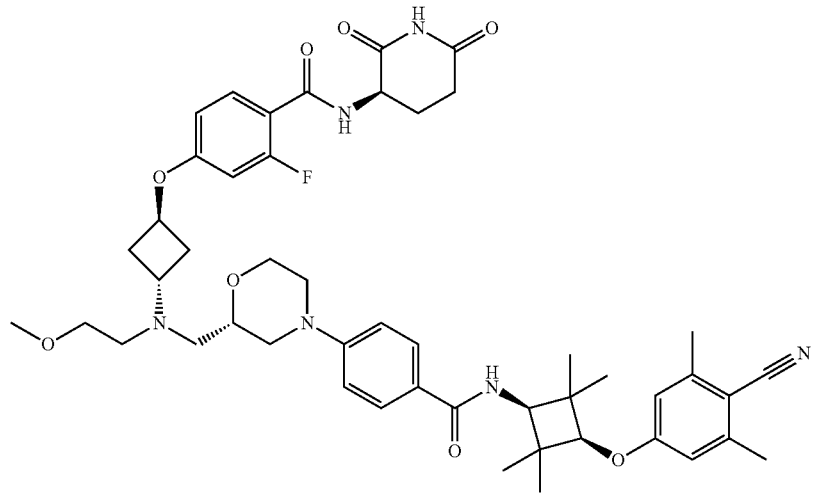 [SMILES: COCCN(C[C@H]1CN(c2ccc(C(=O)N[C@H]3C(C)(C)[C@@H](Oc4cc(C)c(C#N)c(C)c4)C3(C)C)cc2)CCO1)[C@H]1C[C@H](Oc2ccc(C(=O)N[C@@H]3CCC(=O)NC3=O)c(F)c2)C1]
51

-continued
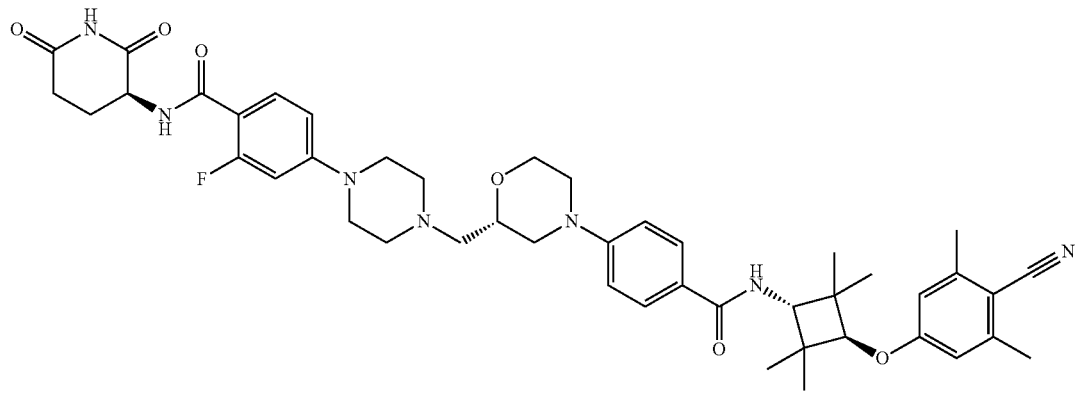 [SMILES: Cc1cc(O[C@H]2C(C)(C)[C@H](NC(=O)c3ccc(N4CCO[C@@H](CN5CCN(c6ccc(C(=O)N[C@H]7CCC(=O)NC7=O)c(F)c6)CC5)C4)cc3)C2(C)C)cc(C)c1C#N]
52
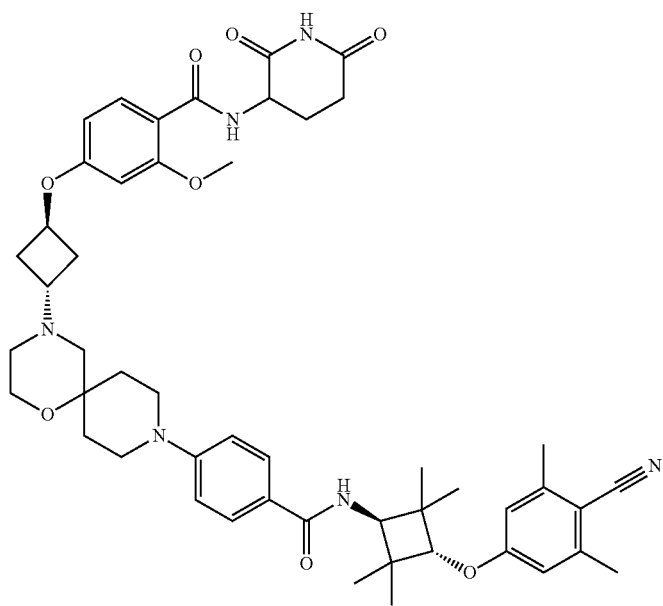 [SMILES: COc1cc(O[C@H]2C[C@H](N3CCOC4(CCN(c5ccc(C(=O)N[C@H]6C(C)(C)[C@H](Oc7cc(C)c(C#N)c(C)c7)C6(C)C)cc5)CC4)C3)C2)ccc1C(=O)NC1CCC(=O)NC1=O]
53
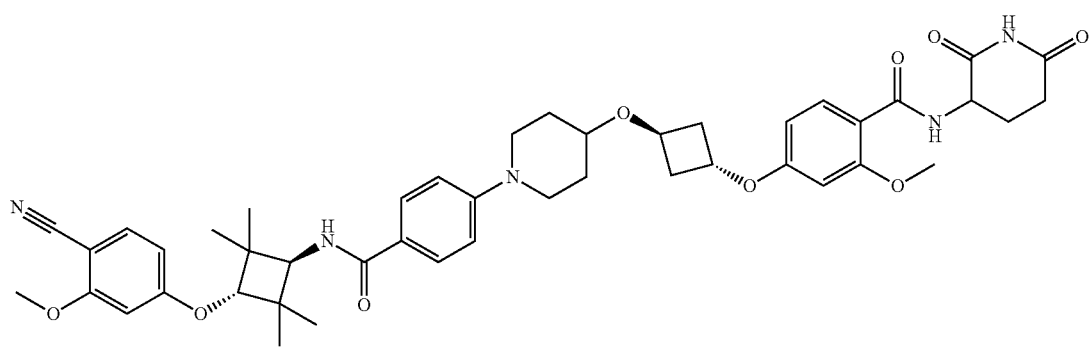 [SMILES: COc1cc(O[C@H]2C(C)(C)[C@H](NC(=O)c3ccc(N4CCC(O[C@H]5C[C@H](Oc6ccc(C(=O)NC7CCC(=O)NC7=O)c(OC)c6)C5)CC4)cc3)C2(C)C)ccc1C#N]
54

-continued
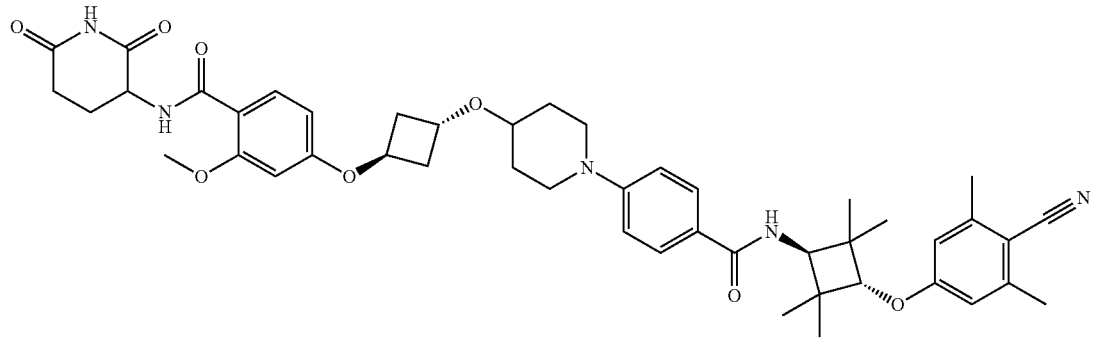 [SMILES: COc1cc(O[C@H]2C[C@H](OC3CCN(c4ccc(C(=O)N[C@H]5C(C)(C)[C@H](Oc6cc(C)c(C#N)c(C)c6)C5(C)C)cc4)CC3)C2)ccc1C(=O)NC1CCC(=O)NC1=O]
55
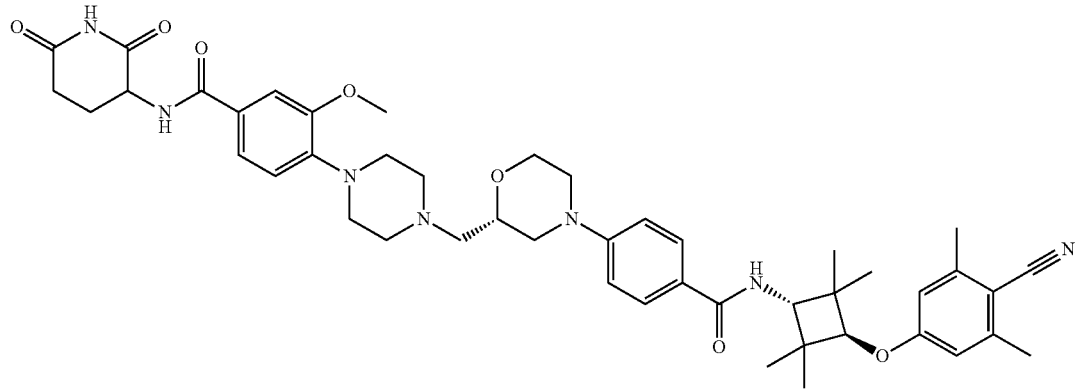 [SMILES: COc1cc(C(=O)NC2CCC(=O)NC2=O)ccc1N1CCN(C[C@H]2CN(c3ccc(C(=O)N[C@H]4C(C)(C)[C@H](Oc5cc(C)c(C#N)c(C)c5)C4(C)C)cc3)CCO2)CC1]
56
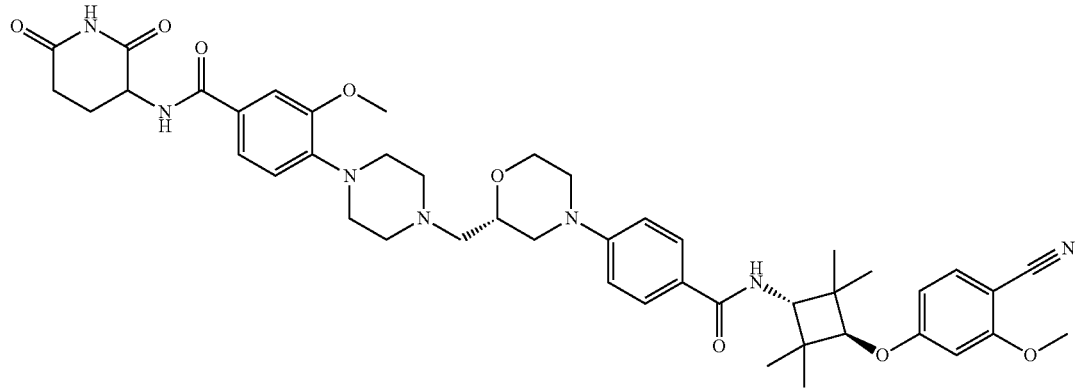 [SMILES: COc1cc(O[C@H]2C(C)(C)[C@H](NC(=O)c3ccc(N4CCO[C@@H](CN5CCN(c6ccc(C(=O)NC7CCC(=O)NC7=O)cc6OC)CC5)C4)cc3)C2(C)C)ccc1C#N]
57
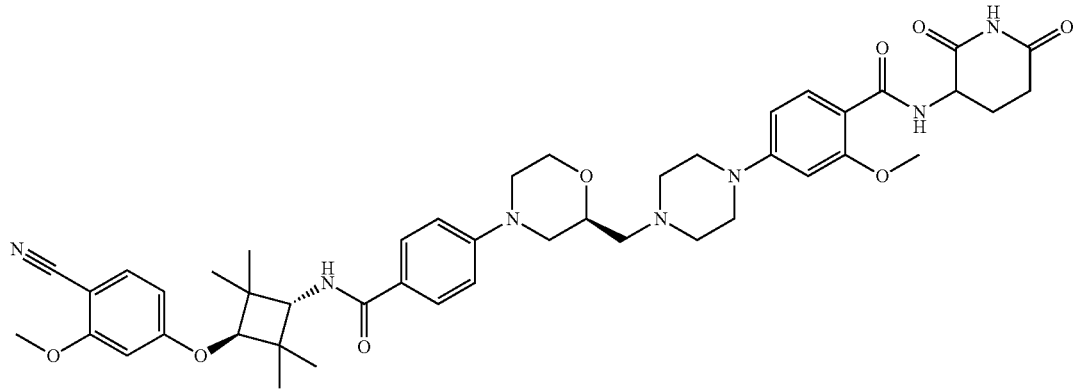 [SMILES: COc1cc(O[C@H]2C(C)(C)[C@H](NC(=O)c3ccc(N4CCO[C@@H](CN5CCN(c6ccc(C(=O)NC7CCC(=O)NC7=O)c(OC)c6)CC5)C4)cc3)C2(C)C)ccc1C#N]
58

59
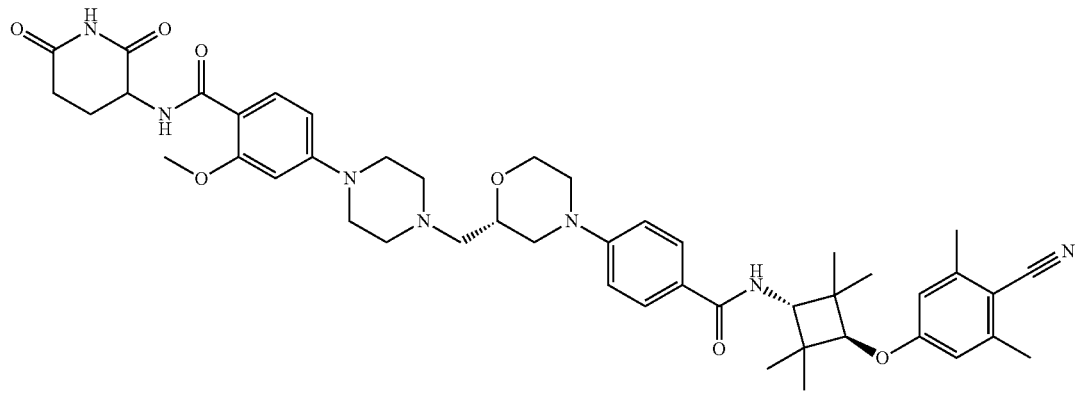 [SMILES: COc1cc(N2CCN(C[C@H]3CN(c4ccc(C(=O)N[C@H]5C(C)(C)[C@H](Oc6cc(C)c(C#N)c(C)c6)C5(C)C)cc4)CCO3)CC2)ccc1C(=O)NC1CCC(=O)NC1=O]
60
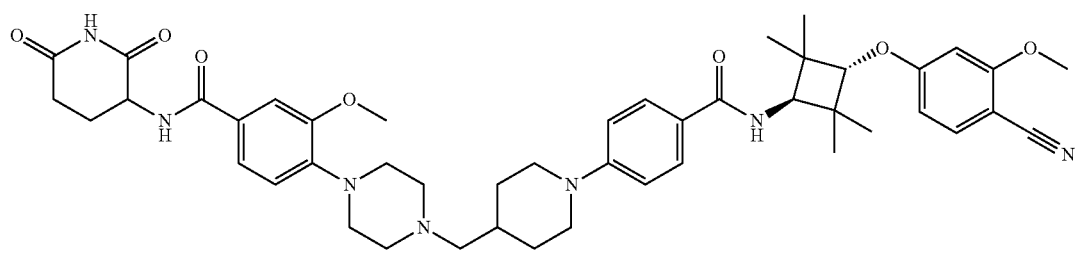 [SMILES: COc1cc(O[C@H]2C(C)(C)[C@H](NC(=O)c3ccc(N4CCC(CN5CCN(c6ccc(C(=O)NC7CCC(=O)NC7=O)cc6OC)CC5)CC4)cc3)C2(C)C)ccc1C#N]
61
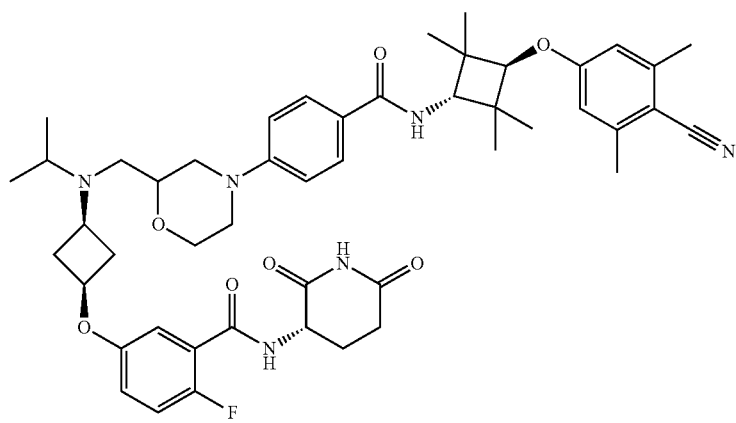 [SMILES: Cc1cc(O[C@H]2C(C)(C)[C@H](NC(=O)c3ccc(N4CCOC(CN(C(C)C)[C@H]5C[C@@H](Oc6ccc(F)c(C(=O)N[C@H]7CCC(=O)NC7=O)c6)C5)C4)cc3)C2(C)C)cc(C)c1C#N]
62
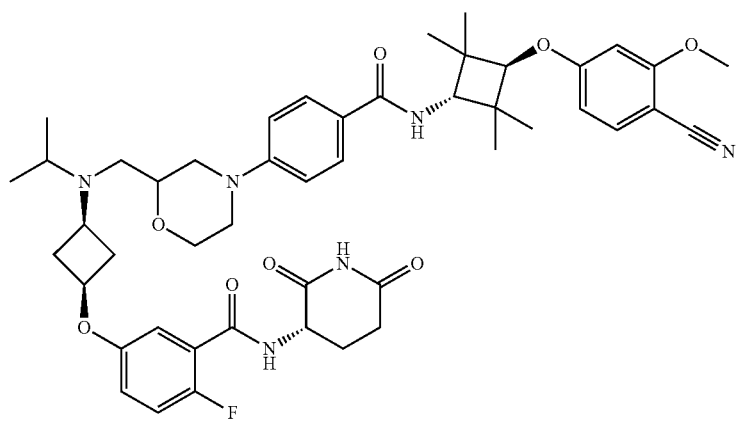 [SMILES: COc1cc(O[C@H]2C(C)(C)[C@H](NC(=O)c3ccc(N4CCOC(CN(C(C)C)[C@H]5C[C@@H](Oc6ccc(F)c(C(=O)N[C@H]7CCC(=O)NC7=O)c6)C5)C4)cc3)C2(C)C)ccc1C#N]

63
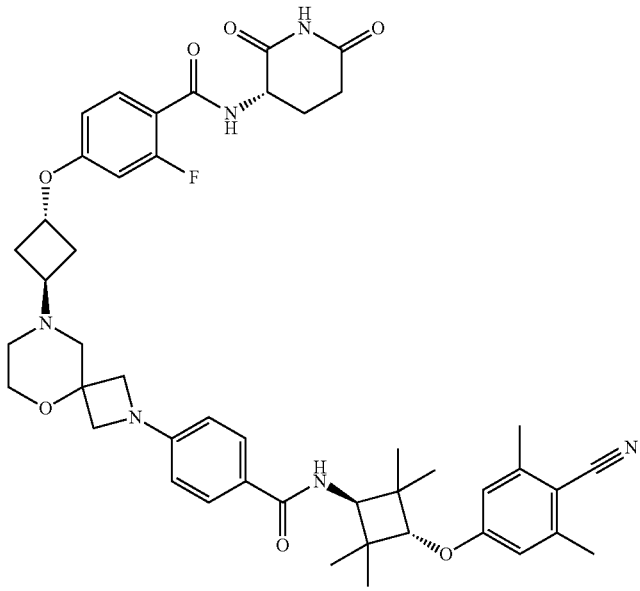
64
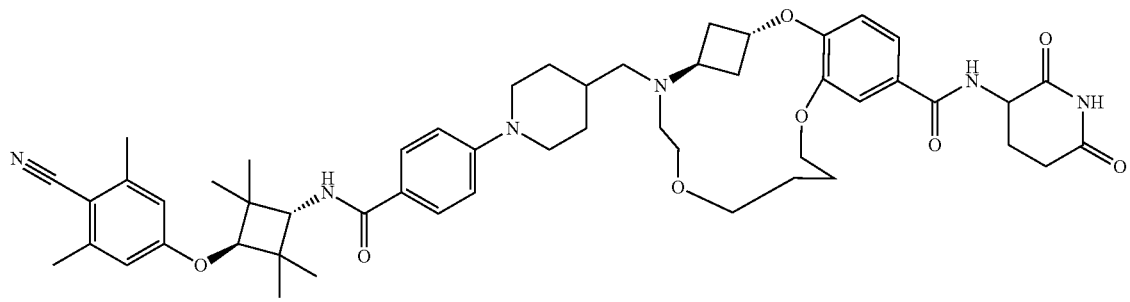
65
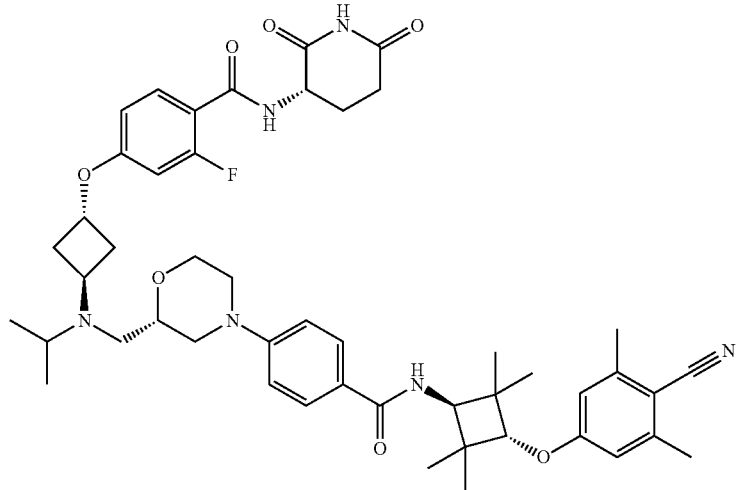

-continued
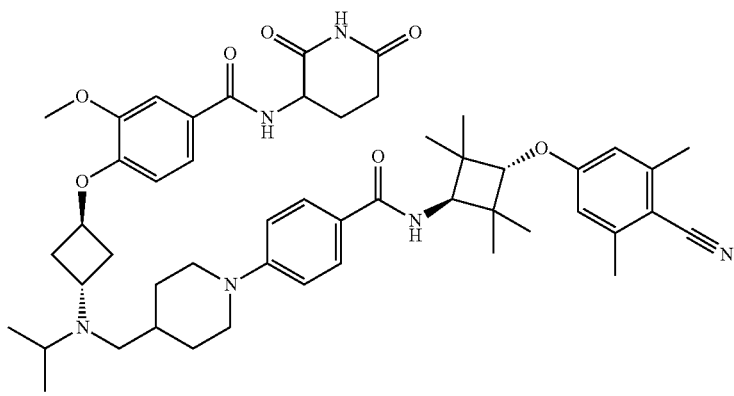
66
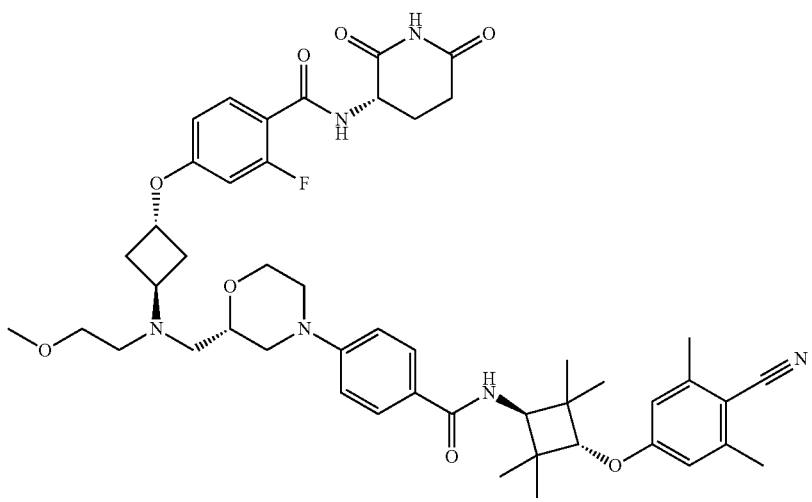
67
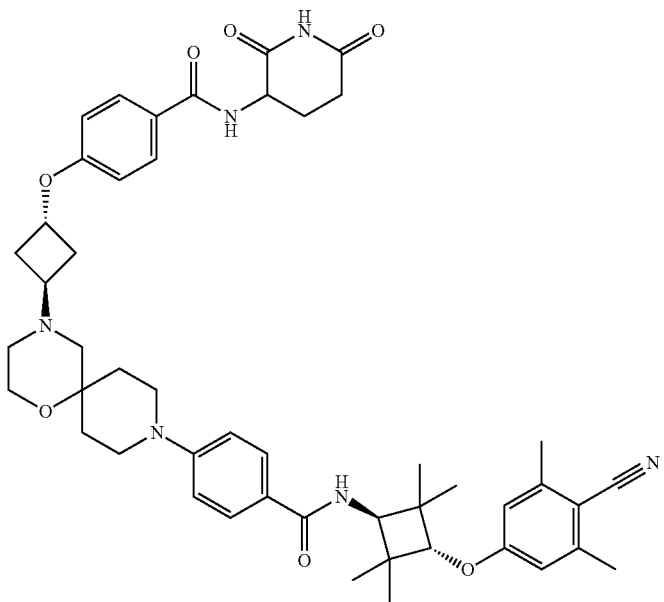
68

-continued
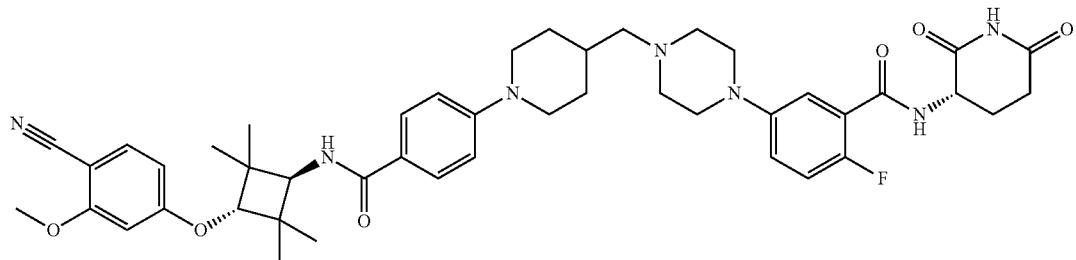
69
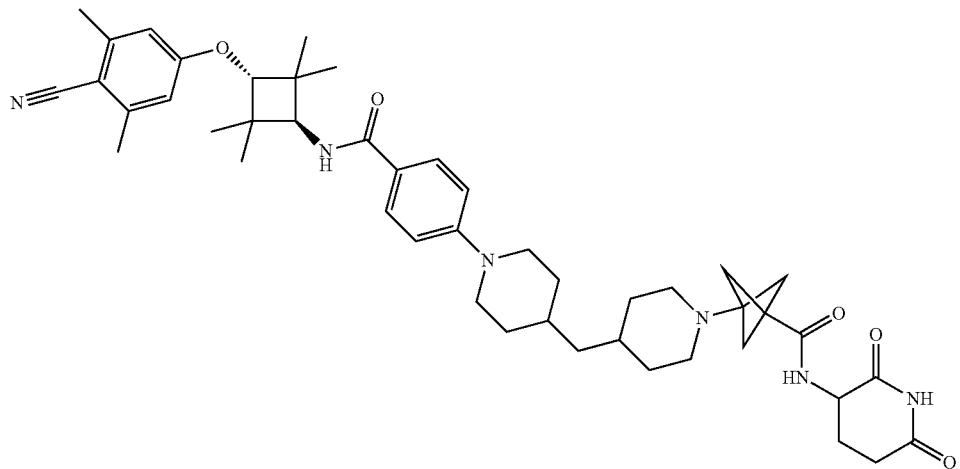
70
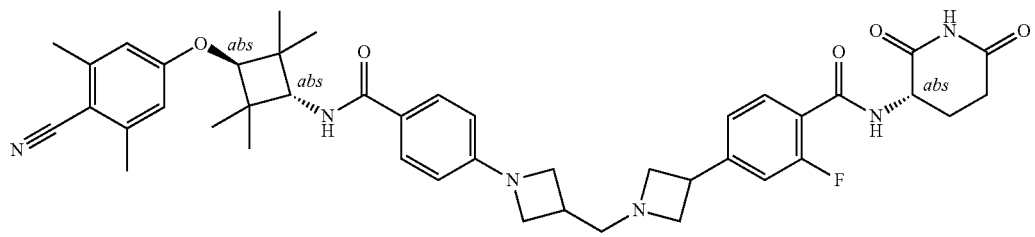
71
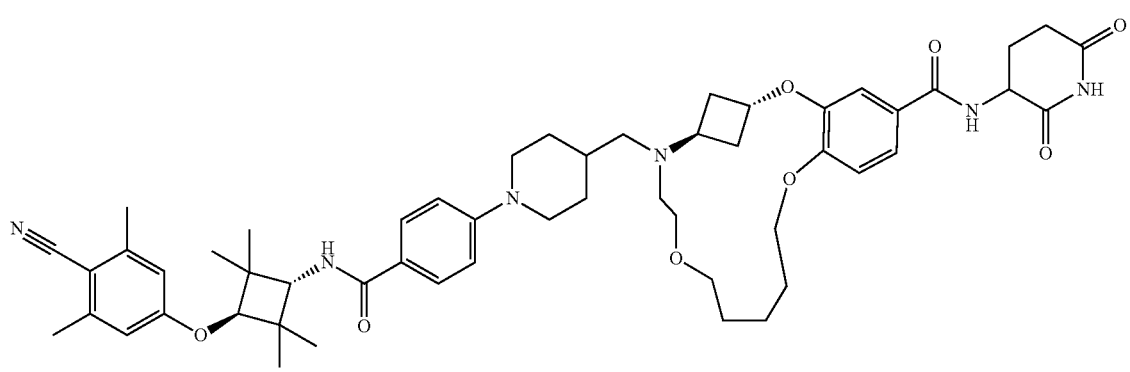
72

73

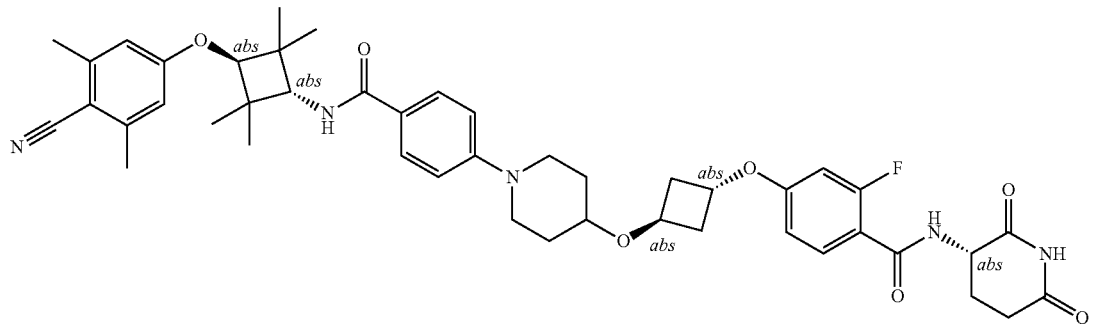

74

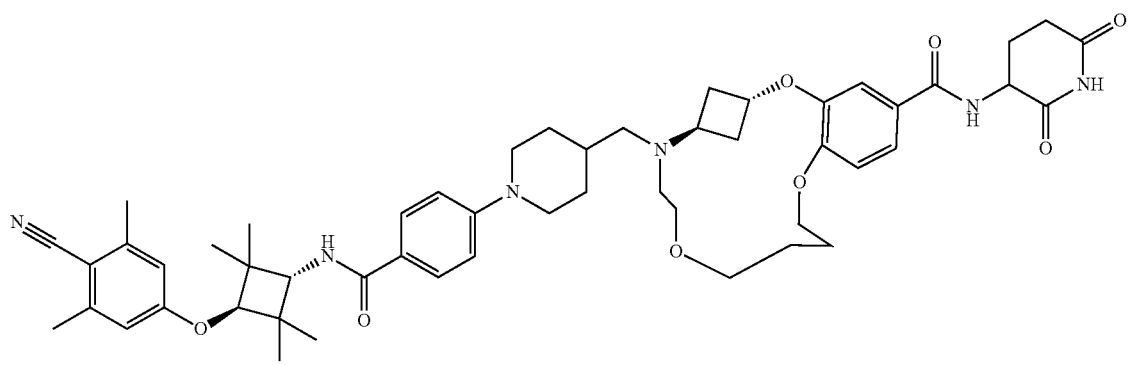

75

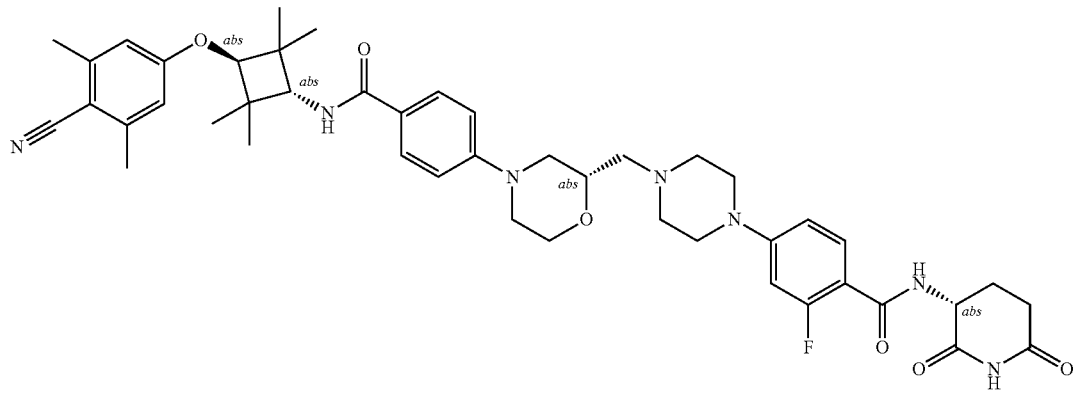

76

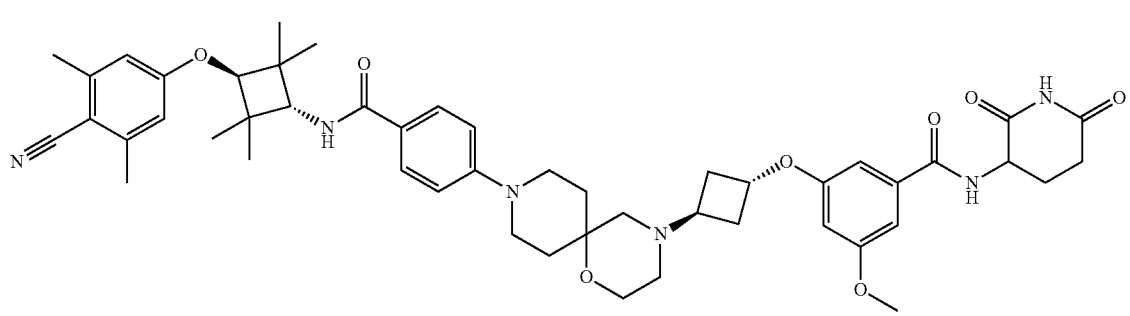

or a pharmaceutically acceptable salt, enantiomer, stereoisomer, solvate, or isotopic derivative thereof.

In one aspect, the application pertains to treating prostate cancer with a compound of the disclosure in combination with another anti-cancer agent. In one embodiment, the prostate cancer treated with the combination of a compound of the disclosure and another anti-cancer agent is metastatic prostate cancer. In one embodiment, the prostate cancer treated with the combination of a compound of the disclosure and another anti-cancer agent is castrate-resistant or castration-resistant prostate cancer. In one embodiment, the prostate cancer treated with the combination of a compound of the disclosure and another anti-cancer agent is metastatic, castrate-resistant prostate cancer. In one embodiment, the other anti-cancer agent is abiraterone, estramustine, docetaxel, ketoconazole, goserelin, histrelin, triptorelin, buserelin, cyproterone, flutamide, bicalutamide, nilutamide, pamidronate, zolendronate, or a pharmaceutically acceptable salt thereof. In one embodiment, the other anti-cancer agent is abiraterone or a pharmaceutically acceptable salt thereof. In one embodiment, the other anti-cancer agent is abiraterone acetate.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its volume prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active agent or compound of the disclosure. In another preferred aspect, an increase in average survival time of a population may also be measured, for example, by calculating for a population the average length of survival following completion of a first round of treatment with an active agent or compound of the disclosure.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured by calculating for a population the average length of survival following initiation of treatment with an active agent or compound of the disclosure. In another preferred aspect, an increase in average survival time of a population may be measured by calculating for a population the average length of survival following completion of a first round of treatment with a compound of the disclosure.

In another aspect, treating cancer results in a decrease in tumor growth rate. Preferably, after treatment, tumor growth rate is reduced by at least 5% relative to growth rate prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured by measuring an increase in the diameter of a tumor after a prior tumor shrinkage that followed treatment. In another preferred aspect, a decrease in tumor regrowth is indicated by failure of tumors to reoccur after treatment has stopped.

The dosages of the compound of the disclosure for any of the methods and uses described herein vary depending on the agent, the age, weight, and clinical condition of the recipient subject, and the experience and judgment of the clinician or practitioner administering the therapy, among other factors affecting the selected dosage.

The therapeutically effective amount of the compound of the disclosure may be administered one or more times over a day for up to 30 or more days, followed by 1 or more days of non-administration of the compound. This type of treatment schedule, i.e., administration of a the compound of the disclosure on consecutive days followed by non-administration of the compound on consecutive days may be referred to as a treatment cycle. A treatment cycle may be repeated as many times as necessary to achieve the intended affect.

In one embodiment, the therapeutically effective amount of the compound of the disclosure is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1,000 mg administered once, twice, three times, four times, or more daily for one, two, three, four, five, six, seven, eight, nine, ten, eleven, twelve, thirteen, fourteen, fifteen, twenty, twenty-five, thirty consecutive days, or, once, twice, three times, four times, or more daily, in single or divided doses, for 2 months, 3 months, 4 months, 5 months, 6 months, or longer.

In one embodiment, the therapeutically effective amount of the compound of the disclosure is about 10 to about 40 mg, about 20 to about 50 mg, about 30 to about 60 mg, about 40 to about 70 mg, about 50 to about 80 mg, about 60 to about 90 mg, about 70 to about 100 mg, about 80 to about 110 mg, about 90 to about 120 mg, about 100 to about 130 mg, about 110 to about 140 mg, about 120 to about 150 mg, about 130 to about 160 mg, about 140 to about 170 mg, about 150 to about 180 mg, about 160 to about 190 mg, about 170 to about 200 mg, about 180 to about 210 mg, about 190 to about 220 mg, about 200 to about 230 mg, about 210 to about 240 mg, about 220 to about 250 mg, about 230 to about 260 mg, about 240 to about 270 mg, about 250 to about 280 mg, about 260 to about 290 mg, about 270 to about 300 mg, about 280 to about 310 mg, about 290 to about 320 mg, about 300 to about 330 mg, about 310 to about 340 mg, about 320 to about 350 mg, about 330 to about 360 mg, about 340 to about 370 mg, about 350 to about 380 mg, about 360 to about 390 mg, about 370 to about 400 mg, about 380 to about 410 mg, about 390 to about 420 mg, about 400 to about 430 mg, about 410 to about 440 mg, about 420 to about 450 mg, about 430 to about 460 mg, about 440 to about 470 mg, about 450 to about 480 mg, about 460 to about 490 mg, about 470 to about 500 mg, about 480 to about 510 mg, about 490 to about 520 mg, about 500 to about 530 mg, about 510 to about 540 mg, about 520 to about 550 mg, about 530 to about 560 mg, about 540 to about 570 mg, about 550 to about 580 mg, about 560 to about 590 mg, about 570 to about 600 mg, about 580 to about 610 mg, about 590 to about 620 mg, about 600 to about 630 mg, about 610 to about 640 mg, about 620 to about 650 mg, about 630 to about 660 mg, about 640 to about 670 mg, about 650 to about 680 mg, about 660 to about 690 mg, about 670 to about 700 mg, about 680 to about 710 mg, about 690 to about 720 mg, about 700 to about 730 mg, about 710 to about 740 mg, about 720 to about 750 mg, about 730 to about 760 mg, about 740 to about 770 mg, about 750 to about 780 mg, about 760 to about 790 mg, about 770 to about 800 mg, about 780 to about 810 mg, about 790 to about 820 mg, about 800 to about 830 mg, about 810 to about 840 mg, about 820 to about 850 mg, about 830 to about 860 mg, about 840 to about 870 mg, about 850 to about 880 mg, about 860 to about 890 mg, about 870 to about 900 mg, about 880 to about 910 mg, about 890 to about 920 mg, about 900 to about 930 mg, about 910 to about 940 mg, about 920 to about 950 mg, about 930 to about 960 mg, about 940 to about 970 mg, about 950 to about 980 mg, about 960 to about 990 mg, or about 970 to about 1,000 mg administered once, twice, three times, four times, or more daily in single or divided doses (which dose may be adjusted for the patient's weight in kg, body surface area in $m^2$, and/or age in years).

In one embodiment, the therapeutically effective amount of the compound of the disclosure is about 70 mg to about 1000 mg administered once, twice, three times, four times, or more daily in single or divided doses (which dose may be adjusted for the patient's weight in kg, body surface area in $m^2$, and/or age in years).

In one embodiment, the therapeutically effective amount of the compound of the disclosure is about 70 mg, 105 mg, 140 mg, 175 mg, 210 mg, 245 mg, 280 mg, 315 mg, 350 mg, 385 mg, 420 mg, 455 mg, 490 mg, 525 mg, 560 mg, 595 mg, 630 mg, 665 mg, or 700 mg administered once, twice, three times, four times, or more daily in single or divided doses (which dose may be adjusted for the patient's weight in kg, body surface area in $m^2$, and/or age in years).

The therapeutically effective amount of the compound of the disclosure can also range from about 0.01 mg/kg per day to about 100 mg/kg per day. In an aspect, therapeutically effective amount of the compound of the disclosure can range from about 0.05 mg/kg per day to about 10 mg/kg per day. In an aspect, therapeutically effective amount of the compound of the disclosure can range from about 0.075 mg/kg per day to about 5 mg/kg per day. In an aspect, therapeutically effective amount of the compound of the disclosure can range from about 0.10 mg/kg per day to about 1 mg/kg per day. In an aspect, therapeutically effective amount of the compound of the disclosure can range from about 0.20 mg/kg per day to about 0.70 mg/kg per day.

In one embodiment, the therapeutically effective amount of the compound of the disclosure is about 0.10 mg/kg per day, about 0.15 mg/kg per day, about 0.20 mg/kg per day, about 0.25 mg/kg per day, about 0.30 mg/kg per day, about 0.35 mg/kg per day, about 0.40 mg/kg per day, about 0.45 mg/kg per day, about 0.50 mg/kg per day, about 0.55 mg/kg per day, about 0.60 mg/kg per day, about 0.65 mg/kg per day, about 0.70 mg/kg per day, about 0.75 mg/kg per day, about 0.80 mg/kg per day, about 0.85 mg/kg per day, about 0.90 mg/kg per day, about 0.95 mg/kg per day, or about 1.00 mg/kg per day.

In one embodiment, the therapeutically effective amount of the compound of the disclosure is about 1.05 mg/kg per day, about 1.10 mg/kg per day, about 1.15 mg/kg per day, about 1.20 mg/kg per day, about 1.25 mg/kg per day, about 1.30 mg/kg per day, about 1.35 mg/kg per day, about 1.40 mg/kg per day, about 1.45 mg/kg per day, about 1.50 mg/kg per day, about 1.55 mg/kg per day, about 1.60 mg/kg per day, about 1.65 mg/kg per day, about 1.70 mg/kg per day, about 1.75 mg/kg per day, about 1.80 mg/kg per day, about 1.85 mg/kg per day, about 1.90 mg/kg per day, about 1.95 mg/kg per day, or about 2.00 mg/kg per day.

In one embodiment, the therapeutically effective amount of the compound of the disclosure is about 2 mg/kg per day, about 2.5 mg/kg per day, about 3 mg/kg per day, about 3.5 mg/kg per day, about 4 mg/kg per day, about 4.5 mg/kg per day, about 5 mg/kg per day, about 5.5 mg/kg per day, about 6 mg/kg per day, about 6.5 mg/kg per day, about 7 mg/kg per day, about 7.5 mg/kg per day, about 8.0 mg/kg per day, about 8.5 mg/kg per day, about 9.0 mg/kg per day, about 9.5 mg/kg per day, or about 10 mg/kg per day.

In one embodiment, the therapeutically effective amount of the compound of the disclosure is administered to the subject once daily. In one embodiment, this daily dose of a compound of the compound of the disclosure may administered to the subject all at once. In one embodiment, this daily dose of the compound of the disclosure may administered to the subject in two portions (i.e., a divided dose). In one embodiment, this daily dose of the compound of the disclosure may administered to the subject in three divided doses. In one embodiment, this daily dose of the compound of the disclosure may administered to the subject in four divided doses. In one embodiment, this daily dose of the compound of the disclosure may be administered to the subject in five or more divided doses. In one embodiment, these portions or divided doses are administered to the subject at regular intervals throughout the day, for example, every 12 hours, every 8 hours, every 6 hours, every 5 hours, every 4 hours, etc.

The therapeutically effective amount of the compound of the disclosure can be estimated initially either in cell culture assays or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the compound of the disclosure or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, once every two weeks, or monthly depending on half-life and clearance rate of the particular formulation.

In one embodiment, for the methods of treating prostate cancer with the combination of the compound of the disclosure and another anti-cancer agent, the therapeutically effective amount of the compound of the disclosure is described herein, and the therapeutically effective amount of the anti-cancer agent is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1,000 mg administered once, twice, three times, four times, or more daily for one, two, three, four, five, six, seven, eight, nine, ten, eleven, twelve, thirteen, fourteen, fifteen, or thirty consecutive days, or, once, twice, three times, four times, or more daily, in single or divided doses, for 2 months, 3 months, 4 months, 5 months, 6 months, or longer.

In one embodiment, for the methods of treating prostate cancer with the combination of the compound of the disclosure and abiraterone, or a pharmaceutically acceptable salt thereof, the therapeutically effective amount of the compound of the disclosure is described herein, and the therapeutically effective amount of abiraterone, or a pharmaceutically acceptable salt thereof, is 0.01, 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1,000 mg administered once, twice, three times, four times, or more daily for one, two, three, four, five, six, seven, eight, nine, ten, eleven, twelve, thirteen, fourteen, fifteen, thirty consecutive days, or, once, twice, three times, four times, or more daily, in single or divided doses, for 2 months, 3 months, 4 months, 5 months, 6 months, or longer. In one embodiment, the abiraterone is abiraterone acetate.

In one embodiment, for the methods of treating prostate cancer with the combination of the compound of the disclosure and abiraterone acetate, the therapeutically effective amount of the compound of the disclosure is described herein, and the therapeutically effective amount of abiraterone acetate is 1,000 mg administered orally once daily for one, two, three, four, five, six, seven, eight, nine, ten, eleven, twelve, thirteen, fourteen, fifteen, twenty, twenty-five, thirty, or more consecutive days, in single or divided doses. In one embodiment, the abiraterone acetate is administered in combination with 5 mg of prednisone administered orally, twice daily. In one embodiment, the combination of the compound of the disclosure and abiraterone acetate is administered to the subject in need thereof in the fasted state. In one embodiment, the subject does not eat for at least two hours before, and at least one hour after, the administration of the combination of the compound of the disclosure and abiraterone acetate.

In one embodiment, the compound of the disclosure and abiraterone acetate are administered to the subject simultaneously. In one embodiment, the compound of the disclosure and abiraterone acetate are administered to the subject sequentially.

In one embodiment, the compound of the disclosure and the anti-cancer agent are administered to the subject in temporal proximity.

In some embodiments, "temporal proximity" means that administration of the compound of the disclosure occurs within a time period before or after the administration of anti-cancer agent, such that the therapeutic effect of the compound of the disclosure overlaps with the therapeutic effect of the anti-cancer agent. In some embodiments, the therapeutic effect of the compound of the disclosure completely overlaps with the therapeutic effect of the anti-cancer agent. In some embodiments, "temporal proximity" means that administration of the compound of the disclosure occurs within a time period before or after the administration of anti-cancer agent, such that there is a synergistic effect between the compound of the disclosure and the anti-cancer agent. In one embodiment, the anti-cancer agent is abiraterone acetate.

"Temporal proximity" may vary according to various factors, including but not limited to, the age, gender, weight, genetic background, medical condition, disease history, and treatment history of the subject to which the therapeutic agents are to be administered; the disease or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, within an hour, within two hours, within four hours, within six hours, within eight hours, within 12 hours, within 18 hours, within 24 hours, within 36 hours, within 2 days, within 3 days, within 4 days, within 5 days, within 6 days, within a week, within 2 weeks, within 3 weeks, within 4 weeks, with 6 weeks, or within 8 weeks. In some embodiments, multiple administration of one therapeutic agent can occur in temporal proximity to a single administration of another therapeutic agent. In some embodiments, temporal proximity may change during a treatment cycle or within a dosing regimen.

Pharmaceutical Compositions

In one embodiment, the compound of the disclosure is formulated for oral administration. For example, in one embodiment, he compound of the disclosure is formulated as a tablet that comprises zero, one, two, or more of each of the following: emulsifier; surfactant; binder; disintegrant; glidant; and lubricant.

In one embodiment, the emulsifier is hypromellose.

In one embodiment, the surfactant is vitamin E polyethylene glycol succinate.

In one embodiment, the binder (also referred to herein as a filler) is selected from the group consisting of microcrystalline cellulose, lactose monohydrate, sucrose, glucose, and sorbitol.

In one embodiment, the disintegrant is croscarmellose sodium.

In one embodiment, the glidant refers to a substance used to promote powder flow by reducing interparticle cohesion. In one embodiment, in the dosage forms of the disclosure, the glidant is selected from the group consisting of silicon dioxide, silica colloidal anhydrous, starch, and talc.

In one embodiment, the lubricant refers to a substance that prevents ingredients from sticking and/or clumping together in the machines used in preparation of the dosage forms of the disclosure. In one embodiment, in the dosage forms of the disclosure, the lubricant is selected from the group consisting of magnesium stearate, sodium stearyl fumarate, stearic acid, and vegetable stearin.

The pharmaceutical compositions containing the compound of the disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the compound of the disclosure into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N. J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound of the disclosure in the required amount in an appropriate solvent with one or a combination of ingredients enumerated above, as required, followed by filtered sterilization. Generally, dispersions are prepared by incorporating the active agent or compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the compound of the disclosure can be incorporated with excipients and used in the form of tablets, troches, or capsules. Oral compositions can also be prepared using a fluid carrier for use as a mouthwash, wherein the agent or compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

For administration by inhalation, the agents or compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents or compounds are formulated into ointments, salves, gels, or creams as generally known in the art.

In one aspect, the compound of the disclosure is prepared with pharmaceutically acceptable carriers that will protect the agent or compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active agent or compound calculated to produce the desired therapeutic effect in association with the required pharmaceutical carrier. The specification for the dosage unit forms of the application are dictated by and directly dependent on the unique characteristics of the compound of the disclosure and the particular therapeutic effect to be achieved.

The pharmaceutical compositions can be included in a container, pack, or dispenser together with instructions for administration.

Illustrative modes of administration for the compound of the disclosure includes systemic or local administration such as oral, nasal, parenteral, transdermal, subcutaneous, vaginal, buccal, rectal or topical administration modes. In one embodiment, the compound of the disclosure is administered orally. In one embodiment, the compound of the disclosure is administered as a tablet, capsule, caplet, solution, suspension, syrup, granule, bead, powder, or pellet.

Illustrative pharmaceutical compositions are tablets and gelatin capsules comprising a salt of the compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the salt such as cyclodextrin, hydroxypropyl-cyclodextrin, PEG400, and/or PEG200.

For preparing pharmaceutical compositions from the compound of the disclosure, or a salt or hydrate thereof, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed salt is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, intrathecal, subcutaneous or intramuscular form, and all using forms well known to those skilled in the pharmaceutical arts.

Pharmaceutical compositions can be prepared according to conventional mixing, granulating or coating methods, respectively, and the present pharmaceutical compositions can contain from about 0.1% to about 99%, from about 5% to about 90%, or from about 1% to about 20% of the disclosed free base or salt by weight or volume.

The pharmaceutical compositions containing the compound of the disclosure may further comprising one or more additional anti-cancer agents, including any of those disclosed herein.

All amounts of any component of an oral dosage form described herein, e.g., a tablet, that are indicated based on % w/w refer to the total weight of the oral dosage form, unless otherwise indicated.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Abbreviations:
ACN: acetonitrile
ADDP: 1,1'-(azodicarbonyl)dipiperidine
BAST: N,N-bis(2-methoxyethyl)aminosulfur trifluoride
Binap: 2,2'-bis(diphenylphosphino)-1,1'-binaphthyl
Boc: tert-butoxycarbonyl
BPO: benzoyl peroxide
Cbz: Carbonylbezyloxy
DAST: diethylaminosulfur trifluoride
DBE: 1,2-dibromoethane
DCE: 1,2-dichloroethane
DCM: dichloromethane
DEAD: diethyl azodicarboxylate
DIAD: diisopropyl azodicarboxylate
DIBAL: disiobutylaluminium hydride
DIEA or DIPEA: diisopropylethylamine
DMA: N,N-dimethylacetamide
DMF: N,N-dimethylformamide
DMP: Dess-Martin periodinane
DMSO: Dimethylsulfoxide
EA: ethyl acetate
EDCI: 1-ethyl-3-(3-dimethylaminopropyl)carbodiimide
HATU: 1-[bis(dimethylamino)methylene]-1H-1,2,3-triazolo[4,5-b]pyridinium 3-oxide hexafluorophosphate
HBTU: N,N,N'N'-tetramethyl-O-(1H-benzotriazol-1-yl)uronium hexafluorophosphate
HMDS: bis(trimethylsilyl)amine
HOBt: hydroxybenzotriazole
HPLC: High Performance Liquid Chromatography
HMPA: hexamethylphosphoramide
LDA: lithium diisopropylamide
LCMS: Liquid Chromatography—Mass Spectrometry
MCPBA: meta-chloroperoxybenzoic acid
MsCl: methanesulfonyl chloride
M.W: microwave
NBS: A-bromosuccinimide
NMM: N-methylmorpholine
NMP: N-methylpyrrolidone
PCC: pyridinium chlorochromate
Pd-118 or Pd(dtpf)Cl$_2$: 1,1'-bis(di-tert-butylphosphino)ferrocene dichloropalladium
Pd(dppf)Cl$_2$: 1,1'-bis(diphenylphosphino)ferrocene dichloropalladium
Pd(dba)$_2$: bis(dibenzylideneacetone)palladium
Pd$_2$(dba)$_3$: Tris(dibenzylideneacetone)dipalladium
PPTS: pyridium p-toluenesulfonate
PTSA: p-toluenesulfonic acid
RuPhos-Pd-G3: XPhos-Pd-G3: [(2-dicyclohexylphosphino-2',6'-diisopropoxy-1,1'-biphenyl)-2-(2'-amino-1,1'-biphenyl)] palladium(II) methanesulfonate
RuPhos-Pd-G2: Chloro[(2-dicyclohexylphosphino-2',6'-diisopropoxy-1,1'-biphenyl)-2-(2'-amino-1,1'-biphenyl)] palladium(II)
SEM-Cl: 2-(trimethylsilyl)ethoxymethyl chloride
SFC: supercritical fluid chromatography
STAB: sodium triacetoxyborohydride
t-BuXPhos-Pd-G3: [(2-di-tert-butylphosphino-2',4',6'-triisopropyl-1,1'-biphenyl)-2-(2'-amino-1,1'-biphenyl)] palladium(II) methanesulfonate
TEA: triethylamine
THF: tetrahydrofuran
TFA: trifluoroacetic acid
TLC: thin layer chromatography
TMP: 2,2,6,6-tetramethylpiperidine
TEMPO: 2,2,6,6-tetramethylpiperidine-N-oxide TosCl or TsCl: p-toluenesulfonyl chloride
TsOH: p-toluenesulfonic acid
XantPhos: 4,5-bis(diphenylphosphino)-9,9-dimethylxanthene
XPhos: 2-dicyclohexylphosphino-2', 4', 6'-triisopropylbiphenyl XPhos-Pd-G3: [(2-dicyclohexylphosphino-2', 4',6'-triisopropyl-1,1'-biphenyl)-2-(2'-amino-1,1'-biphenyl)] palladium(II) methanesulfonate 12354-85-7: bis(pentamethylcyclopentadienylrhodium dichloride)

Example 1—Compounds of the Disclosure

| Compound No. | Compound Structure |
|---|---|
| 1 | 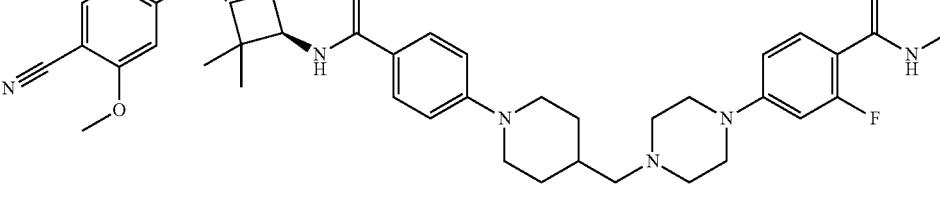 |
| 2 | 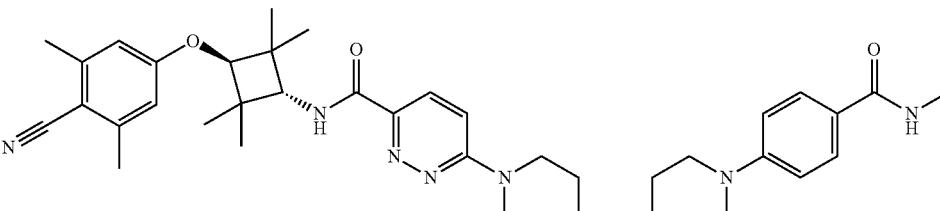 |
| 3 | 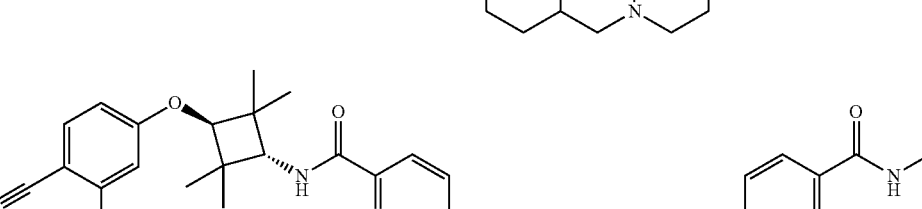 |
| 4 | 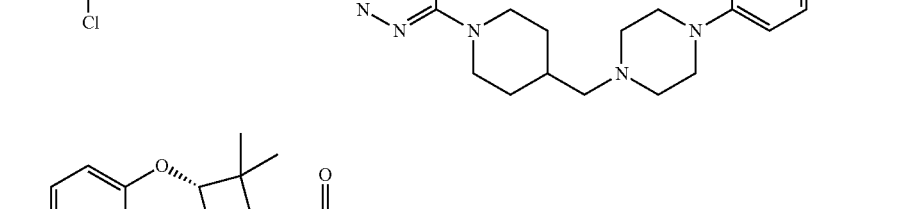 |
| 5 | 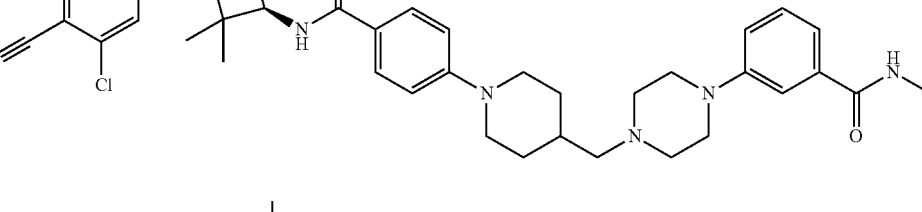 |

-continued

| Compound No. | Compound Structure |
|---|---|
| 6 | 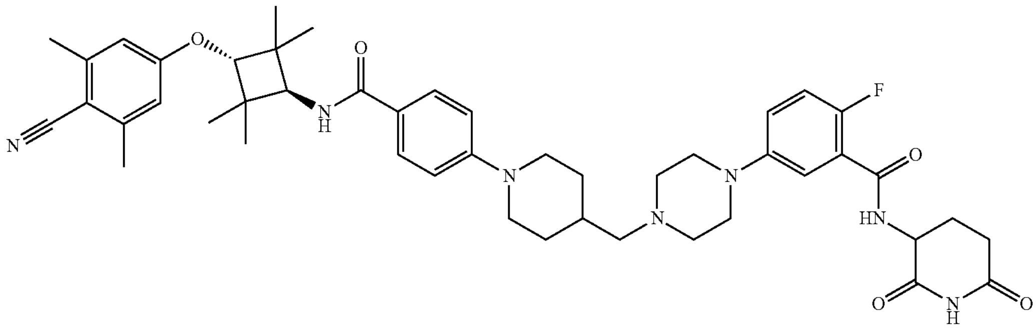 |
| 7 | 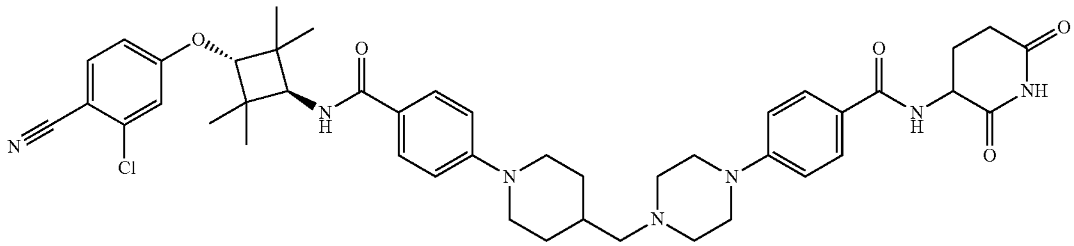 |
| 8 | 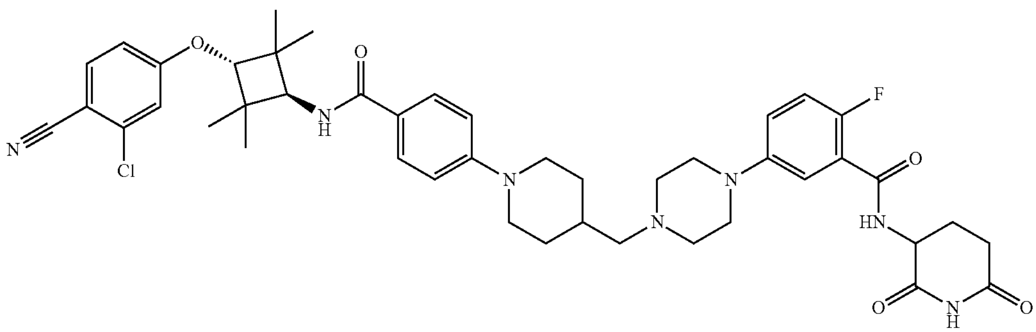 |
| 9 | 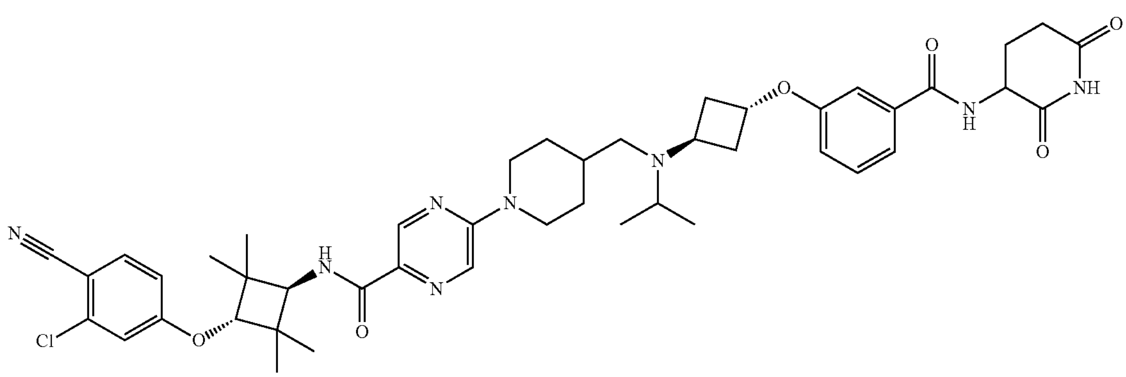 |
| 10 | 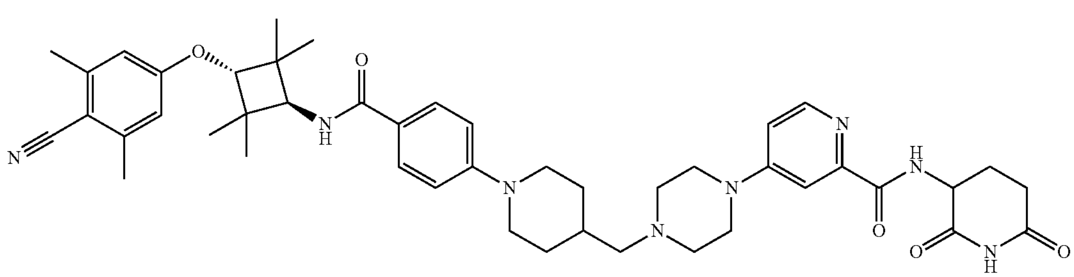 |

-continued
| Compound No. | Compound Structure |
|---|---|
| 11 | 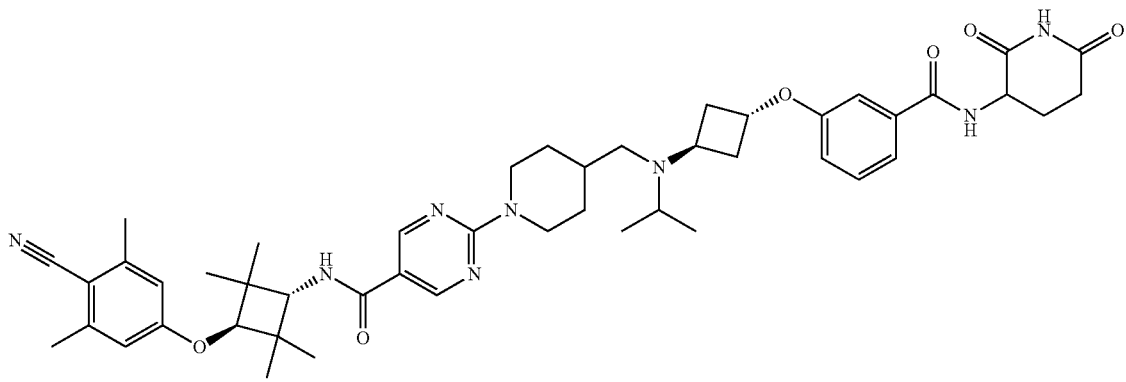 |
| 12 | 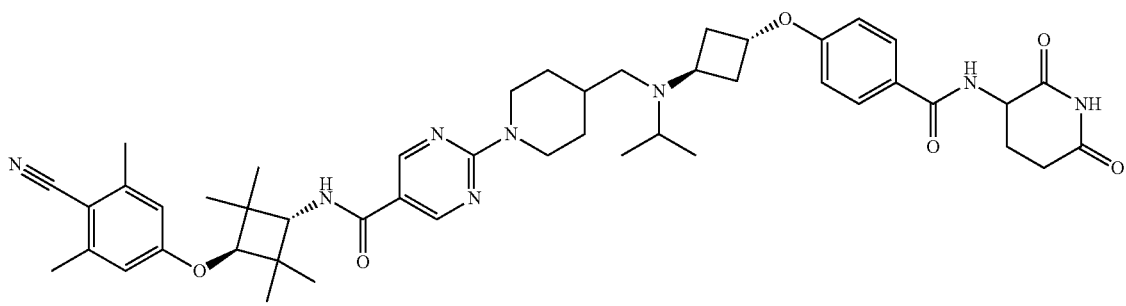 |
| 13 | 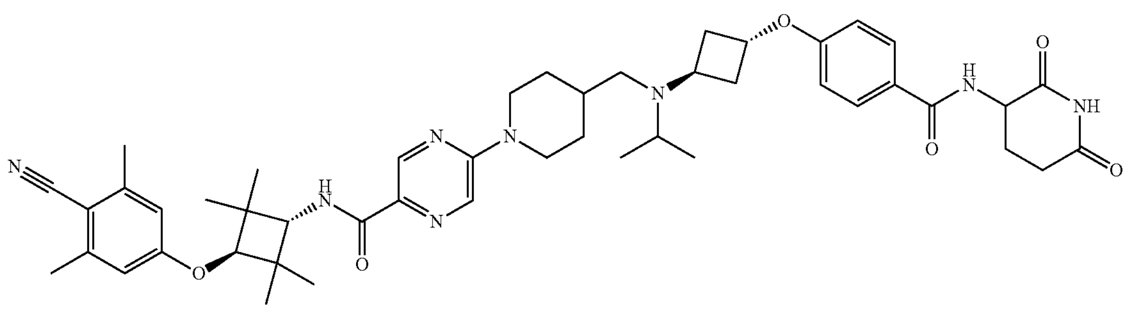 |
| 14 | 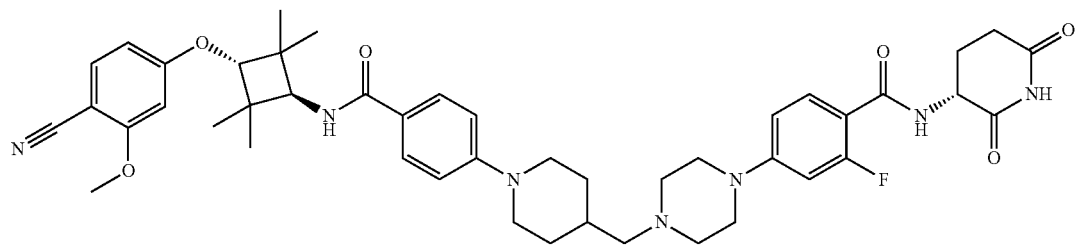 |

| Compound No. | Compound Structure |
|---|---|
| 15 | 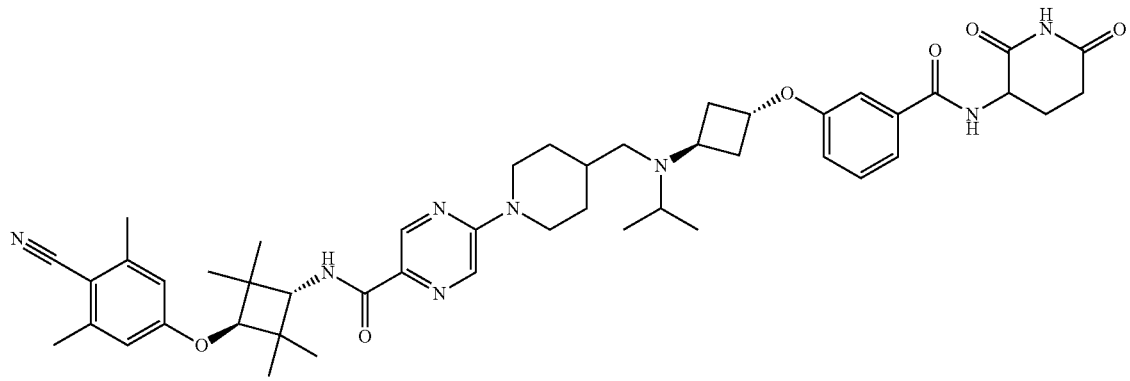 |
| 16 | 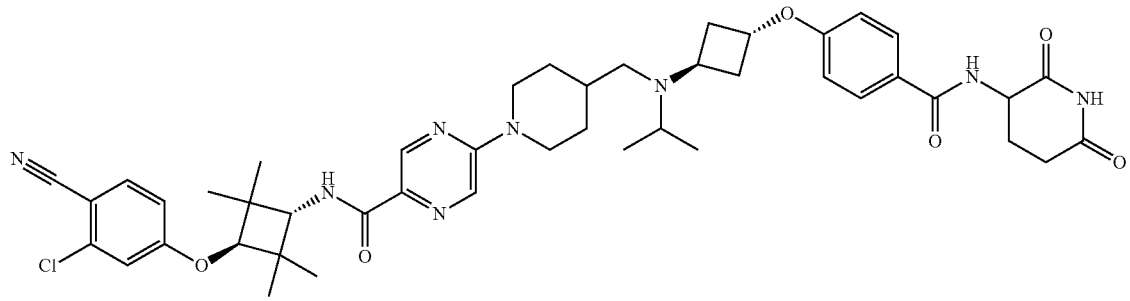 |
| 17 | 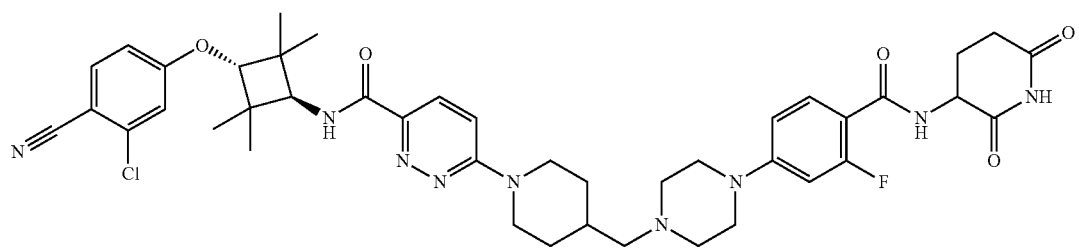 |
| 18 | 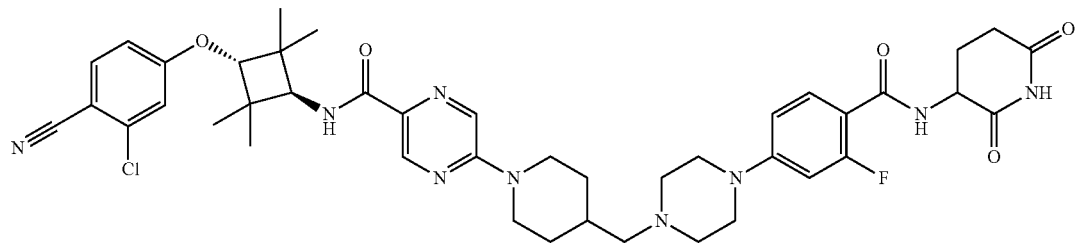 |
| 19 | 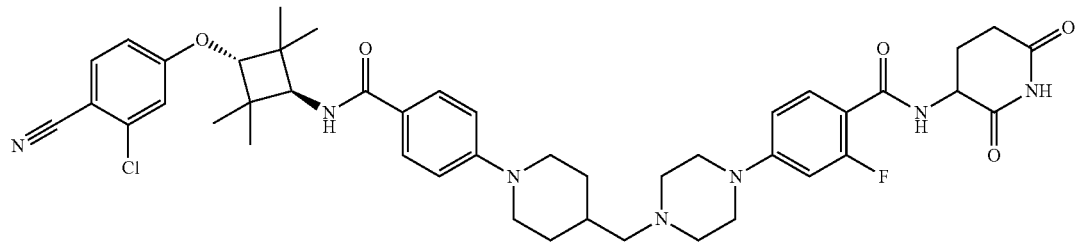 |

| Compound No. | Compound Structure |
|---|---|
| 20 | 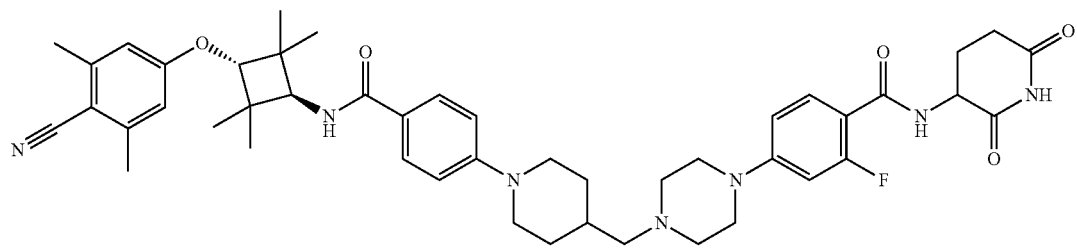 |
| 21 | 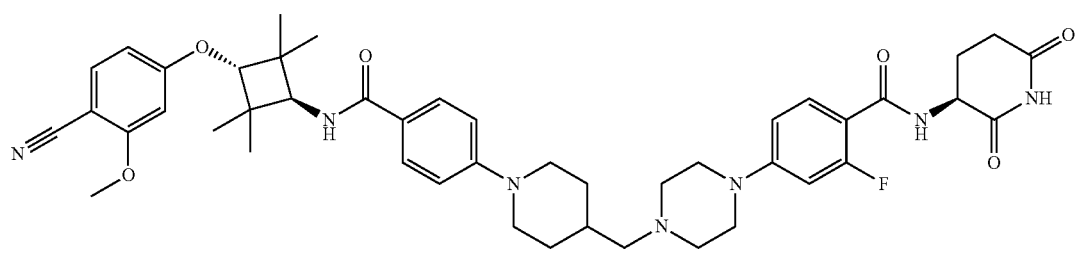 |
| 22 | 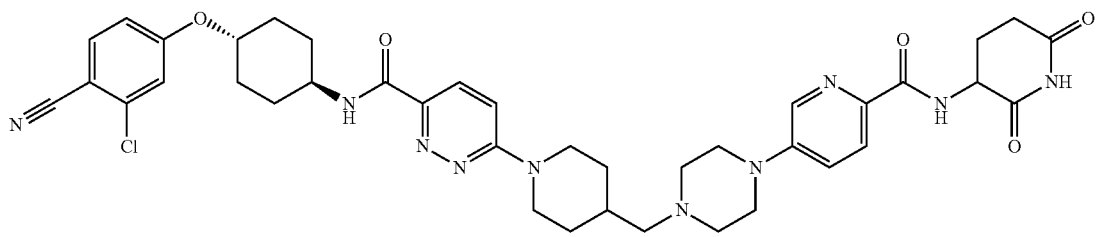 |
| 23 | 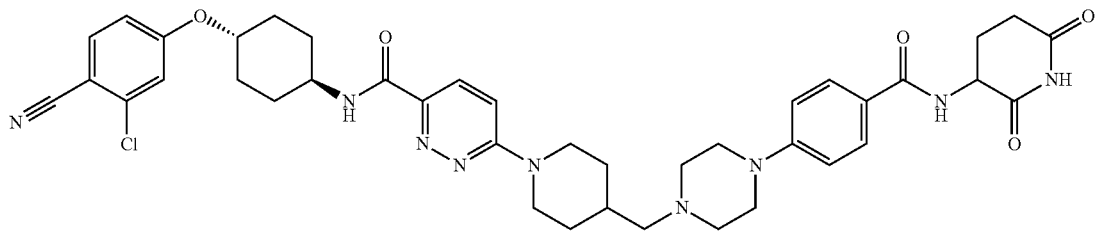 |
| 24 | 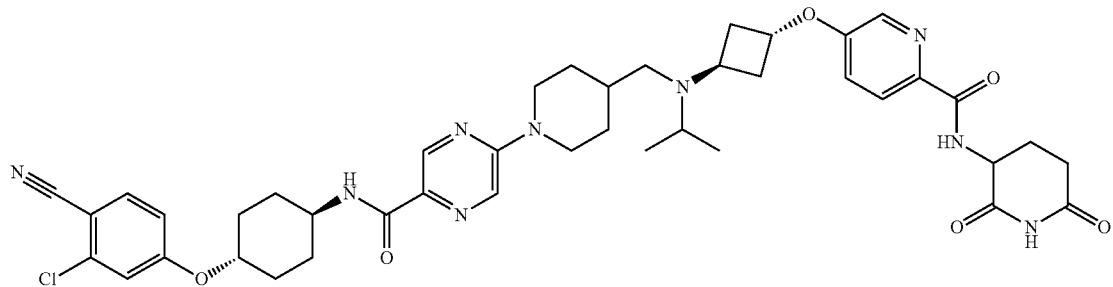 |

-continued
| Compound No. | Compound Structure |
|---|---|
| 25 | 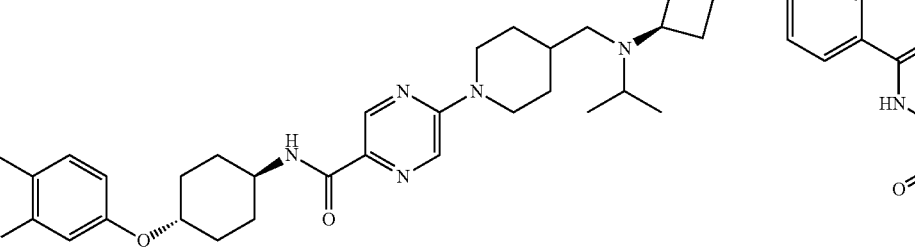 |
| 26 | 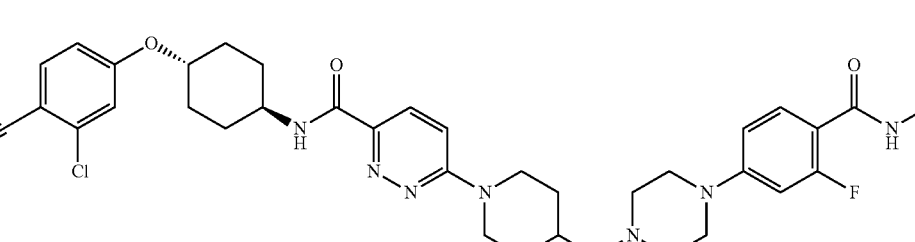 |
| 27 | 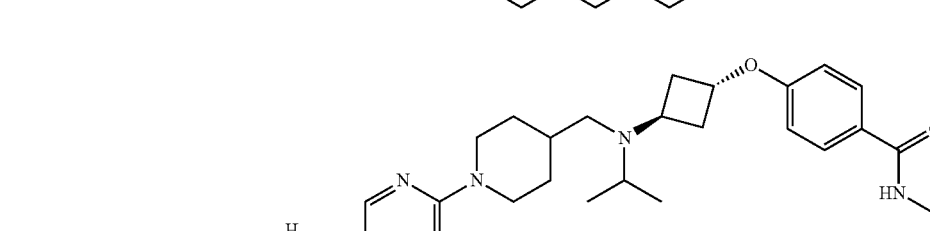 |
| 28 | 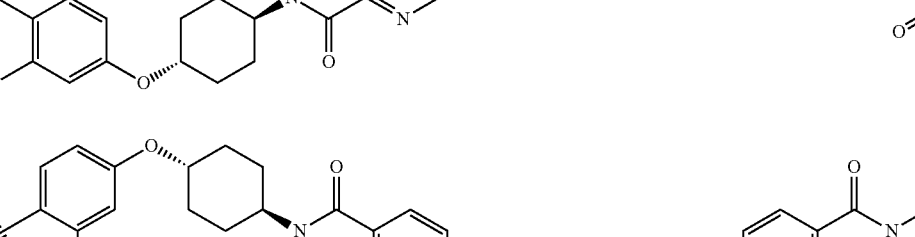 |
| 29 | 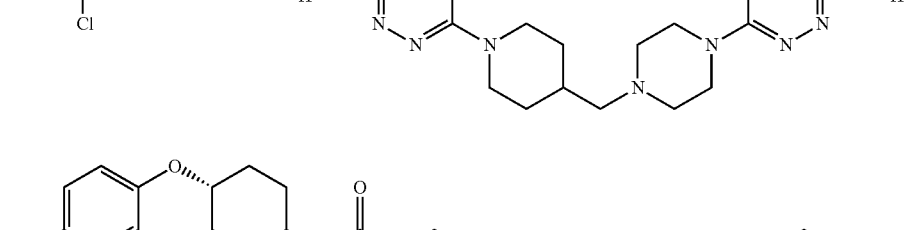 |

-continued
| Compound No. | Compound Structure |
|---|---|
| 30 | 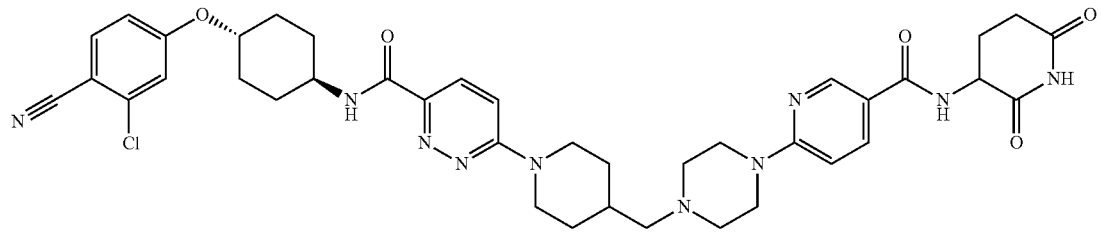 |
| 31 | 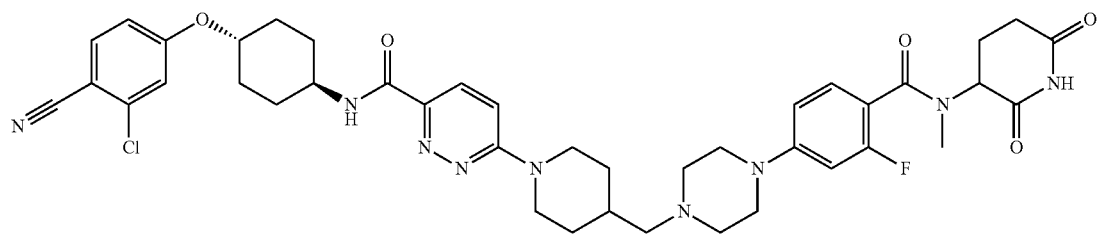 |
| 32 | 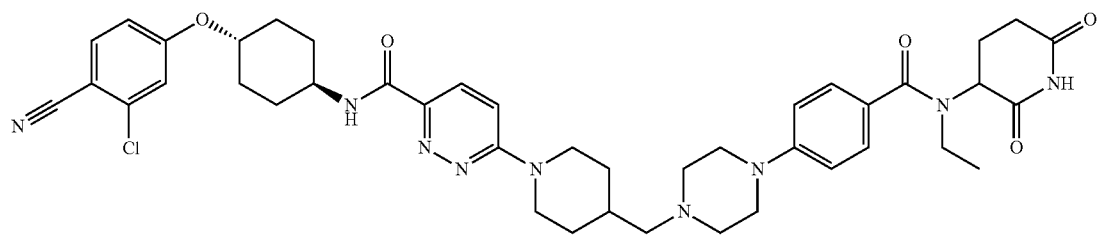 |
| 33 | 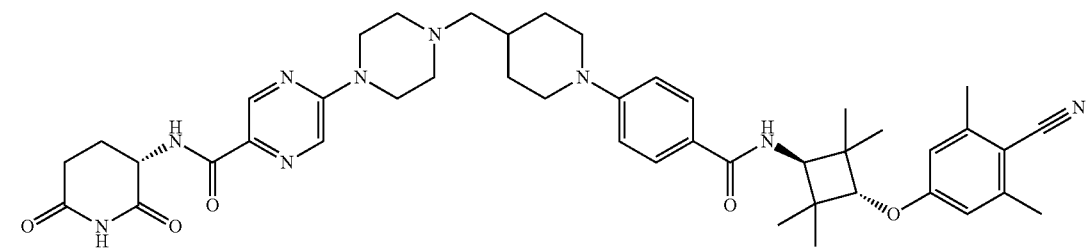 |
| 34 | 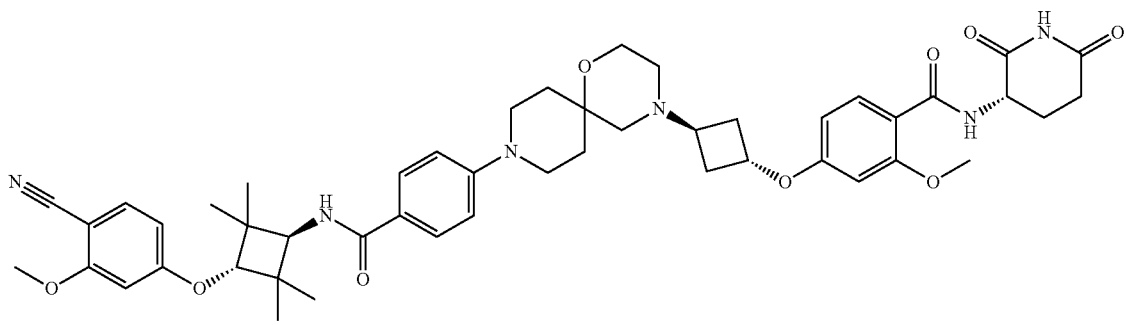 |

| Compound No. | Compound Structure |
|---|---|
| 35 | 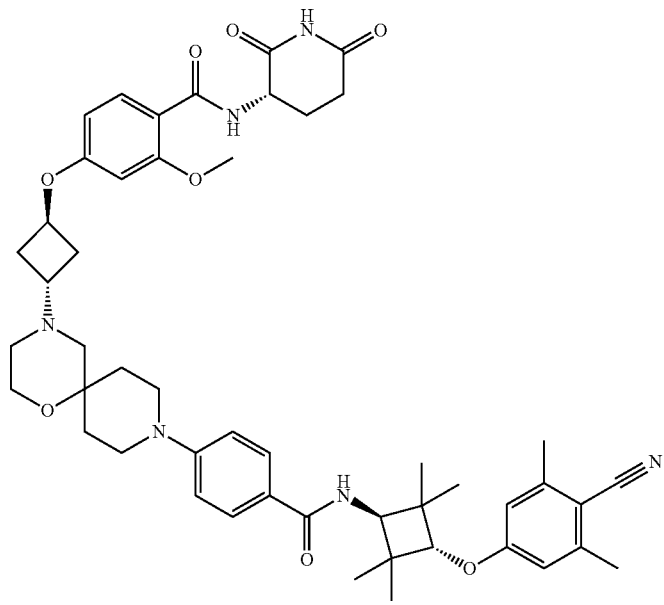 |
| 36 | 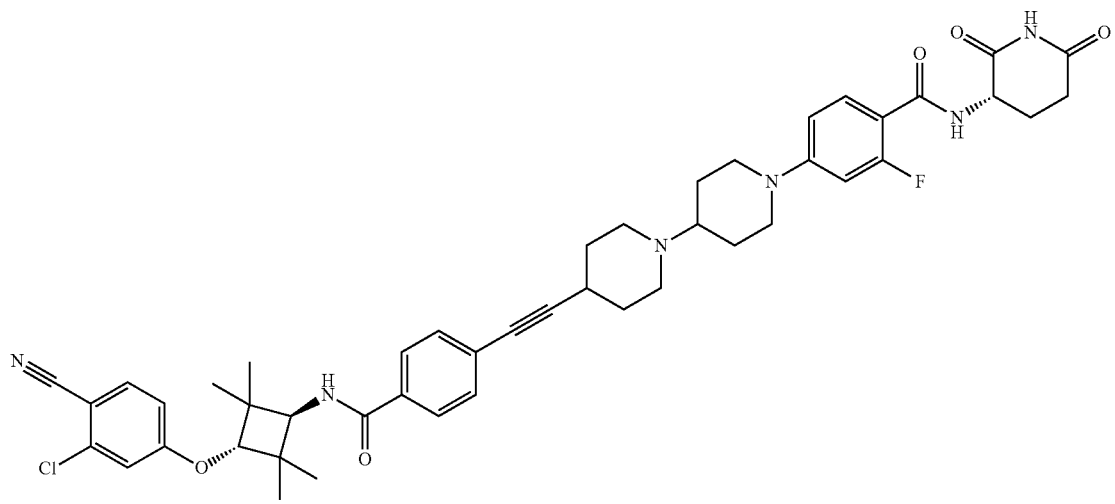 |
| 37 | 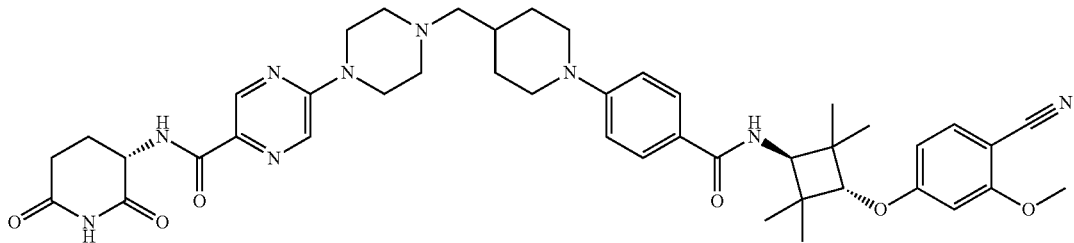 |

| Compound No. | Compound Structure |
| --- | --- |
| 38 | 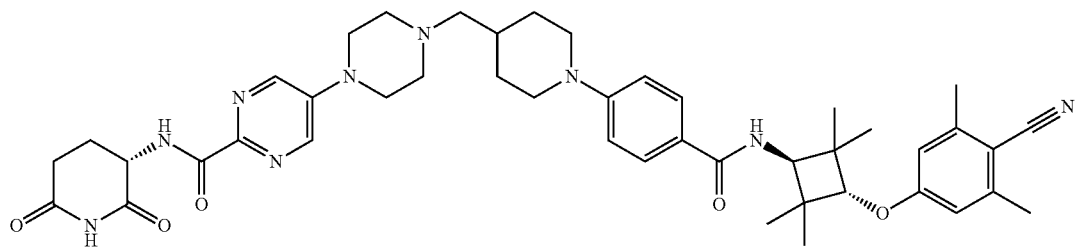 |
| 39 | 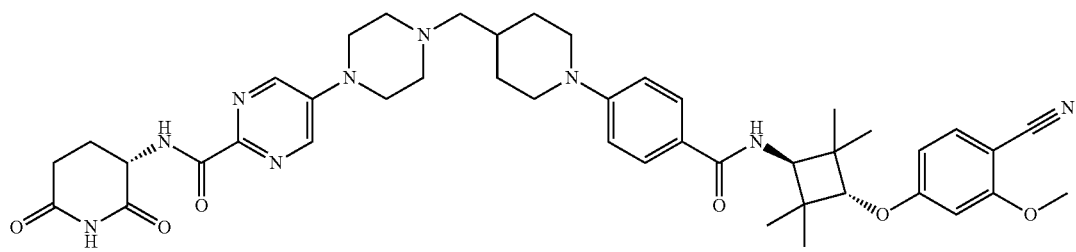 |
| 40 | 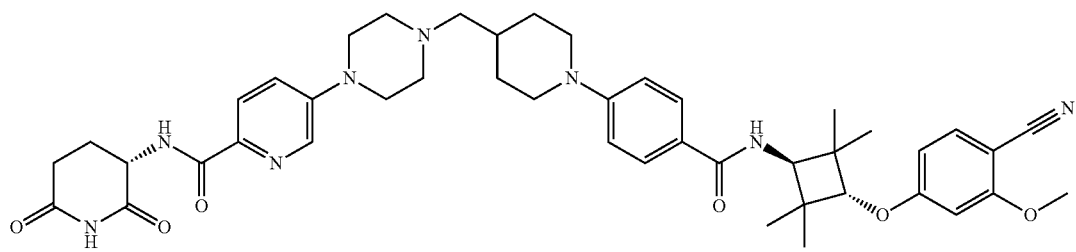 |
| 41 | 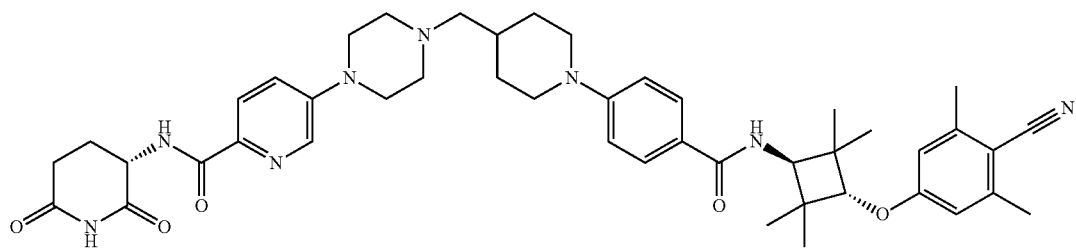 |
| 42 | 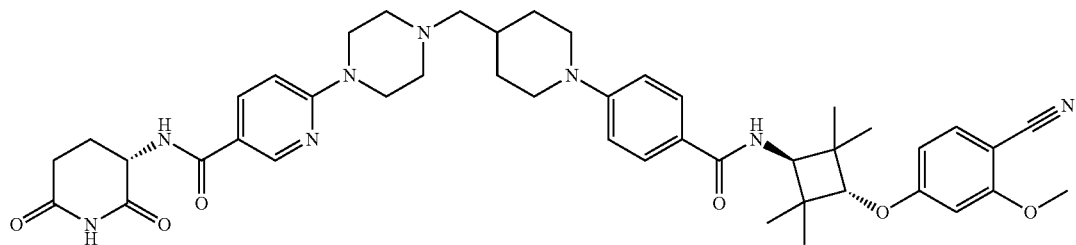 |

| Compound No. | Compound Structure |
|---|---|
| 43 | 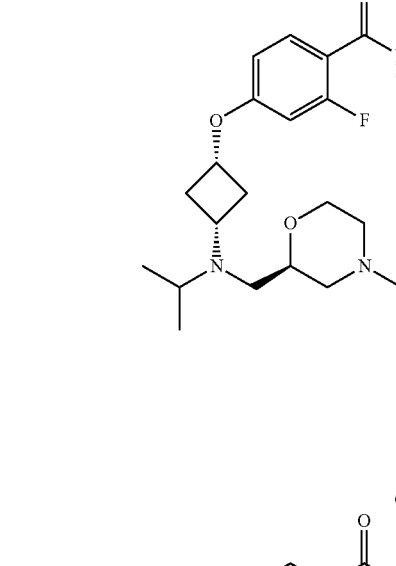 |
| 44 | 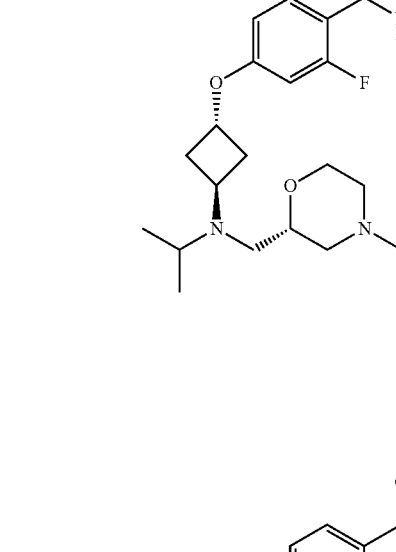 |
| 45 | 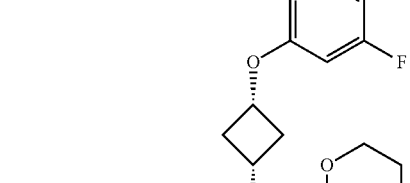 |

| Compound No. | Compound Structure |
|---|---|
| 46 | 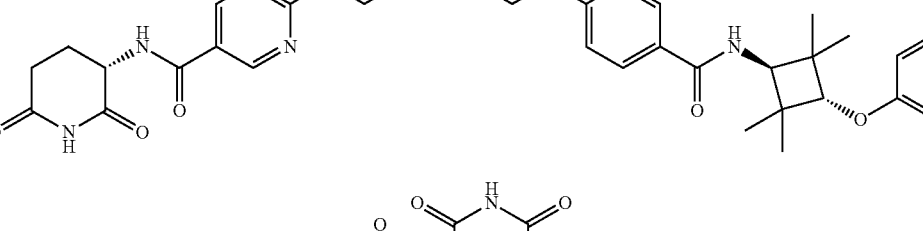 |
| 47 | 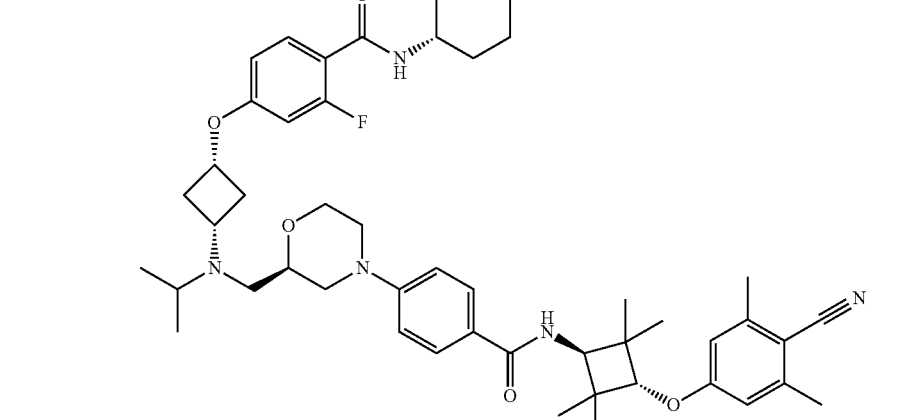 |
| 48 | 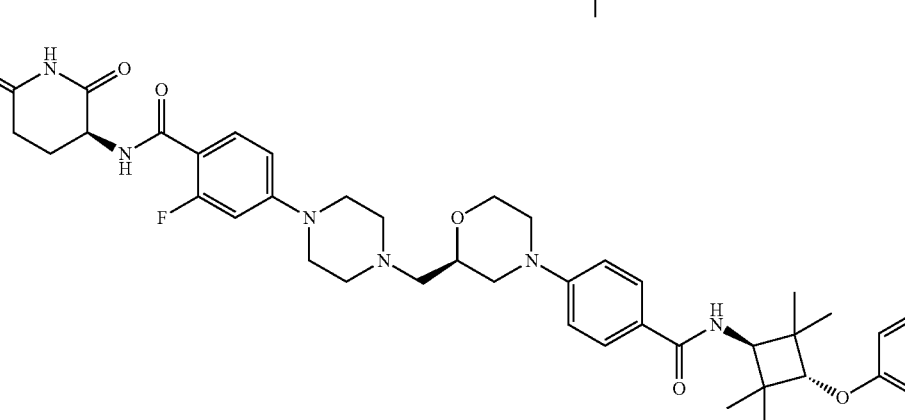 |
| 49 | 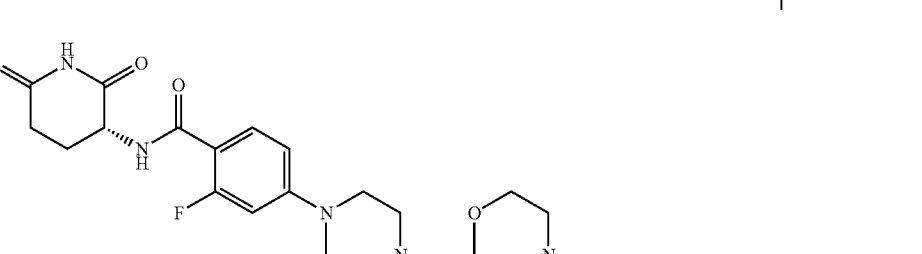 |

| Compound No. | Compound Structure |
|---|---|
| 50 | 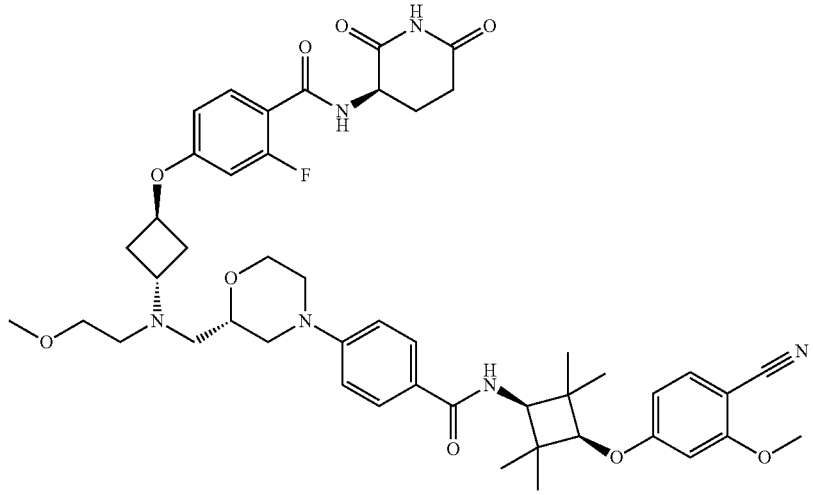 |
| 51 | 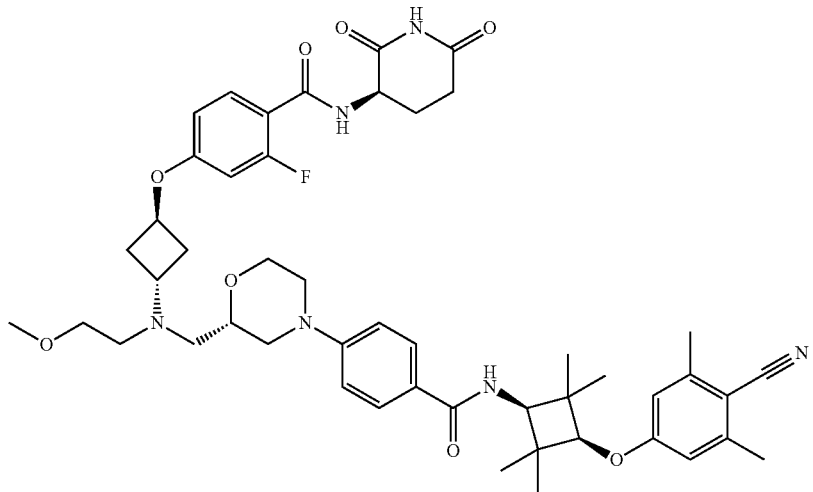 |
| 52 | 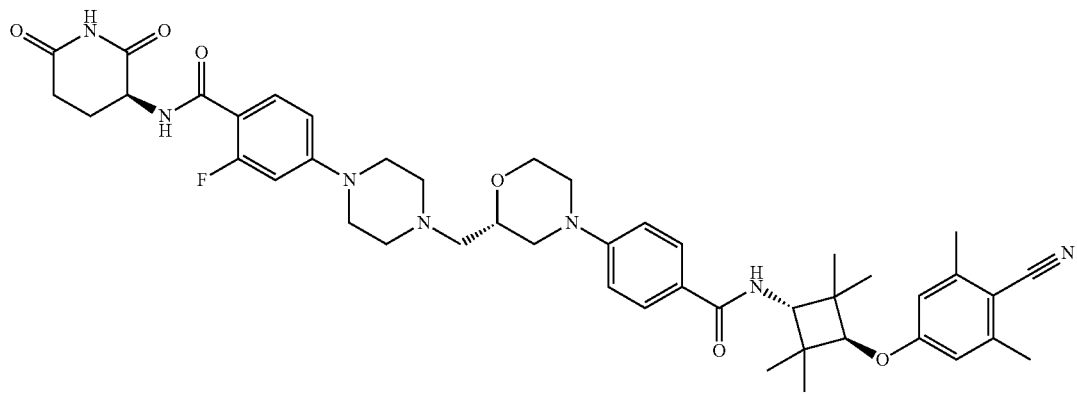 |

| Compound No. | Compound Structure |
|---|---|
| 53 | 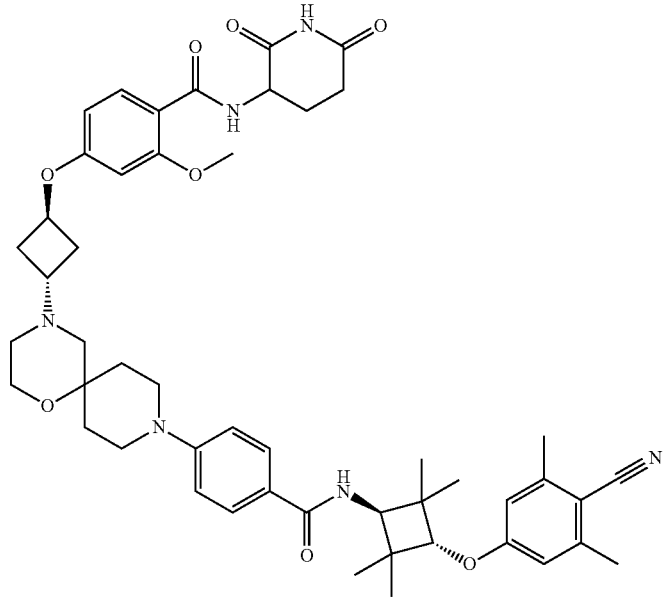 |
| 54 | 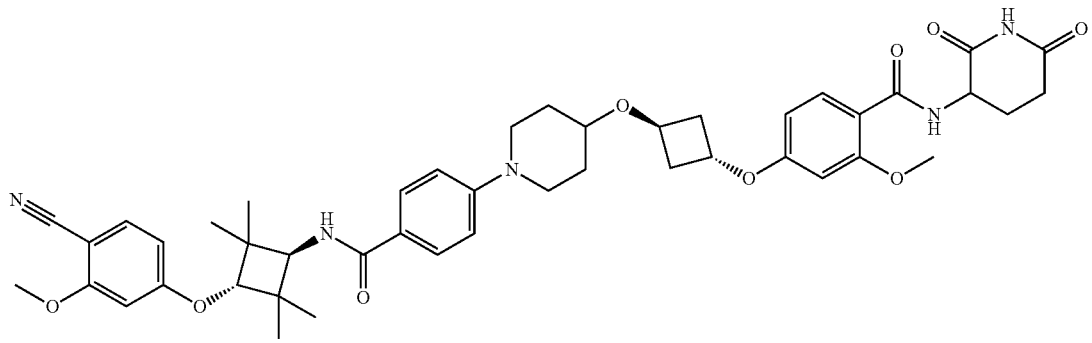 |
| 55 | 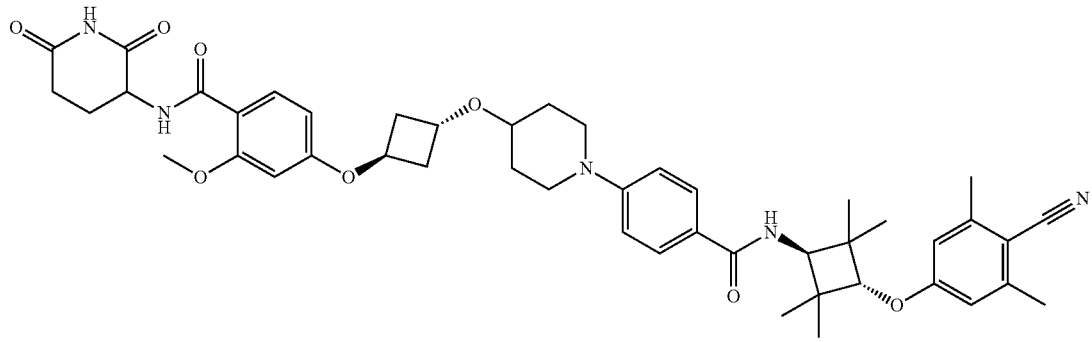 |

| Compound No. | Compound Structure |
|---|---|
| 56 | 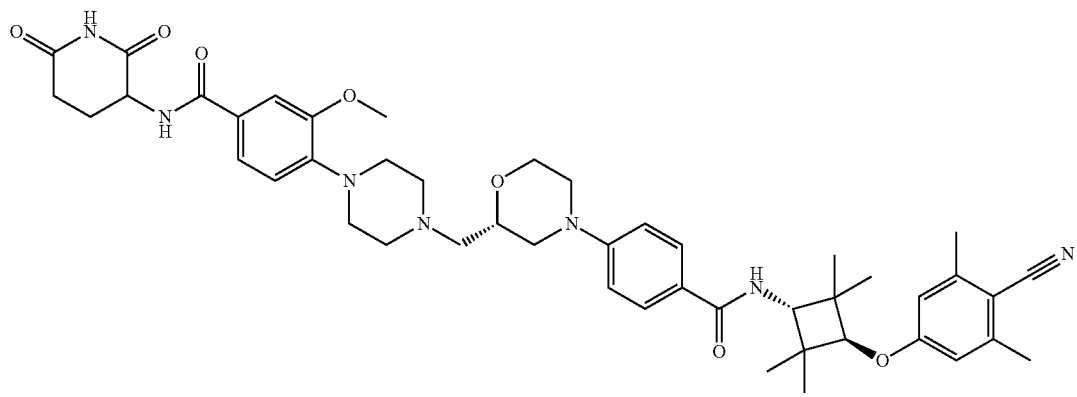 |
| 57 | 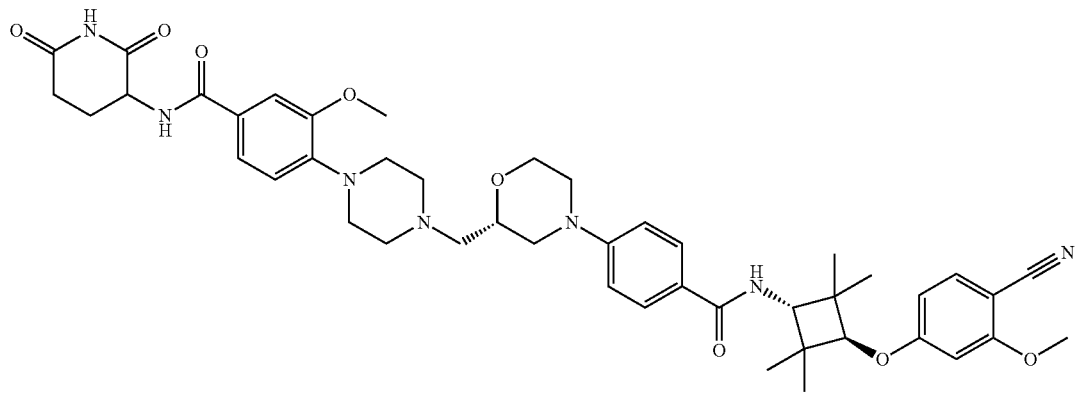 |
| 58 | 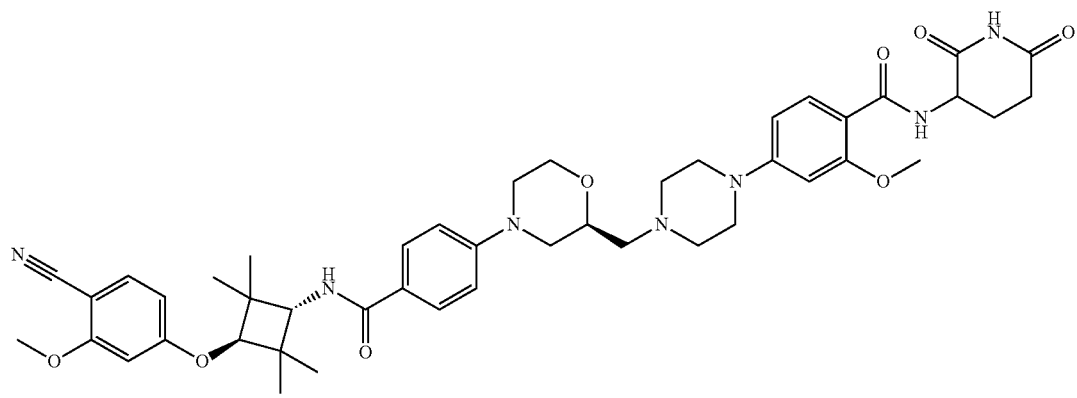 |

| Compound No. | Compound Structure |
|---|---|
| 59 | 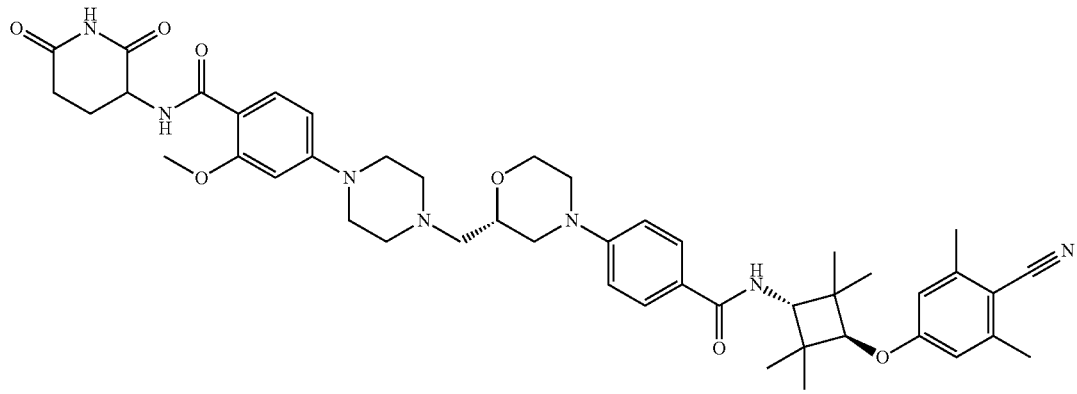 |
| 60 | 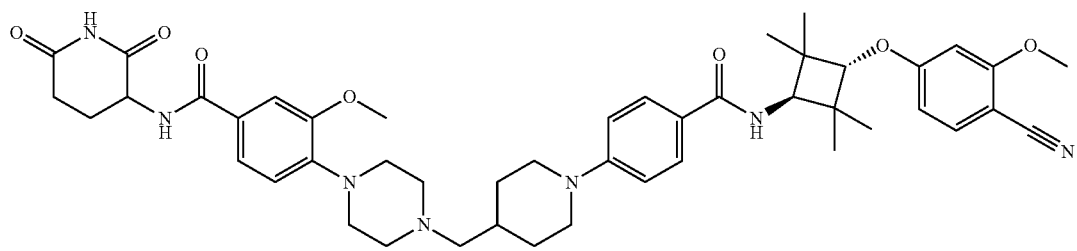 |
| 61 | 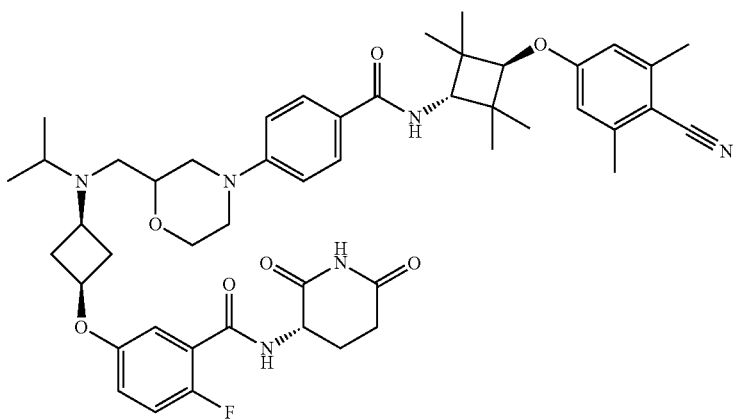 |
| 62 | 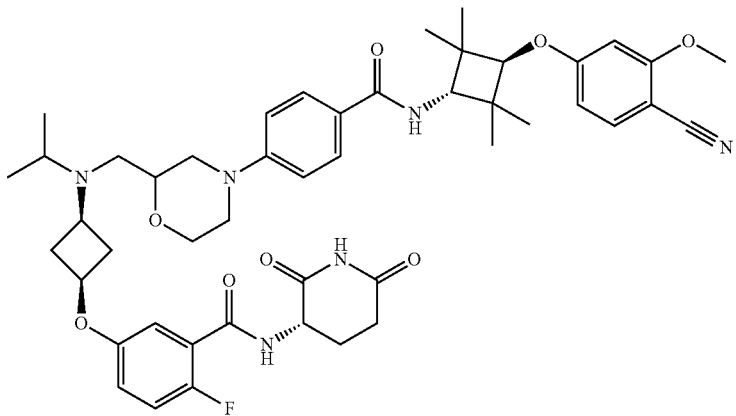 |

-continued
| Compound No. | Compound Structure |
|---|---|
| 63 | 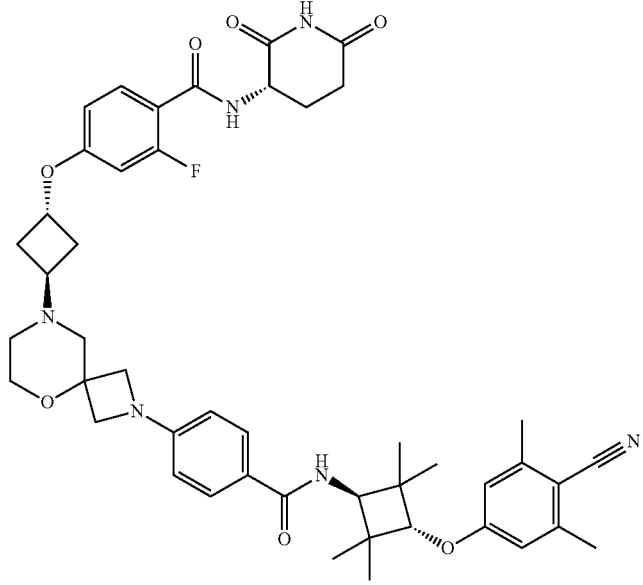 [SMILES: Cc1cc(O[C@H]2C(C)(C)[C@H](NC(=O)c3ccc(N4CC5(C4)CN([C@H]4C[C@H](Oc6ccc(C(=O)N[C@H]7CCC(=O)NC7=O)c(F)c6)C4)CCO5)cc3)C2(C)C)cc(C)c1C#N] |
| 64 | 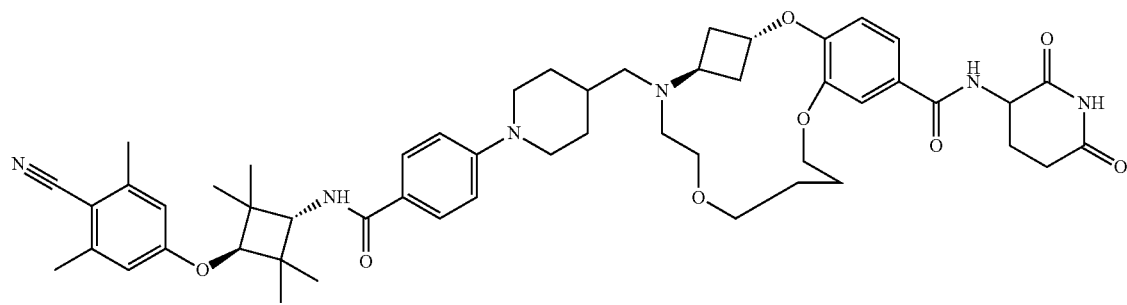 [SMILES: Cc1cc(O[C@H]2C(C)(C)[C@H](NC(=O)c3ccc(N4CCC(CN5CCOCCCCOc6cc(C(=O)NC7CCC(=O)NC7=O)ccc6O[C@H]6C[C@H]5C6)CC4)cc3)C2(C)C)cc(C)c1C#N] |
| 65 | 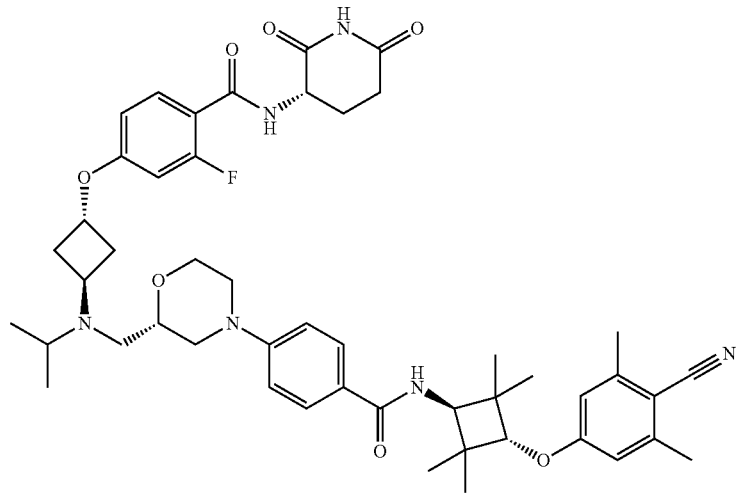 [SMILES: Cc1cc(O[C@H]2C(C)(C)[C@H](NC(=O)c3ccc(N4CCO[C@@H](CN(C(C)C)[C@H]5C[C@H](Oc6ccc(C(=O)N[C@H]7CCC(=O)NC7=O)c(F)c6)C5)C4)cc3)C2(C)C)cc(C)c1C#N] |

| Compound No. | Compound Structure |
|---|---|
| 66 | 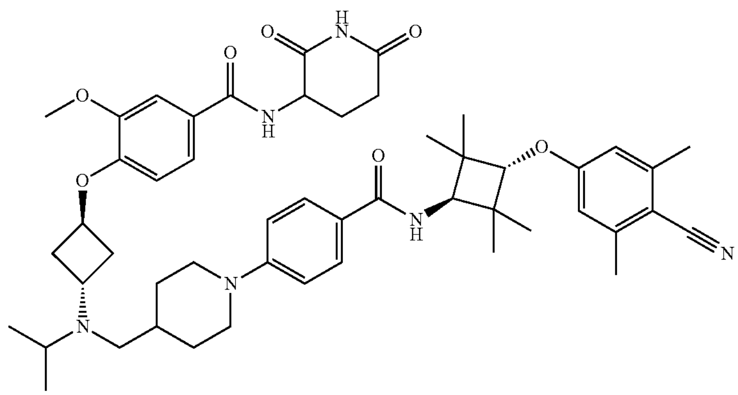 [SMILES: COc1cc(C(=O)NC2CCC(=O)NC2=O)ccc1O[C@H]1C[C@H](N(CC2CCN(c3ccc(C(=O)N[C@H]4C(C)(C)[C@H](Oc5cc(C)c(C#N)c(C)c5)C4(C)C)cc3)CC2)C(C)C)C1] |
| 67 | 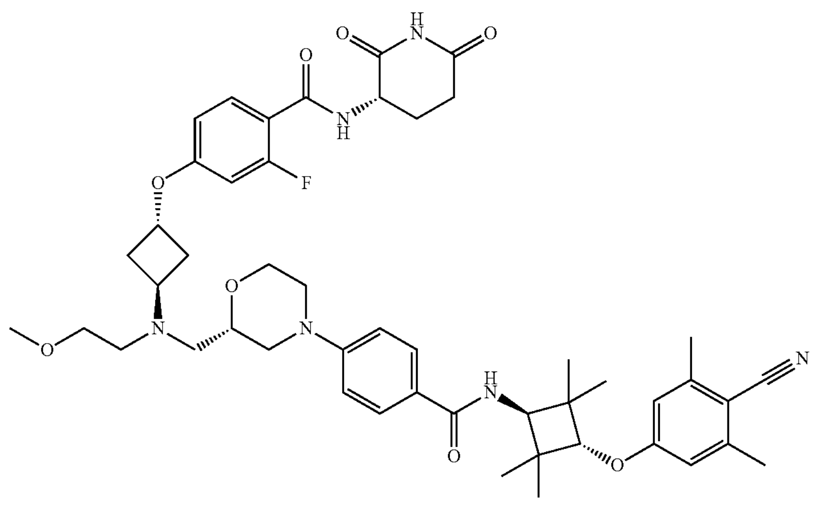 [SMILES: COCCN(C[C@H]1CN(c2ccc(C(=O)N[C@H]3C(C)(C)[C@H](Oc4cc(C)c(C#N)c(C)c4)C3(C)C)cc2)CCO1)[C@H]1C[C@H](Oc2ccc(C(=O)N[C@H]3CCC(=O)NC3=O)c(F)c2)C1] |
| 68 | 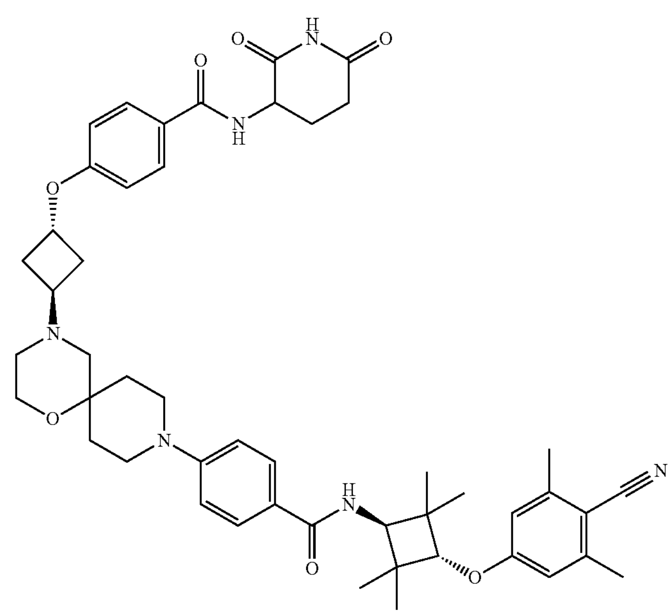 [SMILES: Cc1cc(O[C@H]2C(C)(C)[C@H](NC(=O)c3ccc(N4CCC5(CC4)CN([C@H]4C[C@H](Oc6ccc(C(=O)NC7CCC(=O)NC7=O)cc6)C4)CCO5)cc3)C2(C)C)cc(C)c1C#N] |

US 11,883,393 B2
203                                                                 204
-continued
| Compound No. | Compound Structure |
|---|---|
| 69 | 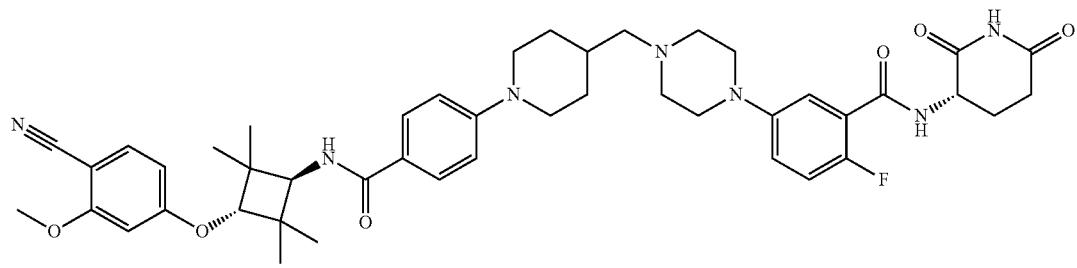 [SMILES: COc1cc(O[C@H]2C(C)(C)[C@H](NC(=O)c3ccc(N4CCC(CN5CCN(c6ccc(F)c(C(=O)N[C@H]7CCC(=O)NC7=O)c6)CC5)CC4)cc3)C2(C)C)ccc1C#N] |
| 70 | 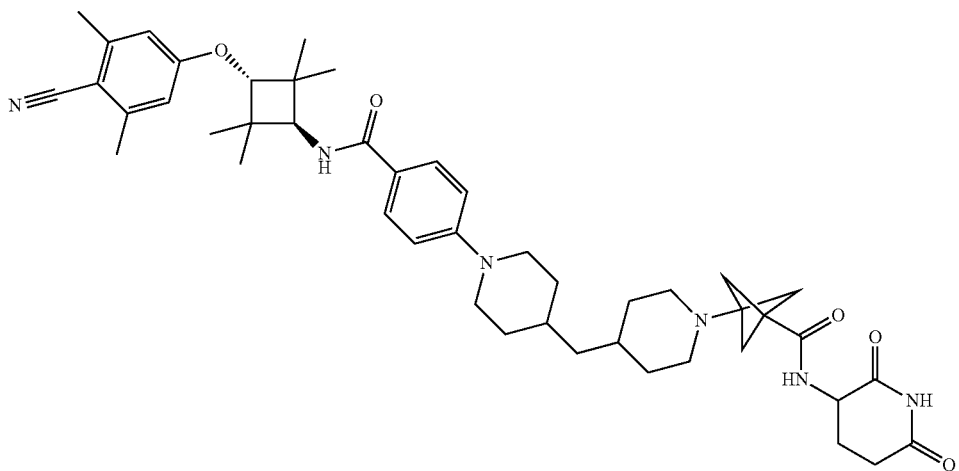 [SMILES: Cc1cc(O[C@H]2C(C)(C)[C@H](NC(=O)c3ccc(N4CCC(CC5CCN(C67CC(C(=O)NC8CCC(=O)NC8=O)(C6)C7)CC5)CC4)cc3)C2(C)C)cc(C)c1C#N] |
| 71 | 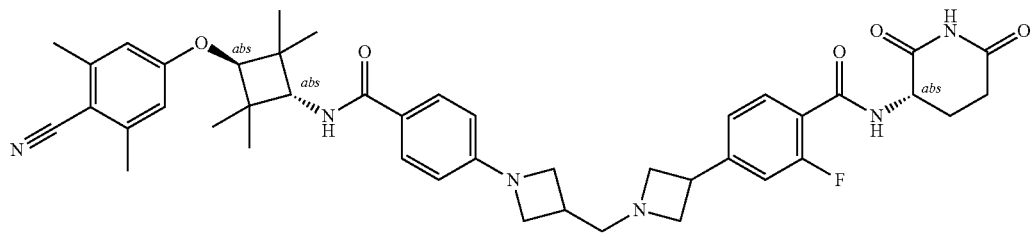 [SMILES: Cc1cc(O[C@H]2C(C)(C)[C@H](NC(=O)c3ccc(N4CC(CN5CC(c6ccc(C(=O)N[C@H]7CCC(=O)NC7=O)c(F)c6)C5)C4)cc3)C2(C)C)cc(C)c1C#N] |
| 72 | 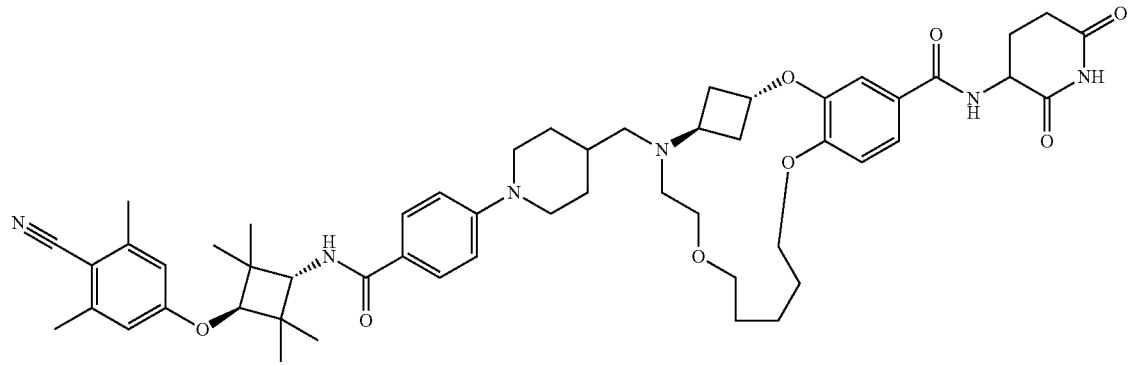 [SMILES: Cc1cc(O[C@H]2C(C)(C)[C@H](NC(=O)c3ccc(N4CCC(CN5CCOCCCCCOc6ccc(C(=O)NC7CCC(=O)NC7=O)cc6O[C@H]6C[C@H]5C6)CC4)cc3)C2(C)C)cc(C)c1C#N] |

-continued
| Compound No. | Compound Structure |
|---|---|
| 73 | 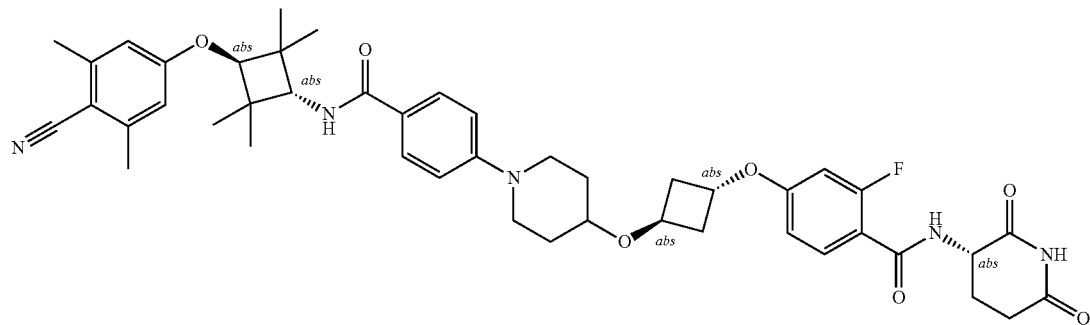 [SMILES: Cc1cc(O[C@H]2C(C)(C)[C@H](NC(=O)c3ccc(N4CCC(O[C@H]5C[C@H](Oc6ccc(C(=O)N[C@H]7CCC(=O)NC7=O)c(F)c6)C5)CC4)cc3)C2(C)C)cc(C)c1C#N] |
| 74 | 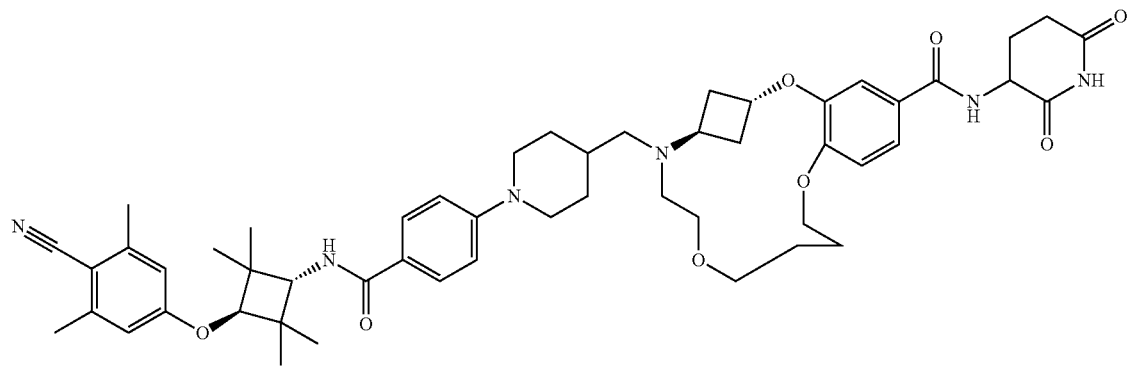 [SMILES: Cc1cc(O[C@H]2C(C)(C)[C@H](NC(=O)c3ccc(N4CCC(CN5CCOCCCCOc6ccc(C(=O)NC7CCC(=O)NC7=O)cc6O[C@H]6C[C@H]5C6)CC4)cc3)C2(C)C)cc(C)c1C#N] |
| 75 | 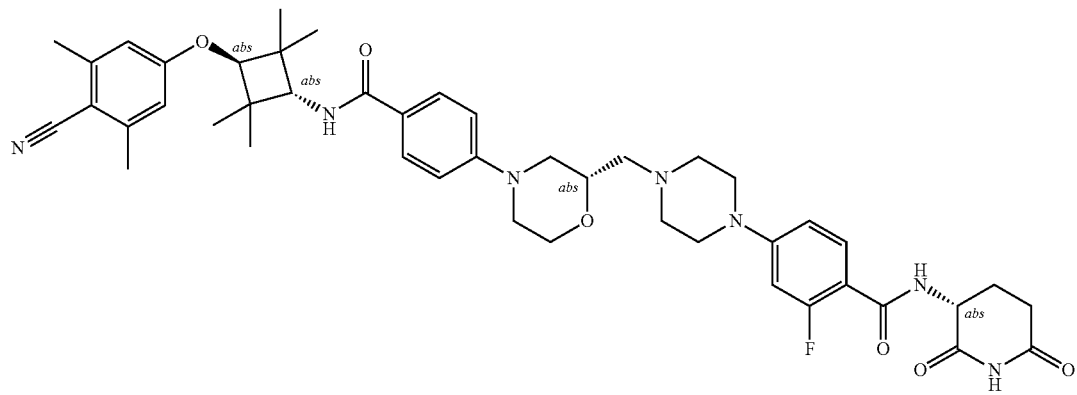 [SMILES: Cc1cc(O[C@H]2C(C)(C)[C@H](NC(=O)c3ccc(N4CCO[C@@H](CN5CCN(c6ccc(C(=O)N[C@@H]7CCC(=O)NC7=O)c(F)c6)CC5)C4)cc3)C2(C)C)cc(C)c1C#N] |
| 76 | 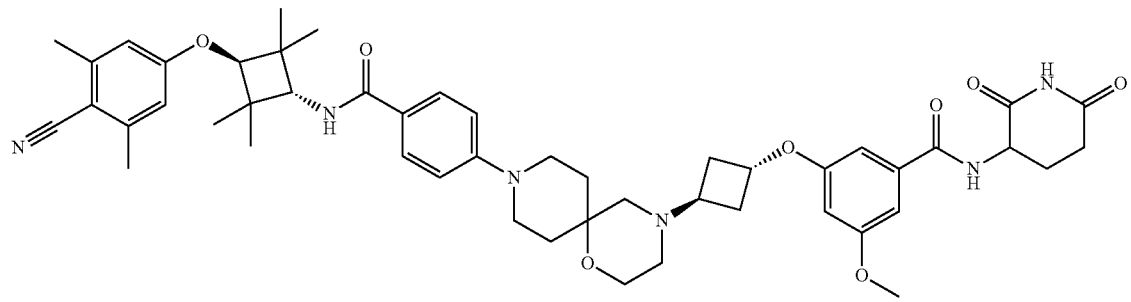 [SMILES: COc1cc(O[C@H]2C[C@H](N3CCOC4(CCN(c5ccc(C(=O)N[C@H]6C(C)(C)[C@H](Oc7cc(C)c(C#N)c(C)c7)C6(C)C)cc5)CC4)C3)C2)cc(C(=O)NC2CCC(=O)NC2=O)c1] |

Example 2—Synthesis of Intermediate 4-((1R,3R)-3-amino-2,2,4,4-tetramethylcyclobutoxy)-2-methoxybenzonitrile

Step 1: Preparation of tert-butyl ((1R,3R)-3-(4-cyano-3-methoxyphenoxy)-2,2,4,4-tetramethylcyclobutyl)carbamate

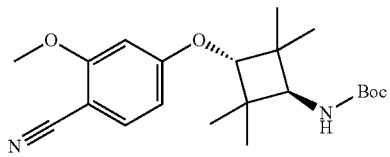 [SMILES: COc1cc(O[C@H]2C(C)(C)[C@H](NC(=O)OC(C)(C)C)C2(C)C)ccc1C#N]

To a solution of tert-butyl N-(3-hydroxy-2,2,4,4-tetramethyl-cyclobutyl)carbamate (10.00 g, 41.09 mmol, 1.00 eq) in dimethylformamide (100 mL) was added sodium hydride (3.29 g, 82.19 mmol, 60% purity, 2.00 eq) at 0° C. for 0.5 h. Then to the mixture was added dropwise a solution of 4-fluoro-2-methoxy-benzonitrile (6.83 g, 45.20 mmol, 1.10 eq) in dimethylformamide (10 mL) at 0° C. The mixture was warmed to 20° C. and stirred at 20° C. for 3.5 h. The reaction mixture was quenched with saturated ammonium chloride solvent (600 mL) and extracted with ethyl acetate (300 mL). The organic layers were washed with brine (300 mL×2), dried over sodium sulfate and concentrated under reduced pressure to give a residue. The residue was purified by column chromatography on silica gel (petroleum ether:ethyl acetate=20:1 to 8:1) to give tert-butyl N-[3-(4-cyano-3-methoxy-phenoxy)-2,2,4,4-tetramethyl-cyclobutyl]carbamate (10.00 g, 26.70 mmol, 64% yield) as a white solid. $^1$H-NMR (400 MHz, DMSO-d$_6$) δ 7.62 (d, J=8.4 Hz, 1H) 6.76-6.59 (m, 2H) 6.50 (d, J=8.4 Hz, 1H) 4.12 (s, 1H) 3.89 (s, 3H) 3.64-3.44 (m, 1H) 1.41 (s, 9H) 1.13 (s, 6H) 1.06 (s, 6H).

Step 2: Preparation of 4-((1R,3R)-3-amino-2,2,4,4-tetramethylcyclobutoxy)-2-methoxybenzonitrile

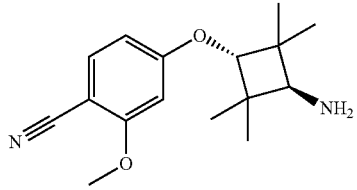 [SMILES: COc1cc(O[C@H]2C(C)(C)[C@H](N)C2(C)C)ccc1C#N]

To a solution of tert-butyl N-[3-(4-cyano-3-methoxy-phenoxy)-2,2,4,4-tetramethyl-cyclobutyl]carbamate (10.00 g, 26.70 mmol, 1.00 eq) in dichloromethane (50 mL) was added hydrochloric acid/dioxane (4 M, 48.00 mL, 7.19 eq). The mixture was stirred at 25° C. for 1 h. The reaction mixture was concentrated under reduced pressure to give 4-(3-amino-2,2,4,4-tetramethyl-cyclobutoxy)-2-methoxy-benzonitrile (8.20 g, 26.38 mmol, 98% yield, hydrochloride salt) as a white solid. $^1$H-NMR (400 MHz, DMSO-d$_6$) δ 8.49 (s, 3H) 7.64 (d, J=8.8 Hz, 1H) 6.63 (d, J=2.0 Hz, 1H) 6.53 (d, J=8.8, 2.0 Hz, 1H) 4.31 (s, 1H) 3.90 (s, 3H) 3.06 (d, J=5.2 Hz, 1H) 1.33 (s, 6H) 1.11 (s, 6H).

Example 3—Synthesis of 4-(4-((1-(4-(((1R,3R)-3-(4-cyano-3-methoxyphenoxy)-2,2,4,4-tetramethylcyclobutyl)carbamoyl)phenyl)piperidin-4-yl)methyl)piperazin-1-yl)-N-2,6-dioxopiperidin-3-yl)-2-fluorobenzamide (compound 1)

Step 1: Preparation of benzyl 4-((1-(tert-butoxycarbonyl)piperidin-4-yl)methyl)piperazine-1-carboxylate

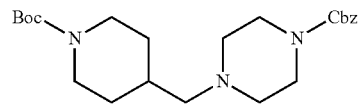 [SMILES: CC(C)(C)OC(=O)N1CCC(CN2CCN(C(=O)OCc3ccccc3)CC2)CC1]

To a solution of tert-butyl 4-formylpiperidine-1-carboxylate (10.00 g, 46.89 mmol, 1.00 eq) in methanol (20 mL) was added benzyl piperazine-1-carboxylate (10.33 g, 46.89 mmol, 9.06 mL, 1.00 eq) at 25° C. and stirred for 10 h. Then the mixture was added sodium cyanoborohydride (4.42 g, 70.33 mmol, 1.50 eq). The mixture was stirred at 25° C. for 2 h. The reaction mixture was concentrated under reduced pressure. The residue was diluted with water (20 mL) and extracted with ethyl acetate (100 mL×3). The combined organic layers were washed with brine (100 mL×3), dried over anhydrous sodium sulfate, filtered and concentrated under reduced pressure to give a residue. The residue was purified by silica gel chromatography (petroleum ether/ethyl acetate=3/1) to give benzyl 4-[(1-tert-butoxycarbonyl-4-piperidyl)methyl]piperazine-1-carboxylate (15.00 g, 35.92 mmol, 76% yield) as a colorless oil. $^1$H-NMR (400 MHz, CD$_3$OD) δ 7.22-7.43 (m, 5H), 5.09-5.14 (m, 2H), 4.03-4.13 (m, 2H), 3.49 (s, 4H), 2.75 (s, 2H), 2.39 (s, 4H), 2.20 (d, J=6 Hz, 2H), 1.63-1.82 (m, 3H), 1.44 (s, 9H), 0.97-1.13 (m, 2H).

Step 2: Preparation of tert-butyl 4-(piperazin-1-ylmethyl) piperidine-1-carboxylate

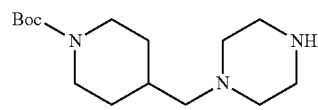

To a mixture of benzyl 4-[(1-tert-butoxycarbonyl-4-piperidyl)methyl]piperazine-1-carboxylate (8.00 g, 19.16 mmol, 1.00 eq) in ethanol (50 mL) was added palladium hydroxide on activated carbon catalyst (2.69 g, 10% purity). The mixture was degassed and purged with hydrogen for 3 times. Then the mixture was stirred at 50° C. for 12 h under hydrogen (50 psi) atmosphere. The reaction mixture was filtered and concentrated under reduced pressure to give tert-butyl 4-(piperazin-1-ylmethyl) piperidine-1-carboxylate (4.50 g, 15.88 mmol, 82% yield) as a black oil. $^1$H-NMR (400 MHz, CD$_3$OD) δ 4.00-4.10 (m, 1H), 3.96-4.12 (m, 1H), 3.29-3.43 (m, 1H), 2.81-2.95 (m, 4H), 2.75 (s, 2H), 2.42 (d, J=2.8 Hz, 3H), 2.19 (d, J=6.8 Hz, 2H), 1.71-1.80 (m, 3H), 1.45 (s, 9H), 1.01-1.12 (m, 2H).

Step 3: Preparation of tert-butyl 4-[[4-(3-fluoro-4-methoxycarbonyl-phenyl)piperazin-1-yl]methyl]piperidine-1-carboxylate

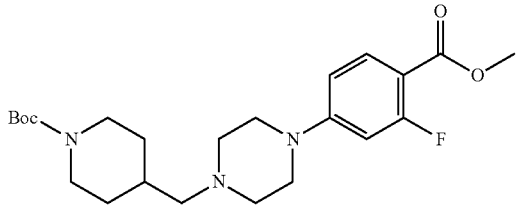 [SMILES: COC(=O)c1ccc(N2CCN(CC3CCN(C(=O)OC(C)(C)C)CC3)CC2)cc1F]

To a solution of methyl 4-bromo-2-fluoro-benzoate (500.00 mg, 2.15 mmol, 1.00 eq) in dioxane (6 mL) was added palladium(II) acetate (24.09 mg, 107.28 μmol, 0.05 eq), bis(diphenylphosphino)-1,1'-binaphthalene (133.60 mg, 214.56 μmol, 0.10 eq), cesium carbonate (1.54 g, 4.72 mmol, 2.20 eq) and tert-butyl 4-(piperazin-1-ylmethyl)piperidine-1-carboxylate (669.00 mg, 2.36 mmol, 1.10 eq) at 110° C. The mixture was stirred at 110° C. for 16 h. The mixture was filtered and the filtrate was concentrated under vacuum to give a residue. The residue was purified by column chromatography on silica gel (petroleum ether/ethyl acetate=8/1 to 1:1) to give tert-butyl 4-[[4-(3-fluoro-4-methoxycarbonyl-phenyl)piperazin-1-yl]methyl]piperidine-1-carboxylate (750.00 mg, 1.72 mmol, 80% yield) as a black brown solid. LC/MS (ESI) m/z: 436.3 [M+1]$^+$; $^1$H-NMR (400 MHz, CDCl$_3$) δ 7.82 (t, J=8.8 Hz, 1H), 6.62 (dd, J=8.8, 2.0, 1H), 6.50 (dd, J=14.8, 2.4, 1H), 4.03-4.09 (m, 1H), 3.88 (s, 3H), 3.23-3.36 (m, 4H), 2.71 (t, J=12.4 Hz, 2H), 2.47-2.57 (m, 4H), 2.22 (d, J=7.2 Hz, 2H), 1.75 (d, J=13.2 Hz, 2H), 1.59-1.71 (m, 2H), 1.46 (s, 9H), 1.02-1.18 (m, 2H).

Step 4: Preparation of methyl 2-fluoro-4-(4-(piperidin-4-ylmethyl) piperazin-1-yl) benzoate

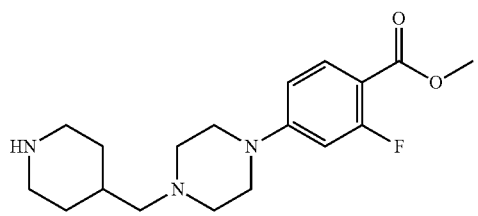 [SMILES: COC(=O)c1ccc(N2CCN(CC3CCNCC3)CC2)cc1F]

To a solution of tert-butyl 4-[[4-(3-fluoro-4-methoxycarbonyl-phenyl)piperazin-1-yl]methyl]piperidine-1-carboxylate (1.00 g, 2.30 mmol, 1.00 eq) in ethyl acetate (10 mL) was added hydrochloride/ethyl acetate (4 M, 574.01 μL, 1.00 eq). The mixture was stirred at 25° C. for 1 h. The mixture was concentrated under reduced pressure to give methyl 2-fluoro-4-[4-(4-piperidylmethyl)piperazin-1-yl] benzoate (850.00 mg, 2.29 mmol, 99% yield, hydrochloride salt) as a white solid. LC/MS (ESI) m/z: 336.1 [M+1]$^+$; $^1$H-NMR (400 MHz, DMSO-d$_6$) δ 8.90 (s, 1H), 8.74 (s, 1H), 7.76 (t, J=8.8 Hz, 1H), 6.91 (d, J=3.2 Hz, 1H), 3.96-4.11 (m, 2H), 3.78 (s, 3H), 3.32-3.39 (m, 2H), 3.27 (d, J=12.8 Hz, 3H), 3.07 (d, J=6.8 Hz, 4H), 2.80-2.93 (m, 2H), 2.17 (s, 1H), 2.01 (d, J=13.6 Hz, 2H), 1.91 (s, 1H), 1.44 (q, J=11.2 Hz, 2H).

Step 5: Preparation of methyl 4-(4-((1-(4-(tert-butoxycarbonyl)phenyl)piperidin-4-yl)methyl)piperazin-1-yl)-2-fluorobenzoate

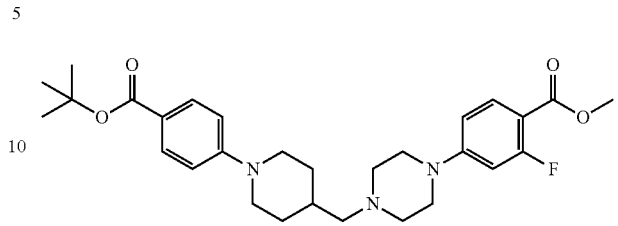

To a solution of methyl 2-fluoro-4-[4-(4-piperidylmethyl)piperazin-1-yl]benzoate (850.00 mg, 2.29 mmol, 1.00 eq, hydrochloric acid) in dioxane (20 mL) were added diacetoxypalladium (51.32 mg, 228.57 μmol, 0.10 eq), 2,2'-bis(diphenylphosphino)-1,1'-binaphthalene (213.49 mg, 342.86 μmol, 0.15 eq), cesium carbonate (1.86 g, 5.71 mmol, 2.50 eq) and tert-butyl 4-bromobenzoate (705.25 mg, 2.74 mmol, 1.20 eq). The mixture was stirred at 110° C. for 12 h under nitrogen atmosphere. The mixture was filtered. The filtrate was concentrated under reduced pressure to give the residue. The residue was purified by column chromatography on gel silica (petroleum ether/ethyl acetate=20/1 to 3/1) to give methyl 4-[4-[[1-(4-tert-butoxycarbonylphenyl)-4-piperidyl]methyl]piperazin-1-yl]-2-fluoro-benzoate (588.00 mg, 1.15 mmol, 50% yield) as a white solid. LC/MS (ESI) m/z 512.2 [M+1]$^+$.

Step 6: Preparation of 4-(4-((1-(4-(tert-butoxycarbonyl)phenyl)piperidin-4-yl)methyl)piperazin-1-yl)-2-fluorobenzoic acid

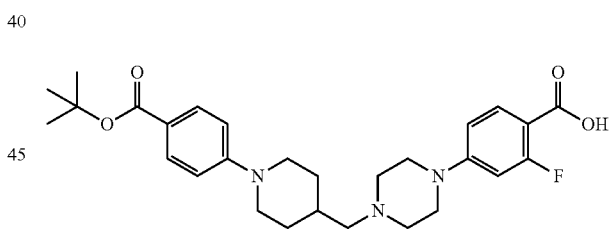

To a solution of methyl 4-[4-[[1-(4-tert-butoxycarbonylphenyl)-4-piperidyl]methyl]piperazin-1-yl]-2-fluorobenzoate (588.00 mg, 1.15 mmol, 1.00 eq) in methanol (8.00 mL) and water (2.00 mL) was added LiOH·H$_2$O (144.68 mg, 3.45 mmol, 3.00 eq). The mixture was stirred at 40° C. for 10 h. The reaction mixture was concentrated under reduced pressure. The residue was adjusted to pH 5-6 by hydrochloric acid (1 M) and extracted with ethyl acetate (30 mL×2). The combined organic layers were washed with brine (20 mL×1), dried over sodium sulfate, filtered and concentrated under reduced pressure to give 4-[4-[[1-(4-tert-butoxycarbonylphenyl)-4-piperidyl]methyl]piperazin-1-yl]-2-fluorobenzoic acid (563.00 mg, 1.13 mmol, 98% yield) as a white solid. LC/MS (ESI) m/z 498.2 [M+1]$^+$.

Step 7: Preparation of tert-butyl 4-(4-((4-(4-((2,6-dioxopiperidin-3-yl)carbamoyl)-3-fluorophenyl)piperazin-1-yl)methyl)piperidin-1-yl)benzoate

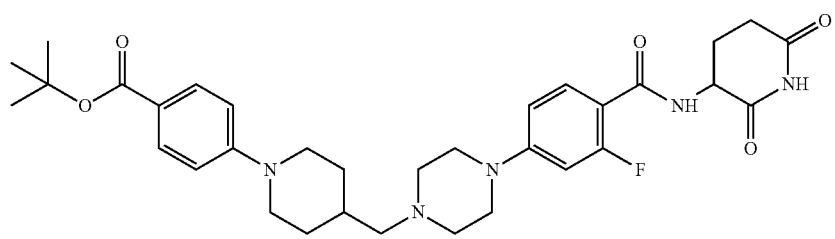 [SMILES: CC(C)(C)OC(=O)c1ccc(N2CCC(CN3CCN(c4ccc(C(=O)NC5CCC(=O)NC5=O)c(F)c4)CC3)CC2)cc1]

To a solution of 4-[4-[[1-(4-tert-butoxycarbonylphenyl)-4-piperidyl]methyl]piperazin-1-yl]-2-fluoro-benzoic acid (563.00 mg, 1.13 mmol, 1.00 eq) in dimethylformamide (6 mL) were added 1-hydroxybenzotriazole (229.32 mg, 1.70 mmol, 1.50 eq), 1-(3-dimethylaminopropyl)-3-ethylcarbodiimide hydrochloride (325.35 mg, 1.70 mmol, 1.5 eq), diisopropylethylamine (731.15 mg, 5.66 mmol, 985.37 μL, 5.00 eq) and 3-aminopiperidine-2,6-dione (223.47 mg, 1.36 mmol, 1.20 eq, hydrochloride salt). The mixture was stirred at 25° C. for 10 h. The reaction mixture was quenched by addition water (50 mL) and a purple solid was separated out. The mixture was filtered to give tert-butyl 4-[4-[[4-[4-[(2,6-dioxo-3-piperidyl)carbamoyl]-3-fluoro-phenyl]piperazin-1-yl]methyl]-1-piperidyl]benzoate (600.00 mg, 987.31 μmol, 87% yield) as a purple solid. LC/MS (ESI) m/z 608.0 [M+1]$^+$; $^1$H-NMR (400 MHz, DMSO-d$_6$) δ 10.83 (s, 1H), 8.03 (t, J=7.2 Hz, 1H), 7.94 (s, 1H), 7.69 (d, J=8.8 Hz, 2H), 7.63 (t, J=9.2 Hz, 1H), 6.92 (d, J=9.2 Hz, 2H), 6.72-6.84 (m, 2H), 4.72 (td, J=12.8, 6.4 Hz, 1H), 3.87 (d, J=12.8 Hz, 2H), 3.28 (s, 4H), 2.88 (s, 3H), 2.81 (br t, J=12.0 Hz, 2H), 2.72 (s, 3H), 2.53 (d, J=4.0 Hz, 2H), 2.11 (dd, J=12.8, 4.0 Hz, 1H), 1.79 (d, J=11.2 Hz, 3H), 1.50 (s, 9H), 1.13-1.24 (m, 2H).

Step 8: Preparation of 4-(4-((4-(4-((2,6-dioxopiperidin-3-yl)carbamoyl)-3-fluorophenyl)piperazin-1-yl)methyl)piperidin-1-yl)benzoic acid

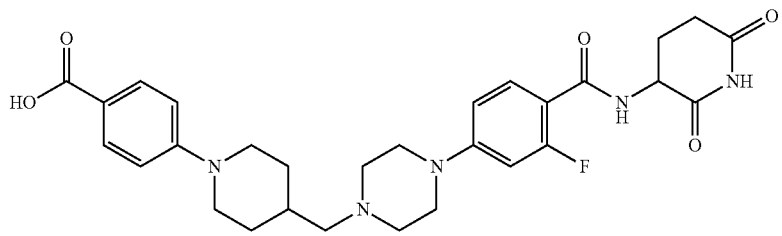 [SMILES: O=C1CCC(NC(=O)c2ccc(N3CCN(CC4CCN(c5ccc(C(=O)O)cc5)CC4)CC3)cc2F)C(=O)N1]

To a solution of tert-butyl 4-[4-[[4-[4-[(2,6-dioxo-3-piperidyl)carbamoyl]-3-fluoro-phenyl]piperazin-1-yl]methyl]-1-piperidyl]benzoate (600.00 mg, 987.31 μmol, 1.00 eq) in ethyl acetate (8 mL) was added hydrochloric acid/ethyl acetate (4 M, 246.83 μL, 1.00 eq). The mixture was stirred at 25° C. for 1 h. The mixture was concentrated under reduced pressure to give 4-[4-[[4-[4-[(2,6-dioxo-3-piperidyl)carbamoyl]-3-fluoro-phenyl]piperazin-1-yl]methyl]-1-piperidyl]benzoic acid (510.00 mg, 924.57 μmol, 93% yield) as a white solid. LC/MS (ESI) m/z 552.2 [M+1]$^+$.

Step 9: Preparation of 4-(4-((1-(4-(((1R,3R)-3-(4-cyano-3-methoxyphenoxy)-2,2,4,4-tetramethylcyclobutyl)carbamoyl)phenyl)piperidin-4-yl)methyl)piperazin-1-yl)-N-(2,6-dioxopiperidin-3-yl)-2-fluorobenzamide

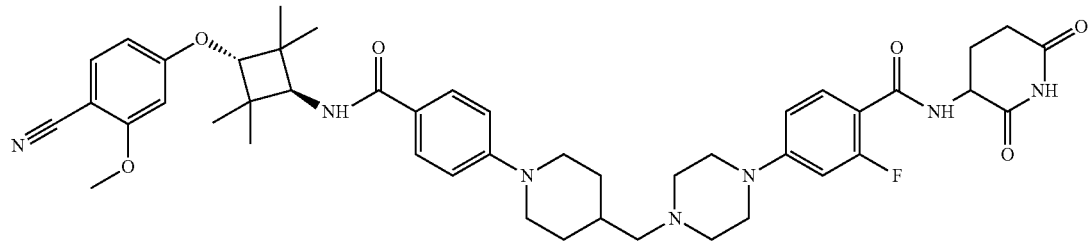 [SMILES: COc1cc(O[C@H]2C(C)(C)[C@H](NC(=O)c3ccc(N4CCC(CN5CCN(c6ccc(C(=O)NC7CCC(=O)NC7=O)c(F)c6)CC5)CC4)cc3)C2(C)C)ccc1C#N]

To a solution of 4-[4-[[4-[4-[(2,6-dioxo-3-piperidyl)carbamoyl]-3-fluoro-phenyl]piperazin-1-yl]methyl]-1-piperidyl]benzoic acid (170.00 mg, 308.19 μmol, 1.00 eq) in dimethylformamide (2 mL) were added 1-hydroxybenzotriazole (54.14 mg, 400.65 μmol, 1.30 eq), 1-(3-dimethylaminopropyl)-3-ethylcarbodiimide hydrochloride (76.80 mg, 400.65 μmol, 1.30 eq), diisopropylethylamine (199.16 mg, 1.54 mmol, 268.41 μL, 5.00 eq) and 4-(3-amino-2,2,4,4-tetramethyl-cyclobutoxy)-2-methoxy-benzonitrile (114.95 mg, 369.83 μmol, 1.20 eq, hydrochloric acid). The mixture was stirred at 25° C. for 24 h. The mixture was filtered to give the filtrate. The filtrate was purified by prep-HPLC to give 4-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]-N-(2,6-dioxo-3-piperidyl)-2-fluoro-benzamide (55.10 mg, 64.42 μmol, 20% yield, 99% purity, formic acid) as a white solid. LC/MS (ESI) m/z 808.3 [M+1]$^+$; $^1$H-NMR (400 MHz, DMSO-d$_6$) δ 10.84 (s, 1H), 8.17 (s, 1H), 8.04 (t, J=7.2 Hz, 1H), 7.74 (d, J=8.8 Hz, 2H), 7.60-7.68 (m, 2H), 7.49 (d, J=9.2 Hz, 1H), 6.96 (d, J=9.2 Hz, 2H), 6.74-6.86 (m, 2H), 6.64 (d, J=2.0 Hz, 1H), 6.55 (dd, J=8.4, 2.0 Hz, 1H), 4.69-4.78 (m, 1H), 4.28 (s, 1H), 4.06 (d, J=9.2 Hz, 1H), 3.91 (s, 3H), 3.86 (d, J=13.2 Hz, 2H), 3.31 (s, 4H), 2.73-2.85 (m, 3H), 2.54 (d, J=4.0 Hz, 1H), 2.49 (s, 4H), 2.21 (d, J=6.8 Hz, 2H), 2.06-2.16 (m, 1H), 1.98-2.05 (m, 1H), 1.76-1.85 (m, 3H), 1.23 (s, 6H), 1.22-1.17 (m, 2H), 1.15 (s, 6H).

Example 4—Synthesis of N-[3-(3-chloro-4-cyanophenoxy)-2,2,4,4-tetramethylcyclobutyl]-6-[4-[(4-[(2,6-dioxopiperidin-3-yl)carbamoyl]phenyl]piperazin-1-yl)methyl]piperidin-1-yl]pyridazine-3-carboxamide (Compound 3)

SCHEME 1. SUMMARY OF THE SYNTHESIS OF COMPOUND 3.

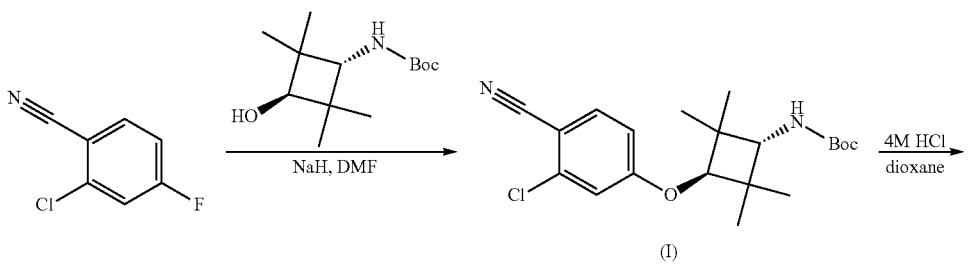

(I)

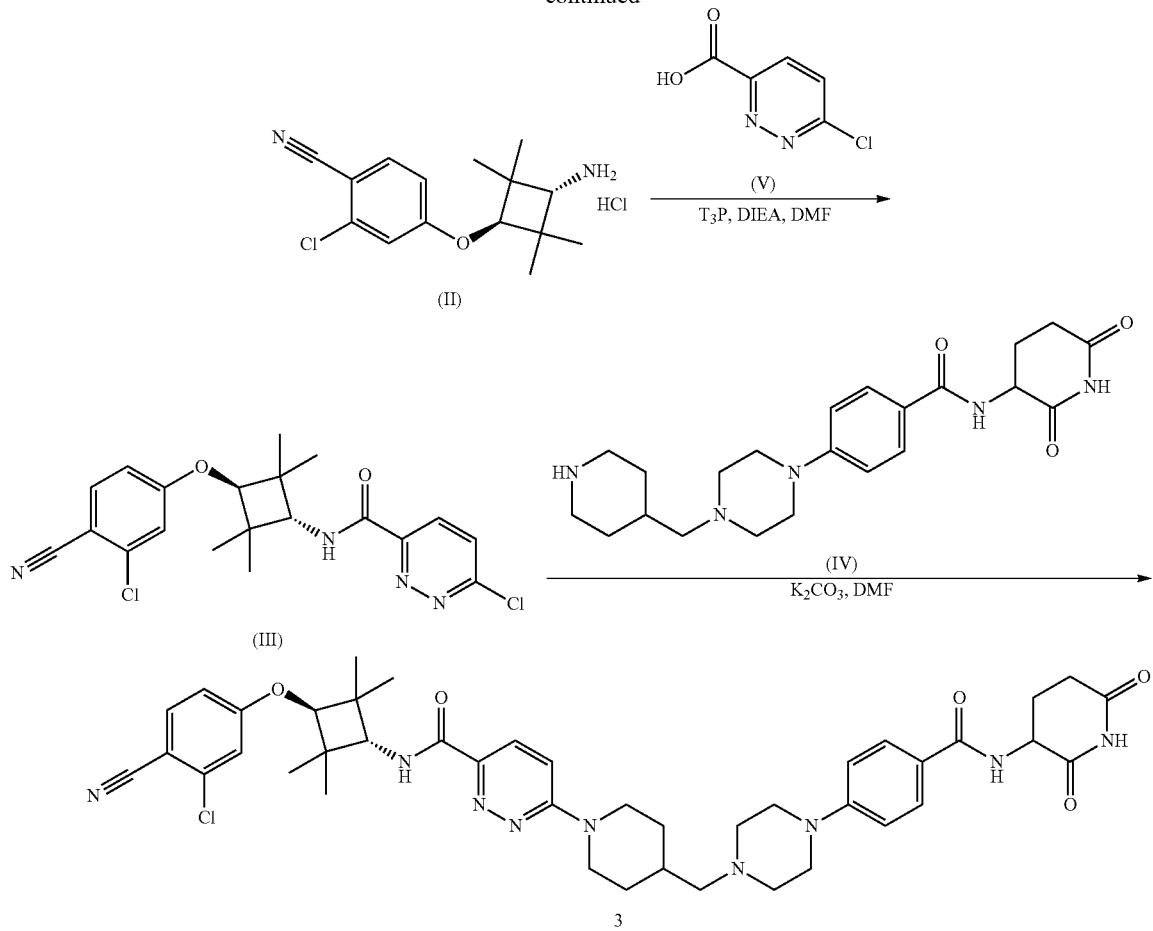

Step 1. Synthesis of tert-butyl N-[(1r,3r)-3-(3-chloro-4-cyanophenoxy)-2,2,4,4-tetramethylcyclobutyl]carbamate (I)

Into a 25-mL round-bottom flask, was placed a solution of tert-butyl N-[(1r,3r)-3-hydroxy-2,2,4,4-tetramethylcyclobutyl]carbamate (312.9 mg, 1.29 mmol, 1 equiv) in DMF (10 mL), to which was added NaH (154.4 mg, 3.86 mmol, 3 equiv, 60%) at 0° C. The resulting mixture was stirred for 15 min and then was added 2-chloro-4-fluorobenzonitrile (200 mg, 1.29 mmol, 1 equiv) at 0° C. The reaction mixture was stirred for 2 hr at 0° C. The reaction was then quenched by the addition of water (45 ml). The resulting mixture was extracted with ethyl acetate (3×50 mL) and the organic layers were combined, washed with brine (50 ml×3), dried over sodium sulfate and concentrated under vacuum to afford 400 mg (crude) of tert-butyl N-[(1r,3r)-3-(3-chloro-4-cyanophenoxy)-2,2,4,4-tetramethylcyclobutyl]carbamate as yellow oil.

LC-MS (ES$^+$): m/z 379.17 [MH$^+$], t$_R$=1.1.46 min, (2.00 minute run).

Step 2. Synthesis of 2-chloro-4-[(1r,3r)-3-amino-2,2,4,4-tetramethylcyclobutoxy]benzonitrile (II)

Into a 25-mL round-bottom flask, was placed a solution of tert-butyl N-[(1r,3r)-3-(3-chloro-4-cyanophenoxy)-2,2,4,4-tetramethylcyclobutyl]carbamate (400 mg, 1.06 mmol, 1 equiv) in a solution of hydrogen chloride in 1,4-dioxane (4 M, 20 mL). The resulting solution was stirred for 2 hr at room temperature. The mixture was concentrated under vacuum to afford 250 mg (crude) of 2-chloro-4-[(1r,3r)-3-amino-2,2,4,4-tetramethylcyclobutoxy]benzonitrile as yellow oil.

Step 3. Synthesis of 6-chloro-N-[(1r,3r)-3-(3-chloro-4-cyanophenoxy)-2,2,4,4-tetramethylcyclobutyl]pyridazine-3-carboxamide (III)

Into a 25-mL round-bottom flask, was placed 2-chloro-4-[(1r,3r)-3-amino-2,2,4,4-tetramethylcyclobutoxy]benzonitrile (250 mg, 0.90 mmol, 1 equiv), 6-chloropyridazine-3-carboxylic acid (142.17 mg, 0.90 mmol, 1 equiv), DIEA (347.70 mg, 2.69 mmol, 3 equiv), T$_3$P (856.00 mg, 2.69 mmol, 3 equiv) in DMF (10 mL). The resulting solution was stirred for 2 hr at room temperature. The reaction was then quenched by the addition of water (20 ml). The resulting mixture was extracted with ethyl acetate (3×50 ml). The combined organic layer was washed with brine (3×50 ml) and concentrated under vacuum. The residue was applied onto a silica gel column eluting with ethyl acetate/petroleum ether (0:100 to 6:1) to afford 250 mg (66.49%) of 6-chloro-N-[(1r,3r)-3-(3-chloro-4-cyanophenoxy)-2,2,4,4-tetramethylcyclobutyl]pyridazine-3-carboxamide as a yellow solid.

LC-MS (ES$^+$): m/z 419.10 [MH$^+$], t$_R$=1.38 min, (2.00 minute run).

Step 4. Synthesis of N-(2, 6-dioxopiperidin-3-yl)-4-[4-[(piperidin-4-yl)methyl]piperazin-1-yl]benzamide (IV)

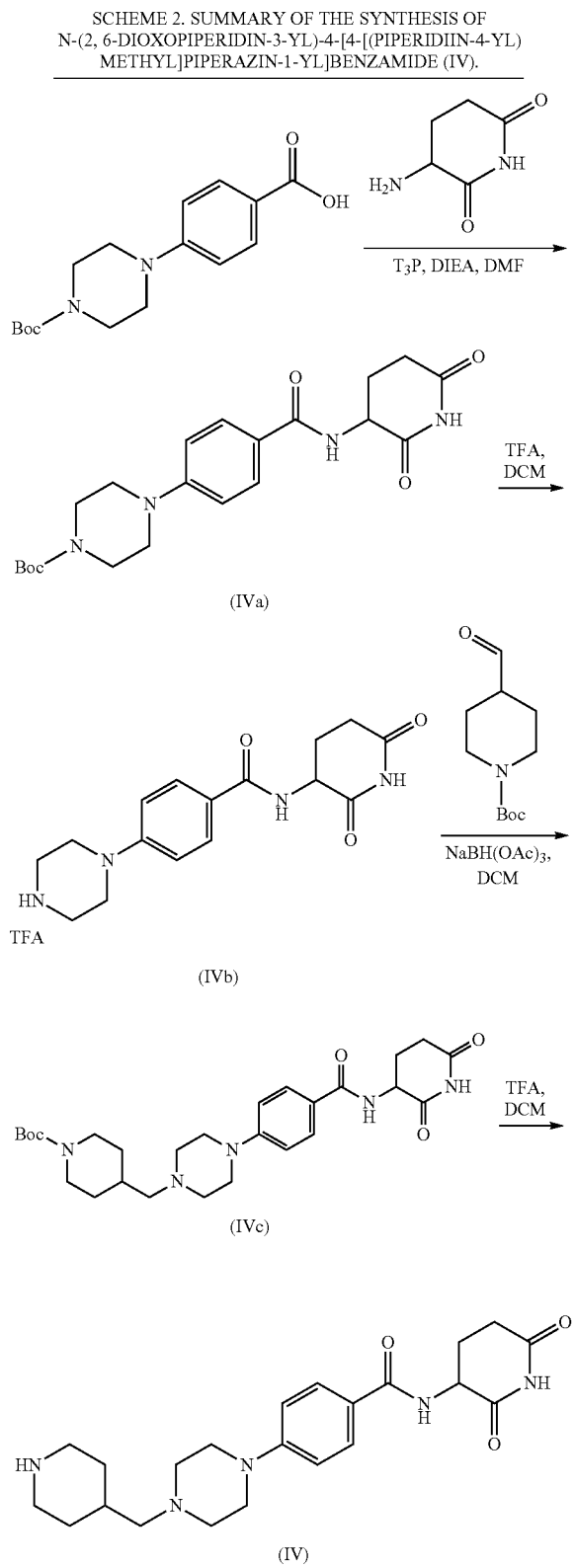

SCHEME 2. SUMMARY OF THE SYNTHESIS OF N-(2, 6-DIOXOPIPERIDIN-3-YL)-4-[4-[(PIPERIDIIN-4-YL)METHYL]PIPERAZIN-1-YL]BENZAMIDE (IV).

Step 4a. Synthesis of tert-butyl 4-[4-[(2,6-dioxopiperidin-3-yl)carbamoyl]phenyl]piperazine-1-carboxylate (IVa)

Into a 100-mL round-bottom flask purged and maintained with an inert atmosphere of nitrogen, was placed 4-[4-[(tert-butoxy)carbonyl]piperazin-1-yl]benzoic acid (1.30 g, 4.24 mmol, 1.00 equiv), 3-aminopiperidine-2,6-dione (543.70 mg, 4.24 mmol, 1.00 equiv), DIEA (1.64 g, 12.73 mmol, 3.00 equiv), T$_3$P (4.05 g, 12.73 mmol, 3.00 equiv) in DMF (20 mL). The resulting solution was stirred for 2 hr at room temperature. The reaction was then quenched by the addition of water (100 ml). The resulting mixture was extracted with ethyl acetate (3×150 mL) and the organic layers were combined, washed with brine, dried over anhydrous sodium sulfate and concentrated under reduced pressure. This resulted in 900 mg (crude) of tert-butyl 4-[4-[(2,6-dioxopiperidin-3-yl)carbamoyl]phenyl]piperazine-1-carboxylate as yellow oil.

Step 4b. Synthesis of N-(2,6-dioxopiperidin-3-yl)-4-(piperazin-1-yl)benzamide (IVb)

Into a 50-mL round-bottom flask, was placed tert-butyl 4-[4-[(2,6-dioxopiperidin-3-yl)carbamoyl]phenyl]piperazine-1-carboxylate (900 mg, 2.16 mmol, 1 equiv) in DCM (20 mL), to which was added TFA (5 ml). The resulting solution was stirred for 1.5 hr at room temperature. The mixture was concentrated under vacuum. This resulted in 600 mg (crude) of N-(2,6-dioxopiperidin-3-yl)-4-(piperazin-1-yl)benzamide as yellow oil.

Step 4c. Synthesis of tert-butyl 4-((4-(4-((2,6-dioxopiperidin-3-yl)carbamoyl)phenyl)piperazin-1-yl)methyl)piperidine-1-carboxylate (IVc)

Into a 100-mL round-bottom flask purged and maintained with an inert atmosphere of nitrogen, was placed N-(2,6-dioxopiperidin-3-yl)-4-(piperazin-1-yl)benzamide (1.00 g, 3.16 mmol, 1.00 equiv), tert-butyl 4-formylpiperidine-1-carboxylate (0.70 g, 3.28 mmol, 1.00 equiv), STAB (2.00 g, 0.01 mmol, 3 equiv) in DCM (25 mL). The resulting solution was stirred for 3 hr at room temperature. The reaction was then quenched by the addition of water (100 ml). The resulting mixture was extracted with ethyl acetate (3×150 mL) and the organic layers were combined, washed with brine, dried over anhydrous sodium sulfate and concentrated under reduced pressure. This resulted in 900 mg (crude) of tert-butyl 4-((4-(4-((2,6-dioxopiperidin-3-yl)carbamoyl)phenyl)piperazin-1-yl)methyl)piperidine-1-carboxylate as yellow oil.

Step 4d. Synthesis of N-(2,6-dioxopiperidin-3-yl)-4-[4-[(piperidin-4-yl)methyl]piperazin-1-yl]benzamide (IV)

Into a 50-mL round-bottom flask, was placed tert-butyl 4-[(4-[4-[(2,6-dioxopiperidin-3-yl)carbamoyl]phenyl]piperazin-1-yl)methyl]piperidine-1-carboxylate (500 mg, 0.97 mmol, 1.00 equiv) in DCM (10 ml), to which was added TFA (3 ml). The resulting solution was stirred for 1.5 hr at room temperature. The mixture was concentrated under vacuum. This resulted in 350 mg (crude) of N-(2,6-dioxopiperidin-3-yl)-4-[4-[(piperidin-4-yl)methyl]piperazin-1-yl] benzamide as yellow oil LC-MS (ES+): m/z 414.30 [MH+], tR=0.703 min, (2.00 minute run). .

Step 5. Synthesis of N-[3-(3-chloro-4-cyanophenoxy)-2,2,4,4-tetramethylcyclobutyl]-6-[4-[(4-[4-[(2,6-dioxopiperidin-3-yl)carbamoyl]phenyl]piperazin-1-yl)methyl]piperidin-1-yl]pyridazine-3-carboxamide (3)

Into a 25-mL round-bottom flask, was placed 6-chloro-N-[(1r,3r)-3-(3-chloro-4-cyanophenoxy)-2,2,4,4-tetramethylcyclobutyl]pyridazine-3-carboxamide (200 mg, 0.48 mmol, 1 equiv), N-(2,6-dioxopiperidin-3-yl)-4-[4-[(piperidin-4-yl)methyl]piperazin-1-yl]benzamide (197.20 mg, 0.48 mmol, 1 equiv), K$_2$CO$_3$ (197.80 mg, 1.43 mmol, 3 equiv) in DMF (11 mL). The resulting mixture was stirred for 12 hr at room temperature. The solids were filtered out and the filtrate was concentrated. The residue was purified by Prep-HPLC with the following conditions: Column, XBridge Prep C18 OBD Column, 5 um, 19*150 mm; Mobile Phase A: Water (with 10 mmol/L NH$_4$HCO$_3$), Mobile Phase B: CH$_3$CN; Gradient: 60% phase B up to 70% in 8 min; Detector, UV. After lyophilization, 27.8 mg (7.32%) of N-[3-(3-chloro-4-cyanophenoxy)-2,2,4,4-tetramethylcyclobutyl]-6-[4-[(4-[4-[(2,6-dioxopiperidin-3-yl)carbamoyl]phenyl]piperazin-1-yl)methyl]piperidin-1-yl]pyridazine-3-carboxamide as a white solid.

$^1$H NMR (300 MHz, DMSO) δ10.81 (s, 1H), 8.46-8.43 (m, 1H), 8.25-8.22 (m, 1H), 7.91-7.89 (m, 1H), 7.83-7.81 (m, 1H), 7.77-7.45 (m, 2H), 7.38-7.35 (m, 1H), 7.25 (s, 1H), 7.05-6.97 (m, 3H), 4.76-4.74 (m, 1H), 4.52-4.46 (m, 3H), 4.02-4.00 (m, 1H), 3.20 (m, 4H), 3.08-3.02 (m, 2H), 2.83-2.76 (m, 1H), 2.60 (m, 4H), 2.23-2.13 (m, 2H), 2.10-2.00 (m, 1H), 1.97-1.84 (m, 4H), 1.28-1.03 (m, 15H); LC-MS (ES$^+$): m/z 796.35 [MH$^+$], t$_R$=1.95 min, (3.00 minute run).

Chemical formula: C$_{42}$H$_{50}$ClN$_9$O$_5$ [796.37]

Example 5—Synthesis of Compound 5

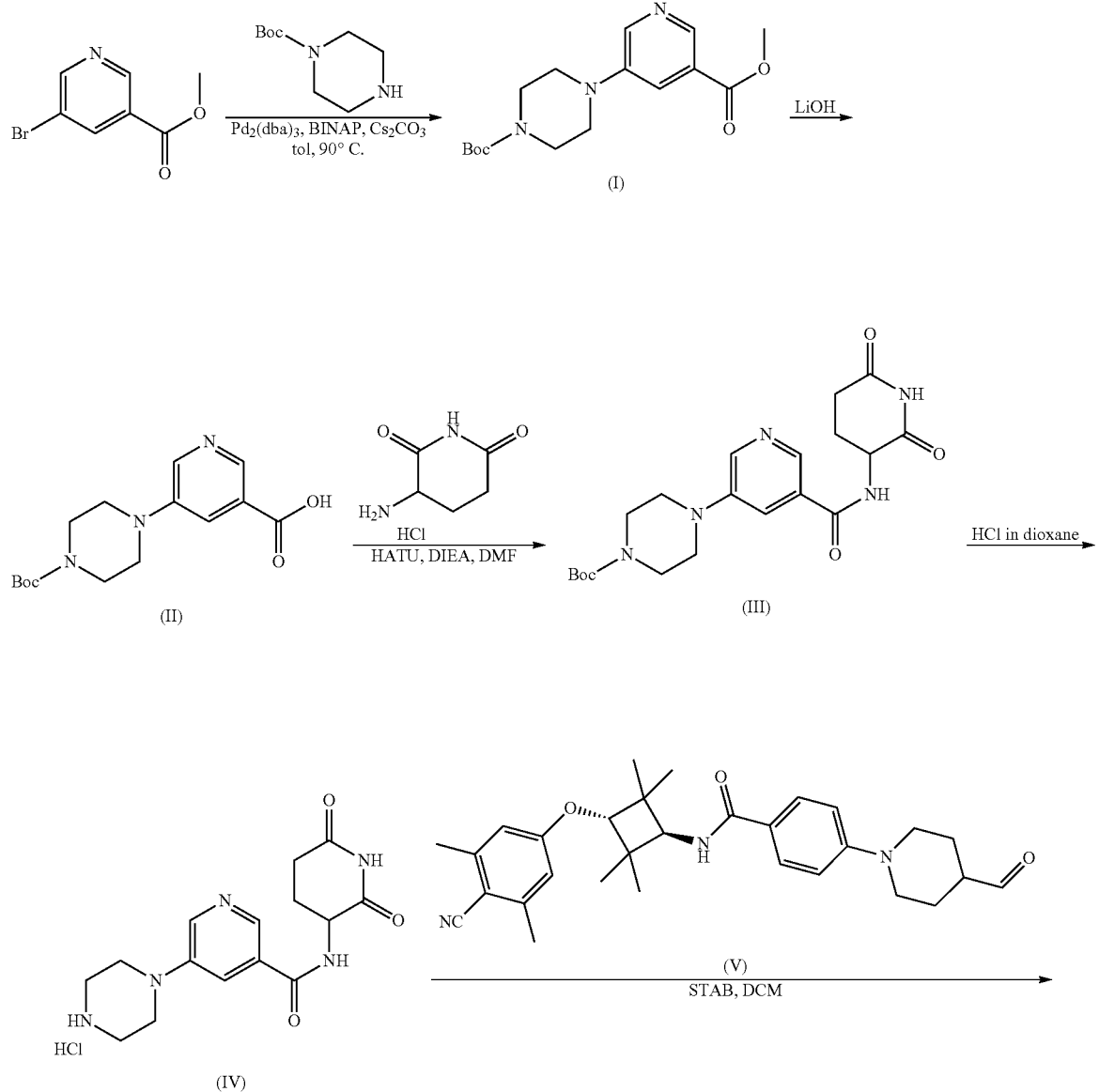

SCHEME 3. SUMMARY OF THE SYNTHESIS OF COMPOUND 5.

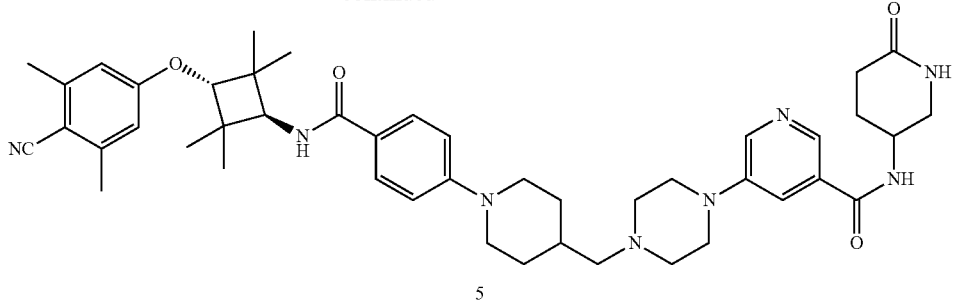

Step 1. Synthesis of tert-butyl 4-[5-(methoxycarbonyl)pyridin-3-yl]piperazine-1-carboxylate (I)

Into a 250 mL round-bottom flask were added methyl 5-bromopyridine-3-carboxylate (2 g, 9.258 mmol, 1 equiv), tert-butyl piperazine-1-carboxylate (1.90 g, 0.010 mmol, 1.1 equiv), Toluene (40 mL, 375.956 mmol, 40.61 equiv) and Cs2CO3 (6.03 g, 18.516 mmol, 2.0 equiv) at room temperature. To the above mixture was added BINAP (0.58 g, 0.926 mmol, 0.1 equiv), Pd2(dba)3 (0.85 g, 0.926 mmol, 0.1 equiv) in portions over 2 min at room temperature. The resulting mixture was stirred for additional overnight at 90° C. The mixture was allowed to cool down to room temperature. The resulting mixture was diluted with ethyl acetate (400 mL). The combined organic layers were washed with brine (1×300 mL), dried over anhydrous Na2SO4. After filtration, the filtrate was concentrated under reduced pressure. The residue was purified by silica gel column chromatography, eluted with hexane/EtOAc (100% to 35%) to afford tert-butyl 4-[5-(methoxycarbonyl)pyridin-3-yl]piperazine-1-carboxylate (1.4 g, 47.05%) as an off-white solid. LC-MS (ES, m/z): 322.00[MH$^+$], t$_R$=0.911 min, (2.00 minute run).

Step 2. Synthesis of 5-(4-(tert-butoxycarbonyl)piperazin-1-yl)nicotinic acid (II)

Into a 50 mL round-bottom flask were added tert-butyl 4-[5-(methoxycarbonyl)pyridin-3-yl]piperazine-1-carboxylate (1.4 g, 4.356 mmol, 1 equiv), MeOH (1.3 mL, 32.109 mmol, 7.37 equiv) and H$_2$O (12 mL, 666.100 mmol, 152.91 equiv) at room temperature. To the stirred solution lithium hydroxide (1.3 g, 54.280 mmol, 12.46 equiv) was added in portions at room temperature. The resulting mixture was stirred for overnight at room temperature. The resulting mixture was diluted with ethyl acetate (30 mL). The resulting mixture was filtered, the filter cake was washed with MeOH (3×50 mL). The filtrate was concentrated under reduced pressure. The crude product was used in the next step directly without further purification. LC-MS (ES, m/z): 308.05[MH$^+$], t$_R$=0.627 min, (2.00 minute run).

Step 3. Synthesis of tert-butyl 4-[5-[(2,6-dioxopiperidin-3-yl)carbamoyl]pyridin-3-yl]piperazine-1-carboxylate (III)

Into a 25 mL round-bottom flask were added 5-[4-[(tert-butoxy)carbonyl]piperazin-1-yl]pyridine-3-carboxylic acid (500 mg, 1.627 mmol, 1 equiv), 3-aminopiperidine-2,6-dione hydrochloride (267.76 mg, 1.627 mmol, 1.00 equiv), DMF (0.00 mL, 0.052 mmol, 0.03 equiv), DIEA (1051.27 mg, 8.134 mmol, 5.0 equiv) and HATU (1237.12 mg, 3.254 mmol, 2.00 equiv) at room temperature. The resulting mixture was stirred for 3 h at room temperature under nitrogen atmosphere. The reaction was quenched by the addition of Water (30 mL) at room temperature. The resulting mixture was extracted with EtOAc (3×50 mL). The combined organic layers were washed with brine (3×30 mL), dried over anhydrous Na2SO4. After filtration, the filtrate was concentrated under reduced pressure. The residue was purified by silica gel column chromatography, eluted with PE/EtOAc (1:1) to afford tert-butyl 4-[5-[(2,6-dioxopiperidin-3-yl)carbamoyl]pyridin-3-yl]piperazine-1-carboxylate (290 mg, 42.70%) as an off-white solid. LC-MS (ES, m/z): 418.05[MH$^+$], t$_R$=0.796 min, (2.00 minute run).

Step 4. Synthesis of N-(2,6-dioxopiperidin-3-yl)-5-(piperazin-1-yl)nicotinamide hydrochloride (IV)

Into a 10 mL round-bottom flask were added tert-butyl 4-[5-[(2,6-dioxopiperidin-3-yl)carbamoyl]pyridin-3-yl]piperazine-1-carboxylate (290 mg), MeOH (2 mL) and HCl (gas) in 1,4-dioxane (3 mL) at room temperature. The resulting mixture was stirred for 2 h at 30° C. under air atmosphere. The resulting mixture was concentrated under vacuum to afford N-(2,6-dioxopiperidin-3-yl)-5-(piperazin-1-yl)pyridine-3-carboxamide hydrochloride (300 mg) as an off-white solid. The crude product was used in the next step directly without further purification.

Step 5. Synthesis of N-(2,6-dioxopiperidin-3-yl)-5-(4-[[1-(4-[[(1r,3r)-3-(4-cyano-3,5-dimethylphenoxy)-2,2,4,4-tetramethylcyclobutyl]carbamoyl]phenyl)piperidin-4-yl]methyl]piperazin-1-yl)pyridine-3-carboxamide (VI)

A solution/mixture of (V), 4-(4-formylpiperidin-1-yl)-N-[(1r,3r)-3-(4-cyano-3,5-dimethylphenoxy)-2,2,4,4-tetramethylcyclobutyl]benzamide (100 mg, 0.205 mmol, 1 equiv), and N-(2,6-dioxopiperidin-3-yl)-5-(piperazin-1-yl)pyridine-3-carboxamide hydrochloride (87.07 mg, 0.246 mmol, 1.2 equiv) in dichloromethane was stirred for 30 min at room temperature under nitrogen atmosphere. To the above mixture was added STAB (130.39 mg, 0.615 mmol, 3.0 equiv) in portions over 5 min at 0° C. The resulting mixture was stirred for additional overnight at room temperature. The mixture was allowed to cool down to 0° C. The reaction was quenched with Water/Ice at 0° C. The resulting mixture was extracted with EtOAc (3×15 mL). The combined organic layers were washed with brine (1×30 mL), dried over anhydrous Na$_2$SO$_4$. After filtration, the filtrate was concentrated under reduced pressure. The crude product was purified by Prep-HPLC with the following conditions (2 #SHIMADZU (HPLC-01)): Column, Xselect CSH OBD Column 30*150 mm 5 um, n; mobile phase, Water (10 MMOL/L NH4HCO3) and ACN (hold 57% PhaseB in 8 min); Detector, UV 254 nm. This resulted in N-(2,6-dioxopiperidin-3-yl)-5-(4-[[1-(4-[[(1r,3r)-3-(4-cyano-3,5-dimethylphenoxy)-

2,2,4,4-tetramethylcyclobutyl]carbamoyl]phenyl)piperidin-4-yl]methyl]piperazin-1-yl)pyridine-3-carboxamide (22.6 mg, 13.97%) as a white solid.

LC-MS (ES, m/z): 789.35[MH$^+$], t$_R$=2.168 min, (3.00 minute run).

1H-NMR: (CD$_3$OD, 300 MHz): δ 8.42 (m, 2H), 7.79 (s, 1H), 7.73 (d, 2H), 7.0 (d, 2H), 6.71 (s, 2H), 4.92-4.89 (m, 1H), 4.23 (s, 1H), 4.11 (m, 1H), 3.91 (d, 2H), 3.38-3.35 (m, 5H), 2.89-2.79 (m, 3H), 2.76-2.74 (m, 1H), 2.69-2.64 (m, 4H), 2.47 (s, 6H), 2.33 (d, 2H), 2.25-2.16 (m, 3H), 1.39-1.31 (m, 3H), 1.28 (s, 6H), 1.21 (s, 6H).

Chemical Formula: C$_{45}$H$_{56}$N$_8$O$_5$ [788.99].

Example 6—Synthesis of 4-(4-((1-(4-(((1R,3R)-3-(4-cyano-3-methoxyphenoxy)-2,2,4,4-tetramethylcyclobutyl)carbamoyl)phenyl)piperidin-4-yl)methyl)piperazin-1-yl)-N—((R)-2,6-dioxopiperidin-3-yl)-2-fluorobenzamide (Compound 14)

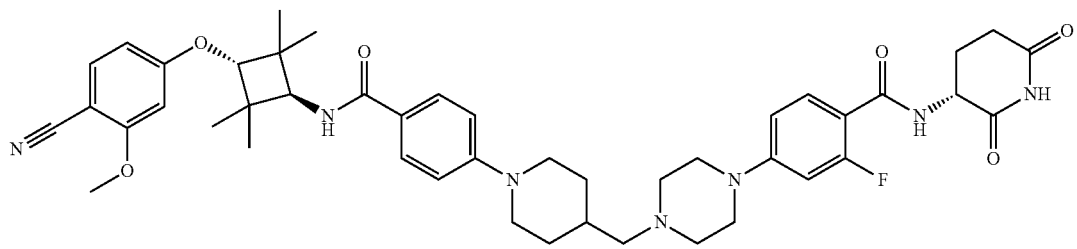 [SMILES: COc1cc(O[C@H]2C(C)(C)[C@H](NC(=O)c3ccc(N4CCC(CN5CCN(c6ccc(C(=O)N[C@@H]7CCC(=O)NC7=O)c(F)c6)CC5)CC4)cc3)C2(C)C)ccc1C#N]

Compound 14 was isolated from Compound 1 (prepared as described in Example 3) using supercritical fluid chromatography. Using the process outlined below in Table 2, 118 mg of Compound 14 was isolated from Compound 1.

TABLE 2

| SFC CONDITIONS FOR ISOLATION OF COMPOUND 14. | |
|---|---|
| Instrument | Waters 80 Q |
| Column | Chiralpak AD 250 × 30 mm I.D., 10 um |
| Mobile Phase | Phase A for Supercritical CO$_2$    Phase B for IPA:ACN = 3:1(0.1% NH3H2O) |
| Isocratic elution | 80% Phase B (20% Phase A) |
| Flow rate | 80 g/min |
| cycle time | 8.2 min |
| Back Pressure | 100 bar to keep the CO$_2$ in Supercritical flow |
| UV | 220 nm |
| Injection | 4.0 ml |

$^1$H NMR (400 MHz, DMSO-d$_6$) δ: 10.84 (s, 1H), 8.05 (t, J=7.2 Hz, 1H), 7.75 (d, J=8.8 Hz, 2H), 7.69-7.60 (m, 2H), 7.51 (d, J=9.2 Hz, 1H), 6.96 (d, J=8.8 Hz, 2H), 6.87-6.74 (m, 2H), 6.65 (d, J=2.0 Hz, 1H), 6.55 (d, J=8.8, 2.0 Hz, 1H), 4.83-4.65 (m, 1H), 4.29 (s, 1H), 4.06 (d, J=9.2 Hz, 1H), 3.95-3.79 (m, 5H), 3.32-3.24 (m, 4H), 2.87-2.72 (m, 3H), 2.56-2.53 (m, 2H), 2.49-2.46 (m, 3H), 2.25-2.17 (m, 2H), 2.17-2.08 (m, 1H), 2.06-2.00 (m, 1H), 1.81 (d, J=12.0 Hz, 3H), 1.27-1.10 (m, 14H).

Example 7—Synthesis of Compound 15

SCHEME 4. SUMMARY OF THE SYNTHESIS OF COMPOUND 15.

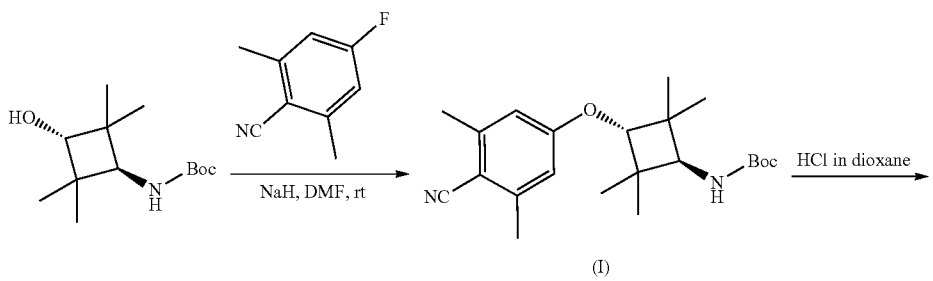

(I)

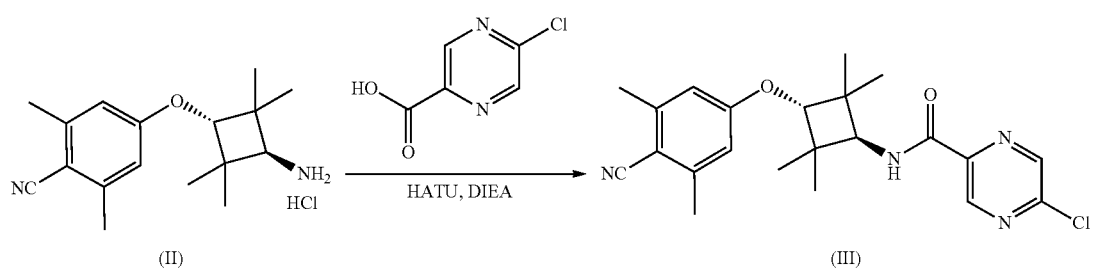

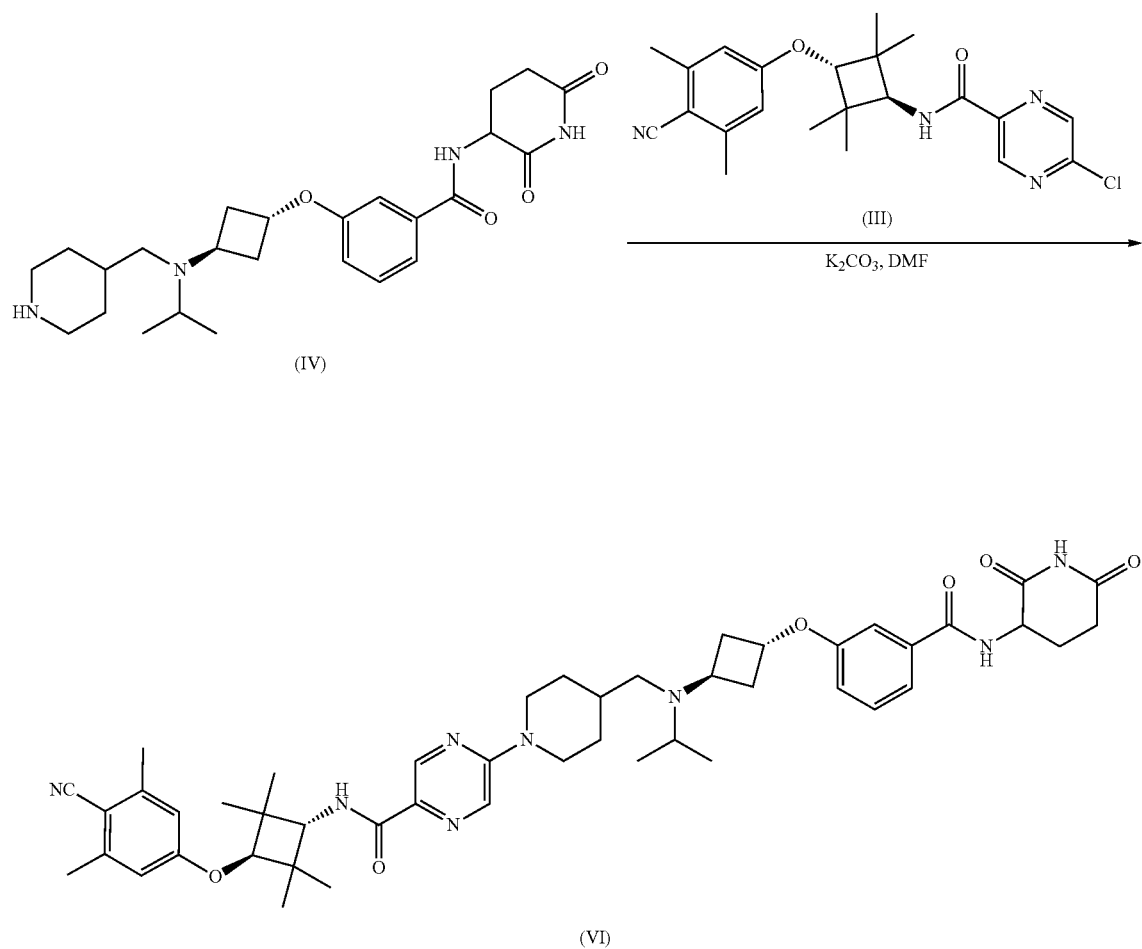

Step 1. Synthesis of tert-butyl N-[(1r,3r)-3-(4-cyano-3,5-dimethylphenoxy)-2,2,4,4-tetramethylcyclobutyl]carbamate (I)

To a solution of tert-butyl N-[(1r, 3 r)-3-hydroxy-2,2,4,4-tetramethylcyclobutyl]carbamate (1.5 g, 6.164 mmol, 1 equiv) in DMF was added sodium hydride (60% in oil, 390 mg) at 0 degrees C. The mixture was stirred for 15 min. 4-fluoro-2,6-dimethylbenzonitrile (1.10 g, 7.397 mmol, 1.20 equiv) was added and the mixture was allowed to warm to RT and stirred for 2 h. The resulting mixture was diluted with ethyl acetate (50 mL). The reaction was quenched by the addition of Water/Ice (20 mL) at 0 degrees C. THE aqueous layer was extracted with EtOAc (2×30 mL). The resulting mixture was washed with 3×50 mL of water. The residue was purified by Prep-TLC (CH2Cl2/MeOH 10:1) to afford tert-butyl N-[(1r,3r)-3-(4-cyano-3,5-dimethylphenoxy)-2,2,4,4-tetramethylcyclobutyl]carbamate (1.8 g, 78.39%) as a light yellow solid.

LC-MS (ES+): m/z 317.00 [MH+−56], $t_R$=1.469 min, (2.00 minute run).

Step 2. Synthesis of 2,6-dimethyl-4-[(1r,3r)-3-amino-2,2,4,4-tetramethylcyclobutoxy]benzonitrile hydrochloride (II)

To a stirred solution of tert-butyl N-[(1r,3r)-3-(4-cyano-3,5-dimethylphenoxy)-2,2,4,4-tetramethylcyclobutyl]carbamate (1.8 g, 4.832 mmol, 1 equiv) in 1,4-dioxane was added 4M HCl in dioxane dropwise portions at room temperature. The resulting mixture was stirred for 1 h at 30 degrees C. The resulting mixture was concentrated under reduced pressure. This resulted in 2,6-dimethyl-4-[(1r,3r)-3-amino-2,2,4,4-tetramethylcyclobutoxy]benzonitrile hydrochloride (1.4 g, 93.81%) as a light yellow solid.

LC-MS (ES$^+$): m/z 273.25 [MH$^+$], $t_R$=0.949 min, (2.00 minute run).

Step 3. Synthesis of 5-chloro-N-[(1r,3r)-3-(4-cyano-3,5-dimethylphenoxy)-2,2,4,4-tetramethylcyclobutyl]pyrazine-2-carboxamide (III)

To a stirred solution of 2,6-dimethyl-4-[(1r,3r)-3-amino-2,2,4,4-tetramethylcyclobutoxy]benzonitrile hydrochloride (500 mg, 1.619 mmol, 1 equiv) and 5-chloropyrazine-2-carboxylic acid (282.33 mg, 1.781 mmol, 1.1 equiv) in DMF were added DIEA (1.05 g, 8.095 mmol, 5 equiv) and HATU (1.85 g, 4.857 mmol, 3 equiv) in portions at room temperature. The resulting mixture was stirred for 1 h at room temperature. The resulting mixture was diluted with ethyl acetate (50 mL). The resulting mixture was washed with 3×40 mL of water. The residue was purified by Prep-TLC (PE/EtOAc 1:1) to afford 5-chloro-N-[(1r,3r)-3-(4-cyano-3,5-dimethylphenoxy)-2,2,4,4-tetramethylcyclobutyl]pyrazine-2-carboxamide (500 mg, 74.80%) as a light yellow solid.

LC-MS (ES$^+$): m/z 413.25 [MH$^+$], $t_R$=1.430 min, (2.00 minute run).

Step 4. Synthesis of 2,2,2-trifluoroacetaldehyde; N-(2,6-dioxopiperidin-3-yl)-3-[(1r,3r)-3-[[(piperidin-4-yl)methyl](propan-2-yl)amino]cyclobutoxy]benzamide (IV)

To a stirred solution of tert-butyl 4-[[(propan-2-yl)[(1r,3r)-3-[3-[(2,6-dioxopiperidin-3-yl)carbamoyl]phenoxy]cyclobutyl]amino]methyl]piperidine-1-carboxylate (100 mg, 1 equiv) in 1,4-dioxane was added HCl (gas) in 1,4-dioxane (5 mL) dropwise portions at room temperature. The resulting mixture was stirred for 2 h at 30° C. The resulting mixture was concentrated under reduced pressure. The crude product was used in the next step directly without further purification.

LC-MS (ES$^+$): m/z 457.27 [MH$^+$], $t_R$=0.806 min, (2.00 minute run).

Step 5. Synthesis of 5-(4-[[(propan-2-yl)[(1r,3r)-3-[3-[(2,6-dioxopiperidin-3-yl)carbamoyl]phenoxy]cyclobutyl]amino]methyl]piperidin-1-yl)-N-[(1r,3r)-3-(4-cyano-3,5-dimethylphenoxy)-2,2,4,4-tetramethylcyclobutyl]pyrazine-2-carboxamide (Compound 3)

To a stirred solution of 2,2,2-trifluoroacetaldehyde; N-(2,6-dioxopiperidin-3-yl)-3-[(1r,3r)-3-[[(piperidin-4-yl)methyl](propan-2-yl)amino]cyclobutoxy]benzamide (100 mg, 0.180 mmol, 1 equiv) and 5-chloro-N-[(1r,3r)-3-(4-cyano-3,5-dimethylphenoxy)-2,2,4,4-tetramethylcyclobutyl]pyrazine-2-carboxamide (81.90 mg, 0.198 mmol, 1.1 equiv) in DMF was added K2CO3 (74.76 mg, 0.541 mmol, 3 equiv) in portions at room temperature. The resulting mixture was stirred for overnight at 60 degrees C. This resulted in 5-(4-[[(propan-2-yl)[(1r,3r)-3-[3-[(2,6-dioxopiperidin-3-yl)carbamoyl]phenoxy]cyclobutyl]amino]methyl]piperidin-1-yl)-N-[(1r,3r)-3-(4-cyano-3,5-dimethylphenoxy)-2,2,4,4-tetramethylcyclobutyl]pyrazine-2-carboxamide (25.8 mg, 17.18%) as a white solid.

$^1$H-NMR (400 MHz, Methanol-d4) δ 8.67 (d, J=1.4 Hz, 1H), 8.24 (d, J=1.3 Hz, 1H), 7.45 (d, J=7.6 Hz, 1H), 7.39 (t, J=7.9 Hz, 1H), 7.32 (s, 1H), 7.04 (d, J=8.3 Hz, 1H), 6.74 (s, 2H), 4.77 (s, 1H), 4.60 (d, J=13.3 Hz, 2H), 4.27 (s, 1H), 4.06 (s, 1H), 3.77 (s, 1H), 3.03 (t, J=12.5 Hz, 3H), 2.84 (dd, J=17.3, 7.4 Hz, 1H), 2.78-2.69 (m, 1H), 2.49 (s, 6H), 2.36 (s, 2H), 2.23 (tt, J=11.6, 7.0 Hz, 4H), 2.00 (d, J=13.1 Hz, 2H), 1.79 (s, 1H), 1.29 (s, 6H), 1.22 (s, 6H), 1.18 (s, 2H), 1.03 (d, J=6.5 Hz, 6H), 0.92 (s, OH), 0.12 (s, 1H).

LC-MS (ES$^+$): m/z 833.55 [MH$^+$], $t_R$=1.646 min, (3.00 minute run).

Example 8—Synthesis of 4-(4-((1-(4-(((1R,3R)-3-(4-cyano-3-methoxyphenoxy)-2,2,4,4-tetramethylcyclobutyl)carbamoyl)phenyl)piperidin-4-yl)methyl)piperazin-1-yl)-N—((S)-2,6-dioxopiperidin-3-yl)-2-fluorobenzamide (Compound 21)

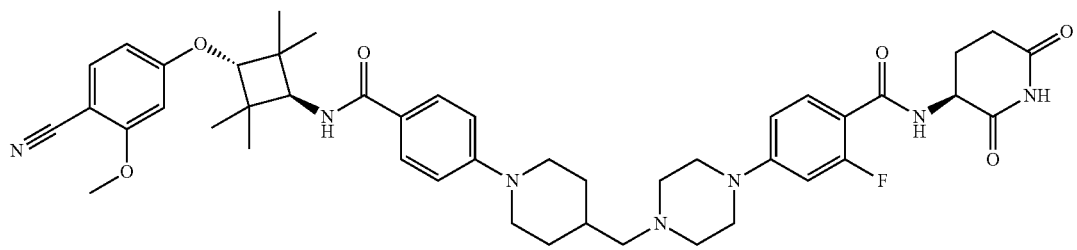 [SMILES: COc1cc(O[C@H]2C(C)(C)[C@H](NC(=O)c3ccc(N4CCC(CN5CCN(c6ccc(C(=O)N[C@H]7CCC(=O)NC7=O)c(F)c6)CC5)CC4)cc3)C2(C)C)ccc1C#N]

Compound 21 was isolated from Compound 1 (prepared as described in Example 3) using supercritical fluid chromatography. Using the process outlined above in Table 2, 71 mg of Compound 21 was isolated from Compound 1.
$^1$H NMR (400 MHz, DMSO-$d_6$) δ: 10.84 (s, 1H), 8.05 (t, J=7.2 Hz, 1H), 7.75 (d, J=8.8 Hz, 2H), 7.69-7.60 (m, 2H), 7.51 (d, J=9.2 Hz, 1H), 6.96 (d, J=8.8 Hz, 2H), 6.87-6.74 (m, 2H), 6.65 (d, J=2.0 Hz, 1H), 6.55 (d, J=8.8, 2.0 Hz, 1H), 4.83-4.65 (m, 1H), 4.29 (s, 1H), 4.06 (d, J=9.2 Hz, 1H), 3.95-3.79 (m, 5H), 3.32-3.24 (m, 4H), 2.87-2.72 (m, 3H), 2.56-2.53 (m, 2H), 2.49-2.46 (m, 3H), 2.25-2.17 (m, 2H), 2.17-2.08 (m, 1H), 2.06-2.00 (m, 1H), 1.81 (d, J=12.0 Hz, 3H), 1.27-1.10 (m, 14H).
Example 9—Synthesis of Compound 23
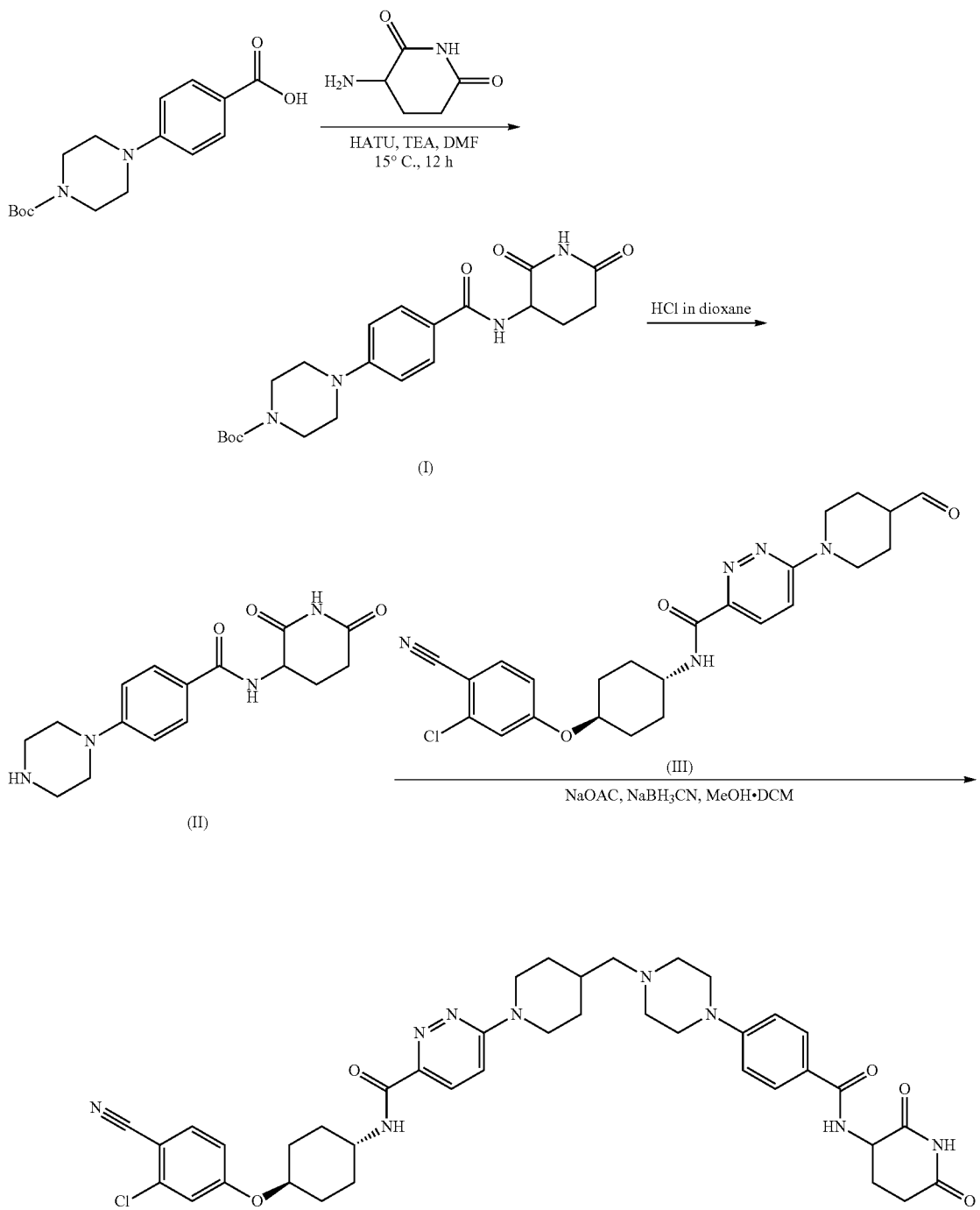

Step 1. Preparation of (I), tert-butyl 4-[4-[(2,6-dioxo-3-piperidyl)carbamoyl]phenyl]piperazine-1-carboxylate

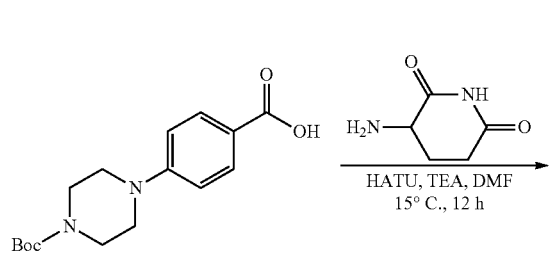

(I)

Step 2. Preparation of (II), N-(2,6-dioxo-3-piperidyl)-4-piperazin-1-yl-benzamide

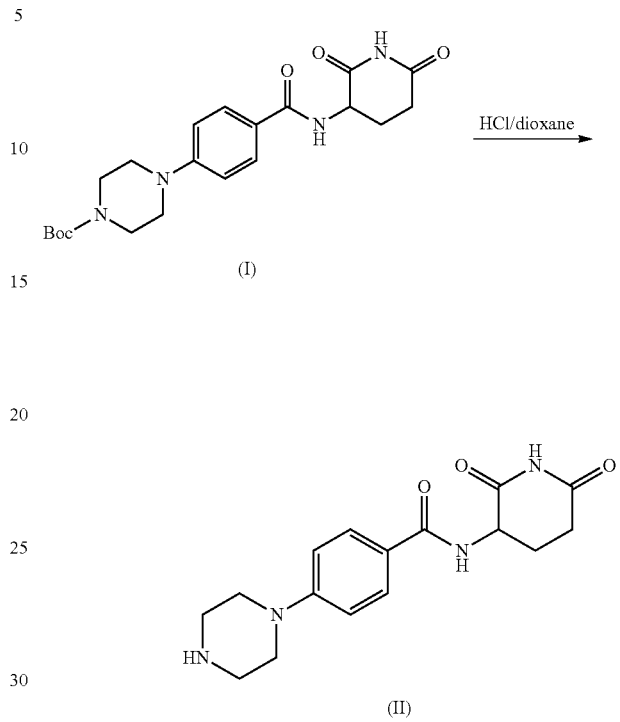

To a solution of 4-(4-tert-butoxycarbonylpiperazin-1-yl)benzoic acid (500 mg, 1.63 mmol, 1 eq) and 3-aminopiperidine-2,6-dione (209 mg, 1.27 mmol, 1 eq, hydrochloride) in N,N-dimethylformamide (3 mL) was added o-(7-azabenzotriazol-1-yl)-n,n,n',n'-tetramethyluronium hexafluorophosphate (930 mg, 2.45 mmol, 1.5 eq) and triethylamine (495 mg, 4.90 mmol, 3 eq). The mixture was stirred at 15° C. for 1 hour. LCMS showed the reaction was completed and desired MS can be detected. Water (100 mL) was poured into the mixture and stirred for 1 minute. The aqueous phase was extracted with ethyl acetate (50 mL×3). The combined organic phase was washed with brine (100 mL×2), dried with anhydrous sodium sulfate, filtered and concentrated in vacuum. The residue was purified by prep-TLC (dichloromethane:methanol=20:1). Compound tert-butyl 4-[4-[(2,6-dioxo-3-piperidyl) carbamoyl]phenyl]piperazine-1-carboxylate (370 mg, 0.88 mmol, 54% yield) was obtained as an off-white solid.

Chemical Formula: $C_{21}H_{28}O_5N_4$, Molecular Weight: 416.47

To a solution of tert-butyl 4-[4-[(2,6-dioxo-3-piperidyl)carbamoyl]phenyl]piperazine-1-carboxylate (370 mg, 0.88 mmol, 1 eq) in dichloromethane (2 mL) was added hydrochloride acid/dioxane (4 M, 10 mL, 45.02 eq). The mixture was stirred at 15° C. for 1 hour. LCMS detected the desired MS. The reaction mixture was filtered and concentrated under reduced pressure to give a residue. The crude product N-(2,6-dioxo-3-piperidyl)-4-piperazin-1-yl-benzamide was used into the next step without further purification. Compound N-(2,6-dioxo-3-piperidyl)-4-piperazin-1-yl-benzamide (300 mg, 0.85 mmol, 95% yield, hydrochloride) was obtained as an off-white solid.

LCMS: MS (ESI) m/z: 317.1 [M+1]$^+$

Chemical Formula: $C16H_{20}O_3N_4$, Molecular Weight: 316.1

Step 3. Preparation of III

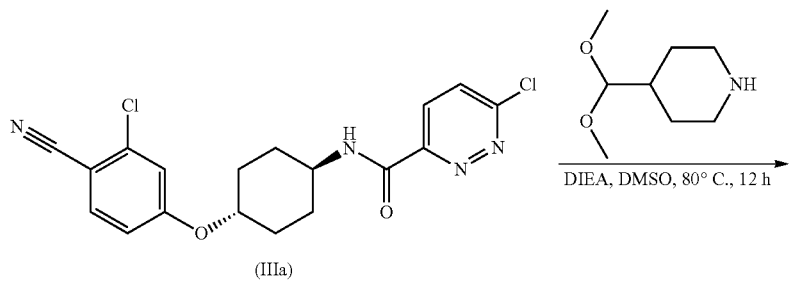

(IIIa)

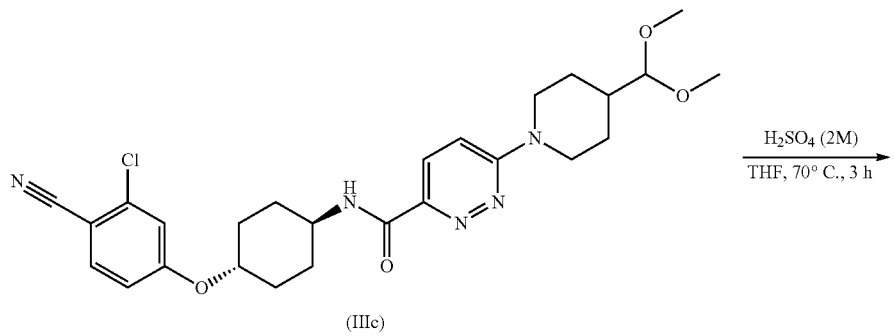

(IIIc)

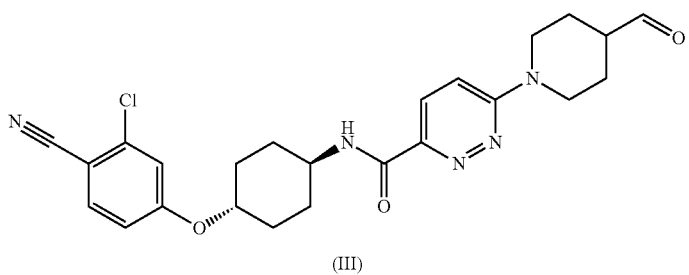

(III)

Preparation of IIIa:

To a solution of methyl 6-chloropyridazine-3-carboxylate (100 g, 579.48 mmol, 1 eq) in tetrahydrofuran (1 L) and water (1 L) was added lithium hydrate (48.63 g, 1.16 mol, 2 eq) in portions. The reaction mixture was stirred at 25° C. for 1 hour. Thin-Layer Chromatography (Petroleum ether: Ethyl acetate=1:1) showed methyl 6-chloropyridazine-3-carboxylate was consumed completely. The reaction mixture was poured into hydrochloric (2.0 M, 600 mL), and extracted with dichloromethane (800 mL*2). The combined organic layers were washed with brine (2 L*3), dried over anhydrous sodium sulfate, filtered and concentrated under reduced pressure. The residue was triturated with ethyl acetate (500 mL). 6-chloropyridazine-3-carboxylic acid (70 g, 436.22 mmol, 75% yield, 98% purity) was obtained as a white solid.

$^1$H NMR: (400 MHz, DMSO-$d_6$),

δ: 14.08 (s, 1H), 8.24 (d, J=9.2 Hz, 1H), 8.09 (d, J=9.2 Hz, 1H).

Chemical Formula: $C_5H_3ClN_2O_2$, Molecular Weight: 158.54.

Total H count from HNMR data: 3

To a solution of 4-(4-aminocyclohexoxy)-2-chloro-benzonitrile (40 g, 139.28 mmol, 1 eq, HCl salt), 6-chloropyridazine-3-carboxylic acid (28.71 g, 181.07 mmol, 1.3 eq) and triethylamine (56.38 g, 557.13 mmol, 4 eq) in dichloromethane (400 mL) was slowly charged with 2,4,6-Tripropyl-1,3,5,2,4,6-trioxatriphosphinane 2,4,6-trioxide (106.36 g, 167.14 mmol, 50% in ethyl acetate, 1.2 eq). The reaction mixture was stirred at 30° C. for 2.5 hr. Thin-Layer Chromatography (Petroleum ether:Ethyl acetate=1:1) indicated 4-(4-aminocyclohexoxy)-2-chloro-benzonitrile was consumed completely. The reaction mixture was poured into saturated sodium bicarbonate solution (3 L), and extracted with dichloromethane (2 L*3). The combined organic layers were washed with brine (4 L*3), dried over anhydrous sodium sulfate, filtered and concentrated under reduced pressure. The residue was triturated with ethyl acetate (500 mL). 6-chloro-N-[4-(3-chloro-4-cyano-phenoxy)cyclohexyl]pyridazine-3-carboxamide (50 g, 125.24 mmol, 90% yield, 98% purity) was obtained as a white solid.

$^1$H NMR: (400 MHz, DMSO-$d_6$),

δ: 9.12 (d, J=8.0 Hz, 1H), 8.22 (d, J=8.8 Hz, 1H), 8.09 (d, J=8.8 Hz, 1H), 7.84 (d, J=8.8 Hz, 1H), 7.38 (d, J=2.4 Hz, 1H), 7.13 (dd, J=2.4, 8.8 Hz, 1H), 4.55-4.49 (m, 1H), 3.92-3.88 (m, 1H), 2.13-2.10 (m, 2H), 1.92-1.89 (m, 2H), 1.72-1.66 (m, 2H), 1.55-1.53 (m, 2H).

Chemical Formula: $C_{18}H_{16}Cl_2N_4O_2$, Molecular Weight: 391.25.

Total H count from HNMR data: 18

Preparation of (IIIc): A solution of 6-chloro-N-[4-(3-chloro-4-cyano-phenoxy)cyclohexyl]pyridazine-3-carboxamide (5 g, 12.78 mmol, 1 eq), 4-(dimethoxymethyl)piperidine (2.03 g, 12.78 mmol, 1 eq) and diisopropyl ethyl amine (4.95 g, 38.34 mmol, 3 eq) in dimethylsulfoxide (50 mL) was stirred at 80° C. for 12 hours. LC-MS showed desired compound was detected. The reaction mixture was poured into (500 mL) water and stirred at 25° C. for 1 hour. The precipitate was collected by filtration and dried under high vacuum. The residue was triturated with ethyl acetate and petroleum ether (30 mL, 1:3) to give N-[4-(3-chloro-4-cyano-phenoxy)cyclohexyl]-6-[4-(dimethoxymethyl)-1-piperidyl]pyridazine-3-carboxamide (3.2 g, 6.23 mmol, 48% yield) as a yellow solid.

LCMS: MS (ESI) m/z: 514.1 [M+1]$^+$.

Chemical Formula: $C_{26}H_{32}ClN_5O_4$, Molecular Weight: 514.02

Preparation of (III)

To a solution of N-[4-(3-chloro-4-cyano-phenoxy)cyclohexyl]-6-[4-(dimethoxymethyl)-1-piperidyl]pyridazine-3-carboxamide (3 g, 5.84 mmol, 1 eq) in tetrahydrofuran (80 mL) was added sulfuric acid (2 M in water, 87 mL, 30 eq). The reaction mixture was stirred at 70° C. for 3 hours. Thin layer chromatography (petroleum ether:ethyl acetate=1:1) indicated reactant 1 was consumed completely. The pH was adjusted to 8 with sodium hydroxide (2 M in water), then extracted with ethyl acetate (50 mL×3). The combined organic layers were washed with brine (50 mL×2), dried over anhydrous sodium sulfate, filtered and concentrated under reduced pressure to give N-[4-(3-chloro-4-cyano-phenoxy)cyclohexyl]-6-(4-formyl-1-piperidyl)pyridazine-3-carboxamide (2.6 g, 5.56 mmol, 95% yield) as a yellow solid.

$^1$H NMR: (400 MHz, DMSO-d$_6$)

δ=9.75-9.55 (m, 1H), 8.62 (d, J=8.4 Hz, 1H), 7.84 (dd, J=9.2, 15.2 Hz, 2H), 7.43-7.33 (m, 2H), 7.14 (dd, J=2.4, 8.8 Hz, 1H), 4.58-4.50 (m, 1H), 4.32 (m, 2H), 3.92-3.78 (m, 1H), 3.33-3.21 (m, 2H), 2.76-2.64 (m, 1H), 2.11 (d, J=10.0 Hz, 2H), 1.98-1.85 (m, 4H), 1.69-1.48 (m, 6H)

Chemical Formula: C$_{24}$H$_{26}$ClN$_5$O$_3$, Molecular Weight: 467.95

Total H count from HNMR data: 26.

Step 4. Preparation of (IV), N-[4-(3-chloro-4-cyano-phenoxy)cyclohexyl]-6-[4-[[4-[4-[(2,6-dioxo-3-piperidyl)carbamoyl]phenyl]piperazin-1-yl]methyl]-1-piperidyl]pyridazine-3-carboxamide To a solution of N-(2,6-dioxo-3-piperidyl)-4-piperazin-1-yl-benzamide (113 mg, 0.32 mmol, 1 eq, HCl) in methanol (2 mL) was added sodium acetate (52 mg, 0.64 mmol, 2 eq). The mixture was stirred at 15° C. for 0.5 h. Then N-[4-(3-chloro-4-cyano-phenoxy)cyclohexyl]-6-(4-formyl-1-piperidyl)pyridazine-3-carboxamide (150 mg, 0.32 mmol, 1 eq) in dichloromethane (2 mL) was added to the mixture, acetic acid (0.5 mL) and sodium cyanoborohydride (40 mg, 0.64 mmol, 2 eq) was added to the mixture, the mixture was stirred at 15° C. for 1 h. LCMS showed the reaction was completed and desired MS can be detected. Water (20 mL) was poured into the mixture and stirred for 1 minute. The aqueous phase was extracted with dichloromethane (10 mL×3). The combined organic phase was dried with anhydrous sodium sulfate, filtered and concentrated in vacuum. The residue was purified by prep-HPLC (column: Phenomenex Synergi C18 150*25*10 um; mobile phase: [water (0.225% FA)-ACN]; B %: 12%-42%, 10 min). Compound N-[4-(3-chloro-4-cyano-phenoxy)cyclohexyl]-6-[4-[[4-[4-[(2,6-dioxo-3-piperidyl)carbamoyl]phenyl]piperazin-1-yl]methyl]-1-piperidyl]pyridazine-3-carboxamide (51.1 mg, 0.06 mmol, 19% yield, 99% purity, formate) was obtained as a white solid.

LCMS: MS (ESI) m/z: 770.3 [M+23]$^+$ $^1$H NMR: (400 MHz, DMSO-d$_6$)

δ: 10.83 (s, 1H), 8.59 (d, J=7.6 Hz, 1H), 8.47 (d, J=7.6 Hz, 1H), 8.20 (s, 1H), 7.85 (d, J=8.8 Hz, 1H), 7.77 (dd, J=8.8, 18.4 Hz, 3H), 7.39 (s, 1H), 7.33 (d, J=9.6 Hz, 1H), 7.13 (d, J=8.4 Hz, 1H), 6.97 (d, J=8.4 Hz, 2H), 4.74 (s, 1H),

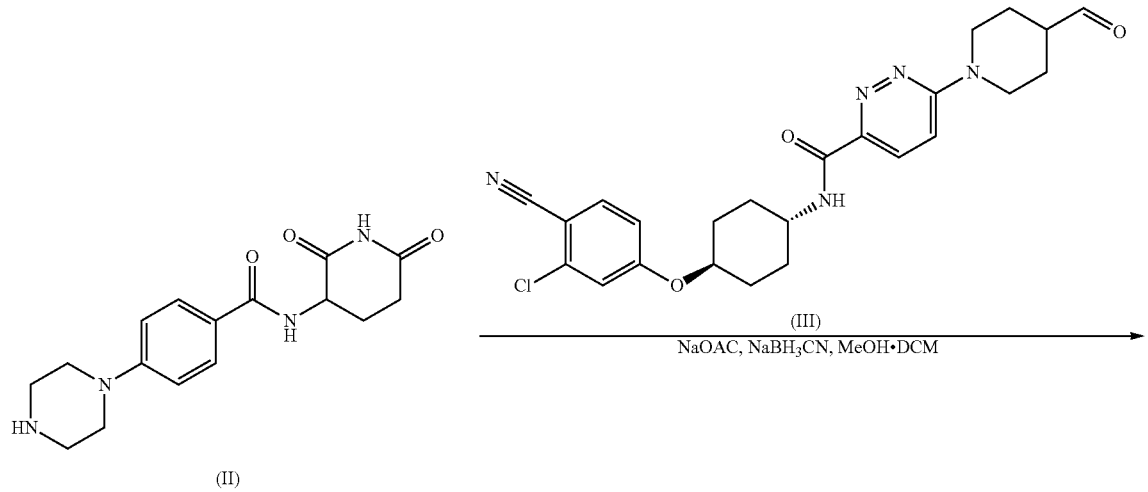

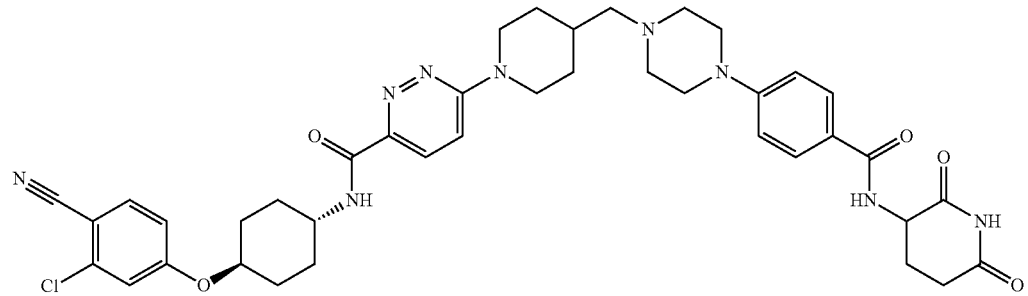

4.59-4.43 (m, 4H), 3.85 (s, 1H), 3.28-3.24 (m, 2H), 3.02 (t, J=12.0 Hz, 2H), 2.85-2.73 (m, 3H), 2.20 (d, J=7.6 Hz, 3H), 2.10 (d, J=9.2 Hz, 4H), 2.02-1.77 (m, 6H), 1.71-1.58 (m, 3H), 1.51 (d, J=12.8 Hz, 3H), 1.12 (d, J=11.6 Hz, 2H)
Chemical Formula: $C_{40}H_{46}ClO_5N_9$, Molecular Weight: 767.33
Example 10—Synthesis of Compound 24
SCHEME 6. SUMMARY OF THE SYNTHESIS OF COMPOUND 24.
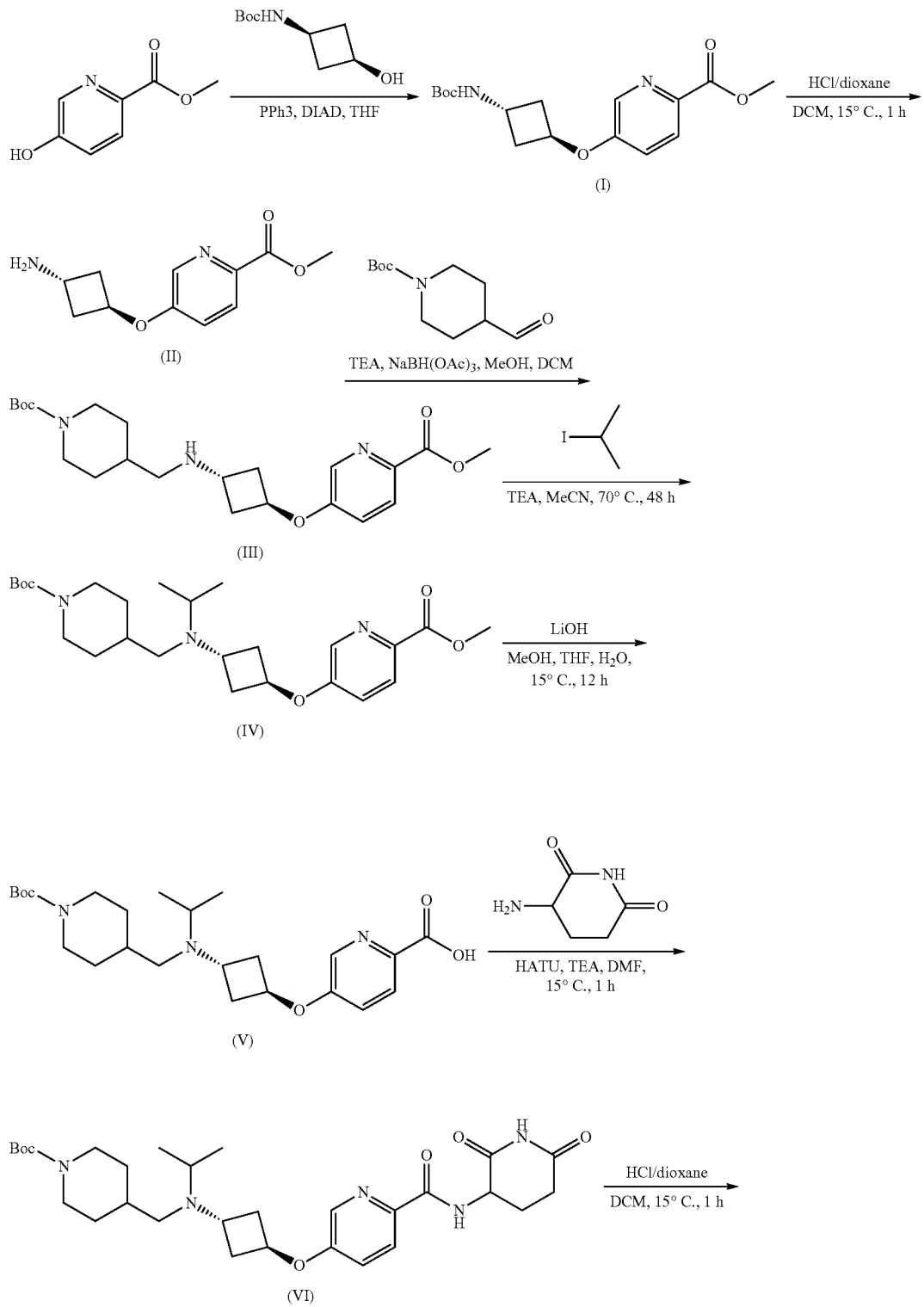

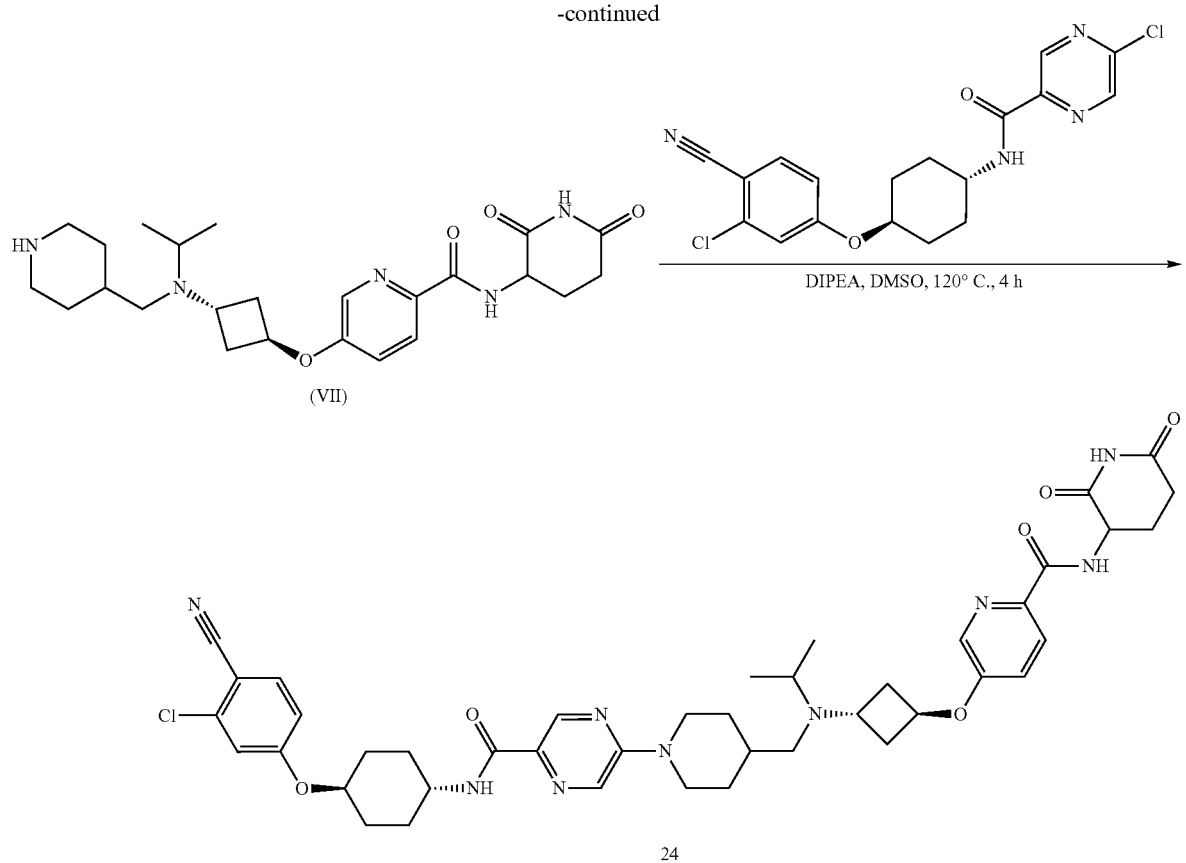

Step 1. Preparation of (I), methyl 5-[3-(tert-butoxy-carbonylamino) cyclobutoxy]pyridine-2-carboxylate To a solution of methyl 5-hydroxypyridine-2-carboxylate (500 mg, 3.27 mmol, 1 eq), tert-butyl N-(3-hydroxycyclobutyl)carbamate (611 mg, 3.27 mmol, 1 eq) and triphenylphosphine (1.28 g, 4.90 mmol, 1.5 eq) in tetrahydrofuran (5 mL) was added diisopropylazodicarboxylate (990 mg, 4.90 mmol, 1.5 eq) at 0° C. The reaction mixture was stirred at 15° C. for 12 hours. LCMS showed desired compound was detected. The reaction mixture was quenched by addition water (30 mL), and extracted with ethyl acetate (50 mL×3). The combined organic layers were washed with brine (80 mL×2), dried over anhydrous sodium sulfate, filtered and concentrated under reduced pressure. The residue was purified by silica gel column chromatography (Petroleum ether/Ethyl acetate=100/1 to 3/1). Methyl 5-[3-(tert-butoxycarbonylamino)cyclobutoxy]pyridine-2-carboxylate (3 g, crude) was obtained as a colorless oil.

LCMS: MS (ESI) m/z: 323.1 [M+1]$^+$

Chemical Formula: $C_{16}H_{22}N_2O_5$, Molecular Weight: 322.36

Step 2. Preparation of (II), methyl 5-(3-aminocyclobutoxy)pyridine-2-carboxylate

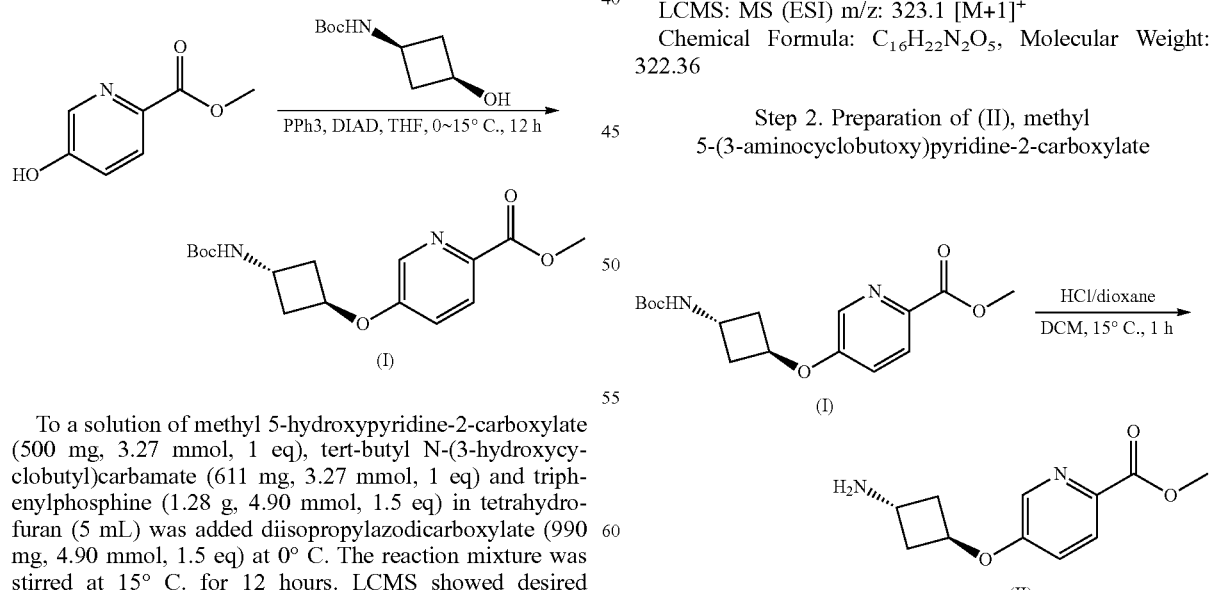

To a solution of methyl 5-[3-(tert-butoxycarbonylamino) cyclobutoxy]pyridine-2-carboxylate (3 g, 9.31 mmol, 1 eq) in dichloromethane (5 mL) was added hydrochloric acid (4

M in dioxane, 3 mL). The reaction mixture was stirred at 15° C. for 1 hour. TLC (Petroleum ether:Ethyl acetate=3:1) indicated methyl 5-[3-(tert-butoxycarbonylamino) cyclobutoxy]pyridine-2-carboxylate was consumed completely. The reaction mixture was concentrated under reduced pressure. The residue was triturated with ethyl acetate (15 mL). methyl 5-(3-aminocyclobutoxy)pyridine-2-carboxylate (760 mg, 2.94 mmol, 31% yield for 2 steps, Hydrochloride) was obtained as a white solid.

$^1$H NMR: (400 MHz, DMSO-$d_6$)

δ: 8.63 (s, 3H), 8.32-8.28 (m, 1H), 8.06-7.99 (m, 1H), 7.36 (dd, J=2.8, 8.8 Hz, 1H), 5.30-5.12 (m, 1H), 3.84 (s, 4H), 2.76-2.64 (m, 2H), 2.48-2.40 (m, 2H), 2.01-1.88 (m, 1H)

Chemical Formula: $C_{11}H_{14}N_2O_3$, Molecular Weight: 222.24

Total H count from HNMR data: 16.

Step 3. Preparation of (III), methyl 5-[3-[(1-tert-butoxycarbonyl-4-piperidyl)methylamino]cyclobutoxy]pyridine-2-carboxylate

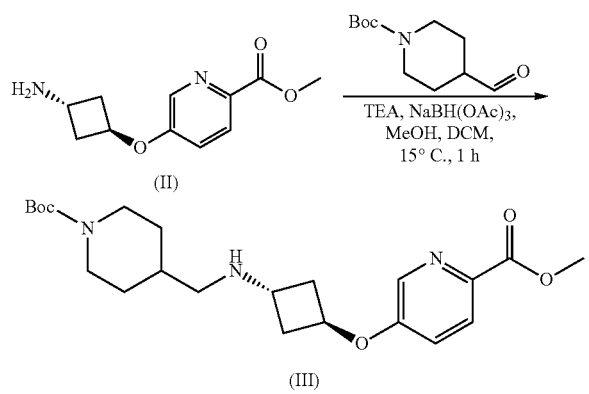

A solution of methyl 5-(3-aminocyclobutoxy)pyridine-2-carboxylate (700 mg, 2.71 mmol, 1 eq, Hydrochloride) and triethylamine (821 mg, 8.12 mmol, 3 eq) in methanol (10 mL) and dichloromethane (10 mL) was stirred at 15° C. for 0.5 hour. Tert-butyl 4-formylpiperidine-1-carboxylate (577 mg, 2.71 mmol, 1 eq) was added. Then sodium borohydride acetate (1.72 g, 8.12 mmol, 3 eq) was added. The reaction mixture was stirred at 15° C. for 0.5 hour. LCMS showed desired compound was detected. The reaction mixture was quenched by water (50 mL), and extracted with dichloromethane (30 mL×3), dried over anhydrous sodium sulfate, filtered and concentrated under reduced pressure. The residue was triturated with ethyl acetate (10 mL). Methyl 5-[3-[(1-tert-butoxycarbonyl-4-piperidyl) methylamino]cyclobutoxy]pyridine-2-carboxylate (460 mg, 1.10 mmol, 40% yield) was obtained as a white solid.

LCMS: MS (ESI) m/z: 418.2 [M+1]$^+$ $^1$H NMR: (400 MHz, DMSO-$d_6$)

δ: 9.28 (s, 2H), 8.32 (d, J=2.8 Hz, 1H), 8.05 (d, J=8.8 Hz, 1H), 7.37 (dd, J=2.8, 8.8 Hz, 1H), 5.29-5.03 (m, 1H), 4.04-3.89 (m, 2H), 3.85 (s, 4H), 2.87-2.78 (m, 2H), 2.76-2.66 (m, 3H), 2.48-2.38 (m, 2H), 1.89 (d, J=19.2 Hz, 1H), 1.76 (d, J=12.0 Hz, 2H), 1.40 (s, 9H), 1.07 (dq, J=4.0, 12.0 Hz, 2H)

Chemical Formula: $C_{20}H_{27}N_5O_5$, Molecular Weight: 417.46

Total H count from HNMR data: 27.

Step 4. Preparation of (IV), methyl 5-[3-[(1-tert-butoxycarbonyl-4-piperidyl)methyl-isopropyl-amino]cyclobutoxy]pyridine-2-carboxylate

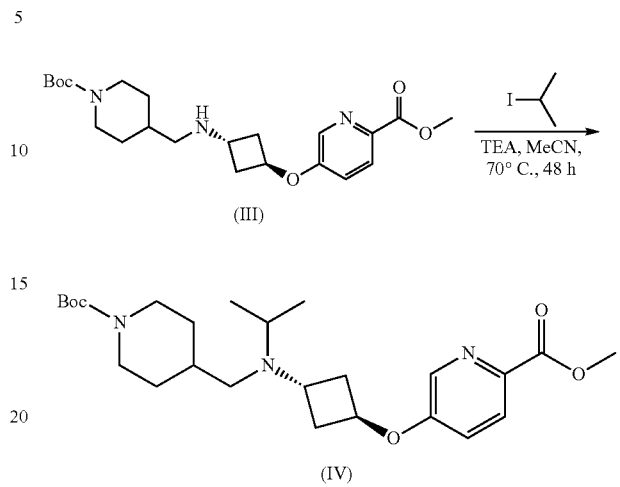

To a solution of methyl 5-[3-[(1-tert-butoxycarbonyl-4-piperidyl)methylamino]cyclobutoxy] pyridine-2-carboxylate (410 mg, 0.97 mmol, 1 eq) and triethylamine (494 mg, 4.89 mmol, 5 eq) in acetonitrile (5 mL) was added 2-iodopropane (1.66 g, 9.77 mmol, 10 eq). The reaction mixture was stirred at 70° C. for 48 h. Thin layer chromatography (Dichloromethane:Methanol=10:1) indicated methyl 5-[3-[(1-tert-butoxycarbonyl-4-piperidyl)methylamino]cyclobutoxy] pyridine-2-carboxylate was consumed completely. The reaction mixture was diluted with ethyl acetate (80 mL), washed with brine (50 mL×3), dried over anhydrous sodium sulfate, filtered and concentrated under reduced pressure. The residue was purified by silica gel column chromatography (Petroleum ether/Ethyl acetate=10/1 to 1/1). Methyl 5-[3-[(1-tert-butoxycarbonyl-4-piperidyl)methyl-isopropyl-amino]cyclobutoxy]pyridine-2-carboxylate (300 mg, 0.64 mmol, 66% yield) was obtained as a yellow solid.

$^1$H NMR: (400 MHz, DMSO-$d_6$)

δ: 8.30 (s, 1H), 8.01 (d, J=7.8 Hz, 1H), 7.34 (d, J=7.2 Hz, 1H), 4.82 (s, 1H), 4.08-3.89 (m, 3H), 3.84 (s, 3H), 3.64 (s, 1H), 3.32 (s, 3H), 2.87 (s, 1H), 2.66 (s, 1H), 2.37 (s, 3H), 2.18 (d, J=13.6 Hz, 4H), 1.99 (s, 1H), 1.70 (d, J=10.4 Hz, 2H), 1.39 (s, 11H), 1.17 (s, 2H), 0.90 (d, J=4.0 Hz, 8H)

Chemical Formula: $C_{25}H_{39}N_3O_5$, Molecular Weight: 461.59

Total H count from HNMR data: 39.

Step 5. Preparation of (V), 5-[3-[(1-tert-butoxycarbonyl-4-piperidyl) methyl-isopropyl-amino]cyclobutoxy]pyridine-2-carboxylic acid

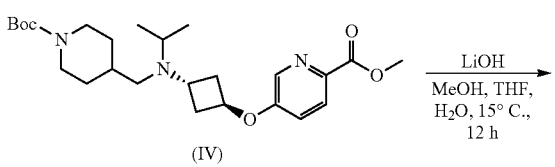

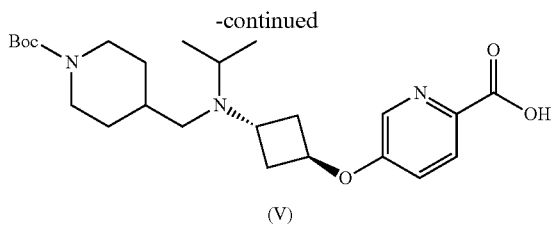

To a solution of methyl 5-[3-[(1-tert-butoxycarbonyl-4-piperidyl)methyl-isopropyl-amino] cyclobutoxy]pyridine-2-carboxylate (300 mg, 0.64 mmol, 1 eq) in methanol (2 mL), tetrahydrofuran (2 mL) and water (2 mL) was added lithium hydroxide (109 mg, 2.60 mmol, 4 eq). The reaction mixture was stirred at 15° C. for 12 hours. LCMS showed desired compound was detected. The reaction mixture was concentrated under reduced pressure. The pH was adjusted to 6 with 1 M hydrochloric acid, and concentrated under reduced pressure. The residue was purified by prep-HPLC (column: Phenomenex Synergi C18 150*25*10 um; mobile phase: [water (0.1% TFA)-ACN]; B %: 23%-53%, 9 min). 5-[3-[(1-tert-butoxycarbonyl-4-piperidyl)methyl-isopropyl-amino]cyclobutoxy]pyridine-2-carboxylic acid (230 mg, 0.40 mmol, 63% yield, Trifluoroacetic acid) was obtained as a white solid.

LCMS: MS (ESI) m/z: 448.4 [M+1]$^+$ $^1$H NMR: (400 MHz, DMSO-d$_6$)

δ: 9.00 (s, 1H), 8.33 (d, J=2.8 Hz, 1H), 8.04 (d, J=8.8 Hz, 1H), 7.42 (dd, J=2.8, 8.8 Hz, 1H), 4.99 (t, J=6.4 Hz, 1H), 4.31-4.09 (m, 1H), 3.96 (d, J=10.0 Hz, 2H), 3.63-3.49 (m, 1H), 3.13-3.01 (m, 1H), 2.98-2.84 (m, 2H), 2.82-2.63 (m, 3H), 2.61-2.53 (m, 1H), 1.90-1.68 (m, 3H), 1.40 (s, 9H), 1.27 (d, J=6.4 Hz, 3H), 1.19 (d, J=6.4 Hz, 3H), 1.12-1.01 (m, 2H)

Chemical Formula: C$_{24}$H$_{37}$N$_3$O, Molecular Weight: 447.57

Total H count from HNMR data: 37.

Step 6. Preparation of (VI), tert-butyl 4-[[[3-[[6-[(2,6-dioxo-3-piperidyl)carbamoyl]-3-pyridyl]oxy]cyclobutyl]-isopropyl-amino]methyl]piperidine-1-carboxylate A solution of 5-[3-[(1-tert-butoxycarbonyl-4-piperidyl)methyl-isopropyl-amino]cyclobutoxy]pyridine-2-carboxylic acid (180 mg, 0.32 mmol, 1 eq, Trifluoroacetic acid), triethylamine (64 mg, 0.64 mmol, 2 eq) and o-(7-azabenzotriazol-1-yl)-n,n,n',n'-tetramethyluronium hexafluorophosphate (182 mg, 0.48 mmol, 1.5 eq) in dimethyl formamide (3 mL) was stirred at 15° C. for 0.5 hours. Then a solution of triethylamine (64 mg, 0.64 mmol, 2 eq) and 3-aminopiperidine-2,6-dione (79 mg, 0.48 mmol, 1.5 eq, Hydrochloric acid) in dimethyl formamide (2 mL) was added. The reaction mixture was stirred at 15° C. for 0.5 hour. LCMS showed desired compound was detected. The reaction mixture was quenched by addition water (50 mL), extracted with ethyl acetate (50 mL×3). The combined organic layers were washed with brine (50 mL×3), dried over anhydrous sodium sulfate, filtered and concentrated under reduced pressure. The residue was purified by silica gel column chromatography (dichloromethane/methanol=100/1 to 20/1). tert-butyl 4-[[[3-[[6-[(2,6-dioxo-3-piperidyl)carbamoyl]-3-pyridyl]oxy]cyclobutyl]-isopropyl-amino]methyl]piperidine-1-carboxylate (160 mg, 0.28 mmol, 89% yield) was obtained as a yellow oil.

LCMS: MS (ESI) m/z: 558.0 [M+1]$^+$ $^1$H NMR: (400 MHz, CHLOROFORM-d)

δ: 8.50 (d, J=6.4 Hz, 1H), 8.21-8.09 (m, 2H), 8.00 (s, 1H), 7.20-7.10 (m, 1H), 4.89-4.64 (m, 2H), 4.30-3.97 (m, 6H), 3.83-3.59 (m, 1H), 2.99-2.82 (m, 3H), 2.75-2.56 (m, 3H), 2.45-2.20 (m, 6H), 2.08-2.03 (m, 6H), 1.78 (d, J=12.4 Hz, 2H), 1.55-1.41 (m, 1H), 1.55-1.41 (m, 10H), 1.30-1.24 (m, 6H), 0.97 (d, J=6.4 Hz, 7H)

Chemical Formula: C$_{29}$H$_{43}$N$_5$O$_6$, Molecular Weight: 557.68

Total H count from HNMR data: 43.

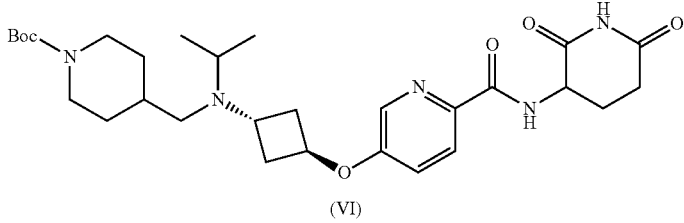

Step 7 Preparation of (VII), N-(2,6-dioxo-3-piperidyl)-5-[3-[isopropyl (4-piperidylmethyl)amino]cyclobutoxy]pyridine-2-carboxamide

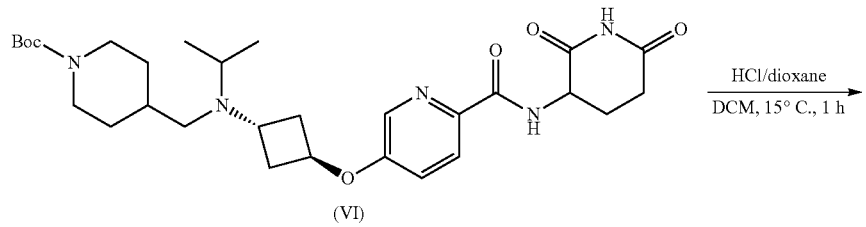

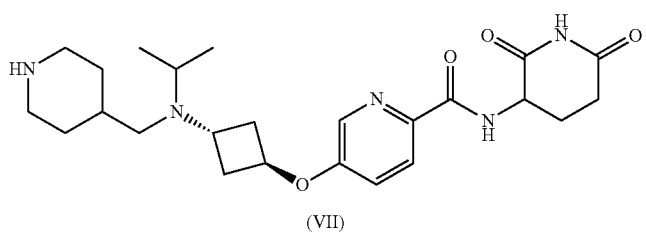

To a solution of tert-butyl 4-[[[3-[[6-[(2,6-dioxo-3-piperidyl)carbamoyl]-3-pyridyl]oxy] cyclobutyl]-isopropyl-amino]methyl]piperidine-1-carboxylate (160 mg, 0.28 mmol, 1 eq) in dichloromethane (5 mL) was added hydrochloric acid (4 M in dioxane, 3 mL). The reaction mixture was stirred at 15° C. for 1 hour. LCMS showed desired compound was detected. The reaction mixture was concentrated under reduced pressure. N-(2,6-dioxo-3-piperidyl)-5-[3-[isopropyl(4-piperidylmethyl)amino]cyclobutoxy]pyridine-2-carboxamide (140 mg, crude, Hydrochloride) was obtained as a gray solid.

LCMS: MS (ESI) m/z: 458.1 [M+1]$^+$

Chemical Formula: $C_{24}H_{35}N_5O_4$, Molecular Weight: 457.57

Step 8. Preparation of Compound No. 24, N-[4-(3-chloro-4-cyano-phenoxy)cyclohexyl]-5-[4-[[[3-[[6-[(2,6-dioxo-3-piperidyl)carbamoyl]-3-pyridyl]oxy]cyclobutyl]-isopropyl-amino]methyl]-1-piperidyl]pyrazine-2-carboxamide

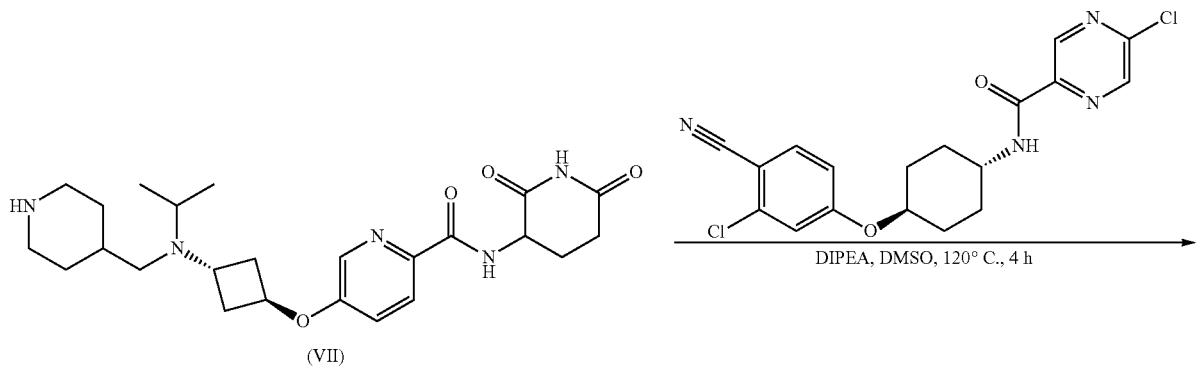

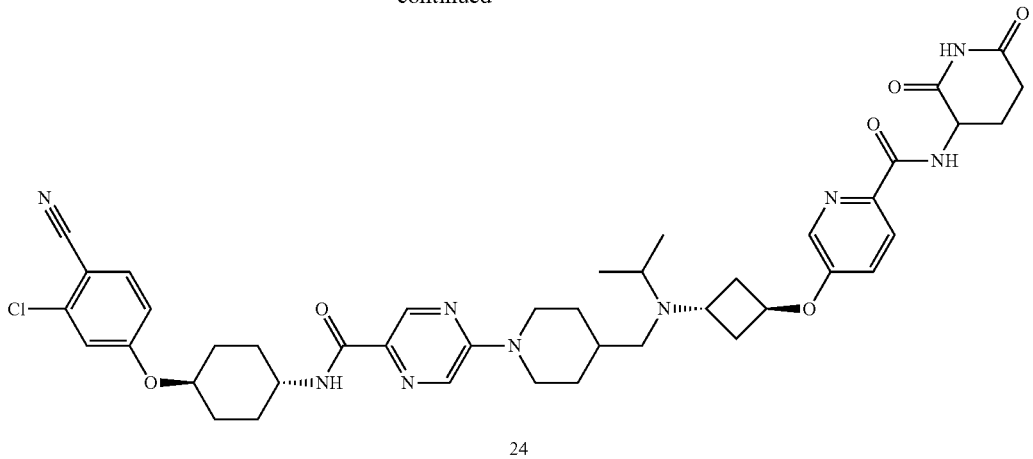

A solution of N-(2,6-dioxo-3-piperidyl)-5-[3-[isopropyl(4-piperidylmethyl)amino]cyclobutoxy]pyridine-2-carboxamide (140 mg, 0.28 mmol, 1 eq, Hydrochloride), 5-chloro-N-[4-(3-chloro-4-cyano-phenoxy)cyclohexyl]pyrazine-2-carboxamide (110 mg, 0.28 mmol, 1 eq) and diisopropyl ethyl amine (109 mg, 0.85 mmol, 3 eq) in dimethylsulfoxide (5 mL) was stirred at 120° C. for 4 hours. LCMS showed desired compound was detected. The reaction mixture was quenched by addition water (50 mL), extracted with ethyl acetate (50 mL×3). The combined organic layers were washed with brine (50 mL×2), dried over anhydrous sodium sulfate, filtered and concentrated under reduced pressure. The residue was purified by prep-HPLC (column: Phenomenex Synergi C18 150*25*10 um; mobile phase: [water (0.225% FA)-ACN]; B %: 21%-48%, 10 min). N-[4-(3-chloro-4-cyano-phenoxy) cyclohexyl]-5-[4-[[[3-[[6-[(2,6-dioxo-3-piperidyl)carbamoyl]-3-pyridyl]oxy]cyclobutyl]-isopropyl-amino]methyl]-1-piperidyl]pyrazine-2-carboxamide (108 mg, 0.12 mmol, 43% yield, 99% purity, formate) was obtained as an off-white solid.

LCMS: MS (ESI) m/z: 812.2 [M+1]$^+$ $^1$H NMR: (400 MHz, DMSO-d$_6$)

δ: 10.84 (s, 1H), 8.84 (d, J=8.4 Hz, 1H), 8.58 (s, 1H), 8.29-8.21 (m, 2H), 8.17 (s, 1H), 8.07-7.95 (m, 2H), 7.85 (d, J=8.8 Hz, 1H), 7.41-7.32 (m, 2H), 7.11 (dd, J=2.4, 8.8 Hz, 1H), 4.90-4.68 (m, 2H), 4.59-4.37 (m, 3H), 3.90-3.58 (m, 2H), 3.02-2.85 (m, 3H), 2.84-2.71 (m, 1H), 2.53 (d, J=2.8 Hz, 2H), 2.44-2.31 (m, 3H), 2.30-1.95 (m, 9H), 1.92-1.79 (m, 4H), 1.73-1.42 (m, 5H), 1.05 (q, J=10.8 Hz, 2H), 0.92 (d, J=6.4 Hz, 6H)

Chemical Formula: C$_{42}$H$_{50}$ClN$_9$O$_6$, Molecular Weight: 812.36

Total H count from HNMR data: 51.

Example 11—Synthesis of Compound 27

SCHEME 7. SUMMARY OF THE SYNTHESIS OF COMPOUND 27.

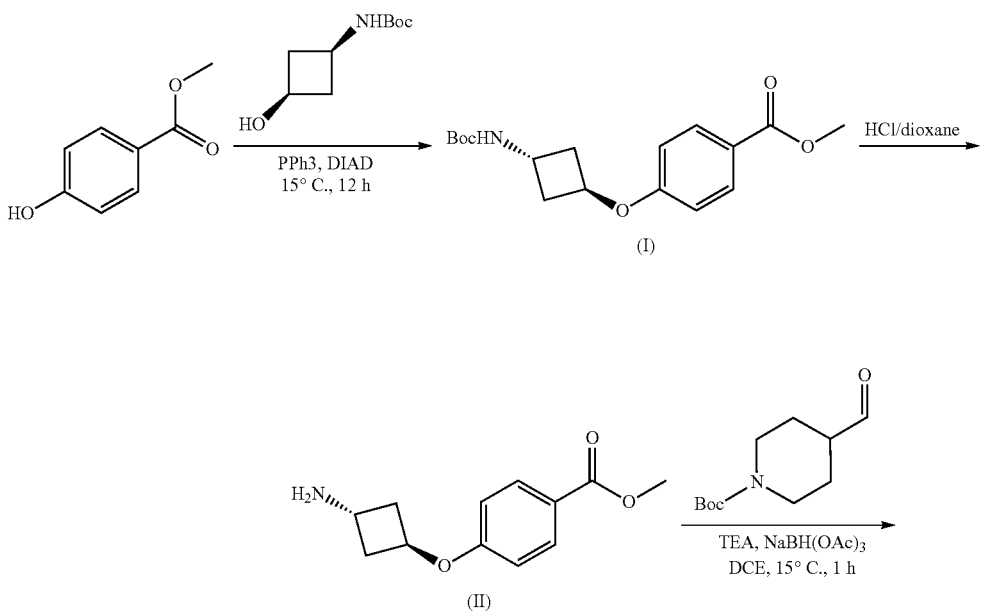

-continued
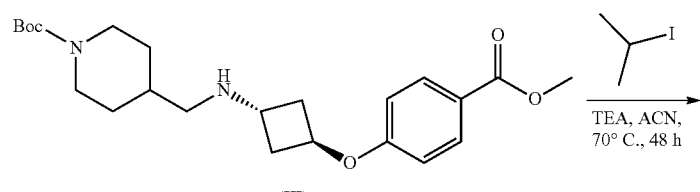
(III)
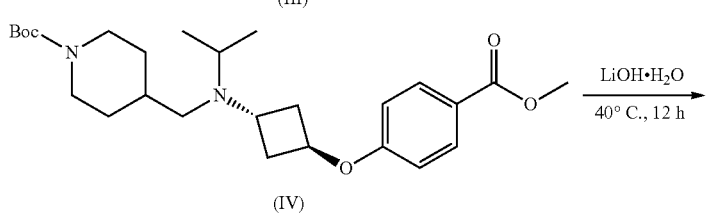
(IV)
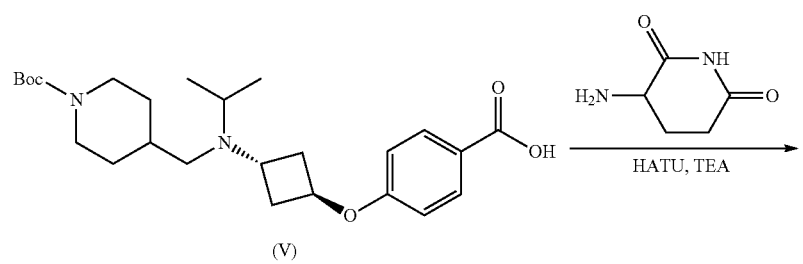
(V)
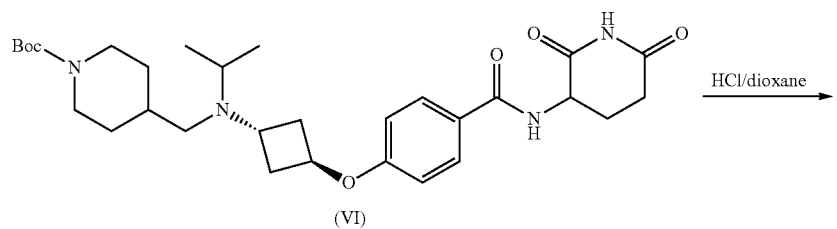
(VI)
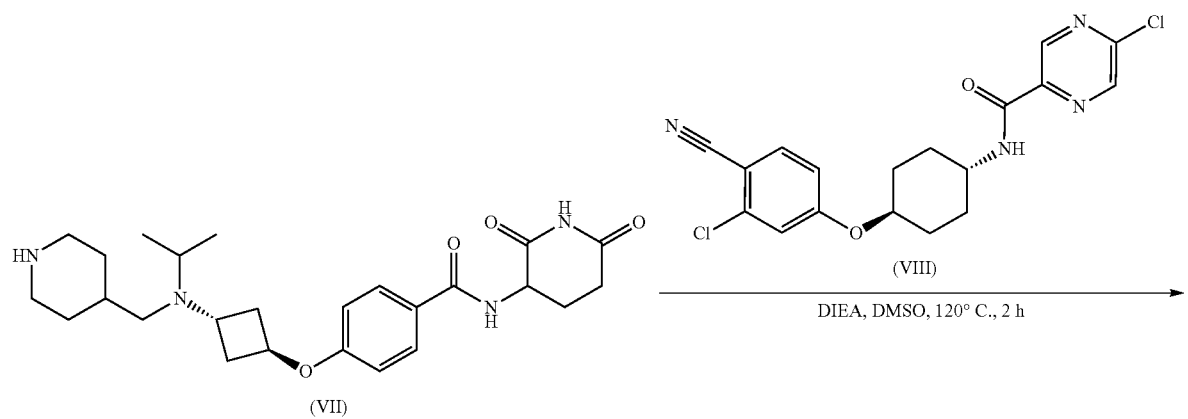
(VII)    (VIII)

-continued

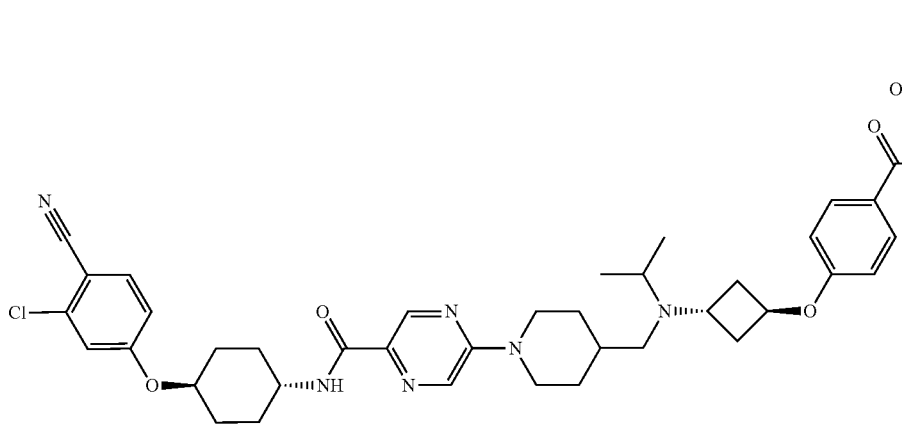

27

Step 1. Preparation of (I), methyl 4-[3-(tert-butoxycarbonylamino)cyclobutoxy]benzoate Step 2. Preparation of (II), methyl 4-(3-aminocyclobutoxy)benzoate

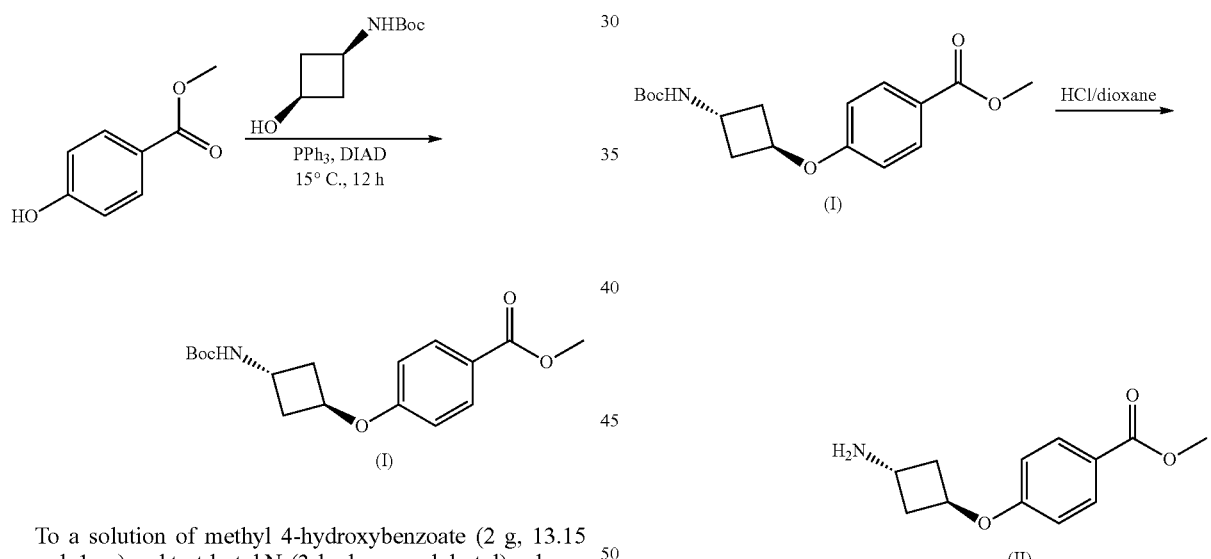

To a solution of methyl 4-hydroxybenzoate (2 g, 13.15 mmol, 1 eq) and tert-butyl N-(3-hydroxycyclobutyl)carbamate (2.46 g, 13.15 mmol, 1 eq) in tetrahydrofuran (150 mL) was added triphenylphosphine (4.14 g, 15.77 mmol, 1.2 eq) and diisopropyl azodicarboxylate (3.19 g, 15.77 mmol, 3.07 mL, 1.2 eq) at 0° C. The mixture was stirred at 15° C. for 12 hours. LCMS detected the desired MS. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The crude product was used into the next step without further purification. Compound methyl 4-[3-(tert-butoxycarbonylamino) cyclobutoxy]benzoate (6 g, crude) was obtained as a yellow oil.

LCMS: MS (ESI) m/z: 266.0 [M−56+1]$^+$

Chemical Formula: $C_{17}H_{23}O_5N$, Molecular Weight: 321.37

To a solution of methyl 4-[3-(tert-butoxycarbonylamino) cyclobutoxy]benzoate (6 g, 18.67 mmol, 1 eq) in dichloromethane (20 mL) was added hydrochloride acid/dioxane (4 M, 93 mL, 20 eq). The mixture was stirred at 20° C. for 12 hours. Thin layer chromatography (dichloromethane:methanol=20:1) indicated the starting material was consumed completely and one new spot formed. The reaction mixture was filtered and concentrated under reduced pressure. The crude product was used into the next step without further purification. Compound methyl 4-(3-aminocyclobutoxy)benzoate (2.5 g, 9.70 mmol, 51% yield, hydrochloride) was obtained as a yellow solid.

Step 3. Preparation of (III), tert-butyl 4-[[[3-(4-methoxycarbonylphenoxy) cyclobutyl]amino]methyl]piperidine-1-carboxylate

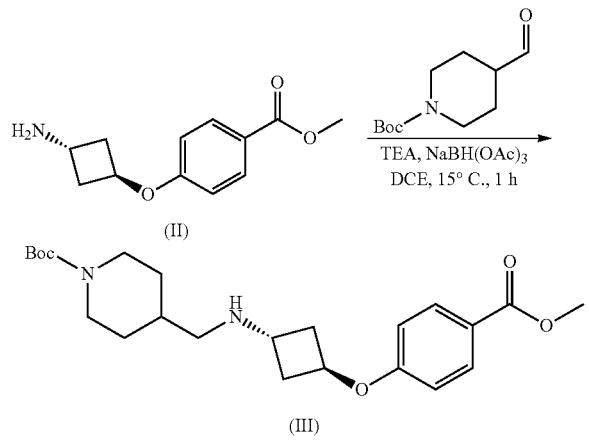

To a solution of methyl 4-(3-aminocyclobutoxy)benzoate (2.5 g, 9.70 mmol, 1 eq, hydrochloride) and tert-butyl 4-formylpiperidine-1-carboxylate (2.07 g, 9.70 mmol, 1 eq) in 1,2-dichloroethane (30 mL) was added triethylamine (1.96 g, 19.40 mmol, 2 eq), the mixture was stirred at 15° C. for 0.5 hours. Then sodium triacetoxyborohydride (6.17 g, 29.10 mmol, 3 eq) was added to the mixture. The mixture was stirred at 15° C. for 0.5 hours. LCMS detected the desired MS. Water (100 mL) was poured into the mixture and stirred for 1 minute. The aqueous phase was extracted with dichloromethane (100 mL×3). The combined organic phase was washed with brine (100 mL×2), dried with anhydrous sodium sulfate, filtered and concentrated in vacuum. The residue was purified by silica gel chromatography (petroleum ether:ethyl acetate=30:1 to 10:1, dichloromethane:methanol=50:1). Compound tert-butyl 4-[[[3-(4-methoxycarbonylphenoxy)cyclobutyl]amino]methyl]piperidine-1-carboxylate (1.6 g, 3.82 mmol, 39% yield) was obtained as a white solid.

LCMS: MS (ESI) m/z: 419.2 [M+1]$^+$

Chemical Formula: $C_{23}H_{34}O_5N_2$, Molecular Weight: 418.53

Step 4. Preparation of (IV), tert-butyl 4-[[isopropyl-[3-(4-methoxycarbonylphenoxy)cyclobutyl]amino]methyl]piperidine-1-carboxylate

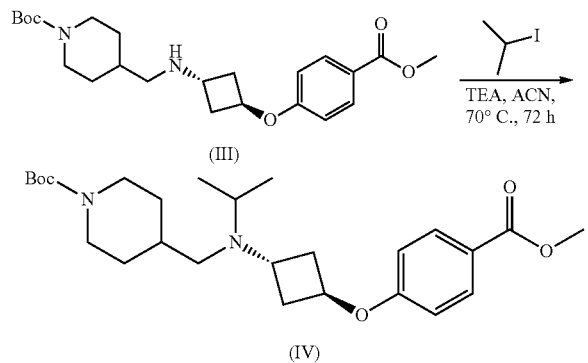

To a solution of tert-butyl 4-[[[3-(4-methoxycarbonylphenoxy)cyclobutyl]amino]methyl] piperidine-1-carboxylate (400 mg, 0.95 mmol, 1 eq) in acetonitrile (5 mL) was added triethylamine (483 mg, 4.78 mmol, 5 eq) and 2-iodopropane (1.62 g, 9.56 mmol, 10 eq). The mixture was stirred at 70° C. for 72 h. Thin layer chromatography (petroleum ether:ethyl acetate=1:1) showed the reactant was consumed completely and one new major spot (R$_f$=0.65) was detected. Water (100 mL) was poured into the mixture and stirred for 1 minute. The aqueous phase was extracted with ethyl acetate (100 mL×3). The combined organic phase was washed with brine (100 mL×2), dried with anhydrous sodium sulfate, filtered and concentrated in vacuum. The residue was purified by silica gel chromatography (petroleum ether:ethyl acetate=50:1 to 0:1). Compound tert-butyl 4-[[isopropyl-[3-(4-methoxycarbonylphenoxy)cyclobutyl]amino]methyl]piperidine-1-carboxylate (325 mg, 0.70 mmol, 36% yield) was obtained as a brown solid.

Step 5. Preparation of (V), 4-[3-[(1-tert-butoxycarbonyl-4-piperidyl) methyl-isopropyl-amino]cyclobutoxy]benzoic acid

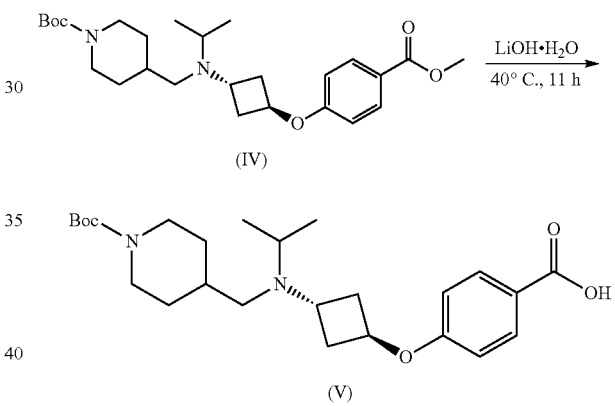

To a solution of tert-butyl 4-[[isopropyl-[3-(4-methoxycarbonylphenoxy)cyclobutyl]amino] methyl]piperidine-1-carboxylate (650 mg, 1.41 mmol, 1 eq) in methanol (5 mL), tetrahydrofuran (5 mL) and water (3 mL) was added lithium hydroxide monohydrate (236 mg, 5.64 mmol, 4 eq). The mixture was stirred at 40° C. for 1 hour. LCMS showed the reactant was not consumed completely. The mixture was stirred at 40° C. for 10 hours. LCMS showed the reaction was completed and desired MS can be detected. The reaction mixture concentrated under reduced pressure. The reaction mixture was adjusted pH to 5 with hydrochloride acid (1M). Water (50 mL) was poured into the mixture and stirred for 1 minute. The aqueous phase was extracted with ethyl acetate (30 mL×3). The combined organic phase was washed with brine (30 mL×2), dried with anhydrous sodium sulfate, filtered and concentrated in vacuum. Compound 4-[3-[(1-tert-butoxycarbonyl-4-piperidyl)methyl-isopropyl-amino]cyclobutoxy]benzoic acid (500 mg, 1.12 mmol, 79% yield) was obtained as a brown solid.

LCMS: MS (ESI) m/z: 447.2 [M+1]$^+$

Chemical Formula: $C_{25}H_{38}O_5N_2$, Molecular Weight: 446.58

Step 6. Preparation of (VI), tert-butyl 4-[[[3-[4-[(2,6-dioxo-3-piperidyl) carbamoyl]phenoxy]cyclobutyl]-isopropyl-amino]methyl]piperidine-1-carboxylate

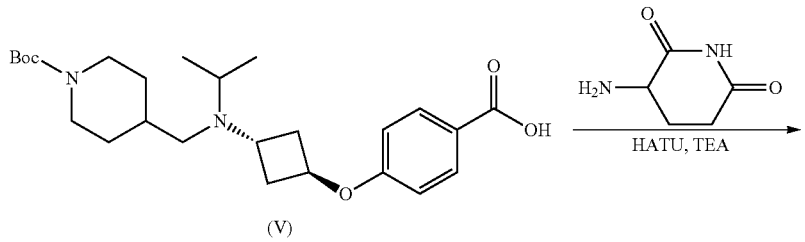

(V)

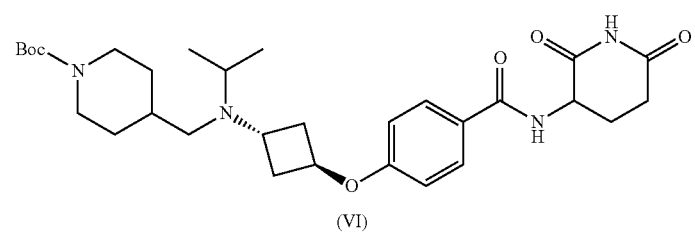

(VI)

To a solution of 4-[3-[(1-tert-butoxycarbonyl-4-piperidyl)methyl-isopropyl-amino]cyclobutoxy]benzoic acid (500 mg, 1.12 mmol, 1 eq) in N,N-dimethylformamide (5 mL) was added o-(7-azabenzotriazol-1-yl)-n,n,n',n'-tetramethyluronium hexafluorophosphate (638 mg, 1.68 mmol, 1.5 eq) and triethylamine (339 mg, 3.36 mmol, 3 eq). Then 3-aminopiperidine-2,6-dione (184 mg, 1.12 mmol, 1 eq, hydrochloride) was added to the mixture. The mixture was stirred at 15° C. for 1 hour. LCMS detected the desired MS. Water (100 mL) was poured into the mixture and stirred for 1 minute. The aqueous phase was extracted with ethyl acetate (50 mL×3). The combined organic phase was washed with brine (100 mL×2), dried with anhydrous sodium sulfate, filtered and concentrated in vacuum. The residue was purified by prep-TLC (dichloromethane:methanol=10:1). Compound tert-butyl 4-[[[3-[4-[(2,6-dioxo-3-piperidyl)carbamoyl]phenoxy]cyclobutyl]-isopropyl-amino]methyl]piperidine-1-carboxylate (100 mg, 0.17 mmol, 16% yield) was obtained as a yellow oil.

LCMS: MS (ESI) m/z: 557.3 [M+1]$^+$

Chemical Formula: $C_{30}H_{44}N_4O_6$, Molecular Weight: 556.69

Step 7. Preparation of (VII), N-(2,6-dioxo-3-piperidyl)-4-[3-[isopropyl(4-piperidylmethyl)amino]cyclobutoxy]benzamide

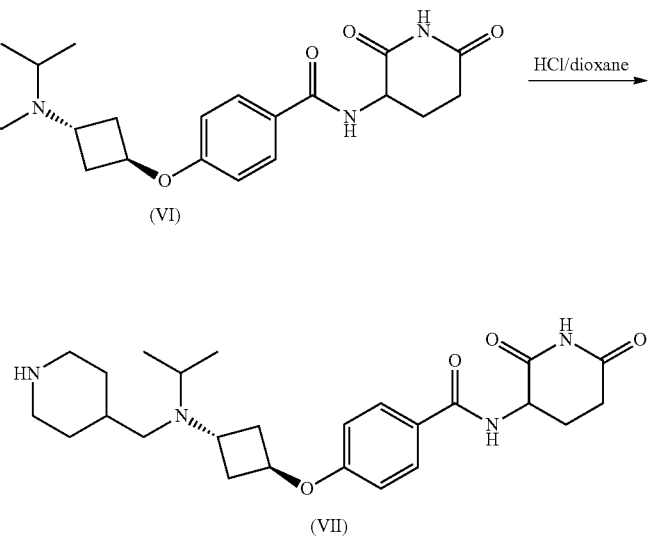

To a solution of tert-butyl 4-[[[3-[4-[(2,6-dioxo-3-piperidyl)carbamoyl]phenoxy]cyclobutyl]-isopropyl-amino]methyl]piperidine-1-carboxylate (100 mg, 0.17 mmol, 1 eq) in dichloromethane (2 mL) was added hydrochloride acid/dioxane (4 M, 4 mL, 89.07 eq). The mixture was stirred at 15° C. for 1 hour. LCMS detected the desired MS. The reaction mixture concentrated under reduced pressure. The crude product was used into the next step without further purification. Compound N-(2,6-dioxo-3-piperidyl)-4-[3-[isopropyl (4-piperidylmethyl)amino]cyclobutoxy]benzamide (70 mg, 0.14 mmol, 79% yield, hydrochloride) was obtained as a brown solid.

LCMS: MS (ESI) m/z: 457.4 [M+1]$^+$

Chemical Formula: $C_{25}H_{36}N_4O_4$, Molecular Weight: 456.27

Step 8. Preparation of Compound 27, N-[4-(3-chloro-4-cyano-phenoxy)cyclohexyl]-6-[4-[[4-[6-[(2,6-dioxo-3-piperidyl)carbamoyl]-3-pyridyl]piperazin-1-yl]methyl]-1-piperidyl]pyridazine-3-carboxamide To a solution of N-(2,6-dioxo-3-piperidyl)-4-[3-[isopropyl(4-piperidylmethyl)amino]cyclobutoxy]benzamide (70 mg, 0.14 mmol, 1 eq, hydrochloride) and (VIII), 5-chloro-N-[4-(3-chloro-4-cyano-phenoxy)cyclohexyl]pyrazine-2-carboxamide (55 mg, 0.14 mmol, 1 eq) in dimethylsulfoxide (2 mL) was added diisopropylethylamine (110 mg, 0.85 mmol, 6 eq). The mixture was stirred at 120° C. for 2 hours. LCMS detected the desired MS. Water (50 mL) was poured into the mixture and stirred for 1 minute. The aqueous phase was extracted with ethyl acetate (20 mL×3). The combined organic phase was washed with brine (20 mL×2), dried with anhydrous sodium sulfate, filtered and concentrated in vacuum. The residue was purified by prep-HPLC (column: Phenomenex Synergi C18 150*25*10 um; mobile phase: [water (0.225% FA)-ACN]; B %: 14%-44%, 10 min). Compound N-[4-(3-chloro-4-cyano-phenoxy)cyclohexyl]-5-[4-[[[3-[4-[(2,6-dioxo-3-piperidyl)carbamoyl]phenoxy]cyclobutyl]-isopropyl-amino]methyl]-1-piperidyl]pyrazine-2-carboxamide (34.4 mg, 0.03 mmol, 27% yield, 98% purity, formate) was obtained as a yellow solid.

LCMS: MS (ESI) m/z: 811.3 [M+1]$^+$
$^1$H NMR: (400 MHz, DMSO-d$_6$)

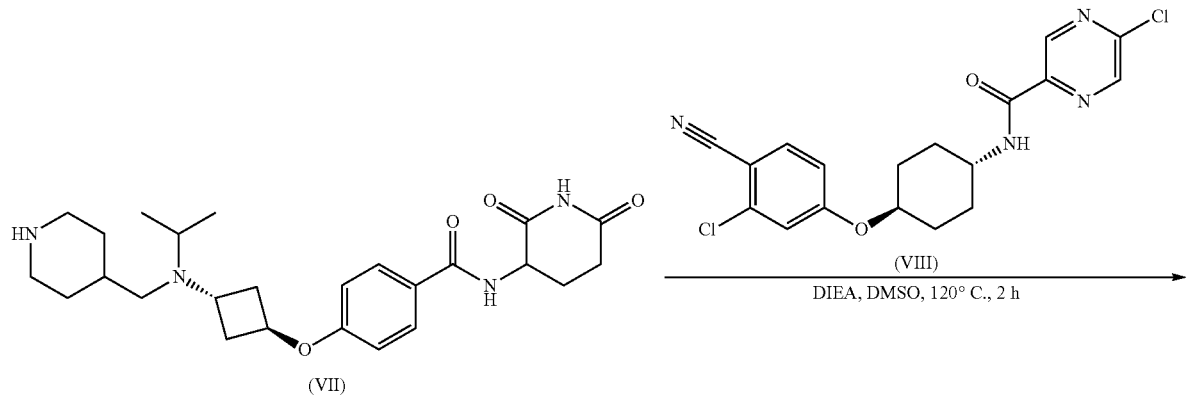

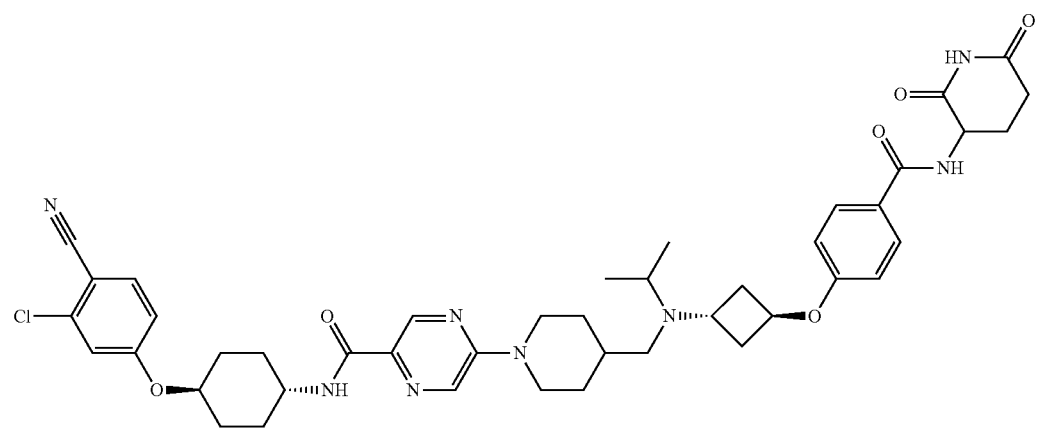

δ: 10.82 (s, 1H), 8.62-8.54 (m, 2H), 8.23 (d, J=8.8 Hz, 2H), 8.04 (d, J=8.0 Hz, 1H), 7.89-7.75 (m, 3H), 7.36 (d, J=2.4 Hz, 1H), 7.12 (dd, J=2.4, 8.8 Hz, 1H), 6.88 (d, J=8.8 Hz, 2H), 4.79-4.68 (m, 2H), 4.49 (d, J=12.4 Hz, 3H), 3.88-3.77 (m, 1H), 3.69-3.67 (m, 1H), 3.01-2.86 (m, 3H), 2.84-2.72 (m, 1H), 2.57-2.52 (m, 1H), 2.38 (d, J=13.8 Hz, 1H), 2.25 (d, J=6.8 Hz, 2H), 2.21-2.03 (m, 6H), 1.96 (dd, J=4.0, 8.8 Hz, 1H), 1.92-1.82 (m, 4H), 1.76-1.41 (m, 5H), 1.13-0.98 (m, 2H), 0.92 (d, J=6.4 Hz, 6H)
Chemical Formula: $C_{43}H_{51}ClO_6N_8$, Molecular Weight: 810.36
Example 12—Synthesis of Compound 28
SCHEME 8. SUMMARY OF SYNTHESIS OF COMPOUND 28.
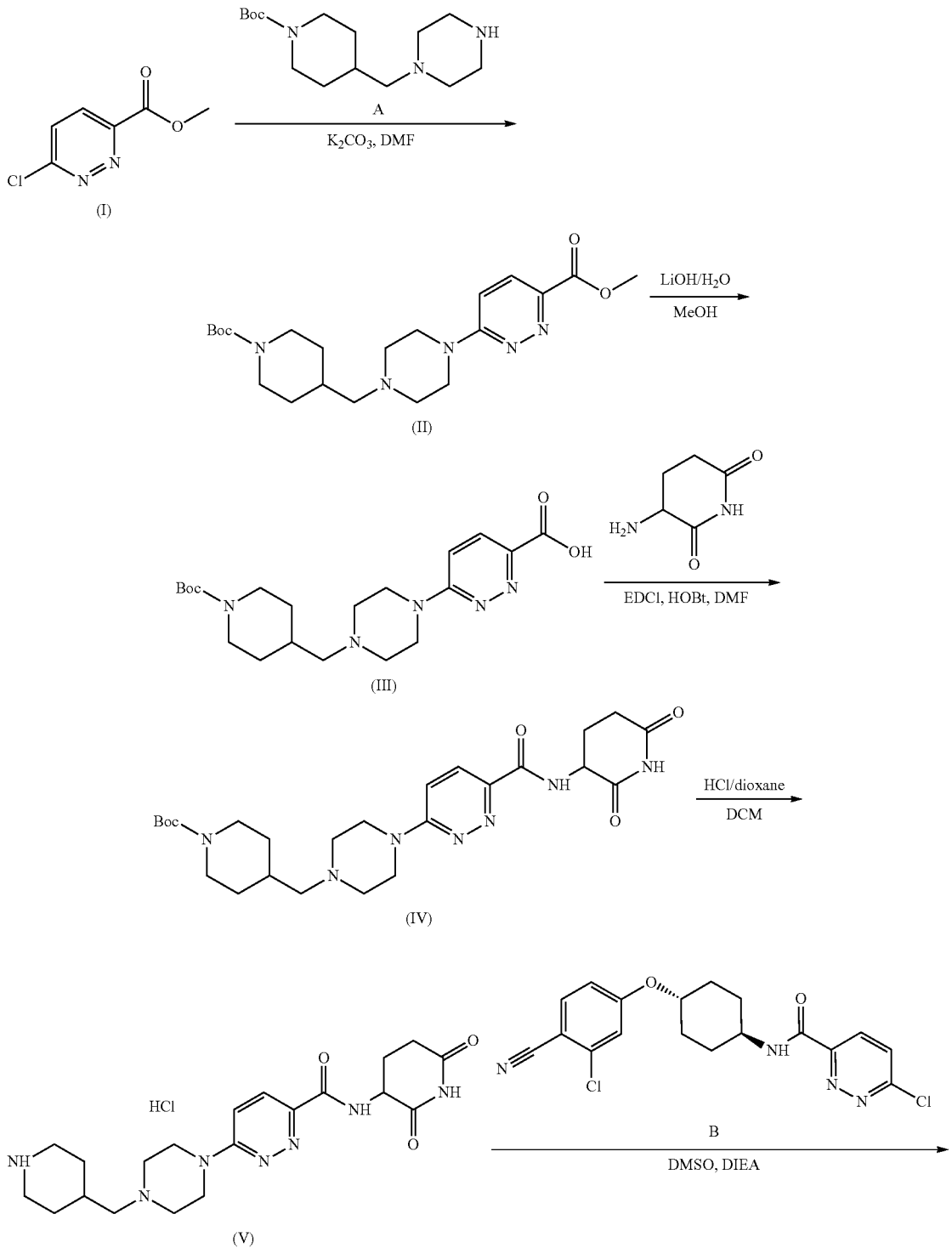

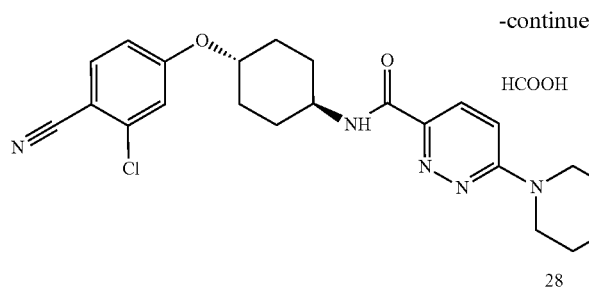
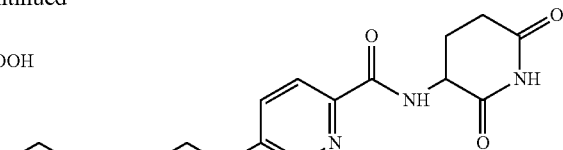

28

Step 1. Preparation of (II), methyl 6-[4-[(1-tert-butoxycarbonyl-4-piperidyl)methyl]piperazin-1-yl]pyridazine-3-carboxylate

Step 2. Preparation of (III), 6-[4-[(1-tert-butoxycarbonyl-4-piperidyl)methyl]piperazin-1-yl]pyridazine-3-carboxylic acid

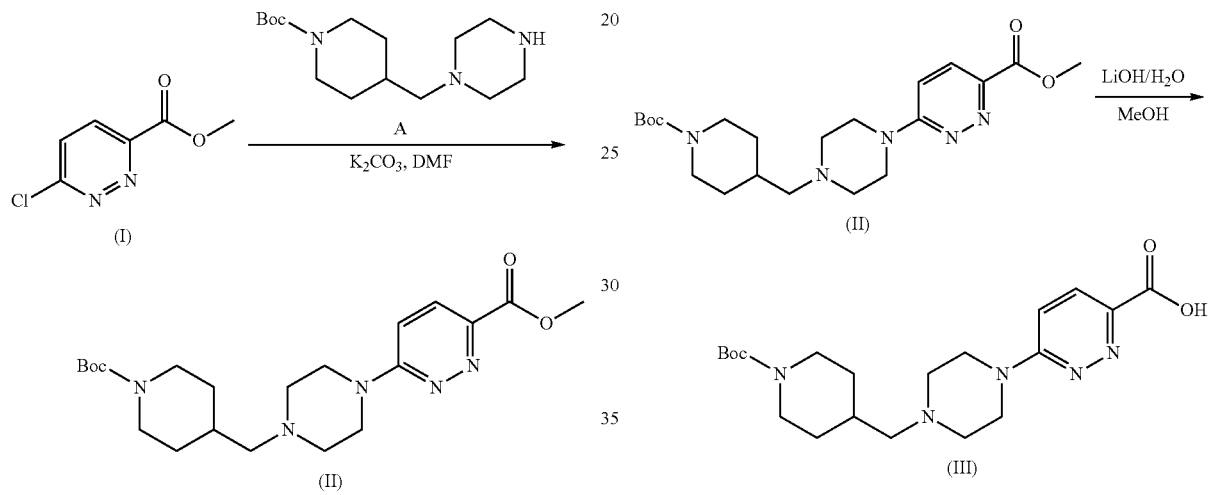

To a solution of (I), methyl 6-chloropyridazine-3-carboxylate (500.00 mg, 2.90 mmol, 1.00 eq) in N,N-dimethylformamide (6 mL) was added potassium carbonate (1.00 g, 7.24 mmol, 2.50 eq) and tert-butyl 4-(piperazin-1-ylmethyl)piperidine-1-carboxylate (A, 903.26 mg, 3.19 mmol, 1.10 eq). The mixture was stirred at 80° C. for 15 h. LCMS showed the desired MS was found and methyl 6-chloropyridazine-3-carboxylate was consumed completely. The mixture was diluted with water (40 mL) and extracted with ethyl acetate (2×30 mL). The combined organic phase was washed with saturated sodium chloride solution (20 mL), dried over sodium sulfate and concentrated under reduced pressure to give a yellow solid. The solid was dissolved with a solution of petroleum ether:ethyl acetate (5:1, 12 mL) and stirred for 0.5 h. Then the suspension solution was filtered and the filter cake was dried under vacuum to give methyl 6-[4-[(1-tert-butoxycarbonyl-4-piperidyl)methyl]piperazin-1-yl]pyridazine-3-carboxylate (880.00 mg, 2.10 mmol, 72% yield) as a light yellow solid, which was used in next step directly.

LCMS: MS (ESI) m/z: 420.2 [M+1]$^+$.

1H NMR: (400 MHz, CDCl3)

δ: 7.88 (d, J=9.6 Hz, 1H), 6.85 (d, J=9.6 Hz, 1H), 4.04-4.20 (m, 2H), 4.00 (s, 3H), 3.75-3.84 (m, 4H), 2.71 (t, J=11.6 Hz, 2H), 2.53 (t, J=4.8 Hz, 4H), 2.23 (d, J=7.2 Hz, 2H), 1.76 (d, J=13.2 Hz, 2H), 1.65-1.71 (m, 1H), 1.46 (s, 9H), 1.04-1.16 (m, 2H).

Chemical Formula: $C_{21}H_{33}N_5O_4$, Molecular Weight: 419.52

To a solution of methyl 6-[4-[(1-tert-butoxycarbonyl-4-piperidyl)methyl]piperazin-1-yl]pyridazine-3-carboxylate (880.00 mg, 2.10 mmol, 1.00 eq) in methanol (10 mL) and water (3 mL) was added lithium hydroxide (264.07 mg, 6.29 mmol, 3.00 eq) at 15° C. The mixture was stirred at 15° C. for 2.5 h. LCMS (EW10815-22-P1A) showed the desired MS was found and methyl 6-[4-[(1-tert-butoxycarbonyl-4-piperidyl)methyl]piperazin-1-yl]pyridazine-3-carboxylate was consumed completely. The mixture was concentrated under vacuum to give a yellow solid. The solid was dissolved with water (10 mL) and adjusted pH to 3 with hydrochloric acid solution (1 M). Then the suspension solution was filtered. The filter cake was dried under vacuum to give 6-[4-[(1-tert-butoxycarbonyl-4-piperidyl)methyl]piperazin-1-yl]pyridazine-3-carboxylic acid (760.00 mg, 1.87 mmol, 89% yield) as a light yellow solid, which was used in next step directly.

LCMS: MS (ESI) m/z: 406.1 [M+1]$^+$.

1H NMR: (400 MHz, DMSO-$d_6$)

δ: 11.30 (br s, 1H), 7.92 (d, J=9.6 Hz, 1H), 7.44 (d, J=9.2 Hz, 1H), 4.57 (d, J=13.2 Hz, 2H), 3.91 (d, J=11.6 Hz, 2H), 3.75 (t, J=12.0 Hz, 2H), 3.60 (d, J=11.2 Hz, 2H), 3.10 (s, 2H), 3.01 (d, J=5.2 Hz, 2H), 2.70-2.87 (m, 2H), 2.04 (d, J=10.4 Hz, 1H), 1.87 (d, J=12.0 Hz, 2H), 1.39 (s, 9H), 1.00-1.15 (m, 2H).

Chemical Formula: $C_{20}H_{31}N_5O_4$, Molecular Weight: 405.49

Step 3. Preparation of (IV), tert-butyl 4-[[4-[6-[(2,6-dioxo-3-piperidyl)carbamoyl]pyridazin-3-yl]piperazin-1-yl]methyl]piperidine-1-carboxylate

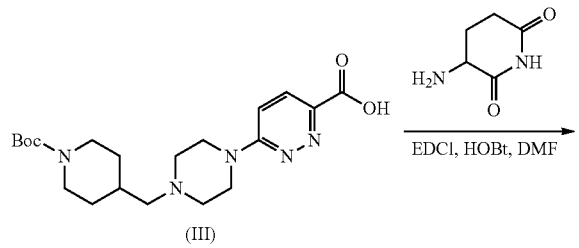

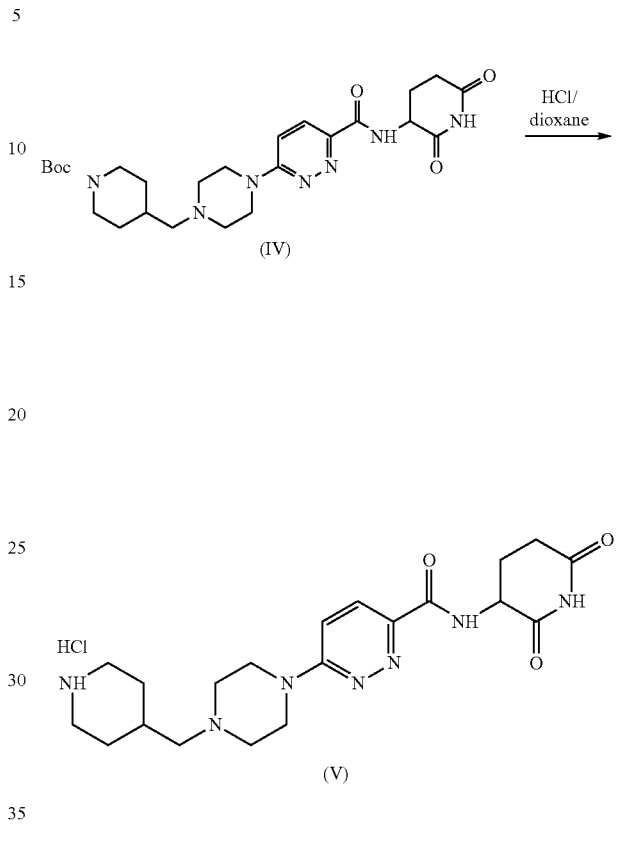

To a solution of 6-[4-[(1-tert-butoxycarbonyl-4-piperidyl)methyl]piperazin-1-yl]pyridazine-3-carboxylic acid (200.00 mg, 493.23 umol, 1.00 eq) in N,N-dimethylformamide (3 mL) were added hydroxybenzotriazole (86.64 mg, 641.20 umol, 1.30 eq), 1-(3-dimethylaminopropyl)-3-ethylcarbodiimide hydrochloride (122.92 mg, 641.20 umol, 1.30 eq), diisopropylethylamine (254.99 mg, 1.97 mmol, 343.65 uL, 4.00 eq), 3-aminopiperidine-2,6-dione; hydrochloride (97.42 mg, 591.88 umol, 1.20 eq) at 15° C. The mixture was stirred at 15° C. for 16 h. LCMS (EW10815-25-P1C2) showed the reaction was completed. The mixture was diluted with water (10 mL) and extracted with ethyl acetate (2×5 mL). The combined organic phases were washed with brine (10 mL), dried over sodium sulfate and concentrated under vacuum to give a residue. The residue was purified by prep-thin layer chromatography (dichloromethane:methanol=10:1) to give tert-butyl 4-[[4-[6-[(2,6-dioxo-3-piperidyl)carbamoyl]pyridazin-3-yl]piperazin-1-yl]methyl]piperidine-1-carboxylate (200.00 mg, 387.89 umol, 79% yield) as a light yellow oil.

LCMS: MS (ESI) m/z: 516.3 [M+1]$^+$.

Step 4. Preparation of (V), N-(2,6-dioxo-3-piperidyl)-6-[4-(4-piperidylmethyl)piperazin-1-yl]pyridazine-3-carboxamide To a solution of tert-butyl 4-[[4-[6-[(2,6-dioxo-3-piperidyl)carbamoyl]pyridazin-3-yl]piperazin-1-yl]methyl]piperidine-1-carboxylate (200.00 mg, 387.89 umol, 1.00 eq) in dichloromethane (2 mL) was added hydrochloride/dioxane (4 M, 2 mL, 20.62 eq) at 15° C. The mixture was stirred at 15° C. for 2 h. Thin layer chromatography (dichloromethane:Methanol=10:1) showed tert-butyl 4-[[4-[6-[(2,6-dioxo-3-piperidyl)carbamoyl]pyridazin-3-yl]piperazin-1-yl]methyl]piperidine-1-carboxylate was consumed completely and a main point was found. The mixture was concentrated under vacuum to give N-(2,6-dioxo-3-piperidyl)-6-[4-(4-piperidylmethyl)piperazin-1-yl]pyridazine-3-carboxamide (160.00 mg, 354.02 umol, 91% yield, hydrochloride salt) as a light yellow solid, which was confirmed by LCMS (EW10815-27-P1C2) and NMR.

LCMS: MS (ESI) m/z: 434.3 [M+19]+.

1H NMR: (400 MHz, DMSO-d6)

δ: 11.40 (br s, 1H), 10.86 (s, 1H), 9.16 (br d, J=8.4 Hz, 1H), 8.86-9.08 (m, 1H), 7.97 (d, J=9.6 Hz, 1H), 7.55 (d, J=9.6 Hz, 1H), 4.81-4.87 (m, 2H), 4.58 (d, J=13.6 Hz, 2H), 3.75 (t, J=12.4 Hz, 2H), 3.64 (d, J=11.6 Hz, 2H), 3.25 (d, J=12.4 Hz, 2H), 3.02-3.18 (m, 4H), 2.76-2.87 (m, 3H), 2.14-2.29 (m, 2H), 1.94-2.09 (m, 3H), 1.40-1.55 (m, 2H).

Chemical Formula: C20H29N7O3, Molecular Weight: 415.19

Total H count from HNMR data: 30.

Step 5. Preparation of Compound 28, N-[4-(3-chloro-4-cyano-phenoxy)cyclohexyl]-6-[4-[[4-[6-[(2,6-dioxo-3-piperidyl)carbamoyl]pyridazin-3-yl]piperazin-1-yl]methyl]-1-piperidyl]pyridazine-3-carboxamide

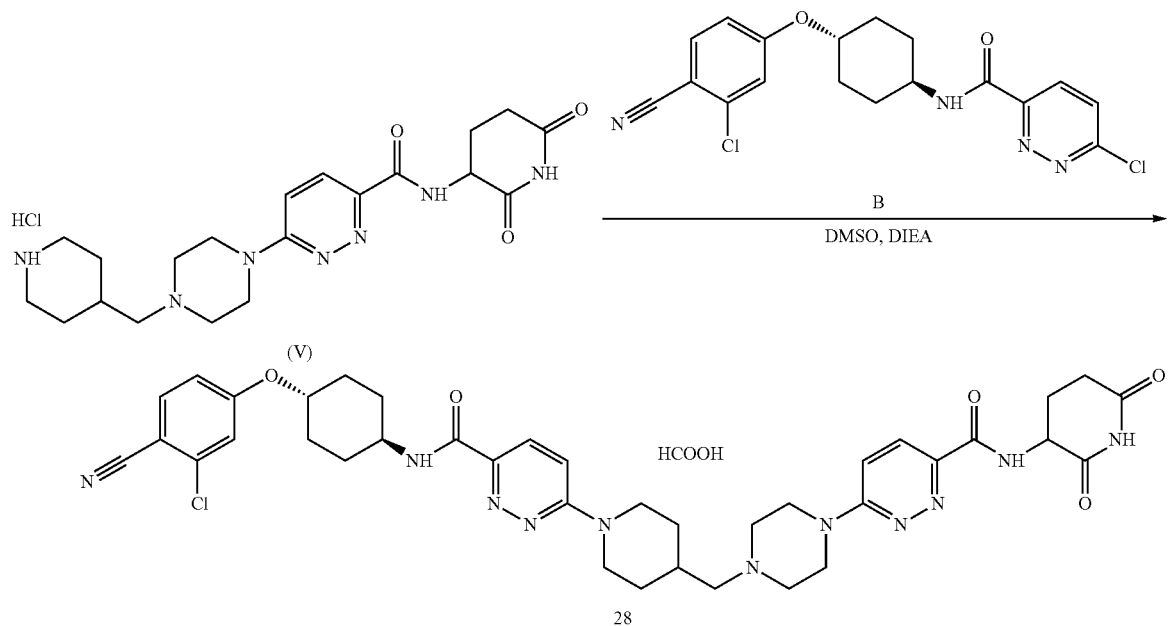

To a solution of N-(2,6-dioxo-3-piperidyl)-6-[4-(4-piperidylmethyl)piperazin-1-yl]pyridazine-3-carboxamide (100.00 mg, 221.26 umol, 1.00 eq, hydrochloride salt) in dimethyl sulfoxide (2 mL) was added diisopropylethylamine (114.39 mg, 885.06 umol, 154.16 uL, 4.00 eq) and 6-chloro-N-[4-(3-chloro-4-cyano-phenoxy)cyclohexyl]pyridazine-3-carboxamide (B, 100.00 mg, 255.59 umol, 1.16 eq) at 100° C. The mixture was stirred at 100° C. for 16 h. LCMS showed the reaction was completed. The mixture was filtered. The filtrate was purified by prep-HPLC (column: Phenomenex Synergi C18 150*25*10 um; mobile phase: [water (0.225% FA)-ACN]; B %: 18%-48%, 10 min) to give N-[4-(3-chloro-4-cyano-phenoxy)cyclohexyl]-6-[4-[[4-[6-[(2,6-dioxo-3-piperidyl)carbamoyl]pyridazin-3-yl]piperazin-1-yl]methyl]-1-piperidyl]pyridazine-3-carboxamide (25.70 mg, 31.17 umol, 14% yield, 99% purity, formate) as a brown solid, which was confirmed by 1H NMR and QC-LCMS QC-LCMS: MS (ESI) m/z: 770.2 [M+1]+.
1H NMR: (400 MHz, DMSO-d6)
δ: 10.83 (br s, 1H), 9.08 (d, J=8.4 Hz, 1H), 8.56 (d, J=8.4 Hz, 1H), 8.30 (s, 1H), 7.86 (dd, J=9.6, 4.0 Hz, 2H), 7.80 (d, J=9.6 Hz, 1H), 7.31-7.39 (m, 3H), 7.13 (dd, J=8.8, 2.4 Hz, 1H), 4.71-4.89 (m, 1H), 4.45-4.59 (m, 3H), 3.80-3.92 (m, 1H), 3.69-3.76 (m, 4H), 3.44-3.58 (m, 4H), 2.97-3.10 (m, 2H), 2.73-2.86 (m, 1H), 2.53-2.58 (m, 1H), 2.18-2.25 (m, 3H), 2.11 (d, J=9.6 Hz, 2H), 1.97-2.04 (m, 1H), 1.83-1.96 (m, 5H), 1.58-1.69 (m, 2H), 1.46-1.58 (m, 2H), 1.07-1.21 (m, 2H).

Chemical Formula: $C_{38}H_{44}CN_{11}O_5$, Molecular Weight: 770.28

Example 13—Synthesis of 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyrazine-2-carboxamide (Compound 33)

SCHEME 8. SUMMARY OF THE SYNTHESIS OF COMPOUND 33

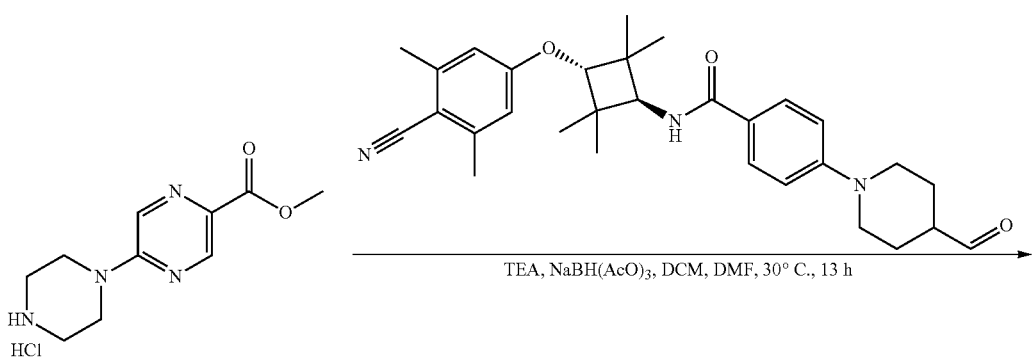

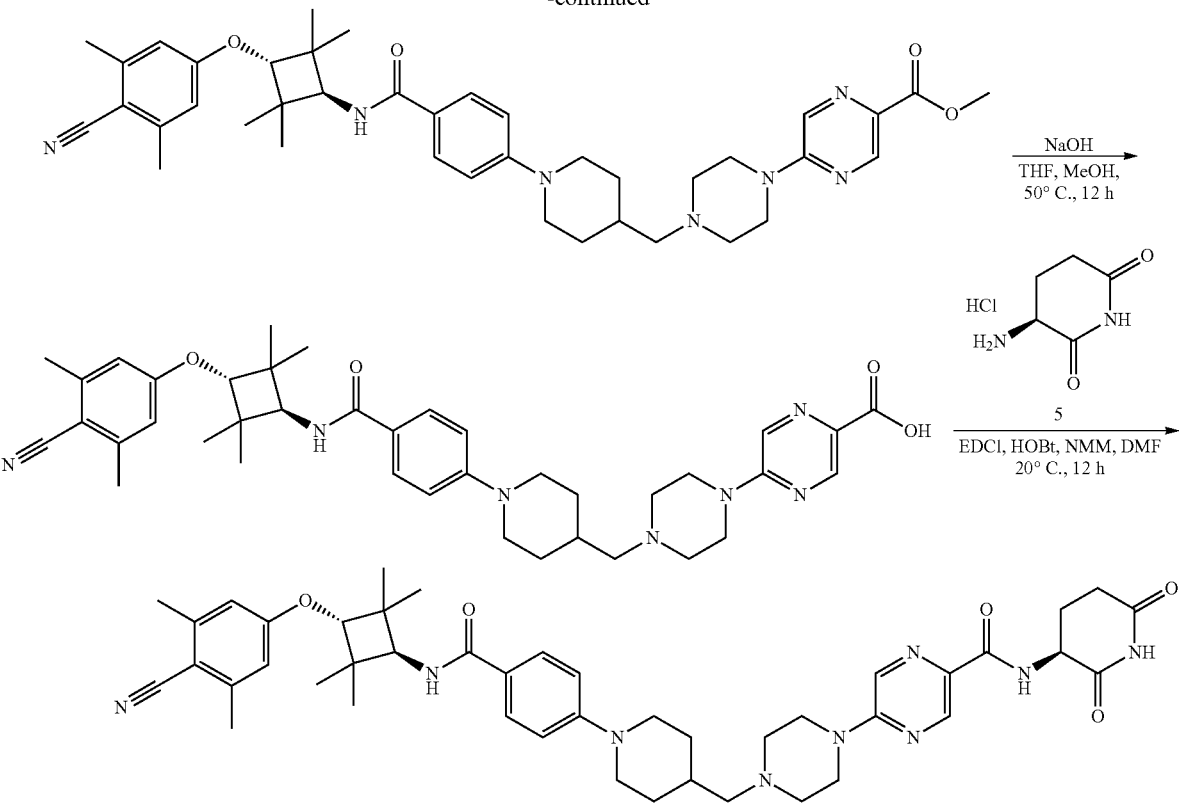
Step 1: Preparation of Methyl-5-(4-((1-(4-(((1r,3r)-3-(4-cyano-3-methoxyphenoxy)-2,2,4,4-tetramethyl-cyclobutyl)carbamoyl)phenyl)piperidin-4-yl)methyl)piperazin-1-yl)pyrazine-2-carboxylate
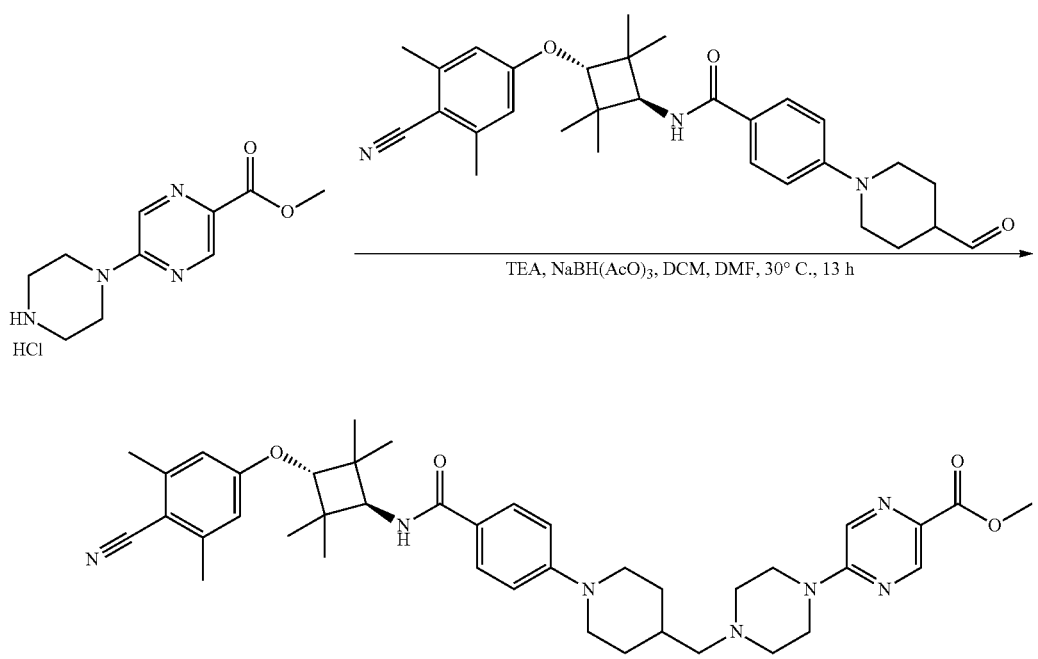

To a solution of methyl 5-piperazin-1-ylpyrazine-2-carboxylate (159 mg, 0.61 mmol, 1.00 eq, hydrochloric acid) in dichloromethane (2 mL) and dimethylformamide (1 mL) was added triethylamine (62 mg, 0.61 mmol, 1.00 eq), acetic acid (36 mg, 0.615 mmol, 1.00 eq) and N-[3-(4-cyano-3,5-dimethyl-phenoxy)-2,2,4,4-tetramethyl-cyclobutyl]-4-(4-formyl-1-piperidyl)benzamide (300 mg, 0.61 mmol, 1.00 eq). The mixture was stirred at 30° C. for 12 h. Then to the mixture was added sodium borohydride acetate (260 mg, 1.23 mmol, 2.00 eq). The mixture was stirred at 30° C. for 1 h. LCMS showed that the reaction was completed. The reaction was added water (50 mL) and extracted with dichloromethane (30 mL×3). The organic layer was dried over sodium sulfate and concentrated under reduced pressure to give the residue. The residue was purified with preparative HPLC (column: Waters Xbridge C18 150*50 mm*10 um; mobile phase: [water (0.05% ammonia hydroxide v/v)-ACN]; B %: 58%-88%, 11.5 min) to give methyl 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyrazine-2-carboxylate (300 mg, 0.43 mmol, 70% yield) as a yellow solid.

MS (ESI) m/z: 694.4 [M+1]$^+$.

Chemical Formula: $C_{40}H_{51}N_7O_4$, Molecular Weight: 693.88

Step 2: Preparation of 5-(4-((1-(4-(((r,3r)-3-(4-cyano-3,5-dimethylphenoxy)-2,2,4,4-tetramethylcyclobutyl)carbamoyl)phenyl)piperidin-4-yl)methyl)piperazin-1-yl)pyrazine-2-carboxylic acid To a solution of methyl 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyrazine-2-carboxylate (300 mg, 0.43 mmol, 1.00 eq) in tetrahydrofuran (5 mL), methanol (5 mL) and water (5 mL) was added sodium hydroxide (138 mg, 3.46 mmol, 8.00 eq). The mixture was stirred at 50° C. for 12 h. LCMS showed that the reaction was completed. The mixture was adjusted with diluted hydrochloric acid (4 M) to pH=5 and filtered to give a white solid. The white solid was further purified with preparative HPLC (column: Waters Xbridge C18 150*50 mm*10 um; mobile phase: [water (10 mM NH4HCO3)-ACN]; B %: 33%-63%, 11.5 min) to give 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyrazine-2-carboxylic acid (200 mg, 0.27 mmol, 64% yield, hydrochloric acid) as a white solid.

MS (ESI) m/z: 678.4 [M−1]$^+$.

Chemical Formula: $C_{39}H_{49}N_7O_4$, Molecular Weight: 679.85

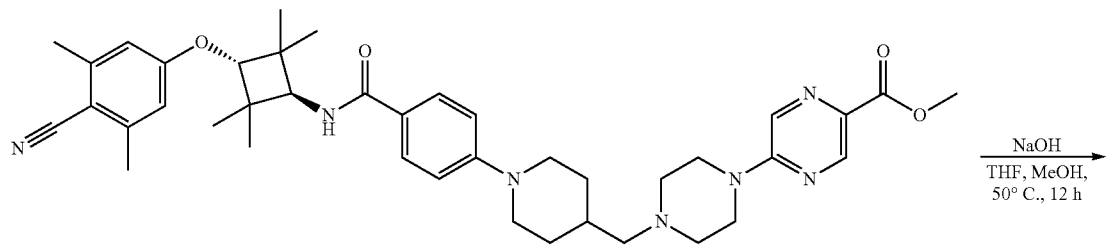

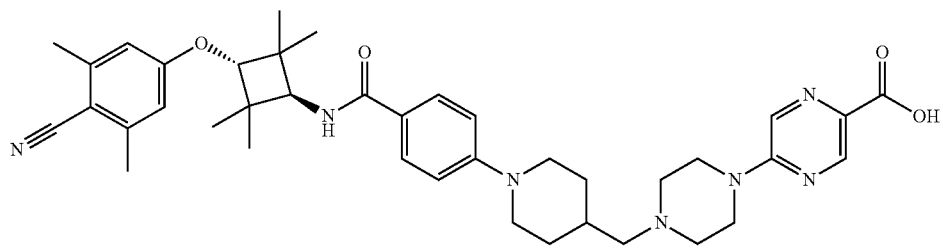

Step 3: Preparation of 5-(4-((1-(4-(((r,3r)-3-(4-cyano-3,5-dimethylphenoxy)-2,2,4,4-tetramethylcyclobutyl)carbamoyl)phenyl)piperidin-4-yl)methyl)piperazin-1-yl)-N—((S)-2,6-dioxopiperidin-3-yl)pyrazine-2-carboxamide, Compound 33

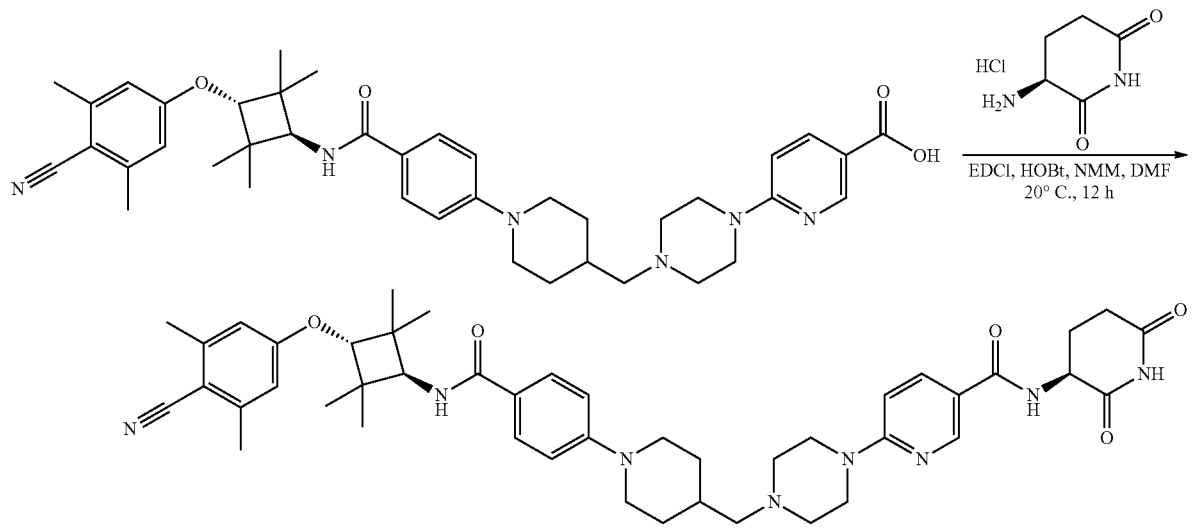

To a solution of 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyrazine-2-carboxylic acid (100 mg, 0.14 mmol, 1.00 eq, hydrochloric acid) in dimethylformamide (2 mL) was added 4-methylmorpholine (74 mg, 0.73 mmol, 5.00 eq), hydroxybenzotriazole (23 mg, 0.17 mmol, 1.20 eq), 3-(ethyliminomethyleneamino)-N,N-dimethyl-propan-1-amine; hydrochloride (33 mg, 0.17 mmol, 1.20 eq) and (3S)-3-aminopiperidine-2,6-dione (36 mg, 0.22 mmol, 1.50 eq, hydrochloric acid). The mixture was stirred at 20° C. for 12 h. LCMS showed that the reaction was completed. The mixture was added dichloromethane (20 mL) and water (20 mL). The mixture was extracted with dichloromethane (20 mL×3). The organic layer was dried over sodium sulfate and concentrated under reduced pressure to give the residue. The residue was purified with preparative HPLC (column: Shim-pack C18 150*25*10 um; mobile phase: [water (0.225% FA)-ACN]; B %: 25%-55%, 10 min) to give 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyrazine-2-carboxamide (52.7 mg, 62.41 umol, 42.43% yield, 99% purity, formate salt) as a white solid MS (ESI) m/z: 790.5 [M+1]$^+$.

$^1$H NMR: (400 MHz, DMSO-d$_6$)

δ:10.86 (s, 1H), 8.70-8.59 (m, 2H), 8.32 (s, 1H), 7.75 (d, J=8.8 Hz, 2H), 7.49 (d, J=9.2 Hz, 1H), 6.97 (d, J=9.2 Hz, 2H), 6.74 (s, 2H), 4.81-4.68 (m, 1H), 4.23 (s, 1H), 4.04 (d, J=9.2 Hz, 1H), 3.87 (br d, J=13.2 Hz, 2H), 3.73 (br s, 5H), 2.87-2.73 (m, 3H), 2.56-2.53 (m, 4H), 2.44 (s, 6H), 2.25-2.17 (m, 3H), 1.99 (br d, J=12.4 Hz, 1H), 1.83 (br d, J=11.6 Hz, 3H), 1.23 (s, 8H), 1.13 (s, 6H).

Chemical Formula: C$_{44}$H$_{55}$N$_9$O$_5$, Molecular Weight: 789.96

Total H count from HNMR data: 55.

Example 14—Synthesis of 4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-N-[(3S)-2,6-dioxo-3-piperidyl]-2-methoxy-benzamide (Compound 34)

Scheme 9. Summary of the Synthesis of Compound 34

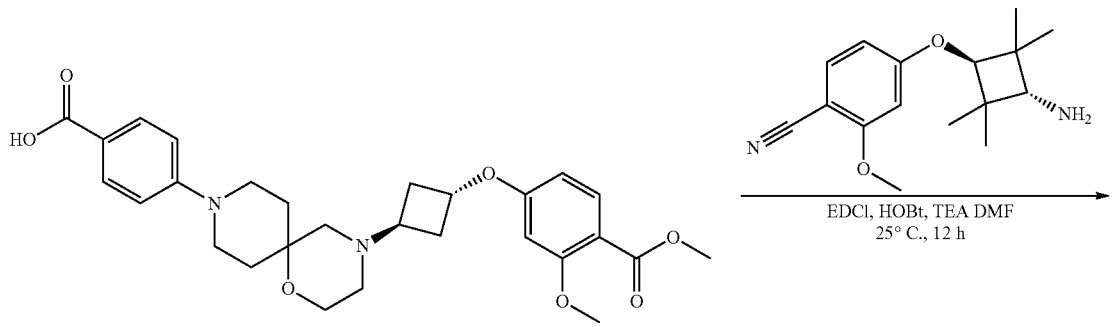

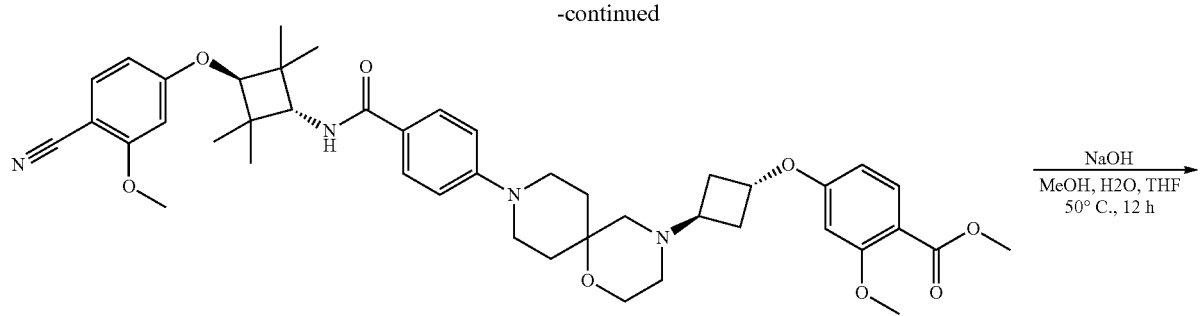
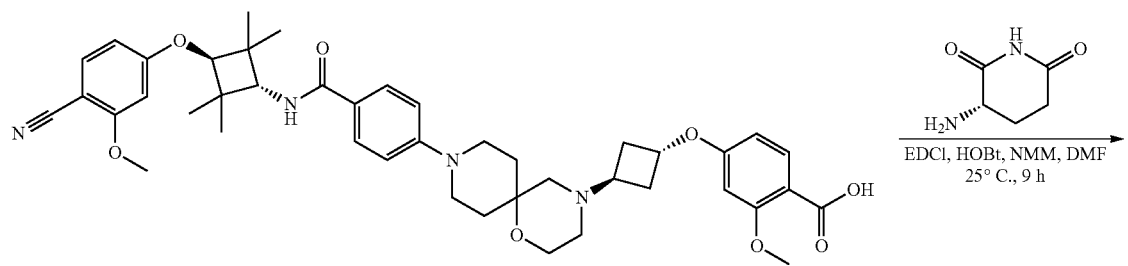
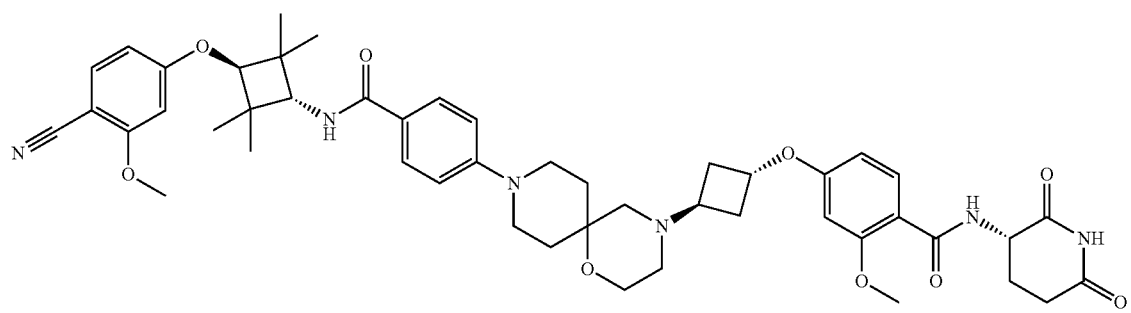
Step 1: Preparation of Methyl-4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoate
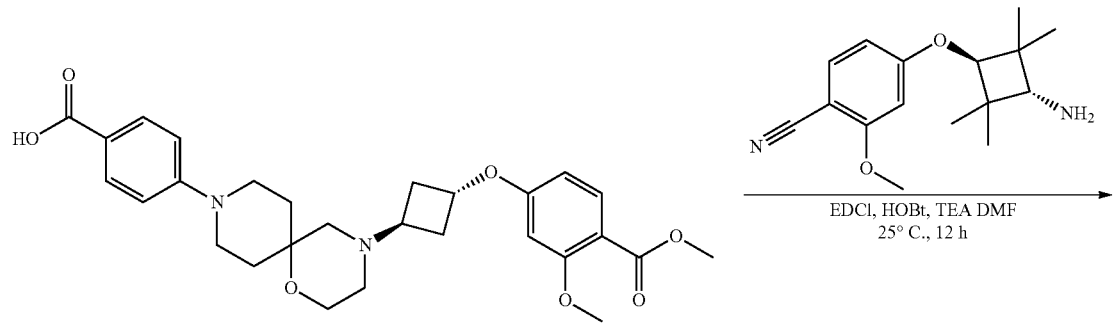

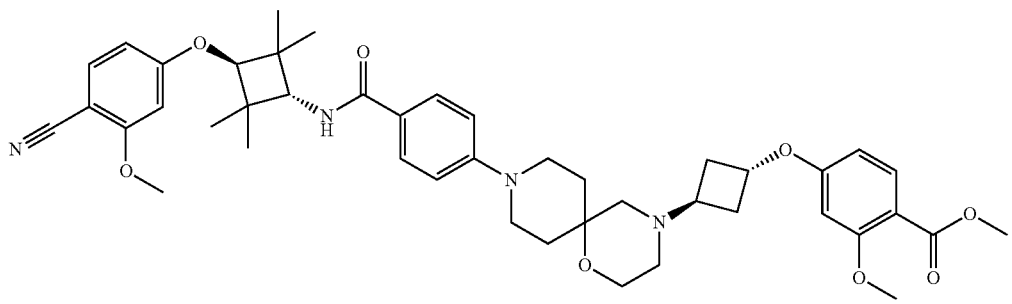

To a mixture of 4-[4-[3-(3-methoxy-4-methoxycarbonyl-phenoxy)cyclobutyl]-1-oxa-4,9-diazaspiro[5.5]undecan-9-yl]benzoic acid (250 mg, 0.49 mmol, 1.00 eq) and triethylamine (248 mg, 2.45 mmol, 0.34 mL, 5.00 eq) in N,N-dimethylformamide (4 mL) was added 3-(ethyliminomethyleneamino)-N,N-dimethyl-propan-1-amine; hydrochloride (113 mg, 0.59 mmol, 1.20 eq), hydroxybenzotriazole (79 mg, 0.59 mmol, 1.20 eq) and 4-(3-amino-2,2,4,4-tetramethyl-cyclobutoxy)-2-methoxy-benzonitrile (134. mg, 0.49 mmol, 1.00 eq, hydrochloric acid). The mixture was stirred at 25° C. for 12 h. LCMS showed the reaction was finished. The reaction mixture was filtered and the filtrate was directly purified by preparative HPLC (Column: Phenomenex luna C18 150*40 mm*15 um, Condition:water (0.225% FA)-ACN) to give methyl 4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoate (180 mg, 0.23 mmol, 48% yield) as a light yellow solid.

MS (ESI) m/z: 767.6 [M+1]$^+$.

Chemical Formula: $C_{44}H_{54}N_4O$, Molecular Weight: 766.92

Step 2: Preparation of 4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoic acid

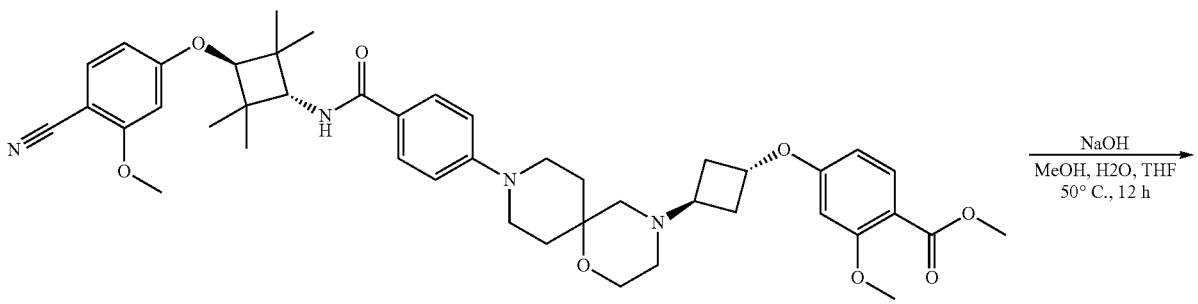

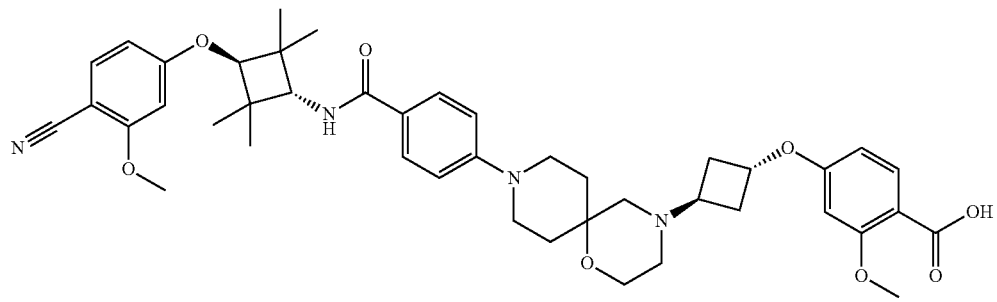

To a mixture of methyl 4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoate (180 mg, 0.23 mmol, 1.00 eq) in methanol (2 mL), water (2 mL) and tetrahydrofuran (2 mL) was added sodium hydroxide (47 mg, 1.17 mmol, 5.00 eq). The mixture was stirred at 50° C. for 12 h. LCMS showed the reaction was finished. Then the reaction mixture was concentrated under reduced pressure to give the residue. The residue was adjust pH=6 with hydrochloric acid (1 M). Then the mixture was filtered. The filtered cake was dried under reduced pressure to give 4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoic acid (160 mg, 0.21 mmol, 91% yield) as a white solid.

MS (ESI) m/z: 753.2 [M+1]$^+$.

Chemical Formula: $C_{43}H_{52}N_4O$, Molecular Weight: 752.89

Step 3: Preparation of 4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-N-[(3S)-2,6-dioxo-3-piperidyl]-2-methoxy-benzamide Compound 34

To a solution of 4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoic acid (160 mg, 0.21 mmol, 1.00 eq) in N,N-dimethylformamide (4 mL) was added 4-methylmorpholine (107 mg, 1.06 mmol, 0.12 mL, 5.00 eq), hydroxybenzotriazole (34 mg, 0.26 mmol, 1.20 eq), 3-(ethyliminomethyleneamino)-N,N-dimethyl-propan-1-amine; hydrochloride (49 mg, 0.26 mmol, 1.20 eq) and (3S)-3-aminopiperidine-2,6-dione (70 mg, 0.43 mmol, 2 eq, hydrochloric acid). The mixture was stirred at 25° C. for 9 h. LCMS showed the reaction was finished. The reaction mixture was filtered. The filtrate was directly purified by preparative HPLC (Column:Phenomenex luna C18 150*40 mm*15 um, Condition:water (0.225% FA)-ACN) to give 4-[3-[9-[4-[[3-(4-cyano-3-methoxy-phenoxy)-2,2,4,4-tetramethyl-cyclobutyl]carbamoyl]phenyl]-1-oxa-4,9-diazaspiro[5.5]undecan-4-yl]cyclobutoxy]-N-[(3S)-2,6-dioxo-3-piperidyl]-2-methoxy-benzamide (130.0 mg, 0.15 mmol, 70% yield, 99% purity) as a off-white solid.

MS (ESI) m/z: 863.3 [M+1]$^+$.

$^1$H NMR: (400 MHz, DMSO-d$_6$)

δ: 10.88 (s, 1H), 8.48 (d, J=6.8 Hz, 1H), 7.86 (d, J=8.8 Hz, 1H), 7.75 (d, J=9.2 Hz, 2H), 7.65 (d, J=8.8 Hz, 1H), 7.50 (d, J=9.2 Hz, 1H), 6.98 (d, J=9.2 Hz, 2H), 6.64 (d, J=2.0 Hz,

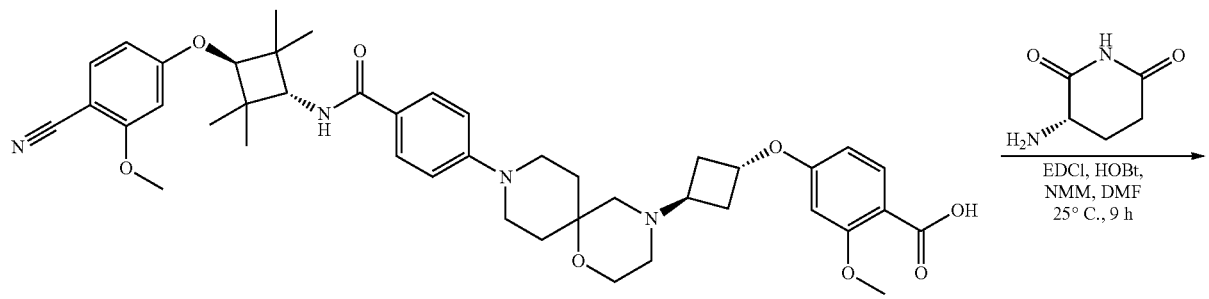

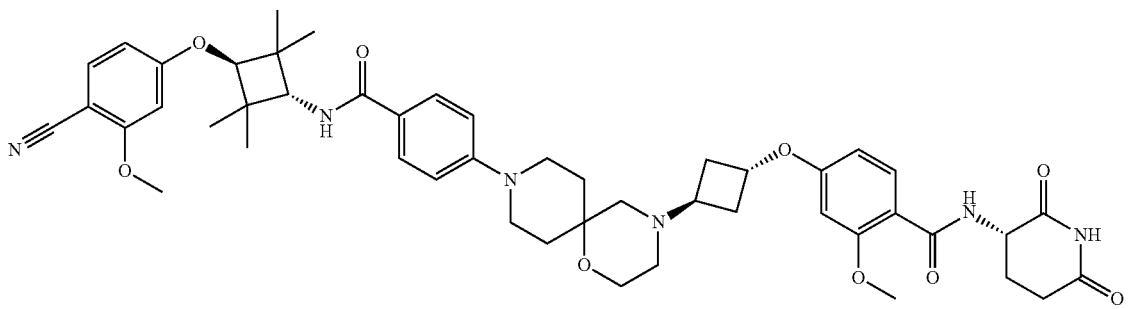

Example 34

1H), 6.57-6.49 (m, 3H), 4.92-4.80 (m, 1H), 4.76-4.67 (m, 1H), 4.31-4.27 (m, 1H), 4.09-4.02 (m, 1H), 3.91 (s, 6H), 3.72-3.66 (m, 2H), 3.55-3.47 (m, 2H), 3.22-3.10 (m, 3H), 2.95-2.70 (m, 3H), 2.43-2.37 (m, 2H), 2.30-2.25 (m, 1H), 2.21-2.07 (m, 6H), 1.97-1.88 (m, 2H), 1.69-1.59 (m, 2H), 1.23 (s, 6H), 1.15 (s, 6H).
Chemical Formula: $C_{48}H_{58}N_6O_9$, Molecular Weight: 863.01
Example 15—Synthesis of 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-N-[(3S)-2,6-dioxo-3-piperidyl]-2-methoxy-benzamide (Compound 35)
Scheme 10. Summary of the Synthesis of Compound 35
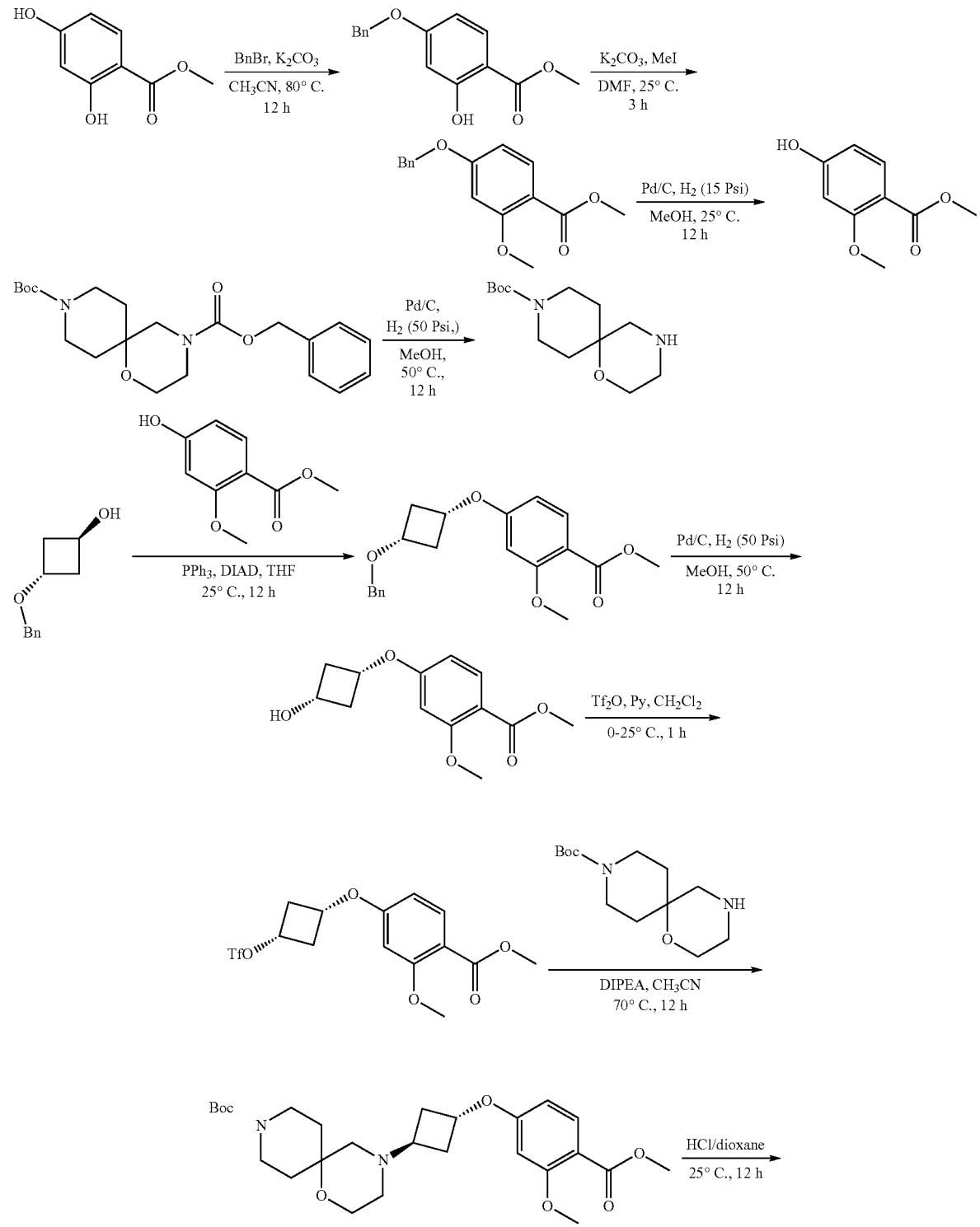

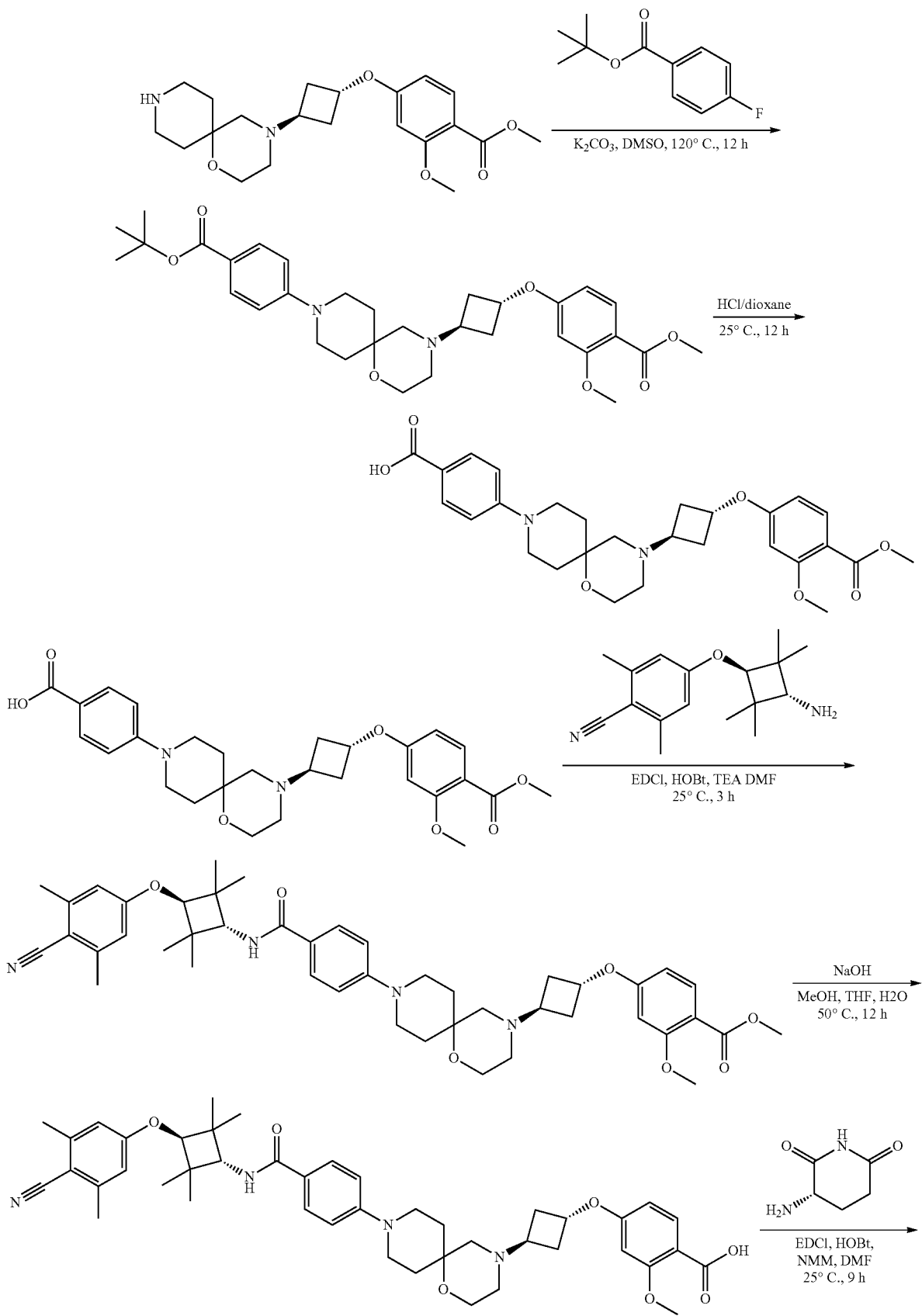

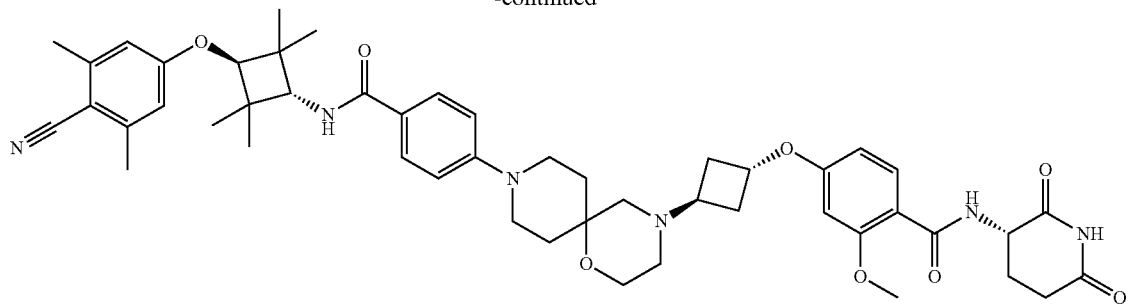

Step 1: Preparation of Methyl 4-benzyloxy-2-hydroxy-benzoate

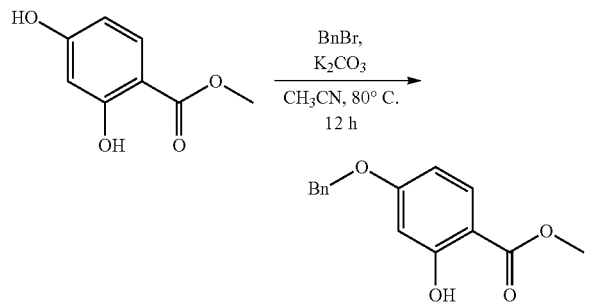

To a solution of methyl 2,4-dihydroxybenzoate (1.00 g, 5.95 mmol, 1.00 eq) and potassium carbonate (1.64 g, 11.89 mmol, 2.00 eq) in acetonitrile (20 mL) was added benzyl bromide (1.02 g, 5.95 mmol, 0.7 mL, 1.00 eq). The mixture was stirred at 80° C. for 12 h under nitrogen atmosphere. LCMS showed that the reaction was finished. The mixture was filtered. The filtrate was concentrated under reduced pressure to give the residue. The crude product was triturated with (petroleum ether:ethyl acetate=25:1, 20 mL) at 25° C. for 0.5 h. The mixture was filtered. The filtered cake was collected and dried under reduced pressure to give methyl 4-benzyloxy-2-hydroxy-benzoate (1.00 g, 3.87 mmol, 65% yield) as white solid, which was used in next step directly.

MS (ESI) m/z: 259.1 [M+1]+.

HNMR: (400 MHz, CDCl$_3$) δ=10.98 (brs, 1H), 7.77 (d, J=8.4 Hz, 1H), 7.50-7.34 (m, 5H), 6.59-6.52 (m, 2H), 5.11 (s, 2H), 3.94 (s, 3H).

Chemical Formula: C$_{15}$H$_{14}$O$_4$, Molecular Weight: 258.27

Step 2: Preparation of Methyl 4-benzyloxy-2-methoxy-benzoate

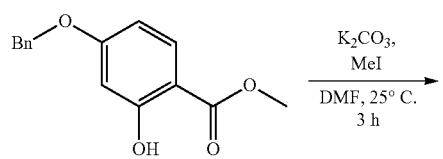

To a mixture of methyl 4-benzyloxy-2-hydroxy-benzoate (1.00 g, 3.87 mmol, 1.00 eq) and potassium carbonate (1.61 g, 11.62 mmol, 3.00 eq) in N,N-dimethylformamide (10 mL) was added methyl iodide (1.28 g, 9.02 mmol, 0.56 mL, 2.33 eq) at 25° C. The mixture was stirred at 25° C. for 3 h. LCMS showed the reaction was finished. The mixture was diluted with ethyl acetate (50 mL×3) and washed with water (50 mL). The organic layers was combined, dried over anhydrous sodium sulfate, filtered and concentrated under reduced pressure to give the crude product. The crude product was triturated with (petroleum ether:ethyl acetate=10:1, 20 mL) at 25° C. for 0.5 h. The mixture was filtered. The filtered cake was collected and dried under reduced pressure to give methyl 4-benzyloxy-2-methoxy-benzoate (0.80 g, 2.94 mmol, 76% yield) as a white solid.

MS (ESI) m/z: 273.1 [M+1]+.

HNMR: (400 MHz, CDCl3) δ=7.88 (d, J=4.0 Hz, 1H), 7.50-7.33 (m, 5H), 6.61-6.50 (m, 2H), 5.13 (s, 2H), 3.87-3.82 (m, 6H).

Chemical Formula: C$_{16}$H$_{16}$O$_4$, Molecular Weight: 272.30

Step 3: Preparation of Methyl 4-hydroxy-2-methoxy-benzoate

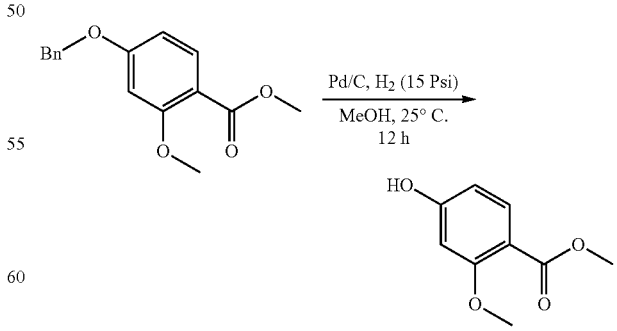

To a solution of methyl 4-benzyloxy-2-methoxy-benzoate (0.80 g, 2.94 mmol, 1.00 eq) in methanol (10 mL) was added palladium carbon (10%, 0.30 g) under nitrogen atmosphere. The suspension was degassed and purged with hydrogen for 3 times. The mixture was stirred under hydrogen atmosphere (15 Psi) at 25° C. for 12 h. Thin layer chromatography (petroleum ether:ethyl acetate=3:1) showed the reaction was finished. The mixture was filtered. The filtrate was concentrated under reduced pressure to give methyl 4-hydroxy-2-methoxy-benzoate (0.51 g, 2.82 mmol, 96% yield) as a white solid, which was used in next step directly.

Chemical Formula: $C_9H_{10}O_4$, Molecular Weight: 182.17

HNMR: (400 MHz, CDCl$_3$) δ=7.81 (d, J=8.4 Hz, 1H), 6.52-6.48 (m, 2H), 3.88 (s, 3H), 3.84 (s, 3H).

Step 4: Preparation of tert-Butyl 1-oxa-4,9-diazaspiro[5.5]undecane-9-carboxylate

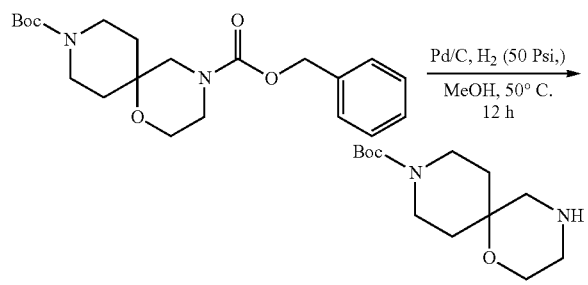

To a mixture of 4-benzyl-9-tert-butyl-1-oxa-4,9-diazaspiro[5.5]undecane-4,9-dicarboxylate (2.00 g, 5.12 mmol, 1.00 eq) in methanol (100 mL) was added palladium carbon (0.40 g, 10% purity) under nitrogen atmosphere. The suspension was degassed and purged with hydrogen for 3 times. The mixture was stirred under hydrogen atmosphere (50 Psi) at 50° C. for 12 h. Thin layer chromatography (petroleum ether:ethyl acetate=3:1) showed that the reaction was finished. Then the reaction mixture was filtered. The filtrate was concentrated under reduce pressure to give tert-butyl 1-oxa-4,9-diazaspiro[5.5]undecane-9-carboxylate (1.10 g, 4.29 mmol, 84% yield) as light yellow oil, which was used in next step directly.

Chemical Formula: $C_{13}H_{24}N_2O_3$, Molecular Weight: 256.34

HNMR: (400 MHz, DMSO-d$_6$) δ=3.62-3.40 (m, 6H), 3.08-2.93 (m, 2H), 2.72-2.58 (m, 2H), 1.88-1.72 (m, 2H), 1.39 (s, 9H), 1.35-1.22 (m, 2H).

Step 5: Preparation of Methyl 4-(3-benzyloxy cyclobutoxy)-2-methoxy-benzoate

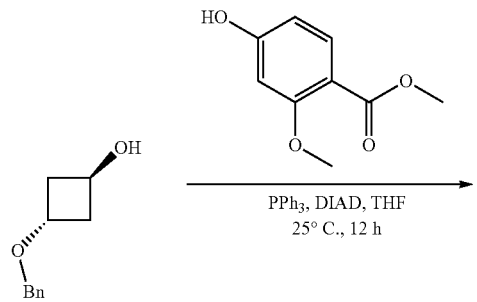

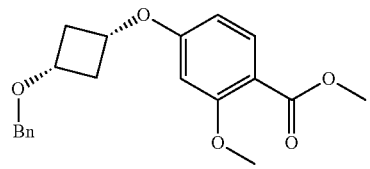

To a solution of methyl 4-hydroxy-2-methoxy-benzoate (1.40 g, 7.69 mmol, 1.00 eq), 3-benzyloxycyclobutanol (1.51 g, 8.45 mmol, 1.10 eq) and triphenylphosphine (3.02 g, 11.53 mmol, 1.50 eq) in tetrahydrofuran (15 mL) was added diisopropyl azodiformate (1.86 g, 9.22 mmol, 1.79 mL, 1.20 eq) at 0° C. The mixture was stirred at 25° C. for 12 h under nitrogen atmosphere. LCMS showed the reaction was finished. The reaction mixture was concentrated under reduced pressure. The residue was purified by column chromatography on silica gel (petroleum ether/ethyl acetate=20/1 to 5/1) to give methyl 4-(3-benzyloxycyclobutoxy)-2-methoxy-benzoate (2.00 g, 5.84 mmol, 76% yield) as a yellow oil.

Chemical Formula: $C_{20}H_{22}O_5$, Molecular Weight: 342.39

LCMS: MS (ESI) m/z: 343.2 [M+1]$^+$.

Step 6: Preparation of Methyl 4-(3-hydroxycyclobutoxy)-2-methoxy-benzoate

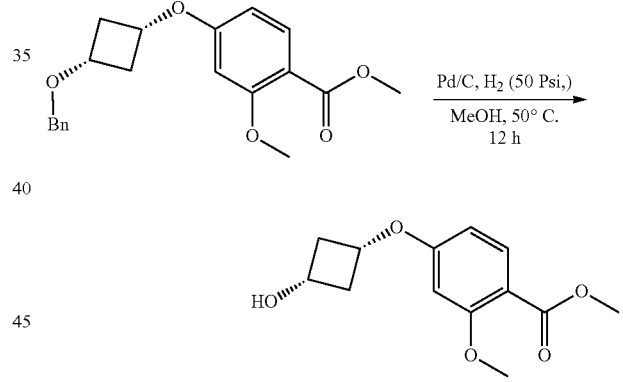

To a mixture of methyl 4-(3-benzyloxycyclobutoxy)-2-methoxy-benzoate (5.00 g, 14.60 mmol, 1.00 eq) in methanol (50 mL) was added palladium carbon (0.50 g, 10% purity) under nitrogen atmosphere. The suspension was degassed and purged with hydrogen for 3 times. The mixture was stirred under hydrogen atmosphere (50 Psi) at 50° C. for 12 h. Thin layer chromatography (petroleum ether:ethyl acetate=3:1) showed the reaction was finished. Then the reaction mixture was filtered. The filtrate was concentrated under reduced pressure to give methyl 4-(3-hydroxycyclobutoxy)-2-methoxy-benzoate (2.70 g, 10.70 mmol, 73% yield) as a white solid.

HNMR: (400 MHz, CDCl$_3$) δ=7.82 (d, J=8.8 Hz, 1H), 6.43 (d, J=2.4 Hz, 1H), 6.37 (dd, J=8.8, 2.4 Hz, 1H), 4.33-4.10 (m, 2H), 3.88 (s, 3H), 3.86 (s, 3H), 2.99-2.95 (m, 2H), 2.17-2.05 (m, 2H), 1.61 (brs, 1H).

Chemical Formula: $C_{13}H_{16}O_5$, Molecular Weight: 252.26

Step 7: Preparation of Methyl 2-methoxy-4-[3-(trifluoromethylsulfonyloxy)cyclobutoxy]benzoate

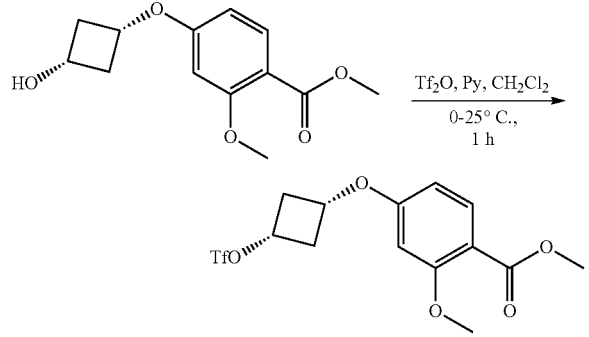

To a mixture of methyl 4-(3-hydroxycyclobutoxy)-2-methoxy-benzoate (2.50 g, 9.91 mmol, 1.00 eq) and pyridine (1.57 g, 19.82 mmol, 1.60 mL, 2.00 eq) in dichloromethane (50 mL) was added trifluoromethane anhydride (3.36 g, 11.89 mmol, 1.96 mL, 1.2 eq) at 0° C. under nitrogen. The mixture was stirred at 25° C. for 1 h. Thin layer chromatography (petroleum ether:ethyl acetate=3:1) showed the reaction was finished. To the mixture was added water (200 mL) and extracted with dichloromethane (50 mL×3). The organic layers were combined, dried over anhydrous sodium sulfate, filtered and concentrated under reduced pressure to give a residue. The residue was purified by column chromatography on silica gel (petroleum ether:ethyl acetate=3:1) to give methyl 2-methoxy-4-[3-(trifluoromethylsulfonyloxy)cyclobutoxy]benzoate (3.00 g, 7.81 mmol, 79% yield) as a yellow solid.

HNMR: (400 MHz, DMSO-$d_6$) δ=7.70 (d, J=8.8 Hz, 1H), 6.54 (d, J=2.0 Hz, 1H), 6.49 (dd, J=8.8, 2.4 Hz, 1H), 5.24-5.21 (m, 1H), 5.05-5.02 (m, 1H), 3.81 (s, 3H), 3.74 (s, 3H), 2.81-2.76 (m, 2H), 2.65-2.55 (m, 2H).

Chemical Formula: $C_{14}H_{15}F_3O_7S$, Molecular Weight: 384.32

Step 8: Preparation of tert-Butyl 4-[3-(3-methoxy-4-methoxycarbonyl-phenoxy)cyclobutyl]-1-oxa-4,9-diazaspiro[5.5]undecane-9-carboxylate

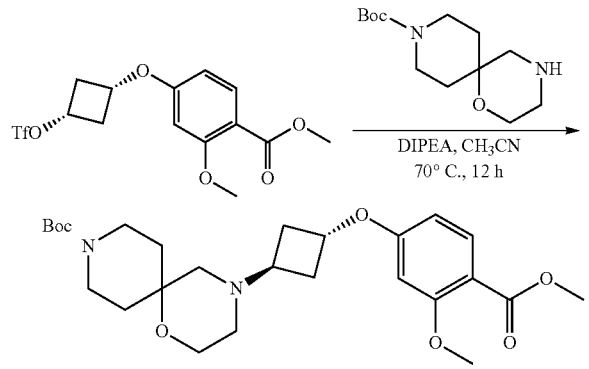

To a solution of tert-butyl 1-oxa-4,9-diazaspiro[5.5]undecane-9-carboxylate (1.00 g, 3.90 mmol, 1.00 eq) in acetonitrile (30 mL) was added methyl 2-methoxy-4-[3-(trifluoromethylsulfonyloxy)cyclobutoxy]benzoate (1.50 g, 3.90 mmol, 1.00 eq) and diisopropylethylamine (2.52 g, 19.51 mmol, 3.40 mL, 5.00 eq). The reaction mixture was stirred at 70° C. for 12 h. LCMS showed the reaction was finished. Then the reaction mixture was concentrated under reduce pressure to give the residue. The residue was purified by column chromatography on silica gel (petroleum ether:ethyl acetate=3:1) to give tert-butyl 4-[3-(3-methoxy-4-methoxycarbonyl-phenoxy)cyclobutyl]-1-oxa-4,9-diazaspiro[5.5]undecane-9-carboxylate (1.50 g, 3.06 mmol, 78% yield) as a yellow oil.

LCMS: MS (ESI) m/z: 491.4 [M+1]$^+$.

HNMR: (400 MHz, DMSO-$d_6$) δ=7.68 (d, J=8.8 Hz, 1H), 6.52 (d, J=2.0 Hz, 1H), 6.44 (dd, J=8.4, 2.4 Hz, 1H), 4.88-4.78 (m, 1H), 3.80 (s, 3H), 3.74 (s, 3H), 3.68-3.54 (m, 4H), 3.12-2.96 (m, 2H), 2.89-2.79 (m, 1H), 2.71-2.63 (m, 1H), 2.46-2.34 (m, 2H), 2.32-2.22 (m, 2H), 2.20-2.09 (m, 3H), 1.85-1.77 (m, 2H), 1.49-1.41 (m, 2H), 1.40 (s, 9H).

Chemical Formula: $C_{26}H_{38}N_2O_7$, Molecular Weight: 490.59

Step 9: Preparation of Methyl 2-methoxy-4-[3-(1-oxa-4,9-diazaspiro[5.5]undecan-4-yl)cyclobutoxy]benzoate

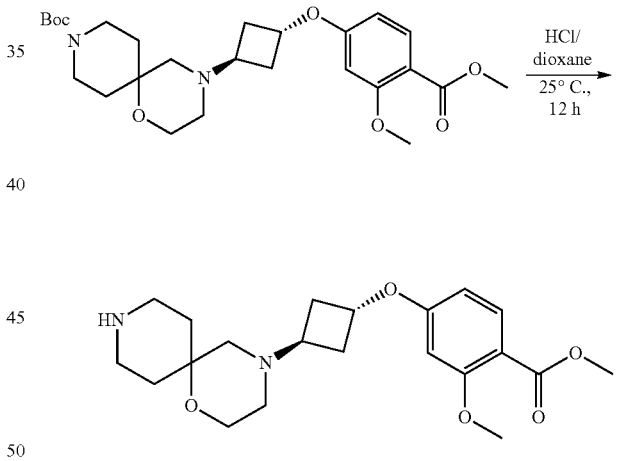

To a mixture of tert-butyl 4-[3-(3-methoxy-4-methoxycarbonyl-phenoxy)cyclobutyl]-1-oxa-4,9-diazaspiro[5.5]undecane-9-carboxylate (1.50 g, 3.06 mmol, 1.00 eq) was added hydrogen chloride/dioxane (4 M, 25 mL, 32.71 eq). The mixture was stirred at 25° C. for 12 h. LCMS showed the reaction was finished. Then the reaction mixture was concentrated under reduce pressure to give methyl 2-methoxy-4-[3-(1-oxa-4,9-diazaspiro[5.5]undecan-4-yl)cyclobutoxy]benzoate (1.30 g, 3.04 mmol, 99% yield, hydrogen chloride) as a light yellow solid.

LCMS: MS (ESI) m/z: 391.3 [M+1]$^+$.

Chemical Formula: $C_{21}H_{30}N_2O_5$, Molecular Weight: 390.47

Step 10: Preparation of Methyl 4-[3-[9-(4-tert-butoxycarbonylphenyl)-1-oxa-4,9-diazaspiro[5.5]undecan-4-yl]cyclobutoxy]-2-methoxybenzoate

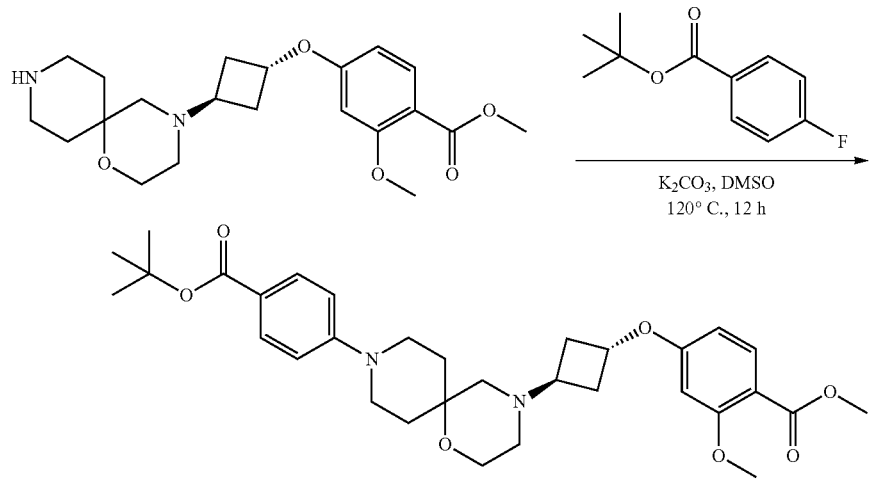

To a mixture of methyl 2-methoxy-4-[3-(1-oxa-4,9-diazaspiro[5.5]undecan-4-yl)cyclobutoxy]benzoate (1.30 g, 3.04 mmol, 1.00 eq, hydrogen chloride) in dimethylsulfoxide (40 mL) was added potassium carbonate (2.10 g, 15.22 mmol, 5.00 eq) and tert-butyl 4-fluorobenzoate (0.90 g, 4.57 mmol, 1.50 eq). The mixture was stirred at 120° C. for 12 h. LCMS showed the reaction mixture was finished. To the solution was added water (200 mL) and extracted with ethyl acetate (50 mL×2). The organic layers was combined, dried over anhydrous sodium sulfate, filtered and concentrated under reduced pressure to give a residue. The residue was purified by preparative HPLC (column: Phenomenex luna C18 250*80 mm*10 um; mobile phase: [water (0.225% FA)-ACN]; B %: 26%-56%, 19 min) to give methyl 4-[3-[9-(4-tert-butoxycarbonylphenyl)-1-oxa-4,9-diazaspiro[5.5]undecan-4-yl]cyclobutoxy]-2-methoxybenzoate (0.55 g, 970.56 umol, 32% yield) as a yellow oil.

LCMS: MS (ESI) m/z: 567.5 [M+1]$^+$.

HNMR: (400 MHz, DMSO-d$_6$) δ=7.88 (d, J=9.2 Hz, 2H), 7.84 (d, J=8.8 Hz, 1H), 6.89 (d, J=9.2 Hz, 2H), 6.43 (d, J=1.6 Hz, 1H), 6.33 (dd, J=8.4, 2.4 Hz, 1H), 4.85-4.77 (m, 1H), 3.90 (s, 3H), 3.87 (s, 3H), 3.82-3.73 (m, 2H), 3.58-3.50 (m, 2H), 3.34-3.22 (m, 2H), 3.01-2.92 (m, 1H), 2.40-2.26 (m, 6H), 2.22-2.14 (m, 2H), 2.12-2.07 (m, 2H), 1.70-1.63 (m, 2H), 1.59 (s, 9H).

Chemical Formula: C$_{32}$H$_{42}$N$_2$O$_7$, Molecular Weight: 566.69

Step 11: Preparation of Methyl 4-[3-[9-(4-tert-butoxycarbonylphenyl)-1-oxa-4,9-diazaspiro[5.5]undecan-4-yl]cyclobutoxy]-2-methoxy-benzoate

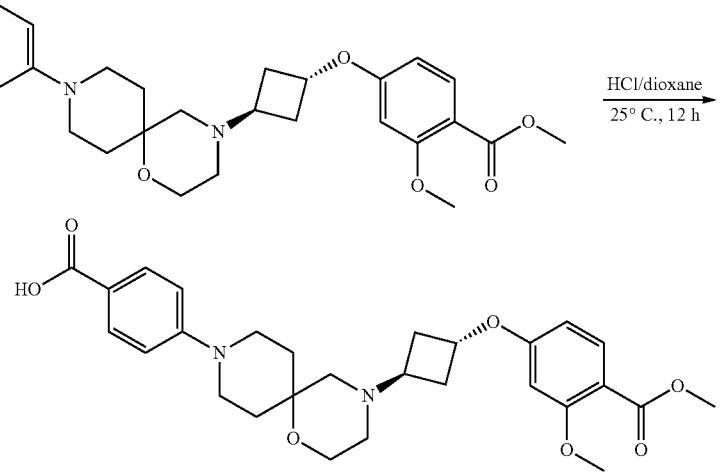

To a compound of methyl 4-[3-[9-(4-tert-butoxycarbonylphenyl)-1-oxa-4,9-diazaspiro[5.5]undecan-4-yl]cyclobutoxy]-2-methoxy-benzoate (550 mg, 0.97 mmol, 1.00 eq) was added hydrogen chloride/dioxane (4 M, 20 mL, 82.43 eq). The mixture was stirred at 25° C. for 12 h. LCMS showed the reaction was finished. The reaction mixture was concentrated under reduced pressure to give 4-[4-[3-(3-methoxy-4-methoxycarbonyl-phenoxy)cyclobutyl]-1-oxa-4,9-diazaspiro[5.5]undecan-9-yl]benzoic acid (500 mg, 0.91 mmol, 94% yield, hydrogen chloride) as a white solid, which was used in next step directly.

LCMS: MS (ESI) m/z: 511.3 [M+1]$^+$.

Chemical Formula: $C_{28}H_{34}N_2O_7$, Molecular Weight: 510.58

Step 12: Preparation of Methyl 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoate 3-(ethyliminomethyleneamino)-N,N-dimethyl-propan-1-amine; hydrochloride (113 mg, 0.59 mmol, 1.20 eq), hydroxybenzotriazole (79 mg, 0.59 mmol, 1.20 eq) and 4-(3-amino-2,2,4,4-tetramethyl-cyclobutoxy)-2,6-dimethyl-benzonitrile (151 mg, 0.49 mmol, 1.00 eq, hydrochloric acid). The mixture was stirred at 25° C. for 3 h. LCMS showed the reaction was finished. The reaction mixture was purified by preparative HPLC (Column: Phenomenex luna C18 150*40 mm*15 um, Condition: water (0.225% FA)-ACN) to give methyl 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoate (200 mg, 0.26 mmol, 53% yield) as a light yellow solid.

LCMS: MS (ESI) m/z: 765.6 [M+1]$^+$.

1HNMR: (400 MHz, CDCl$_3$) δ: 7.82 (d, J=8.4 Hz, 1H), 7.70-7.67 (m, 2H), 6.96-6.90 (m, 2H), 6.59 (s, 2H), 6.45-6.41 (m, 1H), 6.39-6.29 (m, 1H), 6.16-6.09 (m, 1H), 4.87-4.74 (m, 1H), 4.55-4.43 (m, 1H), 4.15-4.11 (m, 1H), 4.05-4.01 (m, 1H), 3.89 (s, 3H), 3.86 (s, 3H), 3.80-3.74 (m, 2H),

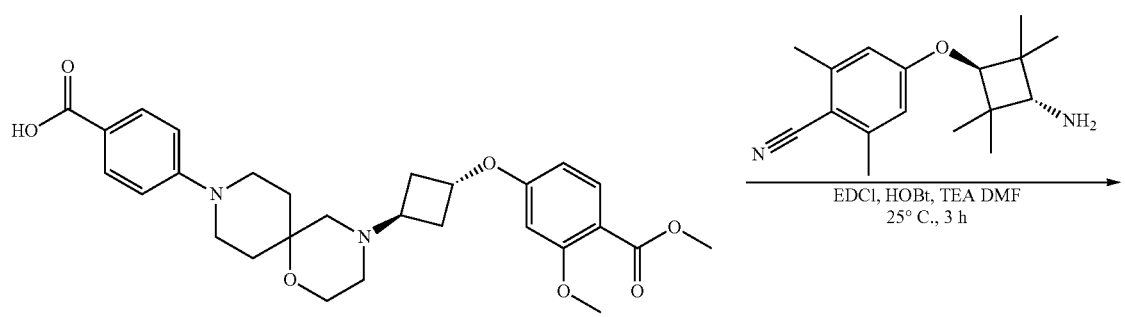

To a mixture of 4-[4-[3-(3-methoxy-4-methoxycarbonyl-phenoxy)cyclobutyl]-1-oxa-4,9-diazaspiro[5.5]undecan-9-yl]benzoic acid (250 mg, 0.49 mmol, 1.00 eq) and triethylamine (248 mg, 2.45 mmol, 0.34 mL, 5.00 eq) in N,N-dimethylformamide (4 mL) was added 3.56-3.47 (m, 2H), 3.31-3.22 (m, 2H), 2.99-2.91 (m, 1H), 2.77-2.67 (m, 1H), 2.49 (s, 6H), 2.40-2.31 (m, 4H), 2.21-2.16 (m, 2H), 2.12-1.99 (m, 4H), 1.26 (s, 6H), 1.22 (s, 6H).

Chemical Formula: $C_{45}H_{56}N_4O_7$, Molecular Weight: 764.95

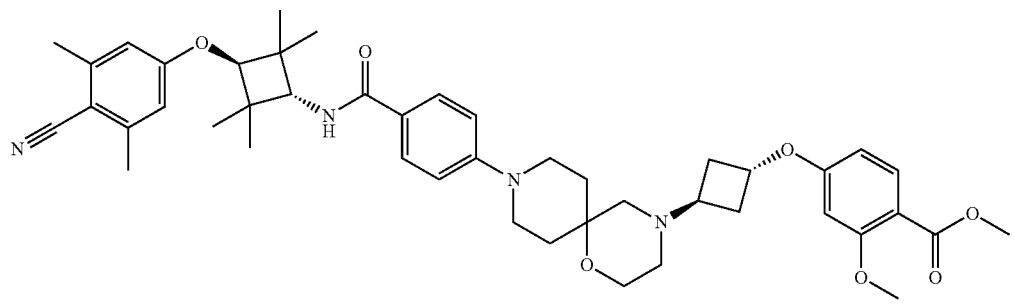

Step 13: Preparation of 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoic acid

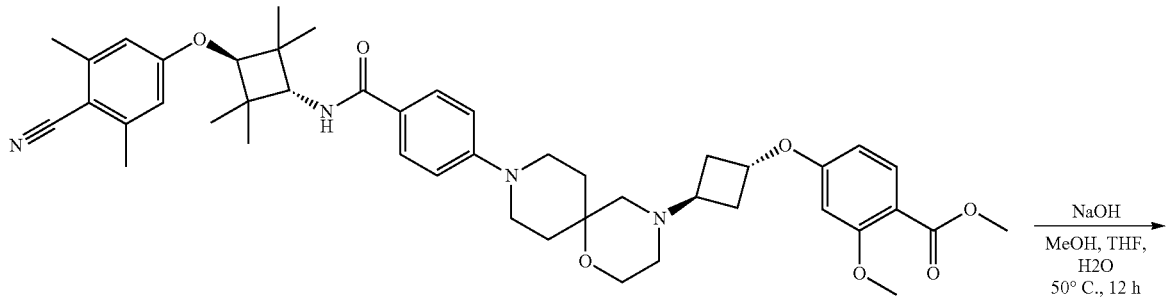

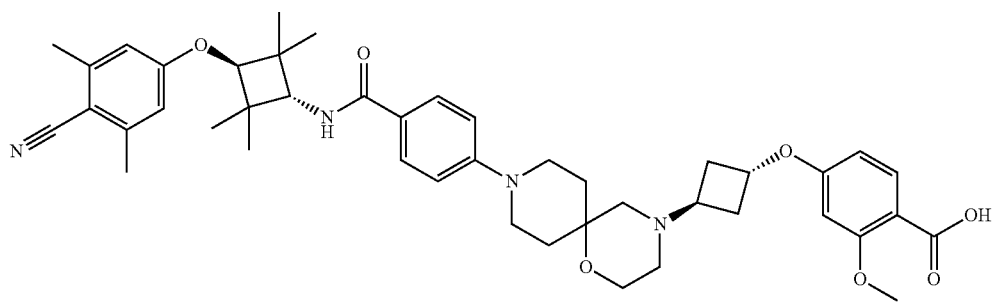

To a mixture of methyl 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoate (200 mg, 0.26 mmol, 1.00 eq) in methanol (2 mL), water (2 mL) and tetrahydrofuran (2 mL) was added sodium hydroxide (52 mg, 1.31 mmol, 5.00 eq). The mixture was stirred at 50° C. for 12 h. LCMS showed the reaction was finished. Then the reaction mixture was concentrated under reduced pressure to give the residue. The residue was adjust pH=6 with hydrochloric acid (1 M). Then the mixture was filtered. The filtered cake was dried under reduced pressure to give 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoic acid (200 mg, crude) as a white solid.

LCMS: MS (ESI) m/z: 751.2 [M+1]$^+$.

Chemical Formula: $C_{44}H_{54}N_4O_7$, Molecular Weight: 750.92

Step 14: Preparation of 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-N-[(3S)-2,6-dioxo-3-piperidyl]-2-methoxy-benzamide, Compound 35

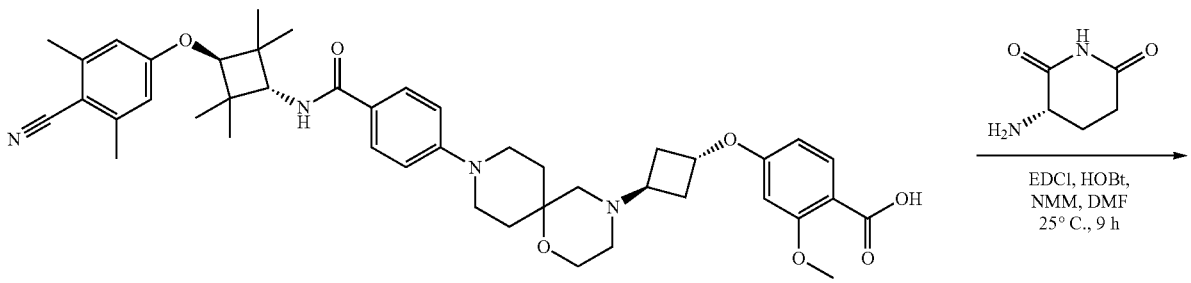

-continued

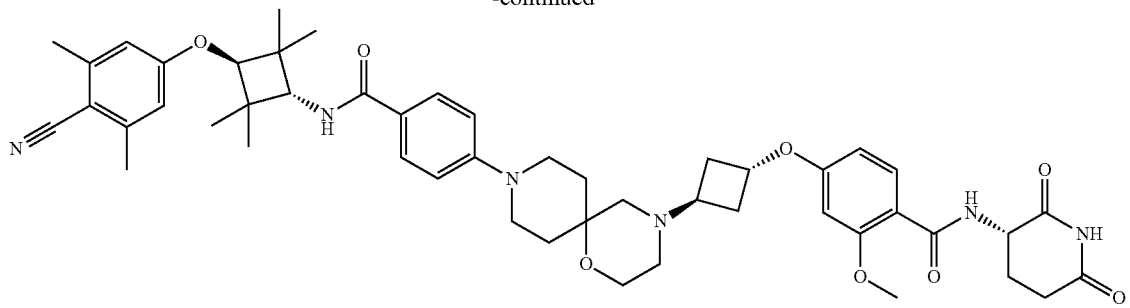

To a solution of 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-2-methoxy-benzoic acid (190.0 mg, 0.25 mmol, 1.00 eq) in N,N-dimethylformamide (4 mL) was added 4-methylmorpholine (128.0 mg, 1.27 mmol, 0.14 mL, 5.00 eq), hydroxybenzotriazole (41 mg, 0.30 mmol, 1.20 eq) and 3-(ethyliminomethyleneamino)-N,N-dimethyl-propan-1-amine; hydrochloride (58 mg, 0.30 mmol, 1.20 eq) and (3S)-3-aminopiperidine-2,6-dione (83 mg, 0.51 mmol, 2.00 eq, hydrochloric acid). The mixture was stirred at 25° C. for 9 h. LCMS showed the reaction was finished. The reaction mixture was filtered. The filtrate was directly purified by preparative HPLC (Column: Phenomenex luna C18 150*40 mm*15 um, Condition:water (0.225% FA)-ACN) to give 4-[3-[9-[4-[[3-(4-cyano-3,5-dimethyl-phenoxy)-2,2,4,4-tetramethyl-cyclobutyl]carbamoyl]phenyl]-1-oxa-4,9-diazaspiro[5.5]undecan-4-yl]cyclobutoxy]-N-[(3S)-2,6-dioxo-3-piperidyl]-2-methoxy-benzamide (104.6 mg, 0.12 mmol, 47% yield, 97% purity) as a off-white solid.
LCMS: MS (ESI) m/z: 861.5 [M+1]$^+$.

HNMR: (400 MHz, DMSO-d$_6$) δ: 10.88 (s, 1H), 8.48 (d, J=6.8 Hz, 1H), 7.86 (d, J=8.8 Hz, 1H), 7.75 (d, J=8.8 Hz, 2H), 7.49 (d, J=8.8 Hz, 1H), 6.98 (d, J=9.2 Hz, 2H), 6.74 (s, 2H), 6.57 (d, J=2.4 Hz, 1H), 6.51 (dd, J=8.4, 2.4 Hz, 1H), 4.87-4.82 (m, 1H), 4.75-4.70 (m, 1H), 4.25-4.23 (m, 1H), 4.07-4.03 (m, 1H), 3.92 (s, 3H), 3.72-3.65 (m, 3H), 3.55-3.47 (m, 4H), 3.22-3.10 (m, 2H), 2.92-2.75 (m, 3H), 2.45-2.39 (m, 7H), 2.32-2.26 (m, 1H), 2.20-2.10 (m, 5H), 2.00-1.81 (m, 2H), 1.71-1.57 (m, 2H), 1.23 (s, 6H), 1.13 (s, 6H).

Chemical Formula: C$_{49}$H$_{60}$N$_6$O, Molecular Weight: 861.04

Example 16—Synthesis of 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyrazine-2-carboxamide (Compound 37)

SCHEME 11. SUMMARY OF THE SYNTHESIS OF COMPOUND 37

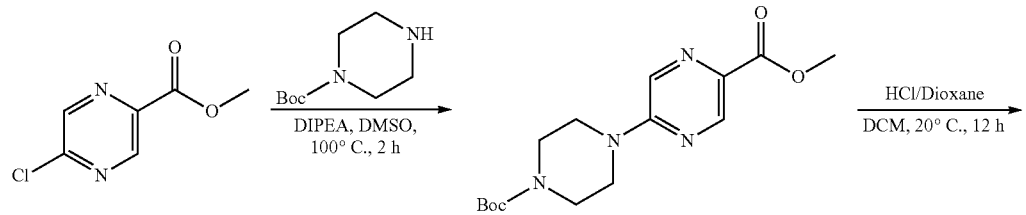

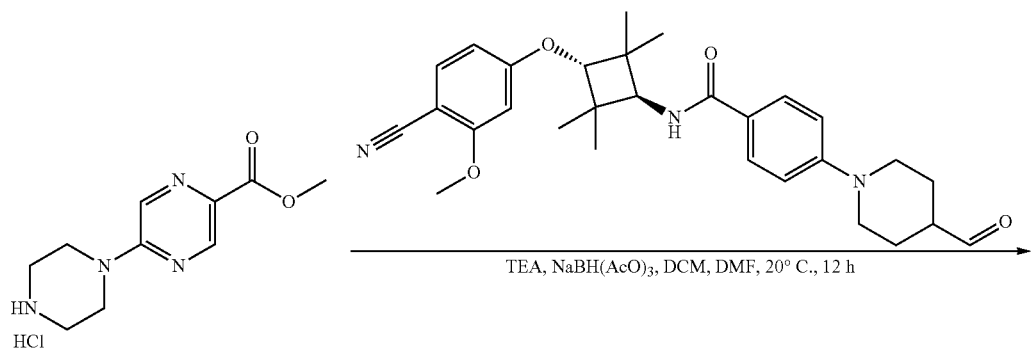

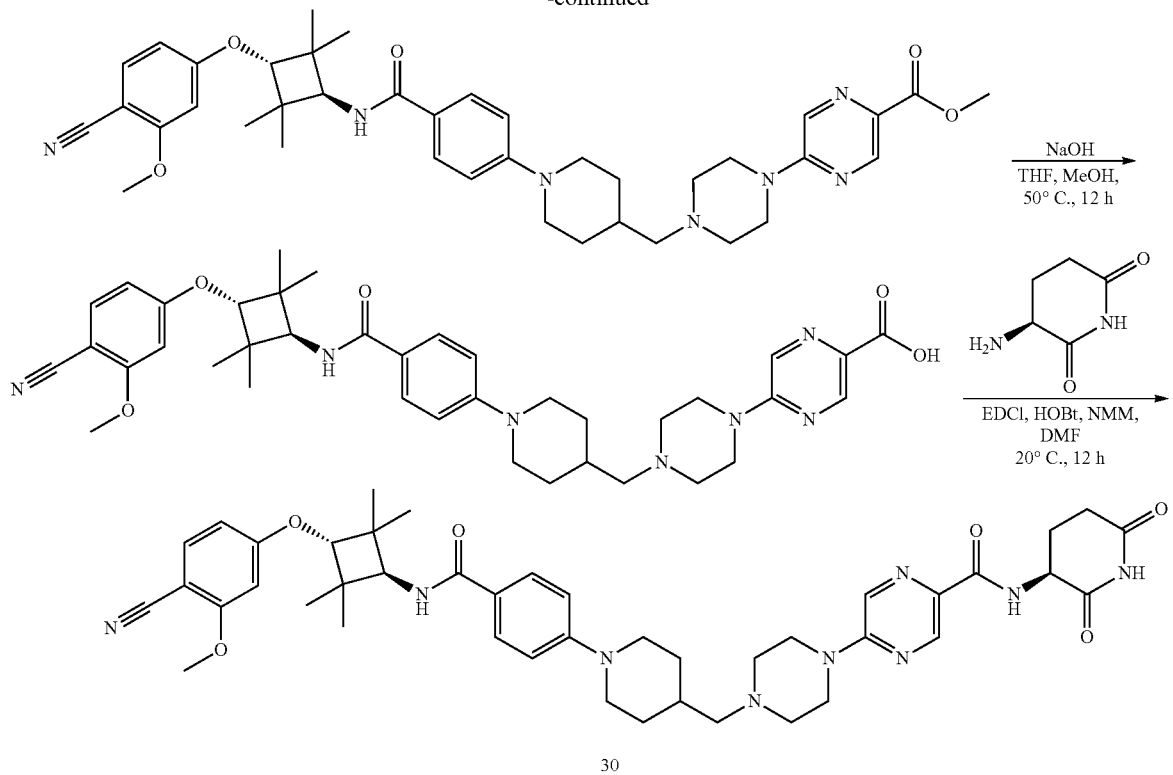

Step 1: Preparation of Methyl 5-(4-(tert-butoxycarbonyl)piperazin-1-yl)pyrazine-2-carboxylate Step 2: Preparation of Methyl 5-(piperazin-1-yl)pyrazine-2-carboxylate

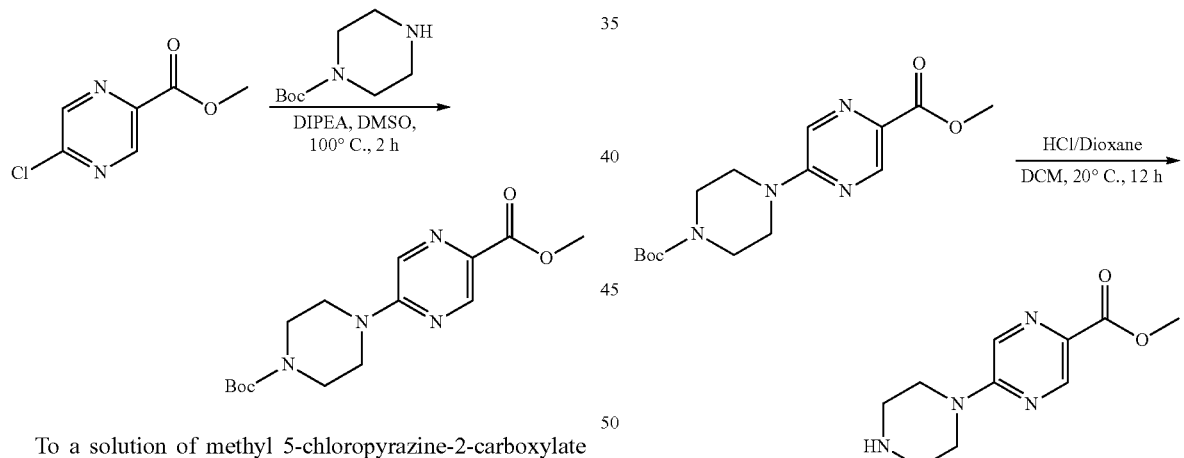

To a solution of methyl 5-chloropyrazine-2-carboxylate (2.00 g, 11.59 mmol, 1.00 eq) in dimethylsulfoxide (20 mL) was added diisopropylethylamine (3.00 g, 23.18 mmol, 4.04 mL, 2.00 eq), tert-butyl piperazine-1-carboxylate (2.16 g, 11.59 mmol, 1.00 eq). The mixture was stirred at 100° C. for 12 h. LCMS showed that the reaction was completed. The mixture was poured into ice water (30 mL) and ethyl acetate (30 mL). The mixture was filtered and the filter cake was concentrated under reduced pressure to give methyl 5-(4-tert-butoxycarbonylpiperazin-1-yl)pyrazine-2-carboxylate (3.50 g, 10.86 mmol, 93% yield) as a yellow solid, which was used in next step directly.

LCMS: MS (ESI) m/z: 323.8 [M+1]$^+$.

$^1$H NMR: (400 MHz, DMSO-$d_6$) δ: 8.81 (d, J=1.2 Hz, 1H), 8.14 (d, J=1.2 Hz, 1H), 3.96 (s, 3H), 3.80-3.68 (m, 4H), 3.63-3.51 (m, 4H), 1.49 (s, 9H).

Chemical Formula: $C_{15}H_{22}N_4O_4$, Molecular Weight: 322.36

To a solution of methyl 5-(4-tert-butoxycarbonylpiperazin-1-yl)pyrazine-2-carboxylate (1.50 g, 4.65 mmol, 1.00 eq) in dichloromethane (30 mL) was added hydrochloric acid/dioxane (4 M, 5 mL, 4.28 eq). The mixture was stirred at 25° C. for 12 h. LCMS showed that the reaction was completed. The mixture was filtered and the filter cake was concentrated under reduced pressure to give methyl 5-piperazin-1-ylpyrazine-2-carboxylate (1.00 g, 3.87 mmol, 83% yield, hydrochloride) as a yellow solid.

LCMS: MS (ESI) m/z: 223.2 [M+1]$^+$.

Chemical Formula: $C_{10}H_{14}N_4O_2$, Molecular Weight: 222.24

Step 3: Preparation of Methyl 5-(4-((1-(4-(((1r,3r)-3-(4-cyano-3-methoxyphenoxy)-2,2,4,4-tetramethyl-cyclobutyl)carbamoyl)phenyl)piperidin-4-yl)methyl)piperazin-1-yl)pyrazine-2-carboxylate

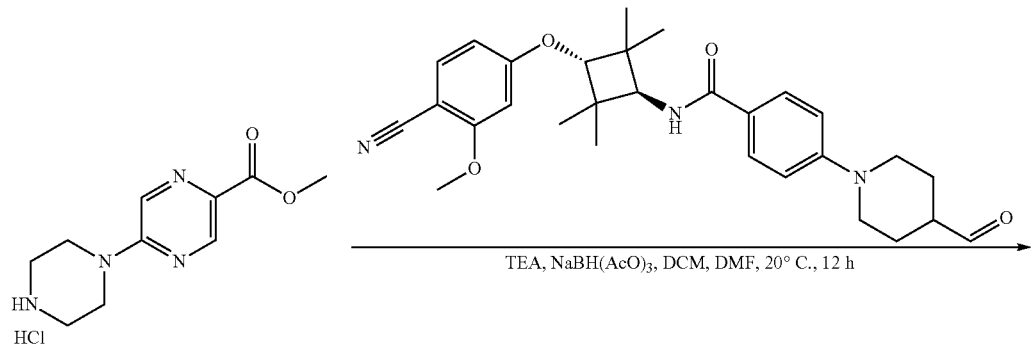

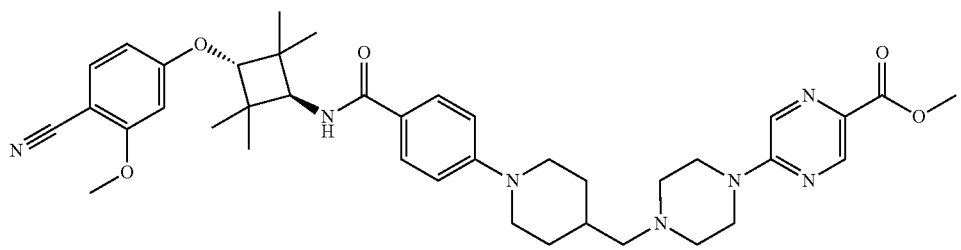

To a solution of methyl 5-piperazin-1-ylpyrazine-2-carboxylate (158 mg, 0.61 mmol, 1.00 eq, hydrochloride) in dichloromethane (2 mL) and dimethyformamide (1 mL) was added triethylamine (62 mg, 0.61 mmol, 1.00 eq), acetate acid (36 mg, 0.61 mmol, 1.00 eq) and N-[3-(4-cyano-3-methoxy-phenoxy)-2,2,4,4-tetramethyl-cyclobutyl]-4-(4-formyl-1-piperidyl)benzamide (300 mg, 0.61 mmol, 1.00 eq). The mixture was stirred at 30° C. for 12 h. Then to the mixture was added sodium borohydride acetate (259 mg, 1.23 mmol, 2.00 eq) and stirred at 30° C. for 1 h. LCMS showed that the reaction was completed. The reaction was added water (20 mL) and extracted with dichloromethane (30 mL×3). The organic layer was dried over sodium sulfate and concentrated under reduced pressure to give a residue. The residue was purified with preparative high performance liquid chromatography (column: Phenomenex luna C18 150*40 mm*15 um; mobile phase: [water (0.1% TFA)-ACN]; B %: 30%-50%, 10 min) to give methyl 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyrazine-2-carboxylate (260 mg, 0.37 mmol, 60% yield) as a yellow solid.

LCMS: MS (ESI) m/z: 696.4 [M+1]$^+$.

Chemical Formula: $C_{39}H_{49}N_7O_5$, Molecular Weight: 695.85

Step 4: Preparation of 5-(4-((1-(4-(((1r,3r)-3-(4-cyano-3-methoxyphenoxy)-2,2,4,4-tetramethylcyclobutyl)carbamoyl)phenyl)piperidin-4-yl)methyl)piperazin-1-yl)pyrazine-2-carboxylic acid

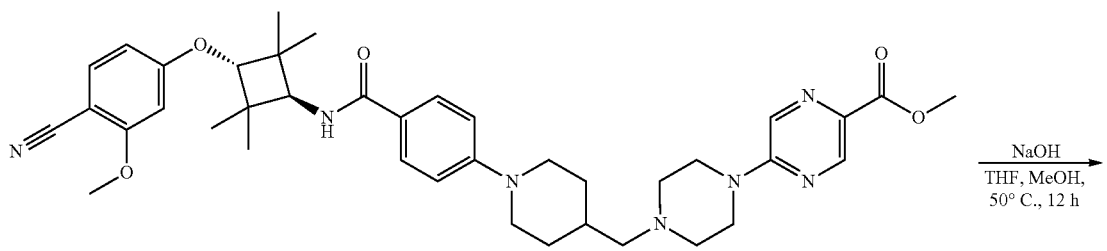

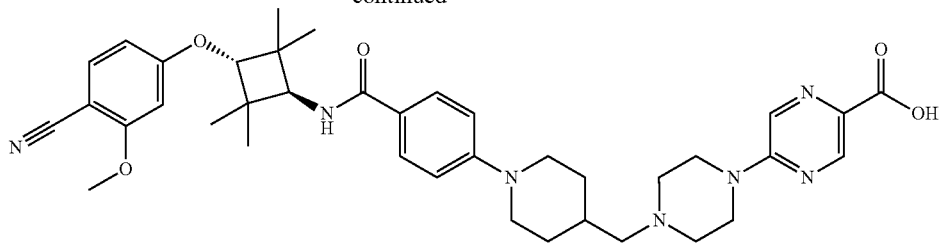

To a solution of methyl 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyrazine-2-carboxylate (260 mg, 0.37 mmol, 1.00 eq) in tetrahydrofuran (5 mL), methanol (5 mL) and water (5 mL) was added sodium hydroxide (119 mg, 2.99 mmol, 8.00 eq). The mixture was stirred at 50° C. for 12 h. LCMS showed that the reaction was completed. The mixture was adjusted with hydrochloric acid (4 M) to pH=5. The mixture was filtered and the filter cake was concentrated under reduced pressure to give 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyrazine-2-carboxylic acid (240 mg, 0.33 mmol, 89% yield, hydrochloride) as a yellow solid.

LCMS: MS (ESI) m/z: 682.1 [M+1]$^+$.

Chemical Formula: $C_{38}H_{47}N_7O_5$, Molecular Weight: 681.82

Step 5: Preparation of 5-(4-((1-(4-(((r,3r)-3-(4-cyano-3-methoxyphenoxy)-2,2,4,4-tetramethylcyclobutyl)carbamoyl)phenyl)piperidin-4-yl)methyl)piperazin-1-yl)-N—((S)-2,6-dioxopiperidin-3-yl) pyrazine-2-carboxamide, Compound 37

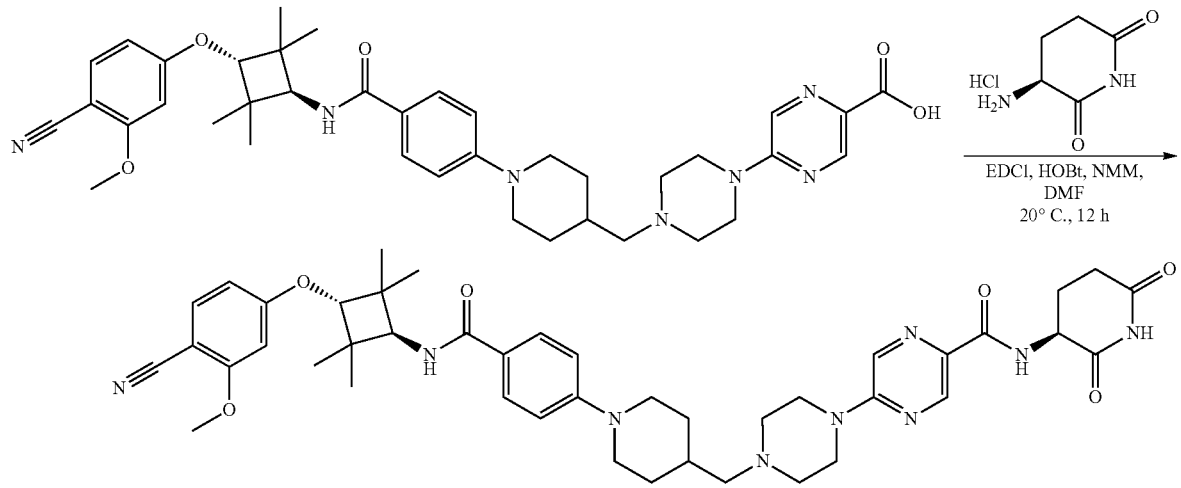

To a solution of 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyrazine-2-carboxylic acid (200 mg, 0.27 mmol, 1.00 eq, hydrochloride) in dimethylformamide (2 mL) was added 4-methylmorpholine (140 mg, 1.39 mmol, 5.00 eq), hydroxybenzotriazole (45 mg, 0.33 mmol, 1.20 eq), 3-(ethyliminomethyleneamino)-N,N-dimethyl-propan-1-amine; hydrochloride (64 mg, 0.33 mmol, 1.20 eq) and (3S)-3-aminopiperidine-2,6-dione (68 mg, 0.41 mmol, 1.50 eq, hydrochloride). The mixture was stirred at 20° C. for 12 h. LCMS showed that the reaction was completed. The mixture was added dichloromethane (20 mL) and water (20 mL). Then the mixture filtered. The filtrate was extracted with dichloromethane (20 mL×3). The organic layer was dried over sodium sulfate and concentrated under reduced pressure to give a residue. The residue was purified with preparative high performance liquid chromatography (column: Shim-pack C18 150*25*10 um; mobile phase: [water (0.225% FA)-ACN]; B %: 22%-52%, 10 min) to give 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyrazine-2-carboxamide (158 mg, 0.19 mmol, 70% yield, 99% purity) as a white solid.

QC-LCMS: (ESI) m/z: 792.5 [M+1]$^+$.

$^1$H NMR: (400 MHz, DMSO-$d_6$) δ: 10.85 (s, 1H), 8.62 (d, J=2.4 Hz, 1H), 8.54 (d, J=8.4 Hz, 1H), 7.97 (dd, J=2.4, 9.2 Hz, 1H), 7.74 (d, J=8.4 Hz, 2H), 7.65 (d, J=8.4 Hz, 1H), 7.50 (d, J=9.2 Hz, 1H), 7.01-6.92 (m, 1H), 6.96 (br d, J=8.8 Hz, 2H), 6.88 (d, J=9.2 Hz, 1H), 6.64 (d, J=2.0 Hz, 1H), 6.54 (dd, J=2.0, 8.8 Hz, 1H), 4.81-4.69 (m, 1H), 4.28 (s, 1H), 4.06 (d, J=9.2 Hz, 1H), 3.91 (s, 3H), 3.86 (br d, J=12.0 Hz, 2H), 3.62 (br s, 4H), 2.79 (br t, J=12.0 Hz, 3H), 2.56 (br d, J=3.6 Hz, 1H), 2.45 (br s, 4H), 2.25-2.05 (m, 3H), 2.02-1.93 (m, 1H), 1.82 (br d, J=12.0 Hz, 3H), 1.23 (s, 8H), 1.15 (s, 6H).

Chemical Formula: $C_{43}H_{53}N_9O_6$, Molecular Weight: 791.94

Total H count from HNMR data: 53.

Example 17—Synthesis of 6-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyridine-3-carboxamide (Compound 38)
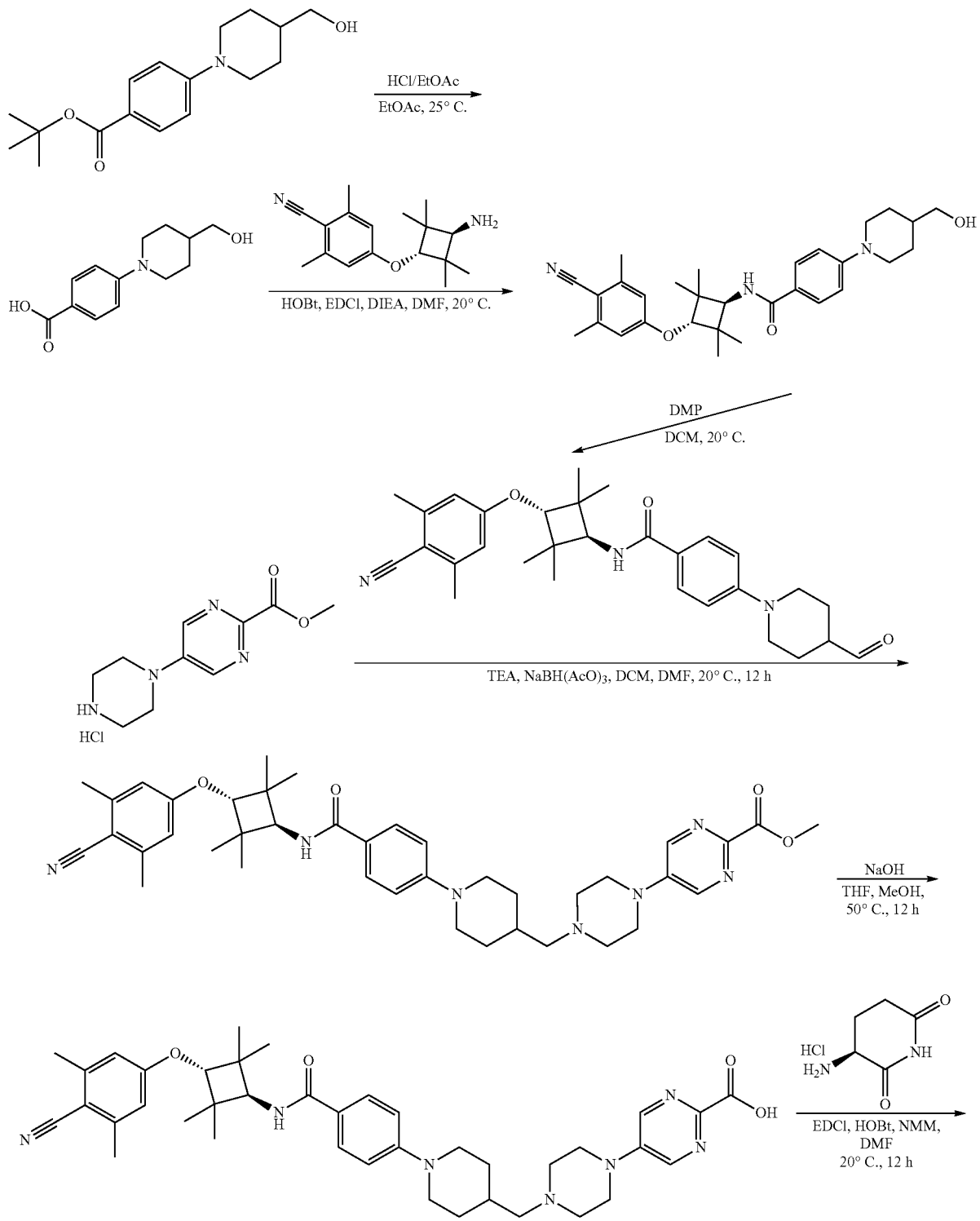
SCHEME 12. SUMMARY OF THE SYNTHESIS OF COMPOUND 38

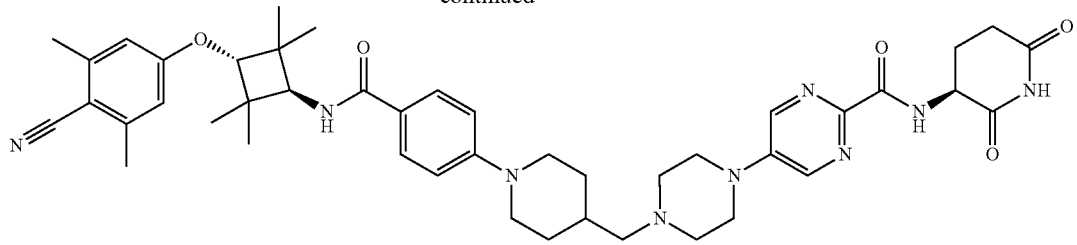

Step 1: Preparation of 4-[4-(hydroxymethyl)-1-piperidyl]benzoic acid

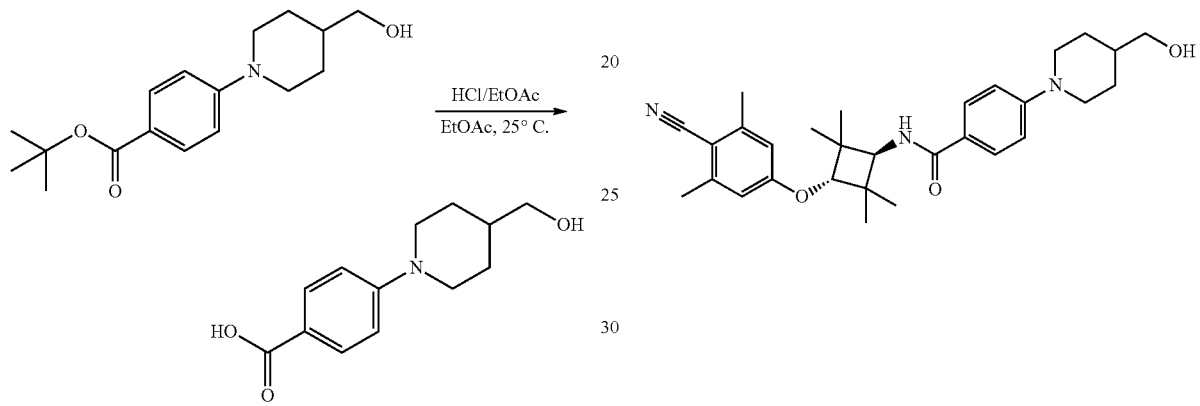

To a solution of tert-butyl 4-[4-(hydroxymethyl)-1-piperidyl]benzoate (5.00 g, 17.16 mmol, 1.00 eq) in ethyl acetate (50 mL) was added hydrochloric acid/ethyl acetate (4 M, 10 mL, 2.33 eq) at 25° C. The mixture was stirred at 25° C. for 35 h. LCMS showed that the reaction was completed. The mixture was concentrated under reduced pressure to give a solid. The solid was washed with ethyl acetate (40 mL) and concentrated under reduced pressure to give 4-[4-(hydroxymethyl)-1-piperidyl]benzoic acid (4.30 g, 16.45 mmol, 96% yield, 90% purity) as a white solid, which was used in next step directly.

LCMS: MS (ESI) m/z: 236.1[M+1]$^+$.

$^1$H NMR: (400 MHz, DMSO-d$_6$) δ: 7.77 (d, J=8.8 Hz, 2H), 7.04 (s, 2H), 3.87 (d, J=12.8 Hz, 2H), 3.28 (d, J=6.0 Hz, 2H), 2.87 (t, J=11.6 Hz, 2H), 1.74 (d, J=12.8 Hz, 2H), 1.55-1.68 (m, 1H), 1.17-1.33 (m, 2H).

Chemical Formula: C$_{13}$H$_{17}$NO$_3$ Molecular Weight: 235.28.

Step 2: Preparation of N-[3-(4-cyano-3,5-dimethyl-phenoxy)-2,2,4,4-tetramethyl-cyclobutyl]-4-[4-(hydroxymethyl)-1-piperidyl]benzamide

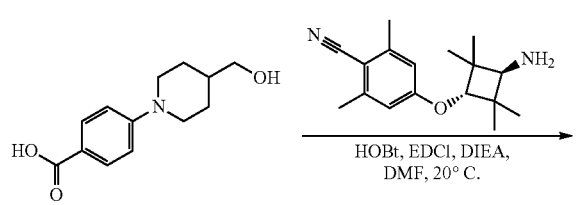

To a solution of 4-[4-(hydroxymethyl)-1-piperidyl]benzoic acid (798.37 mg, 3.39 mmol, 1.31 eq) in N,N-dimethylformamide (10 mL) were added Hydroxybenzotriazole (525.00 mg, 3.89 mmol, 1.50 eq), 1-(3-dimethylaminopropyl)-3-ethylcarbodiimide hydrochloride (744.84 mg, 3.89 mmol, 1.50 eq), diisopropylethylamine (1.67 g, 12.95 mmol, 2.26 mL, 5.00 eq) and 4-(3-amino-2,2,4,4-tetramethyl-cyclobutoxy)-2,6-dimethyl-benzonitrile (800.00 mg, 2.59 mmol, 1.00 eq, hydrochloric acid). The mixture was stirred at 20° C. for 12 h. LCMS showed that 4-(3-amino-2,2,4,4-tetramethyl-cyclobutoxy)-2,6-dimethyl-benzonitrile was consumed completely and the desired MS was found. The mixture was diluted with water (30 mL) and extracted with ethyl acetate (20 mL). The organic layer was washed with brine (2×20 mL), dried over sodium sulfate and concentrated under reduced pressure to give a residue. The residue was purified by column chromatography on silica gel (petroleum ether:ethyl acetate=8:1 to 1:1) to give N-[3-(4-cyano-3,5-dimethyl-phenoxy)-2,2,4,4-tetramethyl-cyclobutyl]-4-[4-(hydroxymethyl)-1-piperidyl]benzamide (510.00 mg, 1.04 mmol, 40% yield) as a white solid.

LCMS: MS (ESI) m/z: 490.4[M+1]$^+$.

$^1$H NMR: (400 MHz, DMSO-d$_6$) δ: 7.73 (d, J=8.8 Hz, 2H), 7.48 (d, J=9.2 Hz, 1H), 6.95 (d, J=8.8 Hz, 2H), 6.73 (s, 2H), 4.49 (t, J=5.2 Hz, 1H), 4.22 (s, 1H), 4.03 (d, J=9.2 Hz, 1H), 3.87 (d, J=13.2 Hz, 2H), 3.27 (t, J=5.6 Hz, 2H), 2.75 (s, 2H), 2.43 (s, 6H), 1.73 (d, J=12.0 Hz, 2H), 1.51-1.64 (m, 1H), 1.21 (s, 6H), 1.14-1.20 (m, 2H), 1.11 (s, 6H).

Chemical Formula: C$_{30}$H$_{39}$N$_3$O$_3$ Molecular Weight: 489.65

Step 3: Preparation of N-[3-(4-cyano-3,5-dimethyl-phenoxy)-2,2,4,4-tetramethyl-cyclobutyl]-4-(4-formyl-1-piperidyl)benzamide

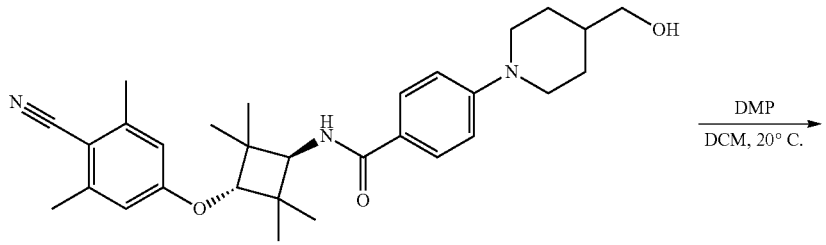

To a solution of N-[3-(4-cyano-3,5-dimethyl-phenoxy)-2,2,4,4-tetramethyl-cyclobutyl]-4-[4-(hydroxymethyl)-1-piperidyl]benzamide (510.00 mg, 1.04 mmol, 1.00 eq) in dichloromethane (10 mL) was added Dess-Martain reagent (662.66 mg, 1.56 mmol, 483.69 uL, 1.50 eq). The mixture was stirred at 20° C. for 3 h. LCMS showed that the reaction was completed. The mixture was quenched with saturated natrium sulfurosum solution and saturated sodium bicarbonate solution (10 mL, 1:1) and then extracted with dichloromethane (15 mL). The organic layer was wished with brine (15 mL), dried over sodium sulfate and concentrated under reduced pressure to give a residue. The residue was purified by column chromatography on silica gel (petroleum ether:ethyl acetate=8:1 to 1:1) to give N-[3-(4-cyano-3,5-dimethyl-phenoxy)-2,2,4,4-tetramethyl-cyclobutyl]-4-(4-formyl-1-piperidyl)benzamide (350.00 mg, 717.75 umol, 69% yield) as a light yellow oil.

LCMS: MS (ESI) m/z: 488.2[M+1]$^+$.

$^1$H NMR: (400 MHz, DMSO-d$_6$)

δ: 9.64 (s, 1H), 7.75 (d, J=8.8 Hz, 2H), 7.50 (d, J=9.2 Hz, 1H), 6.98 (d, J=8.8 Hz, 2H), 6.74 (s, 2H), 4.23 (s, 1H), 4.04 (d, J=9.2 Hz, 1H), 3.72-3.83 (m, 2H), 2.89-3.04 (m, 2H), 2.54-2.63 (m, 1H), 2.43 (s, 6H), 1.88-1.97 (m, 2H), 1.49-1.63 (m, 2H), 1.22 (s, 6H), 1.12 (s, 6H).

Chemical Formula: C$_{30}$H$_{37}$N$_3$O$_3$ Molecular Weight: 487.63

Step 4: Preparation of Methyl 5-(4-((1-(4-(((r,3r)-3-(4-cyano-3,5-dimethylphenoxy)-2,2,4,4-tetramethyl-cyclobutyl)carbamoyl)phenyl)piperidin-4-yl)methyl)piperazin-1-yl)pyrimidine-2-carboxylate

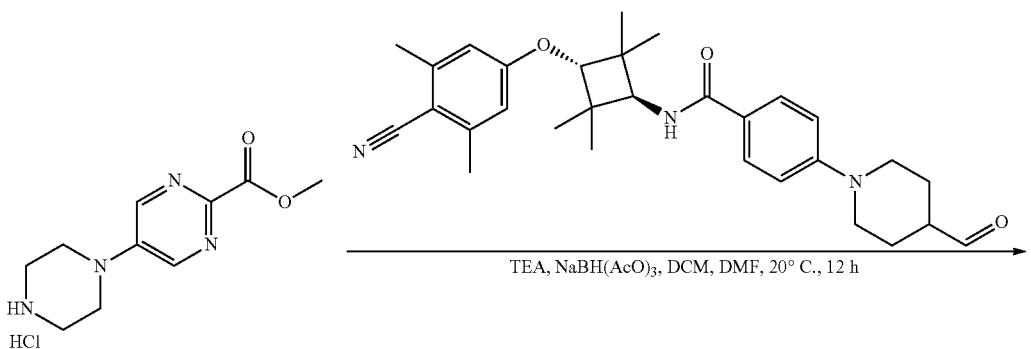

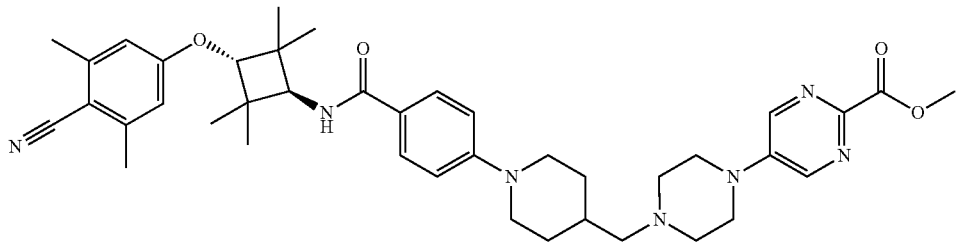

To a solution of methyl 5-piperazin-1-ylpyrimidine-2-carboxylate (106 mg, 0.41 mmol, 1.00 eq, hydrochloride) in dichloromethane (2 mL) and dimethylformamide (1 mL) was added triethylamine (41 mg, 0.41 mmol, 1.00 eq), acetic acid (24 mg, 0.41 mmol, 1.00 eq) and N-[3-(4-cyano-3,5-dimethyl-phenoxy)-2,2,4,4-tetramethyl-cyclobutyl]-4-(4-formyl-1-piperidyl)benzamide (200 mg, 0.41 mmol, 1.00 eq). The mixture was stirred at 30° C. for 12 h. Then to the mixture was added sodium borohydride acetate (173 mg, 0.82 mmol, 2.00 eq) and stirred at 30° C. for 1 h. LCMS showed that the reaction was completed. The reaction was added water (20 mL) and extracted with dichloromethane (30 mL×3). The organic layer was dried over sodium sulfate and concentrated under reduced pressure to give a residue. The residue was purified with preparative high performance liquid chromatography (column: Phenomenex luna C18 150*40 mm*15 um; mobile phase: [water (0.1% TFA)-ACN]; B %: 27%-57%, 10 min) to give methyl 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyrimidine-2-carboxylate (200 mg, 0.28 mmol, 70% yield) as a yellow solid.

LCMS: MS (ESI) m/z: 693.1 [M+1]$^+$.

Chemical Formula: $C_{41}H_{52}N_6O_4$, Molecular Weight: 692.89

Step 5: Preparation of 5-(4-((1-(4-(((r,3r)-3-(4-cyano-3,5-dimethylphenoxy)-2,2,4,4-tetramethylcyclobutyl)carbamoyl)phenyl)piperidin-4-yl)methyl)piperazin-1-yl)pyrimidine-2-carboxylic acid

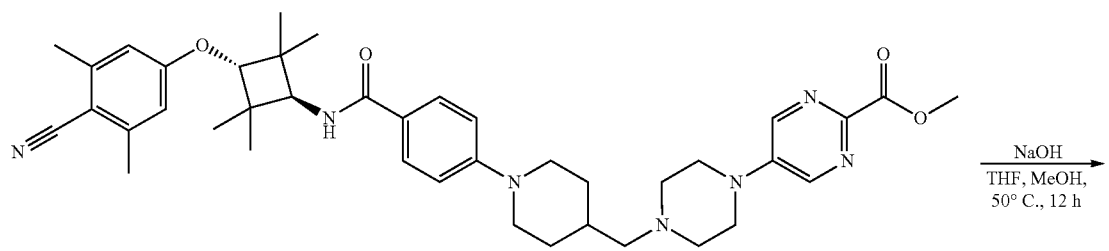

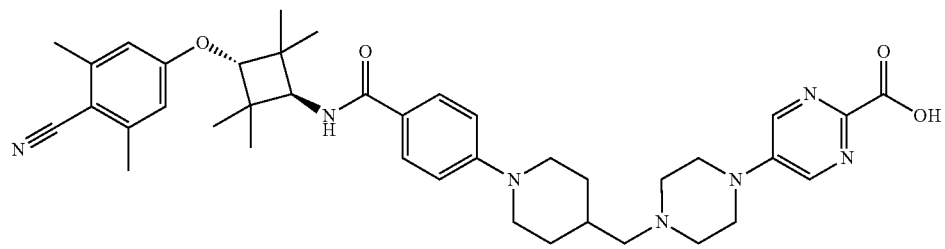

To a solution of methyl 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyrimidine-2-carboxylate (200 mg, 0.28 mmol, 1.00 eq) in tetrahydrofuran (5 mL), methanol (5 mL) and water (5 mL) was added sodium hydroxide (92 mg, 2.31 mmol, 8.00 eq). The mixture was stirred at 50° C. for 12 h. LCMS showed that the reaction was completed. The mixture was adjusted with hydrochloric acid (6 M) to pH=5. The mixture was filtered and the filter cake was concentrated under reduced pressure to give 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyrimidine-2-carboxylic acid (200 mg, 0.027 mmol, 96% yield, hydrochloride) as a yellow solid, which was used in next step directly.

LCMS: MS (ESI) m/z: 679.1 [M+1]$^+$.

Chemical Formula: $C_{40}H_{50}N_6O_4$, Molecular Weight: 678.86

Step 6: Preparation of 6-(4-((1-(4-(((r,3r)-3-(4-cyano-3,5-dimethylphenoxy)-2,2,4,4-tetramethylcyclobutyl)carbamoyl)phenyl)piperidin-4-yl)methyl)piperazin-1-yl)-N—((S)-2,6-dioxopiperidin-3-yl) nicotinamide, Compound 38

(111 mg, 1.10 mmol, 5.00 eq), hydroxybenzotriazole (35 mg, 0.26 mmol, 1.20 eq), 3-(ethyliminomethyleneamino)-N,N-dimethyl-propan-1-amine; hydrochloride (50 mg, 0.26 mmol, 1.20 eq) and (3S)-3-aminopiperidine-2,6-dione (54 mg, 0.33 mmol, 1.50 eq, hydrochloride). The mixture was stirred at 20° C. for 1 h. LCMS showed that the reaction was completed. The mixture was added dichloromethane (20 mL) and water (20 mL). The organic layer was dried over sodium sulfate and concentrated under reduced pressure to give a residue. The residue was purified with preparative high performance liquid chromatography (column: Phenomenex Synergi C18 150*25*10 um; mobile phase: [water (0.225% FA)-ACN]; B %: 30%-60%, 9 min) to give 6-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyridine-3-carboxamide (69.3 mg, 0.08 mmol, 38% yield, 96% purity) as a white solid.

QC-LCMS: MS (ESI) m/z: 789.3 [M+1]$^+$.

$^1$H NMR: (400 MHz, DMSO-d$_6$) δ: 10.84 (s, 1H), 8.61 (d, J=2.4 Hz, 1H), 8.54 (d, J=8.4 Hz, 1H), 8.17 (s, 1H), 7.96 (dd, J=2.4, 9.2 Hz, 1H), 7.73 (d, J=8.8 Hz, 2H), 7.47 (d, J=9.2 Hz, 1H), 6.96 (d, J=8.8 Hz, 2H), 6.87 (d, J=8.8 Hz, 1H), 6.73 (s, 2H), 4.85-4.68 (m, 1H), 4.22 (s, 1H), 4.03 (d, J=9.2 Hz,

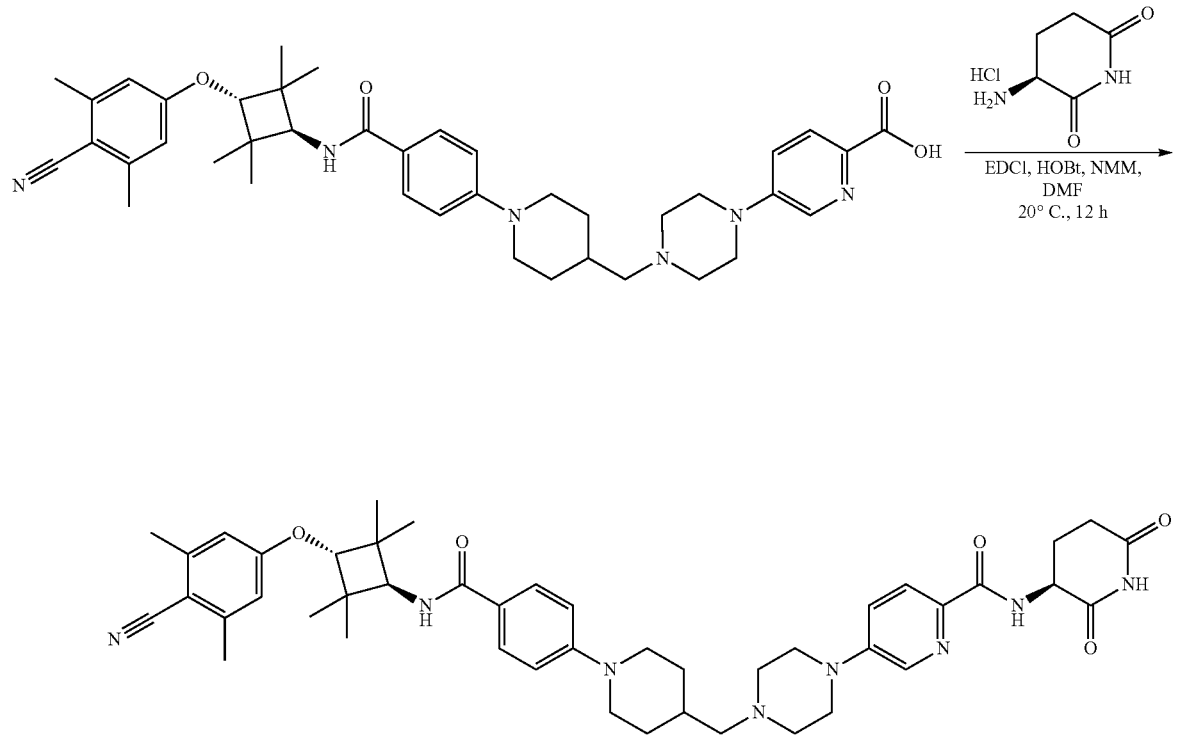

To a solution of 6-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyridine-3-carboxylic acid (150 mg, 0.22 mmol, 1.00 eq, hydrochloride) in dimethylformamide (2 mL) was added 4-methylmorpholine 1H), 3.86 (br d, J=12.4 Hz, 2H), 3.61 (br s, 4H), 2.79 (br t, J=12.4 Hz, 3H), 2.60-2.52 (m, 1H), 2.43 (s, 10H), 2.20 (br d, J=6.4 Hz, 2H), 2.15-2.04 (m, 1H), 1.96 (br d, J=5.6 Hz, 1H), 1.81 (br d, J=11.0 Hz, 3H), 1.21 (s, 8H), 1.12 (s, 6H).

Chemical Formula: $C_{45}H_{56}N_8O$, Molecular Weight: 788.98

Example 18—Synthesis of [4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyrimidine-2-carboxamide (Compound 39)
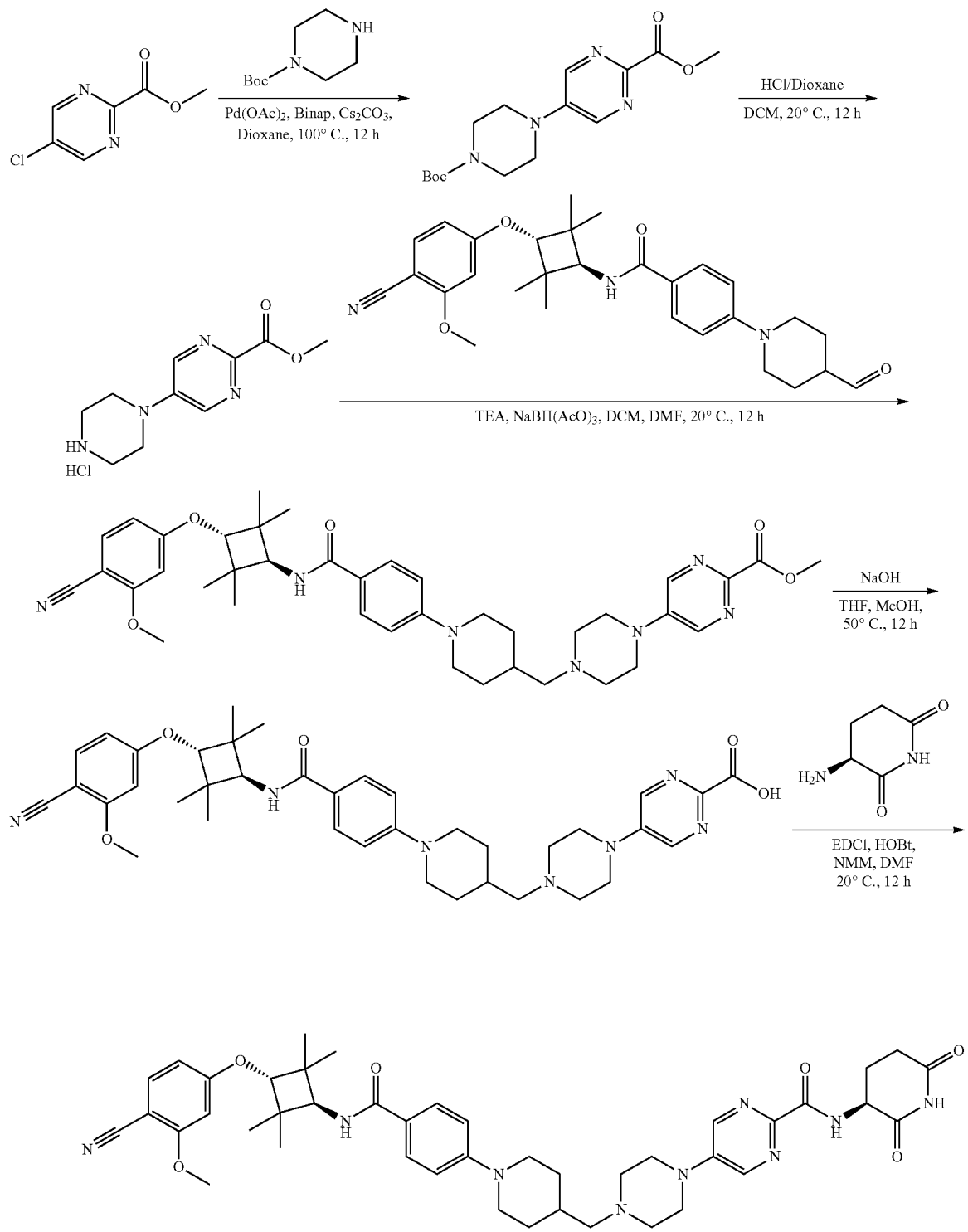

Step 1: Preparation of Methyl 5-(4-(tert-butoxycarbonyl)piperazin-1-yl)pyrimidine-2-carboxylate

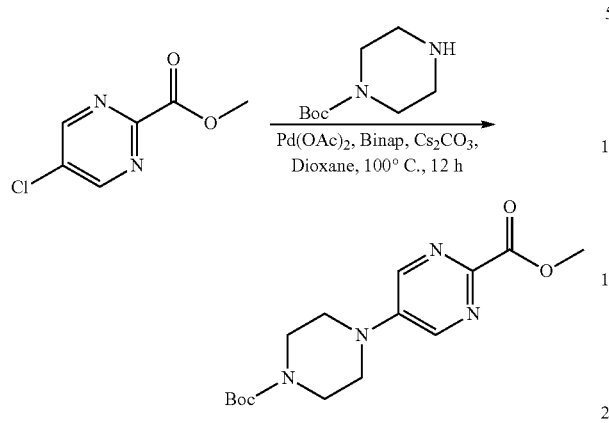

Step 2: Preparation of methyl 5-(piperazin-1-yl)pyrimidine-2-carboxylate

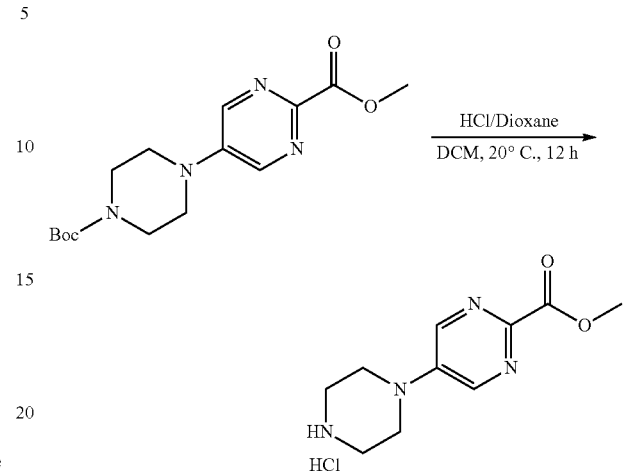

To a solution of methyl 5-bromopyrimidine-2-carboxylate (2.00 g, 9.22 mmol, 1.00 eq) in dioxane (20 mL) was added cesium carbonate (6.01 g, 18.43 mmol, 2.00 eq), tert-butyl piperazine-1-carboxylate (1.72 g, 9.22 mmol, 1.00 eq), palladium acetate (310 mg, 1.38 mmol, 0.15 eq), and (R)-(+)-2,2'-Bis(diphenylphosphino)-1,1'-binaphthyl (860 mg, 1.38 mmol, 0.15 eq). The mixture was stirred at 100° C. for 12 h. LCMS showed that the reaction was completed. The mixture was poured into water (100 mL) and extracted with ethyl acetate (50 mL×3). The organic layer was dried over anhydrous sodium sulfate and concentrated under reduced pressure to give a residue. The residue was purified with column chromatography on silica gel (petroleum ether:ethyl acetate=10:1 to 1:2) to give methyl 5-(4-tert-butoxycarbonylpiperazin-1-yl)pyrimidine-2-carboxylate (1.50 g, 4.65 mmol, 50% yield) as a yellow solid.

LCMS: EW6807-1109-P1A1, MS (ESI) m/z: 323.1 [M+1]$^+$.

Chemical Formula: $C_{15}H_{22}N_4O_4$, Molecular Weight: 322.36

To a solution of methyl 5-(4-tert-butoxycarbonylpiperazin-1-yl)pyrimidine-2-carboxylate (1.50 g, 4.65 mmol, 1.00 eq) in dichloromethane (30 mL) was added hydrochloric acid/dioxane (4 M, 5 mL, 4.28 eq). The mixture was stirred at 25° C. for 12 h. Thin layer chromatography (petroleum ether:ethyl acetate=3:1) showed that the reaction was completed. The mixture was filtered and the filter cake was concentrated under reduced pressure to give methyl 5-piperazin-1-ylpyrimidine-2-carboxylate (1.00 g, 3.87 mmol, 83% yield, hydrochloride) as a yellow solid, which was used in next step directly.

Step 3: Preparation of methyl 5-(4-((1-(4-(((1r,3r)-3-(4-cyano-3-methoxyphenoxy)-2,2,4,4-tetramethylcyclobutyl)carbamoyl)phenyl)piperidin-4-yl)methyl)piperazin-1-yl)pyrimidine-2-carboxylate

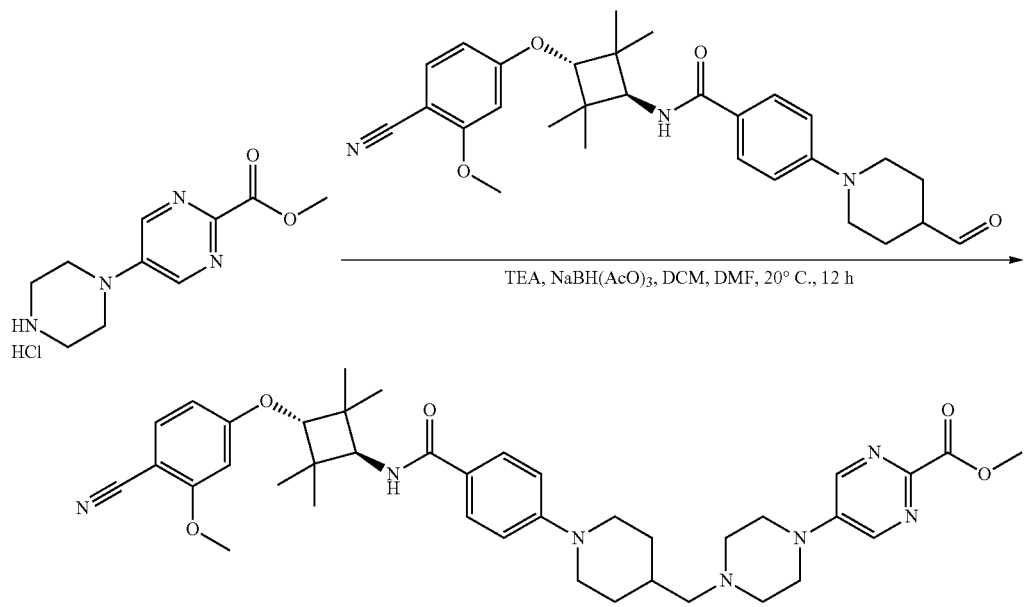

317

To a solution of methyl 5-piperazin-1-ylpyrimidine-2-carboxylate (159 mg, 0.61 mmol, 1.00 eq, hydrochloride) in dichloromethane (2 mL) and dimethyformamide (1 mL) was added triethylamine (62 mg, 0.61 mmol, 1.00 eq), acetate acid (73 mg, 1.23 mmol, 2.00 eq) and N-[3-(4-cyano-3-methoxy-phenoxy)-2,2,4,4-tetramethyl-cyclobutyl]-4-(4-formyl-1-piperidyl)benzamide (301 mg, 0.61 mmol, 1.00 eq). The mixture was stirred at 30° C. for 12 h. Then to the mixture was added sodium borohydride acetate (260 mg, 1.23 mmol, 2.00 eq). The mixture was stirred at 30° C. for 1 h. LCMS showed that the reaction was completed. The reaction was added water (20 mL) and extracted with dichloromethane (30 mL×3). The organic layer was dried over anhydrous sodium sulfate and concentrated under reduced pressure to give a residue. The residue was purified with preparative high performance liquid chromatography (column: Phenomenex luna C18 150*40 mm*15 um; mobile phase: [water (0.1% TFA)-ACN]; B %: 27%-47%, 10 min) to give methyl 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyrimidine-2-carboxylate (200 mg, 0.28 mmol, 46% yield) as a yellow solid.

LCMS: MS (ESI) m/z: 696.0 [M+1]$^+$.

Chemical Formula: $C_{39}H_{49}N_7O$, Molecular Weight: 695.85

Step 4: Preparation of 5-(4-((1-(4-(((1r,3r)-3-(4-cyano-3-methoxyphenoxy)-2,2,4,4-tetramethylcyclobutyl)carbamoyl)phenyl)piperidin-4-yl)methyl)piperazin-1-yl)pyrimidine-2-carboxylic acid To a solution of methyl 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyrimidine-2-carboxylate (200 mg, 0.28 mmol, 1.00 eq) in tetrahydrofuran (5 mL), methanol (5 mL) and water (5 mL) was added sodium hydroxide (91 mg, 2.30 mmol, 8.00 eq). The mixture was stirred at 50° C. for 12 h. LCMS showed that the reaction was completed. The mixture was adjusted with hydrochloric acid (4 M) to pH=5. The mixture was filtered and the filter cake was concentrated under reduced pressure to give 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyrimidine-2-carboxylic acid (200 mg, 0.27 mmol, 96% yield, hydrochloride) as a yellow solid.

LCMS: MS (ESI) m/z: 682.0 [M+1]$^+$.

Chemical Formula: $C_{38}H_{47}N_7O_5$, Molecular Weight: 681.82

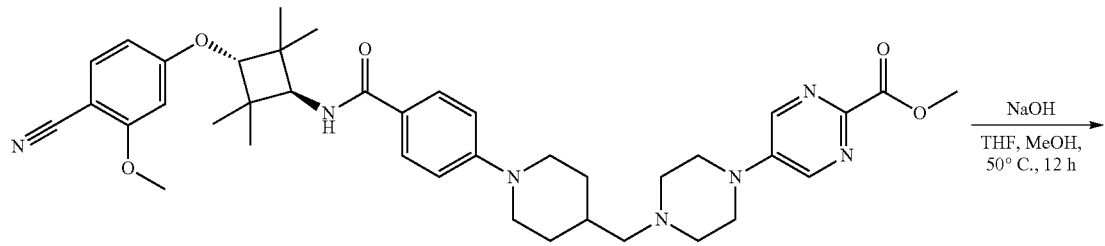

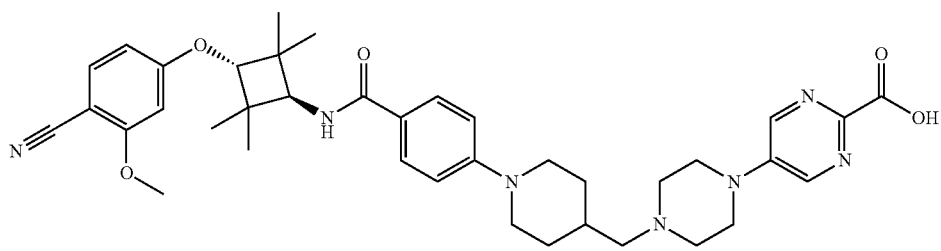

Step 5: Preparation of 5-(4-((1-(4-(((1r,3r)-3-(4-cyano-3-methoxyphenoxy)-2,2,4,4-tetramethylcyclobutyl)carbamoyl)phenyl)piperidin-4-yl)methyl)piperazin-1-yl)-N—((S)-2,6-dioxopiperidin-3-yl)pyrimidine-2-carboxamide, Compound 39

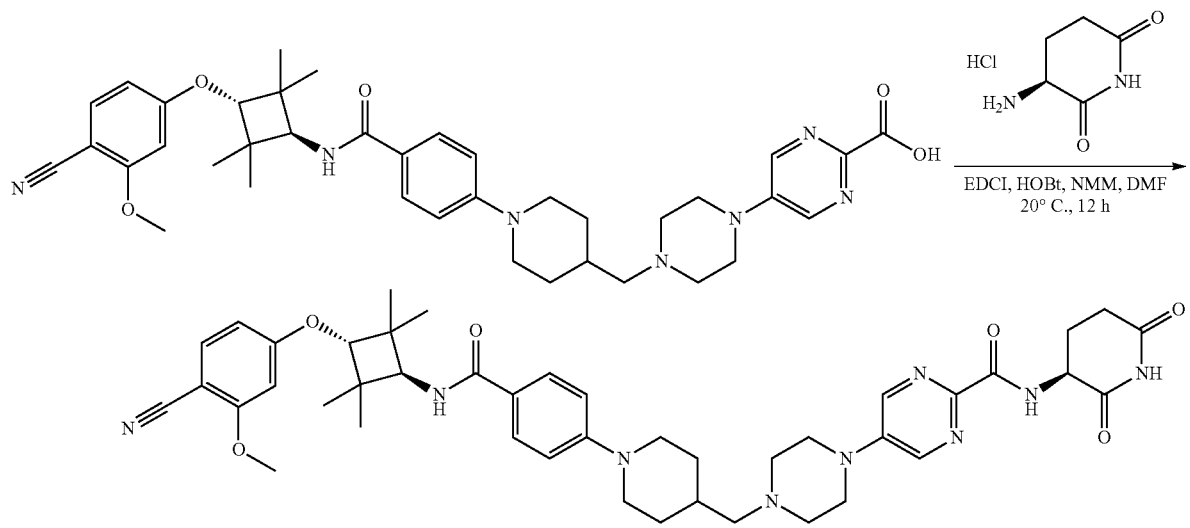

To a solution of 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyrimidine-2-carboxylic acid (200 mg, 0.29 mmol, 1.00 eq, hydrochloride) in dimethylformamide (2 mL) was added 4-methylmorpholine (148 mg, 1.47 mmol, 5.00 eq), hydroxybenzotriazole (47 mg, 0.35 mmol, 1.20 eq), 3-(ethyliminomethyleneamino)-N,N-dimethyl-propan-1-amine; hydrochloride (67 mg, 0.35 mmol, 1.20 eq) and (3S)-3-aminopiperidine-2,6-dione (72 mg, 0.44 mmol, 1.50 eq, hydrochloride). The mixture was stirred at 20° C. for 12 h. LCMS showed that the reaction was completed. The mixture was added dichloromethane (20 mL) and water (20 mL). Then the mixture was filtered. The filtrate was extracted with dichloromethane (20 mL×3). The organic layer was dried over sodium sulfate and concentrated under reduced pressure to give a residue. The residue was purified with preparative high performance liquid chromatography (column: Phenomenex Synergi C18 150*25*10 um; mobile phase: [water (0.225% FA)-ACN]; B %:25%-55%, 10 min) to give 5-(4-((1-(4-(((1r,3r)-3-(4-cyano-3-methoxyphenoxy)-2,2,4,4-tetramethylcyclobutyl)carbamoyl)phenyl)piperidin-4-yl)methyl)piperazin-1-yl)-N—((S)-2,6-dioxopiperidin-3-yl)pyrimidine-2-carboxamide (200.5 mg, 0.22 mmol, 78% yield, 95% purity, formate) as a white solid.

QC-LCMS: (ESI) m/z: 792.5 [M+1]$^+$.

$^1$H NMR: (400 MHz, DMSO-$d_6$) δ: 10.86 (s, 1H), 8.86 (d, J=8.4 Hz, 1H), 8.57 (s, 2H), 8.16 (s, 1H), 7.75 (d, J=8.4 Hz, 2H), 7.49 (d, J=9.2 Hz, 1H), 6.97 (d, J=9.2 Hz, 2H), 6.65 (d, J=2.4 Hz, 1H), 6.55 (dd, J=2.4, 8.4 Hz, 1H), 4.83-4.72 (m, 1H), 4.28 (s, 1H), 4.06 (d, J=9.2 Hz, 1H), 3.92 (s, 3H), 3.88-3.85 (m, 2H), 2.27-2.17 (m, 3H), 2.03-2.01 (m, 1H), 1.84-1.81 (m, 3H), 1.23 (s, 8H), 1.16 (s, 6H).

Chemical Formula: $C_{43}H_{53}N_9O_6$, Molecular Weight: 791.94

Example 19—Synthesis of 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyridine-2-carboxamide (Compound 40)

SCHEME 14. SUMMARY OF THE SYNTHESIS OF COMPOUND 40

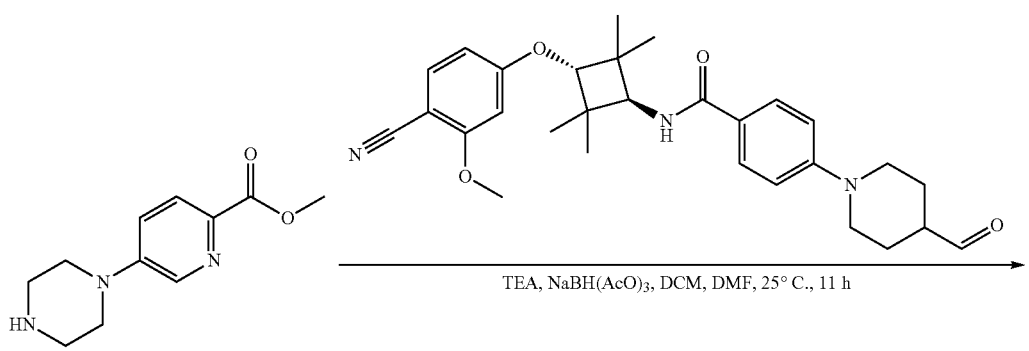

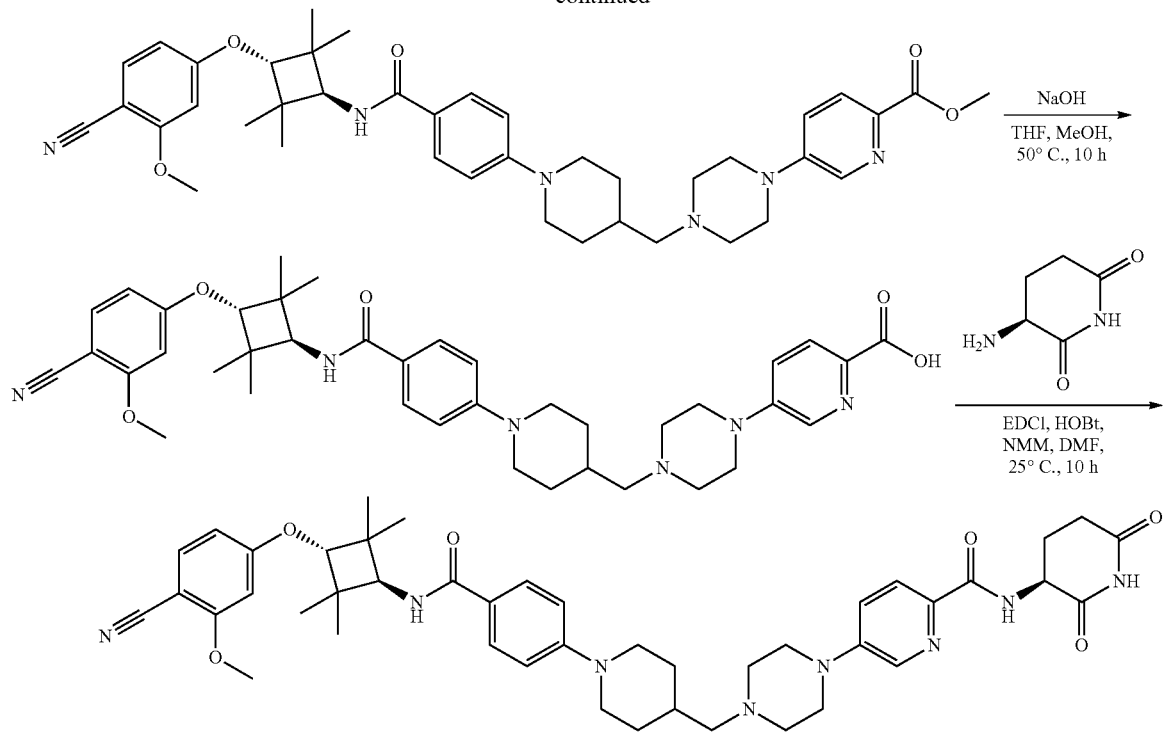

Step 1: Preparation of methyl 5-(4-((1-(4-(((1r,3r)-3-(4-cyano-3-methoxyphenoxy)-2,2,4,4-tetramethyl-cyclobutyl)carbamoyl)phenyl)piperidin-4-yl)methyl)piperazin-1-yl)picolinate and N-[3-(4-cyano-3-methoxy-phenoxy)-2,2,4,4-tetramethyl-cyclobutyl]-4-(4-formyl-1-piperidyl)benzamide (300 mg, 0.61 mmol, 1.00 eq). The mixture was stirred at 25° C. for 10 h. Then to the mixture was added sodium triacetyl borohydride (259 mg, 1.23 mmol, 2.00 eq) and stirred at 25°

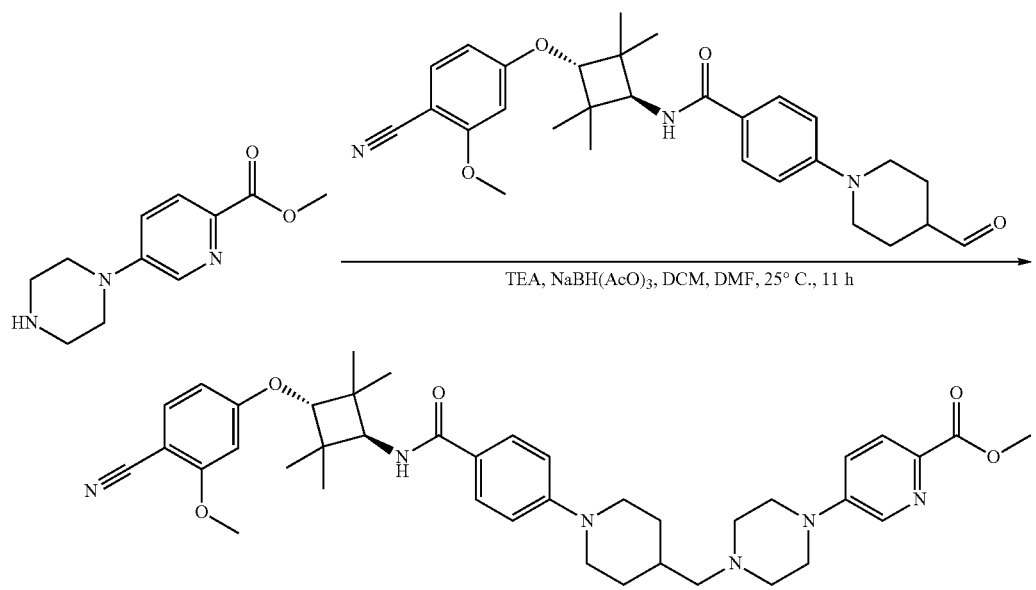

To a solution of methyl 5-piperazin-1-ylpyridine-2-carboxylate (189 mg, 0.73 mmol, 1.20 eq, hydrochloric acid) in dimethylformamide (6 mL) and dichloromethane (2 mL) was added triethylamine (145.40 mg, 1.44 mmol, 0.2 mL, 2.35 eq), acetic acid (210 mg, 3.50 mmol, 0.2 mL, 5.71 eq)

C. for 1 h. LCMS showed the reaction was completed. The mixture was concentrated under reduced pressure to give the residue. The residue was purified by preparative high performance liquid chromatography (column: Phenomenex luna C18 150*25 mm*10 um; mobile phase: [water (0.1%

TFA)-ACN]; B %: 26%-56%, 10 min) to give methyl 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyridine-2-carboxylate (280 mg, 402.96 umol, 66% yield) as a white solid.

LCMS: MS (ESI) m/z: 695.3 [M+1]$^+$

Chemical Formula: $C_{40}H_{50}N_6O_5$ Molecular Weight: 694.86

Step 2: Preparation of 5-(4-((1-(4-(((1r,3r)-3-(4-cyano-3-methoxyphenoxy)-2,2,4,4-tetramethylcyclobutyl)carbamoyl)phenyl)piperidin-4-yl)methyl)piperazin-1-yl)picolinic acid To a solution of methyl 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyridine-2-carboxylate (280 mg, 0.40 mmol, 1.00 eq) in methanol (6 mL) and water (2 mL) was added sodium hydroxide (48.35 mg, 1.21 mmol, 3.00 eq). The mixture was stirred at 50° C. for 10 h. LCMS showed the reaction was completed. The mixture was concentrated under reduced pressure to give the residue. The residue was adjusted to pH=3-4 by hydrochloric acid (1M). Then the mixture was extracted with ethyl acetate (10 mL×2). The organic layer was concentrated under reduced progress to give 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyridine-2-carboxylic acid (170.00 mg, 249.69 umol, 62% yield) as a white solid, which was used into the next step without further purification.

LCMS: MS (ESI) m/z: 681.3 [M+1]$^+$

Chemical Formula: $C_{39}H_{48}N_6O_5$, Molecular Weight: 680.84

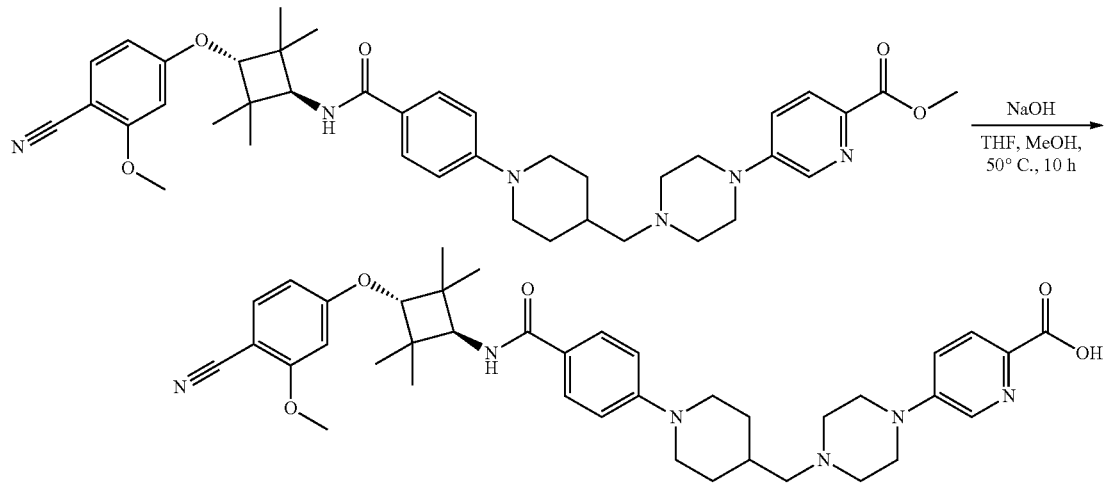

Step 3: Preparation of 5-(4-((1-(4-(((1r,3r)-3-(4-cyano-3-methoxyphenoxy)-2,2,4,4-tetramethylcyclobutyl)carbamoyl)phenyl)piperidin-4-yl)methyl)piperazin-1-yl)-N—((S)-2,6-dioxopiperidin-3-yl)picolinamide, Compound 40

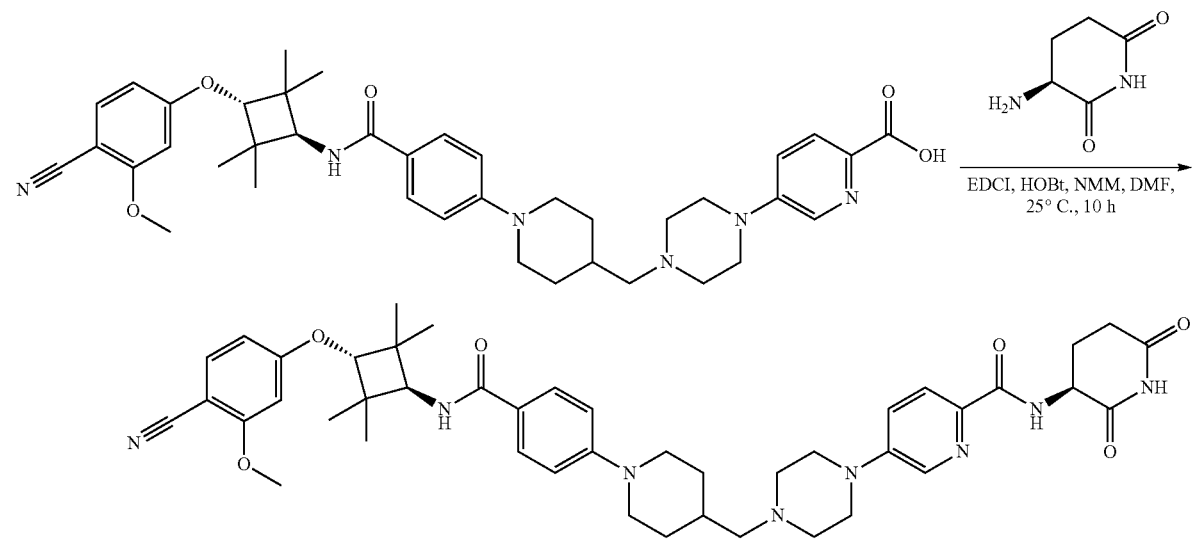 [SMILES: COc1cc(O[C@H]2C(C)(C)[C@H](NC(=O)c3ccc(N4CCC(CN5CCN(c6ccc(C(=O)O)nc6)CC5)CC4)cc3)C2(C)C)ccc1C#N ; N[C@H]1CCC(=O)NC1=O ; COc1cc(O[C@H]2C(C)(C)[C@H](NC(=O)c3ccc(N4CCC(CN5CCN(c6ccc(C(=O)N[C@H]7CCC(=O)NC7=O)nc6)CC5)CC4)cc3)C2(C)C)ccc1C#N]

To a solution of 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]pyridine-2-carboxylic acid (170 mg, 249.69 umol, 1.00 eq) in dimethylformamide (3 mL) was added 1-methylpiperazine (101 mg, 998.78 umol, 109.81 uL, 4.00 eq), 1-hydroxybenzotriazole (51 mg, 374.54 umol, 1.50 eq), 1-(3-dimethylaminopropyl)-3-ethylcarbodiimide hydrochloride (72 mg, 374.54 umol, 1.50 eq) and (3S)-3-aminopiperidine-2,6-dione (82.19 mg, 499.39 umol, 2.00 eq, hydrochloric acid). The mixture was stirred at 25° C. for 10 h. LCMS showed the reaction was completed. The mixture was filtered to give the residue. The residue was purified by preparative high performance liquid chromatography (column: Phenomenex Synergi C18 150*25*10 um; mobile phase: [water (0.225% FA)-ACN]; B %: 20%-50%, 10 min) to give 5-[4-[[1-[4-[[3-(4-cyano-3-methoxy-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyridine-2-carboxamide (70.60 mg, 87.39 umol, 35% yield) as a white solid.

QC-LCMS: MS (ESI) m/z: 791.4 [M+1]$^+$.

$^1$H NMR: (400 MHz, DMSO-d$_6$) δ: 10.85 (s, 1H), 8.73 (d, J=8.4 Hz, 1H), 8.33 (d, J=2.8 Hz, 1H), 7.87 (d, J=8.8 Hz, 1H), 7.74 (d, J=8.8 Hz, 2H), 7.65 (d, J=8.8 Hz, 1H), 7.50 (d, J=9.2 Hz, 1H), 7.43 (dd, J=2.8, 8.4 Hz, 1H), 6.96 (d, J=9.2 Hz, 2H), 6.64 (d, J=2.0 Hz, 1H), 6.54 (dd, J=2.0, 8.8 Hz, 1H), 4.75 (ddd, J=5.2, 7.6, 12.8 Hz, 1H), 4.27 (s, 1H), 4.05 (d, J=9.2 Hz, 1H), 3.91 (s, 3H), 3.87 (br dd, J=2.0, 11.6 Hz, 2H), 3.35 (br s, 4H), 3.30 (br s, 1H), 2.87-2.72 (m, 3H), 2.55 (br s, 2H), 2.53 (br d, J=2.0 Hz, 2H), 2.27-2.14 (m, 3H), 2.05-1.98 (m, 1H), 1.86-1.75 (m, 3H), 1.27-1.18 (m, 8H), 1.15 (s, 6H).

Chemical Formula: C$_{44}$H$_{54}$N$_8$O$_6$, Molecular Weight: 790.95

Example 20—Synthesis of 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyridine-2-carboxamide (Compound 41)

SCHEME 15. SUMMARY OF THE SYNTHESIS OF COMPOUND 41

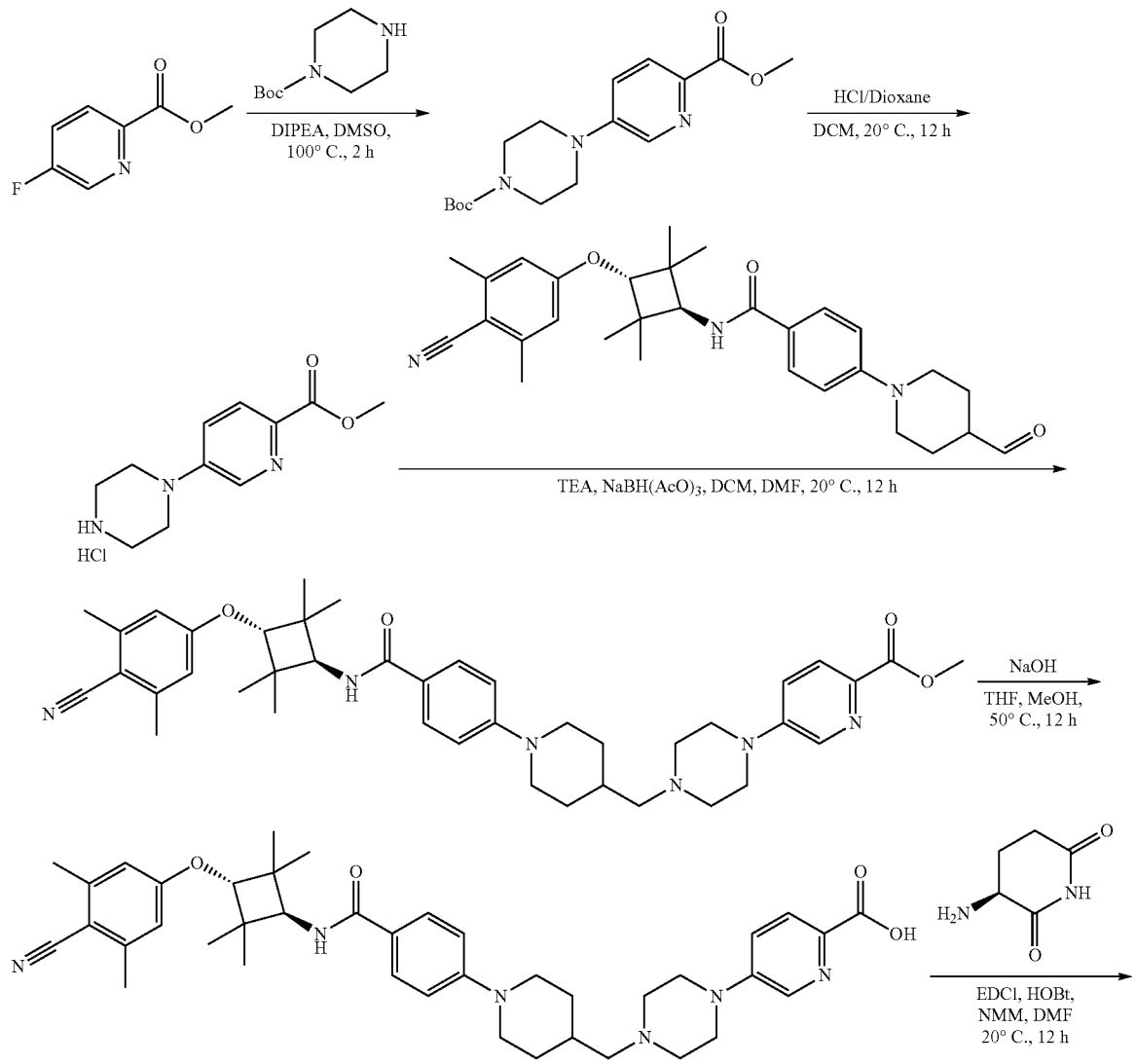

-continued

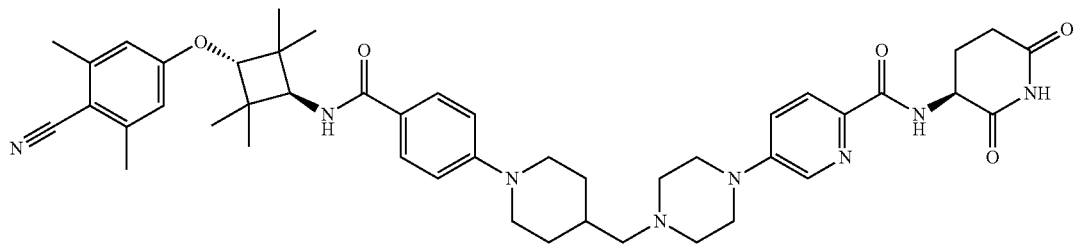

Step 1: Preparation of tert-butyl 4-(6-(methoxycarbonyl)pyridin-3-yl)piperazine-1-carboxylate Step 2: Preparation of methyl 5-(piperazin-1-yl)picolinate

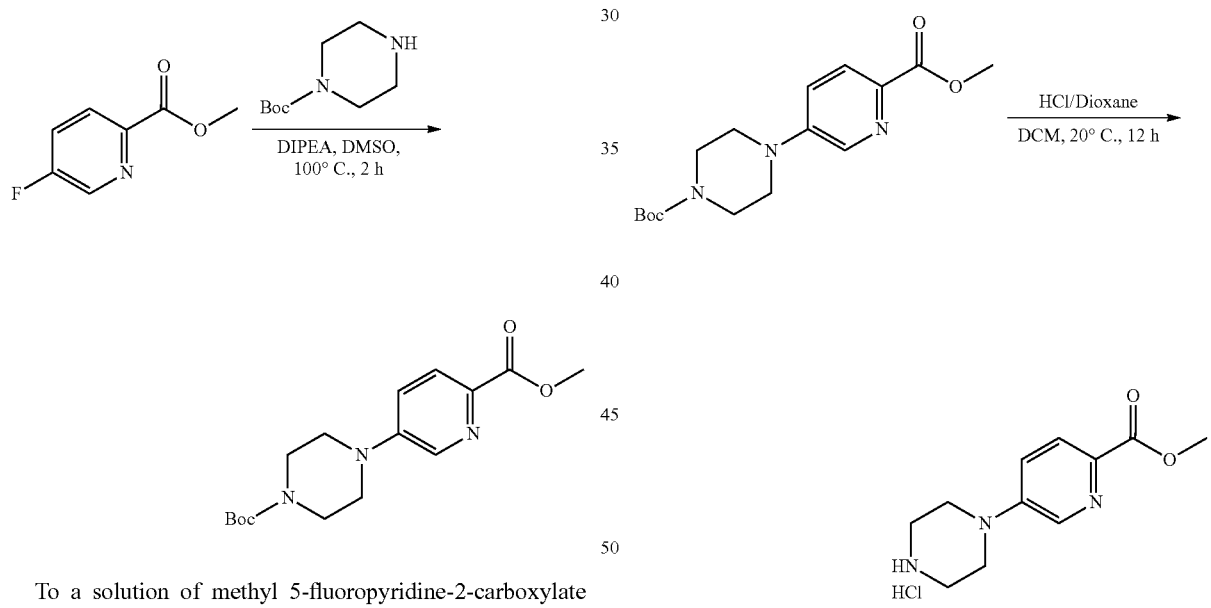

To a solution of methyl 5-fluoropyridine-2-carboxylate (900 mg, 5.80 mmol, 1.00 eq) in dimethylsulfoxide (10 mL) was added diisopropyl ethyl amine (1.50 g, 11.60 mmol, 2.02 mL, 2.00 eq) and tert-butyl piperazine-1-carboxylate (1.08 g, 5.80 mmol, 1.00 eq). The mixture was stirred at 100° C. for 2 h. LCMS showed that the reaction was completed. The mixture was added poured into ice water (20 mL) and ethyl acetate (20 mL) and the filtered cake was concentrated under reduced pressure to give tert-butyl 4-(6-methoxycarbonyl-3-pyridyl)piperazine-1-carboxylate (1.20 g, 3.73 mmol, 64% yield) as a white solid, which was used in next step directly.

LCMS: MS (ESI) m/z: 322.7 [M+1]$^+$.

Chemical Formula: $C_{16}H_{23}N_3O_4$, Molecular Weight: 321.37

To a solution of tert-butyl 4-(6-methoxycarbonyl-3-pyridyl) piperazine-1-carboxylate (1.20 g, 3.73 mmol, 1.00 eq) in dichloromethane (30 mL) was added hydrochloric acid/dioxane (4 M, 4 mL, 4.28 eq). The mixture was stirred at 20° C. for 12 h. LCMS showed that the reaction was completed. The mixture was filtered and the filtered cake concentrated under reduced pressure to give methyl 5-piperazin-1-ylpyridine-2-carboxylate (0.90 g, 3.49 mmol, 93% yield, hydrochloride) as a yellow solid. The solid was used directly to next step.

LCMS: MS (ESI) m/z: 222.2 [M+1]$^+$.

Chemical Formula: $C_{11}H_{15}N_3O_2$, Molecular Weight: 221.26

Step 3: Preparation of methyl 5-(4-((1-(4-(((1r,3r)-3-(4-cyano-3,5-dimethylphenoxy)-2,2,4,4-tetramethylcyclobutyl)carbamoyl)phenyl)piperidin-4-yl)methyl)piperazin-1-yl)picolinate

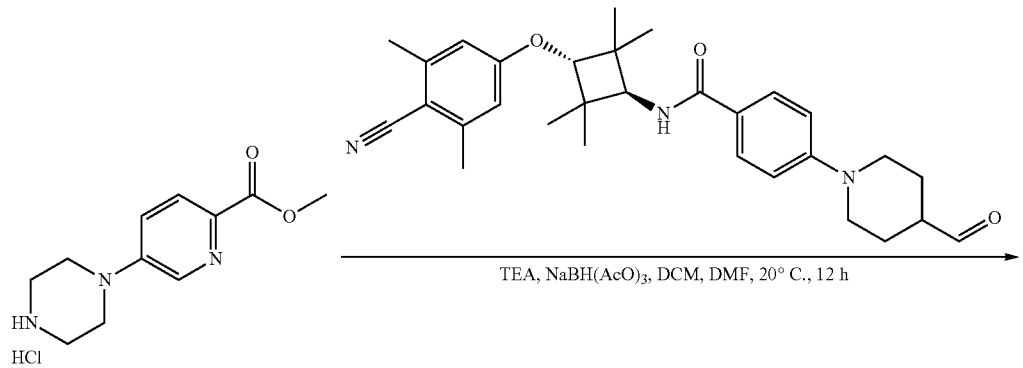

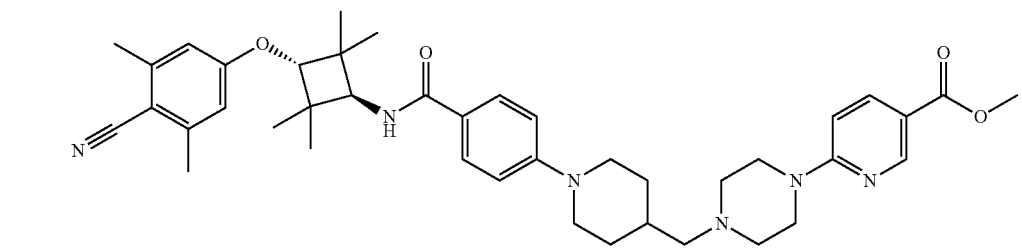

To a solution of methyl 5-piperazin-1-ylpyridine-2-carboxylate (159 mg, 0.61 mmol, 1.00 eq, hydrochloride) in dichloromethane (3 mL) and dimethylformamide (2 mL) was added triethylamine (62 mg, 0.61 mmol, 1.00 eq), acetate acid (37 mg, 0.61 mmol, 1.00 eq) and N-[3-(4-cyano-3,5-dimethyl-phenoxy)-2,2,4,4-tetramethyl-cyclobutyl]-4-(4-formyl-1-piperidyl)benzamide (300 mg, 0.61 mmol, 1.00 eq). The mixture was stirred at 30° C. for 12 h. Then to the mixture was added sodium borohydride acetate (261 mg, 1.23 mmol, 2.00 eq). Then the mixture was stirred at 30° C. for 1 h. LCMS showed that the reaction was completed. The reaction was added water (20 mL) and extracted with dichloromethane (30 mL×3). The organic layer was dried over anhydrous sodium sulfate and concentrated under reduced pressure to give a residue. The residue was purified with preparative high performance liquid chromatography (column: Phenomenex luna C18 150*40 mm*15 um; mobile phase: [water (0.1% TFA)-ACN]; B %: 32%-52%, 10 min) to give methyl 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyridine-2-carboxylate (260 mg, 0.37 mmol, 60% yield) as a yellow solid.

LCMS: MS (ESI) m/z: 693.4 [M+1]$^+$.

Chemical Formula: $C_{41}H_{52}N_6O_4$, Molecular Weight: 692.89

Step 4: Preparation of 5-(4-((1-(4-(((r,3r)-3-(4-cyano-3,5-dimethylphenoxy)-2,2,4,4-tetramethylcyclobutyl)carbamoyl)phenyl)piperidin-4-yl)methyl)piperazin-1-yl)picolinic acid

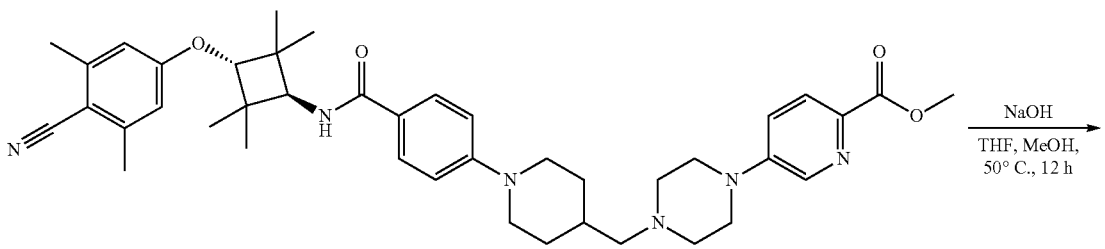

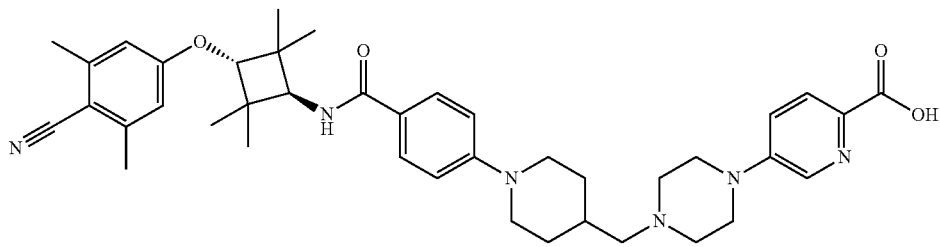

To a solution of methyl 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyridine-2-carboxylate (260 mg, 0.37 mmol, 1.00 eq) in tetrahydrofuran (5 mL), methanol (5 mL) and water (5 mL) was added sodium hydroxide (120 mg, 3.00 mmol, 8.00 eq). The mixture was stirred at 50° C. for 12 h. LCMS showed that the reaction was completed. The mixture was adjusted with diluted hydrochloric acid (6 M) to pH 5. Then the mixture was filtered and the filtered cake was concentrated under reduced pressure to give 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyridine-2-carboxylic acid (200 mg, 0.27 mmol, 74% yield, hydrochloride) as a yellow solid, which was used in next step directly.

LCMS: MS (ESI) m/z: 679.2 [M+1]$^+$.

Chemical Formula: $C_{40}H_{50}N_6O_4$, Molecular Weight: 678.86

Step 5: Preparation of 5-(4-((1-(4-(((r,3r)-3-(4-cyano-3,5-dimethylphenoxy)-2,2,4,4-tetramethylcyclobutyl)carbamoyl)phenyl)piperidin-4-yl)methyl)piperazin-1-yl)-N—((S)-2,6-dioxopiperidin-3-yl)picolinamide, Compound 41

(141 mg, 1.40 mmol, 5.00 eq), hydroxybenzotriazole (45 mg, 0.33 mmol, 1.20 eq) and 3-(ethyliminomethyleneamino)-N,N-dimethyl-propan-1-amine; hydrochloride (64 mg, 0.33 mmol, 1.20 eq) and (3S)-3-aminopiperidine-2,6-dione (69 mg, 0.41 mmol, 1.50 eq, hydrochloride). The mixture was stirred at 20° C. for 12 h. LCMS showed that the reaction was completed. The mixture was added dichloromethane (20 mL) and water (20 mL). The organic layer was dried over sodium sulfate and concentrated under reduced pressure to give a residue. The residue was purified with preparative high performance liquid chromatography (column: Shim-pack C18 150*25*10 um; mobile phase: [water (0.225% FA)-ACN]; B %: 26%-56%, 10 min) to give 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]-N-[(3S)-2,6-dioxo-3-piperidyl]pyridine-2-carboxamide (60.10 mg, 0.07 mmol, 26% yield, 99% purity) as a white solid.

QC-LCMS: MS (ESI) m/z: 791.4 [M+1]$^+$.

$^1$H NMR: (400 MHz, DMSO-d$_6$) δ: 10.85 (s, 1H), 8.73 (d, J=8.0 Hz, 1H), 8.33 (d, J=2.8 Hz, 1H), 8.14 (s, 1H), 7.87 (d, J=8.8 Hz, 1H), 7.74 (d, J=8.8 Hz, 2H), 7.51-7.39 (m, 2H), 6.97 (d, J=9.2 Hz, 2H), 6.74 (s, 2H), 4.81-4.66 (m, 1H), 4.23 (s, 1H), 4.04 (d, J=9.2 Hz, 1H), 3.87 (br d, J=12.0 Hz, 2H),

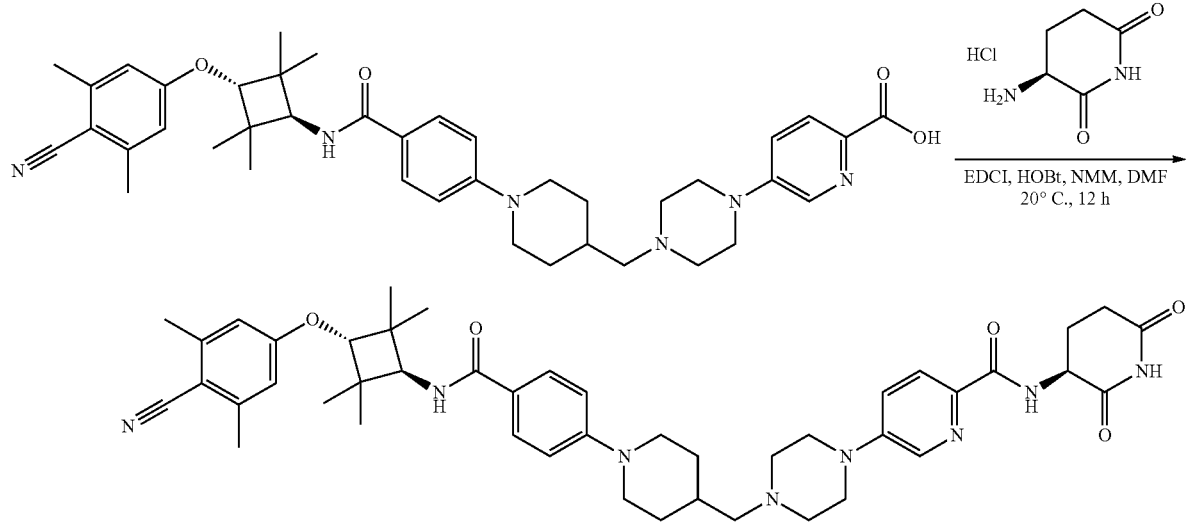 [SMILES: Cc1cc(O[C@H]2C(C)(C)[C@H](NC(=O)c3ccc(N4CCC(CN5CCN(c6ccc(C(=O)O)nc6)CC5)CC4)cc3)C2(C)C)cc(C)c1C#N ; Cl ; N[C@H]1CCC(=O)NC1=O ; Cc1cc(O[C@H]2C(C)(C)[C@H](NC(=O)c3ccc(N4CCC(CN5CCN(c6ccc(C(=O)N[C@H]7CCC(=O)NC7=O)nc6)CC5)CC4)cc3)C2(C)C)cc(C)c1C#N]

To a solution of 5-[4-[[1-[4-[[3-(4-cyano-3,5-dimethyl-phenoxy)-2,2,4,4-tetramethyl-cyclobutyl]carbamoyl]phenyl]-4-piperidyl]methyl]piperazin-1-yl]pyridine-2-carboxylic acid (200 mg, 0.27 mmol, 1.00 eq, hydrochloride) in dimethylformamide (2 mL) was added 4-methylmorpholine 2.53 (br d, J=2.0 Hz, 6H), 2.44 (s, 6H), 2.05-1.96 (m, 1H), 1.82 (br d, J=11.6 Hz, 3H), 1.22 (s, 8H), 1.13 (s, 6H).

Chemical Formula: $C_{45}H_{56}N_8O$, Molecular Weight: 788.98

Example 21—Synthesis of 4-[(2R)-2-([ISOPRO-PYL[(1R,3R)-3-(4-[[(3S)-2,6-dioxopiperidin-3-yl]carbamoyl]-3-fluorophenoxy)cyclobutyl]amino]methyl) morpholin-4-yl]-N-[(1R,3R)-3-(4-cyano-3-methoxyphenoxy)-2,2,4,4-tetramethylcyclobutyl] benzamide (Compound 43) AND 4-[(2S)-2-([isopropyl[(1R,3R)-3-(4-[[(3S)-2,6-dioxopiperidin-3-yl]carbamoyl]-3-fluorophenoxy)cyclobutyl]amino]methyl)morpholin-4-yl]-N-[(1R,3R)-3-(4-cyano-3-methoxyphenoxy)-2,2,4,4-tetramethylcyclobutyl] benzamide (Compound 44)

SCHEME 16. SUMMARY OF THE SYNTHESIS OF COMPOUNDS 43 AND 44

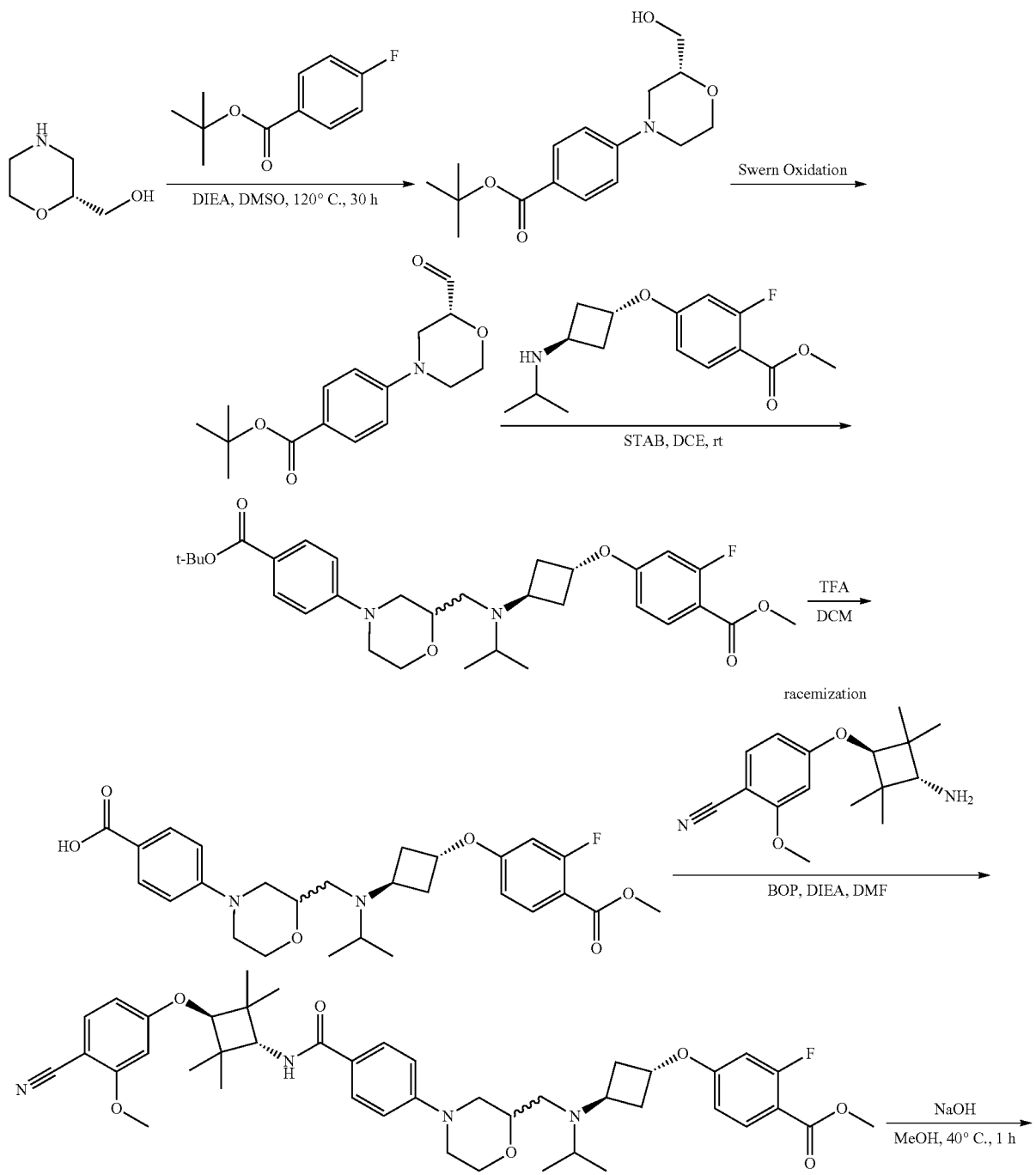

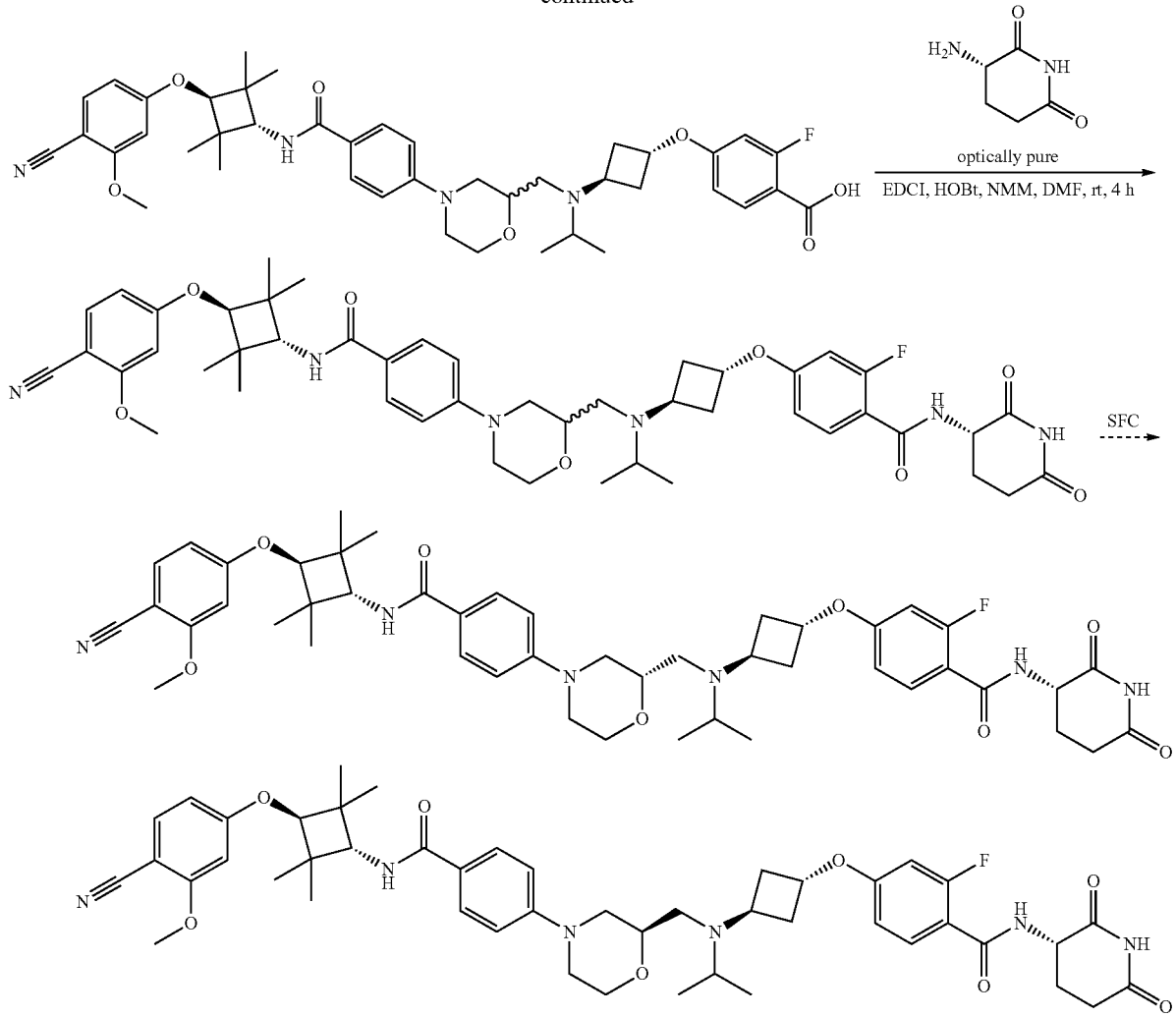

Step 1: Synthesis of tert-butyl 4-[(2R)-2-(hydroxymethyl)morpholin-4-yl]benzoate Into a 250 mL round-bottom flask, was placed (2R)-morpholin-2-ylmethanol (10.0 g, 85.4 mmol, 1.0 equiv), tert-butyl 4-fluorobenzoate (16.7 g, 85.4 mmol, 1.0 equiv), DIEA (33.1 g, 25.1 mmol, 3.0 equiv) in DMSO (25 mL). The resulting solution was stirred for 16 hours at 120° C. in an oil bath. The reaction was then quenched by the addition of 10 mL of water. The resulting solution was extracted with ethyl acetate (50 mL×2) dried over anhydrous sodium sulfate and concentrated. The residue was applied onto a silica gel column with ethyl acetate/petroleum ether (1:1). This resulted in 4.5 g (18%) of tert-butyl 4-[(2R)-2-(hydroxymethyl) morpholin-4-yl]benzoate as yellow oil.

LC-MS (ES+): m/z 294.40[MH+], $t_R$=1.58 min (2.9 minute run).

Step 2: Synthesis of tert-butyl 4-[(2R)-2-formylmorpholin-4-yl]benzoate

Into a 250 mL 3-necked round-bottom flask purged and maintained with an inert atmosphere of nitrogen, was placed DCM (20 mL). This was followed by the addition of (COCl)$_2$ (1.5 mL) at −78. To this was added a solution of DMSO (3 mL) in DCM (6 mL) at −78° C. To the mixture was added a solution of tert-butyl 4-[(2R)-2-(hydroxymethyl) morpholin-4-yl] benzoate (2.0 g) in DCM (10 mL) at −78° C. To the mixture was added a solution of TEA (6 mL) in DCM (15 mL) at −78° C. The resulting solution was stirred for 1.5 hours at −78° C. The reaction was then quenched by the addition of 100 mL of water. The resulting solution was extracted with dichloromethane (100 mL×3) and the organic layers combined. The resulting mixture was washed with x of brine. The mixture was dried over anhydrous sodium sulfate. The solids were filtered out. The resulting mixture was concentrated under vacuum. This resulted in 1.37 g of tert-butyl 4-[(2R)-2-formylmorpholin-4-yl] benzoate as a yellow oil.

Step 3: tert-Butyl 4-[2-([isopropyl][(1r, 3r)-3-[3-fluoro-4-(methoxycarbonyl) phenoxy]cyclobutyl] amino] methyl) morpholin-4-yl]benzoate Into a 100 mL round-bottom flask, was placed tert-butyl 4-[(2R)-2-formylmorpholin-4-yl]benzoate (1.1 g, 3.7 mmol, 1.0 equiv), methyl 2-fluoro-4-[(1r, 3r)-3-(isopropylamino) cyclobutoxy] benzoate (1.1 g, 3.9 mmol, 1.0 equiv) in DCE (3 mL), STAB (2.5 g, 0.1 mmol, 3.0 equiv). The resulting solution was stirred for 2 hours at room temperature. The reaction was then quenched by the addition of 1 mL of water. The resulting solution was extracted with dichloromethane (20 mL×2) dried over anhydrous sodium sulfate and concentrated. The residue was applied onto a silica gel column with ethyl acetate/petroleum ether (1:1). This resulted in 650.0 mg (31%) of tert-butyl 4-[2-([isopropyl[(r, 3r)-3-[3-fluoro-4-(methoxycarbonyl) phenoxy]cyclobutyl] amino] methyl) morpholin-4-yl] benzoate as a yellow solid.

LC-MS (ES$^+$): m/z 557.35[MH$^+$], $t_R$=2.41 min (2.9 minute run)

Step 4: Synthesis of 4-[2-([isopropyl[(1r, 3r)-3-[3-fluoro-4-(methoxycarbonyl) phenoxy]cyclobutyl] amino] methyl) morpholin-4-yl]benzoic acid: Into a 50 mL round-bottom flask, was placed tert-butyl 4-[2-([isopropyl[(1r, 3r)-3-[3-fluoro-4-(methoxycarbonyl) phenoxy] cyclobutyl]amino] methyl) morpholin-4-yl] benzoate (650.0 mg, 1.2 mmol, 1.0 equiv) in DCM (10 mL), trifluoroacetaldehyde (5 mL). The resulting solution was stirred for 1 hour at room temperature. The resulting mixture was concentrated. This resulted in 495.0 mg (84%) of 4-[2-([isopropyl[(1r,3r)-3-[3-fluoro-4-(methoxycarbonyl)phenoxy]cyclobutyl]amino]methyl)morpholin-4-yl]benzoic acid as yellow oil.

LC-MS (ES$^+$): m/z 501.2[MH$^+$], $t_R$=1.32 min (4.9 minute run)

Step 5: Synthesis of methyl 2-fluoro-4-[(1r, 3r)-3-[isopropyl([[4-(4-[[(1r, 3r)-3-(4-cyano-3-methoxyphenoxy)-2, 2, 4, 4-tetramethylcyclobutyl] carbamoyl] phenyl) morpholin-2-yl]methyl]) amino] cyclobutoxy]benzoate: Into a 100-mL round-bottom flask, was placed 4-[2-([isopropyl[(1r,3r)-3-[3-fluoro-4-(methoxycarbonyl)phenoxy]cyclobutyl]amino] methyl) morpholin-4-yl]benzoic acid (495.0 mg, 0.9 mmol, 1.0 equiv), 2-methoxy-4-[(1r,3r)-3-amino-2,2,4,4-tetramethylcyclobutoxy]benzonitrile (271.3 mg, 0.9 mmol, 1.0 equiv) in DMF (5 mL), DIEA (383.4 mg, 2.9 mmol, 3.0 equiv), BOP (524.8 mg, 1.2 mmol, 1.2 equiv). The resulting solution was stirred for 1 hour at room temperature. The reaction was then quenched by the addition of 2 mL of water. The resulting solution was extracted with ethyl acetate (20 mL×2) dried over anhydrous sodium sulfate and concentrated. The residue was applied onto a silica gel column with ethyl acetate/petroleum ether (2:1). This resulted in 435.0 mg (58%) of methyl 2-fluoro-4-[(1r, 3r)-3-[isopropy ([[4-(4-[[(1r, 3r)-3-(4-cyano-3-methoxyphenoxy)-2, 2, 4, 4-tetramethylcyclobutyl] carbamoyl] phenyl) morpholin-2-yl] methyl]) amino] cyclobutoxy]benzoate as a yellow solid.

LC-MS (ES$^+$): m/z 757.2[MH$^+$], $t_R$=3.49 min (4.9 minute run)

Step 6: Synthesis of 2-fluoro-4-[(1r,3r)-3-[isopropyl([[4-(4-[[(1r,3r)-3-(4-cyano-3-methoxyphenoxy)-2,2,4,4-tetramethylcyclobutyl]carbamoyl]phenyl)morpholin-2-yl] methyl])amino]cyclobutoxy]benzoic acid: Into a 100 mL round-bottom flask, was placed methyl 2-fluoro-4-[(1r, 3r)-3-[isopropyl([[4-(4-[[(1r,3r)-3-(4-cyano-3-methoxyphenoxy)-2, 2, 4, 4-tetramethylcyclobutyl] carbamoyl] phenyl) morpholin-2-yl] methyl]) amino] cyclobutoxy]benzoate (435.0 mg, 0.6 mmol, 1.0 equiv) in MeOH (5 mL), caustic soda (91.9 mg, 2.3 mmol, 4.0 equiv) in H$_2$O (2.00 mL). The resulting solution was stirred for 2 hours at room temperature. The resulting solution was extracted with ethyl acetate (20 mL×2) dried over anhydrous sodium sulfate and concentrated. This resulted in 380.0 mg (89%) of 2-fluoro-4-[(r, 3r)-3-[isopropyl ([[4-(4-[[(1r, 3r)-3-(4-cyano-3-methoxyphenoxy)-2, 2, 4, 4-tetramethylcyclobutyl] carbamoyl] henyl) orpholin-2-yl] methyl]) amino] cyclobutoxy] benzoic acid as a yellow solid.

LC-MS (ES$^+$): m/z 743.35[MH$^+$], $t_R$=1.26 min (2.9 minute run)

Step 7a. Synthesis of 4-[(2R)-2-([isopropyl[(1r, 3r)-3-(4-[[(3S)-2, 6-dioxopiperidin-3-yl]carbamoyl]-3-fluorophenoxy) cyclobutyl] amino] methyl) morpholin-4-yl]-N-[(1r, 3r)-3-(4-cyano-3-methoxyphenoxy)-2, 2, 4, 4-tetramethylcyclobutyl] benzamide, Compound 43: Into a 50 mL round-bottom flask, was placed 2-fluoro-4-[(1r, 3r)-3-[isopropyl ([[4-(4-[[(1r, 3r)-3-(4-cyano-3-methoxyphenoxy)-2, 2, 4, 4-tetramethylcyclobutyl] carbamoyl] phenyl) morpholin-2-yl]methyl]) amino] cyclobutoxy]benzoic acid (280.0 mg, 0.4 mmol, 1.0 equiv), (3S)-3-aminopiperidine-2,6-dione (72.4 mg, 0.5 mmol, 1.5 equiv) in DMF (3 mL), NMM (114.4 mg, 1.1 mmol, 3.0 equiv), HOBT (61.1 mg, 0.4 mmol, 1.2 equiv), EDCI (86.7 mg, 0.4 mmol, 1.2 equiv). The resulting solution was stirred for 4 hours at room temperature. The reaction was then quenched by the addition of 1 mL of water. The resulting solution was extracted with ethyl acetate (20 mL×2) dried over anhydrous sodium sulfate and concentrated. The residue was applied onto a silica gel column with dichloromethane/methanol (10:1). The crude product was purified by Chiral-Prep-HPLC with the following conditions: MTBE (0.1% DEA):EtOH=50:50, column: ChiralWHELK-014, Size: 6*50 mm, 3.5 um; This resulted in 74.9 mg (23%) of 4-[(2R)-2-([isopropyl[(1r,3r)-3-(4-[[(3S)-2,6-dioxopiperidin-3-yl]carbamoyl]-3-fluorophenoxy)cyclobutyl]amino]methyl)morpholin-4-yl]-N-[(1r,3r)-3-(4-cyano-3-methoxyphenoxy)-2,2,4,4-tetramethylcyclobutyl] benzamide as a off-white solid.

$^1$H NMR (400 MHz, DMSO-d$_6$) δ 10.90 (s, 1H), 8.45-8.20 (m, 1H), 7.90-7.73 (m, 2H), 7.72-7.60 (m, 2H), 7.59-7.42 (m, 1H), 7.06-6.87 (m, 2H), 6.86-6.70 (m, 2H), 6.69-6.60 (m, 1H), 6.59-6.45 (m, 1H), 4.90-4.69 (m, 2H), 4.33-4.21 (m, 1H), 4.15-4.00 (m, 1H), 3.99-3.83 (m, 4H), 3.82-3.45 (m, 7H), 3.05-2.90 (m, 1H), 2.85-2.70 (m, 2H), 2.46-2.35 (m, 3H), 2.22-1.83 (m, 4H), 1.25-1.20 (m, 7H), 1.18-1.10 (m, 6H), 1.05-0.88 (m, 6H).

LC-MS (ES$^+$): m/z 853.45[MH$^+$], $t_R$=3.61 min (4.9 minute run).

Chemical formula: C$_{47}$H$_{57}$FN$_6$O$_8$ [852.42]

Step 7b. Synthesis of 4-[(2S)-2-([isopropyl[(1r, 3r)-3-(4-[[(3S)-2, 6-dioxopiperidin-3-yl]carbamoyl]-3-fluorophenoxy) cyclobutyl] amino] methyl) morpholin-4-yl]-N-[(1r, 3r)-3-(4-cyano-3-methoxyphenoxy)-2, 2, 4, 4-tetramethylcyclobutyl] benzamide, Compound 44: Into a 50 mL round-bottom flask, was placed 2-fluoro-4-[(1r, 3r)-3-[isopropyl ([[4-(4-[[(1r, 3r)-3-(4-cyano-3-methoxyphenoxy)-2, 2, 4, 4-tetramethylcyclobutyl] carbamoyl] phenyl) morpholin-2-yl]methyl]) amino] cyclobutoxy]benzoic acid (280.0 mg, 0.4 mmol, 1.0 equiv), (3S)-3-aminopiperidine-2,6-dione (72.4 mg, 0.5 mmol, 1.5 equiv) in DMF (3 mL), NMM (114.4 mg, 1.1 mmol, 3.0 equiv), HOBT (61.1 mg, 0.4 mmol, 1.2 equiv), EDCI (86.7 mg, 0.4 mmol, 1.2 equiv). The resulting solution was stirred for 4 hours at room temperature. The reaction was then quenched by the addition of 1 mL of water. The resulting solution was extracted with ethyl acetate (20 mL×2) dried over anhydrous sodium sulfate and concentrated. The residue was applied onto a silica gel column with dichloromethane/methanol (10:1). The crude product was purified by Chiral-Prep-HPLC with the following conditions: MTBE (0.1% DEA):EtOH=50:50, column: ChiralWHELK-014, Size: 6*50 mm, 3.5 um; This resulted in 58.1 mg (18%) of 4-[(2S)-2-([isopropyl[(1r,3r)-3-(4-[[(3S)-2,6-dioxopiperidin-3-yl]carbamoyl]-3-fluorophenoxy)cyclobutyl]amino]methyl)morpholin-4-yl]-N-[(1r,3r)-3-(4-cyano-3-methoxyphenoxy)-2,2,4,4-tetramethylcyclobutyl] benzamide as a off-white solid.

¹H NMR (400 MHz, DMSO-d₆) δ 10.85 (s, 1H), 8.52-8.15 (m, 1H), 7.88-7.72 (m, 2H), 7.71-7.57 (m, 2H), 7.56-7.35 (m, 1H), 7.15-6.87 (m, 2H), 6.86-6.70 (m, 2H), 6.69-6.59 (m, 1H), 6.58-6.40 (m, 1H), 4.95-4.63 (m, 2H), 4.40-4.23 (m, 1H), 4.10-4.00 (m, 1H), 3.99-3.95 (m, 1H), 3.94-3.88 (m, 3H), 3.86-3.75 (m, 1H), 3.70-3.60 (m, 3H), 3.59-3.48 (m, 1H), 3.47-3.40 (m, 1H), 3.05-2.92 (m, 1H), 2.85-2.70 (m, 2H), 2.55-2.50 (m, 2H), 2.48-2.32 (m, 3H), 2.30-2.05 (m, 3H), 2.04-1.90 (m, 1H), 1.30-1.21 (m, 6H), 1.20-1.03 (m, 6H), 1.01-0.80 (m, 6H).

LC-MS (ES⁺): m/z 853.45[MH⁺], $t_R$=2.03 min (2.9 minute run). Chemical formula: $C_{47}H_{57}FN_6O_8$ [852.42]

Example 22—Synthesis of N-[(3R)-2,6-dioxopiperidin-3-yl]-2-fluoro-4-(4-[[(2R)-4-(4-[[(1R,3R)-3-(4-cyano-3,5-dimethylphenoxy)-2,2,4,4-tetramethylcyclobutyl]carbamoyl]phenyl)morpholin-2-yl]methyl]piperazin-1-yl)benzamide (Compound 48) and N-[(3S)-2,6-dioxopiperidin-3-yl]-2-fluoro-4-(4-[[(2R)-4-(4-[[(1R,3R)-3-(4-cyano-3,5-dimethylphenoxy)-2,2,4,4-tetramethylcyclobutyl]carbamoyl]phenyl)morpholin-2-yl]methyl]piperazin-1-yl)benzamide; bis(formic acid) (Compound 49)

SCHEME 17: SUMMARY OF THE SYNTHESIS OF COMPOUNDS 48 AND 49.

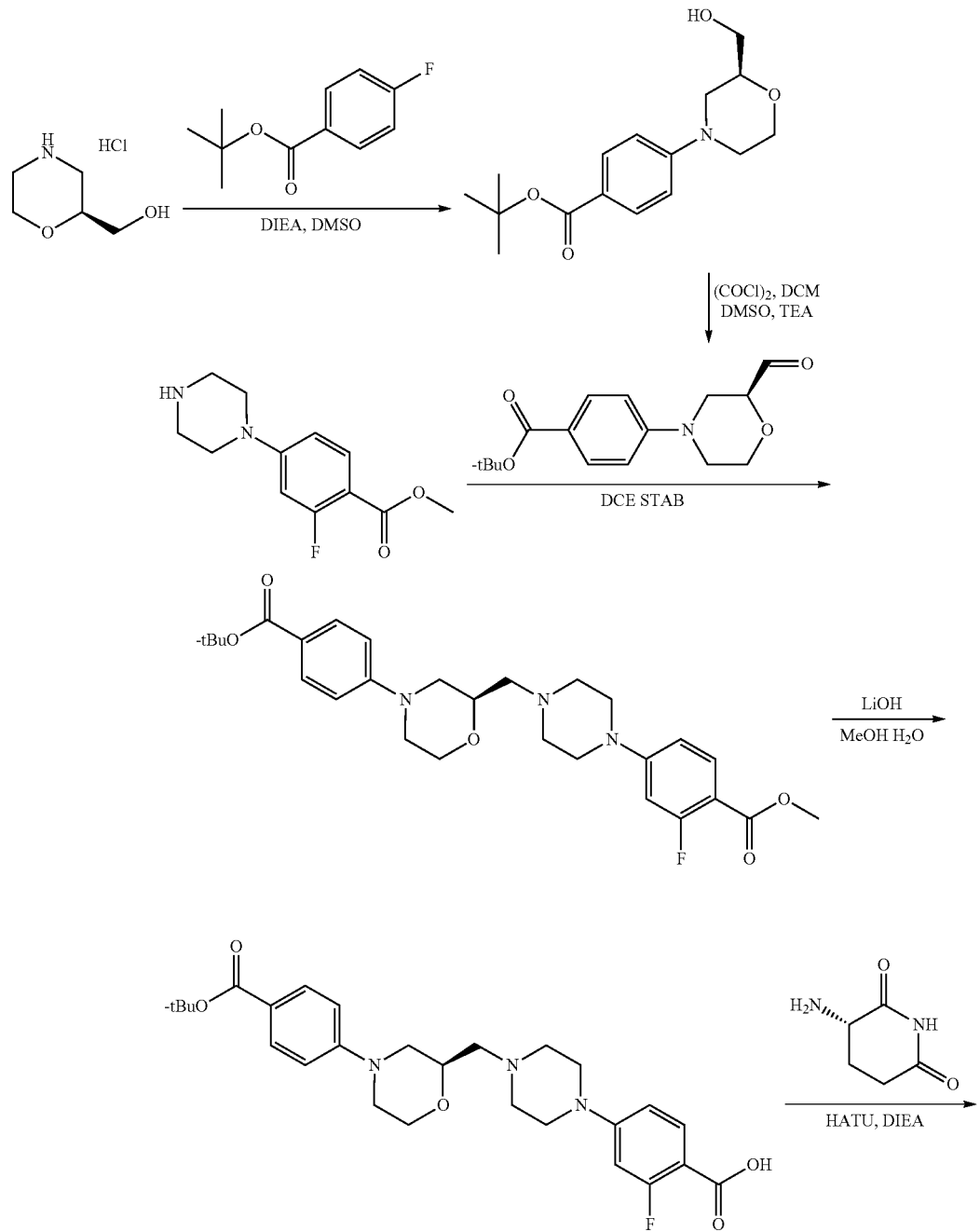

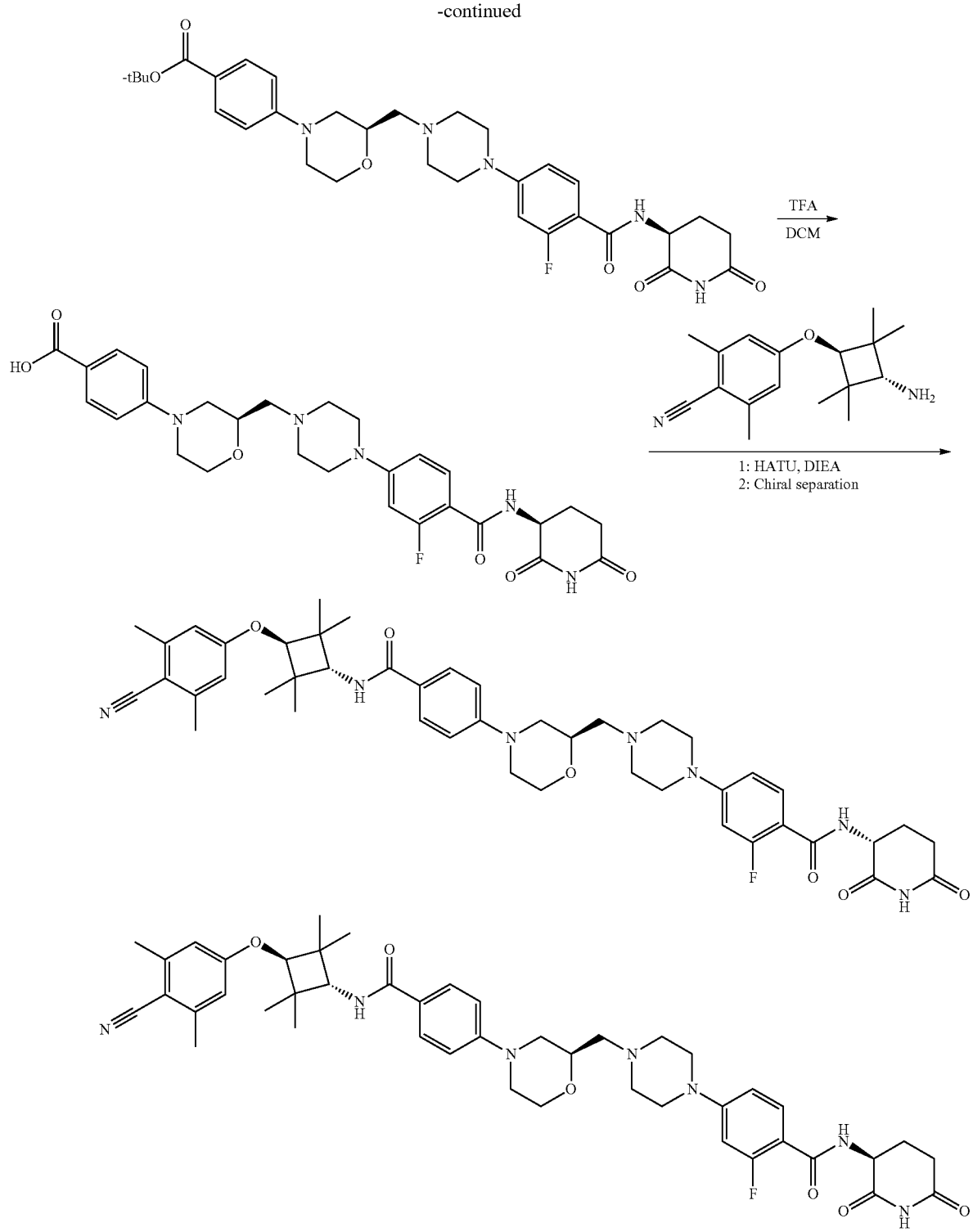

Step 1: Synthesis of tert-butyl 4-[(2S)-2-(hydroxymethyl)morpholin-4-yl]benzoate Into a 50-mL round-bottom flask, was placed [(2S)-morpholin-2-yl]methanol hydrochloride (200.00 mg, 1.30 mmol, 1.00 equiv) in DMSO (8.00 mL), to which was added DIEA (841.37 mg, 6.51 mmol, 5.00 equiv), tert-butyl 4-fluorobenzoate (383.22 mg, 1.95 mmol, 1.50 equiv). The resulting solution was stirred for 30 hr at 120° C. in an oil bath. The reaction mixture was cooled to room temperature. The resulting solution was diluted with 50 mL of DCM. The resulting mixture was washed with 50 mL of H₂O and (3×50 mL) of brine. The mixture was dried over anhydrous sodium sulfate. The solids were filtered out. The resulting mixture was concentrated under vacuum. This resulted in 180 mg (crude) of tert-butyl 4-[(2S)-2-(hydroxymethyl)morpholin-4-yl]benzoate as light yellow oil.

LC-MS (ES$^+$): m/z 294.10 [M+H$^+$], $t_R$=0.93 min (1.9 minute run).

Step 2: Synthesis of tert-butyl 4-[(2S)-2-formylmorpholin-4-yl]benzoate

Into a 100-mL 3-necked round-bottom flask purged and maintained with an inert atmosphere of nitrogen, was placed (COCl)$_2$ (0.40 mL, 4.70 mmol, 9.18 equiv) in DCM (20.00 mL), to which was added DMSO (0.80 mL, 11.26 mmol, 22.03 equiv) in DCM (6.00 mL) over 30 min at –78° C., after completion of the addition, the mixture was stirred at –78° C. for 5 min, followed by addition of a solution of tert-butyl 4-[(2S)-2-(hydroxymethyl)morpholin-4-yl]benzoate (150.00 mg, 0.51 mmol, 1.00 equiv) in DCM (6.00 mL) over 20 min at –78° C., and the resulting mixture was stirred for 20 min, then Et$_3$N (3.50 mL, 25.18 mmol, 49.25 equiv) was added dropwise over 10 min. The resulting solution was allowed to warm to 0° C. and stirred for 1 hr at 0° C. for 30 min. The reaction was then quenched by the addition of 50 mL of water. The resulting solution was diluted with 50 mL of DCM. The resulting mixture was washed with 50 mL of H$_2$O and (3×50 mL) of brine. The mixture was dried over anhydrous sodium sulfate. The solids were filtered out. The resulting mixture was concentrated under vacuum. This resulted in 120 mg (crude) of tert-butyl 4-[(2S)-2-formylmorpholin-4-yl]benzoate as a yellow solid.

Step 3: Synthesis of methyl 4-(4-[[(2R)-4-[4-(tert-butoxycarbonyl)phenyl]morpholin-2-yl]methyl] piperazin-1-yl)-2-fluorobenzoate Into a 100-mL round-bottom flask, was placed tert-butyl 4-[(2S)-2-formymorpholin-4-yl]benzoate (950 mg, 3.26 mmol, 1.00 equiv), DCE (25 mL), MeOH (10 mL), methyl 2-fluoro-4-(piperazin-1-yl)benzoate (780 mg, 3.26 mmol, 1.00 equiv), STAB (690 mg, 3.26 mmol, 1.00 equiv). The resulting solution was stirred for 15 min at room temperature. The resulting mixture was washed with 1×60 mL of Water. The resulting solution was extracted with 3×60 mL of dichloromethane and the organic layers combined and dried over anhydrous sodium sulfate. The solids were filtered out. The resulting mixture was concentrated. The residue was applied onto a silica gel column with ethyl acetate/petroleum ether (0%:100%-30%:70%). This resulted in 515 mg (31%) of methyl 4-(4-[[(2R)-4-[4-(tert-butoxycar-bonyl)phenyl] morpholin-2-yl]methyl]piperazin-1-yl)-2-fluorobenzoate as an off-white solid.

LC-MS (ES$^+$): m/z 514.25 [MH$^+$], $t_R$=0.64 min (1.2 minute run).

Step 4: Synthesis of 4-(4-[[(2R)-4-[4-(tert-butoxycarbonyl)phenyl]morpholin-2-yl]methyl]piperazin-1-yl)-2-fluorobenzoic acid Into a 250-mL round-bottom flask, was placed methyl 4-(4-[[(2R)-4-[4-(tert-butoxycarbonyl)phenyl]morpholin-2-yl]methyl]piperazin-1-yl)-2-fluorobenzoate (540 mg, 1.05 mmol, 1.00 equiv), MeOH (40 mL), H2O (12 mL), LiOH·H2O (880 mg, 21.04 mmol, 20.00 equiv). The resulting solution was stirred for 3 hr at 40° C. The resulting solution was concentrated under vacuum. The pH value of the solution was adjusted to 7 with HCl/H2O (1 mol/L). The solids were collected by filtration. This resulted in 0.39 g (74%) of 4-(4-[[(2R)-4-[4-(tert-butoxycarbonyl)phenyl]morpholin-2-yl]methyl]piperazin-1-yl)-2-fluorobenzoic acid as a light yellow solid.

LC-MS (ES$^+$): m/z 500.30 [MH$^+$], $t_R$=0.79 min (1.5 minute run).

Step 5: Synthesis of tert-butyl 4-[(2R)-2-[[4-(4-[[(3S)-2,6-dioxopiperidin-3-yl]carbamoyl]-3-fluorophenyl) piperazin-1-yl]methyl]morpholin-4-yl]benzoate Into a 100-mL round-bottom flask, was placed 4-(4-[[(2R)-4-[4-(tert-butoxycarbonyl)phenyl]morpholin-2-yl]methyl]piperazin-1-yl)-2-fluorobenzoic acid (330 mg, 0.66 mmol, 1.00 equiv), DMF (20 mL), HATU (380 mg, 0.99 mmol, 1.50 equiv), a solution of DIEA (850 mg 6.62 mmol, 10.00 equiv) in DMF (15 mL), (3S)-3-aminopiperidine-2,6-dione (130 mg, 1.02 mmol, 1.50 equiv). The resulting solution was stirred for 1 hr at room temperature. The reaction was then quenched by the addition of 50 mL of water. The resulting solution was extracted with 3×50 mL of ethyl acetate and the organic layers combined. The resulting mixture was washed with 1×100 mL of brine. The mixture was dried over anhydrous sodium sulfate and concentrated under vacuum. The residue was applied onto a silica gel column with dichloromethane/methanol (15:1). This resulted in 302 mg (74%) of tert-butyl 4-[(2R)-2-[[4-(4-[[(3S)-2,6-dioxopiperidin-3-yl]carbamoyl]-3-fluorophenyl)piperazin-1-yl]methyl]morpholin-4-yl]benzoate as a brown solid.

LC-MS (ES$^+$): m/z 610.30 [MH$^+$], $t_R$=0.57 min (1.2 minute run).

Step 6: Synthesis of 4-[(2R)-2-[[4-(4-[[(3S)-2,6-dioxopiperidin-3-yl]carbamoyl]-3-fluorophenyl)piperazin-1-yl]methyl]morpholin-4-yl]benzoic acid Into a 100-mL round-bottom flask, was placed tert-butyl 4-[(2R)-2-[[4-(4-[[(3S)-2,6-dioxopiperidin-3-yl]carbamoyl]-3-fluorophenyl) piperazin-1-yl]methyl]morpholin-4-yl]benzoate (400 mg, 0.66 mmol, 1.50 equiv), dichloromethane (20 mL), TFA (5 mL). The resulting solution was stirred for 30 min at room temperature. The resulting mixture was concentrated under vacuum. The residue was applied onto a silica gel column with dichloromethane/methanol (5:1). This resulted in 113 mg (30%) of 4-[(2R)-2-[[4-(4-[[(3S)-2,6-dioxopiperidin-3-yl]carbamoyl]-3-fluorophenyl)piperazin-1-yl]methyl]morpholin-4-yl]benzoic acid as a off-white solid.

LC-MS (ES$^+$): m/z 554.20 [MH$^+$], $t_R$=0.45 min (1.2 minute run).

Step 7a: Synthesis of N-[(3R)-2,6-dioxopiperidin-3-yl]-2-fluoro-4-(4-[[(2R)-4-(4-[[(1r,3r)-3-(4-cyano-3,5-dimethylphenoxy)-2,2,4,4-tetramethylcyclobutyl]carbamoyl]phenyl) morpholin-2-yl]methyl] piperazin-1-yl)benzamide, Compound 48

Into a 100-mL round-bottom flask, was placed 4-[(2R)-2-[[4-(4-[[(3S)-2,6-dioxopiperidin-3-yl] carbamoyl]-3-fluorophenyl)piperazin-1-yl]methyl]morpholin-4-yl]benzoic acid (90.00 mg, 0.16 mmol, 1.00 equiv), DMF (12 mL), HATU (92.80 mg, 0.24 mmol, 1.50 equiv), a solution of DIEA (209.90 mg, 1.62 mmol, 10.00 equiv) in DMF (2 mL), 2,6-dimethyl-4-[(1r,3r)-3-amino-2,2,4,4-tetramethylcyclobutoxy]benzonitrile (61.00 mg, 0.20 mmol, 1.20 equiv). The resulting solution was stirred for 10 min at room temperature. The resulting mixture was washed with 1×30 mL of Water. The resulting solution was extracted with 3×30 mL of ethyl acetate and the organic layers combined. The resulting mixture was washed with 1×50 of brine. The mixture was dried over anhydrous sodium sulfate. The solids were filtered out. The resulting mixture was concentrated under vacuum. The residue was applied onto a silica gel column with dichloromethane/methanol (15:1). The crude product was purified by Flash-Prep-HPLC with the following conditions: Column, C18 silica gel; mobile phase, H$_2$O/methanol=100%/0% increasing to H$_2$O/methanol=14%/86% within 45 min; Detector. The product was purified by chiral separation with the following conditions: Column: Chiralpak IC, 2*25 cm, 5um; Mobile Phase A: DCM, Mobile Phase B: EtOH (8 mmol/L NH3·MeOH; Flow rate: 20 mL/min; Gradient: 50% B to 50% B in 11 min; 220/254 nm; This resulted in 21.5 mg of N-[(3R)-2,6-dioxopiperidin-3-yl]-2-fluoro-4-(4-[[(2R)-4-(4-[[(1r,3r)-3-(4-cyano-3,5-dimethylphenoxy)-2,2,4,4-tetramethylcyclobutyl]carbamoyl]phenyl)morpholin-2-yl]methyl]piperazin-1-yl)benzamide (absolute stereochemistry tentatively assigned) as a white solid.

$^1$HNMR (400 MHz, DMSO-d$_6$) δ 10.85 (s, 1H), 8.06 (m, 1H), 7.78 (m, 2H), 7.64 (m, 1H), 7.53 (m, 1H), 7.00 (m, 2H), 6.87-6.72 (m, 4H), 4.73 (s, 1H), 4.23 (s, 1H), 4.04 (m, 3H), 3.77 (m, 5H), 2.77 (m, 3H), 2.60 (m, 6H), 2.43 (s, 5H), 2.18-1.92 (m, 4H), 1.22-1.12 (m, 14H); LC-MS (ES$^+$): m/z 808.25 [M+H+], t$_R$=1.21 min (3.00 minute run).

Chemical Formula: C$_{45}$H$_{54}$FN$_7$O$_6$ [807.41]

Step 7b: Synthesis of N-[(3R)-2,6-dioxopiperidin-3-yl]-2-fluoro-4-(4-[[(2R)-4-(4-[[(1r,3r)-3-(4-cyano-3,5-dimethylphenoxy)-2,2,4,4-tetramethylcyclobutyl]carbamoyl]phenyl)morpholin-2-yl]methyl]piperazin-1-yl)benzamide, Compound 49: Into a 100-mL round-bottom flask, was placed 4-[(2R)-2-[[4-(4-[[(3S)-2,6-dioxopiperidin-3-yl]carbamoyl]-3-fluorophenyl)piperazin-1-yl]methyl]morpholin-4-yl]benzoic acid (90.00 mg, 0.16 mmol, 1.00 equiv), DMF (12 mL), HATU (92.80 mg, 0.24 mmol, 1.50 equiv), a solution of DIEA (209.90 mg, 1.62 mmol, 10.00 equiv) in DMF (2 mL), 2,6-dimethyl-4-[(1r,3r)-3-amino-2,2,4,4-tetramethylcyclo-butoxy]benzonitrile (61.00 mg, 0.20 mmol, 1.20 equiv). The resulting solution was stirred for 10 min at room temperature. The resulting mixture was washed with 1×30 mL of Water. The resulting solution was extracted with 3×30 mL of ethyl acetate and the organic layers combined. The resulting mixture was washed with 1×50 of brine. The mixture was dried over anhydrous sodium sulfate. The solids were filtered out. The resulting mixture was concentrated under vacuum. The residue was applied onto a silica gel column with dichloromethane/methanol (15:1). The crude product (90.00 mg) was purified by Flash-Prep-HPLC with the following conditions (IntelFlash-1): Column, C18 silica gel; mobile phase, H2O/MeOH=100%/0% increasing to H2O/MeOH=14%/86% within 45 min; Detector. The product (60.00 mg) was purified by chiral separation with the following conditions: Column: Chiralpak IC, 2*25 cm, 5um; Mobile Phase A: DCM, Mobile Phase B:EtOH (8 mmol/L NH3·MeOH; Flow rate:20 mL/min; Gradient: 50 B to 50 B in 11 min; 220/254 nm; RT1:5.86; RT2:9.36; The product was obtained. This resulted in 11.2 mg of N-[(3S)-2,6-dioxopiperidin-3-yl]-2-fluoro-4-(4-[[(2R)-4-(4-[[(1r,3r)-3-(4-cyano-3,5-dimethylphenoxy)-2,2,4,4-tetramethylcyclobutyl]carbamoyl]phenyl)morpholin-2-yl]methyl]piperazin-1-yl)benzamide; bis(formic acid) (stereochemistry tentatively assigned) as a white solid.

$^1$H NMR (400 MHz, DMSO-d$_6$) δ 10.85 (s, 1H), 8.06 (m, 1H), 7.78 (m, 2H), 7.64 (m, 1H), 7.53 (m, 1H), 7.00 (m, 2H), 6.87 (m, 1H), 6.72 (m, 3H), 4.73 (s, 1H), 4.23 (s, 1H), 4.04 (m, 2H), 3.43-3.82 (m, 6H), 2.77 (m, 3H), 2.60 (m, 6H), 2.43 (m, 5H), 2.28-1.92 (m, 4H), 1.22 (s, 7H), 1.12 (s, 7H); LC-MS (ES$^+$): m/z 808.20 [M+H+], t$_R$=1.17 min (3.00 minute run).

Chemical Formula: C$_{45}$H$_{54}$FN$_7$O$_6$ [807.41]

Example 23—Synthesis of (3$^1$R,3$^3$R)-4-((1-(4-(((1R,3R)-3-(4-cyano-3,5-dimethylphenoxy)-2,2,4,4-tetramethylcyclobutyl)carbamoyl)phenyl)piperidin-4-yl)methyl)-N-(2,6-dioxopiperidin-3-yl)-2,7,12-trioxa-4-aza-1(1,2)-benzena-3(1,3)-cyclobutanacyclododecaphane-1$^4$-carboxamide (Compound 64)

SCHEME 18: SUMMARY OF THE SYNTHESIS OF COMPOUND 64

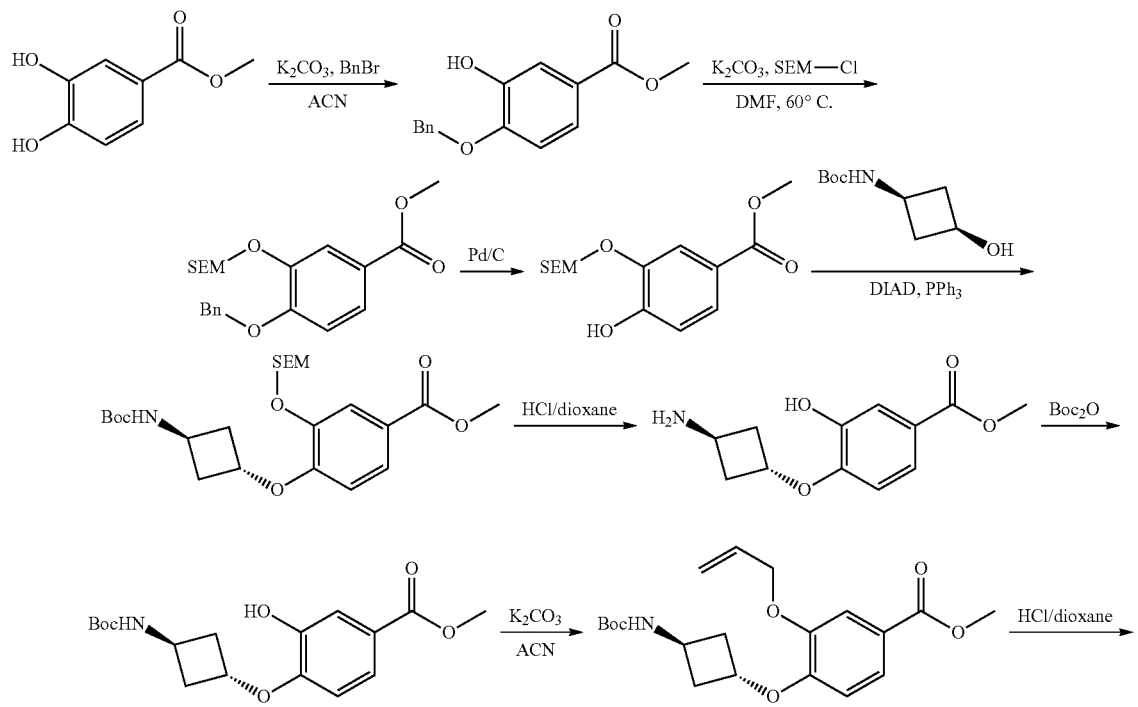

-continued
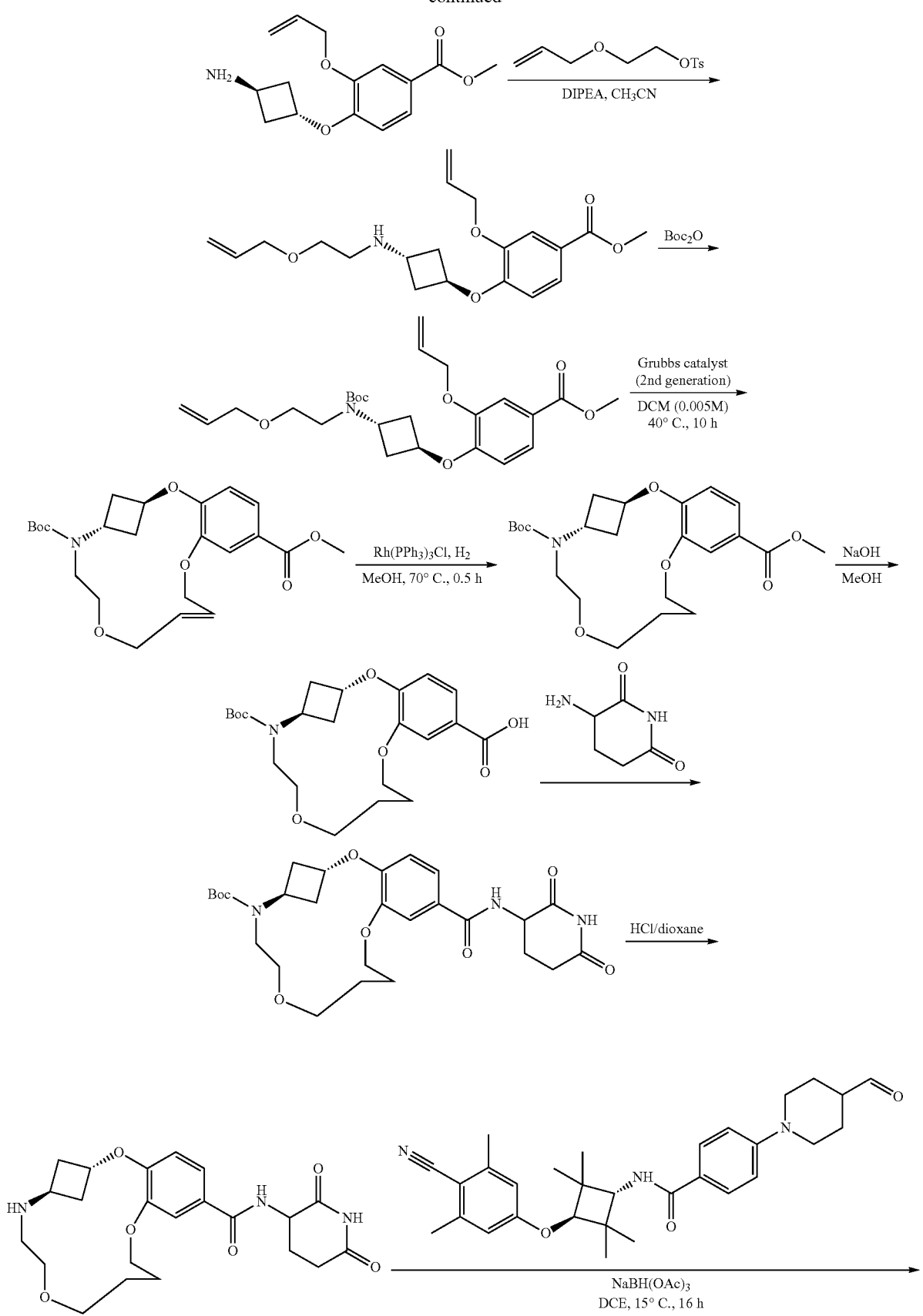

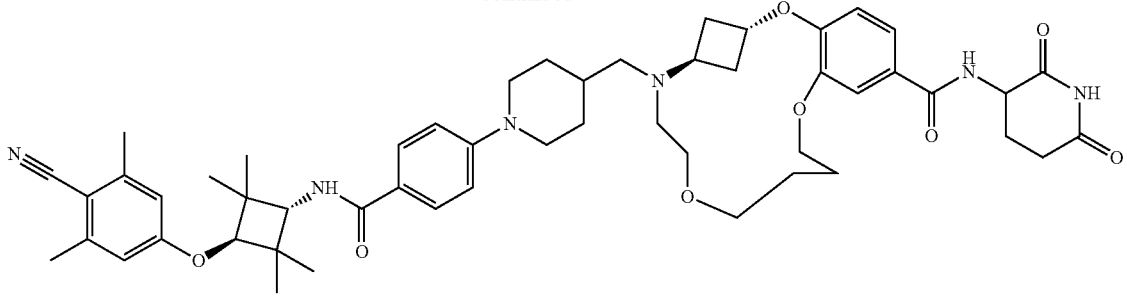

Step 1: Methyl 4-benzyloxy-3-hydroxy-benzoate

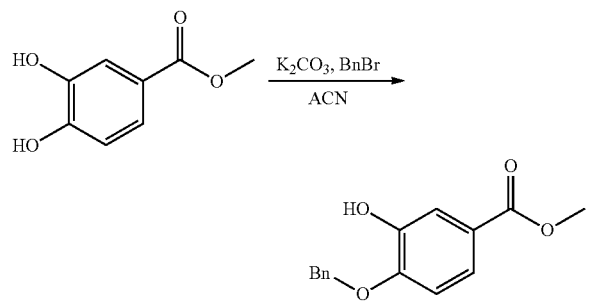

To a solution of methyl 3, 4-dihydroxybenzoate (10.00 g, 59.47 mmol, 1.00 eq) and potassium carbonate (8.22 g, 59.47 mmol, 1.00 eq) in acetonitrile (120 mL) was added benzyl bromide (10.17 g, 59.47 mmol, 7.06 mL, 1.00 eq). The mixture was stirred at 80° C. for 12 h under hydrogen atmosphere. LCMS showed that the reaction was completed. The mixture was filtered. The filtrate was concentrated under reduced pressure to give the residue. The residue was diluted with water (100 mL) and extracted with dichloromethane (200 mL). The organic layer was dried over anhydrous sodium sulfate, filtered and concentrated under reduced pressure to give a residue. The residue was purified by column chromatography on silica gel (petroleum ether:ethyl acetate=20:1 to 10:1) to give methyl 4-benzyloxy-3-hydroxy-benzoate (12.00 g, 46.46 mmol, 78% yield) as a white solid.

LCMS: MS (ESI) m/z: 259.1[M+1]$^+$.

$^1$H NMR: (400 MHz, CDCl3) δ: 7.69-7.57 (m, 2H), 7.50-7.35 (m, 5H), 6.97 (d, J=8.4 Hz, 1H), 5.82-5.70 (m, 1H), 5.19 (s, 2H), 3.94-3.84 (m, 3H).

Chemical Formula: $C_{15}H_{14}O_4$, Molecular Weight: 258.27

Step 2: Preparation of methyl 4-benzyloxy-3-(2-trimethylsilylethoxymethoxy)benzoate

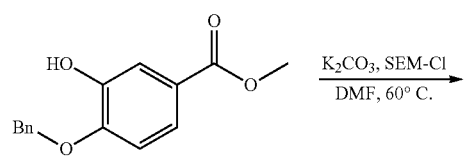

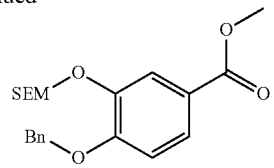

To a solution of methyl 4-benzyloxy-3-hydroxy-benzoate (2.30 g, 8.91 mmol, 1.00 eq) in dimethylformamide (20 mL) was added potassium carbonate (2.46 g, 17.81 mmol, 2.00 eq) and 2-(trimethylsilyl)ethoxymethyl chloride (4.45 g, 26.72 mmol, 4.73 mL, 3.00 eq). The mixture was stirred at 60° C. for 12 h. LCMS showed that the reaction was completed. The reaction mixture was concentrated under reduced pressure to give the residue. The residue was diluted with water (100 mL) and extracted with ethyl acetate (200 mL). The organic layer was dried over anhydrous sodium sulfate, filtered and concentrated under reduced pressure to give a residue. The residue was purified by column chromatography on silica gel (petroleum ether:ethyl acetate=20:1 to 10:1) to give methyl 4-benzyloxy-3-(2-trimethylsilylethoxymethoxy) benzoate (2.30 g, 5.92 mmol, 66% yield) as a colorless oil.

LCMS: MS (ESI) m/z: 411.1[M+23]$^+$.

$^1$H NMR: (400 MHz, CDCl$_3$) δ: 7.83-7.79 (m, 1H), 7.69-7.64 (m, 1H), 7.45-7.34 (m, 5H), 6.95-6.90 (m, 1H), 5.32 (s, 2H), 5.22 (s, 2H), 3.87 (s, 3H), 3.86-3.80 (m, 2H), 0.98-0.94 (m, 2H), 0.00 (s, 9H).

Chemical Formula: $C_{21}H_{28}O_5Si$, Molecular Weight: 388.53

Step 3: Preparation of methyl 4-hydroxy-3-(2-trimethylsilylethoxymethoxy)benzoate

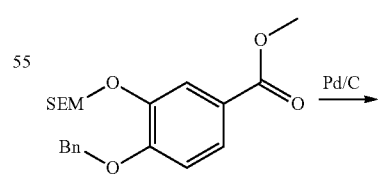

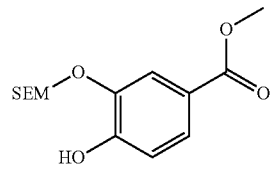

To a solution of methyl 4-benzyloxy-3-(2-trimethylsilylethoxymethoxy)benzoate (6.25 g, 16.09 mmol, 1.00 eq) in methanol (80 mL) was added palladium on activated carbon catalyst (10%, 1.20 g) under nitrogen atmosphere. The suspension was degassed and purged with hydrogen for 3 times. The mixture was stirred under hydrogen atmosphere (15 Psi) at 40° C. for 12 h. Thin layer chromatography (petroleum ether:ethyl acetate=3:1) showed that the reaction was completed. The mixture was filtered. The filtrate was concentrated under reduced pressure to give methyl 4-hydroxy-3-(2-trimethylsilylethoxymethoxy) benzoate (3.70 g, 12.40 mmol, 77% yield) as a colorless oil.

$^1$H NMR: (400 MHz, CDCl$_3$) δ: 7.75 (d, J=2.0 Hz, 1H), 7.70-7.65 (m, 1H), 6.95 (d, J=8.4 Hz, 1H), 5.30-5.24 (m, 2H), 3.87-3.85 (m, 3H), 3.81-3.76 (m, 2H), 1.02-0.96 (m, 2H), 0.01-0.01 (m, 9H).

Chemical Formula: C$_{14}$H$_{22}$O$_5$Si, Molecular Weight: 298.41

Step 4: Preparation of methyl 4-[3-(tert-butoxycarbonylamino)cyclobutoxy]-3-(2-trimethylsilylethoxymethoxy)benzoate

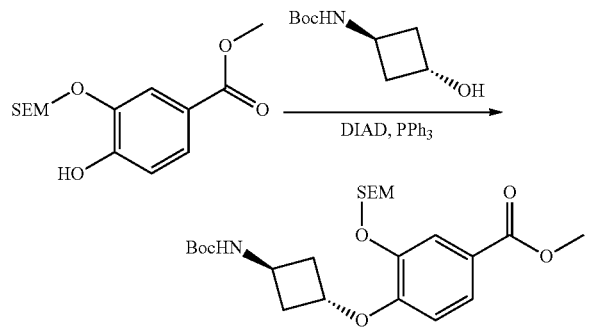 [SMILES: COC(=O)c1ccc(O)c(OCOCC[Si](C)(C)C)c1 ; CC(C)(C)OC(=O)N[C@H]1C[C@H](O)C1 ; COC(=O)c1ccc(O[C@H]2C[C@H](NC(=O)OC(C)(C)C)C2)c(OCOCC[Si](C)(C)C)c1]

To a solution of methyl 4-hydroxy-3-(2-trimethylsilylethoxymethoxy)benzoate (3.70 g, 12.40 mmol, 1.00 eq), tert-butyl ((1s,3s)-3-hydroxycyclobutyl)carbamate (2.32 g, 12.40 mmol, 1.00 eq) and triphenylphosphine (4.88 g, 18.60 mmol, 1.50 eq) in tetrahydrofuran (40 mL) was added diisopropyl azodicarboxylate (3.01 g, 14.88 mmol, 2.89 mL, 1.20 eq) at 0° C. The mixture was stirred at 25° C. for 12 h under nitrogen atmosphere. LCMS showed the starting material was consumed completely. The reaction mixture was concentrated under reduced pressure to give a residue. The residue was purified by column chromatography on silica gel (petroleum ether:ethyl acetate=10:1 to 5:1) to give methyl 4-[3-(tert-butoxycarbonylamino) cyclobutoxy]-3-(2-trimethylsilylethoxymethoxy) benzoate (5.20 g, 11.12 mmol, 89% yield) as a colorless oil.

LCMS: MS (ESI) m/z: 490.3[M+23]$^+$.

$^1$H NMR: (400 MHz, CDCl$_3$) δ: 7.79 (d, J=2.0 Hz, 1H), 7.70-7.63 (m, 1H), 6.64 (d, J=8.4 Hz, 1H), 5.27 (s, 2H), 4.92-4.85 (m, 1H), 4.84-4.70 (m, 1H), 4.34-4.23 (m, 1H), 3.87-3.86 (m, 3H), 3.81 (dd, J=8.8, 7.6 Hz, 2H), 2.70-2.53 (m, 2H), 2.44 (br d, J=6.0 Hz, 2H), 1.26 (d, J=6.0 Hz, 9H), 0.98-0.93 (m, 2H), 0.00 (s, 9H).

Chemical Formula: C$_{23}$H$_{37}$NO$_7$Si, Molecular Weight: 467.63

Step 5: Preparation of methyl 4-(3-aminocyclobutoxy)-3-hydroxy-benzoate

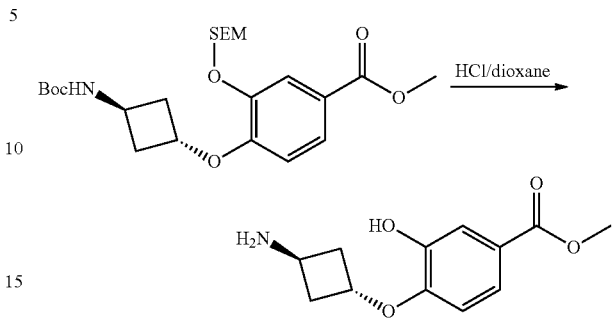

To a solution of methyl 4-[3-(tert-butoxycarbonylamino) cyclobutoxy]-3-(2-trimethylsilylethoxymethoxy)benzoate (5.20 g, 11.12 mmol, 1.00 eq) in dichlormethane (30 mL) was added hydrochloric acid/dioxane (4 M, 24 mL, 8.63 eq). The mixture was stirred at 35° C. for 1 h. Thin layer chromatography (petroleum ether:ethyl acetate=3:1) showed that the reaction was completed. The reaction mixture was concentrated under reduced pressure to give methyl 4-(3-aminocyclobutoxy)-3-hydroxy-benzoate (1.90 g, 6.94 mmol, 62% yield, hydrochloride) as a white solid, which was used in next step directly.

LCMS: MS (ESI) m/z: 238.1[M+1]$^+$ $^1$H NMR: (400 MHz, DMSO-d$_6$) δ: 9.53 (br s, 1H), 8.34 (br s, 3H), 7.47-7.34 (m, 2H), 6.76 (d, J=8.8 Hz, 1H), 5.05 (br d, J=4.4 Hz, 1H), 3.85 (br d, J=5.2 Hz, 1H), 3.79 (s, 3H), 2.71-2.55 (m, 2H), 2.49-2.41 (m, 2H).

Chemical Formula: C$_{12}$H$_{15}$NO$_4$, Molecular Weight: 237.25

Step 6: Preparation of methyl 4-[3-(tert-butoxycarbonylamino)cyclobutoxy]-3-hydroxy-benzoate

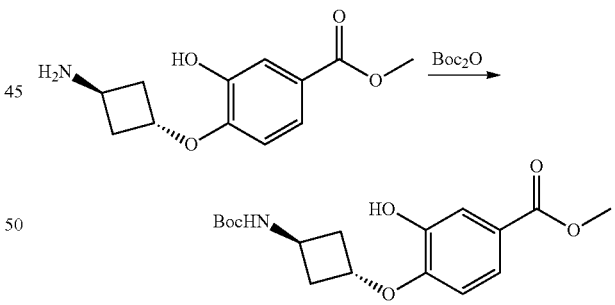

To a solution of methyl 4-(3-aminocyclobutoxy)-3-hydroxy-benzoate (1.90 g, 6.94 mmol, 1.00 eq, hydrochloride) in tetrahydrofuran (20 mL) was added di-tert-butyl dicarbonate (1.67 g, 7.64 mmol, 1.75 mL, 1.10 eq) and triethylamine (1.40 g, 13.88 mmol, 1.93 mL, 2.00 eq). The mixture was stirred at 25° C. for 12 h. Thin layer chromatography (petroleum ether:ethyl acetate=3:1) showed that the reaction was completed. The reaction mixture was concentrated under reduced pressure to remove solvent. The residue was purified by silica gel chromatography (petroleum ether/ethyl acetate=10/1 to 1/1) to give methyl 4-[3-(tert-butoxycarbonylamino)cyclobutoxy]-3-hydroxy-benzoate (1.73 g, 5.13 mmol, 73% yield) as a white solid.

¹H NMR: (400 MHz, CDCl₃) δ: 7.54-7.51 (m, 1H), 7.50-7.46 (m, 1H), 6.55 (d, J=8.4 Hz, 1H), 5.66 (s, 1H), 4.83 (tt, J=6.8, 3.6 Hz, 1H), 4.73 (br d, J=13.6 Hz, 1H), 4.25 (br s, 1H), 3.80 (s, 3H), 2.60-2.51 (m, 2H), 2.45-2.34 (m, 2H), 1.38 (s, 9H).

Chemical Formula: $C_{17}H_{23}NO_6$, Molecular Weight: 337.37

Step 7: Preparation of methyl 3-allyloxy-4-[3-(tert-butoxycarbonylamino)cyclobutoxy]benzoate

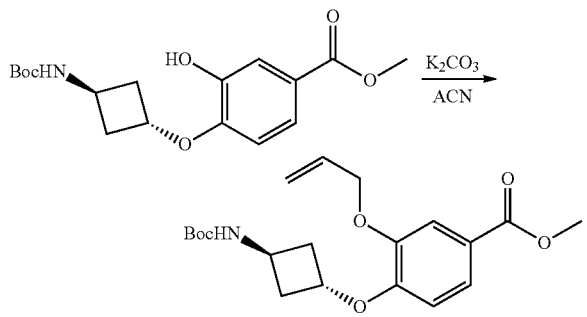

To a solution of methyl 4-[3-(tert-butoxycarbonylamino)cyclobutoxy]-3-hydroxy-benzoate (1.73 g, 5.13 mmol, 1.00 eq) in dimethylformamide (20 mL) was added potassium carbonate (2.13 g, 15.38 mmol, 3.00 eq) and 3-bromoprop-1-ene (806.46 mg, 6.67 mmol, 1.30 eq). The mixture was stirred at 25° C. for 2 h. Then to the mixture was added sodium triacetoxyborohydride (38.57 g, 182.00 mmol, 2.50 eq) and stirred at 25° C. for 4 h. LCMS showed that the reaction was completed. The mixture was filtered. The filtrate was concentrated under reduced pressure to give methyl 3-allyloxy-4-[3-(tert-butoxycarbonylamino)cyclobutoxy]benzoate (1.90 g, 5.03 mmol, 98% yield) as a white solid, which was used in next step directly.

LCMS: MS (ESI) m/z: 278.2[M+1-100]⁺.

¹H NMR: (400 MHz, DMSO-d₆) δ: 7.66-7.61 (m, 1H), 7.58 (d, J=2.0 Hz, 1H), 6.66 (d, J=8.4 Hz, 1H), 6.17-6.06 (m, 1H), 5.47 (dd, J=17.2, 1.6 Hz, 1H), 5.33 (dd, J=10.4, 1.2 Hz, 1H), 4.94-4.86 (m, 1H), 4.65 (br d, J=5.2 Hz, 2H), 4.38-4.26 (m, 1H), 3.90 (s, 3H), 2.74-2.62 (m, 2H), 2.47 (br d, J=6.8 Hz, 2H), 1.47 (s, 9H).

Chemical Formula: $C_{20}H_{27}NO_6$, Molecular Weight: 377.43

Total H count from HNMR data: 26.

Step 8

Preparation of methyl 3-allyloxy-4-(3-aminocyclobutoxy) benzoate

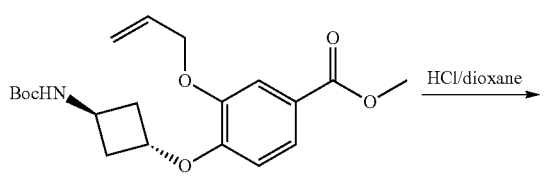

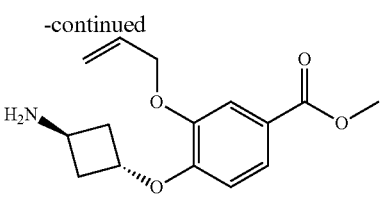

To a solution of methyl 3-allyloxy-4-[3-(tert-butoxycarbonylamino)cyclobutoxy]benzoate (1.90 g, 5.03 mmol, 1.00 eq) in dichlormethane (20 mL) was added hydrochloric acid/dioxane (4 M, 18 mL, 13.72 eq). The mixture was stirred at 25° C. for 1 h. Thin layer chromatography (petroleum ether:ethyl acetate=3:1) showed that the reaction was completed. The reaction mixture was concentrated under reduced pressure to give methyl 3-allyloxy-4-(3-aminocyclobutoxy) benzoate (1.50 g, 4.78 mmol, 94% yield, hydrochloride) as a white solid, which was used in next step directly.

¹H NMR: (400 MHz, DMSO-d₆) δ: 8.51-8.31 (m, 3H), 7.59-7.53 (m, 1H), 7.48 (d, J=2.00 Hz, 1H), 6.82 (d, J=8.4 Hz, 1H), 6.05 (ddt, J=17.2, 10.4, 5.2 Hz, 1H), 5.41 (dq, J=17.2, 1.6 Hz, 1H), 5.27 (dq, J=10.4, 1.6 Hz, 1H), 5.16-5.03 (m, 1H), 4.63 (dt, J=5.2, 1.6 Hz, 2H), 3.88-3.81 (m, 1H), 3.81 (s, 3H), 2.66 (qd, J=7.2, 4.8 Hz, 2H), 2.49-2.42 (m, 2H).

Chemical Formula: $C_{15}H_{19}NO_4$, Molecular Weight: 277.32

Total H count from HNMR data: 20.

Step 9: Preparation of methyl 3-allyloxy-4-[3-(2-allyloxyethylamino)cyclobutoxy]benzoate

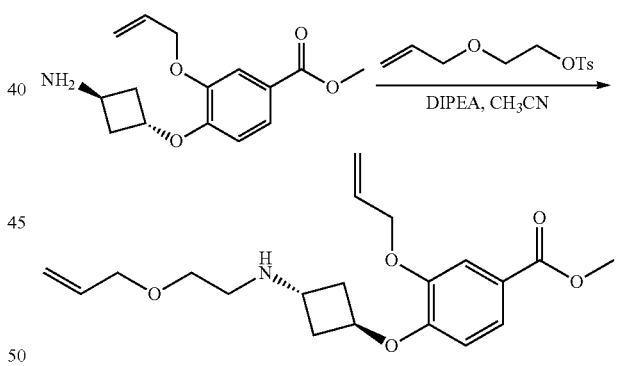

To a solution of methyl 3-allyloxy-4-(3-aminocyclobutoxy) benzoate (900.00 mg, 2.87 mmol, 1.00 eq, hydrochloride) and 2-allyloxyethyl 4-methylbenzenesulfonate (588.15 mg, 2.29 mmol, 0.80 eq) in methyl cyanide (15 mL) was added diisopropylethylamine (1.11 g, 8.60 mmol, 1.50 mL, 3.00 eq). The mixture was stirred at 70° C. for 12 h. LCMS showed that the reaction was completed. The reaction mixture was concentrated under reduced pressure to give methyl 3-allyloxy-4-[3-(2-allyloxyethylamino) cyclobutoxy] benzoate (0.90 g, 2.49 mmol, 86% yield) as a yellow oil, which was used in next step directly.

LCMS: MS (ESI) m/z: 362.3 [M+1]⁺.

¹H NMR: (400 MHz, CDCl₃) δ: 7.71 (d, J=8.0 Hz, 2H), 7.47 (s, 1H), 6.08-5.93 (m, 1H), 5.87-5.73 (m, 1H), 5.42-5.32 (m, 1H), 5.28-5.18 (m, 2H), 5.16-5.05 (m, 1H), 4.91 (td, J=7.2, 3.6 Hz, 1H), 4.60-4.49 (m, 2H), 3.96-3.87 (m,

2H), 3.81 (s, 3H), 3.69-3.60 (m, 3H), 3.06-3.02 (m, 2H), 2.84-2.73 (m, 2H), 2.58-2.46 (m, 2H), 2.00 (s, 1H).

Chemical Formula: $C_{20}H_{27}NO_5$, Molecular Weight: 361.43

Total H count from HNMR data: 27.

Step 10: Preparation of methyl 3-allyloxy-4-[3-[2-allyloxyethyl (tert-butoxycarbonyl) amino] cyclobutoxy] benzoate

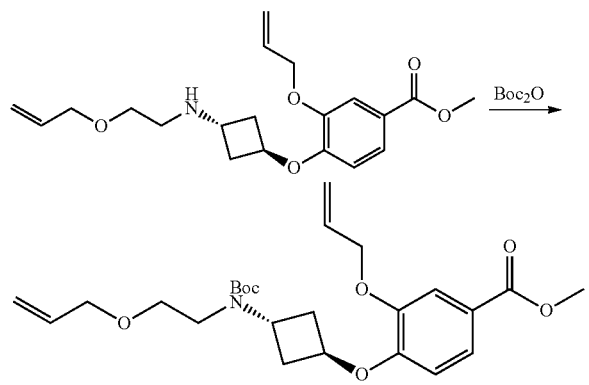

To a solution of methyl 3-allyloxy-4-[3-(2-allyloxyethylamino)cyclobutoxy]benzoate (0.90 g, 2.49 mmol, 1.00 eq) in tetrahydrofuran (10 mL) was added di-tert-butyl dicarbonate (598.00 mg, 2.74 mmol, 629.27 uL, 1.10 eq) and triethylamine (504.00 mg, 4.98 mmol, 693.19 uL, 2.00 eq). The mixture was stirred at 25° C. for 12 h. LCMS showed that the reaction was completed. The reaction mixture was concentrated under reduced pressure. The residue was purified by silica gel chromatography (petroleum ether/ethyl acetate=20/1 to 10/1) to give methyl 3-allyloxy-4-[3-[2-allyloxyethyl (tert-butoxycarbonyl) amino] cyclobutoxy] benzoate (0.53 g, 1.15 mmol, 46% yield) as a colorless oil.

LCMS: MS (ESI) m/z: 362.2[M+1-100]$^+$.

$^1$H NMR: 400 MHz, CDCl$_3$) δ: 7.55 (dd, J=8.4, 2.0 Hz, 1H), 7.51-7.47 (m, 1H), 6.56 (d, J=8.4 Hz, 1H), 6.13-5.49 (m, 1H), 5.82 (ddt, J=17.2, 10.6, 5.6 Hz, 1H), 5.46-5.33 (m, 1H), 5.26-5.15 (m, 2H), 5.10 (dd, J=10.4, 1.6 Hz, 1H), 4.75 (br t, J=6.4 Hz, 1H), 4.61-4.54 (m, 2H), 4.52-4.41 (m, 1H), 3.96-3.86 (m, 2H), 3.81 (s, 3H), 3.49-3.39 (m, 2H), 3.37-3.25 (m, 2H), 2.83-2.59 (m, 2H) 2.57-2.40 (m, 2H), 1.40 (s, 9H).

Chemical Formula: $C_{25}H_{35}NO_7$, Molecular Weight: 461.55

Step 11: Preparation of 4-(tert-butyl) 1$^4$-methyl (3$^1$r,3$^3$r,E)-2,7,12-trioxa-4-aza-1(1,2)-benzena-3(1,3)-cyclobutanacyclododecaphan-9-ene-1$^4$,4-dicarboxylate

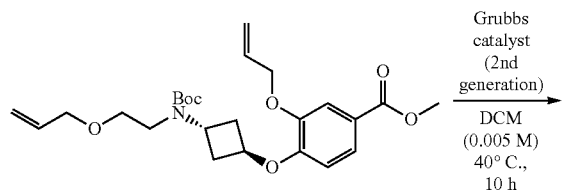

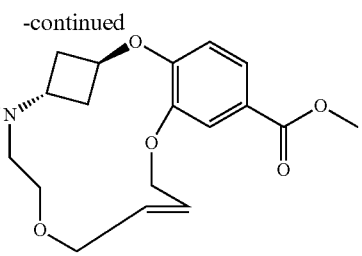

To a solution of methyl 3-allyloxy-4-[3-[2-allyloxyethyl (tert-butoxycarbonyl)amino]cyclobutoxy]benzoate (530.00 mg, 1.15 mmol, 1.00 eq) in dichlormethane (300 mL) was added benzylidene-[1,3-bis(2,4,6-trimethylphenyl)imidazolidin-2-ylidene]-dichloro-ruthenium; tricyclohexylphosphane (234.00 mg, 0.27 mmol, 0.24 eq). The mixture was stirred at 40° C. for 12 h. LCMS showed that the reaction was completed. The reaction mixture was concentrated under reduced pressure. The residue was purified by column chromatography on silica gel (petroleum ether/ethyl acetate=10/1 to 5/1) to give 4-(tert-butyl) 1$^4$-methyl (3$^1$r, 3$^3$r,E)-2,7,12-trioxa-4-aza-1(1,2)-benzena-3(1,3)-cyclobutanacyclododecaphan-9-ene-1$^4$,4-dicarboxylate (110.00 mg, 0.25 mmol, 22% yield) as a yellow oil.

LCMS: EW13161-309-P1B4, MS (ESI) m/z: 334.1[M+1-100]$^+$.

Chemical Formula: $C_{23}H_{31}NO_7$, Molecular Weight: 433.49

Step 12: Preparation of 4-(tert-butyl) 1$^4$-methyl (3$^1$r,3$^3$r)-2,7,12-trioxa-4-aza-1(1,2)-benzena-3(1,3)-cyclobutanacyclododecaphane-1$^4$,4-dicarboxylate

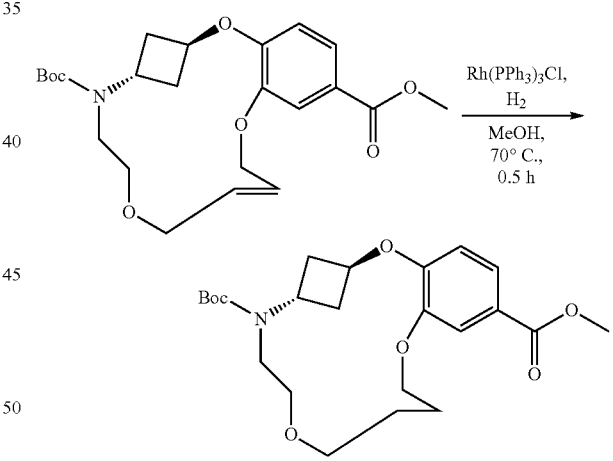

To a solution of O23-tert-butyl 1$^4$-methyl (3$^1$r,3$^3$r,E)-2,7,12-trioxa-4-aza-1(1,2)-benzena-3(1,3)-cyclobutanacyclododecaphan-9-ene-1$^4$,4-dicarboxylate (110.00 mg, 0.25 mmol, 1.00 eq) in methanol (2 mL) was added chlororhodium; triphenylphosphane (23.00 mg, 0.03 mmol, 0.10 eq). The mixture was stirred at 70° C. for 0.5 h under hydrogen atmosphere (15 Psi). LCMS showed that the reaction was completed. The reaction mixture was concentrated under reduced pressure. The residue was purified by preparative thin layer chromatography (petroleum ether/ethyl acetate=3:1, R$_f$=0.4) to give 4-(tert-butyl) 1$^4$-methyl (3$^1$r,3$^3$r)-2,7,12-trioxa-4-aza-1(1,2)-benzena-3(1,3)-cyclobutanacyclododecaphane-1$^4$,4-dicarboxylate (90 mg, 0.21 mmol, 81% yield) as a yellow oil.

LCMS: EW13161-311-P1A, MS (ESI) m/z: 336.4[M+1-100]⁺.

Chemical Formula: $C_{23}H_{33}NO_7$, Molecular Weight: 435.57

Step 13: Preparation of (3¹r,3³r)-4-(tert-butoxycarbonyl)-2,7,12-trioxa-4-aza-1(1,2)-benzena-3(1,3)-cyclobutanacyclododecaphane-1⁴-carboxylic acid

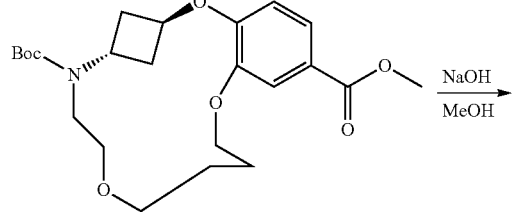

To a solution of 4-(tert-butyl) 1⁴-methyl (3¹r,3³r)-2,7,12-trioxa-4-aza-1(1,2)-benzena-3(1,3)-cyclobutanacyclododecaphane-1⁴,4-dicarboxylate (180.00 mg, 0.41 mmol, 1.00 eq) in methanol (2 mL) and water (0.5 mL) was added sodium hydroxide (66.00 mg, 1.65 mmol, 4.00 eq). The mixture was stirred at 50° C. for 12 h. LCMS showed that the reaction was completed. The reaction mixture was concentrated under reduced pressure. The residue was diluted with water (10 mL) and adjusted pH to 5-6 by hydrochloric acid (1 M). Then the mixture was filtered and concentrated under reduced pressure to give (3¹r,3³r)-4-(tert-butoxycarbonyl)-2,7,12-trioxa-4-aza-1(1,2)-benzena-3(1,3)-cyclobutanacyclododecaphane-1⁴-carboxylic acid (140.00 mg, 0.33 mmol, 80% yield) as a white solid.

LCMS: MS (ESI) m/z: 322.2[M+1-100]⁺.

¹H NMR: (400 MHz, DMSO-d₆) δ: 12.83-12.58 (m, 1H), 7.61-7.51 (m, 2H), 7.15-7.05 (m, 1H), 4.91 (br t, J=5.6 Hz, 1H), 4.50-4.33 (m, 1H), 4.13-4.00 (m, 2H), 3.49-3.43 (m, 2H), 3.41-3.37 (m, 2H), 2.77-2.61 (m, 2H), 2.55-2.52 (m, 2H), 2.30-2.16 (m, 2H), 1.89-1.77 (m, 2H), 1.70-1.59 (m, 2H), 1.45-1.37 (m, 9H).

Chemical Formula: $C_{22}H_{31}NO_7$, Molecular Weight: 421.48

Total H count from HNMR data: 31.

Step 14: Preparation of tert-butyl (3¹r,3³r)-1⁴-((2,6-dioxopiperidin-3-yl)carbamoyl)-2,7,12-trioxa-4-aza-1(1,2)-benzena-3(1,3)-cyclobutanacyclododecaphane-4-carboxylate

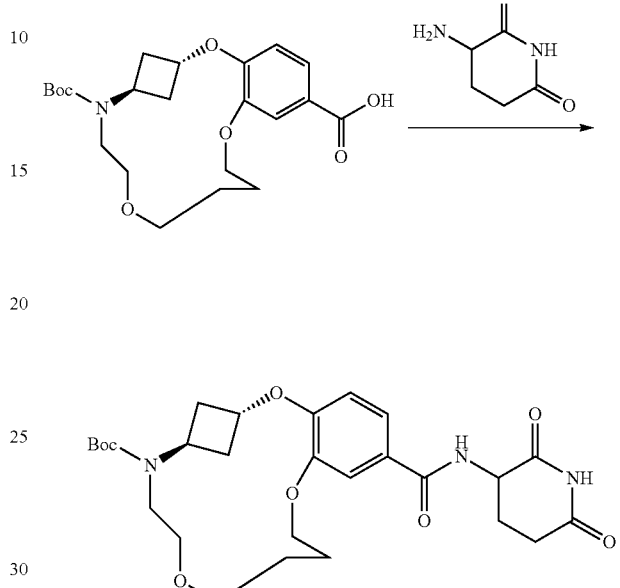

To a solution of (3¹r,3³r)-4-(tert-butoxycarbonyl)-2,7,12-trioxa-4-aza-1(1,2)-benzena-3(1,3)-cyclobutanacyclododecaphane-1⁴-carboxylic acid (140.00 mg, 0.33 mmol, 1.00 eq) in dimethylformamide (2 mL) was added triethylamine (134.00 mg, 1.33 mmol, 184.93 uL, 4.00 eq), 1-hydroxybenzotriazole (58.00 mg, 0.43 mmol, 1.30 eq), 1-(3-dimethylaminopropyl)-3-ethylcarbodiimide hydrochloride (82.00 mg, 0.43 mmol, 1.30 eq) and 3-aminopiperidine-2,6-dione (71.00 mg, 0.43 mmol, 1.30 eq, hydrochloride). The mixture was stirred at 25° C. for 12 h. LCMS showed that the reaction was completed. The reaction mixture was concentrated under reduced pressure. The residue was diluted with water (5 mL) and extracted with ethyl acetate (20 mL). The organic layer was dried over anhydrous sodium sulfate, filtered and concentrated under reduced pressure to give a residue. The residue was purified by silica gel chromatography (petroleum ether/ethyl acetate=5/1 to 0/1) to give tert-butyl (3¹r,3³r)-1⁴-((2,6-dioxopiperidin-3-yl)carbamoyl)-2,7,12-trioxa-4-aza-1(1,2)-benzena-3(1,3)-cyclobutanacyclododecaphane-4-carboxylate (170.00 mg, 0.32 mmol, 96% yield) as a white solid.

LCMS: MS (ESI) m/z: 432.3[M+1-100]⁺.

¹H NMR: (400 MHz, CDCl₃) δ: 8.02-7.89 (m, 1H), 7.43 (d, J=2.0 Hz, 1H), 7.35-7.27 (m, 1H), 6.89 (d, J=8.4 Hz, 1H), 6.82 (br d, J=5.2 Hz, 1H), 4.80 (br s, 1H), 4.66 (dt, J=12.8, 5.2 Hz, 1H), 4.59-4.43 (m, 1H), 4.14 (br d, J=4.0 Hz, 1H), 3.49-3.42 (m, 2H), 3.37 (br t, J=5.2 Hz, 4H), 2.84-2.62 (m, 5H), 2.34 (br t, J=8.4 Hz, 2H), 1.95-1.81 (m, 3H), 1.67 (dt, J=12.8, 6.4 Hz, 2H), 1.41 (s, 9H).

Chemical Formula: $C_{27}H_{37}N_3O$, Molecular Weight: 531.60

Step 15: Preparation of dimethyl 4-[8-[3-[2-(2,6-dioxo-3-piperidyl)-6-methoxy-1,3-dioxo-isoindolin-5-yl]oxycyclobutyl]-5-oxa-2,8-diazaspiro[3.5]nonan-2-yl]benzoic acid

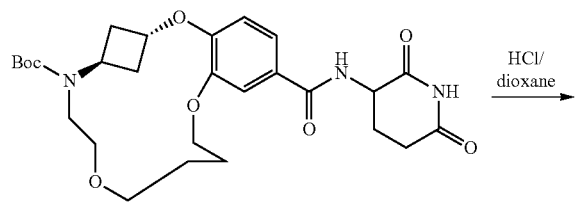

The reaction mixture was concentrated under reduced pressure to give N-(2, 6-dioxo-3-piperidyl)-28,29,30-trioxa-22-azatricycloicosa-,2(13),14-triene-13-carboxamide (148.00 mg, 0.32 mmol, 98% yield, hydrochloride) as a white solid.

LCMS: MS (ESI) m/z: 432.3[M+1]$^+$.

Chemical Formula: $C_{22}H_{29}N_3O_6$, Molecular Weight: 431.48

Step 16: Preparation of (3$^1$r,3$^3$r)-4-((1-(4-(((1r,3r)-3-(4-cyano-3,5-dimethylphenoxy)-2,2,4,4-tetramethylcyclobutyl)carbamoyl)phenyl)piperidin-4-yl)methyl)-N-(2,6-dioxopiperidin-3-yl)-2,7,12-trioxa-4-aza-1(1,2)-benzena-3(1,3)-cyclobutanacyclododecaphane-1$^4$-carboxamide, Compound 64

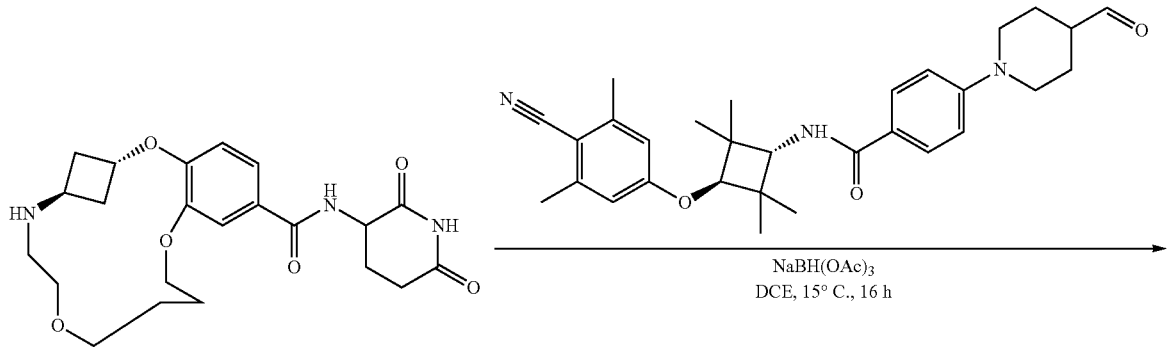

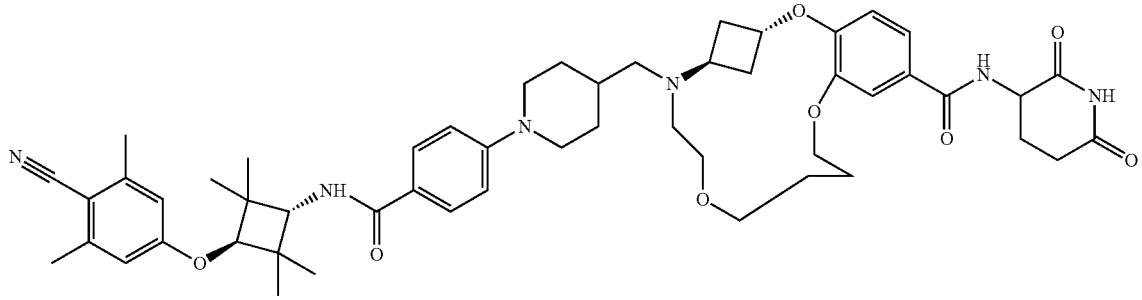

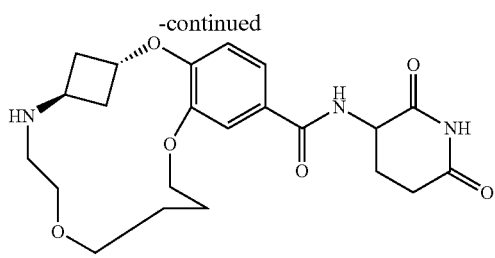

-continued

To a solution of tert-butyl 16-[(2,6-dioxo-3-piperidyl)carbamoyl]-34,35,36-trioxa-29-azatricycloicosa-3,5(16),17-triene-29-carboxylate (170.00 mg, 0.32 mmol, 1.00 eq) in dichlormethane (5 mL) was added hydrochloric acid/dioxane (4 M, 1 mL, 12.51 eq). The mixture was stirred at 25° C. for 1 h. LCMS showed that the reaction was completed.

To a solution of N-(2,6-dioxo-3-piperidyl)-28,29,30-trioxa-22-azatricycloicosa-,2(13),14-triene-13-carboxamide (148.00 mg, 0.31 mmol, 1.00 eq, hydrochloride) in dichlormethane (5 mL) was added N-[3-(4-cyano-3,5-dimethylphenoxy)-2,2,4,4-tetramethyl-cyclobutyl]-4-(4-formyl-1-piperidyl)benzamide (169.00 mg, 0.34 mmol, 1.10 eq), triethylamine (32.00 mg, 0.31 mmol, 44.02 uL, 1.00 eq) and acetic acid (38.00 mg, 0.63 mmol, 36.18 uL, 2.00 eq) at 25° C. The mixture was stirred at 25° C. for 12 h. Then to the mixture was added sodium triacetoxyborohydride (201.00 mg, 0.95 mmol, 3.00 eq) and stirred at 25° C. for 4 h. LCMS showed that the reaction was completed. The reaction mixture was concentrated under reduced pressure. The residue was purified by preparative thin layer chromatography (dichloromethane:methyl alcohol=10:1, R$_f$=0.4) to give a yellow oil. The yellow oil was further purification by preparative HPLC (column: Shim-pack C18 150*25*10 um; mobile phase: [water (0.225% FA)-ACN]; B %: 30%-60%, 10 min) to give (3¹r,3³r)-4-((1-(4-(((1r,3r)-3-(4-cyano-3,5-dimethylphenoxy)-2,2,4,4-tetramethylcyclobutyl)carbamoyl)phenyl)piperidin-4-yl)methyl)-N-(2,6-dioxopiperidin-3-yl)-2,7,12-trioxa-4-aza-1(1,2)-benzena-3(1,3)-cyclobutanacyclododecaphane-1⁴-carboxamide (76.90 mg, 0.08 mmol, 26% yield, 99% purity, formate) as a white solid.

QC-LCMS: MS (ESI) m/z: 903.1[M]⁺.

¹H NMR: (400 MHz, DMSO-$d_6$) δ: 10.88-10.82 (m, 1H), 8.61 (br d, J=8.4 Hz, 1H), 8.25 (s, 1H), 7.78-7.70 (m, 2H), 7.58-7.45 (m, 3H), 7.01-6.9 (m, 3H), 6.74 (s, 2H), 4.83 (s, 2H), 4.23 (s, 1H), 4.16-4.01 (m, 4H), 3.93-3.78 (m, 2H), 3.58-3.47 (m, 2H), 3.39-3.37 (m, 2H), 2.81-2.72 (m, 2H), 2.64-2.54 (m, 1H), 2.44 (s, 6H), 2.31-2.23 (m, 3H), 2.22-2.12 (m, 2H), 2.11-2.03 (m, 4H), 1.96 (dt, J=6.4, 4.0 Hz, 1H), 1.85-1.71 (m, 5H), 1.66-1.54 (m, 3H), 1.12 (s, 6H), 1.17-1.11 (m, 8H).

Chemical Formula: $C_{52}H_{66}N_6O_8$, Molecular Weight: 903.12

Example 24—Synthesis of 3-[4-[[1-[4-[[3-(4-cyano-3,5-dimethyl-phenoxy)-2,2,4,4-tetramethylcyclobutyl]carbamoyl]phenyl]-4-piperidyl]methyl]-1-piperidyl]-N-(2,6-dioxo-3-piperidyl)bicyclo[1.1.1]pentane-1-carboxamide (Compound 70)

SCHEME 19. SUMMARY OF THE SYNTHESIS OF COMPOUND 70

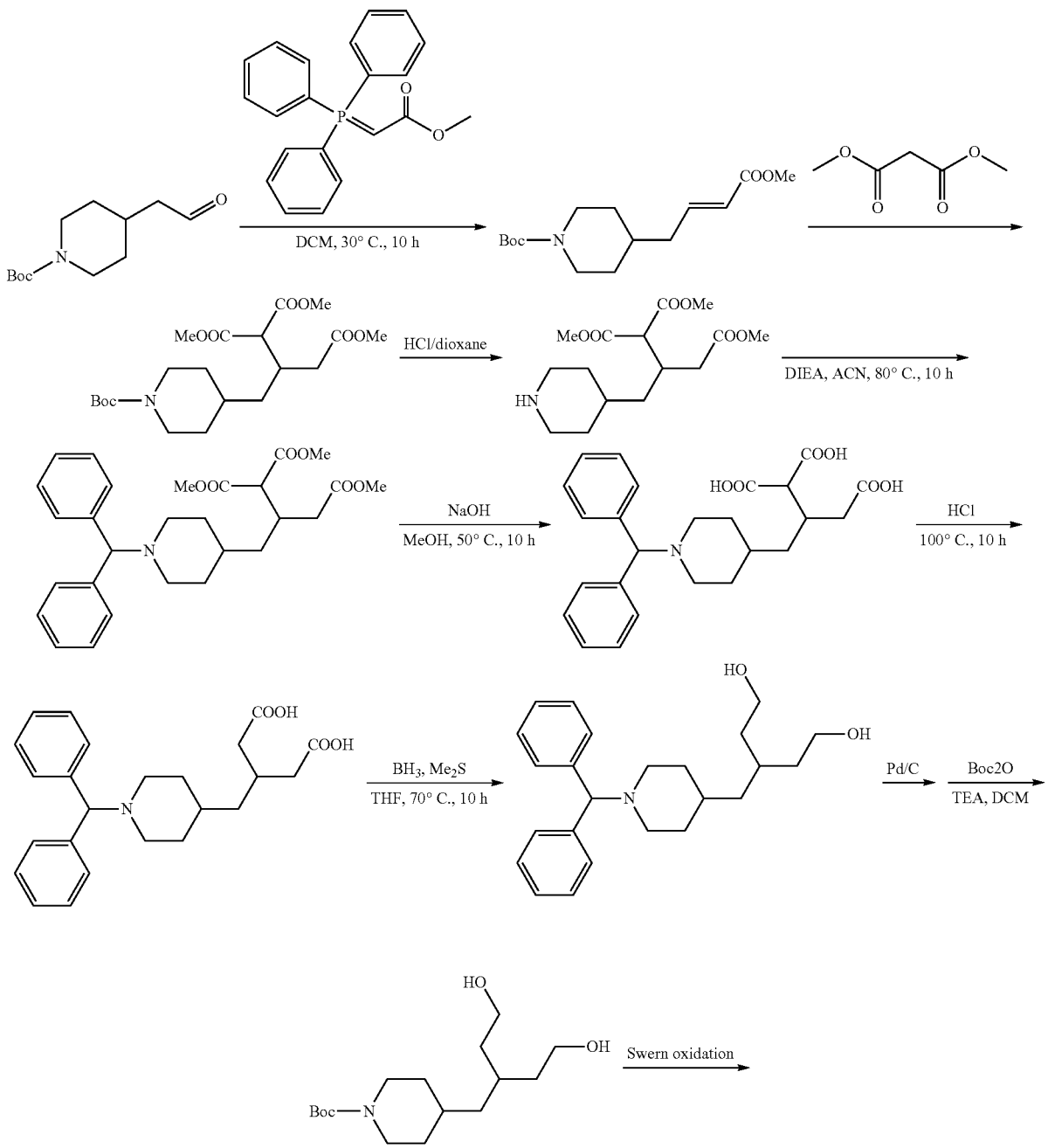

-continued
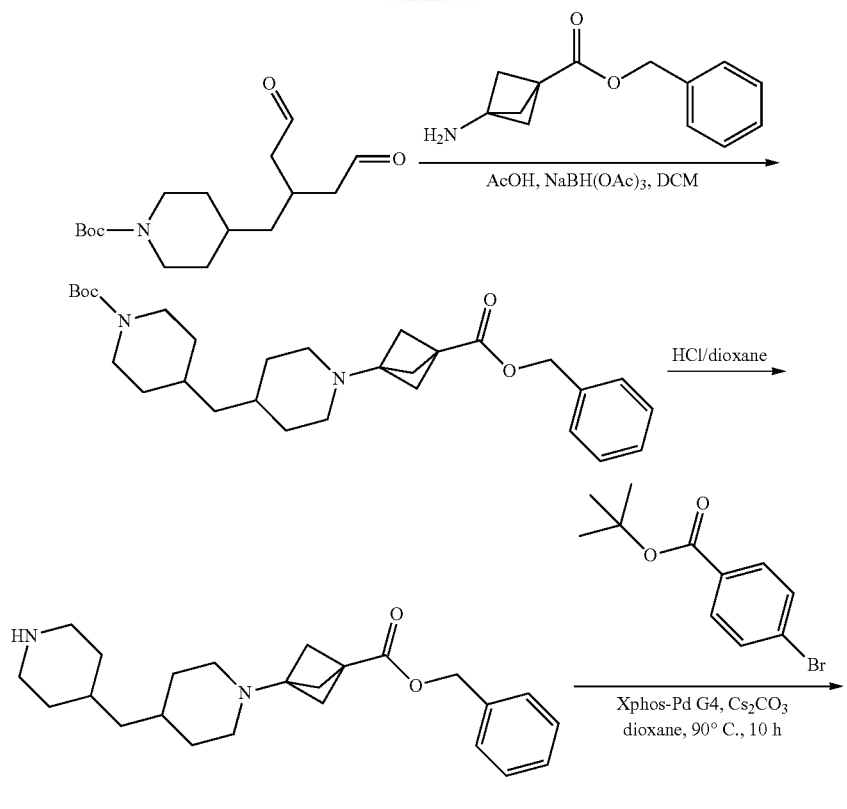
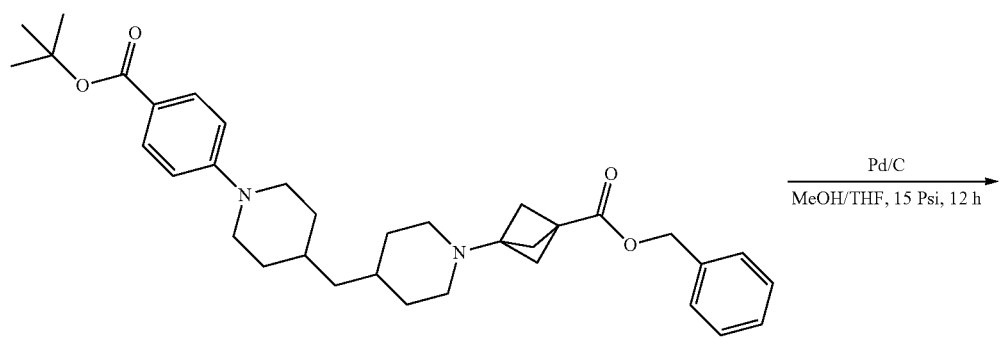
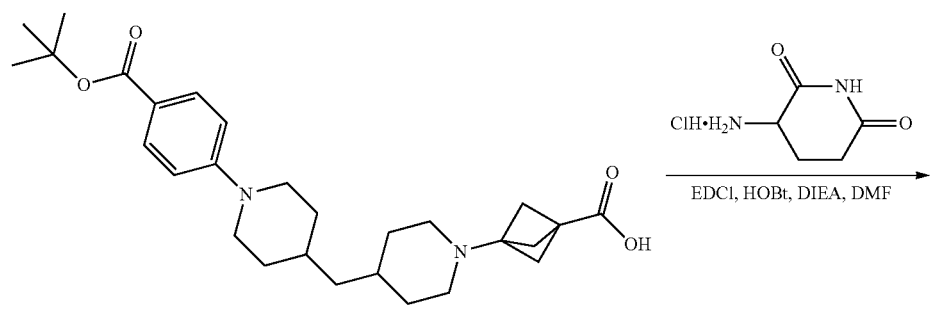

-continued

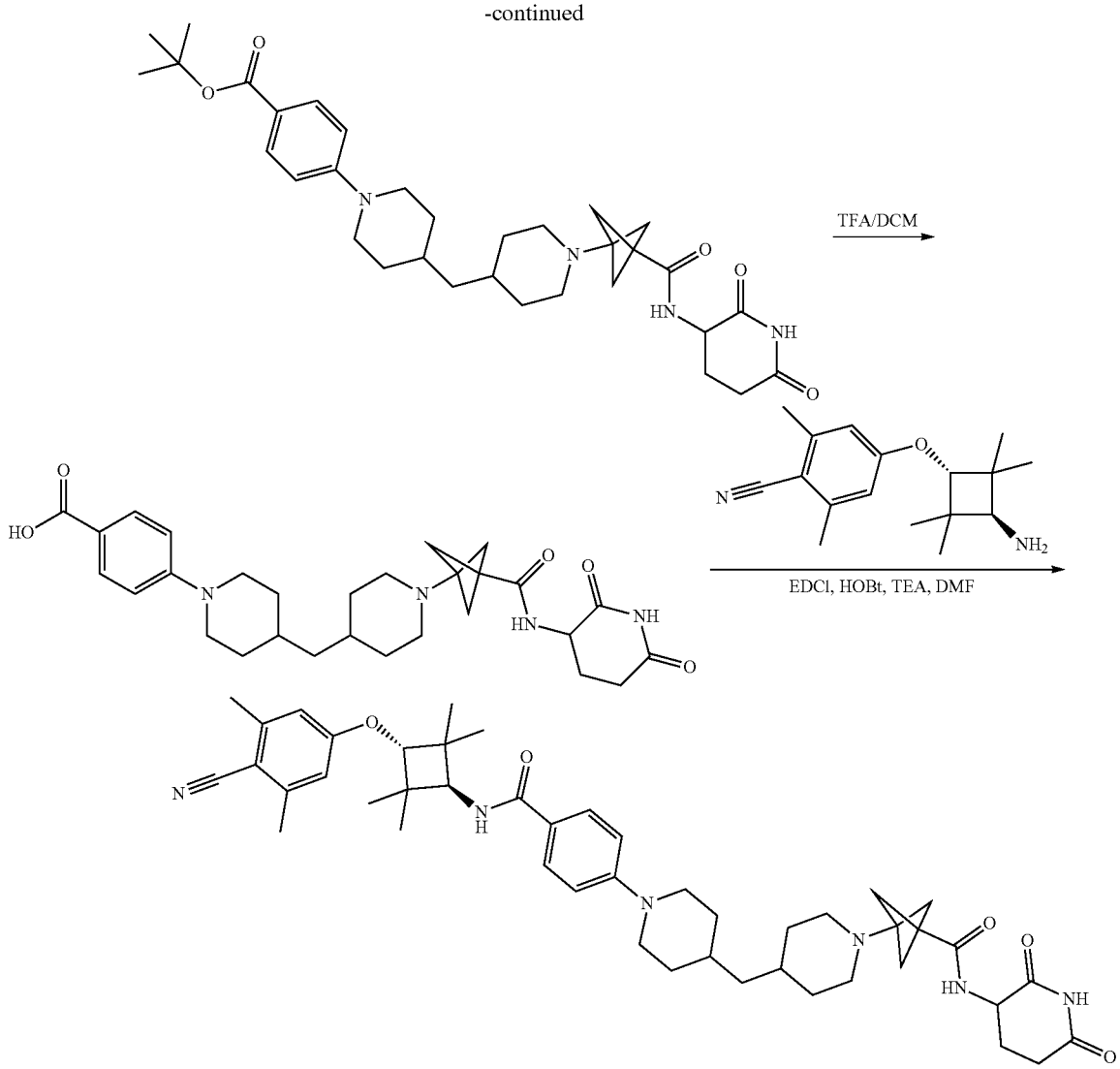

Step 1: Preparation of tert-butyl 4-[(E)-4-methoxy-4-oxo-but-2-enyl]piperidine-1-carboxylate

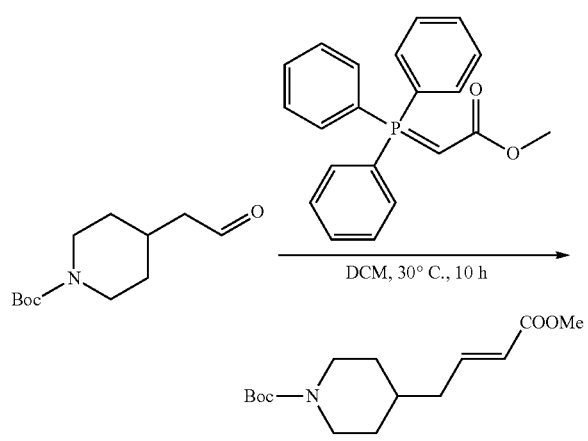

To a solution of tert-butyl 4-(2-oxoethyl)piperidine-1-carboxylate (5.00 g, 22.00 mmol, 1.00 eq) in dichloromethane (100 mL) was added methyl 2-(triphenyl-phosphanylidene)acetate (8.09 g, 24.20 mmol, 1.10 eq). Then the mixture was stirred for 10 h at 30° C. Thin layer chromatography (petroleum ether: ethyl acetate=5:1) showed that the reaction was completed. The mixture was concentrated under reduced pressure to give the residue. The residue was dissolved by (Petroleum ether: ethyl acetate=10:1, 100 mL). Then the mixture was filtered. The filtrate was concentrated under reduced pressure to give tert-butyl 4-[(E)-4-methoxy-4-oxo-but-2-enyl]piperidine-1-carboxylate (6.20 g, 21.88 mmol, 99% yield) as a colorless oil, which was used in next step directly.

$^1$H NMR: (400 MHz, DMSO-d$_6$) δ: 6.79-6.93 (m, 1H), 5.76 (dt, J=15.6, 1.2 Hz, 1H), 3.95-4.07 (m, 2H), 3.66 (s, 3H), 2.61 (td, J=12.8, 2.8 Hz, 2H), 2.04-2.17 (m, 2H), 1.56-1.64 (m, 2H), 1.44-1.56 (m, 1H), 1.38 (s, 9H), 0.99-1.13 (m, 2H).

Chemical Formula: $C_{15}H_{25}NO_4$, Molecular Weight: 283.36

Step 2: Preparation of trimethyl 2-[(1-tertbutoxycarbonyl-4-piperidyl)methyl]propane-1,1,3-tricarboxylate

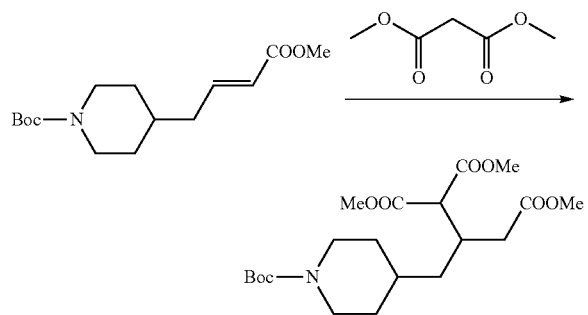

To a solution of cesium carbonate (28.06 g, 86.11 mmol, 4.00 eq) in N,N-dimethylformamide (100 mL) was added dimethyl propanedioate (5.69 g, 43.05 mmol, 4.95 mL, 2.00 eq) at 30° C. The mixture was stirred for 30 min at 30° C. Then to the mixture was added tert-butyl 4-[(E)-4-methoxy-4-oxo-but-2-enyl]piperidine-1-carboxylate (6.10 g, 21.53 mmol, 1.00 eq) and stirred for 10 h at 60° C. Thin layer chromatography (petroleum ether: ethyl acetate=3:1) showed that the reaction was completed. The mixture was diluted with ethyl acetate (300 mL) and washed with water (500 mL). The organic layer was washed with brine (300 mL), dried over sodium sulfate and concentrated under reduced pressure to give the residue. The residue was purified by column chromatography on silica gel (petroleum ether: ethyl acetate=20:1~10:1~5:1) to give trimethyl 2-[(1-tertbutoxycarbonyl-4-piperidyl)methyl]propane-1,1,3-tricarboxylate (8.10 g, 19.50 mmol, 90% yield) as a colorless oil.

$^1$H NMR: (400 MHz, CDCl$_3$) δ: 3.95-4.05 (m, 2H), 3.51-3.72 (m, 11H), 2.55-2.68 (m, 3H), 2.47-2.55 (m, 1H), 2.32-2.40 (m, 1H), 1.60-1.69 (m, 1H), 1.57 (br s, 1H), 1.29-1.43 (m, 10H), 1.23-1.29 (m, 1H), 0.92-1.10 (m, 2H).

Chemical Formula: C$_{20}$H$_{33}$NO$_8$, Molecular Weight: 415.48

Step 3: Preparation of trimethyl 2-(4-piperidylmethyl)propane-1,1,3-tricarboxylate

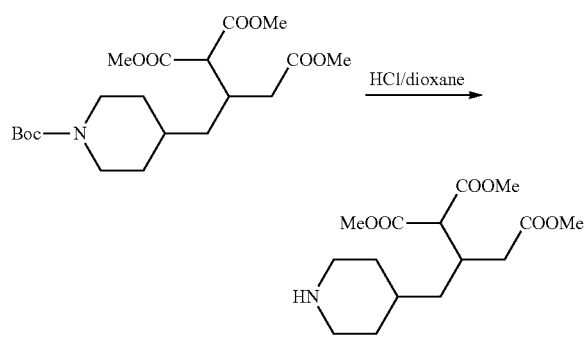 [SMILES: COC(=O)CC(CC1CCN(C(=O)OC(C)(C)C)CC1)C(C(=O)OC)C(=O)OC ; "HCl/dioxane" ; COC(=O)CC(CC1CCNCC1)C(C(=O)OC)C(=O)OC]

To a solution of trimethyl 2-[(1-tert-butoxycarbonyl-4-piperidyl)methyl]propane-1,1,3-tricarboxylate (8.10 g, 19.50 mmol, 1.00 eq) in dichloromethane (100 mL) was added hydrochloric acid/dioxane (4 M, 58 mL, 11.83 eq). Then the mixture was stirred for 30 min at 30° C. Thin layer chromatography (petroleum ether: ethyl acetate=1:1) showed that the reaction was completed. The mixture was concentrated under reduced pressure to give trimethyl 2-(4-piperidylmethyl)propane-1,1,3-tricarboxylate (6.80 g, 19.33 mmol, 99% yield, hydrochloride salt) as a white solid, which was used in next step directly.

Step 4: Preparation of trimethyl 2-[(1-benzhydryl-4-piperidyl)methyl]propane-1,1,3-tricarboxylate

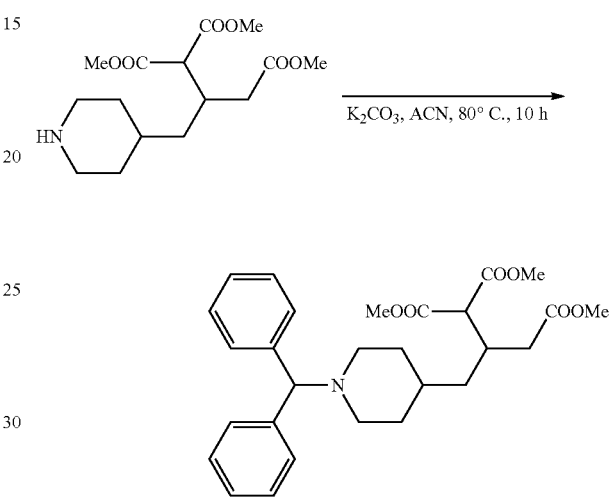

To a solution of trimethyl 2-(4-piperidylmethyl)propane-1,1,3-tricarboxylate (6.80 g, 21.56 mmol, 1.00 eq, hydrochloride salt) in acetonitrile (100 mL) was added potassium iodide (357.94 mg, 2.16 mmol, 0.10 eq), potassium carbonate (8.94 g, 64.69 mmol, 3.00 eq) and [bromo(phenyl)methyl]benzene (6.39 g, 25.88 mmol, 1.20 eq). Then the mixture was stirred for 10 h at 80° C. Thin layer chromatography (petroleum ether: ethyl acetate=1:1) showed that the reaction was completed. The mixture was filtered. The filtrate was concentrated under reduced pressure to give the residue. The residue was purified by column chromatography on silica gel (petroleum ether: ethyl acetate=10:1~5:1~1:1) to give trimethyl 2-[(1-benzhydryl-4-piperidyl)methyl]propane-1,1,3-tricarboxylate (8.30 g, 17.23 mmol, 79% yield) as a colorless oil.

Step 5: Preparation of 2-[(1-benzhydryl-4-piperidyl)methyl]propane-1,1,3-tricarboxylic acid

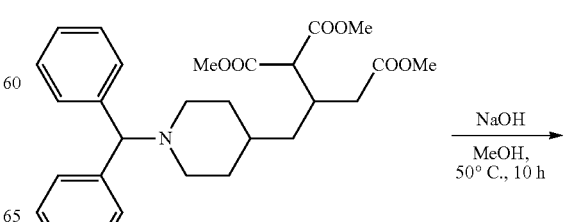

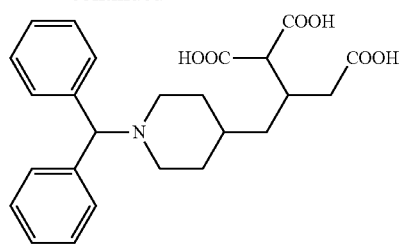

To a solution of trimethyl 2-[(1-benzhydryl-4-piperidyl)methyl]propane-1,1,3-tricarboxylate (8.3 g, 17.23 mmol, 1.00 eq) in water (25 mL) and methanol (100 mL) was added sodium hydroxide (2.76 g, 68.94 mmol, 4.00 eq). Then the mixture was stirred for 1 h at 100° C. LCMS showed that the reaction was completed. The mixture was concentrated under reduced pressure to give 2-[(1-benzhydryl-4-piperidyl)methyl]propane-1,1,3-tricarboxylic acid (7.50 g, 17.06 mmol, 99% yield) as a white solid was used in next step directly.

LCMS: MS (ESI) m/z: 440.2[M+1]$^+$.

Step 6 Preparation of: 3-[(1-benzhydryl-4-piperidyl)methyl]pentanedioic acid

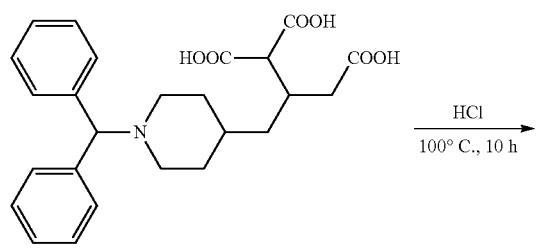

To a solution of 2-[(1-benzhydryl-4-piperidyl)methyl]propane-1,1,3-tricarboxylic acid (7.50 g, 17.06 mmol, 1.00 eq) in water (50 mL) was added hydrochloric acid (12 M, 7 mL, 4.98 eq). Then the mixture was stirred for 10 h at 100° C. LCMS showed that the reaction was completed. The mixture was diluted with water (50 mL) and filtered. The filtrate cake was concentrated under reduced pressure to give 3-[(1-benzhydryl-4-piperidyl)methyl]pentanedioic acid (5.00 g, 12.64 mmol, 74% yield) as a white solid, which was used in next step directly.

LCMS: MS (ESI) m/z: 396.2[M+1]$^+$.

Chemical Formula: $C_{24}H_{29}NO_4$, Molecular Weight: 395.49

Step 7: Preparation of 3-[(1-benzhydryl-4-piperidyl)methyl]pentane-1,5-diol

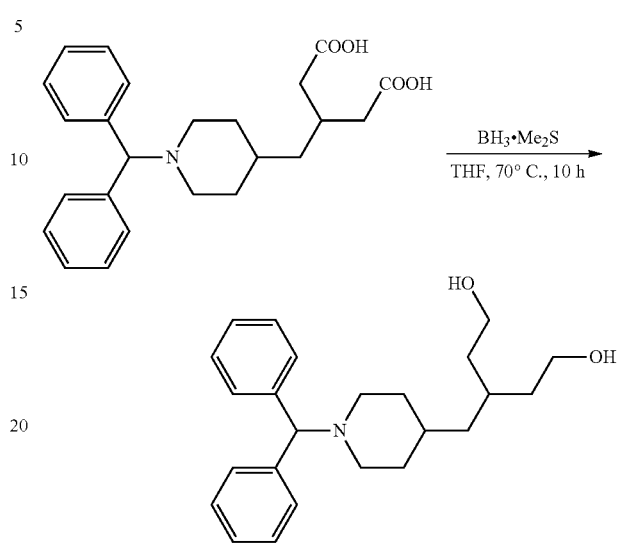

To a solution of 3-[(1-benzhydryl-4-piperidyl)methyl]pentanedioic acid (5.0 g, 12.64 mmol, 1.00 eq) in tetrahydrofuran (300 mL) was added dropwise borane dimethyl sulfide complex (10 M, 3.79 mL, 3.00 eq) at 0° C. Then the mixture was stirred for 10 h at 80° C. LCMS showed that the reaction was completed. The mixture was quenched with hydrochloride/methanol (4 M, 20 mL). The mixture was stirred for 1 h at 60° C. Then the mixture was concentrated under reduced pressure to give the residue. The residue was purified by column chromatography on silica gel (dichloromethane: methyl alcohol methanol=100:1~40:1~20:1) to give 3-[(1-benzhydryl-4-piperidyl)methyl]pentane-1,5-diol (3.10 g, 8.43 mmol, 66% yield) as a white solid.

LCMS: MS (ESI) m/z: 368.2[M+1]$^+$.

Chemical Formula: $C_{24}H_{33}NO_2$, Molecular Weight: 367.52

Step 8: Preparation of tert-butyl 4-[4-hydroxy-2-(2-hydroxyethyl)butyl]piperidine-1-carboxylate

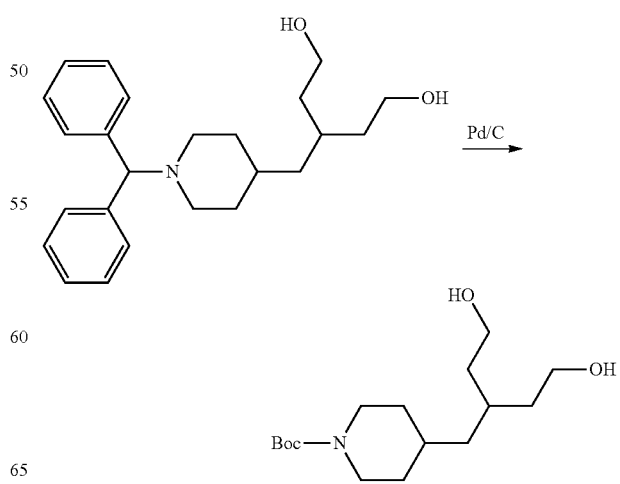

To a solution of 3-[(1-benzhydryl-4-piperidyl)methyl]pentane-1,5-diol (3.10 g, 8.43 mmol, 1.00 eq) in ethyl acetate (50 mL) was added triethylamine (1.71 g, 16.87 mmol, 2.35 mL, 2.00 eq), di-tert-butyl dicarbonate (2.21 g, 10.12 mmol, 2.33 mL, 1.20 eq) and palladium on activated carbon catalyst (200 mg, 10% purity). Then the mixture was purged and degassed with hydrogen for three times. The mixture was stirred for 10 h at 30° C. under hydrogen atmosphere (15 Psi). LCMS showed that the reaction was completed. The mixture was filtered. The filtrate was concentrated under reduced pressure to give the residue. The residue was purified by column chromatography on silica gel (petroleum ether: ethyl acetate=10:1~1:1) to give tert-butyl 4-[4-hydroxy-2-(2-hydroxyethyl)butyl]piperidine-1-carboxylate (1.70 g, 5.64 mmol, 66% yield) as a colorless oil.

LCMS: MS (ESI) m/z: 302.2[M+1]$^+$.

Chemical Formula: $C_{16}H_{31}NO_4$, Molecular Weight: 301.42

Step 9: Preparation of tert-butyl 4-[4-oxo-2-(2-oxoethyl)butyl]piperidine-1-carboxylate

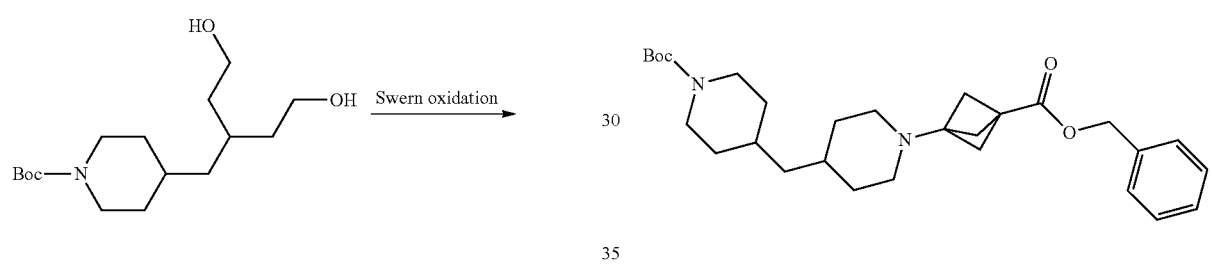

To a solution of Oxalyl chloride (2.74 g, 21.56 mmol, 1.89 mL, 10.00 eq) in dichloromethane (5 mL) was added dropwised a solution of dimethylsulfoxide (2.02 g, 25.88 mmol, 2.02 mL, 12.00 eq) in dichloromethane (5 mL) at −70° C. The mixture was stirred for 0.5 h at −70° C. Then to the mixture was added a solution of tert-butyl 4-[4-hydroxy-2-(2-hydroxyethyl)butyl]piperidine-1-carboxylate (650 mg, 2.16 mmol, 1.00 eq) in dichloromethane (5 mL) at −70° C. The mixture was stirred for 3 h at −70° C. Then to the mixture was added triethylamine (4.36 g, 43.13 mmol, 6.00 mL, 20.00 eq) at −70° C. dropwise. The mixture was stirred at 25° C. for 12 h. Thin layer chromatography (petroleum ether: ethyl acetate=5:1) showed that the reaction was completed. The mixture was quenched with water (30 mL) and extracted with dichloromethane (30 mL). The organic layer was washed with brine (30 mL), dried over sodium sulfate and concentrated under reduced pressure to give the residue. The residue was purified by column chromatography on silica gel (petroleum ether: ethyl acetate=30:1~20:1~5:1) to give tert-butyl 4-[4-oxo-2-(2-oxoethyl)butyl]piperidine-1-carboxylate (630 mg, 2.12 mmol, 98% yield) as a colorless oil.

Step 10: Preparation of: tert-butyl 4-[[1-(1-benzyloxycarbonyl-3-bicyclo[1.1.1]pentanyl)-4-piperidyl]methyl]piperidine-1-carboxylate

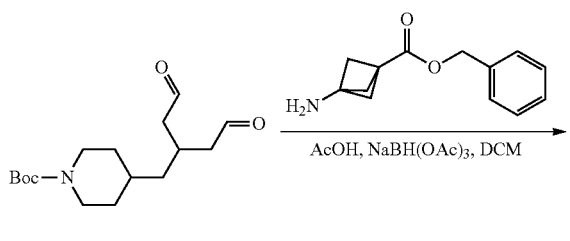

To a solution of benzyl 3-aminobicyclo[1.1.1]pentane-1-carboxylate (591.25 mg, 2.33 mmol, 1.10 eq, hydrochloride salt) in dichloromethane (10 mL) was added sodium acetate (347.57 mg, 4.24 mmol, 2.00 eq) and tert-butyl 4-[4-oxo-2-(2-oxoethyl)butyl]piperidine-1-carboxylate (630 mg, 2.12 mmol, 1.00 eq). The mixture was stirred for 30 min at 30° C. Then to the mixture was added sodium triacetoxyborohydride (897.97 mg, 4.24 mmol, 2.00 eq) and stirred for 0.5 h at 30° C. LCMS showed that the reaction was completed. The mixture was quenched with water (50 mL) and extracted with dichloromethane (50 mL). The organic layer was washed with brine (50 mL), dried over sodium sulfate and concentrated under reduced pressure to give the residue. The residue was purified by column chromatography on silica gel (Petroleum ether: Ethyl acetate=10:1~5:1~1:1) to give tert-butyl 4-[[1-(1-benzyloxycarbonyl-3-bicyclo[1.1.1]pentanyl)-4-piperidyl]methyl]piperidine-1-carboxylate (560 mg, 1.16 mmol, 54% yield) as a colorless oil.

LCMS: MS (ESI) m/z: 483.3[M+1]$^+$.

$^1$H NMR: (400 MHz, CDCl$_3$) δ: 7.31-7.42 (m, 5H), 5.14 (s, 2H), 3.97-4.14 (m, 2H), 2.88 (br d, J=11.6 Hz, 2H), 2.68 (br t, J=12.4 Hz, 2H), 2.09 (s, 6H), 1.95-2.04 (m, 2H), 1.62-1.74 (m, 4H), 1.45-1.51 (m, 10H), 1.30-1.38 (m, 1H), 1.14-1.25 (m, 4H), 1.06 (qd, J=12.4, 4.4 Hz, 2H).

Chemical Formula: $C_{29}H_{42}N_2O_4$, Molecular Weight: 482.65

Step 11: Preparation of benzyl 3-[4-(4-piperidylmethyl)-1-piperidyl]bicyclo[1.1.1]pentane-1-carboxylate

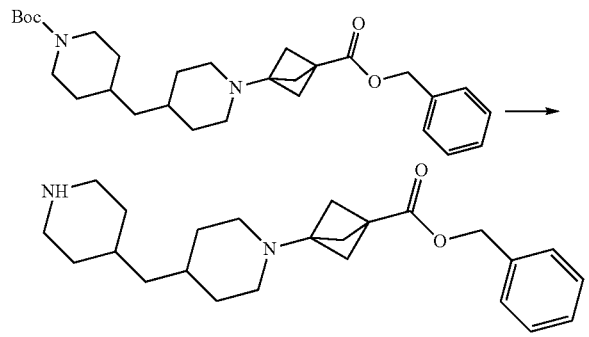

To a solution of tert-butyl 4-[[1-(1-benzyloxycarbonyl-3-bicyclo[1.1.1]pentanyl)-4-piperidyl]methyl]piperidine-1-carboxylate (560 mg, 1.16 mmol, 1.00 eq) in dichloromethane (10 mL) was added hydrochloric acid/dioxane (4 M, 4 mL, 15.32 eq). Then the mixture was stirred for 0.5 h at 30° C. Thin layer chromatography (petroleum ether: ethyl acetate=1:1) showed that the reaction was completed. The mixture was concentrated under reduced pressure to give benzyl 3-[4-(4-piperidylmethyl)-1-piperidyl]bicyclo[1.1.1]pentane-1-carboxylate (480 mg, 1.15 mmol, 98% yield, hydrochloride salt) as a white solid, which was used in next step directly.

$^1$H NMR: (400 MHz, DMSO-d$_6$) δ: 11.78-12.03 (m, 1H), 8.68-9.15 (m, 2H), 7.28-7.49 (m, 5H), 5.15 (s, 2H), 3.32 (br d, J=12.0 Hz, 2H), 3.21 (br d, J=12.0 Hz, 2H), 2.79 (quin, J=12.0 Hz, 4H), 2.29-2.37 (m, 6H), 1.70-1.88 (m, 4H), 1.54-1.68 (m, 2H), 1.37-1.51 (m, 2H), 1.21-1.36 (m, 2H), 1.14 (br t, J=7.2 Hz, 2H).

Chemical Formula: C$_{24}$H$_{36}$Cl$_2$N$_2$O$_2$, Molecular Weight: 455.46

Step 12: Preparation of benzyl 3-[4-[[1-(4-tertbutoxycarbonylphenyl)-4-piperidyl]methyl]-1-piperidyl]bicyclo[1.1.1]pentane-1-carboxylate

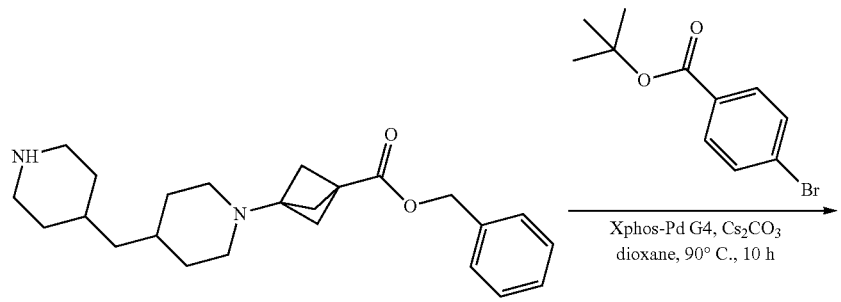

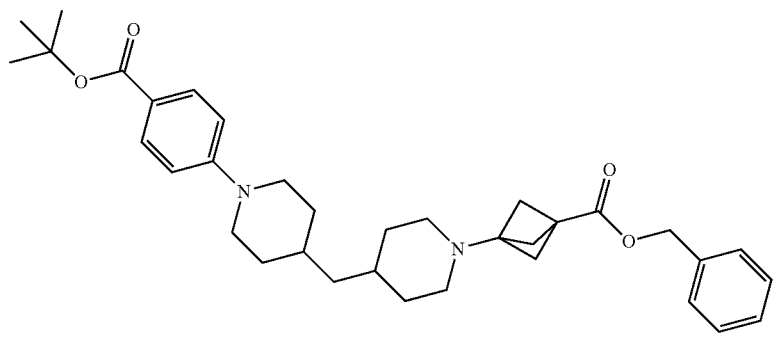

To a solution of benzyl 3-[4-(4-piperidylmethyl)-1-piperidyl]bicyclo[1.1.1]pentane-1-carboxylate (100 mg, 0.24 mmol, 1.00 eq, hydrochloride salt) in dioxane (8 mL) was added methanesulfonato(2-dicyclohexylphosphino-2,4,6-tri-i-propyl-1,1-biphenyl)(2-methylamino-1,1-biphenyl-2-yl)palladium(II) (21 mg, 0.02 mmol, 0.10 eq) and tert-butyl 4-bromobenzoate (123 mg, 0.48 mmol, 2.00 eq), cesium carbonate (233 mg, 0.72 mmol, 3.00 eq). Then the mixture was stirred for 10 h at 100° C. LCMS showed that the reaction was completed. The mixture was concentrated under reduced pressure to remove dioxane. The residue was diluted with ethyl acetate (50 mL) and washed with water (50 mL). The organic layer was washed with brine (50 mL), dried over sodium sulfate and concentrated under reduced pressure to give the residue. The residue was purified by column chromatography on silica gel (petroleum ether: ethyl acetate=10:1~5:1~1:1) to give benzyl 3-[4-[[1-(4-tertbutoxycarbonylphenyl)-4-piperidyl]methyl]-1-piperidyl]bicyclo[1.1.1]pentane-1-carboxylate (130 mg, 232.66 umol, 48% yield) as a yellow solid.

LCMS: MS (ESI) m/z: 483.3[M+1]$^+$.

$^1$H NMR: (400 MHz, DMSO-d$_6$) δ: 7.81-7.93 (m, 2H), 7.31-7.45 (m, 5H), 6.86 (d, J=9.2 Hz, 2H), 5.15 (s, 2H), 3.85 (br d, J=12.8 Hz, 2H), 2.86-2.99 (m, 2H), 2.81 (td, J=12.4, 2.4 Hz, 2H), 1.95-2.20 (m, 8H), 1.74 (br t, J=12.8 Hz, 4H), 1.53-1.65 (m, 10H), 1.31-1.46 (m, 1H), 1.25-1.31 (m, 4H), 1.17-1.24 (m, 2H).

Chemical Formula: C$_{29}$H$_{42}$N$_2$O$_4$, Molecular Weight: 482.65

Step 13: Preparation of 3-[4-[[1-(4-tert-butoxycarbonylphenyl)-4-piperidyl]methyl]-1-piperidyl]bicyclo[1.1.1]pentane-1-carboxylic acid

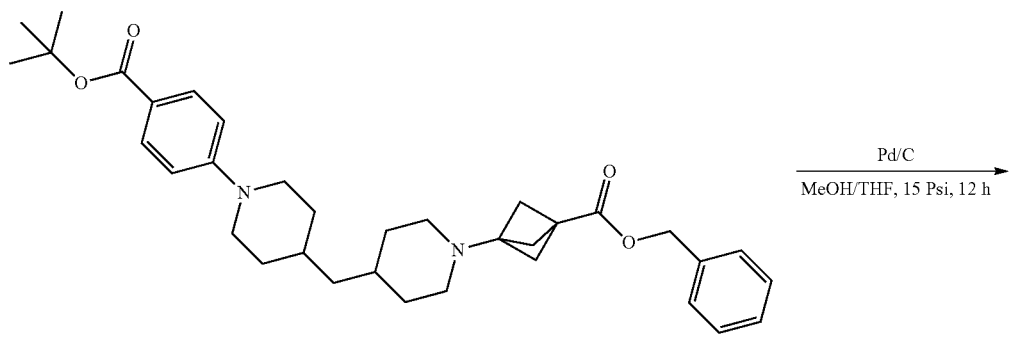

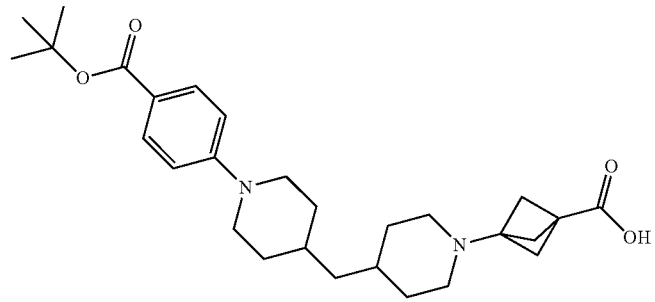

To a solution of benzyl 3-[4-[[1-(4-tert-butoxycarbonylphenyl)-4-piperidyl]methyl]-1-piperidyl]bicyclo[1.1.1]pentane-1-carboxylate (100 mg, 0.18 mmol, 1.00 eq) in the mixed solvent of methanol (15 mL) and tetrahydrofuran (5 mL) was added palladium on activated carbon (100 mg, 10% purity) in the atmosphere of hydrogen (15 psi). The mixture was stirred at 40° C. for 4 h. LCMS indicated the desired mass of the product was detected. The mixture was filtered and the filtrate was evaporated under vacuum to give 3-[4-[[1-(4-tert-butoxycarbonylphenyl)-4-piperidyl]methyl]-1-piperidyl]bicyclo[1.1.1]pentane-1-carboxylic acid (83 mg, crude) as a light yellow solid.

LCMS: MS (ESI) m/z: 469.3[M+1]$^+$.

Chemical Formula: $C_{28}H_{40}N_2O_4$, Molecular Weight: 468.63

Step 14: tert-butyl 4-[4-[[1-[1-[(2,6-dioxo-3-piperidyl)carbamoyl]-3-bicyclo[1.1.1]pentanyl]-4-piperidyl]methyl]-1-piperidyl]benzoate To a solution of 3-[4-[[1-(4-tert-butoxycarbonylphenyl)-4-piperidyl]methyl]-1-piperidyl]bicyclo[1.1.1]pentane-1-carboxylic acid (83 mg, 0.17 mmol, 1.00 eq) and 3-aminopiperidine-2,6-dione (29 mg, 0.17 mmol, 1.00 eq, hydrochloride salt) in dimethylformamide (5 mL) was added hydroxybenzotriazole (35 mg, 0.27 mmol, 1.50 eq), 1-(3-dimethylaminopropyl)-3-ethylcarbodiimide hydrochloride (51 mg, 0.26 mmol, 1.50 eq) and diisopropylethylamine (115 mg, 0.89 mmol, 5.00 eq). The mixture was stirred at 25° C. for 3 h. LCMS indicated that the reaction worked well. Then the mixture was stirred at 25° C. for further 2 h. To the mixture was added water (20 mL) and extracted with ethyl acetate (5 mL×3). The combined organic layers were concentrated under reduced pressure to get a residue. The residue was purified through preparative thin layer chromatography (dichloromethane:methanol=20:1) to give tert-butyl 4-[4-[[1-[1-[(2,6-dioxo-3-piperidyl)carbamoyl]-3-bicyclo[1.1.1]pentanyl]-4-piperidyl]methyl]-1-piperidyl]benzoate (63 mg, 0.11 mmol, 60% yield, 98% purity) as a white solid.

LCMS: MS (ESI) m/z: 579.3[M+1]$^+$.

Chemical Formula: $C_{33}H_{46}N_4O$, Molecular Weight: 578.74

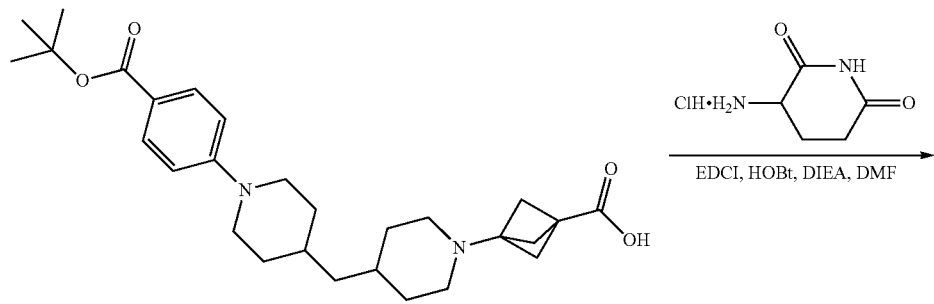

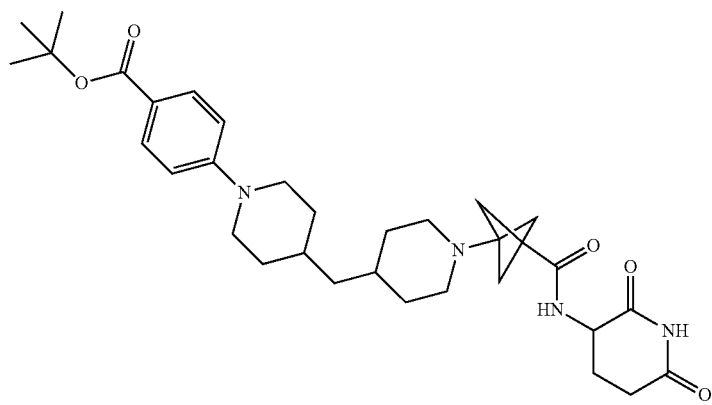

Step 15: Preparation of 4-[4-[[1-[1-[(2,6-dioxo-3-piperidyl)carbamoyl]-3-bicyclo[1.1.1]pentanyl]-4-piperidyl]methyl]-1-piperidyl]benzoic acid

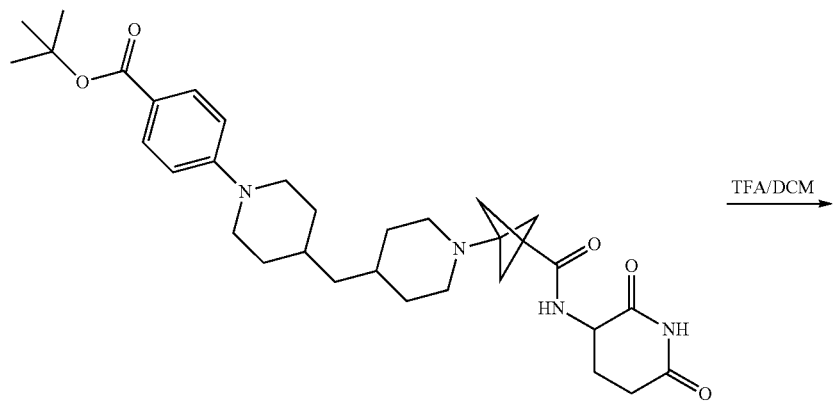

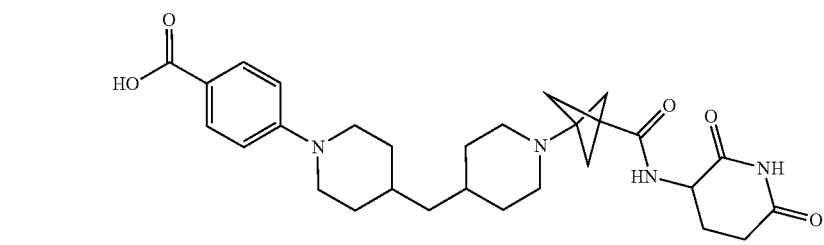

To a solution of tert-butyl 4-[4-[[1-[1-[(2,6-dioxo-3-piperidyl)carbamoyl]-3-bicyclo[1.1.1]pentanyl]-4-piperidyl]methyl]-1-piperidyl]benzoate (40 mg, 0.07 mmol, 1.00 eq) in dichloromethane (4 mL) was added trifluoroacetic acid (1.5 mL). The mixture was stirred at 20° C. for 2 h. The reaction mixture was concentrated under reduced pressure to give 4-[4-[[1-[1-[(2,6-dioxo-3-piperidyl)carbamoyl]-3-bicyclo[1.1.1]pentanyl]-4-piperidyl]methyl]-1-piperidyl]benzoic acid (43 mg, crude, trifluoroacetic salt) as a light yellow oil, which was used for next step directly.

LCMS: MS (ESI) m/z: 523.2[M+1]$^+$.

Chemical Formula: $C_{29}H_{38}N_4O$, Molecular Weight: 522.64

Step 16: Preparation of 3-[4-[[1-[4-[[3-(4-cyano-3,5-dimethyl-phenoxy)-2,2,4,4-tetramethylcyclobutyl]carbamoyl]phenyl]-4-piperidyl]methyl]-1-piperidyl]-N-(2,6-dioxo-3-piperidyl)bicyclo[1.1.1]pentane-1-carboxamide, Compound 70

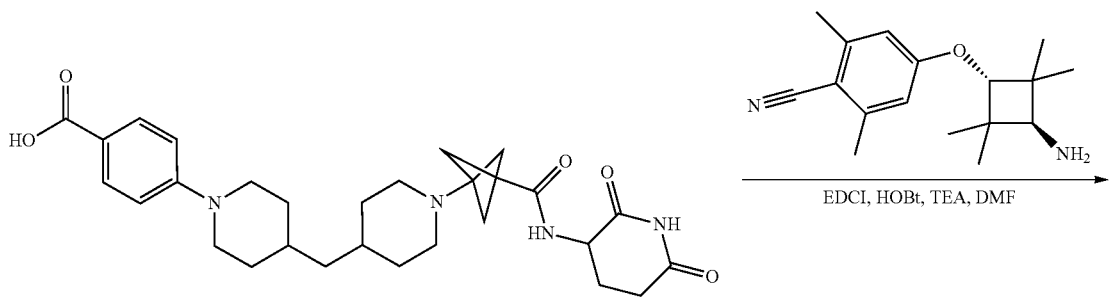

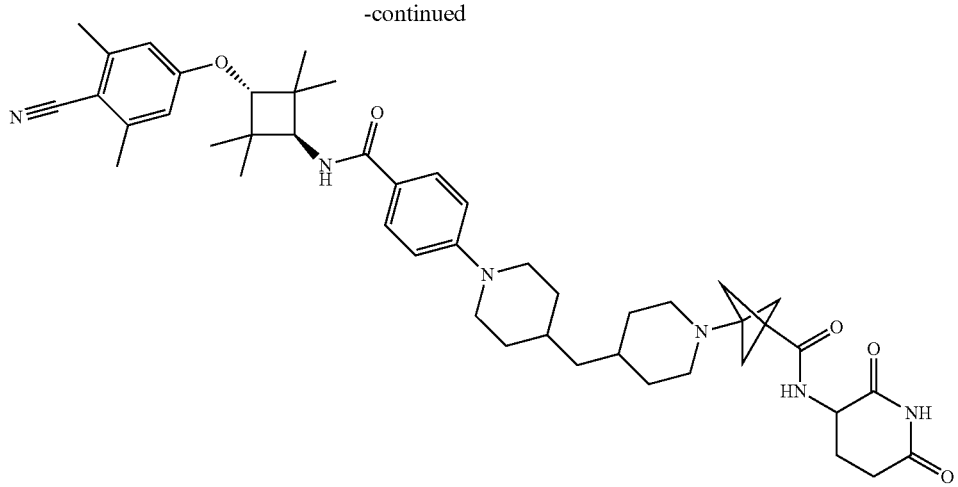

To a solution of 4-[4-[[1-[1-[(2,6-dioxo-3-piperidyl)carbamoyl]-3-bicyclo[1.1.1]pentanyl]-4-piperidyl]methyl]-1-piperidyl]benzoic acid (43 mg, 0.07 mmol, 1.00 eq, trifluoroacetic salt) and 4-(3-amino-2,2,4,4-tetramethylcyclobutoxy)-2,6-dimethylbenzonitrile (33 mg, 0.11 mmol, 1.50 eq, hydrochloride) in dimethylformamide (2 mL) was added diisopropylethylamine (44 mg, 0.33 mmol, 5.00 eq), hydroxybenzotriazole (14 mg, 0.10 mmol, 1.50 eq), 1-(3-dimethylaminopropyl)-3-ethylcarbodiimide hydrochloride (19 mg, 0.10 mmol, 1.50 eq). Then the mixture was stirred for 2 h at 30° C. LCMS showed that the reaction was completed. The mixture was filtered. The filtrate was purified by preparative high performance liquid chromatography (column: Phenomenex Synergi C18 150*25*10 um; mobile phase: [water (0.225% FA)-ACN]; B %: 30%-51%, 7 min) to give 3-[4-[[1-[4-[[3-(4-cyano-3,5-dimethyl-phenoxy)-2,2,4,4-tetramethylcyclobutyl]carbamoyl]phenyl]-4-piperidyl]methyl]-1-piperidyl]-N-(2,6-dioxo-3-piperidyl)bicyclo[1.1.1]pentane-1-carboxamide (16.6 mg, 0.02 mmol, 30% yield, 96% purity) as a white solid.

QC-LCMS: MS (ESI) m/z: 777.3[M+1]$^+$.

$^1$H NMR: (400 MHz, DMSO-d$_6$) δ: 10.67-10.92 (m, 1H), 8.01 (d, J=8.4 Hz, 1H), 7.73 (d, J=8.8 Hz, 2H), 7.47 (d, J=9.2 Hz, 1H), 6.95 (d, J=9.0 Hz, 2H), 6.66-6.78 (m, 2H), 4.48-4.59 (m, 1H), 4.23 (s, 1H), 4.04 (d, J=9.0 Hz, 1H), 3.84 (br d, J=12.2 Hz, 2H), 2.70-2.84 (m, 5H), 2.39-2.48 (m, 7H), 1.80-2.04 (m, 10H), 1.61-1.76 (m, 4H), 1.50-1.60 (m, 1H), 1.26-1.39 (m, 1H), 1.22 (s, 6H), 1.10-1.18 (m, 10H), 1.00-1.10 (m, 2H).

Chemical Formula: C$_{46}$H$_{60}$N$_6$O$_5$, Molecular Weight: 777.01

Example 25—$^1$H NMR and Mass Spectroscopy

The $^1$H NMR and mass spectroscopy data for the compounds of the disclosure is provided below in Table 3.

TABLE 3

$^1$H NMR AND MASS SPECTROSCOPY DATA FOR THE COMPOUNDS OF THE DISCLOSURE

| Compound No. | Compound Name | Exact Mass | Observed m/z [M + 1]$^+$ | $^1$H NMR Data |
|---|---|---|---|---|
| 1 | 4-(4-((1-(4-(((1R,3R)-3-(4-cyano-3-methoxyphenoxy)-2,2,4,4-tetramethylcyclobutyl)carbamoyl)phenyl)piperidin-4-yl)methyl)piperazin-1-yl)-N-(2,6-dioxopiperidin-3-yl)-2-fluorobenzamide | 807.411961 | 808.63 | $^1$H NMR (400 MHz, DMSO-d$_6$) δ 10.84 (s, 1H), 8.17 (s, 1H), 8.04 (t, J = 7.2 Hz, 1H), 7.74 (d, J = 8.8 Hz, 2H), 7.60-7.68 (m, 2H), 7.49 (d, J = 9.2 Hz, 1H), 6.96 (d, J = 9.2 Hz, 2H), 6.74-6.86 (m, 2H), 6.64 (d, J = 2.0 Hz, 1H), 6.55 (dd, J = 8.4, 2.0 Hz, 1H), 4.69-4.78 (m, 1H), 4.28 (s, 1H), 4.06 (d, J = 9.2 Hz, 1H), 3.91 (s, 3H), 3.86 (d, J = 13.2 Hz, 2H), 3.31 (s, 4H), 2.73-2.85 (m, 3H), 2.54 (d, J = 4.0 Hz, 1H), 2.49 (s, 4H), 2.21 (d, J = 6.8 Hz, 2H), 2.06-2.16 (m, 1H), 1.98-2.05 (m, 1H), 1.76-1.85 (m, 3H), 1.23 (s, 6H), 1.22-1.17 (m, 2H), 1.15 (s, 6H). |
| 2 | N-((1R,3R)-3-(4-cyano-3,5-dimethylphenoxy)-2,2,4,4-tetramethylcyclobutyl)-6-(4-((4-(4-((2,6- | 789.432616 | 790.7533333 | $^1$H NMR (300 MHz, CDCl$_3$) δ 8.13 (m, 1H), 8.00-7.97 (m, 1H), 7.87 (m, 1H), 7.76-7.74 (m, 2H), 7.01-6.92 (m, 1H), 6.89-6.84 (m, 3H), 6.58 (m, 2H), 4.77-4.71 (m, 1H), 4.57-4.52 (m, 2H), 4.19-4.16 (m, 1H), 4.05 (m, 1H), 3.33-3.29 |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | dioxopiperidin-3-yl)carbamoyl)phenyl)piperazin-1-yl)methyl)piperidin-1-yl)pyridazine-3-carboxamide | | | (m, 3H), 3.12-3.07 (m, 2H), 2.85-2.82 (m, 3H), 2.80-2.75 (m, 3H), 2.49 (m, 5H), 2.28-2.22 (m, 2H), 2.01-1.91 (m, 2H), 1.39-1.11 (m, 19H). |
| 3 | N-((1R,3R)-3-(3-chloro-4-cyanophenoxy)-2,2,4,4-tetramethylcyclobutyl)-6-(4-((4-(4-((2,6-dioxopiperidin-3-yl)carbamoyl)phenyl)piperazin-1-yl)methyl)piperidin-1-yl)pyridazine-3-carboxamide | 795.362343 | 796.68 | ¹H NMR (300 MHz, DMSO) δ 10.81 (s, 1H), 8.46-8.43 (m, 1H), 8.25-8.22 (m, 1H), 7.91-7.89 (m, 1H), 7.83-7.81 (m, 1H), 7.77-7.45 (m, 2H), 7.38-7.35 (m, 1H), 7.25 (s, 1H), 7.05-6.97 (m, 3H), 4.76-4.74 (m,1H), 4.52-4.46 (m, 3H), 4.02-4.00 (m, 1H), 3.20 (m, 4H), 3.08-3.02 (m, 2H), 2.83-2.76 (m, 1H), 2.60 (m, 4H), 2.23-2.13 (m, 2H), 2.10-2.00 (m, 1H), 1.97-1.84 (m, 4H), 1.28-1.03 (m, 15H). |
| 4 | 3-(4-((1-(4-(((1R,3R)-3-(3-chloro-4-cyanophenoxy)-2,2,4,4-tetramethylcyclobutyl)carbamoyl)phenyl)piperidin-4-yl)methyl)piperazin-1-yl)-N-(2,6-dioxopiperidin-3-yl)benzamide | 793.371845 | 794.69 | ¹H NMR (400 MHz, DMSO-d₆) δ 10.86 (s, 1H), 8.68 (d, J = 8.4 Hz, 1H), 8.15 (s, 1H), 7.91 (d, J = 8.8 Hz, 1H), 7.75 (d, J = 8.8 Hz, 2H), 7.48 (d, J = 8.8 Hz, 1H), 7.41 (s, 1H), 7.27-7.36 (m, 2H), 7.22 (d, J = 2.4 Hz, 1H), 7.10-7.15 (m, 1H), 7.02 (dd, J = 8.8, 2.4, 1H), 6.97 (d, J = 8.8 Hz, 2H), 4.72-4.84 (m, 1H), 4.33 (s, 1H), 4.06 (d, J = 9.2 Hz, 1H), 3.87 (d, J = 13.2 Hz, 2H), 3.16-3.28 (m, 6H), 2.75-2.88 (m, 3H), 2.53-2.61 (m, 4H), 2.22-2.29 (m, 2H), 2.07-2.20 (m, 1H), 1.93-2.03 (m, 1H), 1.76-1.86 (m, 3H), 1.23 (s, 6H), 1.20 (s, 1H), 1.14 (s, 6H). |
| 5 | 5-(4-((1-(4-(((1R,3R)-3-(4-cyano-3,5-dimethylphenoxy)-2,2,4,4-tetramethylcyclobutyl)carbamoyl)phenyl)piperidin-4-yl)methyl)piperazin-1-yl)-N-(2,6-dioxopiperidin-3-yl)nicotinamide | 788.437367 | 789.63 | ¹H NMR (CD₃OD, 300 MHz) δ 8.42 (m, 2H), 7.79 (s, 1H), 7.73 (d, 2H), 7.0 (d, 2H), 6.71 (s, 2H), 4.92-4.89 (m, 1H), 4.23 (s, 1H), 4.11 (m, 1H), 3.91 (d, 2H), 3.38-3.35 (m, 5H), 2.89-2.79 (m, 3H), 2.76-2.74 (m, 1H), 2.69-2.64 (m, 4H), 2.47 (s, 6H), 2.33 (d, 2H), 2.25-2.16 (m, 3H), 1.39-1.31 (m, 3H), 1.28 (s, 6H), 1.21 (s, 6H). |
| 6 | 5-(4-((1-(4-(((1R,3R)-3-(4-cyano-3,5-dimethylphenoxy)-2,2,4,4-tetramethylcyclobutyl)carbamoyl)phenyl)piperidin-4-yl)methyl)piperazin-1-yl)-N-(2,6-dioxopiperidin-3-yl)-2-fluorobenzamide | 805.432696 | 806.635 | ¹H NMR (400 MHz, Methanol-d₄) δ 8.29 (s, 3H), 7.75 (d, J = 8.7 Hz, 1H), 7.02 (d, J = 8.9 Hz, 1H), 6.73 (s, 1H), 4.24 (s, 0H), 3.93 (s, 1H), 3.36 (s, 3H), 2.90 (d, J = 12.4 Hz, 3H), 2.49 (s, 3H), 1.37-1.27 (m, 6H), 1.22 (s, 3H). |
| 7 | N-((1R,3R)-3-(3-chloro-4-cyanophenoxy)-2,2,4,4-tetramethylcyclobutyl)-4-(4-((4-(4-((2,6-dioxopiperidin-3-yl)carbamoyl)phenyl)piperazin-1-yl)methyl)piperidin-1-yl)benzamide | 793.371845 | 794.69 | ¹H NMR (400 MHz, DMSO-d₆) δ 10.82 (s, 1H), 8.47 (d, J = 8.4 Hz, 1H), 8.14 (s, 1H), 7.90 (d, J = 8.8 Hz, 1H), 7.75 (t, J = 8.8 Hz, 4H), 7.48 (d, J = 9.2 Hz, 1H), 7.21 (d, J = 2.4 Hz, 1H), 7.02-6.95 (m, 5H), 4.79-4.70 (m, 1H), 4.32 (s, 1H), 4.05 (d, J = 9.2 Hz, 1H), 3.86 (br d, J = 12.4 Hz, 2H), 3.29-3.27 (m, 6H), 2.80 (br t, J = 12.0 Hz, 3H), 2.57-2.52 (m, 4H), 2.24 (br s, 2H), 2.15-2.07 (m, 1H), 1.99-1.92 (m, 1H), 1.84-1.76 (m, 3H), 1.22 (s, 6H), 1.18 (br d, J = 4.8 Hz, 1H), 1.13 (s, 6H). |
| 8 | 5-(4-((1-(4-(((1R,3R)-3-(3-chloro-4-cyanophenoxy)-2,2,4,4-tetramethylcyclobutyl)carbamoyl)phenyl) | 811.362424 | 812.68 | ¹H NMR (400 MHz, Chloroform-d) δ 7.92 (s, 1H), 7.70 (d, J = 8.8 Hz, 2H), 7.64-7.55 (m, 2H), 7.13-7.04 (m, 2H), 6.98 (d, J = 2.4 Hz, 1H), 6.93 (d, J = 8.8 Hz, 2H), 6.83 (dd, J = 8.7, 2.4 Hz, 1H), 6.12 (d, J = 8.1 Hz, 1H), 4.80 (dt, J = |

TABLE 3-continued

¹H NMR AND MASS SPECTROSCOPY DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | piperidin-4-yl)methyl)piperazin-1-yl)-N-(2,6-dioxopiperidin-3-yl)-2-fluorobenzamide | | | 11.6, 5.3 Hz, 1H), 4.17 (d, J = 8.1 Hz, 1H), 4.06 (s, 1H), 3.87 (d, J = 12.7 Hz, 2H), 3.22 (s, 3H), 2.86 (s, 3H), 2.85-2.68 (m, 1H), 2.61 (s, 3H), 2.30 (s,1H), 2.01 (tt, J = 12.7, 6.0 Hz, 1H), 1.93 (d, J = 14.4 Hz, 1H), 1.26 (d, J = 17.1 Hz, 14H), 0.92-0.83 (m, 1H), 0.13-0.04 (m, 1H), 0.09 (s, 14H). |
| 9 | N-((1R,3R)-3-(3-chloro-4-cyanophenoxy)-2,2,4,4-tetramethylcyclobutyl)-5-(4-((((1R,3R)-3-(3-((2,6-dioxopiperidin-3-yl)carbamoyl)phenoxy)cyclobutyl)(isopropyl)amino)methyl)piperidin-1-yl)pyrazine-2-carboxamide | 838.393309 | 839.7166667 | ¹H NMR (400 MHz, DMSO-d₆) δ 10.87 (s, 1H), 8.74 (d, J = 8.4 Hz, 1H), 8.57-8.64 (m, 1H), 8.27-8.39 (m, 2H), 7.91 (d, J = 8.8 Hz, 1H), 7.81 (d, J = 9.2 Hz, 1H), 7.44 (br d, J = 7.6 Hz, 1H), 7.29-7.42 (m, 2H), 7.25 (d, J = 2.4 Hz, 1H), 6.95-7.10 (m, 2H), 4.67-4.82 (m, 1.6H), 4.31-4.58 (m, 3.5H), 3.96 (d, J = 8.8 Hz, 1H), 3.56-3.69 (m, 1H), 2.75-3.02 (m, 5H), 2.34-2.41 (m, 2H), 2.25 (br d, J = 6.8 Hz, 2H), 2.10-2.19 (m, 2.5H), 1.93-2.10 (m, 1.6H), 1.86 (br d, J = 10.5 Hz, 2H), 1.70 (br s, 1H), 1.19 (s, 6H), 1.13 (s, 6H), 0.99-1.11 (m, 2H), 0.93 (br d, J = 6.4 Hz, 6H). |
| 10 | 4-(4-((1-(4-((((1R,3R)-3-(4-cyano-3,5-dimethylphenoxy)-2,2,4,4-tetramethylcyclobutyl)carbamoyl)phenyl)piperidin-4-yl)methyl)piperazin-1-yl)-N-(2,6-dioxopiperidin-3-yl)picolinamide | 788.437367 | 789.75 | ¹H NMR (400 MHz, Chloroform-d) δ 8.77 (d, J = 7.0 Hz, 1H), 8.27 (d, J = 5.9 Hz, 1H), 7.99 (s, 1H), 7.70 (d, J = 8.9 Hz, 2H), 7.63 (d, J = 2.7 Hz, 1H), 6.94 (d, J = 8.8 Hz, 2H), 6.77 (dd, J = 6.0, 2.7 Hz, 1H), 6.60 (s, 2H), 6.13 (d, J = 8.1 Hz, 1H), 4.80 (dt, J = 12.5, 6.1 Hz, 1H), 4.15 (d, J = 8.1 Hz, 1H), 4.04 (s,1H), 3.87 (d, J = 12.6 Hz, 2H), 2.92-2.74 (m, 4H), 2.65-2.56 (m, 1H), 2.50 (s, 6H), 2.34 (s, 1H), 2.15-1.99 (m, 1H), 1.95 (s,2H), 1.82 (s, 1H), 1.25 (d, J = 14.1 Hz, 12H), 0.85 (s, 1H), 0.13-0.04 (m, 1H), 0.09 (s, 12H). |
| 11 | N-((1R,3R)-3-(4-cyano-3,5-dimethylphenoxy)-2,2,4,4-tetramethylcyclobutyl)-2-(4-((((1R,3R)-3-(3-((2,6-dioxopiperidin-3-yl)carbamoyl)phenoxy)cyclobutyl)(isopropyl)amino)methyl)piperidin-1-yl)pyrimidine-5-carboxamide | 832.463582 | 833.79 | ¹H NMR (400 MHz, Methanol-d₄) δ 8.74 (s, 2H), 7.48-7.41 (m, 1H), 7.39 (t, J = 7.8 Hz, 1H), 7.32 (t, J = 2.0 Hz, 1H), 7.08-7.00 (m, 1H), 6.73 (s, 2H), 4.77 (t, J = 6.4 Hz, 1H), 4.23 (s, 1H), 4.13 (s, 1H), 3.76 (s, 1H), 2.98 (t, J = 12.4 Hz, 2H), 2.89-2.79 (m, 1H), 2.73 (dt, J = 17.6, 3.7 Hz, 1H), 2.49 (s, 6H), 2.35 (s, 1H), 2.28 (s, 3H), 2.27-2.21 (m, 1H), 2.21 (t, J = 7.5 Hz, 1H), 1.96 (d, J = 12.6 Hz, 2H), 1.77 (s, 1H), 1.29 (s, 6H), 1.22 (s, 6H), 1.11 (d, J = 12.1 Hz, 2H), 1.03 (d, J = 6.6 Hz, 6H). |
| 12 | N-((1R,3R)-3-(4-cyano-3,5-dimethylphenoxy)-2,2,4,4-tetramethylcyclobutyl)-2-(4-(((((1R,3R)-3-(4-((2,6-dioxopiperidin-3-yl)carbamoyl)phenoxy)cyclobutyl)(isopropyl)amino)methyl)piperidin-1-yl)pyrimidine-5-carboxamide | 832.463582 | 833.79 | ¹H NMR (400 MHz, Methanol-d₄) δ 8.75 (s, 2H), 7.89-7.82 (m, 2H), 6.91 (d, J = 8.9 Hz, 2H), 6.73 (s, 2H), 4.92 (s, 1H), 4.88 (s, 2H), 4.78 (d, J = 6.4 Hz, 1H), 4.23 (s, 1H), 4.13 (s, 1H), 3.76 (t, J = 8.1 Hz, 1H), 3.04 (s, 1H), 2.98 (t, J = 12.6 Hz, 2H), 2.83 (dt, J = 11.8, 6.5 Hz, 1H), 2.77-2.67 (m, 1H), 2.49 (s, 6H), 2.35 (d, J = 6.7 Hz, 2H), 2.22 (ddd, J = 16.9, 14.2, 8.4 Hz, 5H), 1.96 (d, J = 13.0 Hz, 2H), 1.77 (s, 1H), 1.40 (s, 0H), 1.29 (s, 6H), 1.22 (s, 6H), 1.16-1.07 (m, 2H), 1.03 (d, J = 6.6 Hz, 6H), 0.12 (d, J = 2.5 Hz, 1H). |
| 13 | N-((1R,3R)-3-(4-cyano-3,5-dimethylphenoxy)-2,2,4,4-tetramethylcyclobutyl)-5-(4-(((((1R,3R)-3-(4-((2,6-dioxopiperidin-3-yl)carbamoyl)phenoxy)cyclobutyl)(isopropyl) | 832.463582 | 833.79 | ¹H NMR (400 MHz, Methanol-d₄) δ 8.68 (d, J = 1.3 Hz, 1H), 8.25 (d, J = 1.4 Hz, 1H), 7.86 (d, J = 8.7 Hz, 2H), 6.92 (d, J = 8.7 Hz, 2H), 6.74 (s, 2H), 4.79 (s, 1H), 4.61 (d, J = 12.2 Hz, 2H), 4.27 (s, 1H), 4.06 (s, 1H), 3.04 (t, J = 12.6 Hz, 2H), 2.83 (dd, J = 11.6, 6.8 Hz, 1H), 2.77-2.68 (m, 1H), 2.49 (s, 6H), 2.33 (s, 7H), 2.27-2.16 (m, 2H), 2.08-1.96 (m, 3H), |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | amino)methyl)piperidin-1-yl)pyrazine-2-carboxamide | | | 1.82 (s, 2H), 1.29 (s, 7H), 1.24 (s, 5H), 1.22 (s, 6H), 1.06 (s, 5H), 0.92 (s, 1H), 0.12 (s, 1H). |
| 14 | 4-(4-((1-(4-(((1R,3R)-3-(4-cyano-3-methoxyphenoxy)-2,2,4,4-tetramethylcyclobutyl)carbamoyl)phenyl)piperidin-4-yl)methyl)piperazin-1-yl)-N-((R)-2,6-dioxopiperidin-3-yl)-2-fluorobenzamide | 807.412 | 808.54 | ¹H NMR (400 MHz, DMSO-d6) δ: 10.84 (s, 1H), 8.05 (t, J = 7.2 Hz, 1H), 7.75 (d, J = 8.8 Hz, 2H), 7.69-7.60 (m, 2H), 7.51 (d, J = 9.2 Hz, 1H), 6.96 (d, J = 8.8 Hz, 2H), 6.87-6.74 (m, 2H), 6.65 (d, J = 2.0 Hz, 1H), 6.55 (d, J = 8.8, 2.0 Hz, 1H), 4.83-4.65 (m, 1H), 4.29 (s, 1H), 4.06 (d, J = 9.2 Hz, 1H), 3.95-3.79 (m, 5H), 3.32-3.24 (m, 4H), 2.87-2.72 (m, 3H), 2.56-2.53 (m, 2H), 2.49-2.46 (m, 3H), 2.25-2.17 (m, 2H), 2.17-2.08 (m, 1H), 2.06-2.00 (m, 1H), 1.81 (d, J = 12.0 Hz, 3H), 1.27-1.10 (m, 14H). |
| 15 | N-((1R,3R)-3-(4-cyano-3,5-dimethylphenoxy)-2,2,4,4-tetramethylcyclobutyl)-5-(4-(((1R,3R)-3-(3-((2,6-dioxopiperidin-3-yl)carbamoyl)phenoxy)cyclobutyl)(isopropyl)amino)methyl)piperidin-1-yl)pyrazine-2-carboxamide | 832.463582 | 833.79 | ¹H NMR (400 MHz, Methanol-d₄) δ 8.67 (d, J = 1.4 Hz, 1H), 8.24 (d, J = 1.3 Hz, 1H), 7.45 (d, J = 7.6 Hz, 1H), 7.39 (t, J = 7.9 Hz, 1H), 7.32 (s, 1H), 7.04 (d, J = 8.3 Hz, 1H), 6.74 (s, 2H), 4.77 (s, 1H), 4.60 (d, J = 13.3 Hz, 2H), 4.27 (s, 1H), 4.06 (s, 1H), 3.77 (s, 1H), 3.03 (t, J = 12.5 Hz, 3H), 2.84 (dd, J = 17.3, 7.4 Hz, 1H), 2.78-2.69 (m, 1H), 2.49 (s, 6H), 2.36 (s, 2H), 2.23 (tt, J = 11.6, 7.0 Hz, 4H), 2.00 (d, J = 13.1 Hz, 2H), 1.79 (s, 1H), 1.29 (s, 6H), 1.22 (s, 6H), 1.18 (s, 2H), 1.03 (d, J = 6.5 Hz, 6H), 0.92 (s, 0H), 0.12 (s, 1H). |
| 16 | N-((1R,3R)-3-(3-chloro-4-cyanophenoxy)-2,2,4,4-tetramethylcyclobutyl)-5-(4-((((1R,3R)-3-(4-((2,6-dioxopiperidin-3-yl)carbamoyl)phenoxy)cyclobutyl)(isopropyl)amino)methyl)piperidin-1-yl)pyrazine-2-carboxamide | 838.393309 | 839.72 | ¹H NMR (400 MHz, Methanol-d₄) δ 8.67 (d, J = 1.3 Hz, 1H), 8.24 (d, J = 1.3 Hz, 1H), 7.89-7.81 (m, 2H), 7.75 (d, J = 8.8 Hz, 1H), 7.17 (d, J = 2.4 Hz, 1H), 7.01 (dd, J = 8.8, 2.5 Hz, 1H), 6.91 (d, J = 8.8 Hz, 2H), 4.77 (s, 1H), 4.60 (d, J = 13.4 Hz, 2H), 4.33 (s, 1H), 4.09 (s, 1H), 3.76 (t, J = 8.1 Hz, 1H), 3.03 (t, J = 12.4 Hz, 3H), 2.85 (ddd, J = 18.5, 11.7, 6.7 Hz, 1H), 2.77-2.68 (m, 1H), 2.45 (s, 2H), 2.35 (d, J = 7.1 Hz, 2H), 2.32-2.15 (m, 4H), 2.00 (d, J = 13.0 Hz, 2H), 1.78 (s, 2H), 1.30 (s, 7H), 1.23 (s, 6H), 1.16 (dd, J = 12.2, 8.6 Hz, 2H), 1.03 (d, J = 6.6 Hz, 6H), 0.91 (s, 1H), 0.11 (d, J = 4.4Hz, 0H). |
| 17 | N-((1R,3R)-3-(3-chloro-4-cyanophenoxy)-2,2,4,4-tetramethylcyclobutyl)-6-(4-((4-(4-((2,6-dioxopiperidin-3-yl)carbamoyl)-3-fluorophenyl)piperazin-1-yl)methyl)piperidin-1-yl)pyridazine-3-carboxamide | 813.352922 | 814.67 | ¹H NMR (400 MHz, DMSO-d₆) δ 10.85 (s, 1H), 8.25 (d, J = 9.2 Hz, 1H), 8.16 (s, 1H), 8.05 (t, J = 7.2 Hz, 1H), 7.91 (d, J = 8.8 Hz, 1H), 7.82 (d, J = 9.6 Hz, 1H), 7.64 (t, J = 8.8 Hz, 1H), 7.37 (d, J = 9.6 Hz, 1H), 7.26 (d, J = 2.4 Hz, 1H), 7.04 (dd, J = 8.8, 2.4 Hz, 1H), 6.75-6.87 (m, 2H), 4.69-4.79 (m, 1H), 4.45-4.55 (m, 3H), 4.01 (d, J = 9.2 Hz, 1H), 3.34-3.49 (m, 4H), 3.05 (t, J = 11.6 Hz, 2H), 2.72-2.84 (m, 1H), 2.51-2.56 (m, 4H), 2.21 (d, J = 6.8 Hz, 2H), 2.07-2.16 (m, 1H), 1.98-2.05 (m, 1H), 1.94 (s, 1H), 1.85 (d, J = 13.2 Hz, 2H), 1.23 (s, 6H), 1.15 (s, 9H). |
| 18 | N-((1R,3R)-3-(3-chloro-4-cyanophenoxy)-2,2,4,4-tetramethylcyclobutyl)-5-(4-((4-(4-((2,6-dioxopiperidin-3-yl)carbamoyl)-3-fluorophenyl)piperazin-1-yl)methyl)piperidin-1-yl)pyrazine-2-carboxamide | 813.352922 | 814.67 | ¹H NMR (400 MHz, DMSO-d₆) δ 10.85 (s, 1H), 8.61 (s, 1H), 8.34 (s, 1H), 8.06 (t, J = 7.2 Hz, 1H), 7.91 (s, 1H), 7.81 (d, J = 9.2 Hz, 1H), 7.64 (t, J = 9.2 Hz, 1H), 7.25 (d, J = 2.4 Hz, 1H), 7.03 (dd, J = 8.8, 2.4 Hz, 1H), 6.72-6.87 (m, 2H), 4.67-4.79 (m, 1H), 4.40-4.54 (m, 3H), 3.96 (d, J = 8.8 Hz, 1H), 3.27-3.32 (m, 4H), 3.02 (t, J = 11.6 Hz, 2H), 2.71-2.85 (m, 1H), 2.51-2.58 (m, 4H), 2.22 (d, J = 6.0 Hz, 2H), 2.08-2.16 (m, 1H), 1.89-2.06 (m, 2H), 1.84 (d, J = 12.8 Hz, 2H), 1.05-1.25 (m, 15H). |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| 19 | 4-(4-((1-(4-(((1R,3R)-3-(3-chloro-4-cyanophenoxy)-2,2,4,4-tetramethylcyclobutyl)carbamoyl)phenyl)piperidin-4-yl)methyl)piperazin-1-yl)-N-(2,6-dioxopiperidin-3-yl)-2-fluorobenzamide | 811.362424 | 812.68 | ¹H NMR (400 MHz, DMSO-d₆) δ 10.84 (s, 1H), 8.21 (s, 1H), 8.04 (t, J = 7.2 Hz, 1H), 7.91 (d, J = 8.8 Hz, 1H), 7.74 (d, J = 8.8 Hz, 2H), 7.64 (t, J = 9.2 Hz, 1H), 7.48 (d, J = 9.2 Hz, 1H), 7.21 (d, J = 2.4 Hz, 1H), 6.93-7.05 (m, 3H), 6.75-6.86 (m, 2H), 4.69-4.78 (m, 1H), 4.33 (s, 1H), 4.06 (d, J = 9.2 Hz, 1H), 3.86 (d, J = 13.2 Hz, 2H), 3.34-3.42 (m, 4H), 2.72-2.84 (m, 3H), 2.54 (d, J = 4.0 Hz, 1H), 2.52-2.57 (m, 1H), 2.49 (s, 2H), 2.45-2.50 (m, 1H), 2.21 (d, J = 6.8 Hz, 2H), 2.07-2.16 (m, 1H), 1.98-2.06 (m, 1H), 1.75-1.85 (m, 3H), 1.22 (s, 8H), 1.12-1.15 (m, 1H), 1.13 (s, 5H). |
| 20 | 4-(4-((1-(4-(((1R,3R)-3-(4-cyano-3,5-dimethylphenoxy)-2,2,4,4-tetramethylcyclobutyl)carbamoyl)phenyl)piperidin-4-yl)methyl)piperazin-1-yl)-N-(2,6-dioxopiperidin-3-yl)-2-fluorobenzamide | 805.432696 | 806.74 | ¹H NMR (400 MHz, DMSO-d₆) δ 10.85 (s, 1H), 8.27 (s, 1H), 8.06 (t, J = 7.2 Hz, 1H), 7.74 (d, J = 8.8 Hz, 2H), 7.64 (t, J = 9.2 Hz, 1H), 7.48 (d, J = 9.6 Hz, 1H), 6.96 (d, J = 8.8 Hz, 2H), 6.76-6.86 (m, 2H), 6.72-6.75 (m, 2H), 4.69-4.79 (m, 1H), 4.23 (s, 1H), 4.04 (d, J = 9.6 Hz, 1H), 3.86 (d, J = 12.8 Hz, 2H), 3.37-3.46 (m, 4H), 2.74-2.83 (m, 3H), 2.44 (s, 8H), 1.96-2.25 (m, 5H), 1.81 (d, J = 11.6 Hz, 3H), 1.22 (s, 6H), 1.16 (s, 2H), 1.12 (s, 6H), 1.04 (s, 2H). |
| 21 | 4-(4-((1-(4-(((1R,3R)-3-(4-cyano-3-methoxyphenoxy)-2,2,4,4-tetramethylcyclobutyl)carbamoyl)phenyl)piperidin-4-yl)methyl)piperazin-1-yl)-N-((S)-2,6-dioxopiperidin-3-yl)-2-fluorobenzamide | 807.412 | 808.45 | ¹H NMR (400 MHz, DMSO-d6) δ: 10.84 (s, 1H), 8.05 (t, J = 7.2 Hz, 1H), 7.75 (d, J = 8.8 Hz, 2H), 7.69-7.60 (m, 2H), 7.51 (d, J = 9.2 Hz, 1H), 6.96 (d, J = 8.8 Hz, 2H), 6.87-6.74 (m, 2H), 6.65 (d, J = 2.0 Hz, 1H), 6.55 (d, J = 8.8, 2.0 Hz, 1H), 4.83-4.65 (m, 1H), 4.29 (s, 1H), 4.06 (d, J = 9.2 Hz, 1H), 3.95-3.79 (m, 5H), 3.32-3.24 (m, 4H), 2.87-2.72 (m, 3H), 2.56-2.53 (m, 2H), 2.49-2.46 (m, 3H), 2.25-2.17 (m, 2H), 2.17-2.08 (m, 1H), 2.06-2.00 (m, 1H), 1.81 (d, J = 12.0 Hz, 3H), 1.27-1.10 (m, 14H). |
| 22 | N-((1R,4R)-4-(3-chloro-4-cyanophenoxy)cyclohexyl)-6-(4-((4-(6-((2,6-dioxopiperidin-3-yl)carbamoyl)pyridin-3-yl)piperazin-1-yl)methyl)piperidin-1-yl)pyridazine-3-carboxamide | 768.3263 | 769.52 | ¹H NMR (400 MHz, DMSO-d₆) δ 10.85 (s, 1H), 8.73 (d, J = 8.4 Hz, 1H), 8.59 (d, J = 8.4 Hz, 1H), 8.32 (d, J = 2.8 Hz, 1H), 8.16 (s, 1H), 7.86 (dd, J = 2.8, 8.8 Hz, 2H), 7.80 (d, J = 9.6 Hz, 1H), 7.42 (dd, J = 2.8, 8.8 Hz, 1H), 7.39 (d, J = 2.4 Hz, 1H), 7.33 (d, J = 9.6 Hz, 1H), 7.13 (dd, J = 2.4, 8.8 Hz, 1H), 4.80-4.69 (m, 1H), 4.58-4.44 (m, 3H), 3.91-3.79 (m, 1H), 3.02 (t, J = 11.6 Hz, 2H), 2.86-2.73 (m, 1H), 2.52 (d, J = 1.6 Hz, 9H), 2.26-2.15 (m, 3H), 2.10 (d, J = 10.0 Hz, 2H), 2.05-1.97 (m, 1H), 1.96-1.85 (m, 4H), 1.82 (s, 1H), 1.71-1.58 (m, 2H), 1.57-1.44 (m, 2H), 1.20-1.07 (m, 2H). |
| 23 | N-((1R,4R)-4-(3-chloro-4-cyanophenoxy)cyclohexyl)-6-(4-((4-(4-((2,6-dioxopiperidin-3-yl)carbamoyl)phenyl)piperazin-1-yl)methyl)piperidin-1-yl)pyridazine-3-carboxamide | 767.331 | 768.52 | ¹H NMR (400 MHz, DMSO-d₆) δ 10.83 (s, 1H), 8.59 (d, J = 7.6 Hz, 1H), 8.47 (d, J = 7.6 Hz, 1H), 8.20 (s, 1H), 7.85 (d, J = 8.8 Hz, 1H), 7.77 (dd, J = 8.8, 18.4 Hz, 3H), 7.39 (s, 1H), 7.33 (d, J = 9.6 Hz, 1H), 7.13 (d, J = 8.4 Hz, 1H), 6.97 (d, J = 8.4 Hz, 2H), 4.74 (s, 1H), 4.59-4.43 (m, 4H), 3.85 (s, 1H), 3.28-3.24 (m, 2H), 3.02 (t, J = 12.0 Hz, 2H), 2.85-2.73 (m, 3H), 2.20 (d, J = 7.6 Hz, 3H), 2.10 (d, J = 9.2 Hz, 4H), 2.02-1.77 (m, 6H), 1.71-1.58 (m, 3H), 1.51 (d, J = 12.8 Hz, 3H), 1.12 (d, J = 11.6 Hz, 2H). |
| 24 | N-((1R,4R)-4-(3-chloro-4-cyanophenoxy)cyclohexyl)-5-(4-((((1R,3R)-3-((6-((2,6- | 811.3573 | 812.49 | ¹H NMR (400 MHz, DMSO-d₆) δ 10.84 (s, 1H), 8.84 (d, J = 8.4 Hz, 1H), 8.58 (s, 1H), 8.29-8.21 (m, 2H), 8.17 (s, 1H), 8.07-7.95 (m, 2H), 7.85 (d, J = 8.8 Hz, 1H), 7.41-7.32 (m, 2H), 7.11 (dd, J = 2.4, |

TABLE 3-continued

¹H NMR AND MASS SPECTROSCOPY DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | dioxopiperidin-3-yl)carbamoyl)pyridin-3-yl)oxy)cyclobutyl)(isopropyl)amino)methyl)piperidin-1-yl)pyrazine-2-carboxamide | | | 8.8 Hz, 1H), 4.90-4.68 (m, 2H), 4.59-4.37 (m, 3H), 3.90-3.58 (m, 2H), 3.02-2.85 (m, 3H), 2.84-2.71 (m, 1H), 2.53 (d, J = 2.8 Hz, 2H), 2.44-2.31 (m, 3H), 2.30-1.95 (m, 9H), 1.92-1.79 (m, 4H), 1.73-1.42 (m, 5H), 1.05 (q, J = 10.8 Hz, 2H), 0.92 (d, J = 6.4 Hz, 6H). |
| 25 | N-((1R,4R)-4-(3-chloro-4-cyanophenoxy)cyclohexyl)-5-(4-((((1R,3R)-3-(4-((2,6-dioxopiperidin-3-yl)carbamoyl)-3-fluorophenoxy)cyclobutyl)(isopropyl)amino)methyl)piperidin-1-yl)pyrazine-2-carboxamide | 828.3526 | 829.49 | 1H NMR (400 MHz, DMSO-d₆) δ 10.83 (s, 1H), 8.58 ( s, 1H), 8.25-8.24 (d, J = 4 Hz 2H), 8.19 (s, 1H), 7.86-7.84 (d, J = 8 Hz 1H), 7.66 (s, 1H) 7.36 (s, 1H), 7.13-7.10 (d, J = 12 Hz 2H) 7.46-4.74 (d, J = 8 Hz 2H), 4.52-4.47 (m, 3H), 3.81 (s, 1H), 2.95 (m, 3H), 2.52-2.49 (m, 2H), 2.25-2.24 (m, 6H), 2.07-1.96 (m, 2H), 1.83-1.82 (m, 4H), 1.58-1.52 (m, 4H), 1.07 ( s, 2H), 0.93 (s, 6H). |
| 26 | N-((1R,4R)-4-(3-chloro-4-cyanophenoxy)cyclohexyl)-6-(4-((4-(4-((2,6-dioxopiperidin-3-yl)carbamoyl)-3-fluorophenyl)piperazin-1-yl)methyl)piperidin-1-yl)pyridazine-3-carboxamide | 785.3216 | 786.58 | ¹H NMR (400 MHz, DMSO-d₆) δ 10.85 (s, 1H), 8.61 (d, J = 8.2 Hz, 1H), 8.05 (t, J = 7.2 Hz, 1H), 7.86 (d, J = 8.8 Hz, 1H), 7.80 (d, J = 9.6 Hz, 1H), 7.63 (t, J = 9.2 Hz, 1H), 7.39 (d, J = 2.4 Hz, 1H), 7.33 (d, J = 9.6 Hz, 1H), 7.14 (dd, J = 2.0, 8.8 Hz, 1H), 6.87-6.73 (m, 2H), 4.77-4.68 (m, 1H), 4.58-4.44 (m, 3H), 3.86 (d, J = 8.8 Hz, 1H), 3.30 (s, 7H), 3.02 (t, J = 12.0 Hz, 2H), 2.83-2.72 (m, 1H), 2.47-2.45 (m, 2H), 2.47-2.40 (m, 1H), 2.20 (d, J = 7.2 Hz, 2H), 2.10 (d, J = 4.8 Hz, 3H), 2.00 (d, J = 10.4 Hz, 1H), 1.94-1.79 (m, 5H), 1.70-1.58 (m, 2H), 1.57-1.44 (m, 2H), 1.20-1.06 (m, 2H). |
| 27 | N-((1R,4R)-4-(3-chloro-4-cyanophenoxy)cyclohexyl)-5-(4-((((1r,3r)-3-(4-((2,6-dioxopiperidin-3-yl)carbamoyl)phenoxy)cyclobutyl)(isopropyl)amino)methyl)piperidin-1-yl)pyrazine-2-carboxamide | 810.362 | 811.57 | ¹H NMR (400 MHz, DMSO-d₆) δ 10.82 (s, 1H), 8.62-8.54 (m, 2H), 8.23 (d, J = 8.8 Hz, 2H), 8.04 (d, J = 8.0 Hz, 1H), 7.89-7.75 (m, 3H), 7.36 (d, J = 2.4 Hz, 1H), 7.12 (dd, J = 2.4, 8.8 Hz, 1H), 6.88 (d, J = 8.8 Hz, 2H), 4.79-4.68 (m, 2H), 4.49 (d, J = 12.4 Hz, 3H), 3.88-3.77 (m, 1H), 3.69-3.67 (m, 1H), 3.01-2.86 (m, 3H), 2.84-2.72 (m, 1H), 2.57-2.52 (m, 1H), 2.38 (d, J = 13.8 Hz, 1H), 2.25 (d, J = 6.8 Hz, 2H), 2.21-2.03 (m, 6H), 1.96 (dd, J = 4.0, 8.8 Hz, 1H), 1.92-1.82 (m, 4H), 1.76-1.41 (m, 5H), 1.13-0.98 (m, 2H), 0.92 (d, J = 6.4 Hz, 6H). |
| 28 | N-((1R,4R)-4-(3-chloro-4-cyanophenoxy)cyclohexyl)-6-(4-((4-(6-((2,6-dioxopiperidin-3-yl)carbamoyl)pyridazin-3-yl)piperazin-1-yl)methyl)piperidin-1-yl)pyridazine-3-carboxamide | 769.3215 | 770.63 | ¹H NMR (400 MHz, DMSO-d₆) δ 10.83 (br s, 1H), 9.08 (d, J = 8.4 Hz, 1H), 8.56 (d, J = 8.4 Hz, 1H), 8.30 (s, 1H), 7.86 (dd, J = 9.6, 4.0 Hz, 2H), 7.80 (d, J = 9.6 Hz, 1H), 7.31-7.39 (m, 3H), 7.13 (dd, J = 8.8, 2.4 Hz, 1H), 4.71-4.89 (m, 1H), 4.45-4.59 (m, 3H), 3.80-3.92 (m, 1H), 3.69-3.76 (m, 4H), 3.44-3.58 (m, 4H), 2.97-3.10 (m, 2H), 2.73-2.86 (m, 1H), 2.53-2.58 (m, 1H), 2.18-2.25 (m, 3H), 2.11 (d, J = 9.6 Hz, 2H), 1.97-2.04 (m, 1H), 1.83-1.96 (m, 5H), 1.58-1.69 (m, 2H), 1.46-1.58 (m, 2H), 1.07-1.21 (m, 2H). |
| 29 | N-((1R,4R)-4-(3-chloro-4-cyanophenoxy)cyclohexyl)-6-(4-((4-(3-((2,6-dioxopiperidin-3-yl)carbamoyl)phenyl)piperazin-1-yl)methyl)piperidin-1-yl)pyridazine-3-carboxamide | 767.331 | 768.64 | ¹H NMR (400 MHz, DMSO-d₆) δ 10.86 (s, 1H), 8.52-8.75 (m, 2H), 8.19 (s, 1H), 7.77-7.88 (m, 2H), 7.38 (d, J = 2.4 Hz, 2H), 7.24-7.36 (m, 3H), 7.08-7.15 (m, 2H), 4.71-4.84 (m, 1H), 4.43-4.60 (m, 3H), 3.85 (d, J = 8.0 Hz, 1H), 3.44-3.63 (m, 4H), 3.19 (s, 4H), 3.02 (t, J = 10.4 Hz, 2H), 2.73-2.87 (m, 1H), 2.55 (d, J = 4.0 Hz, 1H), 2.21 (d, J = 7.2 Hz, 2H), 2.05-2.17 (m, 3H), 1.76-2.04 (m, 6H), 1.44-1.70 (m, 4H), 1.03-1.21 (m, 2H). |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| 30 | N-((1R,4R)-4-(3-chloro-4-cyanophenoxy)cyclohexyl)-6-(4-((4-(5-((2,6-dioxopiperidin-3-yl)carbamoyl)pyridin-2-yl)piperazin-1-yl)methyl)piperidin-1-yl)pyridazine-3-carboxamide | 768.3263 | 769.64 | $^1$H NMR (400 MHz, DMSO-$d_6$) δ 10.84 (br s, 1H), 8.61 (br s, 1H), 8.56 (dd, J = 16.0, 8.0 Hz, 2H), 7.96 (d, J = 7.6 Hz, 1H), 7.85 (d, J = 8.8 Hz, 1H), 7.80 (d, J = 8.8 Hz, 1H), 7.38 (s, 1H), 7.33 (d, J = 9.6 Hz, 1H), 7.13 (d, J = 7.2 Hz, 1H), 6.87 (d, J = 8.8 Hz, 1H), 4.74 (br s, 1H), 4.48 (d, J = 12.4 Hz, 3 H), 3.85 (br s, 1H), 3.61 (s, 4H), 3.02 (t, J = 12.4 Hz, 2H), 2.79 (br t, J = 12.4 Hz, 1H), 2.58-2.53 (m, 1H), 2.44 (s, 4H), 2.19 (br d, J = 4.8 Hz, 2H), 2.10 (br d, J = 8.8 Hz, 3H), 2.00-1.78 (m, 6H), 1.69-1.59 (m, 2H), 1.51 (br d, J = 11.2 Hz, 2H), 1.13 (br d, J = 11.2 Hz, 2H). |
| 31 | N-((1R,4R)-4-(3-chloro-4-cyanophenoxy)cyclohexyl)-6-(4-((4-(4-((2,6-dioxopiperidin-3-yl)(methyl)carbamoyl)-3-fluorophenyl)piperazin-1-yl)methyl)piperidin-1-yl)pyridazine-3-carboxamide | 799.3373 | 800.66 | $^1$H NMR (400 MHz, DMSO-$d_6$) δ 10.86 (s, 1H), 8.56 (d, J = 8.0 Hz, 1H), 8.21 (s, 1H), 7.76-7.88 (m, 2H), 7.38 (d, J = 2.4 Hz, 1H), 7.32 (d, J = 9.6 Hz, 1H), 7.20 (t, J = 8.4 Hz, 1H), 7.10-7.16 (m, 1H), 6.72-6.85 (m, 2H), 4.90-5.23 (m, 1H), 4.44-4.58 (m, 3H), 3.78-3.95 (m, 1H), 3.24 (s, 4H), 3.02 (t, J = 12.0 Hz, 2H), 2.79 (s, 4H), 2.28-2.73 (m, 1H), 2.42-2.49 (m, 4H), 2.34-2.41 (m, 1H), 2.04-2.25 (m, 4H), 1.87-1.96 (m, 4H), 1.83 (d, J = 13.6 Hz, 2H), 1.58-1.70 (m, 2H), 1.45-1.57 (m, 2H), 1.08-1.18 (m, 2H). |
| 32 | N-((1R,4R)-4-(3-chloro-4-cyanophenoxy)cyclohexyl)-6-(4-((4-(4-((2,6-dioxopiperidin-3-yl)(ethyl)carbamoyl)phenyl)piperazin-1-yl)methyl)piperidin-1-yl)pyridazine-3-carboxamide | 795.3623 | 796.68 | $^1$H NMR (400 MHz, DMSO-$d_6$) δ 10.72 (s, 1H), 8.57 (d, J = 8.4 Hz, 1H), 8.30 (s, 1H), 7.76-7.89 (m, 2H), 7.38 (d, J = 2.4 Hz, 1H), 7.33 (d, J = 9.6 Hz, 1H), 7.25 (d, J = 8.4 Hz, 2H), 7.13 (dd, J = 8.8, 2.20 Hz, 1H), 6.95 (d, J = 8.4 Hz, 2H), 4.41-4.56 (m, 3H), 4.28 (s, 1H), 3.86 (d, J = 7.6 Hz, 1H), 3.22 (s, 11H), 2.94-3.09 (m, 3H), 2.69 (d, J = 12.4 Hz, 1H), 2.20 (d, J = 6.4 Hz, 2H), 2.10 (d, J = 10.8 Hz, 2H), 1.77-2.00 (m, 6H), 1.44-1.66 (m, 4H), 1.13 (t, J = 6.8 Hz, 5H). |
| 33 | N-[(3S)-2,6-dioxopiperidin-3-yl]-5-(4-{[1-(4-{[(1r,3r)-3-(4-cyano-3,5-dimethylphenoxy)-2,2,4,4-tetramethylcyclobutyl]carbamoyl}phenyl)piperidin-4-yl]methyl}piperazin-1-yl)pyrazine-2-carboxamide | 789.433 | 790.80 | |
| 34 | N-[(1r,3r)-3-(4-cyano-3-methoxyphenoxy)-2,2,4,4-tetramethylcyclobutyl]-4-{4-[(1r,3r)-3-(4-{[(3S)-2,6-dioxopiperidin-3-yl]carbamoyl}-3-methoxyphenoxy)cyclobutyl]-1-oxa-4,9-diazaspiro[5.5]undecan-9-yl}benzamide | 862.427 | 863.80 | |
| 35 | N-[(3S)-2,6-dioxopiperidin-3-yl]-2-methoxy-4-[(1r,3r)-3-[9-(4-{[(1r,3r)-3-(4-cyano-3,5-dimethylphenoxy)-2,2,4,4-tetramethylcyclobutyl]carbamoyl}phenyl)-1- | 860.447 | 861.80 | |

TABLE 3-continued

¹H NMR AND MASS SPECTROSCOPY DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | oxa-4,9-diazaspiro[5.5]undecan-4-yl]cyclobutoxy]benzamide | | | |
| 36 | N-[(3S)-2,6-dioxopiperidin-3-yl]-2-fluoro-4-{4-[2-(4-{[(1r,3r)-3-(3-chloro-4-cyanophenoxy)-2,2,4,4-tetramethylcyclobutyl]carbamoyl}phenyl)ethynyl]-[1,4'-bipiperidin]-1'-yl}benzamide | 820.352 | 821.20 | (400 MHz, DMSO-d₆) δ: 10.81 (br s, 1H), 8.29 (s, 1H), 8.02 (t, J = 7.2 Hz, 1H), 7.93-7.85 (m, 2H), 7.80 (d, J = 8.4 Hz, 2H), 7.61 (t, J = 9.2 Hz, 1H), 7.46 (d, J = 8.4 Hz, 2H), 7.20 (d, J = 2.4 Hz, 1H), 7.00 (dd, J = 2.4, 8.8 Hz, 1H), 6.83-6.70 (m, 2H), 4.75-4.66 (m, 1H), 4.31 (s, 1H), 4.05 (d, J = 9.2 Hz, 1H), 3.91 (br d, J = 12.4 Hz, 2H), 2.84-2.73 (m, 5H), 2.64 (br s, 1H), 2.36-2.30 (m, 2H), 2.16-2.07 (m, 1H), 2.04-1.94 (m, 1H), 1.87 (br d, J = 9.6 Hz, 2H), 1.79 (br d, J = 11.2 Hz, 2H), 1.65-1.56 (m, 2H), 1.51-1.41 (m, 2H), 1.21 (s, 6H), 1.17-1.11 (m, 8H). |
| 37 | N-[(3S)-2,6-dioxopiperidin-3-yl]-5-(4-{[1-(4-{[(1r,3r)-3-(4-cyano-3-methoxyphenoxy)-2,2,4,4-tetramethylcyclobutyl]carbamoyl}phenyl)piperidin-4-yl]methyl}piperazin-1-yl)pyrazine-2-carboxamide | 791.412 | 792.30 | |
| 38 | N-[(3S)-2,6-dioxopiperidin-3-yl]-5-(4-{[1-(4-{[(1r,3r)-3-(4-cyano-3,5-dimethylphenoxy)-2,2,4,4-tetramethylcyclobutyl]carbamoyl}phenyl)piperidin-4-yl]methyl}piperazin-1-yl)pyrimidine-2-carboxamide | 789.433 | 790.40 | |
| 39 | N-[(3S)-2,6-dioxopiperidin-3-yl]-5-(4-{[1-(4-{[(1r,3r)-3-(4-cyano-3-methoxyphenoxy)-2,2,4,4-tetramethylcyclobutyl]carbamoyl}phenyl)piperidin-4-yl]methyl}piperazin-1-yl)pyrimidine-2-carboxamide | 791.412 | 792.40 | |
| 40 | N-[(3S)-2,6-dioxopiperidin-3-yl]-5-(4-{[1-(4-{[(1r,3r)-3-(4-cyano-3-methoxyphenoxy)-2,2,4,4-tetramethylcyclobutyl]carbamoyl}phenyl)piperidin-4-yl]methyl}piperazin-1-yl)pyridine-2-carboxamide | 790.417 | 791.70 | |
| 41 | N-[(3S)-2,6-dioxopiperidin-3-yl]-5-(4-{[1-(4-{[(1r,3r)-3-(4-cyano-3,5-dimethylphenoxy)-2,2,4,4-tetramethylcyclobutyl]carbamoyl}phenyl) | 788.437 | 789.80 | |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | piperidin-4-yl]methyl}piperazin-1-yl)pyridine-2-carboxamide | | | |
| 42 | N-[(3S)-2,6-dioxopiperidin-3-yl]-6-(4-{[1-(4-{[(1r,3r)-3-(4-cyano-3-methoxyphenoxy)-2,2,4,4-tetramethylcyclobutyl]carbamoyl}phenyl)piperidin-4-yl]methyl}piperazin-1-yl)pyridine-3-carboxamide | 790.417 | 791.80 | (400 MHz, DMSO-d6) δ: 10.85 (s, 1H), 8.62 (d, J = 2.4 Hz, 1H), 8.54 (d, J = 8.4 Hz, 1H), 7.97 (dd, J = 2.4, 9.2 Hz, 1H), 7.74 (d, J = 8.4 Hz, 2H), 7.65 (d, J = 8.4 Hz, 1H), 7.50 (d, J = 9.2 Hz, 1H), 7.01-6.92 (m, 1H), 6.96 (br d, J = 8.8 Hz, 2H), 6.88 (d, J = 9.2 Hz, 1H), 6.64 (d, J = 2.0 Hz, 1H), 6.54 (dd, J = 2.0, 8.7 Hz, 1H), 4.81-4.69 (m, 1H), 4.28 (s, 1H), 4.06 (d, J = 9.2 Hz, 1H), 3.91 (s, 3H), 3.86 (br d, J = 12.0 Hz, 2H), 3.62 (br s, 4H), 2.79 (br t, J = 12.0 Hz, 3H), 2.56 (br d, J = 3.6 Hz, 1H), 2.45 (br s, 4H), 2.25-2.05 (m, 3H), 2.02-1.93 (m, 1H), 1.82 (br d, J = 12.0 Hz, 3H), 1.23 (s, 8H), 1.15 (s, 6H). |
| 43 | 4-[(2R)-2-{[(propan-2-yl)[(1r,3r)-3-(4-{[(3S)-2,6-dioxopiperidin-3-yl]carbamoyl}-3-fluorophenoxy)cyclobutyl]amino]methyl}morpholin-4-yl]-N-[(1r,3r)-3-(4-cyano-3-methoxyphenoxy)-2,2,4,4-tetramethylcyclobutyl]benzamide | 852.422 | 853.80 | |
| 44 | 4-[(2S)-2-{[(propan-2-yl)[(1r,3r)-3-(4-{[(3S)-2,6-dioxopiperidin-3-yl]carbamoyl}-3-fluorophenoxy)cyclobutyl]amino]methyl}morpholin-4-yl]-N-[(1r,3r)-3-(4-cyano-3-methoxyphenoxy)-2,2,4,4-tetramethylcyclobutyl]benzamide | 852.422 | 853.30 | |
| 45 | 4-[(2R)-2-{[(2-methoxyethyl)[(1r,3r)-3-(4-{[(3S)-2,6-dioxopiperidin-3-yl]carbamoyl}-3-fluorophenoxy)cyclobutyl]amino]methyl}morpholin-4-yl]-N-[(1r,3r)-3-(4-cyano-3,5-dimethylphenoxy)-2,2,4,4-tetramethylcyclobutyl]benzamide | 866.438 | 867.42 | (400 MHz, DMSO, ppm) δ 10.85 (s, 1H), 8.30 (m, 1H), 7.78 (d, J = 8.4 Hz, 2H), 7.67 (t, J = 8.6 Hz, 1H), 7.51 (d, J = 9.2 Hz, 1H), 6.98 (d, J = 8.5 Hz, 2H), 6.73 (m, 4H), 4.80 (m, 2H), 4.22 (s, 1H), 4.07 (m, 2H), 3.95 (d, J = 11.2 Hz, 1H), 3.76 (m, 4H), 3.41 (m, 2H), 3.25 (m, 4H), 2.77 (m, 1H), 2.68 (m, 4H), 2.57 (m, 1H), 2.43 (m, 9H), 2.41 (m, 3H), 2.20 (m, 1H), 2.17 (m, 6H), 1.21 (m, 1H), 1.12 (s, 6H) |
| 46 | N-[(3S)-2,6-dioxopiperidin-3-yl]-6-(4-{[1-(4-{[(1r,3r)-3-(4-cyano-3,5-dimethylphenoxy)-2,2,4,4-tetramethylcyclobutyl]carbamoyl}phenyl)piperidin-4-yl]methyl}piperazin-1-yl)pyridine-3-carboxamide | 788.437 | 789.43 | (400 MHz, DMSO-d6)δ: 10.84 (s, 1H), 8.61 (d, J = 2.4 Hz, 1H), 8.54 (d, J = 8.4 Hz, 1H), 8.17 (s, 1H), 7.96 (dd, J = 2.4, 9.2 Hz, 1H), 7.73 (d, J = 8.8 Hz, 2H), 7.47 (d, J = 9.2 Hz, 1H), 6.96 (d, J = 8.8 Hz, 2H), 6.87 (d, J = 8.8 Hz, 1H), 6.73 (s, 2H), 4.85-4.68 (m, 1H), 4.22 (s, 1H), 4.03 (d, J = 9.2 Hz, 1H), 3.86 (br d, J = 12.4 Hz, 2H), 3.61 (br s, 4H), 2.79 (br t, J = 12.4 Hz, 3H), 2.60-2.52 (m, 1H), 2.43 (s, 10H), 2.20 (br d, J = 6.4 Hz, 2H), 2.15-2.04 (m, 1H), 1.96 (br d, J = 5.6 Hz, 1H), 1.81 (br d, J = 11.2 Hz, 3H), 1.21 (s, 8H), 1.12 (s, 6H). |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| 47 | 4-[(2R)-2-{[(propan-2-yl)[(1r,3r)-3-(4-{[(3S)-2,6-dioxopiperidin-3-yl]carbamoyl}-3-fluorophenoxy)cyclobutyl]amino]methyl}morpholin-4-yl]-N-[(1r,3r)-3-(4-cyano-3,5-dimethylphenoxy)-2,2,4,4-tetramethylcyclobutyl]benzamide | 850.443 | 851.43 | |
| 48 | N-[(3S)-2,6-dioxopiperidin-3-yl]-2-fluoro-4-(4-{[(2R)-4-(4-{[(1r,3r)-3-(4-cyano-3,5-dimethylphenoxy)-2,2,4,4-tetramethylcyclobutyl]carbamoyl}phenyl)morpholin-2-yl]methyl}piperazin-1-yl)benzamide | 807.412 | 808.41 | |
| 49 | N-[(3R)-2,6-dioxopiperidin-3-yl]-2-fluoro-4-(4-{[(2R)-4-(4-{[(1r,3r)-3-(4-cyano-3,5-dimethylphenoxy)-2,2,4,4-tetramethylcyclobutyl]carbamoyl}phenyl)morpholin-2-yl]methyl}piperazin-1-yl)benzamide | 807.412 | 808.40 | |
| 50 | 4-[(2S)-2-{[(2-methoxyethyl)[(1r,3r)-3-(4-{[(3R)-2,6-dioxopiperidin-3-yl]carbamoyl}-3-fluorophenoxy)cyclobutyl]amino]methyl}morpholin-4-yl]-N-[(1r,3r)-3-(4-cyano-3-methoxyphenoxy)-2,2,4,4-tetramethylcyclobutyl]benzamide | 868.417 | 869.40 | |
| 51 | 4-[(2S)-2-{[(2-methoxyethyl)[(1r,3r)-3-(4-{[(3R)-2,6-dioxopiperidin-3-yl]carbamoyl}-3-fluorophenoxy)cyclobutyl]amino]methyl}morpholin-4-yl]-N-[(1r,3r)-3-(4-cyano-3,5-dimethylphenoxy)-2,2,4,4-tetramethylcyclobutyl]benzamide | 866.438 | 867.43 | (400 MHz, DMSO, ppm) δ 10.85 (s, 1H), 8.30 (m, 1H), 7.78 (d, J = 8.4 Hz, 2H), 7.67 (t, J = 8.6 Hz, 1H), 7.51 (d, J = 9.2 Hz, 1H), 6.98 (d, J = 8.5 Hz, 2H), 6.73 (m, 4H), 4.80 (m, 2H), 4.22 (s, 1H), 4.07 (m, 2H), 3.95 (d, J = 11.2 Hz, 1H), 3.76 (m, 4H), 3.41 (m, 2H), 3.25 (m, 4H), 2.77 (m, 1H), 2.68 (m, 4H), 2.57 (m, 1H), 2.43 (m, 9H), 2.41 (m, 3H), 2.20 (m, 1H), 2.17 (m, 6H), 1.21 (m, 1H), 1.12 (s, 6H). |
| 52 | N-[(3S)-2,6-dioxopiperidin-3-yl]-2-fluoro-4-(4-{[(2S)-4-(4-{[(1r,3r)-3-(4-cyano-3,5-dimethylphenoxy)-2,2,4,4-tetramethylcyclobutyl]carbamoyl}phenyl) | 807.412 | 808.41 | |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | morpholin-2-yl]methyl}piperazin-1-yl)benzamide | | | |
| 53 | N-(2,6-dioxopiperidin-3-yl)-2-methoxy-4-[(1r,3r)-3-[9-(4-{[(1r,3r)-3-(4-cyano-3,5-dimethylphenoxy)-2,2,4,4-tetramethylcyclobutyl]carbamoyl}phenyl)-1-oxa-4,9-diazaspiro[5.5]undecan-4-yl]cyclobutoxy]benzamide | 860.447 | 861.44 | ¹HNMR (400 MHz, DMSO-d6) δ 10.88 (s, 1H), 8.48 (m, 1H), 7.96 (s, 1H), 7.86 (m, 3H), , 7.49 (m, 1H), 6.98 (m, 2H), 6.74 (s, 2H), 6.57 (m , 2H), 4.84 (m, 1H), 4.73 (m, 1H), 4.23 (s, 1H), 4.04 (m, 1H), 3.91 (s, 3H), 3.69 (s, 2H), 3.51 (m, 2H), 3.15 (m, 2H), 2.90 (s, 3H), 2.77-2.72 (m, 4H), 2.44 (s, 9H), 2.33 (m, 2H), 2.18 (m, 6H), 1.92 (m, 2H), 1.63 (m, 2H), 1.23 (m, 9H), 1.13 (s, 7H) |
| 54 | N-[(1r,3r)-3-(4-cyano-3-methoxyphenoxy)-2,2,4,4-tetramethylcyclobutyl]-4-{4-[(1r,3r)-3-{4-[(2,6-dioxopiperidin-3-yl)carbamoyl]-3-methoxyphenoxy}cyclobutoxy]piperidin-1-yl}benzamide | 807.384 | 808.38 | |
| 55 | N-(2,6-dioxopiperidin-3-yl)-2-methoxy-4-[(1r,3r)-3-{[1-(4-{[(1r,3r)-3-(4-cyano-3,5-dimethylphenoxy)-2,2,4,4-tetramethylcyclobutyl]carbamoyl}phenyl)piperidin-4-yl]oxy}cyclobutoxy]benzamide | 805.405 | 806.40 | |
| 56 | N-(2,6-dioxopiperidin-3-yl)-3-methoxy-4-(4-{[(2S)-4-(4-{[(1r,3r)-3-(4-cyano-3,5-dimethylphenoxy)-2,2,4,4-tetramethylcyclobutyl]carbamoyl}phenyl)morpholin-2-yl]methyl}piperazin-1-yl)benzamide | 819.432 | 820.55 | (400 MHz, DMSO-d6) δ 10.86 (s, 1H), 9.92 (s, 1H), 8.67-8.65 (m, 1H), 7.83-7.81 (m, 2H), 7.56-7.49 (m, 3H), 7.04-7.02 (m, 3H), 6.74 (m, 2H), 4.80-4.77 (m, 1H), 4.24 (s, 1H), 4.14 (m, 1H), 4.07-4.05 (m, 2H), 3.89-3.82 (s, 3H), 3.79-3.63 (m, 4H), 3.42-3.21 (m, 5H), 3.18-3.05 (m, 3H), 2.85-2.77 (m, 2H), 2.44 (m, 6H), 2.21-1.89 (m, 4H), 1.21 (m, 6H), 1.18 (m, 6H). |
| 57 | N-(2,6-dioxopiperidin-3-yl)-3-methoxy-4-(4-{[(2S)-4-(4-{[(1r,3r)-3-(4-cyano-3-methoxyphenoxy)-2,2,4,4-tetramethylcyclobutyl]carbamoyl}phenyl)morpholin-2-yl]methyl}piperazin-1-yl)benzamide | 821.411 | 822.47 | (400 MHz, DMSO-d6) δ 10.86 (s, 1H), 9.84 (s, 1H), 8.67-8.64 (m, 1H), 7.84-7.81 (m, 2H), 7.67-7.65 (m, 1H), 7.58-7.52 (m, 3H), 7.04-7.01 (m, 3H), 6.65 (s, 1H), 6.56-6.54 (m, 1H), 4.74 (m, 1H), 4.29 (s, 1H), 4.16-3.91 (m, 4H), 3.88 (m, 5H), 3.85-3.73 (m, 4H), 3.70-3.64 (m, 4H), 3.42-3.22 (m, 3H), 3.18-2.92 (m, 2H), 2.91- 2.72 (m, 2H), 2.23-2.08 (m, 2H), 2.00-1.92 (m, 1H), 1.24-1.15 (m, 12H). |
| 58 | N-(2,6-dioxopiperidin-3-yl)-2-methoxy-4-(4-{[(2S)-4-(4-{[(1r,3r)-3-(4-cyano-3-methoxyphenoxy)-2,2,4,4-tetramethylcyclobutyl]carbamoyl}phenyl)morpholin-2-yl]methyl}piperazin-1-yl)benzamide | 821.411 | 822.54 | (400 MHz, DMSO-d6) δ 10.88 (s, 1H), 10.15 (s, 1H), 8.48 (s, 1H), 7.83 (m, 3H), 7.66-7.57 (m, 2H), 7.03-7.01 (m, 2H), 6.65-6.54 (m, 4H), 4.72 (s, 1H), 4.29 (s, 1H), 4.15- 4.06 (m, 5H), 3.95-3.92 (m, 4H), 3.80-3.53 (m, 6H), 3.42 (m, 3H), 3.25 (m, 4H), 2.84-2.77 (m, 2H), 2.68 (m, 1H), 2.13-2.08 (m, 2H), 1.24- 1.16 (m, 12H). |
| 59 | N-(2,6-dioxopiperidin-3-yl)-2-methoxy-4-(4-{[(2S)-4-(4-{[(1r,3r)-3-(4-cyano-3,5-dimethylphenoxy)- | 819.432 | 820.55 | (300 MHz, Chloroform-d) δ 8.65 (s, 1H), 8.09-8.01 (m, 2H), 7.73 (m, 2H), 6.94 (m, 2H), 6.58-6.14 (m, 4H), 4.79-4.75 (m, 1H), 4.14-3.88 (m, 7H), 3.81-3.44 (m, 5H), 2.94-2.66 (m, 10H), 2.46 (m, |

TABLE 3-continued

¹H NMR AND MASS SPECTROSCOPY DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | 2,2,4,4-tetramethylcyclobutyl]carbamoyl}phenyl)morpholin-2-yl]methyl}piperazin-1-yl)benzamide | | | 4H), 2.37-1.83 (m, 3H), 1.25-1.12 (m, 16H). |
| 60 | N-(2,6-dioxopiperidin-3-yl)-3-methoxy-4-(4-{[1-(4-{[(1r,3r)-3-(4-cyano-3-methoxyphenoxy)-2,2,4,4-tetramethylcyclobutyl]carbamoyl}phenyl)piperidin-4-yl]methyl}piperazin-1-yl)benzamide | 819.432 | 820.55 | (400 MHz, Methanol-d4) δ 7.77-7.69 (m, 2H), 7.52 (d, J = 8.6 Hz, 1H), 7.52-7.45 (m, 2H), 7.04-6.95 (m, 3H), 6.63 (d, J = 2.2 Hz, 1H), 6.56 (dd, J = 8.6, 2.2 Hz, 1H), 4.86 (d, J = 6.8 Hz, 1H), 4.26 (s, 1H), 4.13 (s, 1H), 3.93 (d, J = 4.4 Hz, 7H), 3.89 (s, 1H), 3.67-3.55 (m, 1H), 3.17 (s, 4H), 2.90-2.81 (m, 2H), 2.84-2.77 (m, 1H), 2.77-2.63 (m, 1H), 2.66-2.61 (m, 4H), 2.32 (d, J = 6.9 Hz, 2H), 2.26-2.13 (m, 2H), 1.96-1.80 (m, 2H), 1.43-1.29 (m, 3H), 1.29 (s, 6H), 1.24 (s, 6H). |
| 61 | 4-(2-{[(propan-2-yl)[(1r,3r)-3-(3-{[(3S)-2,6-dioxopiperidin-3-yl]carbamoyl}-4-fluorophenoxy)cyclobutyl]amino]methyl}morpholin-4-yl)-N-[(1r,3r)-3-(4-cyano-3,5-dimethylphenoxy)-2,2,4,4-tetramethylcyclobutyl]benzamide | 850.443 | 851.30 | (400 MHz, DMSO-d6) δ = 10.89 (s, 1H), 8.55 (dd, J = 8.0, 3.2 Hz, 1H), 7.79 (d, J = 8.8 Hz, 2H), 7.54 (d, J = 9.2 Hz, 1H), 7.28-7.20 (m, 1H), 7.08-6.95 (m, 4H), 6.78-6.71 (m, 2H), 4.80-4.68 (m, 2H), 4.23 (s, 1H), 4.07-4.02 (m, 1H), 4.00-3.93 (m, 1H), 3.83-3.77 (m, 1H), 3.74-3.48 (m, 5H), 3.05-2.94 (m, 1H), 2.84-2.73 (m, 2H), 2.58-2.53 (m, 2H), 2.48-2.35 (m, 9H), 2.21-2.05 (m, 3H), 2.04-1.95 (m, 1H), 1.22 (s, 6H), 1.12 (s,6H), 1.02-0.90 (m, 6H). |
| 62 | 4-(2-{[(propan-2-yl)[(1r,3r)-3-(3-{[(3S)-2,6-dioxopiperidin-3-yl]carbamoyl}-4-fluorophenoxy)cyclobutyl]amino]methyl}morpholin-4-yl)-N-[(1r,3r)-3-(4-cyano-3-methoxyphenoxy)-2,2,4,4-tetramethylcyclobutyl]benzamide | 852.422 | 853.30 | (400 MHz, DMSO-d6) δ = 10.89 (s, 1H), 8.55 (dd, J = 8.0, 3.2 Hz, 1H), 8.16 (s, 1H), 7.79 (d, J = 8.8 Hz, 2H), 7.66 (d, J = 8.4 Hz, 1H), 7.56 (d, J = 9.6 Hz, 1H), 7.28-7.21 (m, 1H), 7.08-6.94 (m, 4H), 6.64 (d, J = 2.4 Hz, 1H), 6.54 (dd, J = 8.8, 2.4 Hz, 1H), 4.80-4.68 (m, 2H), 4.27 (s, 1H), 4.10-4.04 (m, 1H), 4.01-3.94 (m, 1H), 3.91 (s, 3H), 3.85-3.77 (m, 1H), 3.73-3.50 (m, 5H), 3.03-2.96 (m, 1H), 2.86-2.73 (m, 2H), 2.57-2.53 (m, 2H), 2.46-2.35 (m, 3H), 2.21-2.05 (m, 3H), 2.04-1.97 (m, 1H), 1.23 (s, 6H), 1.15 (s, 6H), 1.04-0.90 (m, 6H). |
| 63 | N-[(1r,3r)-3-(4-cyano-3,5-dimethylphenoxy)-2,2,4,4-tetramethylcyclobutyl]-4-{8-[(1r,3r)-3-(4-{[(3S)-2,6-dioxopiperidin-3-yl]carbamoyl}-3-fluorophenoxy)cyclobutyl]-5-oxa-2,8-diazaspiro[3.5]nonan-2-yl}benzamide | 820.396 | 821.80 | (400 MHz, DMSO-d6) δ 10.85 (s, 1H), 8.40-8.21 (m, 1H), 7.86-7.70 (m, 2H, 7.69-7.65 (m, 1H), 7.55-7.38 (m, 1H), 6.90-6.78 (m, 2H), 6.77-6.68 (m, 2H), 6.55-6.42 (m, 2H), 4.91-4.78 (m, 1H), 4.77-4.70 (m,1H), 4.27-4.19 (m, 1H), 4.07-4.00 (m, 1H), 3.97-3.88 (m, 2H), 3.75-3.60 (m, 4H), 3.55-3.32 (m, 5H), 3.30-3.28 (m, 2H), 3.17-2.92 (m, 1H), 2.85-2.72 (m, 1H) ,2.45-2.38 (m, 6H), 2.22-2.05 (m, 3H), 2.04-1.94 (m, 1H), 1.26-1.17 (m, 6H), 1.16-1.05 (m, 6H). |
| 64 | (1r,18r)-N-(2,6-dioxopiperidin-3-yl)-17-{[1-(4-{[(1r,3r)-3-(4-cyano-3,5-dimethylphenoxy)-2,2,4,4-tetramethylcyclobutyl]carbamoyl}phenyl)piperidin-4-yl]methyl}-2,9,14-trioxa-17-azatricyclo[16.1.1.0³,⁸]icosa-3(8),4,6-triene-6-carboxamide | 902.494 | 903.48 | 2H),7.69-7.65 (m, 1H), 7.55-7.38 (m, |
| 65 | 4-[(2S)-2-{[(propan-2-yl)[(1r,3r)-3-(4-{[(3S)-2,6-2,2,4,4- | 850.443 | 851.44 | (300 MHz, DMSO-d6) δ 10.80 (s, 1H), 8.30 (s, 1H), 7.90-7.80 (m, 2H),7.65 (s, 1H), 7.50 (s, 1H), 7.10-6.91 (m, 2H), |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | dioxopiperidin-3-yl]carbamoyl}-3-fluorophenoxy)cyclobutyl]amino]methyl}morpholin-4-yl]-N-[(1r,3r)-3-(4-cyano-3,5-dimethylphenoxy)-2,2,4,4-tetramethylcyclobutyl]benzamide | | | 1H), 6.90-6.78 (m, 2H), 6.77-6.68 (m, 6.82-6.72 (m, 3H), 4.92-4.73 (m, 2H), 4.17 (s, 1H), 4.0-3.91 (m, 2H), 3.92-3.53 (m, 5H), 2.58 (s, 1H), 2.50-2.48 (m, 7H), 2.43-2.41 (m, 6H), 2.21-2.03(m, 3H), 1.30-1.20 (m, 8H), 1.15-1.03 (m, 7H), 1.00-0.95 (m, 3H), 0.95-0.90 (m, 3H) |
| 66 | N-(2,6-dioxopiperidin-3-yl)-3-methoxy-4-[(1r,3r)-3-[(propan-2-yl)({1-(4-{[(1r,3r)-3-(4-cyano-3,5-dimethylphenoxy)-2,2,4,4-tetramethylcyclobutyl]carbamoyl}phenyl)piperidin-4-yl]methyl})amino]cyclobutoxy]benzamide | 860.484 | 861.61 | (400 MHz, Methanol-d4) δ 7.55 (d, J = 8.9 Hz, 2H), 7.35-7.26 (m, 2H), 6.81 (d, J = 8.9 Hz, 2H), 6.60 (d, J = 8.4 Hz, 1H), 6.53 (s, 2H), 4.59 (s, 1H), 4.05 (s, 1H), 3.93 (s, 1H), 3.74 (s, 3H), 3.72 (s, 1H), 3.60 (s, 1H), 2.84 (s, 1H), 2.63 (t, J = 10.3 Hz, 3H), 2.53 (dt, J = 17.5, 3.7 Hz, 1H), 2.29 (s, 6H), 2.17 (s, 2H), 2.12 (s, 3H), 2.07-1.96 (m, 2H), 1.76 (d, J = 12.6 Hz, 2H), 1.44 (s, 2H), 1.11 (s, 1H), 1.09 (s, 6H), 1.08 (s, 3H), 1.03 (s, 6H), 0.84 (d, J = 6.5 Hz, 6H), 0.71 (s, 1H), −0.06--0.12 (m, 2H), −0.18 (s, 37H), −0.18 (d, J = 6.7 Hz, 2H). |
| 67 | 4-[(2S)-2-{[(2-methoxyethyl)[(1r,3r)-3-(4-{[(3S)-2,6-dioxopiperidin-3-yl]carbamoyl}-3-fluorophenoxy)cyclobutyl]amino]methyl}morpholin-4-yl]-N-[(1r,3r)-3-(4-cyano-3,5-dimethylphenoxy)-2,2,4,4-tetramethylcyclobutyl]benzamide | 866.438 | 867.43 | |
| 68 | N-[(1r,3r)-3-(4-cyano-3,5-dimethylphenoxy)-2,2,4,4-tetramethylcyclobutyl]-4-{4-[(1r,3r)-3-{4-[(2,6-dioxopiperidin-3-yl)carbamoyl]phenoxy}cyclobutyl]-1-oxa-4,9-diazaspiro[5.5]undecan-9-yl}benzamide | 830.437 | 831.43 | (300 MHz, DMSO-d6) δ 10.83 (s, 1H), 9.34 (s, 1H), 8.67-8.55 (m, 1H), 7.90-7.68 (m, 4H), 7.42-7.52 (m, 2H), 7.02-6.82 (m, 4H), 6.82 (s, 1H), 4.90-4.69 (m, 2H), 4.21 (s, 1H), 4.07-4.01 (m, 1H), 3.68 (s, 2H), 3.58-3.43 (m, 2H), 3.30-3.17 (m, 2H), 2.91-2.62 (m, 3H), 2.49-2.36 (m, 8H), 2.22-2.03 (m, 4H), 3.96 (s, 3H), 3.81-3.77 (m, 2H), 2.94-2.81 (m, 1H) 2.78-2.71 (m, 2H), 2.65-2.60 (m, 1H), 2.58-2.51 (m, 6H), 2.00-1.82 (m, 2H), 2.70-2.62 (m, 2H), 1.35-1.00 (m, 12H). |
| 69 | N-[(3S)-2,6-dioxopiperidin-3-yl]-2-fluoro-5-(4-{1-(4-{[(1r,3r)-3-(4-cyano-3-methoxyphenoxy)-2,2,4,4-tetramethylcyclobutyl]carbamoyl}phenyl)piperidin-4-yl]methyl}piperazin-1-yl)benzamide | 807.412 | 808.30 | (400 MHz, DMSO-d6) δ: 10.87 (s, 1H), 8.48 (dd, J = 8.2, 3.6 Hz, 1H), 7.75 (d, J = 8.8 Hz, 2 H), 7.66 (d, J = 8.4 Hz, 1H), 7.49 (d, J = 8.8 Hz, 1H), 7.18-7.11 (m, 3H), 6.96 (br d, J = 8.8 Hz, 2 H), 6.64 (s, 1H), 6.55 (dd, J = 8.8, 2.0 Hz, 1H), 4.79-4.71 (m, 1H), 4.28 (s, 1H),4.07-4.04 (m, 1H), 3.92 (s, 3 H), 3.87 (br d, J = 12.4 Hz, 2 H), 3.13 (br d, J = 4.4 Hz, 5 H), 2.83-2.75 (m, 6 H), 2.22 (br d, J = 6.0 Hz, 2 H), 2.14-1.99 (m, 3 H), 1.81 (br d, J = 12.0 Hz, 3 H), 1.23 (s, 8 H), 1.16 (s,6 H). |
| 70 | rac-N-(2,6-dioxopiperidin-3-yl)-3-(4-{1-(4-{[(1r,3r)-3-(4-cyano-3,5-dimethylphenoxy)-2,2,4,4-tetramethylcyclobutyl]carbamoyl}phenyl)pip | 776.463 | 777.50 | (400 MHz, DMSO-d6) δ: 10.67-10.92 (m, 1H), 8.01 (d, J = 8.4 Hz, 1H), 7.73 (d, J = 8.8 Hz, 2 H), 7.47 (d, J = 9.2 Hz, 1H), 6.95 (d, J = 9.0 Hz, 2 H), 6.66-6.78 (m, 2 H), 4.48-4.59 (m, 1H), 4.23 (s, 1H), 4.04 (d, J = 9.0 Hz, 1H), 3.84 (br d, J = 12.2 Hz, 2 H), 2.70-2.84 (m, 5 H), 2.39-2.48 (m, 7 H), 1.80-2.04 (m, |

TABLE 3-continued

¹H NMR AND MASS SPECTROSCOPY DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | eridin-4-yl]methyl}piperidin-1-yl)bicyclo[1.1.1]pentane-1-carboxamide | | | 10H), 1.61-1.76 (m, 4 H), 1.50-1.60 (m, 1H), 1.26-1.39 (m, 1H), 1.22 (s, 6 H), 1.10-1.18 (m, 10 H), 1.00-1.10 (m, 2H). |
| 71 | N-[(3S)-2,6-dioxopiperidin-3-yl]-2-fluoro-4-(1-{[1-(4-{[(1r,3r)-3-(4-cyano-3,5-dimethylphenoxy)-2,2,4,4-tetramethylcyclobutyl]carbamoyl}phenyl)azetidin-3-yl]methyl}azetidin-3-yl)benzamide | 748.375 | 749.25 | (400 MHz, DMSO-d6) δ 10.87 (s, 1H), 8.49 (m, 1H), 7.72 (d, 2H), 7.65 (t, 1H), 7.42 (d, 1H), 7.35-7.24 (m, 2H), 6.73 (s, 2H), 6.45-6.38 (m, 2H), 4.76 (m, 1H), 4.22 (s, 1H), 4.03-3.96 (t, 3H), 3.66 (m, 3H), 3.56 (m, 2H), 3.15 (t, 2H), 2.78 (d, 4H), 2.55 (d, 5H), 2.04-1.99 (m, 2H), 1.22 (d, 7H), 1.11 (s,6H). |
| 72 | (1r,19r)-N-(2,6-dioxopiperidin-3-yl)-18-{[1-(4-{[(1r,3r)-3-(4-cyano-3,5-dimethylphenoxy)-2,2,4,4-tetramethylcyclobutyl]carbamoyl}phenyl)piperidin-4-yl]methyl}-2,9,15-trioxa-18-azatricyclo[17.1.1.0³,⁸]henicosa-3(8),4,6-triene-5-carboxamide | 916.510 | 917.50 | (400 MHz, DMSO-d6) δ: 10.85 (s, 1H), 8.58 (d, J = 8.0 Hz, 1H), 8.14 (s,1H), 7.73 (d, J = 8.8 Hz, 2H), 7.55-7.43 (m, 2H), 7.40 (d, J = 2.0 Hz, 1H), 7.10 (d, J = 8.8 Hz, 1H), 6.95 (d, J = 9.2 Hz, 2H), 6.74 (s, 2H), 4.89 (s, 1H), 4.79-4.68 (m, 1H), 4.23 (s, 1H), 4.15 (d, J = 1.2 Hz, 2H), 4.07-4.01 (m, 1H), 4.01-3.91 (m, 1H), 3.85 (d, J = 12.4 Hz, 2H), 3.44 (d, J = 1.2 Hz, 2H), 2.86-2.71 (m, 3H), 2.71-2.63 (m, 2H), 2.60-2.54 (m, 1H), 2.44 (s, 7H), 2.33 (td, J = 1.6, 3.6 Hz, 1H), 2.31-2.21 (m, 2H), 2.16-1.91 (m, 6H), 1.85-1.74 (m, 2H), 1.72-1.56 (m, 5H), 1.51-1.38 (m, 2H), 1.22 (s, 6H), 1.12 (s, 8H) |
| 73 | N-[(1r,3r)-3-(4-cyano-3,5-dimethylphenoxy)-2,2,4,4-tetramethylcyclobutyl]-4-{4-[(1r,3r)-3-(4-{[(3S)-2,6-dioxopiperidin-3-yl]carbamoyl}-3-fluorophenoxy)cyclobutoxy]piperidin-1-yl}benzamide | 793.385 | 794.38 | (400 MHz, DMSO-d6) δ 11.05 (s, 1H), 8.39-8.12 (m, 1H), 7.90-7.60 (m, 2H),7.58-7.33 (m, 1H), 7.10-6.88 (m, 2H), 6.87-6.61 (m, 3H), 5.12-4.80 (m, 1H), 4.79-4.60 (m, 1H), 4.50-4.30 (m, 1H), 4.29-4.15 (m,1H), 4.10-3.95 (m, 1H), 3.75-3.60 (m, 2H), 3.58-3.50 (m, 1H), 3.30-3.10 (m, 2H), 3.05-2.90 (m, 2H), 2.85-2.70 (m, 1H), 2.45-2.25 (m, 8H), 2.20-1.80 (m, 4H) ,1.60-1.40 (m, 2H), 1.30-1.03 (m, 12H), 0.90-0.71 (m, 1H). |
| 74 | (1r,18r)-N-(2,6-dioxopiperidin-3-yl)-17-{[1-(4-{[(1r,3r)-3-(4-cyano-3,5-dimethylphenoxy)-2,2,4,4-tetramethylcyclobutyl]carbamoyl}phenyl)piperidin-4-yl]methyl}-2,9,14-trioxa-17-azatricyclo[16.1.1.0³,⁸]icosa-3(8),4,6-triene-5-carboxamide | 902.494 | 903.48 | (400 MHz, DMSO-d6) δ = 10.84 (s, 1H), 8.60 (d, J = 8.0 Hz, 1H), 7.73 (br d, J = 8.8 Hz, 2H), 7.55-7.41 (m, 3H), 7.12 (d, J = 8.4 Hz, 1H), 6.95 (br d, J = 8.8 Hz, 2H), 6.74 (s, 2H), 4.85-4.68 (m, 2H), 4.23 (s, 1H), 4.15-4.01 (m, 4H), 3.85 (br d, J = 12.0 Hz, 2H), 3.51 (br s, 2H), 3.42 - 3.41 (m, 1H), 2.77 (br s, 2H), 2.63 (br s, 3H), 2.44 (s, 6H), 2.34 (br s, 1H), 2.27 (br d, J = 6.4 Hz, 2H), 2.18-2.01 (m, 5H), 1.98-1.92 (m, 1H), 1.91-1.71 (m, 5H), 1.71-1.53 (m, 3H), 1.22 (s, 6H), 1.12 (s, 8H) |
| 75 | N-[(3R)-2,6-dioxopiperidin-3-yl]-2-fluoro-4-(4-{[(2S)-4-(4-{[(1r,3r)-3-(4-cyano-3,5-dimethylphenoxy)-2,2,4,4-tetramethylcyclobutyl]carbamoyl}phenyl)morpholin-2-yl]methyl}piperazin-1-yl)benzamide | 807.412 | 808.40 | |
| 76 | N-(2,6-dioxopiperidin-3-yl)-3-methoxy-5-[(1r,3r)-3-[9-(4-{[(1r,3r)-3-(4-cyano-3,5-dimethylphenoxy)-2,2,4,4-tetramethylcyclobutyl] | 860.447 | 861.44 | (400 MHz, DMSO-d6) δ 10.87 (s, 1H), 8.73-8.71 (m, 1H), 7.76-7.74 (m, 2H), 7.50-7.48 (m, 1H), 7.03-6.91 (m, 4H), 6.74 (s, 2H), 6.55 (s, 1H), 4.81-4.74 (m, 2H), 4.23 (s, 1H), 4.05-4.03 (m, 1H), 3.79 (s, 3H), 3.67 (m, 2H), 3.52-3.49 (m, 2H), 3.18-3.12 (m, 2H), 2.90-2.74 (m, |

TABLE 3-continued

¹H NMR AND MASS SPECTROSCOPY
DATA FOR THE COMPOUNDS OF THE DISCLOSURE

| Compound No. | Compound Name | Exact Mass | Observed m/z [M + 1]⁺ | ¹H NMR Data |
|---|---|---|---|---|
| | carbamoyl}phenyl)-1-oxa-4,9-diazaspiro[5.5]undecan-4-yl]cyclobutoxy]benzamide | | | 2H), 2.44-2.40 (m, 6H), 2.38 (m, 3H), 2.37 (m, 2H), 2.29-2.18 (m, 5H), 1.98-1.87 (m, 3H), 1.64-1.52 (m, 2H), 1.22 (m, 6H), 1.12 (m, 6H). |

Example 26—Bioactivity Data for the Compounds of the Disclosure

AR ELISA Assay Protocol

Compounds were evaluated in this assay in LNCaP and/or VCaP cells utilizing similar protocols. The protocols used with VCaP cells are described below. The androgen receptor ELISA assay was performed using PathScan AR Sandwich ELISA (Cell Signaling Catalog #12850) according to the following assay steps:

VCaP cells were seeded at 40,000 cells/well at a volume of 100 µL/well in VCaP assay medium [Phenol red free RPMI (Gibco Cat #11835-030); 5% Charcoal Stripped (Dextran treated) FBS (Omega Scientific, Cat #FB-04); 1% penstrep (Life Technologies, Gibco Cat #: 10378-016)] in Corning 3904 plates. The cells were incubated for a minimum of 3 days. Cells were dosed with PROTACs diluted in 0.01% DMSO and the drug treatment was allowed for 5 hours.

AR ELISA (Cell Signaling) was performed as follows. 1× Cell Signaling Cell lysis buffer was made (Catalogue #9803; comes with the kit). Media from the treated wells is aspirated, and 100 µL 1× cell lysis buffer/well is added. The cells were placed on a shaker for 10 minutes at 4° C. Twenty microliters of lysate was transferred to 100 µl of Diluent in ELISA plate (0.15 µg/ml-0.075 µg/ml). The lysate-diluent mixture was shaken for 30 minutes at 37° C. Allow mouse AR antibody, anti-mouse antibody, TMB, and STOP solution to come to room temperature. The 1×ELISA buffer included in kit was made and loaded in the reservoir. Media from the plates was discarded, the ELISA plate tapped hard on paper towel, and washed 4×200 µl ELISA wash buffer using a plate washer.

One-hundred (100) µL/well of mouse AR detection Ab was added; the plates were covered and shaken at 37° C. for 1 hour; media was discarded from the plates, the plates were tapped on a paper towel, washed 4× with 200 µL ELISA wash buffer with a plate washer.

One-hundred (100) µL/well of anti-mouse—HRP conjugated Ab (comes with the kit) was added; the plates were covered and shaken at 37° C. for 30 minutes; the TMB reagent was allowed to come to room temperature; the media was discard from the plate, the plates were tapped on paper towel, washed 4× with 200 µL of ELISA wash buffer; the plates were tapped the plates on paper towel. One-hundred (100) L of TMB was added and the plates shaken for 2 minutes—while watching for color development. One-hundred (100) L Stop solution was added when light blue color developed. Plates were shaken and read at 450 nM.

Progression of prostate cancer in patients treated with anti-androgen therapy usually involves one of several mechanisms of enhanced Androgen Receptor (AR) signaling, including increased intratumoral androgen synthesis, increased AR expression and AR mutations. PROTACs (PROteolysis TArgeting Chimera), which use bi-functional molecules that simultaneously bind a target of choice and an E3 ligase, cause ubiquitination via induced proximity and degradation of the targeted, pathological protein. As opposed to traditional target inhibition, which is a competitive process, degradation is a progressive process. As such, it is less susceptible to increases in endogenous ligand, target expression, or mutations in the target. Thus, this technology appears to be ideal for addressing the mechanisms of AR resistance in patients with prostate cancer. Data was analyzed and plotted using GraphPad Prism software.

AR Immunofluorescence Staining of Cells for the High Content Imager was performed as follows: Following treatment of the cells with compound (using the central 60 wells of a 96-well plate), media was removed by aspiration, followed by addition of 50 µL per well of 4% paraformaldehyde (PFA) in PBS supplemented with 2 mM MgCl2 and 2 mM CaCl2). Fixed cells were incubated at RT for 15 minutes. For particularly low adherence cell lines (e.g., VCaP), a 2× solution of 8% PFA was added directly to wells instead. Cells were washed once with 200 µL PBS/well. To permeabilize cells 50 µL/well of 0.1% Triton X-100 in PBS was added and incubated for 5 minutes. Cells were washed once with 200 µL PBSS/well. 100 µL/well of Licor Odyssey Blocking Buffer was added for 1 hour at 20° C. Wells were aspirated and AR antibody (1:1000 in Licor Odyssey blocking buffer; 50 µL/well; CST 5153s) was added. Plates were incubated overnight at 4° C. Plates were washed 3 times with 200 µL PBS/well. The appropriate secondary antibody was added (50 µL/well; diluted in Licor Odyssey blocking buffer) and incubated for 1 hour at RT in the dark as prepared below using Anti-rabbit FITC (1:5000; 488 nM) and Phalloidin-Alexafluor 648 (1:500; 648 nM). Cells were washed once with 200 µL PBS/well. 50 µL DAPI or Hoechst 33342 diluted 1:1000 in Licor Odyssey blocking buffer was added to the wells. Cells were washed 3 times with 200 µL PBS/well. The plates were covered with a clear plastic sealer and refrigerated in the dark until ready to analyze. The cells were analyzed using a Molecular Devices IXM high content imager and analyzed using Molecular Devices metaXpress software suite.

TABLE 4

BIOACTIVITY DATA FOR THE COMPOUNDS OF THE DISCLOSURE

| Compound No. | High Content VCaP DC$_{50}$ (nM) | High Content VCaP D$_{max}$ (%) | ELISA VCaP DC$_{50}$ (nM) | ELISA VCaP D$_{max}$ (%) |
|---|---|---|---|---|
| 1 | ++++ | A | nd | — |
| 2 | nd | — | ++++ | A |
| 3 | nd | — | ++++ | A |
| 4 | nd | — | ++++ | C |
| 5 | nd | — | ++++ | C |

TABLE 4-continued

BIOACTIVITY DATA FOR THE COMPOUNDS OF THE DISCLOSURE

| Compound No. | High Content VCaP $DC_{50}$ (nM) | High Content VCaP $D_{max}$ (%) | ELISA VCaP $DC_{50}$ (nM) | ELISA VCaP $D_{max}$ (%) |
|---|---|---|---|---|
| 6 | nd | — | ++++ | B |
| 7 | nd | — | ++++ | A |
| 8 | nd | — | ++++ | C |
| 9 | nd | — | + | C |
| 10 | nd | — | ++++ | B |
| 11 | nd | — | ++++ | B |
| 12 | nd | — | ++++ | A |
| 13 | nd | — | +++ | B |
| 14 | +++ | C | nd | — |
| 15 | nd | — | +++ | C |
| 16 | nd | — | +++ | C |
| 17 | ++++ | B | nd | — |
| 18 | +++ | B | nd | — |
| 19 | ++++ | A | nd | — |
| 20 | ++++ | A | nd | — |
| 21 | ++++ | A | nd | — |
| 22 | ++++ | A | — | — |
| 23 | ++++ | A | — | — |
| 24 | ++++ | A | — | — |
| 25 | ++++ | B | — | — |
| 26 | ++++ | A | — | — |
| 27 | ++++ | A | — | — |
| 28 | ++++ | A | — | — |
| 29 | ++++ | C | — | — |
| 30 | ++++ | A | — | — |
| 31 | ++++ | B | — | — |
| 32 | + | C | — | — |
| 33 | ++++ | A | — | — |
| 34 | ++++ | A | — | — |
| 35 | ++++ | A | — | — |
| 36 | ++++ | A | — | — |
| 37 | ++++ | A | — | — |
| 38 | ++++ | A | — | — |
| 39 | ++++ | A | — | — |
| 40 | ++++ | A | — | — |
| 41 | ++++ | A | — | — |
| 42 | ++++ | A | — | — |
| 43 | ++++ | A | — | — |
| 44 | ++++ | A | — | — |
| 45 | ++++ | A | — | — |
| 46 | ++++ | A | — | — |
| 47 | ++++ | A | — | — |
| 48 | ++++ | A | — | — |
| 49 | ++++ | A | — | — |
| 50 | ++++ | A | — | — |
| 51 | ++++ | A | — | — |
| 52 | ++++ | A | — | — |
| 53 | ++++ | A | — | — |
| 54 | ++++ | A | — | — |
| 55 | ++++ | A | — | — |
| 56 | ++++ | A | — | — |
| 57 | ++++ | A | — | — |
| 58 | ++++ | A | — | — |
| 59 | ++++ | A | — | — |
| 60 | ++++ | A | — | — |
| 61 | ++++ | B | — | — |
| 62 | ++++ | B | — | — |
| 63 | ++++ | B | — | — |
| 64 | ++++ | B | — | — |
| 65 | ++++ | B | — | — |
| 66 | ++++ | B | — | — |
| 67 | +++ | A | — | — |
| 68 | +++ | B | — | — |
| 69 | ++ | A | — | — |
| 70 | ++++ | C | — | — |
| 71 | ++++ | B | — | — |
| 72 | +++ | C | — | — |
| 73 | +++ | C | — | — |
| 74 | ++++ | C | — | — |
| 75 | +++ | C | — | — |
| 76 | +++ | C | — | — |

++++: $DC_{50}$ <1 nM;
+++: 1 nM <= $DC_{50}$ <10 nM;
++: 10 nM <= $DC_{50}$ <100 nM;
+: $DC_{50}$ >= 100
A: $D_{max}$ >= 70%;
B: 50 <= $D_{max}$ <70; .
C: $D_{max}$ <50
nd = not detected;
"—" = not tested

---

The invention claimed is:
1. A compound that is:

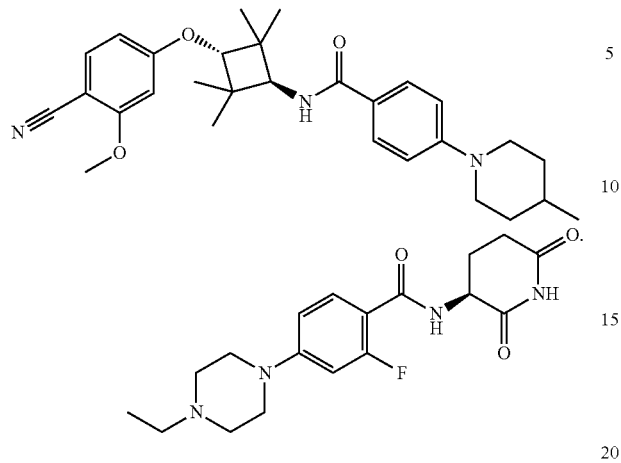

2. A pharmaceutically acceptable salt of a compound that is:

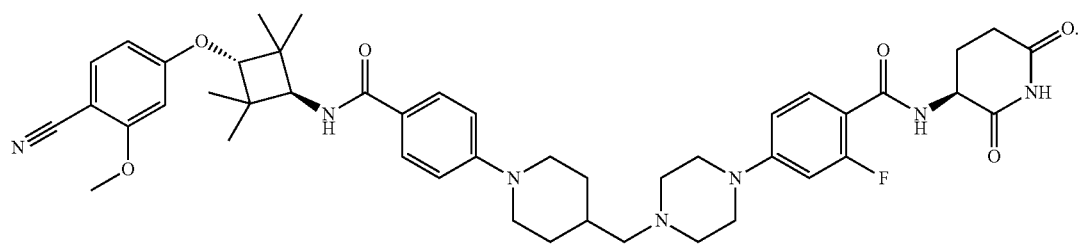 [SMILES: COc1cc(O[C@H]2C(C)(C)[C@H](NC(=O)c3ccc(N4CCC(CN5CCN(c6ccc(C(=O)N[C@H]7CCC(=O)NC7=O)c(F)c6)CC5)CC4)cc3)C2(C)C)ccc1C#N]

3. A pharmaceutical composition comprising a compound and one or more pharmaceutically acceptable excipients, wherein the compound is:

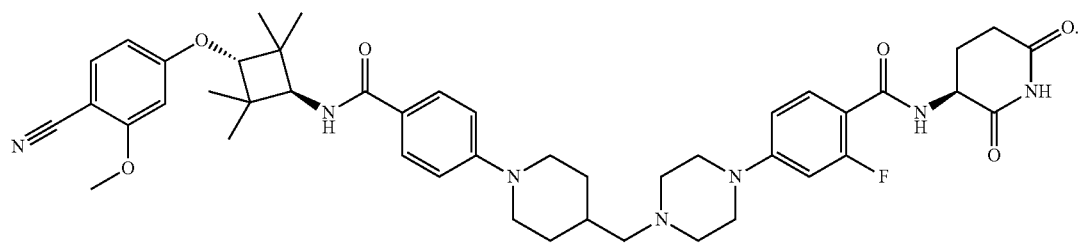 [SMILES: COc1cc(O[C@H]2C(C)(C)[C@H](NC(=O)c3ccc(N4CCC(CN5CCN(c6ccc(C(=O)N[C@H]7CCC(=O)NC7=O)c(F)c6)CC5)CC4)cc3)C2(C)C)ccc1C#N]

4. A pharmaceutical composition comprising a pharmaceutically acceptable salt of a compound and one or more pharmaceutically acceptable excipients, wherein the compound is:

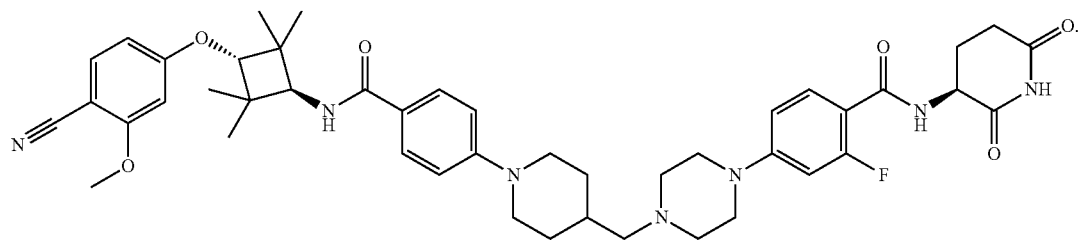 [SMILES: COc1cc(O[C@H]2C(C)(C)[C@H](NC(=O)c3ccc(N4CCC(CN5CCN(c6ccc(C(=O)N[C@H]7CCC(=O)NC7=O)c(F)c6)CC5)CC4)cc3)C2(C)C)ccc1C#N]

* * * * *

UNITED STATES PATENT AND TRADEMARK OFFICE
CERTIFICATE OF CORRECTION

PATENT NO. : 11,883,393 B2
APPLICATION NO. : 17/126501
DATED : January 30, 2024
INVENTOR(S) : Lawrence B. Snyder et al.

Page 1 of 1

It is certified that error appears in the above-identified patent and that said Letters Patent is hereby corrected as shown below:

In the Claims

At Column 417, in Claim number 1, at Line numbers 3-20, the structure of the compound is indicated as:

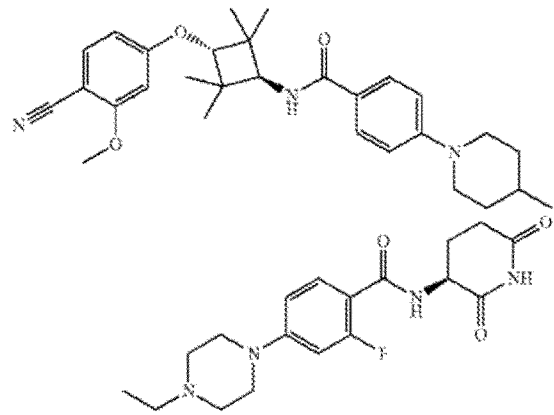

Should be:

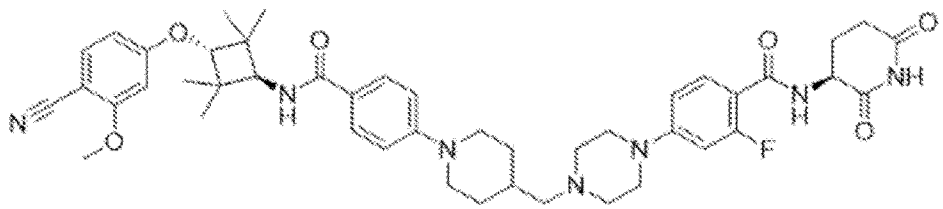

Signed and Sealed this
Twenty-sixth Day of March, 2024

Katherine Kelly Vidal
*Director of the United States Patent and Trademark Office*